US011584747B2

(12) United States Patent
Velaparthi et al.

(10) Patent No.: US 11,584,747 B2
(45) Date of Patent: Feb. 21, 2023

(54) SUBSTITUTED PYRIDOPYRIMIDINONYL COMPOUNDS USEFUL AS T CELL ACTIVATORS

(71) Applicant: BRISTOL-MYERS SQUIBB COMPANY, Princeton, NJ (US)

(72) Inventors: Upender Velaparthi, Princeton Junction, NJ (US); Richard E. Olson, Cambridge, MA (US); Chetan Padmakar Darne, Ewing, NJ (US); Bireshwar Dasgupta, Doylestown, PA (US); Jayakumar Sankara Warrier, Bangalore (IN); Hasibur Rahaman, Bangalore (IN); Prasada Rao Jalagam, Bangalore (IN); Saumya Roy, Bangalore (IN); Denise Christine Grunenfelder, Boston, MA (US)

( * ) Notice: Subject to any disclaimer, the term of this patent is extended or adjusted under 35 U.S.C. 154(b) by 185 days.

(21) Appl. No.: 17/004,058

(22) Filed: Aug. 27, 2020

(65) Prior Publication Data

US 2021/0061802 A1   Mar. 4, 2021

Related U.S. Application Data

(60) Provisional application No. 62/892,799, filed on Aug. 28, 2019.

(51) Int. Cl.
C07D 471/04   (2006.01)

(52) U.S. Cl.
CPC .................................. C07D 471/04 (2013.01)

(58) Field of Classification Search
CPC ..................................................... C07D 471/04
See application file for complete search history.

(56) References Cited

U.S. PATENT DOCUMENTS

| | | | |
|---|---|---|---|
| 4,324,893 | A | 4/1982 | Scotese et al. |
| 7,084,141 | B2 | 8/2006 | Gaeta et al. |
| 7,173,036 | B2 | 2/2007 | Sircar et al. |
| 7,220,856 | B2 | 5/2007 | Dunning et al. |
| 7,279,481 | B2 | 10/2007 | Falchi et al. |
| 7,381,401 | B2 | 6/2008 | Gajewski |
| 9,050,334 | B2 | 6/2015 | Gaweco et al. |
| 9,133,164 | B2 | 9/2015 | Gaweco et al. |
| 10,532,042 | B2 | 1/2020 | Lanman et al. |
| 10,669,272 | B2 | 6/2020 | Velaparthi et al. |
| 2005/0124604 | A1 | 6/2005 | Sircar et al. |
| 2005/0266510 | A1 | 12/2005 | Gajewski |
| 2008/0139551 | A1 | 6/2008 | Sircar et al. |
| 2011/0281908 | A1 | 11/2011 | Sun et al. |
| 2015/0224142 | A1 | 8/2015 | Albelda et al. |
| 2018/0334454 | A1 | 11/2018 | Lanman et al. |
| 2020/0115384 | A1 | 4/2020 | Wu et al. |

FOREIGN PATENT DOCUMENTS

| | | |
|---|---|---|
| WO | 2004056824 A2 | 7/2004 |
| WO | 2004074218 A2 | 9/2004 |
| WO | 2004087880 A2 | 10/2004 |
| WO | 2005009967 A2 | 2/2005 |
| WO | 2005021546 A1 | 3/2005 |
| WO | 2007109251 A2 | 9/2007 |
| WO | 2007132948 A1 | 11/2007 |
| WO | 2007136125 A1 | 11/2007 |
| WO | 2010042489 A2 | 4/2010 |
| WO | 2010088408 A2 | 8/2010 |
| WO | 2012009649 A1 | 1/2012 |
| WO | 2012142498 A2 | 10/2012 |
| WO | 2013118071 A1 | 8/2013 |
| WO | 2016164675 A1 | 10/2016 |
| WO | 2017106607 A1 | 6/2017 |
| WO | 2017177037 A1 | 10/2017 |
| WO | 2018119183 A2 | 6/2018 |

(Continued)

OTHER PUBLICATIONS

Pinedo et al. (2000).*
McMahon et al. (2000).*
Avila-Flores, A. et al., "Predominant Contribution of DGKζ over DGKα in the Control of PKC/PDK-1-Regulated Functions in T Cells", Immunology and Cell Biology (2017) 95: 549-563.
Barraza et al., "Discovery of Anthranilamides as a Novel Class of Inhyibitors of Neurotropic Alphavirus Replication", Bioorg. Med. Chem 23 (2015) 1569-1587.
Boroda et al., "Dual Activites of Ritanserin and R59022 as DGKα inhibitors and Serotonin Receptor Antagonists" Biochemical Pharmacology 123 (2017) 29-39.
Chen et al., "Diacylglycerol Kinases in T Cell Tolerance and Effector Function", Frontiers in Cell and Development Biology 2016 4, 130.

(Continued)

*Primary Examiner* — Paul V Ward
(74) *Attorney, Agent, or Firm* — Gary Greenblatt

(57) ABSTRACT

Disclosed are compounds of Formula (I):

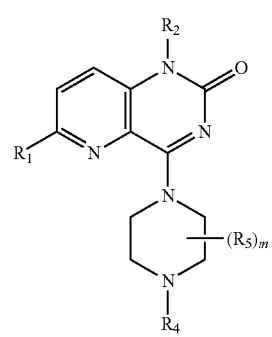

or a salt thereof, wherein: $R_1$, $R_2$, $R_4$, $R_5$, and m are defined herein. Also disclosed are methods of using such compounds to inhibit the activity of one or both of diacylglycerol kinase alpha (DGKα) and diacylglycerol kinase zeta (DGKζ), and pharmaceutical compositions comprising such compounds. These compounds are useful in the treatment of viral infections and proliferative disorders, such as cancer.

33 Claims, No Drawings

Specification includes a Sequence Listing.

(56) References Cited

FOREIGN PATENT DOCUMENTS

| WO | 2018134685 A2 | 7/2018 |
|---|---|---|
| WO | 19005883 A1 | 1/2019 |
| WO | 20006016 A1 | 1/2020 |

OTHER PUBLICATIONS

Dagia et al., "A fluorinated Analog of ISO-1 blocks the Recognition and Biological Function of MIF and is Orally Efficacious in a Murine Model of Colitis" Eur. J. Pharmacology 607 (2009) 201-212.

Database Registry Chemical Abstracts Service: Database RN 2249638-34-2 (Entered STN Nov. 19, 2018).

Facciabene, et al. "T-Regulartory Cells: Key Players in Tumor Immune Escape and Angiogenesis" Cancer Res. 72(9) 2162-2171 (2012).

Franks et al., "The Ligand Binding Landscape of Diacylglycerol Kinases" Cell Chem Bio 24, 870-880 (2017).

Ganesan et al., "Comprehensive in vitro Characterization of PD-L1 Small Molecule Inhibitors", Scientirfic Reports 9, Article No. 12392 (2019).

International Search Report for PCT Application PCT/US2020/048070, dated Oct. 22, 2020.

Jing et al., "T Cells Deficient In Diacylglycerol Kinase Z are Resistance to PD-1 Inhibition and Help Create Persistent Host Immunity to Leukemia" Cancer Res 77(20) 5676-5686 (2017).

Krishna et al., "Regulation of Lipid Signaling by Diacylglycerol Kinases During T Cell Development and Function" Front Immunolog. (2013) 4: Article 178.

Liu et al., "A Novel Diacylglycerol Kinase a-Selective Inhibitor CU-3, Induces Cancer Cell Apoptosis and Enhances mmune Response" J. Lipid Res. 57, 368-379 (2016).

McCloud et al., "Deconstructing Lipid Kinase Inhibitors By Chemical Proteomics" Biochem. 2018, 57, 231-236.

McLean et al., "Fragment Screening of Inhibitors for MIF Tautomerase Reveals a Cryptic Surface Binding Site" Bio. Med Chem. Lett. 20 (2010) 1821-1824.

Mellman et al. "Cancer Immunotherapy Comes of Age" Nature 480 480-489 (2011).

Merida et al., "Redundant and Specialized Roles for Diacylglycerol Kinases a and (in the Control of T cell Functions" Science Signaling 8 (374), re6 (2015).

Merida I., Arranz-Nicolás J., et al., "Diacylglycerol Kinase Malfunction in Human Disease and the Search for Specific Inhibitors", Handbook of Experimental Pharmacology. Springer, Berlin, Heidelberg (2019). First Online: Jun. 22, 2019.

Mizoguchi et al., "Alterations in Signal Transduction Molecules in T Lumphocytes from Tumor-Bearing Mice" (1992) Science 258:1795-98.

Noessner, "DGK-α: A Checkpoint in Cancer-Mediated Immuno-Inhibition and Target for Immunotherapy" Front Cell Dev Bio 2017 5, Article 16.

Olenchock et al., "Disruption of the Diacylglycerol Metabolism Impairs the Induction of T cell Anergy", Nature Immunology 7(11) 1174-1181 (2006).

Prinz et al., "High DGK-α and Disabled MAPK Pathways Cause Dysfunction of Human Tumor-Infiltrating CD8+ T Cells that Is Reversible by Pharmacologic Intervention", J Immunology 188(12) 5990-6000 (2012).

Purow, B. "Molecular Pathways: Targeting Diacylglycerol Kinase Aplha in Cancer" Clin. Cancer Res. 21(22) 5008-5012 (2015).

Riese et al., "Decreased Diacylglycerol Metabolism Enhances ERK Activation and Augments DC8+ T Cell Functional Responses", J Bio Chem 286(7) 5254-5265 (2011).

Riese et al., "Diacylglycerol Kinases (DGKs): Novel Targets for Improving T Cell Activity in Cancer" Frontiers Cell Dev Bio (2016) 4, Article 108.

Santilli et al., "2-Oxo-1,8-naphthyridine-3-carboxylic Acid Derivatives with Potent Gastric Antisecretory Properties" J. Med. Chem. 1987, 30, 2270-2277.

Sjoblom et al. "The Consensus Coding Sequences of Human Breast and Colorectal Cancers" Science 314 268-274 (2006).

Topalian et al., "Targetomg the PD-1/B7-H1(PD-L1) Pathway to Activate Anti-tumor Immunity", Curr. Opin. Immunol. 2012, 24:207-212.

Velnati et al., "Identification of a Novel DGKα Inhibitor for XLP-1 Therapy by Virtual Screening", Eur J Med Chem 164 (2019) 378-390.

Wesley et al., "Diacylglycerol Kinase ζ (DGKζ) and Casitas b-Lineage Proto-Oncogene b-Deficient Mice Have Similar Functional Outcomes in T Cells but DGK ζ-Deficient Mice have Increased T Cell Activatin and Tumor Clearance" ImmunoHorizons 2018 2 94) 107-118.

Zha Y et al., "T Cell Anergy is Reversed by Active Ras and is Regulated by Diacylglycerol Kinase-α" Nature Immunology, (2006) 7(11) 1166-1173; Erratum 7(12) 1343.

* cited by examiner

SEQUENCE LISTING

<160> NUMBER OF SEQ ID NOS: 4

<210> SEQ ID NO 1
<211> LENGTH: 2256
<212> TYPE: DNA
<213> ORGANISM: Homo sapiens

<400> SEQUENCE: 1

```
atggccaagg agaggggcct aataagcccc agtgattttg cccagctgca aaaatacatg    60
gaatactcca ccaaaaaggt cagtgatgtc ctaaagctct cgaggatgg cgagatggct   120
aaatatgtcc aaggagatgc cattgggtac gagggattcc agcaattcct gaaaatctat   180
ctcgaagtgg ataatgttcc cagacaccta agcctggcac tgtttcaatc ctttgagact   240
ggtcactgct aaatgagac aaatgtgaca aagatgtgg tgtgtctcaa tgatgtttcc   300
tgctactttt cccttctgga gggtggtcgg ccagaagaca agttagaatt caccttcaag   360
ctgtacgaca cggacagaaa tgggatcctg gacagctcag aagtggacaa aattatccta   420
cagatgatgc gagtggctga ataccctggat tgggatgtgt ctgagctgag gccgattctt   480
caggagatga tgaaagagat tgactatgat ggcagtggct ctgtctctca agctgagtgg   540
gtccgggctg gggccaccac cgtgccactg ctagtgctgc tgggtctgga gatgactctg   600
aaggacgacg gcagcacat gtggaggccc aagaggttcc ccagaccagt ctactgcaat   660
ctgtgcgagt caagcattgg tcttggcaaa cagggactga gctgtaacct gtcaagtac   720
actgttcacg accagtgtgc catgaaagcc ctgccttgtg aagtcagcac ctatgccaag   780
tctcggaagg acattggtgt ccaatcacat gtgtgggtgc gaggaggctg tgagtccggg   840
cgctgcgacc gctgtcagaa aaagatccgg atctaccaca gtctgaccgg gctgcattgt   900
gtatggtgcc acctagagat ccacgatgac tgcctgcaag cggtgggcca tgagtgtgac   960
tgtgggctgc tccgggatca catcctgcct ccatcttcca tctatccag tgtcctggcc  1020
tctgaccgg atcgtaaaaa tagcaaaaca agccagaaga ccatggatga tttaaatttg  1080
agcacctctg aggctctgcg gattgaccct gttcctaaca cccacccact tctcgtcttt  1140
```

-continued

```
gtcaatccta agagtggcgg gaagcagggg cagagggtgc tctggaagtt ccagtatata   1200
ttaaaccctc gacaggtgtt caacctccta aaggatggtc ctgagatagg gctccgatta   1260
ttcaaggatg ttcctgatag ccggattttg gtgtgtggtg gagacggcac agtaggctgg   1320
attctagaga ccattgacaa agctaacttg ccagttttgc ctcctgttgc tgtgttgccc   1380
ctgggtactg gaaatgatct ggctcgatgc ctaagatggg gaggaggtta tgaaggacag   1440
aatctggcaa agatcctcaa ggatttagag atgagtaaag tggtacatat ggatcgatgg   1500
tctgtggagg tgatacctca acaaactgaa gaaaaagtg acccagtccc ctttcaaatc   1560
atcaataact acttctctat tggcgtggat gcctctattg ctcatcgatt ccacatcatg   1620
cgagagaaat atccggagaa gttcaacagc agaatgaaga caagctatg gtacttcgaa   1680 tttgccacat ctgaatccat cttctcaaca tgcaaaaagc tggaggagtc tttgacagtt   1740
gagatctgtg gaaaccgct ggatctgagc aacctgtccc tagaaggcat cgcagtgcta   1800
aacatcccta gcatgcatgg tggctccaac ctctggggtg ataccaggag accccatggg   1860
gatatctatg ggatcaacca ggcctttaggt gctacagcta aagtcatcac cgaccctgat   1920
atcctgaaaa cctgtgtacc agacctaagt gacaagagac tggaagtggt tgggctggag   1980
ggtgcaattg agatgggcca aatctatacc aagctcaaga atgctggacg tcggctggcc   2040
aagtgctctg agatcacctt ccacaccaca aaaacccttc ccatgcaaat tgacggagaa   2100
ccctggatgc agacgccctg tacaatcaag atcacccaca gaaccagat gcccatgctc   2160 atgggcccac cccccgctc caccaatttc tttggcttct tgagcggatc ctcggagaca   2220
gtgcggtttc agggacacca ccaccatcac cactga                             2256
```

<210> SEQ ID NO 2
<211> LENGTH: 737
<212> TYPE: PRT
<213> ORGANISM: Homo sapiens

<400> SEQUENCE: 2

```
Met Ala Ser Pro Ser Asp Phe Ala Gln Leu Gln Lys Tyr Met Glu Tyr
1               5                   10                  15

Ser Thr Lys Lys Val Ser Asp Val Leu Lys Leu Phe Glu Asp Gly Glu
            20                  25                  30

Met Ala Lys Tyr Val Gln Gly Asp Ala Ile Gly Tyr Glu Gly Phe Gln
        35                  40                  45

Gln Phe Leu Lys Ile Tyr Leu Glu Val Asp Asn Val Pro Arg His Leu
    50                  55                  60

Ser Leu Ala Leu Phe Gln Ser Phe Glu Thr Gly His Cys Leu Asn Glu
65                  70                  75                  80

Thr Asn Val Thr Lys Asp Val Val Cys Leu Asn Asp Val Ser Cys Tyr
                85                  90                  95

Phe Ser Leu Leu Glu Gly Gly Arg Pro Glu Asp Lys Leu Glu Phe Thr
            100                 105                 110

Phe Lys Leu Tyr Asp Thr Asp Arg Asn Gly Ile Leu Asp Ser Ser Glu
        115                 120                 125

Val Asp Lys Ile Ile Leu Gln Met Met Arg Val Ala Glu Tyr Leu Asp
    130                 135                 140

Trp Asp Val Ser Glu Leu Arg Pro Ile Leu Gln Glu Met Met Lys Glu
145                 150                 155                 160

Ile Asp Tyr Asp Gly Ser Gly Ser Val Ser Gln Ala Glu Trp Val Arg
                165                 170                 175
```

```
Ala Gly Ala Thr Thr Val Pro Leu Leu Val Leu Leu Gly Leu Glu Met
            180                 185                 190

Thr Leu Lys Asp Asp Gly Gln His Met Trp Arg Pro Lys Arg Phe Pro
        195                 200                 205

Arg Pro Val Tyr Cys Asn Leu Cys Glu Ser Ser Ile Gly Leu Gly Lys
    210                 215                 220

Gln Gly Leu Ser Cys Asn Leu Cys Lys Tyr Thr Val His Asp Gln Cys
225                 230                 235                 240

Ala Met Lys Ala Leu Pro Cys Glu Val Ser Thr Tyr Ala Lys Ser Arg
                245                 250                 255

Lys Asp Ile Gly Val Gln Ser His Val Trp Val Arg Gly Gly Cys Glu
            260                 265                 270

Ser Gly Arg Cys Asp Arg Cys Gln Lys Lys Ile Arg Ile Tyr His Ser
        275                 280                 285

Leu Thr Gly Leu His Cys Val Trp Cys His Leu Glu Ile His Asp Asp
    290                 295                 300

Cys Leu Gln Ala Val Gly His Glu Cys Asp Cys Gly Leu Leu Arg Asp
305                 310                 315                 320

His Ile Leu Pro Pro Ser Ser Ile Tyr Pro Ser Val Leu Ala Ser Gly
                325                 330                 335

Pro Asp Arg Lys Asn Ser Lys Thr Ser Gln Lys Thr Met Asp Asp Leu
            340                 345                 350

Asn Leu Ser Thr Ser Glu Ala Leu Arg Ile Asp Pro Val Pro Asn Thr
        355                 360                 365

His Pro Leu Leu Val Phe Val Asn Pro Lys Ser Gly Gly Lys Gln Gly
    370                 375                 380

Gln Arg Val Leu Trp Lys Phe Gln Tyr Ile Leu Asn Pro Arg Gln Val
385                 390                 395                 400

Phe Asn Leu Leu Lys Asp Gly Pro Glu Ile Gly Leu Arg Leu Phe Lys
                405                 410                 415

Asp Val Pro Asp Ser Arg Ile Leu Val Cys Gly Gly Asp Gly Thr Val
            420                 425                 430

Gly Trp Ile Leu Glu Thr Ile Asp Lys Ala Asn Leu Pro Val Leu Pro
        435                 440                 445

Pro Val Ala Val Leu Pro Leu Gly Thr Gly Asn Asp Leu Ala Arg Cys
    450                 455                 460

Leu Arg Trp Gly Gly Gly Tyr Glu Gly Gln Asn Leu Ala Lys Ile Leu
465                 470                 475                 480

Lys Asp Leu Glu Met Ser Lys Val Val His Met Asp Arg Trp Ser Val
                485                 490                 495

Glu Val Ile Pro Gln Gln Thr Glu Glu Lys Ser Asp Pro Val Pro Phe
            500                 505                 510

Gln Ile Ile Asn Asn Tyr Phe Ser Ile Gly Val Asp Ala Ser Ile Ala
        515                 520                 525

His Arg Phe His Ile Met Arg Glu Lys Tyr Pro Glu Lys Phe Asn Ser
    530                 535                 540

Arg Met Lys Asn Lys Leu Trp Tyr Phe Glu Phe Ala Thr Ser Glu Ser
545                 550                 555                 560

Ile Phe Ser Thr Cys Lys Lys Leu Glu Glu Ser Leu Thr Val Glu Ile
                565                 570                 575

Cys Gly Lys Pro Leu Asp Leu Ser Asn Leu Ser Leu Glu Gly Ile Ala
            580                 585                 590
```

```
Val Leu Asn Ile Pro Ser Met His Gly Gly Ser Asn Leu Trp Gly Asp
            595                 600                 605

Thr Arg Arg Pro His Gly Asp Ile Tyr Gly Ile Asn Gln Ala Leu Gly
        610                 615                 620

Ala Thr Ala Lys Val Ile Thr Asp Pro Asp Ile Leu Lys Thr Cys Val
625                 630                 635                 640

Pro Asp Leu Ser Asp Lys Arg Leu Glu Val Val Gly Leu Glu Gly Ala
                645                 650                 655

Ile Glu Met Gly Gln Ile Tyr Thr Lys Leu Lys Asn Ala Gly Arg Arg
            660                 665                 670

Leu Ala Lys Cys Ser Glu Ile Thr Phe His Thr Thr Lys Thr Leu Pro
        675                 680                 685

Met Gln Ile Asp Gly Glu Pro Trp Met Gln Thr Pro Cys Thr Ile Lys
690                 695                 700

Ile Thr His Lys Asn Gln Met Pro Met Leu Met Gly Pro Pro Arg
705                 710                 715                 720

Ser Gly Ser Ser Glu Thr Val Arg Phe Gln Gly His His His His
                725                 730                 735

His

<210> SEQ ID NO 3
<211> LENGTH: 2838
<212> TYPE: PRT
<213> ORGANISM: Homo sapiens

<400> SEQUENCE: 3

Ala Thr Gly Gly Ala Gly Cys Cys Gly Cys Gly Gly Ala Cys Gly
1               5                   10                  15

Gly Thr Ala Gly Cys Cys Cys Cys Gly Ala Gly Gly Cys Cys Cys Gly
                20                  25                  30

Gly Ala Gly Cys Ala Gly Cys Gly Ala Cys Thr Cys Cys Gly Ala Gly
                35                  40                  45

Thr Cys Gly Gly Cys Thr Thr Cys Cys Gly Cys Cys Thr Cys Gly Thr
        50                  55                  60

Cys Cys Ala Gly Cys Gly Gly Cys Thr Cys Cys Gly Ala Gly Cys Gly
65                  70                  75                  80

Cys Gly Ala Cys Gly Cys Cys Gly Gly Thr Cys Cys Gly Ala Gly
                85                  90                  95

Cys Cys Gly Gly Ala Cys Ala Ala Gly Gly Cys Cys Gly Cys Cys
                100                 105                 110

Gly Gly Cys Gly Ala Cys Thr Cys Ala Ala Cys Ala Ala Gly Cys Gly
        115                 120                 125

Gly Cys Gly Cys Thr Thr Cys Cys Gly Gly Gly Cys Thr Gly
        130                 135                 140

Cys Gly Gly Cys Thr Cys Thr Thr Cys Gly Gly Gly Cys Ala Cys Ala
145                 150                 155                 160

Gly Gly Ala Ala Ala Gly Cys Cys Ala Thr Ala Cys Gly Cys Ala Ala
                165                 170                 175

Gly Thr Cys Gly Gly Cys Cys Thr Cys Ala Gly Cys Ala Cys
            180                 185                 190

Cys Thr Gly Gly Cys Cys Cys Cys Cys Thr Cys Cys Gly Cys
        195                 200                 205

Cys Cys Ala Cys Cys Cys Thr Gly Gly Gly Cys Cys Cys Cys
210                 215                 220
```

-continued

```
Gly Thr Gly Cys Ala Gly Cys Gly Ala Gly Thr Cys Ala Gly Ala Gly
225                 230                 235                 240

Cys Gly Gly Cys Ala Gly Ala Thr Cys Cys Gly Gly Ala Gly Thr Ala
                245                 250                 255

Cys Ala Gly Thr Gly Gly Ala Cys Thr Gly Gly Ala Gly Cys Gly Ala
            260                 265                 270

Gly Thr Cys Ala Gly Cys Gly Ala Cys Ala Thr Ala Thr Gly Gly Gly
        275                 280                 285

Gly Ala Gly Cys Ala Cys Ala Thr Cys Thr Gly Gly Thr Thr Cys Gly
    290                 295                 300

Ala Gly Ala Cys Cys Ala Ala Cys Gly Thr Gly Thr Cys Cys Gly Gly
305                 310                 315                 320

Gly Gly Ala Cys Thr Thr Cys Thr Gly Cys Thr Ala Cys Gly Thr Thr
                325                 330                 335

Gly Gly Gly Gly Ala Gly Cys Ala Gly Thr Ala Cys Thr Gly Thr Gly
            340                 345                 350

Thr Ala Gly Cys Cys Ala Gly Gly Ala Thr Gly Cys Thr Gly Cys Ala
        355                 360                 365

Gly Ala Ala Gly Thr Cys Ala Gly Thr Gly Thr Cys Thr Cys Gly Ala
    370                 375                 380

Ala Gly Ala Ala Ala Gly Thr Gly Cys Gly Cys Ala Gly Cys Cys Thr
385                 390                 395                 400

Gly Cys Ala Ala Gly Ala Thr Thr Gly Thr Gly Gly Thr Gly Cys Ala
                405                 410                 415

Cys Ala Cys Gly Cys Cys Cys Thr Gly Cys Ala Thr Cys Gly Ala Gly
            420                 425                 430

Cys Ala Gly Cys Thr Gly Gly Ala Gly Ala Ala Gly Ala Thr Ala Ala
        435                 440                 445

Ala Thr Thr Thr Cys Cys Gly Cys Thr Gly Thr Ala Ala Gly Cys Cys
    450                 455                 460

Gly Thr Cys Cys Thr Thr Cys Cys Gly Thr Gly Ala Ala Thr Cys Ala
465                 470                 475                 480

Gly Gly Cys Thr Cys Cys Ala Gly Gly Ala Ala Thr Gly Thr Cys Cys
                485                 490                 495

Gly Cys Gly Ala Gly Cys Cys Ala Ala Cys Cys Thr Thr Thr Gly Thr
            500                 505                 510

Ala Cys Gly Gly Cys Ala Cys Cys Ala Cys Thr Gly Gly Gly Thr Ala
        515                 520                 525

Cys Ala Cys Ala Gly Ala Cys Gly Ala Cys Gly Cys Cys Ala Gly Gly
    530                 535                 540

Ala Cys Gly Gly Cys Ala Ala Gly Thr Gly Thr Cys Gly Gly Cys Ala
545                 550                 555                 560

Cys Thr Gly Thr Gly Gly Gly Ala Ala Gly Gly Gly Ala Thr Thr Cys
                565                 570                 575

Cys Ala Gly Cys Ala Gly Ala Ala Gly Thr Thr Cys Ala Cys Cys Thr
            580                 585                 590

Thr Cys Cys Ala Cys Ala Gly Cys Ala Ala Gly Gly Ala Gly Ala Thr
        595                 600                 605

Thr Gly Thr Gly Gly Cys Cys Ala Thr Cys Ala Gly Cys Thr Gly Cys
    610                 615                 620

Thr Cys Gly Thr Gly Gly Thr Gly Cys Ala Ala Gly Cys Ala Gly Gly
625                 630                 635                 640

Cys Ala Thr Ala Cys Cys Ala Cys Ala Gly Cys Ala Ala Gly Gly Thr
```

|  | | 645 | | | | 650 | | | | 655 | | |
|---|---|---|---|---|---|---|---|---|---|---|---|---|

Gly Thr Cys Cys Thr Gly Cys Thr Thr Cys Ala Thr Gly Cys Thr Gly
                    660                 665                 670

Cys Ala Gly Cys Ala Gly Ala Thr Cys Gly Ala Gly Gly Ala Gly Cys
                675                 680                 685

Cys Gly Thr Gly Cys Thr Cys Gly Cys Thr Gly Gly Gly Gly Gly Thr
            690                 695                 700

Cys Cys Ala Cys Gly Cys Ala Gly Cys Cys Gly Thr Gly Gly Thr Cys
705                 710                 715                 720

Ala Thr Cys Cys Gly Cys Cys Cys Ala Cys Cys Thr Gly Gly Thr Ala
                725                 730                 735

Thr Cys Cys Thr Cys Gly Cys Gly Cys Cys Cys Gly Gly Gly Ala Gly
            740                 745                 750

Gly Cys Cys Cys Ala Gly Ala Ala Thr Ala Cys Thr Cys Thr Thr Gly
        755                 760                 765

Ala Ala Ala Gly Cys Ala Ala Gly Cys Ala Ala Gly Ala Ala Gly Ala
    770                 775                 780

Ala Gly Ala Ala Gly Ala Gly Gly Gly Cys Ala Thr Cys Cys Thr Thr
785                 790                 795                 800

Cys Ala Ala Gly Ala Gly Gly Ala Ala Gly Thr Cys Cys Ala Gly Cys
                805                 810                 815

Ala Ala Gly Ala Ala Ala Gly Gly Gly Cys Cys Thr Gly Ala Gly Gly
            820                 825                 830

Ala Gly Gly Gly Cys Cys Gly Cys Thr Gly Gly Ala Gly Ala Cys Cys
        835                 840                 845

Cys Thr Thr Cys Ala Thr Cys Ala Thr Cys Ala Gly Gly Cys Cys Cys
850                 855                 860

Ala Cys Cys Cys Cys Cys Thr Cys Cys Cys Cys Gly Cys Thr Cys Ala
865                 870                 875                 880

Thr Gly Ala Ala Gly Cys Cys Cys Cys Thr Gly Cys Thr Gly Gly Thr
                885                 890                 895

Gly Thr Thr Thr Gly Thr Gly Ala Ala Cys Cys Cys Cys Ala Ala Gly
            900                 905                 910

Ala Gly Thr Gly Gly Gly Gly Cys Ala Ala Cys Cys Ala Gly Gly Gly
        915                 920                 925

Gly Thr Gly Cys Ala Ala Ala Gly Ala Thr Cys Ala Thr Cys Cys Ala
    930                 935                 940

Gly Thr Cys Thr Thr Thr Cys Cys Thr Cys Thr Gly Thr Ala Thr Ala
945                 950                 955                 960

Cys Thr Cys Ala Ala Thr Cys Cys Cys Gly Ala Cys Ala Ala Gly Ala
                965                 970                 975

Thr Cys Thr Thr Cys Gly Ala Cys Thr Gly Ala Gly Cys Cys Gly Ala
            980                 985                 990

Gly Gly Gly Ala Gly Gly Gly Cys Cys Cys Ala Ala Gly Gly Ala Gly
        995                 1000                1005

Gly Cys Gly Cys Thr Gly Gly Ala Gly Ala Thr Gly Thr Ala Cys Gly
        1010                1015                1020

Cys Gly Cys Ala Ala Ala Gly Thr Gly Cys Ala Cys Ala Ala Cys Cys
        1025                1030                1035

Cys Thr Gly Cys Gly Gly Ala Thr Cys Cys Thr Gly Gly Cys Gly Gly
        1040                1045                1050

Thr Gly Cys Gly Gly Gly Gly Cys Gly Ala Cys Gly Gly Cys
        1055                1060                1065

```
Ala Cys Gly Gly Thr Gly Gly Cys Gly Gly Ala Thr Cys
1070            1075            1080

Cys Thr Cys Thr Cys Cys Ala Cys Cys Cys Thr Gly Gly Ala Cys
1085            1090            1095

Cys Ala Gly Cys Thr Ala Cys Gly Cys Cys Thr Gly Ala Ala Gly
1100            1105            1110

Cys Cys Gly Cys Cys Ala Cys Cys Cys Cys Thr Gly Thr Thr
1115            1120            1125

Gly Cys Cys Ala Thr Cys Cys Thr Gly Cys Cys Cys Thr Gly
1130            1135            1140

Gly Gly Thr Ala Cys Thr Gly Gly Cys Ala Ala Cys Gly Ala Cys
1145            1150            1155

Thr Thr Gly Gly Cys Cys Cys Gly Ala Ala Cys Cys Thr Cys
1160            1165            1170

Ala Ala Cys Thr Gly Gly Gly Thr Gly Gly Gly Gly Cys
1175            1180            1185

Thr Ala Cys Ala Cys Ala Gly Ala Thr Gly Ala Gly Cys Cys Thr
1190            1195            1200

Gly Thr Gly Thr Cys Cys Ala Ala Gly Ala Thr Cys Cys Thr Cys
1205            1210            1215

Thr Cys Cys Cys Ala Cys Gly Thr Gly Ala Gly Gly Ala Gly
1220            1225            1230

Gly Gly Gly Ala Ala Cys Gly Thr Gly Thr Ala Cys Ala Gly
1235            1240            1245

Cys Thr Gly Gly Ala Cys Cys Gly Cys Thr Gly Gly Ala Cys
1250            1255            1260

Cys Thr Cys Cys Ala Cys Gly Cys Thr Gly Ala Gly Cys Cys Cys
1265            1270            1275

Ala Ala Cys Cys Cys Cys Gly Ala Gly Gly Cys Ala Gly Gly Gly
1280            1285            1290

Cys Cys Thr Gly Ala Gly Gly Ala Cys Cys Gly Ala Gly Ala Thr
1295            1300            1305

Gly Ala Ala Gly Gly Cys Gly Cys Cys Ala Cys Cys Gly Ala Cys
1310            1315            1320

Cys Gly Gly Thr Thr Gly Cys Cys Cys Cys Thr Gly Gly Ala Thr
1325            1330            1335

Gly Thr Cys Thr Thr Cys Ala Ala Cys Ala Ala Cys Thr Ala Cys
1340            1345            1350

Thr Thr Cys Ala Gly Cys Cys Thr Gly Gly Gly Cys Thr Thr Thr
1355            1360            1365

Gly Ala Cys Gly Cys Cys Cys Ala Cys Gly Thr Cys Ala Cys Cys
1370            1375            1380

Cys Thr Gly Gly Ala Gly Thr Thr Cys Cys Ala Cys Gly Ala Gly
1385            1390            1395

Thr Cys Thr Cys Gly Ala Gly Ala Gly Gly Cys Cys Ala Ala Cys
1400            1405            1410

Cys Cys Ala Gly Ala Gly Ala Ala Ala Thr Thr Cys Ala Ala Cys
1415            1420            1425

Ala Gly Cys Cys Gly Cys Thr Thr Thr Cys Gly Gly Ala Ala Thr
1430            1435            1440

Ala Ala Gly Ala Thr Gly Thr Thr Cys Thr Ala Cys Gly Cys Cys
1445            1450            1455
```

-continued

```
Gly Gly Gly Ala Cys Ala Gly Cys Thr Thr Cys Thr Cys Thr
    1460                1465                1470

Gly Ala Cys Thr Thr Cys Cys Thr Gly Ala Thr Gly Gly Cys
    1475                1480                1485

Ala Gly Cys Thr Cys Cys Ala Ala Gly Gly Ala Cys Cys Thr Gly
    1490                1495                1500

Gly Cys Cys Ala Ala Gly Cys Ala Cys Ala Thr Cys Cys Gly Ala
    1505                1510                1515

Gly Thr Gly Gly Thr Gly Thr Gly Thr Gly Ala Thr Gly Gly Ala
    1520                1525                1530

Ala Thr Gly Gly Ala Cys Thr Thr Gly Ala Cys Thr Cys Cys Cys
    1535                1540                1545

Ala Ala Gly Ala Thr Cys Cys Ala Gly Gly Ala Cys Cys Thr Gly
    1550                1555                1560

Ala Ala Ala Cys Cys Cys Cys Ala Gly Thr Gly Thr Gly Thr Thr
    1565                1570                1575

Gly Thr Thr Thr Thr Cys Cys Thr Gly Ala Ala Cys Ala Thr Cys
    1580                1585                1590

Cys Cys Cys Ala Gly Gly Thr Ala Cys Thr Gly Thr Gly Cys Gly
    1595                1600                1605

Gly Gly Cys Ala Cys Cys Ala Thr Gly Cys Cys Cys Thr Gly Gly
    1610                1615                1620

Gly Gly Cys Cys Ala Cys Cys Cys Thr Gly Gly Gly Ala Gly
    1625                1630                1635

Cys Ala Cys Cys Ala Cys Gly Ala Cys Thr Thr Thr Gly Ala Gly
    1640                1645                1650

Cys Cys Cys Cys Ala Gly Cys Gly Gly Cys Ala Thr Gly Ala Cys
    1655                1660                1665

Gly Ala Cys Gly Gly Cys Thr Ala Cys Cys Thr Cys Gly Ala Gly
    1670                1675                1680

Gly Thr Cys Ala Thr Thr Gly Gly Cys Thr Thr Cys Ala Cys Cys
    1685                1690                1695

Ala Thr Gly Ala Cys Gly Thr Cys Gly Thr Thr Gly Gly Cys Cys
    1700                1705                1710

Gly Cys Gly Cys Thr Gly Cys Ala Gly Gly Thr Gly Gly Gly Cys
    1715                1720                1725

Gly Gly Ala Cys Ala Cys Gly Gly Cys Gly Ala Gly Cys Gly Gly
    1730                1735                1740

Cys Thr Gly Ala Cys Gly Cys Ala Gly Thr Gly Thr Cys Gly Cys
    1745                1750                1755

Gly Ala Gly Gly Thr Gly Gly Thr Gly Cys Thr Cys Ala Cys Cys
    1760                1765                1770

Ala Cys Ala Thr Cys Cys Ala Ala Gly Gly Cys Cys Ala Thr Cys
    1775                1780                1785

Cys Cys Gly Gly Thr Gly Cys Ala Gly Gly Thr Gly Gly Ala Thr
    1790                1795                1800

Gly Gly Cys Gly Ala Gly Cys Cys Thr Gly Cys Ala Ala Gly
    1805                1810                1815

Cys Thr Thr Gly Cys Ala Gly Cys Cys Thr Cys Ala Cys Gly Cys
    1820                1825                1830

Ala Thr Cys Cys Gly Cys Ala Thr Cys Gly Cys Cys Thr Gly
    1835                1840                1845

Cys Gly Cys Ala Ala Cys Cys Ala Gly Gly Cys Cys Ala Cys Cys
```

-continued 1850 1855 1860

Ala Thr Gly Gly Thr Gly Cys Ala Gly Ala Ala Gly Gly Cys Cys
1865 1870 1875

Ala Ala Gly Cys Gly Gly Cys Gly Gly Ala Gly Cys Gly Cys Cys
1880 1885 1890

Gly Cys Cys Cys Cys Cys Cys Thr Gly Cys Ala Cys Ala Gly Cys
1895 1900 1905

Gly Ala Cys Cys Ala Gly Cys Ala Gly Cys Cys Gly Gly Thr Gly
1910 1915 1920

Cys Cys Ala Gly Ala Gly Cys Ala Gly Thr Thr Gly Cys Gly Cys
1925 1930 1935

Ala Thr Cys Cys Ala Gly Gly Thr Gly Ala Gly Thr Cys Gly Cys
1940 1945 1950

Gly Thr Cys Ala Gly Cys Ala Thr Gly Cys Ala Cys Gly Ala Cys
1955 1960 1965

Thr Ala Thr Gly Ala Gly Gly Cys Cys Cys Thr Gly Cys Ala Cys
1970 1975 1980

Thr Ala Cys Gly Ala Cys Ala Ala Gly Gly Ala Gly Cys Ala Gly
1985 1990 1995

Cys Thr Cys Ala Ala Gly Gly Ala Gly Gly Cys Cys Thr Cys Thr
2000 2005 2010

Gly Thr Gly Cys Cys Gly Cys Thr Gly Gly Gly Cys Ala Cys Thr
2015 2020 2025

Gly Thr Gly Gly Thr Gly Gly Thr Cys Cys Cys Ala Gly Gly Ala
2030 2035 2040

Gly Ala Cys Ala Gly Thr Gly Ala Cys Cys Thr Ala Gly Ala Gly
2045 2050 2055

Cys Thr Cys Thr Gly Cys Cys Gly Thr Gly Cys Cys Cys Ala Cys
2060 2065 2070

Ala Thr Thr Gly Ala Gly Ala Gly Ala Cys Thr Cys Cys Ala Gly
2075 2080 2085

Cys Ala Gly Gly Ala Gly Cys Cys Cys Gly Ala Thr Gly Gly Thr
2090 2095 2100

Gly Cys Thr Gly Gly Ala Gly Cys Cys Ala Ala Gly Thr Cys Cys
2105 2110 2115

Cys Cys Gly Ala Cys Ala Thr Gly Cys Cys Ala Gly Ala Ala Ala
2120 2125 2130

Cys Thr Gly Thr Cys Cys Cys Cys Cys Ala Ala Gly Thr Gly Gly
2135 2140 2145

Thr Gly Cys Thr Thr Cys Cys Thr Gly Gly Ala Cys Gly Cys Cys
2150 2155 2160

Ala Cys Cys Ala Cys Thr Gly Cys Cys Ala Gly Cys Cys Gly Cys
2165 2170 2175

Thr Thr Cys Thr Ala Cys Ala Gly Gly Ala Thr Cys Gly Ala Cys
2180 2185 2190

Cys Gly Ala Gly Cys Cys Cys Ala Gly Gly Ala Gly Cys Ala Cys
2195 2200 2205

Cys Thr Cys Ala Ala Cys Thr Ala Thr Gly Thr Gly Ala Cys Thr
2210 2215 2220

Gly Ala Gly Ala Thr Cys Gly Cys Ala Cys Ala Gly Gly Ala Thr
2225 2230 2235

Gly Ala Gly Ala Thr Thr Thr Ala Thr Ala Thr Cys Cys Thr Gly
2240 2245 2250

-continued

```
Gly Ala Cys Cys Cys Thr Gly Ala Gly Cys Gly Cys Thr Gly
2255                2260                2265
Gly Gly Gly Gly Cys Ala Thr Cys Gly Gly Cys Cys Cys Gly Gly
2270                2275                2280
Cys Cys Thr Gly Ala Cys Cys Thr Cys Cys Cys Ala Ala Cys Cys
2285                2290                2295
Cys Cys Cys Ala Cys Thr Thr Cys Cys Cys Cys Thr Cys Thr Cys
2300                2305                2310
Cys Cys Cys Ala Cys Cys Thr Cys Ala Cys Cys Cys Thr Gly Cys
2315                2320                2325
Thr Cys Ala Cys Cys Cys Ala Cys Gly Cys Cys Cys Cys Gly Gly
2330                2335                2340
Thr Cys Ala Cys Thr Gly Cys Ala Ala Gly Gly Gly Ala Thr
2345                2350                2355
Gly Cys Thr Gly Cys Ala Cys Cys Cys Cys Cys Thr Cys Ala Ala
2360                2365                2370
Gly Gly Thr Gly Ala Ala Gly Ala Gly Cys Thr Gly Ala Thr Thr
2375                2380                2385
Gly Ala Gly Gly Cys Thr Gly Cys Cys Ala Ala Gly Ala Gly Gly
2390                2395                2400
Ala Ala Cys Gly Ala Cys Thr Thr Cys Thr Gly Thr Ala Ala Gly
2405                2410                2415
Cys Thr Cys Cys Ala Gly Gly Ala Gly Cys Thr Gly Cys Ala Cys
2420                2425                2430
Cys Gly Ala Gly Cys Thr Gly Gly Gly Gly Gly Cys Gly Ala Cys
2435                2440                2445
Cys Thr Cys Ala Thr Gly Cys Ala Cys Cys Gly Ala Gly Ala Cys
2450                2455                2460
Gly Ala Gly Cys Ala Gly Ala Gly Thr Cys Gly Cys Ala Cys Gly
2465                2470                2475
Cys Thr Cys Cys Thr Gly Cys Ala Cys Cys Ala Cys Gly Cys Ala
2480                2485                2490
Gly Thr Cys Ala Gly Cys Ala Cys Thr Gly Gly Cys Ala Gly Cys
2495                2500                2505
Ala Ala Gly Gly Ala Thr Gly Thr Gly Gly Thr Cys Cys Gly Cys
2510                2515                2520
Thr Ala Cys Cys Thr Gly Cys Thr Gly Gly Ala Cys Cys Ala Cys
2525                2530                2535
Gly Cys Cys Cys Cys Cys Cys Ala Gly Ala Gly Ala Thr Cys
2540                2545                2550
Cys Thr Thr Gly Ala Thr Gly Cys Gly Gly Thr Gly Gly Ala Gly
2555                2560                2565
Gly Ala Ala Ala Ala Cys Gly Gly Gly Ala Gly Ala Cys Cys
2570                2575                2580
Thr Gly Thr Thr Thr Gly Cys Ala Cys Cys Ala Ala Gly Cys Ala
2585                2590                2595
Gly Cys Gly Gly Cys Cys Cys Thr Gly Gly Gly Cys Cys Ala Gly
2600                2605                2610
Cys Gly Cys Ala Cys Cys Ala Thr Cys Thr Gly Cys Cys Ala Cys
2615                2620                2625
Thr Ala Cys Ala Thr Cys Gly Thr Gly Gly Ala Gly Gly Cys Cys
2630                2635                2640
```

```
Gly Gly Gly Gly Cys Cys Thr Cys Gly Cys Thr Cys Ala Thr Gly
    2645                2650                2655

Ala Ala Gly Ala Cys Ala Gly Ala Cys Cys Ala Gly Cys Ala Gly
    2660                2665                2670

Gly Gly Cys Gly Ala Cys Ala Cys Thr Cys Cys Cys Cys Gly Gly
    2675                2680                2685

Cys Ala Gly Cys Gly Gly Gly Cys Thr Gly Ala Gly Ala Ala Gly
    2690                2695                2700

Gly Cys Thr Cys Ala Gly Gly Ala Cys Ala Cys Cys Gly Ala Gly
    2705                2710                2715

Cys Thr Gly Gly Cys Cys Gly Cys Cys Thr Ala Cys Cys Thr Gly
    2720                2725                2730

Gly Ala Gly Ala Ala Cys Cys Gly Gly Cys Ala Gly Cys Ala Cys
    2735                2740                2745

Thr Ala Cys Cys Ala Gly Ala Thr Gly Ala Thr Cys Cys Ala Gly
    2750                2755                2760

Cys Gly Gly Gly Ala Gly Gly Ala Cys Cys Ala Gly Gly Ala Gly
    2765                2770                2775

Ala Cys Gly Gly Cys Thr Gly Thr Gly Gly Gly Ala Thr Cys Cys
    2780                2785                2790

Thr Cys Gly Gly Ala Gly Ala Cys Ala Gly Thr Gly Cys Gly Gly
    2795                2800                2805

Thr Thr Thr Cys Ala Gly Gly Gly Ala Cys Ala Cys Cys Ala Cys
    2810                2815                2820

Cys Ala Cys Cys Ala Thr Cys Ala Cys Cys Ala Cys Thr Gly Ala
    2825                2830                2835

<210> SEQ ID NO 4
<211> LENGTH: 945
<212> TYPE: PRT
<213> ORGANISM: Homo sapiens

<400> SEQUENCE: 4

Met Glu Pro Arg Asp Gly Ser Pro Glu Ala Arg Ser Ser Asp Ser Glu
1               5                   10                  15

Ser Ala Ser Ala Ser Ser Ser Gly Ser Glu Arg Asp Ala Gly Pro Glu
            20                  25                  30

Pro Asp Lys Ala Pro Arg Arg Leu Asn Lys Arg Arg Phe Pro Gly Leu
        35                  40                  45

Arg Leu Phe Gly His Arg Lys Ala Ile Thr Lys Ser Gly Leu Gln His
    50                  55                  60

Leu Ala Pro Pro Pro Thr Pro Gly Ala Pro Cys Ser Glu Ser Glu
65              70                  75                  80

Arg Gln Ile Arg Ser Thr Val Asp Trp Ser Glu Ser Ala Thr Tyr Gly
                85                  90                  95

Glu His Ile Trp Phe Glu Thr Asn Val Ser Gly Asp Phe Cys Tyr Val
            100                 105                 110

Gly Glu Gln Tyr Cys Val Ala Arg Met Leu Gln Lys Ser Val Ser Arg
        115                 120                 125

Arg Lys Cys Ala Ala Cys Lys Ile Val Val His Thr Pro Cys Ile Glu
    130                 135                 140

Gln Leu Glu Lys Ile Asn Phe Arg Cys Lys Pro Ser Phe Arg Glu Ser
145                 150                 155                 160

Gly Ser Arg Asn Val Arg Glu Pro Thr Phe Val Arg His His Trp Val
                165                 170                 175
```

-continued

```
His Arg Arg Arg Gln Asp Gly Lys Cys Arg His Cys Gly Lys Gly Phe
            180                 185                 190

Gln Gln Lys Phe Thr Phe His Ser Lys Glu Ile Val Ala Ile Ser Cys
        195                 200                 205

Ser Trp Cys Lys Gln Ala Tyr His Ser Lys Val Ser Cys Phe Met Leu
    210                 215                 220

Gln Gln Ile Glu Glu Pro Cys Ser Leu Gly Val His Ala Ala Val Val
225                 230                 235                 240

Ile Pro Pro Thr Trp Ile Leu Arg Ala Arg Arg Pro Gln Asn Thr Leu
                245                 250                 255

Lys Ala Ser Lys Lys Lys Arg Ala Ser Phe Lys Arg Lys Ser Ser
            260                 265                 270

Lys Lys Gly Pro Glu Glu Gly Arg Trp Arg Pro Phe Ile Ile Arg Pro
        275                 280                 285

Thr Pro Ser Pro Leu Met Lys Pro Leu Leu Val Phe Val Asn Pro Lys
    290                 295                 300

Ser Gly Gly Asn Gln Gly Ala Lys Ile Ile Gln Ser Phe Leu Trp Tyr
305                 310                 315                 320

Leu Asn Pro Arg Gln Val Phe Asp Leu Ser Gln Gly Gly Pro Lys Glu
                325                 330                 335

Ala Leu Glu Met Tyr Arg Lys Val His Asn Leu Arg Ile Leu Ala Cys
            340                 345                 350

Gly Gly Asp Gly Thr Val Gly Trp Ile Leu Ser Thr Leu Asp Gln Leu
        355                 360                 365

Arg Leu Lys Pro Pro Pro Val Ala Ile Leu Pro Leu Gly Thr Gly
    370                 375                 380

Asn Asp Leu Ala Arg Thr Leu Asn Trp Gly Gly Gly Tyr Thr Asp Glu
385                 390                 395                 400

Pro Val Ser Lys Ile Leu Ser His Val Glu Glu Gly Asn Val Val Gln
                405                 410                 415

Leu Asp Arg Trp Asp Leu His Ala Glu Pro Asn Pro Glu Ala Gly Pro
            420                 425                 430

Glu Asp Arg Asp Glu Gly Ala Thr Asp Arg Leu Pro Leu Asp Val Phe
        435                 440                 445

Asn Asn Tyr Phe Ser Leu Gly Phe Asp Ala His Val Thr Leu Glu Phe
    450                 455                 460

His Glu Ser Arg Glu Ala Asn Pro Glu Lys Phe Asn Ser Arg Phe Arg
465                 470                 475                 480

Asn Lys Met Phe Tyr Ala Gly Thr Ala Phe Ser Asp Phe Leu Met Gly
                485                 490                 495

Ser Ser Lys Asp Leu Ala Lys His Ile Arg Val Val Cys Asp Gly Met
            500                 505                 510

Asp Leu Thr Pro Lys Ile Gln Asp Leu Lys Pro Gln Cys Val Val Phe
        515                 520                 525

Leu Asn Ile Pro Arg Tyr Cys Ala Gly Thr Met Pro Trp Gly His Pro
    530                 535                 540

Gly Glu His His Asp Phe Glu Pro Gln Arg His Asp Asp Gly Tyr Leu
545                 550                 555                 560

Glu Val Ile Gly Phe Thr Met Thr Ser Leu Ala Ala Leu Gln Val Gly
                565                 570                 575

Gly His Gly Glu Arg Leu Thr Gln Cys Arg Glu Val Val Leu Thr Thr
            580                 585                 590
```

-continued

```
Ser Lys Ala Ile Pro Val Gln Val Asp Gly Glu Pro Cys Lys Leu Ala
        595                 600                 605
Ala Ser Arg Ile Arg Ile Ala Leu Arg Asn Gln Ala Thr Met Val Gln
610                 615                 620
Lys Ala Lys Arg Arg Ser Ala Ala Pro Leu His Ser Asp Gln Gln Pro
625                 630                 635                 640
Val Pro Glu Gln Leu Arg Ile Gln Val Ser Arg Val Ser Met His Asp
                645                 650                 655
Tyr Glu Ala Leu His Tyr Asp Lys Glu Gln Leu Lys Glu Ala Ser Val
            660                 665                 670
Pro Leu Gly Thr Val Val Pro Gly Asp Ser Asp Leu Glu Leu Cys
        675                 680                 685
Arg Ala His Ile Glu Arg Leu Gln Gln Glu Pro Asp Gly Ala Gly Ala
        690                 695                 700
Lys Ser Pro Thr Cys Gln Lys Leu Ser Pro Lys Trp Cys Phe Leu Asp
705                 710                 715                 720
Ala Thr Thr Ala Ser Arg Phe Tyr Arg Ile Asp Arg Ala Gln Glu His
                725                 730                 735
Leu Asn Tyr Val Thr Glu Ile Ala Gln Asp Ile Tyr Ile Leu Asp
            740                 745                 750
Pro Glu Leu Leu Gly Ala Ser Ala Arg Pro Asp Leu Pro Thr Pro Thr
        755                 760                 765
Ser Pro Leu Pro Thr Ser Pro Cys Ser Pro Thr Pro Arg Ser Leu Gln
        770                 775                 780
Gly Asp Ala Ala Pro Pro Gln Gly Glu Glu Leu Ile Glu Ala Ala Lys
785                 790                 795                 800
Arg Asn Asp Phe Cys Lys Leu Gln Glu Leu His Arg Ala Gly Gly Asp
                805                 810                 815
Leu Met His Arg Asp Glu Gln Ser Arg Thr Leu Leu His His Ala Val
            820                 825                 830
Ser Thr Gly Ser Lys Asp Val Val Arg Tyr Leu Leu Asp His Ala Pro
        835                 840                 845
Pro Glu Ile Leu Asp Ala Val Glu Glu Asn Gly Glu Thr Cys Leu His
        850                 855                 860
Gln Ala Ala Ala Leu Gly Gln Arg Thr Ile Cys His Tyr Ile Val Glu
865                 870                 875                 880
Ala Gly Ala Ser Leu Met Lys Thr Asp Gln Gln Gly Asp Thr Pro Arg
                885                 890                 895
Gln Arg Ala Glu Lys Ala Gln Asp Thr Glu Leu Ala Ala Tyr Leu Glu
            900                 905                 910
Asn Arg Gln His Tyr Gln Met Ile Gln Arg Glu Asp Gln Glu Thr Ala
        915                 920                 925
Val Gly Ser Ser Glu Thr Val Arg Phe Gln Gly His His His His
        930                 935                 940
His
945
```

SUBSTITUTED PYRIDOPYRIMIDINONYL COMPOUNDS USEFUL AS T CELL ACTIVATORS

CROSS REFERENCE

This application claims the benefit of U.S. Provisional Application Ser. No. 62/892,799 filed Aug. 28, 2019 which is incorporated herein in its entirety.

DESCRIPTION

The present invention generally relates to substituted pyridopyrimidinonyl compounds that activate T cells, promote T cell proliferation, and/or exhibit antitumor activity. Provided herein are substituted pyridopyrimidinonyl compounds, compositions comprising such compounds, and methods of their use. The invention further pertains to pharmaceutical compositions comprising at least one compound according to the invention that are useful for the treatment of proliferative disorders, such as cancer, and viral infections.

BACKGROUND OF THE INVENTION

Human cancers harbor numerous genetic and epigenetic alterations, generating neoantigens potentially recognizable by the immune system (Sjoblom et al. (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities. However, although an endogenous immune response to cancer is observed in preclinical models and patients, this response is ineffective, and established cancers are viewed as "self" and tolerated by the immune system. Contributing to this state of tolerance, tumors may exploit several distinct mechanisms to actively subvert anti-tumor immunity. These mechanisms include dysfunctional T-cell signaling (Mizoguchi et al., (1992) *Science* 258:1795-98), suppressive regulatory cells (Facciabene et al., (2012) *Cancer Res.* 72:2162-71), and the co-opting of endogenous "immune checkpoints", which serve to down-modulate the intensity of adaptive immune responses and protect normal tissues from collateral damage, by tumors to evade immune destruction (Topalian et al., (2012) *Curr. Opin. Immunol.* 24:1-6; Mellman et al. (2011) *Nature* 480:480-489).

Diacylglycerol kinases (DGKs) are lipid kinases that mediate the conversion of diacylglycerol to phosphatidic acid thereby terminating T cell functions propagated through the TCR signaling pathway. Thus, DGKs serve as intracellular checkpoints and inhibition of DGKs are expected to enhance T cell signaling pathways and T cell activation. Supporting evidence include knock-out mouse models of either DGKα or DGKζ which show a hyper-responsive T cell phenotype and improved anti-tumor immune activity (Riese M. J. et al., *Journal of Biological Chemistry*, (2011) 7: 5254-5265; Zha Y et al., *Nature Immunology*, (2006) 12:1343; Olenchock B. A. et al., (2006) 11: 1174-81). Furthermore tumor infiltrating lymphocytes isolated from human renal cell carcinoma patients were observed to over-express DGKα which resulted in inhibited T cell function (Prinz, P. U. et al., *J Immunology* (2012) 12:5990-6000).

Thus, DGKα and DGKζ are viewed as targets for cancer immunotherapy (Riese M. J. et al., *Front Cell Dev Biol.* (2016) 4: 108; Chen, S. S. et al., *Front Cell Dev Biol.* (2016) 4: 130; Avila-Flores, A. et al., *Immunology and Cell Biology* (2017) 95: 549-563; Noessner, E., *Front Cell Dev Biol.* (2017) 5: 16; Krishna, S., et al., *Front Immunology* (2013) 4:178; Jing, W. et al., *Cancer Research* (2017) 77: 5676-5686.

There remains a need for compounds useful as inhibitors of one or both of DGKα and DGKζ. Additionally, there remains a need for compounds useful as inhibitors of one of both of DGKα and DGKζ that have selectivity over other diacylglycerol kinases, protein kinases, and/or other lipid kinases.

Accordingly, an agent that is safe and effective in restoring T cell activation, lowering antigen threshold, enhancing antitumor functionality, and/or overcoming the suppressive effects of one or more endogenous immune checkpoints, such as PD-1, LAG-3 and TGFβ, would be an important addition for the treatment of patients with proliferative disorders, such as cancer, as well as viral infections.

SUMMARY OF THE INVENTION

Applicants have found compounds that have activity as inhibitors of one or both of DGKα and DGKζ. Further, applicants have found compounds that have activity as inhibitors of one or both of DGKα and DGKζ and have selectivity over other diacylglycerol kinases, protein kinases, and/or other lipid kinases. These compounds are provided to be useful as pharmaceuticals with desirable stability, bioavailability, therapeutic index, and toxicity values that are important to their drugability.

The present invention provides substituted pyridopyrimidinonyl compounds of Formula (I), which are useful as inhibitors of DGKα, DGKζ, or both DGKα and DGKζ, including salts and prodrugs thereof.

The present invention also provides pharmaceutical compositions comprising a compound of Formula (I) and/or a pharmaceutically acceptable salt thereof and a pharmaceutically acceptable carrier.

The present invention also provides a method of treating a disease or disorder associated with the activity of DGKα, DGKζ, or both DGKα and DGKζ, the method comprising administering to a mammalian patient a compound of Formula (I) and/or a pharmaceutically acceptable salt thereof.

The present invention also provides processes and intermediates for making the compounds of Formula (I) and/or salts thereof.

The present invention also provides a compound of Formula (I) and/or a pharmaceutically acceptable salt thereof, for use in therapy.

The present invention also provides the use of the compounds of Formula (I) and/or pharmaceutically acceptable salts thereof, for the manufacture of a medicament for the treatment of proliferative disorders, such as cancer and viral infections.

The compounds of Formula (I) and compositions comprising the compounds of Formula (I) may be used in treating, preventing, or curing viral infections and various proliferative disorders, such as cancer. Pharmaceutical compositions comprising these compounds are useful in treating, preventing, or slowing the progression of diseases or disorders in a variety of therapeutic areas, such as viral infections and cancer.

These and other features of the invention will be set forth in expanded form as the disclosure continues.

DETAILED DESCRIPTION

The first aspect of the present invention provides at least one compound of Formula (I):

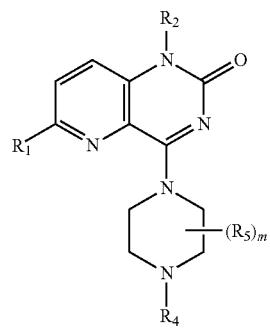

or a salt thereof, wherein:

$R_1$ is H, F, Cl, Br, —CN, —OH, $C_{1-3}$ alkyl substituted with zero to 4 $R_{1a}$, $C_{3-4}$ cycloalkyl substituted with zero to 4 $R_{1a}$, $C_{1-3}$ alkoxy substituted with zero to 4 $R_{1a}$, —$NR_aR_a$, —$S(O)_nR_e$, or —$P(O)R_eR_e$;

each $R_{1a}$ is independently F, Cl, —CN, —OH, —$OCH_3$, or —$NR_aR_a$;

each $R_a$ is independently H or $C_{1-3}$ alkyl;

each $R_e$ is independently $C_{3-4}$ cycloalkyl or $C_{1-3}$ alkyl substituted with zero to 4 $R_{1a}$;

$R_2$ is H, $C_{1-3}$ alkyl substituted with zero to 4 $R_{2a}$, or $C_{3-4}$ cycloalkyl substituted with zero to 4 $R_{2a}$;

each $R_{2a}$ is independently F, Cl, —CN, —OH, —$O(C_{1-2}$ alkyl), $C_{3-4}$ cycloalkyl, $C_{3-4}$ alkenyl, or $C_{3-4}$ alkynyl;

$R_4$ is —$CH_2R_{4a}$, —$CH_2CH_2R_{4a}$, —$CH_2CHR_{4a}R_{4d}$, —$CHR_{4a}R_{4b}$, or —$CR_{4a}R_{4b}R_{4c}$;

$R_{4a}$ and $R_{4b}$ are independently:

(i) —CN or $C_{1-6}$ alkyl substituted with zero to 4 substituents independently selected from F, Cl, —CN, —OH, —$OCH_3$, —$SCH_3$, $C_{1-3}$ fluoroalkoxy, —$NR_aR_a$, —$S(O)_2R_e$, or —$NR_aS(O)_2R_e$;

(ii) $C_{3-8}$ carbocyclyl, 4- to 10-membered heterocyclyl, phenyl, or 5-to 10-membered heteroaryl, each substituted with zero to 4 substituents independently selected from F, Cl, Br, —CN, —OH, $C_{1-6}$ alkyl, $C_{1-3}$ fluoroalkyl, $C_{1-2}$ bromoalkyl, $C_{1-2}$ cyanoalkyl, $C_{1-4}$ hydroxyalkyl, —$(CH_2)_{1-2}O(C_{1-3}$ alkyl), $C_{1-4}$ alkoxy, $C_{1-3}$ fluoroalkoxy, $C_{1-3}$ cyanoalkoxy, —$O(C_{1-4}$ hydroxyalkyl), —$O(CR_xR_x)_{1-3}O(C_{1-3}$ alkyl), $C_{1-3}$ fluoroalkoxy, —$O(CH_2)_{1-3}NR_cR_c$, —$OCH_2CH=CH_2$, —$OCH_2C\equiv CH$, —$C(O)(C_{1-4}$ alkyl), —$C(O)OH$, —$C(O)O(C_{1-4}$ alkyl), —$NR_cR_c$, —$CH_2NR_aR_a$, —$NR_aS(O)_2(C_{1-3}$ alkyl), —$NR_aC(O)(C_{1-3}$ alkyl), —$(CR_xR_x)_{0-2}NR_aC(O)O(C_{1-4}$ alkyl), —$P(O)(C_{1-3}$ alkyl)$_2$, —$S(O)_2(C_{1-3}$ alkyl), —$(CR_xR_x)_{1-2}(C_{3-4}$ cycloalkyl), —$(CR_xR_x)_{1-2}$(morpholinyl), —$(CR_xR_x)_{1-2}$(difluoromorpholinyl), —$(CR_xR_x)_{1-2}$(dimethylmorpholinyl), —$(CR_xR_x)_{1-2}$(oxaazabicyclo[2.2.1]heptanyl), —$(CR_xR_x)_{1-2}$(oxaazaspiro[3.3]heptanyl), —$(CR_xR_x)_{1-2}$(methylpiperazinonyl), —$(CR_xR_x)_{1-2}$(acetylpiperazinyl), —$(CR_xR_x)_{1-2}$(piperidinyl), —$(CR_xR_x)_{1-2}$(difluoropiperidinyl), —$(CR_xR_x)_{1-2}$(methoxypiperidinyl), —$(CR_xR_x)_{1-2}$(hydroxypiperidinyl), —$O(CR_xR_x)_{0-2}(C_{3-6}$ cycloalkyl), —$O(CR_xR_x)_{0-2}$(methylcyclopropyl), —$O(CR_xR_x)_{0-2}$((ethoxycarbonyl)cyclopropyl), —$O(CR_xR_x)_{0-2}$(oxetanyl), —$O(CR_xR_x)_{0-2}$(methylazetidinyl), —$O(CR_xR_x)_{0-2}$(tetrahydropyranyl), —$O(CR_xR_x)_{1-2}$(morpholinyl), —$O(CR_xR_x)_{0-2}$(thiazolyl), cyclopropyl, cyanocyclopropyl, methylazetidinyl, acetylazetidinyl, (tert-butoxycarbonyl)azetidinyl, triazolyl, tetrahydropyranyl, morpholinyl, thiophenyl, methylpiperidinyl, dioxolanyl, pyrrolidinonyl, and $R_d$; or (iii) $C_{1-4}$ alkyl substituted with one cyclic group selected from $C_{3-6}$ cycloalkyl, 4- to 10-membered heterocyclyl, mono- or bicyclic aryl, or 5-to 10-membered heteroaryl, said cyclic group substituted with zero to 3 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, —$OCH_2CH=CH_2$, —$OCH_2C\equiv CH$, —$NR_cR_c$, —$NR_aS(O)_2(C_{1-3}$ alkyl), —$NR_aC(O)(C_{1-3}$ alkyl), —$NR_aC(O)O(C_{1-4}$ alkyl), and $C_{3-6}$ cycloalkyl;

or $R_{4a}$ and $R_{4b}$ together with the carbon atom to which they are attached form a $C_{3-6}$ cycloalkyl or a 3- to 6-membered heterocyclyl, each substituted with zero to 3 $R_f$;

each $R_f$ is independently F, Cl, Br, —OH, —CN, $C_{1-6}$ alkyl, $C_{1-3}$ fluoroalkyl, $C_{1-3}$ alkoxy, $C_{1-3}$ fluoroalkoxy, —$OCH_2CH=CH_2$, —$OCH_2C\equiv CH$, —$NR_cR_c$, or a cyclic group selected from $C_{3-6}$ cycloalkyl, 3- to 6-membered heterocyclyl, phenyl, monocyclic heteroaryl, and bicyclic heteroaryl, each cyclic group substituted with zero to 3 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, and —$NR_cR_c$;

$R_{4c}$ is $C_{1-6}$ alkyl or $C_{3-6}$ cycloalkyl, each substituted with zero to 4 substituents independently selected from F, Cl, —OH, $C_{1-2}$ alkoxy, $C_{1-2}$ fluoroalkoxy, and —CN;

$R_{4d}$ is —$OCH_3$;

each $R_c$ is independently H or $C_{1-2}$ alkyl;

$R_d$ is phenyl substituted with zero to 1 substituent selected from F, Cl, —CN, —$CH_3$, and —$OCH_3$;

each $R_5$ is independently CN, $C_{1-6}$ alkyl substituted with zero to 4 $R_g$, $C_{2-4}$ alkenyl substituted with zero to 4 $R_g$, $C_{2-4}$ alkynyl substituted with zero to 4 $R_g$, $C_{3-4}$ cycloalkyl substituted with zero to 4 $R_g$, phenyl substituted with zero to 4 $R_g$, oxadiazolyl substituted with zero to 3 $R_g$, pyridinyl substituted with zero to 4 $R_g$, —$(CH_2)_{1-2}$(4- to 10-membered heterocyclyl substituted with zero to 4 $R_g$), —$(CH_2)_{1-2}NR_cC(O)(C_{1-4}$ alkyl), —$(CH_2)_{1-2}NR_cC(O)O(C_{1-4}$ alkyl), —$(CH_2)_{1-2}NR_cS(O)_2(C_{1-4}$ alkyl), —$C(O)(C_{1-4}$ alkyl), —$C(O)OH$, —$C(O)O(C_{1-4}$ alkyl), —$C(O)O(C_{3-4}$ cycloalkyl), —$C(O)NR_aR_a$, or —$C(O)NR_a(C_{3-4}$ cycloalkyl);

each $R_g$ is independently F, Cl, —CN, —OH, $C_{1-3}$ alkoxy, $C_{1-3}$ fluoroalkoxy, —$O(CH_2)_{1-20}(C_{1-2}$ alkyl), or $NR_cR_c$;

m is zero, 1, 2, or 3; and n is zero, 1, or 2.

The second aspect of the present invention provides at least one compound of Formula (I):

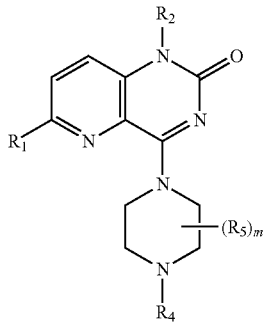

or a salt thereof, wherein:

R$_1$ is H, F, Cl, Br, —CN, C$_{1-3}$ alkyl substituted with zero to 4 R$_{1a}$, C$_{3-4}$ cycloalkyl substituted with zero to 4 R$_{1a}$, C$_{1-3}$ alkoxy substituted with zero to 4 R$_{1a}$, —NR$_a$R$_a$, —S(O)$_n$R$_e$, or —P(O)R$_e$R$_e$;

each R$_{1a}$ is independently F, Cl, —CN, —OH, —OCH$_3$, or —NR$_a$R$_a$;

each R$_a$ is independently H or C$_{1-3}$ alkyl;

each R$_e$ is independently C$_{3-4}$ cycloalkyl or C$_{1-3}$ alkyl substituted with zero to 4 R$_{1a}$;

R$_2$ is H, C$_{1-3}$ alkyl substituted with zero to 4 R$_{2a}$, or C$_{3-4}$ cycloalkyl substituted with zero to 4 R$_{2a}$;

each R$_{2a}$ is independently F, Cl, —CN, —OH, —O(C$_{1-2}$ alkyl), C$_{3-4}$ cycloalkyl, C$_{3-4}$ alkenyl, or C$_{3-4}$ alkynyl;

R$_4$ is —CH$_2$R$_{4a}$, —CH$_2$CH$_2$R$_{4a}$, —CH$_2$CHR$_{4a}$R$_{4d}$, —CHR$_{4a}$R$_{4b}$, or —CR$_{4a}$R$_{4b}$R$_{4c}$;

R$_{4a}$ and R$_{4b}$ are independently:

(i) C$_{1-6}$ alkyl substituted with zero to 4 substituents independently selected from F, Cl, —CN, —OH, —OCH$_3$, —SCH$_3$, C$_{1-3}$ fluoroalkoxy, —NR$_a$R$_a$, —S(O)$_2$R$_e$, or —NR$_a$S(O)$_2$R$_e$;

(ii) C$_{3-6}$ cycloalkyl, heterocyclyl, phenyl, or heteroaryl, each substituted with zero to 4 substituents independently selected from F, Cl, Br, —CN, —OH, C$_{1-6}$ alkyl, C$_{1-3}$ fluoroalkyl, C$_{1-4}$ hydroxyalkyl, —(CH$_2$)$_{1-20}$(C$_{1-3}$ alkyl), C$_{1-4}$ alkoxy, —O(C$_{1-4}$ hydroxyalkyl), —O(CH$_2$)$_{1-3}$O(C$_{1-3}$ alkyl), C$_{1-3}$ fluoroalkoxy, —O(CH$_2$)$_{1-3}$NR$_c$R$_c$, —OCH$_2$CH=CH$_2$, —OCH$_2$C≡CH, —C(O)(C$_{1-4}$ alkyl), —C(O)OH, —C(O)O(C$_{1-4}$ alkyl), —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), —P(O)(C$_{1-3}$ alkyl)$_2$, —S(O)$_2$(C$_{1-3}$ alkyl), —O(CH$_2$)$_{1-2}$(C$_{3-6}$ cycloalkyl), —O(CH$_2$)$_{1-2}$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, thiophenyl, methylpiperidinyl, and R$_d$; or (iii) C$_{1-4}$ alkyl substituted with one cyclic group selected from C$_{3-6}$ cycloalkyl, heterocyclyl, aryl, and heteroaryl, said cyclic group substituted with zero to 3 substituents independently selected from F, Cl, Br, —OH, —CN, C$_{1-6}$ alkyl, C$_{1-3}$ fluoroalkyl, C$_{1-3}$ alkoxy, C$_{1-3}$ fluoroalkoxy, —OCH$_2$CH=CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), and C$_{3-6}$ cycloalkyl;

or R$_{4a}$ and R$_{4b}$ together with the carbon atom to which they are attached form a C$_{3-6}$ cycloalkyl or a 3- to 6-membered heterocyclyl, each substituted with zero to 3 R$_f$;

each R$_f$ is independently F, Cl, Br, —OH, —CN, C$_{1-6}$ alkyl, C$_{1-3}$ fluoroalkyl, C$_{1-3}$ alkoxy, C$_{1-3}$ fluoroalkoxy, —OCH$_2$CH=CH$_2$, —OCH$_2$C≡CH, —NR$_c$R$_c$, or a cyclic group selected from C$_{3-6}$ cycloalkyl, 3- to 6-membered heterocyclyl, phenyl, monocyclic heteroaryl, and bicyclic heteroaryl, each cyclic group substituted with zero to 3 substituents independently selected from F, Cl, Br, —OH, —CN, C$_{1-6}$ alkyl, C$_{1-3}$ fluoroalkyl, C$_{1-3}$ alkoxy, C$_{1-3}$ fluoroalkoxy, and —NR$_c$R$_c$;

R$_{4c}$ is C$_{1-6}$ alkyl or C$_{3-6}$ cycloalkyl, each substituted with zero to 4 substituents independently selected from F, Cl, —OH, C$_{1-2}$ alkoxy, C$_{1-2}$ fluoroalkoxy, and —CN;

R$_{4d}$ is —OCH$_3$;

each R$_c$ is independently H or C$_{1-2}$ alkyl;

R$_d$ is phenyl substituted with zero to 1 substituent selected from F, Cl, —CN, —CH$_3$, and —OCH$_3$;

each R$_5$ is independently —CN, C$_{1-6}$ alkyl substituted with zero to 4 R$_g$, C$_{2-4}$ alkenyl substituted with zero to 4 R$_g$, C$_{2-4}$ alkynyl substituted with zero to 4 R$_g$, C$_{3-4}$ cycloalkyl substituted with zero to 4 R$_g$, phenyl substituted with zero to 4 R$_g$, oxadiazolyl substituted with zero to 3 R$_g$, pyridinyl substituted with zero to 4 R$_g$, —(CH$_2$)$_{1-2}$(4- to 10-membered heterocyclyl substituted with zero to 4 R$_g$), —(CH$_2$)$_{1-2}$NR$_c$C(O)(C$_{1-4}$ alkyl), —(CH$_2$)$_{1-2}$NR$_c$C(O)O (C$_{1-4}$ alkyl), —(CH$_2$)$_{1-2}$NR$_c$S(O)$_2$(C$_{1-4}$ alkyl), —C(O)(C$_{1-4}$ alkyl), —C(O)OH, —C(O)O(C$_{1-4}$ alkyl), —C(O)O (C$_{3-4}$ cycloalkyl), —C(O)NR$_a$R$_a$, or —C(O)NR$_a$(C$_{3-4}$ cycloalkyl);

each R$_g$ is independently F, Cl, —CN, —OH, C$_{1-3}$ alkoxy, C$_{1-3}$ fluoroalkoxy, —O(CH$_2$)$_{1-20}$(C$_{1-2}$ alkyl), or —NR$_c$R$_c$;

m is zero, 1, 2, or 3; and n is zero, 1, or 2.

In one embodiment, a compound of Formula (I) or a salt thereof is provided wherein: R$_1$ is H, F, Cl, Br, —CN, —OH, C$_{1-3}$ alkyl substituted with zero to 4 R$_{1a}$, cyclopropyl substituted with zero to 3 R$_{1a}$, C$_{1-3}$ alkoxy substituted with zero to 3 R$_{1a}$, —NR$_a$R$_a$, —S(O)$_n$CH$_3$, or —P(O)(CH$_3$)$_2$; R$_2$ is H or C$_{1-2}$ alkyl substituted with zero to 2 R$_{2a}$; each R$_{2a}$ is independently F, Cl, —CN, —OH, —O(C$_{1-2}$ alkyl), cyclopropyl, C$_{3-4}$ alkenyl, or C$_{3-4}$ alkynyl; R$_{4a}$ and R$_{4b}$ are independently: (i) —CN or C$_{1-4}$ alkyl substituted with zero to 4 substituents independently selected from F, Cl, —CN, —OH, —OCH$_3$, —SCH$_3$, C$_{1-3}$ fluoroalkoxy, and —NR$_a$R$_a$; (ii) C$_{3-6}$ carbocyclyl, 4- to 10-membered heterocyclyl, phenyl, or 5-to 10-membered heteroaryl, each substituted with zero to 4 substituents independently selected from F, Cl, Br, —CN, —OH, C$_{1-6}$ alkyl, C$_{1-3}$ fluoroalkyl, C$_{1-2}$ bromoalkyl, C$_{1-2}$ cyanoalkyl, C$_{1-2}$ hydroxyalkyl, —CH$_2$NR$_a$R$_a$, —(CH$_2$)$_{1-20}$(C$_{1-2}$ alkyl), —(CH$_2$)$_{1-2}$NR$_x$C(O)O(C$_{1-2}$ alkyl), C$_{1-4}$ alkoxy, —O(C$_{1-4}$ hydroxyalkyl), —O(CR$_x$R$_x$)$_{1-2}$O(C$_{1-2}$ alkyl), C$_{1-3}$ fluoroalkoxy, C$_{1-3}$ cyanoalkoxy, —O(CH$_2$)$_{1-2}$NR$_c$R$_c$, —OCH$_2$CH=CH$_2$, —OCH$_2$C≡CH, —C(O)(C$_{1-4}$ alkyl), —C(O)OH, —C(O)O(C$_{1-4}$ alkyl), —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), —P(O)(C$_{1-2}$ alkyl)$_2$, —S(O)$_2$ (C$_{1-3}$ alkyl), —(CH$_2$)$_{1-2}$(C$_{3-4}$ cycloalkyl), —CR$_x$R$_x$(morpholinyl), —CR$_x$R$_x$(difluoromorpholinyl), —CR$_x$R$_x$(dimethylmorpholinyl), —CR$_x$R$_x$(oxaazabicyclo[2.2.1] heptanyl), —CR$_x$R$_x$(oxaazaspiro[3.3]heptanyl), —CR$_x$R$_x$ (methylpiperazinonyl), —CR$_x$R$_x$(acetylpiperazinyl), —CR$_x$R$_x$(piperidinyl), —CR$_x$R$_x$(difluoropiperidinyl), —CR$_x$R$_x$(methoxypiperidinyl), —CR$_x$R$_x$(hydroxypiperidinyl), —O(CH$_2$)$_{0-2}$(C$_{3-4}$ cycloalkyl), —O(CH$_2$)$_{0-2}$(methylcyclopropyl), —O(CH$_2$)$_{0-2}$((ethoxycarbonyl)cyclopropyl), —O(CH$_2$)$_{0-2}$(oxetanyl), —O(CH$_2$)$_{0-2}$(methylazetidinyl), —O(CH$_2$)$_{1-2}$(morpholinyl), —O(CH$_2$)$_{0-2}$(tetrahydropyranyl), —O(CH$_2$)$_{0-2}$(thiazolyl), cyclopropyl, cyanocyclopropyl, methylazetidinyl, acetylazetidinyl, (tert-butoxycarbonyl)azetidinyl, dioxolanyl, pyrrolidinonyl, triazolyl, tetrahydropyranyl, morpholinyl, thiophenyl, methylpiperidinyl, and $R_d$; or (iii) $C_{1-3}$ alkyl substituted with one cyclic group selected from $C_{3-6}$ cycloalkyl, 4- to 10-membered heterocyclyl, phenyl, and heteroaryl, said cyclic group substituted with zero to 3 substituents independently selected from F, Cl, Br, —OH, —CN, $C_{1-3}$ alkyl, $C_{1-2}$ fluoroalkyl, $C_{1-3}$ alkoxy, $C_{1-2}$ fluoroalkoxy, —OCH$_2$CH=CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), and $C_{3-4}$ cycloalkyl; or $R_{4a}$ and $R_{4b}$ together with the carbon atom to which they are attached, form a $C_{3-6}$ cycloalkyl or a 3- to 6-membered heterocyclyl, each substituted with zero to 3$R_f$; each $R_f$ is independently F, Cl, Br, —OH, —CN, $C_{1-4}$ alkyl, $C_{1-2}$ fluoroalkyl, $C_{1-3}$ alkoxy, $C_{1-2}$ fluoroalkoxy, —OCH$_2$CH=CH$_2$, —OCH$_2$C≡CH, —NR$_c$R$_c$, or a cyclic group selected from $C_{3-6}$ cycloalkyl, 3- to 6-membered heterocyclyl, phenyl, monocyclic heteroaryl, and bicyclic heteroaryl, each cyclic group substituted with zero to 3 substituents independently selected from F, Cl, Br, —OH, —CN, $C_{1-4}$ alkyl, $C_{1-2}$ fluoroalkyl, $C_{1-3}$ alkoxy, $C_{1-2}$ fluoroalkoxy, and NR$_c$R$_c$; $R_{4c}$ is $C_{1-4}$ alkyl or $C_{3-6}$ cycloalkyl, each substituted with zero to 4 substituents independently selected from F, Cl, —OH, $C_{1-2}$ alkoxy, $C_{1-2}$ fluoroalkoxy, and —CN; each $R_5$ is independently —CN, $C_{1-5}$ alkyl substituted with zero to 4 $R_g$, $C_{2-3}$ alkenyl substituted with zero to 4 $R_g$, $C_{2-3}$ alkynyl substituted with zero to 4 $R_g$, $C_{3-4}$ cycloalkyl substituted with zero to 4 $R_g$, phenyl substituted with zero to 3 $R_g$, oxadiazolyl substituted with zero to 3 $R_g$, pyridinyl substituted with zero to 3 $R_g$, —(CH$_2$)$_{1-2}$(4- to 10-membered heterocyclyl substituted with zero to 4 $R_g$), —(CH$_2$)$_{1-2}$NR$_c$C(O)(C$_{1-4}$ alkyl), —(CH$_2$)$_{1-2}$NR$_c$C(O)O(C$_{1-4}$ alkyl), —(CH$_2$)$_{1-2}$NR$_c$S(O)$_2$(C$_{1-4}$ alkyl), —C(O)(C$_{1-4}$ alkyl), —C(O)OH, —C(O)O(C$_{1-4}$ alkyl), —C(O)O(C$_{3-4}$ cycloalkyl), —C(O)NR$_a$R$_a$, or —C(O)NR$_a$(C$_{3-4}$ cycloalkyl);

each $R_x$ is independently H or —CH$_3$; and m is 1, 2, or 3.

In one embodiment, a compound of Formula (I) or a salt thereof is provided wherein: $R_1$ is H, F, Cl, Br, —CN, $C_{1-3}$ alkyl substituted with zero to 4 $R_{1a}$, cyclopropyl substituted with zero to 3 $R_{1a}$, $C_{1-3}$ alkoxy substituted with zero to 3 $R_{1a}$, —NR$_a$R$_a$, —S(O)$_n$CH$_3$, or —P(O)(CH$_3$)$_2$; each $R_{1a}$ is independently F, Cl, or —CN; each $R_a$ is independently H or $C_{1-3}$ alkyl; $R_2$ is H or $C_{1-2}$ alkyl substituted with zero to 2 $R_{2a}$; each $R_{2a}$ is independently F, Cl, —CN, —OH, —O(C$_{1-2}$ alkyl), cyclopropyl, $C_{3-4}$ alkenyl, or $C_{3-4}$ alkynyl; $R_{4a}$ and $R_{4b}$ are independently: (i) $C_{1-4}$ alkyl substituted with zero to 4 substituents independently selected from F, Cl, —CN, —OH, —OCH$_3$, —SCH$_3$, $C_{1-3}$ fluoroalkoxy, and —NR$_a$R$_a$; (ii) $C_{3-6}$ cycloalkyl, 4- to 10-membered heterocyclyl, phenyl, or 5-to 10-membered heteroaryl, each substituted with zero to 4 substituents independently selected from F, Cl, Br, —CN, —OH, $C_{1-6}$ alkyl, $C_{1-3}$ fluoroalkyl, —CH$_2$OH, —(CH$_2$)$_{1-2}$O(C$_{1-2}$ alkyl), $C_{1-4}$ alkoxy, —O(C$_{1-4}$ hydroxyalkyl), —O(CH$_2$)$_{1-2}$O(C$_{1-2}$ alkyl), $C_{1-3}$ fluoroalkoxy, —O(CH$_2$)$_{1-2}$NR$_c$R$_c$, —OCH$_2$CH=CH$_2$, —OCH$_2$C≡CH, —C(O)(C$_{1-4}$ alkyl), —C(O)OH, —C(O)O(C$_{1-4}$ alkyl), —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), —P(O)(C$_{1-2}$ alkyl)$_2$, —S(O)$_2$(C$_{1-3}$ alkyl), —O(CH$_2$)$_{1-2}$(C$_{3-4}$ cycloalkyl), —O(CH$_2$)$_{1-2}$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, thiophenyl, methylpiperidinyl, and $R_d$; or (iii) $C_{1-3}$ alkyl substituted with one cyclic group selected from $C_{3-6}$ cycloalkyl, heterocyclyl, phenyl, and heteroaryl, said cyclic group substituted with zero to 3 substituents independently selected from F, Cl, Br, —OH, —CN, $C_{1-3}$ alkyl, $C_{1-2}$ fluoroalkyl, $C_{1-3}$ alkoxy, $C_{1-2}$ fluoroalkoxy, —OCH$_2$CH=CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), and $C_{3-4}$ cycloalkyl; or $R_{4a}$ and $R_{4b}$ together with the carbon atom to which they are attached, form a $C_{3-6}$ cycloalkyl or a 3- to 6-membered heterocyclyl, each substituted with zero to 3 $R_f$; each $R_f$ is independently F, Cl, Br, —OH, —CN, =O, $C_{1-4}$ alkyl, $C_{1-2}$ fluoroalkyl, $C_{1-3}$ alkoxy, $C_{1-2}$ fluoroalkoxy, —OCH$_2$CH=CH$_2$, —OCH$_2$C≡CH, —NR$_c$R$_c$, or a cyclic group selected from $C_{3-6}$ cycloalkyl, 3- to 6-membered heterocyclyl, phenyl, monocyclic heteroaryl, and bicyclic heteroaryl, each cyclic group substituted with zero to 3 substituents independently selected from F, Cl, Br, —OH, —CN, $C_{1-4}$ alkyl, $C_{1-2}$ fluoroalkyl, $C_{1-3}$ alkoxy, $C_{1-2}$ fluoroalkoxy, and —NR$_c$R$_c$; $R_{4c}$ is $C_{1-4}$ alkyl or $C_{3-6}$ cycloalkyl, each substituted with zero to 4 substituents independently selected from F, Cl, —OH, $C_{1-2}$ alkoxy, $C_{1-2}$ fluoroalkoxy, and —CN; each $R_5$ is independently —CN, $C_{1-5}$ alkyl substituted with zero to 4 $R_g$, $C_{2-3}$ alkenyl substituted with zero to 4 $R_g$, $C_{2-3}$ alkynyl substituted with zero to 4 $R_g$, $C_{3-4}$ cycloalkyl substituted with zero to 4 $R_g$, phenyl substituted with zero to 3 $R_g$, oxadiazolyl substituted with zero to 3 $R_g$, pyridinyl substituted with zero to 3 $R_g$, —(CH$_2$)$_{1-2}$(heterocyclyl substituted with zero to 4 $R_g$), —(CH$_2$)$_{1-2}$NR$_c$C(O)(C$_{1-4}$ alkyl), —(CH$_2$)$_{1-2}$NR$_c$C(O)O(C$_{1-4}$ alkyl), —C(O)(C$_{1-4}$ alkyl), —(CH$_2$)$_{1-2}$NR$_c$S(O)$_2$(C$_{1-4}$ alkyl), —C(O)OH, —C(O)O(C$_{1-4}$ alkyl), —C(O)O(C$_{3-4}$ cycloalkyl), —C(O)NR$_a$R$_a$, or —C(O)NR$_a$(C$_{3-4}$ cycloalkyl); and m is 1, 2, or 3.

In one embodiment, a compound of Formula (I) or a salt thereof is provided wherein: $R_1$ is Cl or —CN; $R_2$ is —CH$_3$; $R_4$ is —CH$_2$R$_{4a}$ or —CHR$_{4a}$R$_{4b}$; $R_{4a}$ is cyclopropyl, cyclobutyl, cyclohexyl, bicyclo[1.1.1]pentanyl, phenyl, pyridinyl, pyrimidinyl, oxadiazolyl, benzo[d][1,3]dioxolyl, or oxodihydrobenzo[d]oxazolyl, each substituted with zero to 3 substituents independently selected from F, Cl, —CN, —CH$_3$, —CH(CH$_3$)$_2$, —CF$_3$, —OCH$_3$, —OCH(CH$_3$)$_2$, —OCHF$_2$, —OCF$_3$, —OCH$_2$(cyclopropyl), and cyclopropyl; $R_{4b}$ is: (i) —CH$_3$ and —CH$_2$CH$_3$; or (ii) phenyl, isoxazolyl, oxadiazolyl, or thiazolyl, each substituted with zero to 3 substituents independently selected from F, Cl, —CH$_3$, —C(CH$_3$)$_3$, —CF$_3$, —OCF$_3$, and cyclopropyl; each $R_5$ is independently —CH$_3$, —CH$_2$CH$_3$, —CH$_2$OH, or —CH$_2$OCH$_3$; and m is 2.

In one embodiment, a compound of Formula (I) or a salt thereof is provided wherein: $R_1$ is Cl, —CN, —OH, —CHF$_2$, —CH$_2$OH, —CH$_2$OCH$_3$, —OCH$_3$, —OCH$_2$CH$_3$, —OCHF$_2$, —OCH$_2$CH$_2$OCH$_3$, or —OCH$_2$CH$_2$N(CH$_3$)$_2$; $R_2$ is H, —CH$_3$, or —CD$_3$; $R_4$ is —CH$_2$R$_{4a}$ or —CHR$_{4a}$R$_{4b}$; $R_{4a}$ is cyclohexyl, phenyl, pyridinyl, pyrimidinyl, oxadiazolyl, benzo[d][1,3]dioxolyl, or oxodihydrobenzo[d]oxazolyl, each substituted with zero to 3 substituents independently selected from F, Cl, Br, —CN, —CH$_3$, —CH(CH$_3$)$_2$, —C(CH$_3$)$_3$, —CH$_2$OH, —CHF$_2$, —CF$_3$, —CH$_2$Br, —CH$_2$NH$_2$, —CH$_2$NHC(O)OCH$_3$, —C(CH$_3$)$_2$CN, —OCH$_3$, —OCD$_3$, —OCH$_2$CH$_3$, —OCH(CH$_3$)$_2$, —OCHF$_2$, —OCF$_3$, —OCH$_2$CH$_2$CF$_3$, —OC(CH$_3$)$_2$CN, —OC(CH$_3$)$_2$CH$_2$OH, —OC(CH$_3$)$_2$CH$_2$OCH$_3$, —N(CH$_3$)$_2$, —C(O)OCH$_3$, cyclopropyl, cyanocyclopropyl, methylcyclopropyl, —O(cyclopropyl), —O((ethoxycarbonyl)cyclopropyl), morpholinyl, pyrrolidinonyl, tetrahydropyranyl, dioxolanyl, —CH$_2$(morpholinyl), —CH$_2$(difluoromorpholinyl), —CH$_2$(dimethylmorpholinyl), —CH$_2$(oxaazabicyclo[2.2.1]heptanyl), —CH$_2$(oxaazaspiro[3.3]heptanyl), —CH$_2$(methylpiperazinonyl), —CH$_2$(acetylpiperazinyl), —CH$_2$(piperidinyl), —CH$_2$(difluoropiperidinyl), —CH$_2$ (methoxypiperidinyl), —CH$_2$(hydroxypiperidinyl), —C(CH$_3$)$_2$(morpholinyl), —OCH$_2$(cyclopropyl), —OCH$_2$(methylcyclopropyl), —OCH$_2$(methylazetidinyl), —OCH$_2$(oxetanyl), —OCH$_2$(tetrahydropyranyl), —OCH$_2$(thiazolyl), or —OCH$_2$CH$_2$(cyclopropyl); R$_{4b}$ is: (i) —CN, —CH$_3$, —CH$_2$CH$_3$, —CH$_2$CH$_2$CH$_3$, or —CH(CH$_3$)$_2$; or (ii) phenyl, isoxazolyl, oxadiazolyl, thiazolyl, or triazolyl, each substituted with zero to 3 substituents independently selected from F, Cl, Br, —CH$_3$, —C(CH$_3$)$_3$, —CF$_3$, —OCF$_3$, and cyclopropyl; each R$_5$ is independently —CH$_3$, —CH$_2$CH$_3$, —CH$_2$CH$_2$CH$_3$, —CH$_2$OH, —CH$_2$OCH$_3$, —CH$_2$OCH$_2$CH$_3$, —CH$_2$NH$_2$, —CH$_2$N$_3$, or —CH$_2$NHC(O)OCH$_3$; and m is 2.

In one embodiment, a compound of Formula (I) or a salt thereof is provided wherein R$_1$ is H, F, Cl, Br, —CN, —OH, C$_{1-3}$ alkyl substituted with zero to 4 R$_{1a}$, cyclopropyl substituted with zero to 3 R$_{1a}$, C$_{1-3}$ alkoxy substituted with zero to 3 R$_{1a}$, —NR$_a$R$_a$, —S(O)$_n$CH$_3$, or —P(O)(CH$_3$)$_2$. Included in this embodiment are compounds in which R$_1$ is Cl, —CN, —OH, —CHF$_2$, —CH$_2$OH, —CH$_2$OCH$_3$, —OCH$_3$, —OCH$_2$CH$_3$, —OCHF$_2$, —OCH$_2$CH$_2$OCH$_3$, or —OCH$_2$CH$_2$N(CH$_3$)$_2$.

In one embodiment, a compound of Formula (I) or a salt thereof is provided wherein R$_1$ is H, F, Cl, Br, —CN, C$_{1-3}$ alkyl substituted with zero to 4 R$_{1a}$, cyclopropyl substituted with zero to 3 R$_{1a}$, C$_{1-3}$ alkoxy substituted with zero to 3 R$_{1a}$, —NR$_a$R$_a$, —S(O)$_n$CH$_3$, or —P(O)(CH$_3$)$_2$. Included in this embodiment are compounds in which R$_1$ is H, F, Cl, Br, —CN, —CH$_3$, cyclopropyl, —OCH$_3$, or —NH$_2$. Also included in this embodiment are compounds in which R$_1$ is Cl or —CN. Further, included in this embodiment are compounds in which R$_1$ is —CN.

In one embodiment, a compound of Formula (I) or a salt thereof is provided wherein R$_2$ is H, C$_{1-2}$ alkyl substituted with zero to 4 R$_{2a}$, or C$_{3-4}$ cycloalkyl substituted with zero to 2 R$_{2a}$. Included in this embodiment are compounds in which R$_2$ is H or C$_{1-2}$ alkyl substituted with zero to 2 R$_{2a}$. Also included in this embodiment are compounds in which R$_2$ is H or CH$_3$. Further, included in this embodiment are compounds in which R$_1$ is —CH$_3$. Additionally, included in this embodiment are compounds in which R$_2$ is H, —CH$_3$, or —CD$_3$.

In one embodiment, a compound of Formula (I) or a salt thereof is provided wherein R$_2$ is H.

In one embodiment, a compound of Formula (I) or a salt thereof is provided wherein R$_2$ is —CH$_3$.

In one embodiment, a compound of Formula (I) or a salt thereof is provided wherein R$_2$ is —CD$_3$.

In one embodiment, a compound of Formula (I) or a salt thereof is provided wherein R$_4$ is —CH$_2$R$_{4a}$ or —CH$_2$CH$_2$R$_{4a}$. Included in this embodiment are compounds in which R$_4$ is —CH$_2$R$_{4a}$ or —CD$_2$R$_{4a}$. Also included in this embodiment are compounds in which R$_{4a}$ is phenyl, pyridinyl, tetrahydropyranyl, benzoxazinyl, benzo[d][1,3]dioxolyl, benzoxazinonyl, indazolyl, indolyl, or quinolinyl, each substituted with zero to 3 substituents independently selected from F, Cl, Br, —CN, —OH, —CH$_3$, —CH$_2$CH$_3$, —CH(CH$_3$)$_2$, —C(CH$_3$)$_3$, —CHF$_2$, —CF$_3$, —OCH$_3$, —OCH$_2$CH$_3$, —OCH(CH$_3$)$_2$, —OCHF$_2$, —OCF$_3$, —C(O)CH$_3$, —C(O)OC(CH$_3$)$_3$, —N(CH$_3$)$_2$, cyanocyclopropyl, and phenyl. Further, included in this embodiment are compounds in which R$_{4a}$ is phenyl, pyridinyl, or benzo[d][1,3]dioxolyl, each substituted with zero to 3 substituents independently selected from F, Cl, —CN, —CH$_3$, —CH(CH$_3$)$_2$, —CF$_3$, —OCH$_3$, —OCH(CH$_3$)$_2$, —OCHF$_2$, —OCF$_3$, —OCH$_2$(cyclopropyl), and cyclopropyl.

In one embodiment, a compound of Formula (I) or a salt thereof is provided wherein R$_4$ is —CH$_2$R$_{4a}$. Included in this embodiment are compounds in which R$_{4a}$ is phenyl, pyridinyl, tetrahydropyranyl, benzoxazinyl, benzo[d][1,3]dioxolyl, benzoxazinonyl, indazolyl, indolyl, or quinolinyl, each substituted with zero to 3 substituents independently selected from F, Cl, Br, —CN, —OH, —CH$_3$, —CH$_2$CH$_3$, —CH(CH$_3$)$_2$, —C(CH$_3$)$_3$, —CHF$_2$, —CF$_3$, —OCH$_3$, —OCH$_2$CH$_3$, —OCH(CH$_3$)$_2$, —OCHF$_2$, —OCF$_3$, —C(O) CH$_3$, —C(O)OC(CH$_3$)$_3$, —N(CH$_3$)$_2$, cyanocyclopropyl, and phenyl. Also included in this embodiment are compounds in which R$_{4a}$ is phenyl, pyridinyl, or benzo[d][1,3]dioxolyl, each substituted with zero to 3 substituents independently selected from F, Cl, —CN, —CH$_3$, —CH(CH$_3$)$_2$, —CF$_3$, —OCH$_3$, —OCH(CH$_3$)$_2$, —OCHF$_2$, —OCF$_3$, —OCH$_2$(cyclopropyl), and cyclopropyl.

In one embodiment, a compound of Formula (I) or a salt thereof is provided wherein R$_4$ is —CH$_2$R$_{4a}$; and R$_{4a}$ is C$_{3-8}$ carbocyclyl, 4- to 10-membered heterocyclyl, phenyl, or 5-to 10-membered heteroaryl, each substituted with zero to 4 substituents independently selected from F, Cl, Br, —CN, —OH, C$_{1-6}$ alkyl, C$_{1-3}$ fluoroalkyl, C$_{1-2}$ bromoalkyl, C$_{1-2}$ cyanoalkyl, C$_{1-4}$ hydroxyalkyl, —(CH$_2$)$_{1-2}$O(C$_{1-3}$ alkyl), C$_{1-4}$ alkoxy, C$_{1-3}$ fluoroalkoxy, C$_{1-3}$ cyanoalkoxy, —O(C$_{1-4}$ hydroxyalkyl), —O(CR$_x$R$_x$)$_{1-3}$O(C$_{1-3}$ alkyl), C$_{1-3}$ fluoroalkoxy, —O(CH$_2$)$_{1-3}$NR$_c$R$_c$, —OCH$_2$CH=CH$_2$, —OCH$_2$C≡CH, —C(O)(C$_{1-4}$ alkyl), —C(O)OH, —C(O)O (C$_{1-4}$ alkyl), —NR$_c$R$_c$, —CH$_2$NR$_a$R$_a$, —NR$_a$S(O)$_2$(C$_{1-3}$ alkyl), —NR$_a$C(O)(C$_{1-3}$ alkyl), —(CR$_x$R$_x$)$_{0-2}$NR$_a$C(O)O (C$_{1-4}$ alkyl), —P(O)(C$_{1-3}$ alkyl)$_2$, —S(O)$_2$(C$_{1-3}$ alkyl), —(CR$_x$R$_x$)$_{1-2}$(C$_{3-4}$ cycloalkyl), —(CR$_x$R$_x$)$_{1-2}$(morpholinyl), —(CR$_x$R$_x$)$_{1-2}$(difluoromorpholinyl), —(CR$_x$R$_x$)$_{1-2}$(dimethylmorpholinyl), —(CR$_x$R$_x$)$_{1-2}$(oxaazabicyclo[2.2.1]heptanyl), (CR$_x$R$_x$)$_{1-2}$(oxaazaspiro[3.3]heptanyl), —(CR$_x$R$_x$)$_{1-2}$ (methylpiperazinonyl), —(CR$_x$R$_x$)$_{1-2}$(acetylpiperazinyl), —(CR$_x$R$_x$)$_{1-2}$(piperidinyl), —(CR$_x$R$_x$)$_{1-2}$(difluoropiperidinyl), —(CR$_x$R$_x$)$_{1-2}$(methoxypiperidinyl), —(CR$_x$R$_x$)$_{1-2}$(hydroxypiperidinyl), —O(CR$_x$R$_x$)$_{0-2}$(C$_{3-6}$ cycloalkyl), —O(CR$_x$R$_x$)$_{0-2}$(methylcyclopropyl), —O(CR$_x$R$_x$)$_{0-2}$ ((ethoxycarbonyl)cyclopropyl), —O(CR$_x$R$_x$)$_{0-2}$(oxetanyl), —O(CR$_x$R$_x$)$_{0-2}$(methylazetidinyl), —O(CR$_x$R$_x$)$_{0-2}$(tetrahydropyranyl), —O(CR$_x$R$_x$)$_{1-2}$(morpholinyl), —O(CR$_x$R$_x$)$_{0-2}$ (thiazolyl), cyclopropyl, cyanocyclopropyl, methylazetidinyl, acetylazetidinyl, (tert-butoxycarbonyl)azetidinyl, triazolyl, tetrahydropyranyl, morpholinyl, thiophenyl, methylpiperidinyl, dioxolanyl, pyrrolidinonyl, and R$_d$.

In one embodiment, a compound of Formula (I) or a salt thereof is provided wherein R$_4$ is —CH$_2$R$_{4a}$; and R$_{4a}$ is C$_{3-6}$ cycloalkyl, 4- to 10-membered heterocyclyl, phenyl, or 5-to 10-membered heteroaryl, each substituted with zero to 4 substituents independently selected from F, Cl, Br, —CN, —OH, C$_{1-6}$ alkyl, C$_{1-3}$ fluoroalkyl, C$_{1-2}$ bromoalkyl, C$_{1-2}$ cyanoalkyl, C$_{1-2}$ hydroxyalkyl, —CH$_2$NR$_a$R$_a$, —(CH$_2$)$_{1-2}$O (C$_{1-2}$ alkyl), —(CH$_2$)$_{1-2}$NR$_x$C(O)O(C$_{1-2}$ alkyl), C$_{1-4}$ alkoxy, —O(C$_{1-4}$ hydroxyalkyl) —O(CR$_x$R$_x$)$_{1-2}$O(C$_{1-2}$ alkyl), C$_{1-3}$ fluoroalkoxy, C$_{1-3}$ cyanoalkoxy, —O(CH$_2$)$_{1-2}$NR$_c$R$_c$, —OCH$_2$CH=CH$_2$, —OCH$_2$C≡CH, —C(O)(C$_{1-4}$ alkyl), —C(O)OH, —C(O)O(C$_{1-4}$ alkyl), —NR$_c$R$_c$, —NR$_a$S(O)$_2$ (C$_{1-3}$ alkyl), —NR$_a$C(O)(C$_{1-3}$ alkyl), —NR$_a$C(O)O(C$_{1-4}$ alkyl), —P(O)(C$_{1-2}$ alkyl)$_2$, —S(O)$_2$(C$_{1-3}$ alkyl), —(CH$_2$)$_{1-2}$(C$_{3-4}$ cycloalkyl), —CR$_x$R$_x$(morpholinyl), —CR$_x$R$_x$(difluoromorpholinyl), —CR$_x$R$_x$(dimethylmorpholinyl), —CR$_x$R$_x$(oxaazabicyclo[2.2.1]heptanyl), —CR$_x$R$_x$(oxaazaspiro[3.3]heptanyl), —CR$_x$R$_x$(methylpiperazinonyl), —CR$_x$R$_x$(acetylpiperazinyl), —CR$_x$R$_x$(piperidinyl), —CR$_x$R$_x$(difluoropiperidinyl), —CR$_x$R$_x$ (methoxypiperidinyl), —CR$_x$R$_x$(hydroxypiperidinyl), —O(CH$_2$)$_{0-2}$(C$_{3-4}$ cycloalkyl), —O(CH$_2$)$_{0-2}$(methylcyclopropyl), —O(CH$_2$)$_{0-2}$((ethoxycarbonyl)cyclopropyl), —O(CH$_2$)$_{0-2}$(oxetanyl), —O(CH$_2$)$_{0-2}$(methylazetidinyl), —O(CH$_2$)$_{1-2}$(morpholinyl), —O(CH$_2$)$_{0-2}$(tetrahydropyranyl), —O(CH$_2$)$_{0-2}$(thiazolyl), cyclopropyl, cyanocyclopropyl, methylazetidinyl, acetylazetidinyl, (tert-butoxycarbonyl)azetidinyl, dioxolanyl, pyrrolidinonyl, triazolyl, tetrahydropyranyl, morpholinyl, thiophenyl, methylpiperidinyl, and R$_d$. Included in this embodiment are compounds in which R$_{4a}$ is cyclohexyl, phenyl, or benzo[d][1,3]dioxolyl, each substituted with 1 to 3 substituents independently selected from F, Cl, —CH(CH$_3$)$_2$, —CF$_3$, —OCH$_2$CH$_3$, —OCF$_3$, cyclopropyl, and —OCH$_2$(cyclopropyl).

In one embodiment, a compound of Formula (I) or a salt thereof is provided wherein R$_4$ is —CHR$_{4a}$R$_{4b}$; R$_{4a}$ is: (i) C$_{3-6}$ cycloalkyl, heterocyclyl, phenyl, or heteroaryl, each substituted with zero to 4 substituents independently selected from F, Cl, Br, —CN, —OH, C$_{1-6}$ alkyl, C$_{1-3}$ fluoroalkyl, C$_{1-4}$ hydroxyalkyl, (CH$_2$)$_{1-2}$O(C$_{1-3}$ alkyl), C$_{1-4}$ alkoxy, —O(C$_{1-4}$ hydroxyalkyl), —O(CH$_2$)$_{1-3}$O(C$_{1-3}$ alkyl), C$_{1-3}$ fluoroalkoxy, —O(CH$_2$)$_{1-3}$NR$_c$R$_c$, —OCH$_2$CH=CH$_2$, —OCH$_2$C≡CH, —C(O)(C$_{1-4}$ alkyl), —C(O)OH, —C(O)O(C$_{1-4}$ alkyl), —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), —P(O)(C$_{1-3}$ alkyl)$_2$, —S(O)$_2$(C$_{1-3}$ alkyl), —O(CH$_2$)$_{1-2}$(C$_{3-6}$ cycloalkyl), —O(CH$_2$)$_{1-2}$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, thiophenyl, methylpiperidinyl, and R$_d$; or (ii) C$_{1-4}$ alkyl substituted with one cyclic group selected from C$_{3-6}$ cycloalkyl, heterocyclyl, aryl, and heteroaryl, said cyclic group substituted with zero to 3 substituents independently selected from F, Cl, Br, —OH, —CN, C$_{1-6}$ alkyl, C$_{1-3}$ fluoroalkyl, C$_{1-3}$ alkoxy, C$_{1-3}$ fluoroalkoxy, —OCH$_2$CH=CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), and C$_{3-6}$ cycloalkyl; and R$_{4b}$ is phenyl or heteroaryl, each substituted with zero to 4 substituents independently selected from F, Cl, Br, —CN, —OH, C$_{1-6}$ alkyl, C$_{1-3}$ fluoroalkyl, C$_{1-4}$ hydroxyalkyl, —(CH$_2$)$_{1-2}$O(C$_{1-3}$ alkyl), C$_{1-4}$ alkoxy, —O(C$_{1-4}$ hydroxyalkyl), —O(CH$_2$)$_{1-3}$O(C$_{1-3}$ alkyl), C$_{1-3}$ fluoroalkoxy, —O(CH$_2$)$_{1-3}$NR$_c$R$_c$, —OCH$_2$CH=CH$_2$, —OCH$_2$C≡CH, —C(O)(C$_{1-4}$ alkyl), —C(O)OH, —C(O)O(C$_{1-4}$ alkyl), —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), —P(O)(C$_{1-3}$ alkyl)$_2$, —S(O)$_2$(C$_{1-3}$ alkyl), —O(CH$_2$)$_{1-2}$(C$_{3-6}$ cycloalkyl), —O(CH$_2$)$_{1-2}$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, thiophenyl, and methylpiperidinyl. Included this embodiment are compounds in which R$_{4a}$ is (i) C$_{3-6}$ cycloalkyl, heterocyclyl, phenyl, or heteroaryl, each substituted with zero to 4 substituents independently selected from F, Cl, Br, —CN, —OH, C$_{1-6}$ alkyl, C$_{1-3}$ fluoroalkyl, —CH$_2$OH, —(CH$_2$)$_{1-2}$O(C$_{1-2}$ alkyl), —C$_{1-4}$ alkoxy, —O(C$_{1-4}$ hydroxyalkyl), —O(CH$_2$)$_{1-20}$(C$_{1-2}$ alkyl), C$_{1-3}$ fluoroalkoxy, —O(CH$_2$)$_{1-2}$NR$_c$R$_c$, —OCH$_2$CH=CH$_2$, —OCH$_2$C≡CH, —C(O)(C$_{1-4}$ alkyl), —C(O)OH, —C(O)O(C$_{1-4}$ alkyl), —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), —P(O)(C$_{1-2}$ alkyl)$_2$, —S(O)$_2$(C$_{1-3}$ alkyl), —O(CH$_2$)$_{1-2}$(C$_{3-4}$ cycloalkyl), —O(CH$_2$)$_{1-2}$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, thiophenyl, methylpiperidinyl, and R$_d$; or (ii) C$_{1-3}$ alkyl substituted with one cyclic group selected from C$_{3-6}$ cycloalkyl, heterocyclyl, phenyl, and heteroaryl, said cyclic group substituted with zero to 3 substituents independently selected from F, Cl, Br, —OH, —CN, C$_{1-3}$ alkyl, C$_{1-2}$ fluoroalkyl, C$_{1-3}$ alkoxy, fluoroalkoxy, —OCH$_2$CH=CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), and C$_{3-4}$ cycloalkyl; and R$_{4b}$ is phenyl, isoxazolyl, oxadiazolyl, or thiazolyl, each substituted with zero to 3 substituents independently selected from F, Cl, —CH$_3$, —C(CH$_3$)$_3$, —CF$_3$, —OCF$_3$, and cyclopropyl. Also included in this embodiment are compounds in which R$_{4a}$ is phenyl, pyridinyl, or benzo[d][1,3]dioxolyl, each substituted with zero to 3 substituents independently selected from F, Cl, —CN, —CH$_3$, —CH(CH$_3$)$_2$, —CF$_3$, —OCH$_3$, —OCH(CH$_3$)$_2$, —OCHF$_2$, —OCF$_3$, —OCH$_2$(cyclopropyl), and cyclopropyl; and R$_{4b}$ is phenyl, isoxazolyl, oxadiazolyl, or thiazolyl, each substituted with zero to 3 substituents independently selected from F, Cl, —CH$_3$, —C(CH$_3$)$_3$, —CF$_3$, —OCF$_3$, and cyclopropyl.

In one embodiment, a compound of Formula (I) or a salt thereof is provided wherein R$_4$ is —CHR$_{4a}$R$_{4b}$; R$_{4a}$ is: (i) C$_{3-6}$ carbocyclyl, 4- to 10-membered heterocyclyl, phenyl, or 5-to 10-membered heteroaryl, each substituted with zero to 4 substituents independently selected from F, Cl, Br, —CN, —OH, C$_{1-6}$ alkyl, C$_{1-3}$ fluoroalkyl, C$_{1-2}$ bromoalkyl, C$_{1-2}$ cyanoalkyl, C$_{1-4}$ hydroxyalkyl, —(CH$_2$)$_{1-20}$(C$_{1-3}$ alkyl), C$_{1-4}$ alkoxy, C$_{1-3}$ fluoroalkoxy, C$_{1-3}$ cyanoalkoxy, —O(C$_{1-4}$ hydroxyalkyl), —O(CR$_x$R$_x$)$_{1-3}$O(C$_{1-3}$ alkyl), C$_{1-3}$ fluoroalkoxy, —O(CH$_2$)$_{1-3}$NR$_c$R$_c$, —OCH$_2$CH=CH$_2$, —OCH$_2$C≡CH, —C(O)(C$_{1-4}$ alkyl), —C(O)OH, —C(O)O(C$_{1-4}$ alkyl), —NR$_c$R$_c$, —CH$_2$NR$_a$R$_a$, —NR$_a$S(O)$_2$(C$_{1-3}$ alkyl), —NR$_a$C(O)(C$_{1-3}$ alkyl), —(CR$_x$R$_x$)$_{0-2}$NR$_a$C(O)O(C$_{1-4}$ alkyl), —P(O)(C$_{1-3}$ alkyl)$_2$, —S(O)$_2$(C$_{1-3}$ alkyl), —(CR$_x$R$_x$)$_{1-2}$(C$_{3-4}$ cycloalkyl), —(CR$_x$R$_x$)$_{1-2}$(morpholinyl), —(CR$_x$R$_x$)$_{1-2}$(difluoromorpholinyl), —(CR$_x$R$_x$)$_{1-2}$(dimethylmorpholinyl), —(CR$_x$R$_x$)$_{1-2}$(oxaazabicyclo[2.2.1]heptanyl), (CR$_x$R$_x$)$_{1-2}$(oxaazaspiro[3.3]heptanyl), —(CR$_x$R$_x$)$_{1-2}$(methylpiperazinonyl), —(CR$_x$R$_x$)$_{1-2}$(acetylpiperazinyl), —(CR$_x$R$_x$)$_{1-2}$(piperidinyl), —(CR$_x$R$_x$)$_{1-2}$(difluoropiperidinyl), —(CR$_x$R$_x$)$_{1-2}$(methoxypiperidinyl), —(CR$_x$R$_x$)$_{1-2}$(hydroxypiperidinyl), —O(CR$_x$R$_x$)$_{0-2}$(C$_{3-6}$ cycloalkyl), —O(CR$_x$R$_x$)$_{0-2}$(methylcyclopropyl), —O(CR$_x$R$_x$)$_{0-2}$((ethoxycarbonyl)cyclopropyl), —O(CR$_x$R$_x$)$_{0-2}$(oxetanyl), —O(CR$_x$R$_x$)$_{0-2}$(methylazetidinyl), —O(CR$_x$R$_x$)$_{0-2}$(tetrahydropyranyl), —O(CR$_x$R$_x$)$_{1-2}$(morpholinyl), —O(CR$_x$R$_x$)$_{0-2}$(thiazolyl), cyclopropyl, cyanocyclopropyl, methylazetidinyl, acetylazetidinyl, (tert-butoxycarbonyl)azetidinyl, triazolyl, tetrahydropyranyl, morpholinyl, thiophenyl, methylpiperidinyl, dioxolanyl, pyrrolidinonyl, and R$_d$; or (ii) C$_{1-4}$ alkyl substituted with one cyclic group selected from C$_{3-6}$ carbocyclyl, 4- to 10-membered heterocyclyl, 6- to 10-membered aryl, or 5-to 10-membered heteroaryl, said cyclic group substituted with zero to 3 substituents independently selected from F, Cl, Br, —OH, —CN, C$_{1-6}$ alkyl, C$_{1-3}$ fluoroalkyl, C$_{1-3}$ alkoxy, C$_{1-3}$ fluoroalkoxy, —OCH$_2$CH=CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), and C$_{3-6}$ cycloalkyl; and R$_{4b}$ is phenyl, isoxazolyl, oxadiazolyl, thiazolyl, or triazolyl, each substituted with zero to 3 substituents independently selected from F, Cl, Br, —CH$_3$, —C(CH$_3$)$_3$, —CF$_3$, —OCF$_3$, and cyclopropyl.

In one embodiment, a compound of Formula (I) or a salt thereof is provided wherein R$_4$ is —CHR$_{4a}$R$_{4b}$; R$_{4a}$ is (i) C$_{3-6}$ cycloalkyl, heterocyclyl, phenyl, or heteroaryl, each substituted with zero to 4 substituents independently selected from F, Cl, Br, —CN, —OH, C$_{1-6}$ alkyl, C$_{1-3}$ fluoroalkyl, C$_{1-4}$ hydroxyalkyl, —(CH$_2$)$_{1-2}$O(C$_{1-3}$ alkyl), C$_{1-4}$ alkoxy, —O(C$_{1-4}$ hydroxyalkyl), —O(CH$_2$)$_{1-3}$O(C$_{1-3}$ alkyl), C$_{1-3}$ fluoroalkoxy, —O(CH$_2$)$_{1-3}$NR$_c$R$_c$, —OCH$_2$CH=CH$_2$, —OCH$_2$C≡CH, —C(O)(C$_{1-4}$ alkyl), —C(O)OH, —C(O)O(C$_{1-4}$ alkyl), —NR$_c$R$_c$, —NR$_a$S(O)$_2$ (C$_{1-3}$ alkyl), —NR$_a$C(O)(C$_{1-3}$ alkyl), —NR$_a$C(O)O(C$_{1-4}$ alkyl), —P(O)(C$_{1-3}$ alkyl)$_2$, —S(O)$_2$(C$_{1-3}$ alkyl), —O(CH$_2$)$_{1-2}$(C$_{3-6}$ cycloalkyl), —O(CH$_2$)$_{1-2}$(morpholinyl), cyclopropyl, cyanocyclopropyl, methylazetidinyl, acetylazetidinyl, (tert-butoxycarbonyl)azetidinyl, triazolyl, tetrahydropyranyl, morpholinyl, thiophenyl, methylpiperidinyl, and R$_d$; or (ii) C$_{1-4}$ alkyl substituted with one cyclic group selected from C$_{3-6}$ cycloalkyl, heterocyclyl, mono- or bicyclic aryl, and heteroaryl, said cyclic group substituted with zero to 3 substituents independently selected from F, Cl, Br, —OH, —CN, C$_{1-6}$ alkyl, C$_{1-3}$ fluoroalkyl, C$_{1-3}$ alkoxy, C$_{1-3}$ fluoroalkoxy, —OCH$_2$CH=CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), and C$_{3-6}$ cycloalkyl; and R$_{4b}$ is C$_{1-6}$ alkyl substituted with zero to 4 substituents independently selected from F, Cl, —CN, —OH, —OCH$_3$, —SCH$_3$, C$_{1-3}$ fluoroalkoxy, —NR$_a$R$_a$, —S(O)$_2$R$_e$, or —NR$_a$S(O)$_2$R$_e$. Included in this embodiment are compounds in which R$_{4a}$ is C$_{3-6}$ cycloalkyl, heterocyclyl, phenyl, or heteroaryl, each substituted with zero to 4 substituents independently selected from F, Cl, Br, —CN, —OH, C$_{1-6}$ alkyl, C$_{1-3}$ fluoroalkyl, —CH$_2$OH, —(CH$_2$)$_{1-2}$O(C$_{1-2}$ alkyl), C$_{1-4}$ alkoxy, —O(C$_{1-4}$ hydroxyalkyl), —O(CH$_2$)$_{1-2}$O(C$_{1-2}$ alkyl), C$_{1-3}$ fluoroalkoxy, —O(CH$_2$)$_{1-2}$NR$_c$R$_c$, —OCH$_2$CH=CH$_2$, —OCH$_2$C≡CH, —C(O)(C$_{1-4}$ alkyl), —C(O)OH, —C(O)O (C$_{1-4}$ alkyl), —NR$_c$R$_c$, —NR$_a$S(O)$_2$(C$_{1-3}$ alkyl), —NR$_a$C (O)(C$_{1-3}$ alkyl), —NR$_a$C(O)O(C$_{1-4}$ alkyl), —P(O)(C$_{1-2}$ alkyl)$_2$, —S(O)$_2$(C$_{1-3}$ alkyl), —O(CH$_2$)$_{1-2}$(C$_{3-4}$ cycloalkyl), —O(CH$_2$)$_{1-2}$(morpholinyl), cyclopropyl, cyanocyclopropyl, methylazetidinyl, acetylazetidinyl, (tert-butoxycarbonyl) azetidinyl, triazolyl, tetrahydropyranyl, morpholinyl, thiophenyl, methylpiperidinyl, and R$_d$; or (ii) C$_{1-3}$ alkyl substituted with one cyclic group selected from C$_{3-6}$ cycloalkyl, heterocyclyl, phenyl, and heteroaryl, said cyclic group substituted with zero to 3 substituents independently selected from F, Cl, Br, —OH, —CN, C$_{1-3}$ alkyl, C$_{1-2}$ fluoroalkyl, C$_{1-3}$ alkoxy, C$_{1-2}$ fluoroalkoxy, —OCH$_2$CH=CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), and C$_{3-4}$ cycloalkyl; and R$_{4b}$ is C$_{1-4}$ alkyl substituted with zero to 4 substituents independently selected from F, Cl, —CN, —OH, —OCH$_3$, —SCH$_3$, C$_{1-3}$ fluoroalkoxy, and —NR$_a$R$_a$. Also included in this embodiment are compounds in which R$_{4a}$ is phenyl, pyridinyl, or benzo[d][1,3]dioxolyl, each substituted with zero to 3 substituents independently selected from F, Cl, —CN, —CH$_3$—, —CH(CH$_3$)$_2$, —CF$_3$, —OCH$_3$, —OCH(CH$_3$)$_2$, —OCHF$_2$, —OCF$_3$, —OCH$_2$(cyclopropyl), and cyclopropyl; and R$_{4b}$ is —CH$_3$ and —CH$_2$CH$_3$.

In one embodiment, a compound of Formula (I) or a salt thereof is provided wherein R$_4$ is —CHR$_{4a}$R$_{4b}$; R$_{4a}$ is (i) C$_{3-8}$ carbocyclyl, 4- to 10-membered heterocyclyl, phenyl, or 5-to 10-membered heteroaryl, each substituted with zero to 4 substituents independently selected from F, Cl, Br, —CN, —OH, C$_{1-6}$ alkyl, C$_{1-3}$ fluoroalkyl, C$_{1-2}$ bromoalkyl, C$_{1-2}$ cyanoalkyl, C$_{1-4}$ hydroxyalkyl, —(CH$_2$)$_{1-2}$O(C$_{1-3}$ alkyl), C$_{1-4}$ alkoxy, C$_{1-3}$ fluoroalkoxy, C$_{1-3}$ cyanoalkoxy, —O(C$_{1-4}$ hydroxyalkyl), —O(CR$_x$R$_x$)$_{1-3}$O(C$_{1-3}$ alkyl), C$_{1-3}$ fluoroalkoxy, —O(CH$_2$)$_{1-3}$NR$_c$R$_c$, —OCH$_2$CH=CH$_2$, —OCH$_2$C≡CH, —C(O)(C$_{1-4}$ alkyl), —C(O)OH, —C(O)O (C$_{1-4}$ alkyl), —NR$_c$R$_c$, —CH$_2$NR$_a$R$_a$, —NR$_a$S(O)$_2$(C$_{1-3}$ alkyl), —NR$_a$C(O)(C$_{1-3}$ alkyl), —(CR$_x$R$_x$)$_{0-2}$NR$_a$C(O)O (C$_{1-4}$ alkyl), —P(O)(C$_{1-3}$ alkyl)$_2$, —S(O)$_2$(C$_{1-3}$ alkyl), —(CR$_x$R$_x$)$_{1-2}$(C$_{3-4}$ cycloalkyl), —(CR$_x$R$_x$)$_{1-2}$(morpholinyl), —(CR$_x$R$_x$)$_{1-2}$(difluoromorpholinyl), —(CR$_x$R$_x$)$_{1-2}$(dimethylmorpholinyl), —(CR$_x$R$_x$)$_{1-2}$(oxaazabicyclo[2.2.1]heptanyl), (CR$_x$R$_x$)$_{1-2}$(oxaazaspiro[3.3]heptanyl), —(CR$_x$R$_x$)$_{1-2}$ (methylpiperazinonyl), —(CR$_x$R$_x$)$_{1-2}$(acetylpiperazinyl), —(CR$_x$R$_x$)$_{1-2}$(piperidinyl), —(CR$_x$R$_x$)$_{1-2}$(difluoropiperidinyl), —(CR$_x$R$_x$)$_{1-2}$(methoxypiperidinyl), —(CR$_x$R$_x$)$_{1-2}$(hydroxypiperidinyl), —O(CR$_x$R$_x$)$_{0-2}$(C$_{3-6}$ cycloalkyl), —O(CR$_x$R$_x$)$_{0-2}$(methylcyclopropyl), —O(CR$_x$R$_x$)$_{0-2}$ ((ethoxycarbonyl)cyclopropyl), —O(CR$_x$R$_x$)$_{0-2}$(oxetanyl), —O(CR$_x$R$_x$)$_{0-2}$(methylazetidinyl), —O(CR$_x$R$_x$)$_{0-2}$(tetrahydropyranyl), —O(CR$_x$R$_x$)$_{1-2}$(morpholinyl), —O(CR$_x$R$_x$)$_{0-2}$ (thiazolyl), cyclopropyl, cyanocyclopropyl, methylazetidinyl, acetylazetidinyl, (tert-butoxycarbonyl)azetidinyl, triazolyl, tetrahydropyranyl, morpholinyl, thiophenyl, methylpiperidinyl, dioxolanyl, pyrrolidinonyl, and R$_d$; or (ii) C$_{1-4}$ alkyl substituted with one cyclic group selected from C$_{3-6}$ cycloalkyl, 4- to 10-membered heterocyclyl, mono- or bicyclic aryl, or 5-to 10-membered heteroaryl, said cyclic group substituted with zero to 3 substituents independently selected from F, Cl, Br, —OH, —CN, C$_{1-6}$ alkyl, C$_{1-3}$ fluoroalkyl, C$_{1-3}$ alkoxy, C$_{1-3}$ fluoroalkoxy, —OCH$_2$CH=CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C (O)O(C$_{1-4}$ alkyl), and C$_{3-6}$ cycloalkyl; and R$_{4b}$ is —CN or C$_{1-6}$ alkyl substituted with zero to 4 substituents independently selected from F, Cl, —CN, —OH, —OCH$_3$, —SCH$_3$, C$_{1-3}$ fluoroalkoxy, —NR$_a$R$_a$, —S(O)$_2$R$_e$, or —NR$_a$S(O)$_2$R$_e$. Included in this embodiment are compounds in which R$_{4a}$ is (i) C$_{3-6}$ carbocyclyl, 4- to 10-membered heterocyclyl, phenyl, or 5-to 10-membered heteroaryl, each substituted with zero to 4 substituents independently selected from F, Cl, Br, —CN, —OH, C$_{1-6}$ alkyl, C$_{1-3}$ fluoroalkyl, C$_{1-2}$ bromoalkyl, C$_{1-2}$ cyanoalkyl, C$_{1-2}$ hydroxyalkyl, —CH$_2$NR$_a$R$_a$, —(CH$_2$)$_{1-2}$O(C$_{1-2}$ alkyl), —(CH$_2$)$_{1-2}$NR$_x$C(O)O(C$_{1-2}$ alkyl), C$_{1-4}$ alkoxy, —O(C$_{1-4}$ hydroxyalkyl), —O(CR$_x$R$_x$)$_{1-2}$O(C$_{1-2}$ alkyl), C$_{1-3}$ fluoroalkoxy, C$_{1-3}$ cyanoalkoxy, —O(CH$_2$)$_{1-2}$NR$_c$R$_c$, —OCH$_2$CH=CH$_2$, —OCH$_2$C≡CH, —C(O)(C$_{1-4}$ alkyl), —C(O)OH, —C(O)O(C$_{1-4}$ alkyl), —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), —P(O)(C$_{1-2}$ alkyl)$_2$, —S(O)$_2$ (C$_{1-3}$ alkyl), —(CH$_2$)$_{1-2}$(C$_{3-4}$ cycloalkyl), —CR$_x$R$_x$(morpholinyl), —CR$_x$R$_x$(difluoromorpholinyl), —CR$_x$R$_x$(dimethylmorpholinyl), —CR$_x$R$_x$(oxaazabicyclo[2.2.1] heptanyl), —CR$_x$R$_x$(oxaazaspiro[3.3]heptanyl), —CR$_x$R$_x$ (methylpiperazinonyl), —CR$_x$R$_x$(acetylpiperazinyl), —CR$_x$R$_x$(piperidinyl), —CR$_x$R$_x$(difluoropiperidinyl), —CR$_x$R$_x$(methoxypiperidinyl), —CR$_x$R$_x$(hydroxypiperidinyl), —O(CH$_2$)$_{0-2}$(C$_{3-4}$ cycloalkyl), —O(CH$_2$)$_{0-2}$(methylcyclopropyl), —O(CH$_2$)$_{0-2}$((ethoxycarbonyl)cyclopropyl), —O(CH$_2$)$_{0-2}$(oxetanyl), —O(CH$_2$)$_{0-2}$(methylazetidinyl), —O(CH$_2$)$_{1-2}$(morpholinyl), —O(CH$_2$)$_{0-2}$(tetrahydropyranyl), —O(CH$_2$)$_{0-2}$(thiazolyl), cyclopropyl, cyanocyclopropyl, methylazetidinyl, acetylazetidinyl, (tert-butoxycarbonyl)azetidinyl, dioxolanyl, pyrrolidinonyl, triazolyl, tetrahydropyranyl, morpholinyl, thiophenyl, methylpiperidinyl, and R$_d$; or (ii) C$_{1-3}$ alkyl substituted with one cyclic group selected from C$_{3-6}$ cycloalkyl, 4- to 10-membered heterocyclyl, mono- or bicyclic aryl, or 5-to 10-membered heteroaryl, said cyclic group substituted with zero to 3 substituents independently selected from F, Cl, Br, —OH, —CN, C$_{1-3}$ alkyl, C$_{1-2}$ fluoroalkyl, C$_{1-3}$ alkoxy, C$_{1-2}$ fluoroalkoxy, —OCH$_2$CH=CH$_2$, —OCH$_2$C≡CH, —NR$_c$R$_c$, —NR$_a$S(O)$_2$(C$_{1-3}$ alkyl), —NR$_a$C(O)(C$_{1-3}$ alkyl), —NR$_a$C (O)O(C$_{1-4}$ alkyl), and C$_{3-4}$ cycloalkyl; and R$_{4b}$ is —CN or C$_{1-4}$ alkyl substituted with zero to 4 substituents independently selected from F, Cl, —CN, —OH, —OCH$_3$, —SCH$_3$, C$_{1-3}$ fluoroalkoxy, and —NR$_a$R$_a$.

In one embodiment, a compound of Formula (I) or a salt thereof is provided wherein $R_4$ is —$CHR_{4a}R_{4b}$; and $R_{4b}$ is —CN, —$CH_3$, —$CH_2CH_3$, —$CH_2CH_2CH_3$, or —$CH(CH_3)_2$.

In one embodiment, a compound of Formula (I) or a salt thereof is provided wherein $R_4$ is —$CHR_{4a}R_{4b}$; and $R_{4b}$ is —CN, —$CH_3$, or —$CH_2CH_3$.

In one embodiment, a compound of Formula (I) or a salt thereof is provided wherein $R_4$ is —$CHR_{4a}R_{4b}$; and $R_{4b}$ is —CN.

In one embodiment, a compound of Formula (I) or a salt thereof is provided wherein $R_4$ is —$CHR_{4a}R_{4b}$; and $R_{4b}$ is —$CH_3$ or —$CH_2CH_3$.

In one embodiment, a compound of Formula (I) or a salt thereof is provided wherein $R_4$ is —$CHR_{4a}R_{4b}$; and $R_{4b}$ is $CH_3$.

In one embodiment, a compound of Formula (I) or a salt thereof is provided wherein $R_4$ is —$CHR_{4a}R_{4b}$; and $R_{4b}$ is —$CH_2CH_3$.

In one embodiment, a compound of Formula (I) or a salt thereof is provided wherein m is 1, 2, or 3; and each $R_5$ is independently —CN, $C_{1-5}$ alkyl substituted with zero to 4 $R_g$, $C_{2-3}$ alkenyl substituted with zero to 4 $R_g$, $C_{2-3}$ alkynyl substituted with zero to 4 $R_g$, $C_{3-4}$ cycloalkyl substituted with zero to 4 $R_g$, phenyl substituted with zero to 3 $R_g$, oxadiazolyl substituted with zero to 3 $R_g$, pyridinyl substituted with zero to 3 $R_g$, —$(CH_2)_{1-2}$(4- to 10-membered heterocyclyl substituted with zero to 4 $R_g$), —$(CH_2)_{1-2}NR_cC(O)(C_{1-4}$ alkyl), —$(CH_2)_{1-2}NR_cC(O)O(C_{1-4}$ alkyl), —$(CH_2)_{1-2}NR_cS(O)_2(C_{1-4}$ alkyl), —$C(O)(C_{1-4}$ alkyl), —C(O)OH, —$C(O)O(C_{1-4}$ alkyl), —$C(O)O(C_{3-4}$ cycloalkyl), —$C(O)NR_aR_a$, or —$C(O)NR_a(C_{3-4}$ cycloalkyl). Included in this embodiment are compounds in which each $R_5$ is independently —$CH_3$, —$CH_2CH_3$, —$CH_2OH$, or —$CH_2OCH_3$.

In one embodiment, a compound of Formula (I) or a salt thereof is provided wherein m is zero.

In one embodiment, a compound of Formula (I) or a salt thereof is provided wherein m is 1, 2, or 3. Included in this embodiment are compounds in which m is 1 or 2.

Also included in this embodiment are compounds in which m is 1.

In one embodiment, a compound of Formula (I) or a salt thereof is provided wherein m is 2 or 3. Included in this embodiment are compounds in which m is 2.

In one embodiment, a compound of Formula (I) or a salt thereof is provided wherein m is 3.

In one embodiment, a compound of Formula (I) or a salt thereof is provided having the structure of Formula (II):

(II)

wherein one, two, or three of $R_{5a}$, $R_{5b}$, $R_{5c}$, and $R_{5d}$ are each $R_5$ and the remainder of $R_{5a}$, $R_{5b}$, $R_{5c}$, and $R_{5d}$ are each hydrogen. Included in this embodiment are compounds in which each $R_5$ is independently —CN, —$CH_3$, —$CH_2CH_3$, —$CH(CH_3)_2$, —$CHC(CH_3)_2$, —$CH_2F$, —$C(CH_3)_2F$, —$CF(CH_3)CH(CH_3)_2$, —$CH_2OH$, —$C(CH_3)_2OH$, —$C(CH_3)(OH)CH(CH_3)_2$, —$CH_2OCH_3$, —$C(O)C(CH_3)_2$, —C(O)OH, —$C(O)OCH_3$, —$C(O)OC(CH_3)_2$, —$C(O)NH_2$, —C(O)NH(cyclopropyl), —C(O)O(cyclopropyl), cyclopropyl, phenyl, methyloxadiazolyl, or methylpyridinyl. Also included in this embodiment are compounds in which each $R_5$ is independently —$CH_3$, —$CH_2CH_3$, —$CH_2CH_2CH_3$, —$CH_2OH$, —$CH_2OCH_3$, —$CH_2OCH_2CH_3$, —$CH_2NH_2$, —$CH_2N_3$, or —$CH_2NHC(O)OCH_3$.

In one embodiment, a compound of Formula (I) or a salt thereof is provided having the structure of Formula (III):

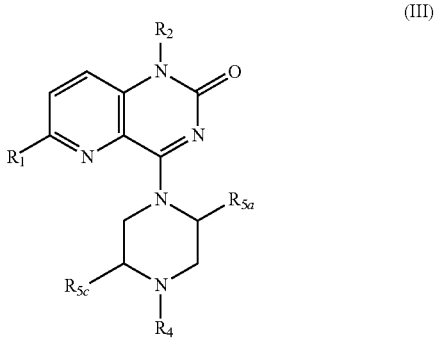

(III)

wherein $R_{5a}$ and $R_{5c}$ are each $R_5$ and $R_{5b}$ and $R_{5d}$ are each hydrogen. Included in this embodiment are compounds in which (i) $R_{5a}$ is —$CH_3$ or —$CH_2CH_3$ and $R_{5c}$ is —$CH_3$ or —$CH_2CH_3$; or (ii) —$R_{5a}$ is —$CH_3$ and $R_{5c}$ is —$CH_2OH$ or —$CH_2OCH_3$.

In one embodiment, a compound of Formula (III) or a salt thereof is provided wherein $R_{5a}$ is —$CH_3$ and $R_{5c}$ is —$CH_3$.

In one embodiment, a compound of Formula (III) or a salt thereof is provided wherein $R_{5a}$ is —$CH_3$ and $R_{5c}$ is —$CH_2CH_3$.

In one embodiment, a compound of Formula (III) or a salt thereof is provided wherein $R_{5a}$ is —$CH_2CH_3$ and $R_{5c}$ is —$CH_3$.

In one embodiment, a compound of Formula (III) or a salt thereof is provided wherein $R_{5a}$ is —$CH_2CH_3$ and $R_{5c}$ is —$CH_2CH_3$.

In one embodiment, a compound of Formula (III) or a salt thereof is provided wherein $R_{5a}$ is —$CH_3$ and $R_{5c}$ is —$CH_2OH$.

In one embodiment, a compound of Formula (III) or a salt thereof is provided wherein $R_{5a}$ is —$CH_3$ and $R_{5c}$ is —$CH_2OCH_3$.

In one embodiment, a compound of Formula (III) or a salt thereof is provided wherein $R_{5a}$ is —$CH_3$ and $R_{5c}$ is —$CH_2OCH_2CH_3$.

In one embodiment, a compound of Formula (III) or a salt thereof is provided wherein $R_{5a}$ is —$CH_3$ and $R_{5c}$ is —$CH_2CH_2CH_3$.

In one embodiment, a compound of Formula (III) or a salt thereof is provided wherein $R_{5a}$ is —$CH_3$ and $R_{5c}$ is —$CH_2N_3$.

In one embodiment, a compound of Formula (III) or a salt thereof is provided wherein $R_{5a}$ is —$CH_3$ and $R_{5c}$ is —$CH_2NH_2$.

In one embodiment, a compound of Formula (III) or a salt thereof is provided wherein $R_{5a}$ is —$CH_3$ and $R_{5c}$ is —$CH_2NHC(O)OCH_3$.

In one embodiment, a compound of Formula (III) or a salt thereof is provided wherein $R_{5a}$ is —CH$_2$OH and $R_{5c}$ is —CH$_3$.

In one embodiment, a compound of Formula (III) or a salt thereof is provided wherein $R_{5a}$ is —CH$_2$OCH$_3$ and $R_{5c}$ is —CH$_3$.

In one embodiment, a compound of Formula (I) or a salt thereof is provided having the structure:

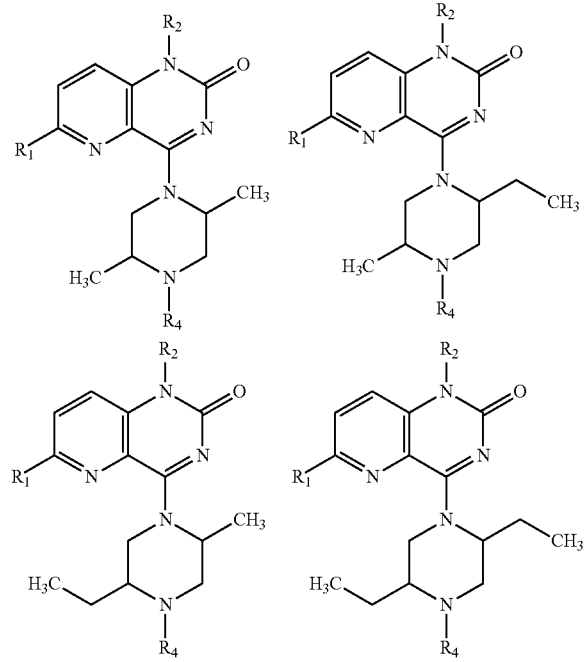

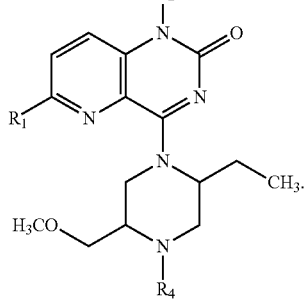

-continued

In one embodiment, a compound of Formula (I) or a salt thereof is provided having the structure:

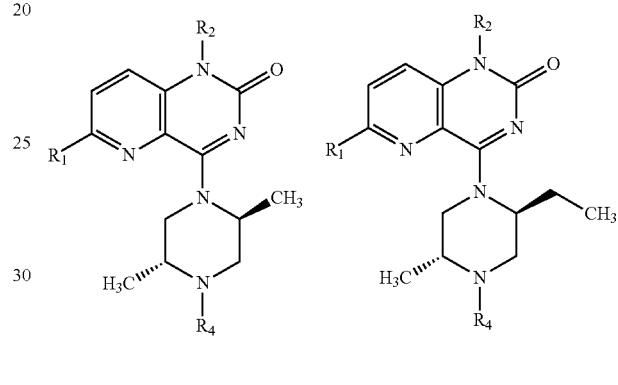

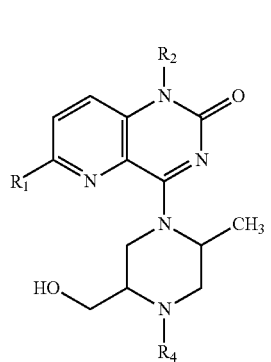

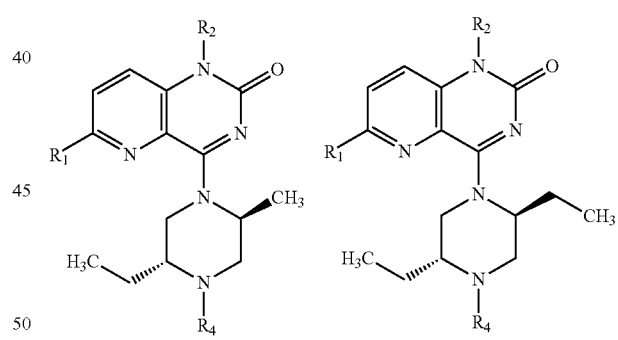

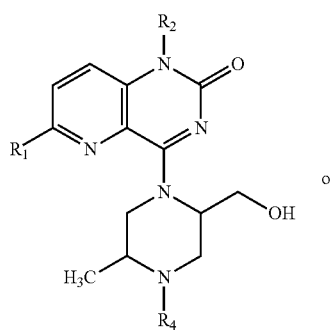

or

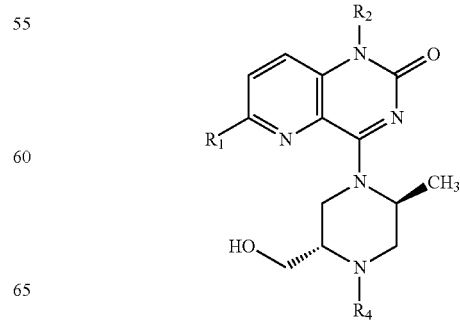

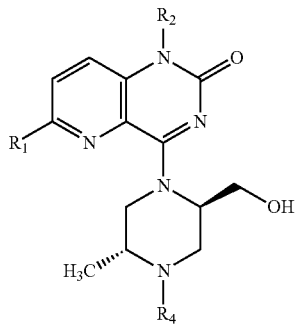
or
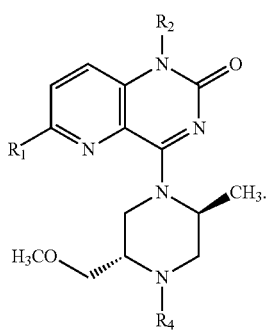
In one embodiment, a compound of Formula (I) or a salt thereof is provided having the structure:
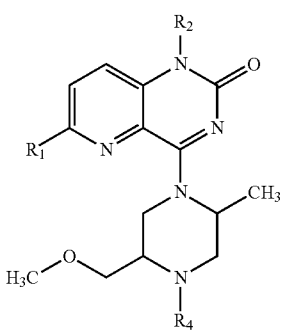
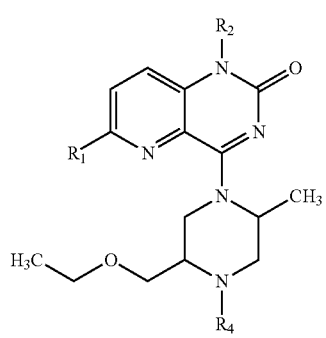
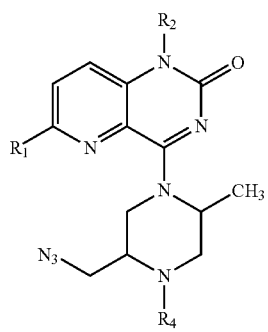 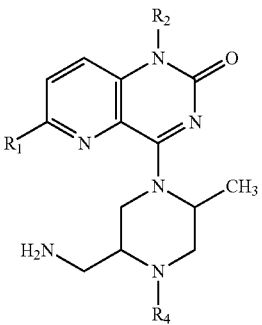
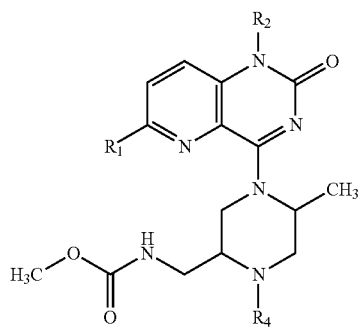
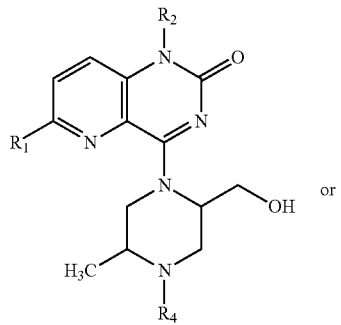
or
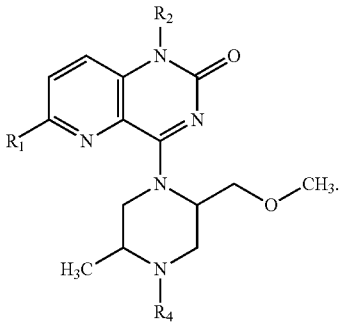

In one embodiment, a compound of Formula (I) or a salt thereof is provided having the structure:
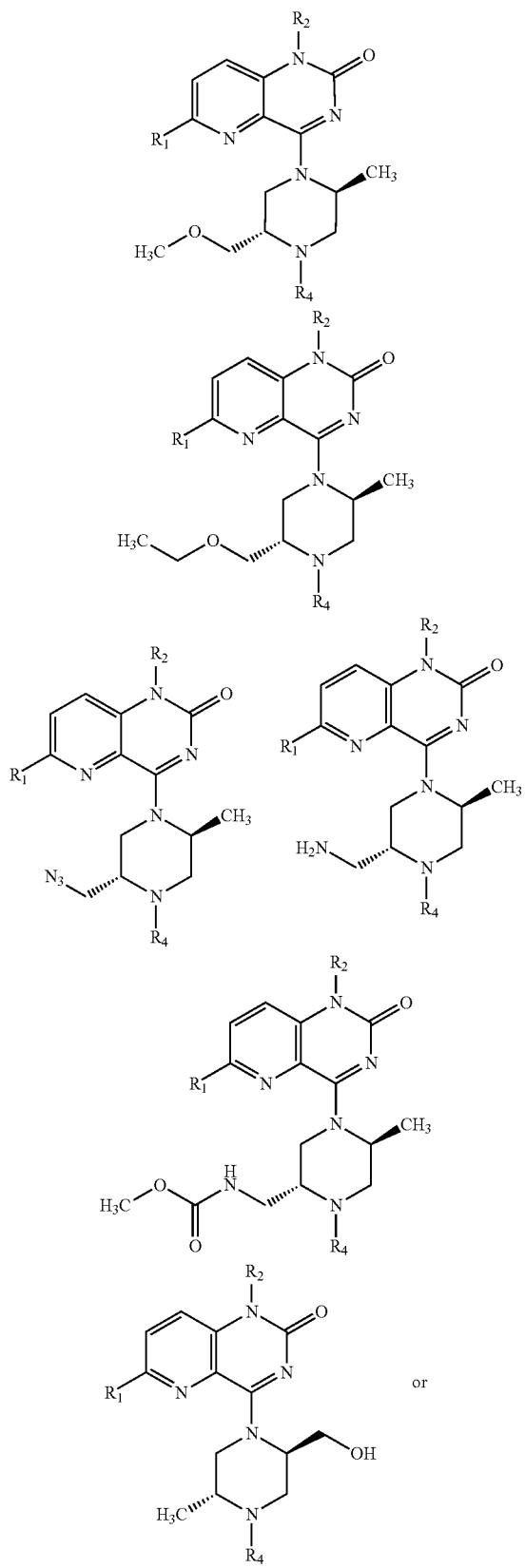
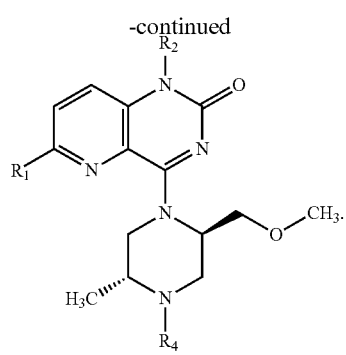
In one embodiment, a compound of Formula (I) or a salt thereof is provided wherein $R_4$ is:
(i)
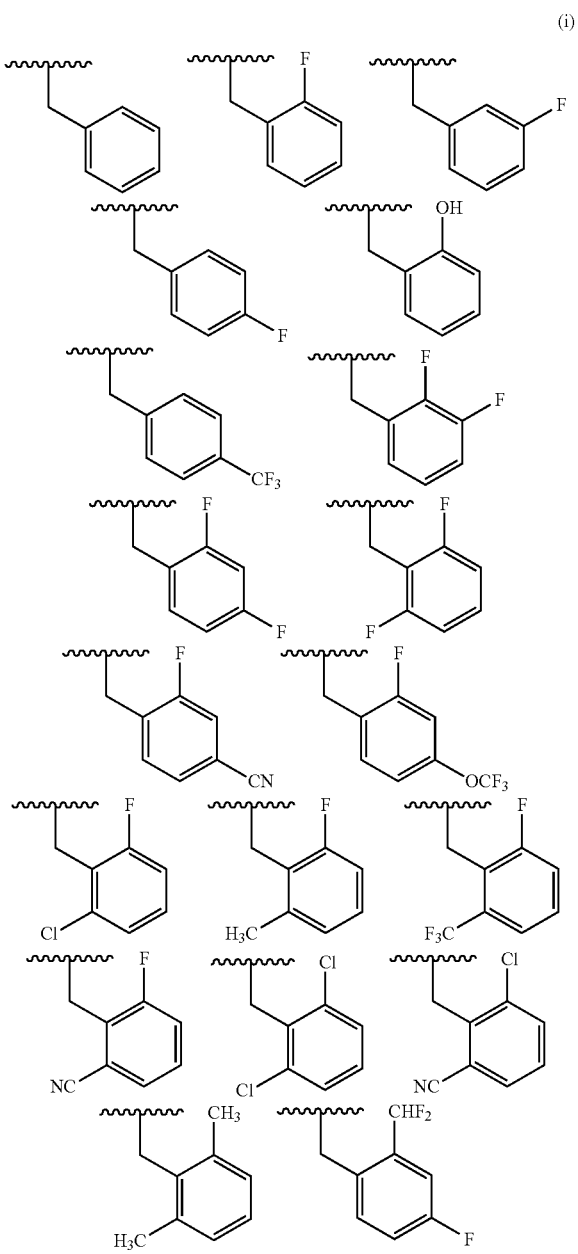

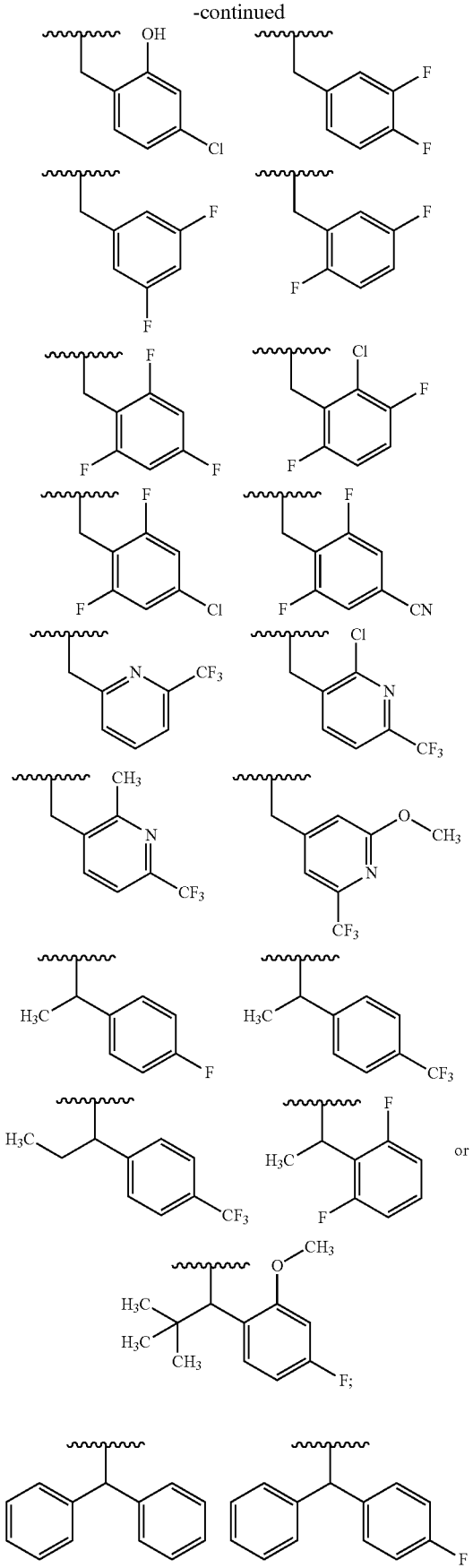
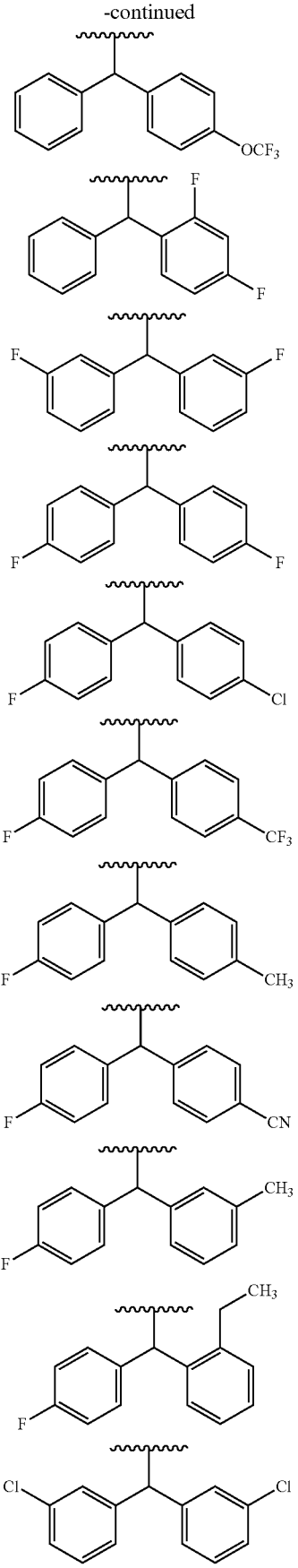

-continued
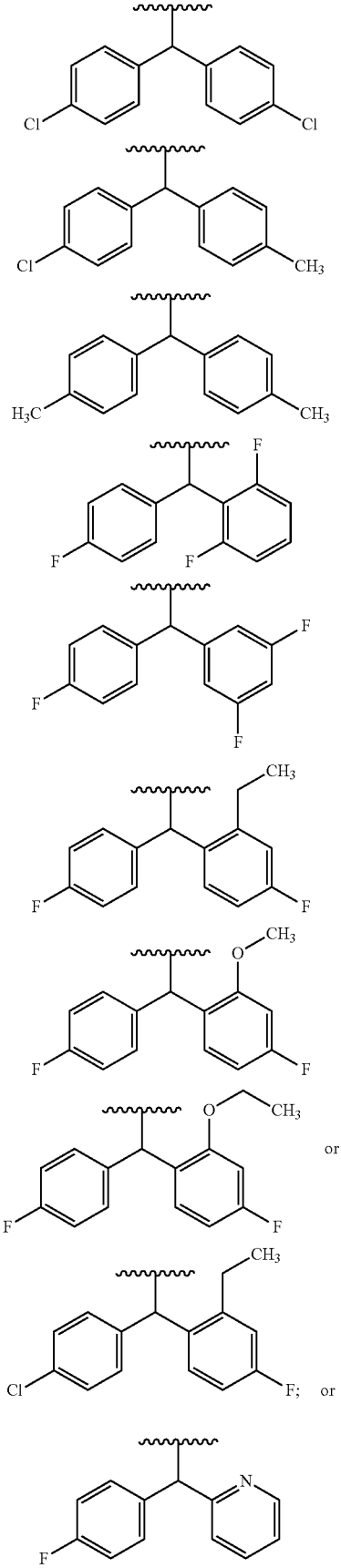
or
(iii)
-continued
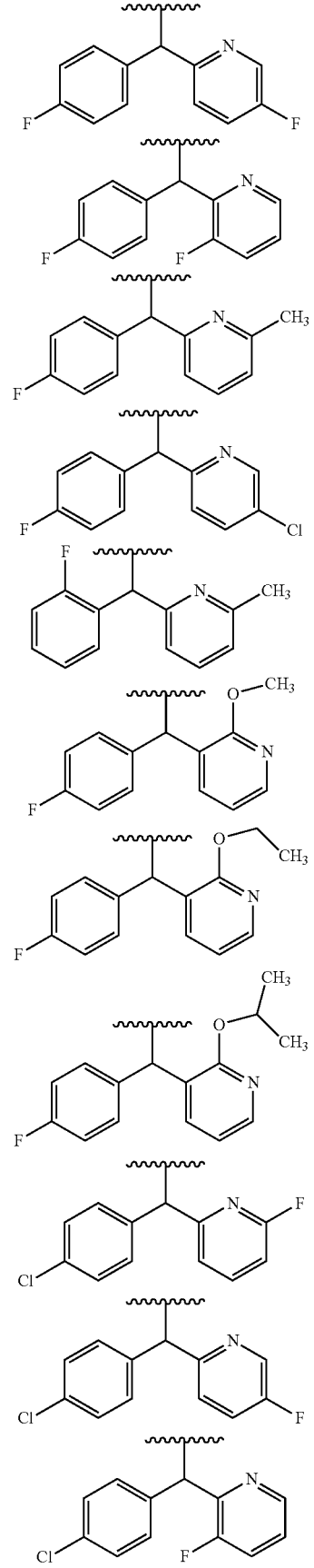

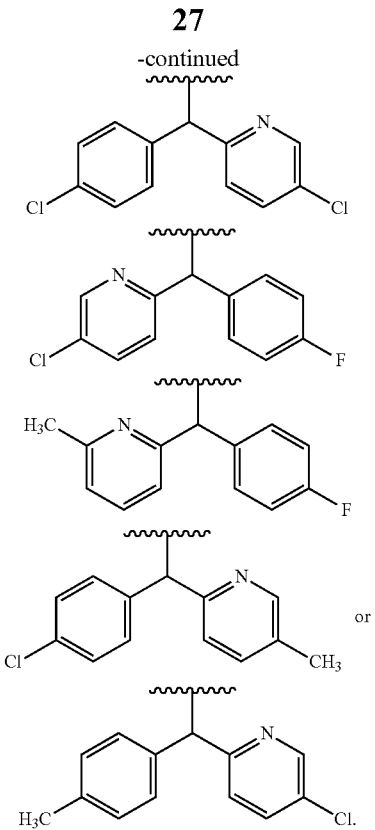

Included in this embodiment are compounds in which $R_1$ is H, Br, —CN, or —OCH$_3$; and $R_2$ is —CH$_3$.

In one embodiment, a compound of Formula (I) or a salt thereof is provided wherein $R_4$ is:

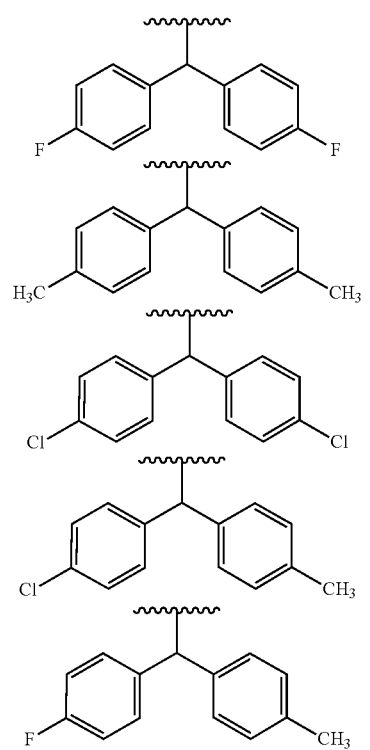

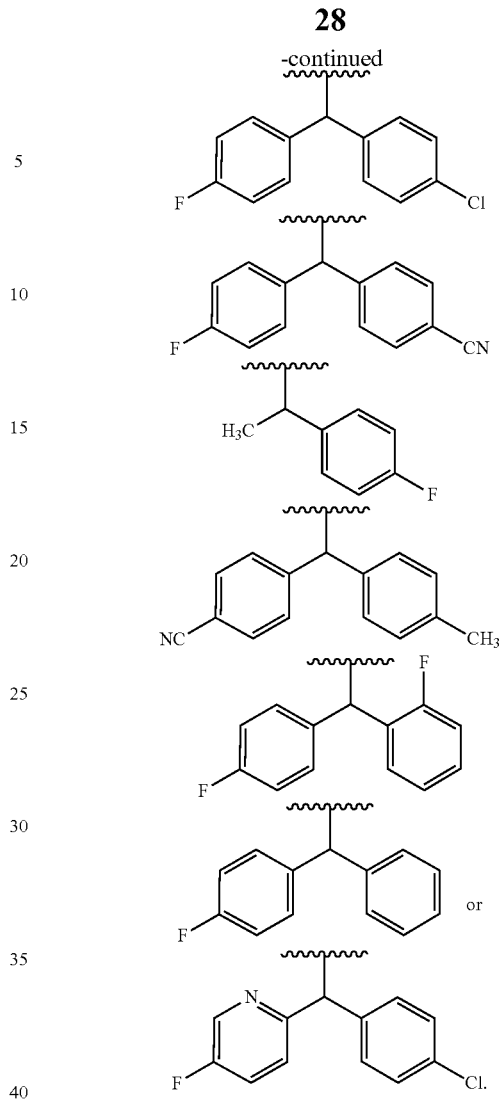

Included in this embodiment are compounds in which $R_1$ is H, Br, —CN, or —OCH$_3$; and $R_2$ is —CH$_3$. Also included in this embodiment are compounds in which $R_1$ is —CN; and $R_2$ is —CH$_3$.

In one embodiment, a compound of Formula (I) or a salt thereof is provided wherein $R_1$ is —CN; and $R_2$ is —CH$_3$.

In one embodiment, a compound of Formula (III) or a salt thereof is provided wherein $R_1$ is —CN; and $R_2$ is —CH$_3$.

In one embodiment, a compound of Formula (III) or a salt thereof is provided wherein $R_1$ is —CN; $R_2$ is —CH$_3$; $R_{5a}$ is —CH$_3$; and $R_{5c}$ is —CH$_3$.

In one embodiment, a compound of Formula (III) or a salt thereof is provided wherein $R_1$ is —CN; $R_2$ is —CH$_3$; $R_{5a}$ is —CH$_3$; and $R_{5c}$ is —CH$_2$CH$_3$.

In one embodiment, a compound of Formula (III) or a salt thereof is provided wherein $R_1$ is —CN; $R_2$ is CH$_3$; $R_{5a}$ is —CH$_3$; and $R_{5c}$ is —CH$_2$CH$_2$CH$_3$.

In one embodiment, a compound of Formula (III) or a salt thereof is provided wherein $R_1$ is —CN; $R_2$ is —CH$_3$; $R_{5a}$ is —CH$_2$CH$_3$; and $R_{5c}$ is —CH$_2$CH$_3$.

In one embodiment, a compound of Formula (III) or a salt thereof is provided wherein $R_1$ is —CN; $R_2$ is —CH$_3$; $R_{5a}$ is —CH$_3$; and $R_{5c}$ is —CH$_3$, —CH$_2$CH$_3$, or —CH$_2$CH$_2$CH$_3$.

In one embodiment, a compound of Formula (I) or a salt thereof is provided wherein $R_1$ is —CN; $R_2$ is —CH$_3$; $R_4$ is —CHR$_{4a}$R$_{4b}$; and $R_{4b}$ is —CH$_3$.

In one embodiment, a compound of Formula (I) or a salt thereof is provided wherein $R_1$ is —CN; $R_2$ is —CH$_3$; $R_4$ is —CHR$_{4a}$R$_{4b}$; and R$_{4b}$ is —CH$_2$CH$_3$.

In one embodiment, a compound of Formula (I) or a salt thereof is provided wherein $R_1$ is —CN; $R_2$ is —CH$_3$; $R_4$ is —CHR$_{4a}$R$_{4b}$; and R$_{4b}$ is —CH$_2$CH$_2$CH$_3$.

In one embodiment, a compound of Formula (I) or a salt thereof is provided wherein $R_1$ is —CN; $R_2$ is CH$_3$; $R_4$ is —CHR$_{4a}$R$_{4b}$; and R$_{4b}$ is —CH$_3$, —CH$_2$CH$_3$, or —CH$_2$CH$_2$CH$_3$.

In one embodiment, a compound of Formula (I) or a salt thereof is provided wherein $R_4$ is —CHR$_{4a}$R$_{4b}$; and R$_{4a}$ is phenyl substituted with 1 to 2 substituents independently selected from F, Cl, —CF$_3$—OCF$_3$, or —OCH$_2$(cyclopropyl). Included in this embodiment are compounds in which $R_1$ is —CN; and $R_2$ is —CH$_3$.

In one embodiment, a compound of Formula (I) or a salt thereof is provided wherein $R_4$ is —CHR$_{4a}$R$_{4b}$; R$_{4a}$ is phenyl substituted —CF$_3$ or —OCF$_3$; and R$_{4b}$ is —CH$_3$, —CH$_2$CH$_3$, or —CH$_2$CH$_2$CH$_3$. Included in this embodiment are compounds in which $R_1$ is —CN; and $R_2$ is —CH$_3$.

In one embodiment, a compound of Formula (I) or a salt thereof is provided wherein $R_4$ is —CHR$_{4a}$R$_{4b}$; R$_{4a}$ is phenyl substituted —CF$_3$ or —OCF$_3$; and R$_{4b}$ is —CH$_3$. Included in this embodiment are compounds in which $R_1$ is —CN; and $R_2$ is —CH$_3$.

In one embodiment, a compound of Formula (I) or a salt thereof is provided wherein $R_4$ is —CHR$_{4a}$R$_{4b}$; R$_{4a}$ is phenyl substituted —CF$_3$ or —OCF$_3$; and R$_{4b}$ is —CH$_2$CH$_3$. Included in this embodiment are compounds in which $R_1$ is —CN; and $R_2$ is —CH$_3$.

In one embodiment, a compound of Formula (I) or a salt thereof is provided wherein $R_4$ is —CHR$_{4a}$R$_{4b}$; R$_{4a}$ is phenyl substituted —CF$_3$ or —OCF$_3$; and R$_{4b}$ is —CH$_2$CH$_2$CH$_3$. Included in this embodiment are compounds in which $R_1$ is —CN; and $R_2$ is —CH$_3$.

In one embodiment, a compound of Formula (I) or a salt thereof is provided wherein $R_4$ is —CHR$_{4a}$R$_{4b}$; R$_{4a}$ is phenyl substituted with 1 to 2 substituents independently selected from F, Cl, —CF$_3$—OCF$_3$, or —OCH$_2$(cyclopropyl); and R$_{4b}$ is —CH$_3$, —CH$_2$CH$_3$, or —CH$_2$CH$_2$CH$_3$. Included in this embodiment are compounds in which $R_1$ is —CN; and $R_2$ is CH$_3$.

In one embodiment, a compound of Formula (I) or a salt thereof is provided wherein $R_4$ is —CHR$_{4a}$R$_{4b}$; and R$_{4a}$ is pyridinyl. Included in this embodiment are compounds in which $R_1$ is —CN; and $R_2$ is —CH$_3$.

In one embodiment, a compound of Formula (I) or a salt thereof is provided wherein $R_4$ is —CHR$_{4a}$R$_{4b}$; and R$_{4a}$ pyridinyl substituted with —CF$_3$. Included in this embodiment are compounds in which $R_1$ is —CN; and $R_2$ is —CH$_3$.

In one embodiment, a compound of Formula (I) or a salt thereof is provided wherein $R_4$ is —CHR$_{4a}$R$_{4b}$; R$_{4a}$ is pyridinyl; and R$_{4a}$ is phenyl substituted with Cl. Included in this embodiment are compounds in which $R_1$ is —CN; and $R_2$ is —CH$_3$.

In one embodiment, a compound of Formula (I) or a salt thereof is provided wherein $R_4$ is —CHR$_{4a}$R$_{4b}$; R$_{4a}$ is pyridinyl substituted with —CF$_3$; and R$_{4b}$ is phenyl substituted with F. Included in this embodiment are compounds in which $R_1$ is —CN; and $R_2$ is —CH$_3$.

In one embodiment, a compound of Formula (I) or a salt thereof is provided wherein $R_4$ is CHR$_{4a}$R$_{4b}$; one of R$_{4a}$ and R$_{4b}$ is phenyl substituted with F; and the other of R$_{4a}$ and R$_{4b}$ is oxadiazolyl substituted with cyclopropyl. Included in this embodiment are compounds in which $R_1$ is —CN; and $R_2$ is —CH$_3$.

In one embodiment, a compound of Formula (I) or a salt thereof is provided wherein said compound is: 4-((2S,5R)-4-((2,2-difluorobenzo[d][1,3]dioxol-5-yl)methyl)-2,5-diethylpiperazin-1-yl)-1-methyl-2-oxo-1,2-dihydropyrido[3,2-d]pyrimidine-6-carbonitrile (13); 4-((2S,5R)-2,5-diethyl-4-(2-fluoro-4-(trifluoromethoxy)benzyl) piperazin-1-yl)-1-methyl-2-oxo-1,2-dihydropyrido[3,2-d]pyrimidine-6-carbonitrile (27); 4-((2S,5R)-5-ethyl-2-methyl-4-(4-(trifluoromethoxy)benzyl)piperazin-1-yl)-1-methyl-2-oxo-1,2-dihydropyrido[3,2-d]pyrimidine-6-carbonitrile (54); 4-((2S,5R)-((2,2-difluorobenzo[d][1,3]dioxol-5-yl)methyl)-5-ethyl-2-methylpiperazin-1-yl)-1-methyl-2-oxo-1,2-dihydropyrido[3,2-d]pyrimidine-6-carbonitrile (55); 4-((2S,5R)-5-ethyl-4-(2-fluoro-4-(trifluoromethoxy)benzyl)-2-methylpiperazin-1-yl)-1-methyl-2-oxo-1,2-dihydropyrido[3,2-d]pyrimidine-6-carbonitrile (62); 4-((2S,5R)-2,5-dimethyl-4-(3,4,5-trifluorobenzyl)piperazin-1-yl)-1-methyl-2-oxo-1,2-dihydropyrido[3,2-d]pyrimidine-6-carbonitrile (130); 4-((2 S,5R)-4-(3,4-difluorobenzyl)-2,5-dimethylpiperazin-1-yl)-1-methyl-2-oxo-1,2-dihydropyrido[3,2-d]pyrimidine-6-carbonitrile (133); 4-((2S,5R)-4-(2-chloro-4,5-difluorobenzyl)-2,5-dimethylpiperazin-1-yl)-1-methyl-2-oxo-1,2-dihydropyrido[3,2-d]pyrimidine-6-carbonitrile (134); 4-((2S,5R)-4-((2,2-difluorobenzo[d][1,3]dioxol-5-yl)methyl)-2,5-dimethylpiperazin-1-yl)-1-methyl-2-oxo-1,2-dihydropyrido[3,2-d]pyrimidine-6-carbonitrile (135); 4-((2S,5R)-4-(2-chloro-4-fluorobenzyl)-2,5-dimethylpiperazin-1-yl)-1-methyl-2-oxo-1,2-dihydropyrido[3,2-d]pyrimidine-6-carbonitrile (136); 4-((2S,5R)-4-(4-isopropylbenzyl)-2,5-dimethylpiperazin-1-yl)-1-methyl-2-oxo-1,2-dihydropyrido[3,2-d]pyrimidine-6-carbonitrile (137); 4-((2S,5R)-4-(4-(cyclopropylmethoxy)benzyl)-2,5-diethylpiperazin-1-yl)-1-methyl-2-oxo-1,2-dihydropyrido[3,2-d]pyrimidine-6-carbonitrile (185); 4-((2S,5R)-2,5-diethyl-4-(2-fluoro-4-(trifluoromethyl)benzyl)piperazin-1-yl)-1-methyl-2-oxo-1,2-dihydropyrido[3,2-d]pyrimidine-6-carbonitrile (204); 4-((2S,5R)-2,5-diethyl-4-(4-(trifluoromethyl)benzyl) piperazin-1-yl)-1-methyl-2-oxo-1,2-dihydropyrido[3,2-d] pyrimidine-6-carbonitrile (205); 4-((2S,5R)-4-(4-cyclopropyl-2-fluorobenzyl)-2,5-diethylpiperazin-1-yl)-1-methyl-2-oxo-1,2-dihydropyrido[3,2-d]pyrimidine-6-carbonitrile (242); 4-((2S,5R)-4-((4,4-difluorocyclohexyl)methyl)-2,5-diethylpiperazin-1-yl)-1-methyl-2-oxo-1,2-dihydropyrido[3,2-d]pyrimidine-6-carbonitrile (269); or 4-((2S,5R)-4-(4-ethoxybenzyl)-5-ethyl-2-methylpiperazin-1-yl)-1-methyl-2-oxo-1,2-dihydropyrido[3,2-d]pyrimidine-6-carbonitrile (310).

In one embodiment, a compound of Formula (I) or a salt thereof is provided wherein said compound is: 4-((2S,5R)-2,5-diethyl-4-((4-fluorophenyl)(5-(trifluoromethyl) pyridin-2-yl)methyl) piperazin-1-yl)-1-methyl-2-oxo-1,2-dihydropyrido[3,2-d] pyrimidine-6-carbonitrile (1-2); 4-((2S,5R)-2,5-diethyl-4-((4-fluorophenyl)(isoxazol-3-yl) methyl) piperazin-1-yl)-1-methyl-2-oxo-1,2-dihydropyrido[3,2-d] pyrimidine-6-carbonitrile (34-35); 4-((2S,5R)-4-((5-cyclopropylisoxazol-3-yl)(4-(trifluoromethoxy) phenyl) methyl)-2,5-diethylpiperazin-1-yl)-1-methyl-2-oxo-1,2-dihydropyrido[3,2-d] pyrimidine-6-carbonitrile (42-43); 4-((2S,5R)-5-ethyl-4-((4-fluorophenyl)(5-(trifluoromethyl) pyridin-2-yl)methyl)-2-methylpiperazin-1-yl)-1-methyl-2-oxo-1,2-dihydropyrido[3,2-d]pyrimidine-6-carbonitrile (46-47); 4-((2S,5R)-4-((4-cyclopropylthiazol-2-yl)(4-fluorophenyl)methyl)-5-ethyl-2-methylpiperazin-1-yl)-1-methyl-2-oxo-1,2-dihydropyrido[3,2-d]pyrimidine-6-carbonitrile (50-51); 4-((2S,5R)-5-ethyl-4-((4-fluorophenyl) (6-(trifluoromethyl)pyridin-2-yl)methyl)-2-methylpiperazin-1-yl)-1-methyl-2-oxo-1,2-dihydropyrido

[3,2-d]pyrimidine-6-carbonitrile (65-66); 4-((2S,5R)-5-ethyl-4-((4-fluorophenyl)(isoxazol-3-yl)methyl)-2-methylpiperazin-1-yl)-1-methyl-2-oxo-1,2-dihydropyrido[3,2-d]pyrimidine-6-carbonitrile (73-74); 4-((2 S,5R)-4-((5-cyclopropylpyridin-2-yl)(4-fluorophenyl)methyl)-5-ethyl-2-methylpiperazin-1-yl)-1-methyl-2-oxo-1,2-dihydropyrido[3,2-d]pyrimidine-6-carbonitrile (75-76); 4-((2S,5R)-5-ethyl-4-((4-fluorophenyl)(pyridin-2-yl)methyl)-2-methylpiperazin-1-yl)-1-methyl-2-oxo-1,2-dihydropyrido[3,2-d]pyrimidine-6-carbonitrile (87-88); 4-((2S,5R)-5-ethyl-2-methyl-4-(pyridin-2-yl(4-(trifluoromethoxy)phenyl)methyl)piperazin-1-yl)-1-methyl-2-oxo-1,2-dihydropyrido[3,2-d]pyrimidine-6-carbonitrile (93-94); 4-((2S,5R)-4-((4-chlorophenyl) (pyridin-2-yl)methyl)-5-ethyl-2-methylpiperazin-1-yl)-1-methyl-2-oxo-1,2-dihydropyrido[3,2-d]pyrimidine-6-carbonitrile (95-96); 4-((2S,5R)-5-ethyl-4-((4-fluorophenyl)(6-(trifluoromethyl)pyridin-3-yl)methyl)-2-methylpiperazin-1-yl)-1-methyl-2-oxo-1,2-dihydropyrido[3,2-d]pyrimidine-6-carbonitrile (97-98); 4-((2S,5R)-4-((5-cyclopropylisoxazol-3-yl)(4-(trifluoromethoxy)phenyl)methyl)-5-ethyl-2-methylpiperazin-1-yl)-1-methyl-2-oxo-1,2-dihydropyrido[3,2-d]pyrimidine-6-carbonitrile (99-100); 4-((2S,5R)-4-((5-cyclopropylisoxazol-3-yl)(4-fluorophenyl)methyl)-5-ethyl-2-methylpiperazin-1-yl)-1-methyl-2-oxo-1,2-dihydropyrido[3,2-d]pyrimidine-6-carbonitrile (101-102); 4-((2S,5R)-4-((2-cyclopropylthiazol-5-yl)(4-fluorophenyl)methyl)-5-ethyl-2-methylpiperazin-1-yl)-1-methyl-2-oxo-1,2-dihydropyrido[3,2-d]pyrimidine-6-carbonitrile (103-104); 6-chloro-4-((2S,5R)-4-((3-cyclopropyl-1,2,4-oxadiazol-5-yl)(4-fluorophenyl) methyl)-2,5-dimethylpiperazin-1-yl)-1-methylpyrido[3,2-d]pyrimidin-2(1H)-one (105); 4-((2 S,5R)-4-((3-cyclopropyl-1,2,4-oxadiazol-5-yl)(4-fluorophenyl)methyl)-2,5-dimethylpiperazin-1-yl)-1-methyl-2-oxo-1,2-dihydropyrido[3,2-d]pyrimidine-6-carbonitrile (106-107); 4-((2 S,5R)-4-((3-(tert-butyl)-1,2,4-oxadiazol-5-yl)(4-fluorophenyl)methyl)-2,5-dimethylpiperazin-1-yl)-1-methyl-2-oxo-1,2-dihydropyrido[3,2-d]pyrimidine-6-carbonitrile (108-109); 4-((2S,5R)-4-((3-cyclopropyl-1,2,4-oxadiazol-5-yl)(4-fluorophenyl)methyl)-2,5-dimethylpiperazin-1-yl)-1-methyl-2-oxo-1,2-dihydropyrido[3,2-d]pyrimidine-6-carbonitrile (110-111); 4-((2S,5R)-4-((3-cyclopropyl-1,2,4-oxadiazol-5-yl)(4-fluorophenyl)methyl)-5-ethyl-2-methylpiperazin-1-yl)-1-methyl-2-oxo-1,2-dihydropyrido[3,2-d]pyrimidine-6-carbonitrile (112-113); 4-((2S,5R)-2-ethyl-4-((4-fluorophenyl)(5-(trifluoromethyl)pyridin-2-yl)methyl)-5-methylpiperazin-1-yl)-1-methyl-2-oxo-1,2-dihydropyrido[3,2-d]pyrimidine-6-carbonitrile (114-115); 4-((2S,5R)-2-ethyl-4-((4-fluorophenyl)(6-(trifluoromethyl)pyridin-2-yl) methyl)-5-methylpiperazin-1-yl)-1-methyl-2-oxo-1,2-dihydropyrido[3,2-d]pyrimidine-6-carbonitrile (120-121); 4-((2S,5R)-4-(bis(4-fluorophenyl)methyl)-2,5-dimethylpiperazin-1-yl)-1-methyl-2-oxo-1,2-dihydropyrido[3,2-d]pyrimidine-6-carbonitrile (124-125); 4-((2S,5R)-4-((4-fluorophenyl)(5-(trifluoromethyl)pyridin-2-yl)methyl)-2,5-dimethylpiperazin-1-yl)-1-methyl-2-oxo-1,2-dihydropyrido[3,2-d]pyrimidine-6-carbonitrile (126-127); 4-((2S,5R)-4-((4-cyclopropylthiazol-2-yl)(4-fluorophenyl) methyl)-2,5-dimethylpiperazin-1-yl)-1-methyl-2-oxo-1,2-dihydropyrido[3,2-d] pyrimidine-6-carbonitrile (158-159); 4-((2S,5R)-4-((4-fluorophenyl)(isoxazol-3-yl) methyl)-2,5-dimethylpiperazin-1-yl)-1-methyl-2-oxo-1,2-dihydropyrido[3,2-d] pyrimidine-6-carbonitrile (162-163); 4-((2S,5R)-4-((5-cyclopropylisoxazol-3-yl)-4-(trifluoromethoxy)phenyl) methyl)-2,5-dimethylpiperazin-1-yl)-1-methyl-2-oxo-1,2-dihydropyrido[3,2-d]pyrimidine-6-carbonitrile (164-165); 4-((2S,5R)-4-((4-fluorophenyl) (2-(trifluoromethyl)thiazol-4-yl)methyl)-2,5-dimethylpiperazin-1-yl)-1-methyl-2-oxo-1,2-dihydropyrido[3,2-d]pyrimidine-6-carbonitrile (170-171); 4-((2S,5S)-4-((4-fluorophenyl) (5-(trifluoromethyl)pyridin-2-yl)methyl)-5-(methoxymethyl)-2-methylpiperazin-1-yl)-1-methyl-2-oxo-1,2-dihydropyrido[3,2-d]pyrimidine-6-carbonitrile (178-179); 6-chloro-4-((2S,5S)-4-((4-fluorophenyl)(5-(trifluoromethyl)pyridin-2-yl)methyl)-5-(hydroxymethyl)-2-methylpiperazin-1-yl)-1-methylpyrido[3,2-d]pyrimidin-2(1H)-one (180); 4-((2 S,5 S)-4-((4-fluorophenyl)(5-(trifluoromethyl)pyridin-2-yl)methyl)-5-(hydroxymethyl)-2-methylpiperazin-1-yl)-1-methyl-2-oxo-1,2-dihydropyrido[3,2-d] pyrimidine-6-carbonitrile (181-182); 4-((2S,5R)-2,5-diethyl-4-((4-fluorophenyl)(2-(trifluoromethyl) thiazol-4-yl)methyl) piperazin-1-yl)-1-methyl-2-oxo-1,2-dihydropyrido[3,2-d] pyrimidine-6-carbonitrile (210-211); 4-((2S,5R)-4((6-(difluoromethyl)pyridin-2-yl)(4-fluorophenyl) methyl)-2,5-diethylpiperazin-1-yl)-1-methyl-2-oxo-1,2-dihydropyrido[3,2-d]pyrimidine-6-carbonitrile (257-258); 4-((2S,5R)-4-((3-bromo-1-methyl-1H-1,2,4-triazol-5-yl)(4-fluorophenyl) methyl)-2,5-diethylpiperazin-1-yl)-1-methyl-2-oxo-1,2-dihydropyrido[3,2-d]pyrimidine-6-carbonitrile (293); 4-(2S,5R)-4-((3-cyclopropyl-1-methyl-1H-1,2,4-triazol-5-yl)(4-fluorophenyl)methyl)-2,5-diethylpiperazin-1-yl)-1-methyl-2-oxo-1,2-dihydropyrido[3,2-d]pyrimidine-6-carbonitrile (294-295); 4-((2S,5R)-5-ethyl-4-((4-fluorophenyl)(2-(trifluoromethyl)thiazol-4-yl)methyl)-2-methylpiperazin-1-yl)-1-methyl-2-oxo-1,2-dihydropyrido[3,2-d]pyrimidine-6-carbonitrile (296-297); 4-((2 S,5R)-4-((6-(difluoromethyl) pyridin-2-yl)(4-fluorophenyl)methyl)-5-ethyl-2-methylpiperazin-1-yl)-1-methyl-2-oxo-1,2-dihydropyrido[3,2-d]pyrimidine-6-carbonitrile (315-316); 6-chloro-4-((2S,5R)-4-((5-cyclopropyl-1,2,4-oxadiazol-3-yl)(4-fluorophenyl)methyl)-2,5-diethylpiperazin-1-yl)-1-methylpyrido[3,2-d]pyrimidin-2(1H)-one (370); 4-((2S,5R)-4-((5-cyclopropyl-1,2,4-oxadiazol-3-yl)(4-fluorophenyl)methyl)-2,5-diethylpiperazin-1-yl)-1-methyl-2-oxo-1,2-dihydropyrido[3,2-d]pyrimidine-6-carbonitrile (371-372); 4-((2 S, 5R)-4-(bis(4-chlorophenyl)methyl)-2,5-dimethylpiperazin-1-yl)-1-methyl-2-oxo-1,2-dihydropyrido[3,2-d]pyrimidine-6-carbonitrile (373-374); 4-((2S,5R)-4-((4-cyanophenyl)(4-fluorophenyl)methyl)-2,5-dimethylpiperazin-1-yl)-1-methyl-2-oxo-1,2-dihydropyrido[3,2-d]pyrimidine-6-carbonitrile (375); or 4-((2S,5R)-4-((4-fluorophenyl)(3-(trifluoromethyl)bicyclo[1.1.1]pentan-1-yl) methyl)-2,5-dimethylpiperazin-1-yl)-1-methyl-2-oxo-1,2-dihydropyrido[3,2-d]pyrimidine-6-carbonitrile (450-452).

In one embodiment, a compound of Formula (I) or a salt thereof is provided wherein said compound is: 4-((2S,5R)-4-(1-(4-cyclopropylphenyl)ethyl)-2,5-dimethylpiperazin-1-yl)-1-methyl-2-oxo-1,2-dihydropyrido[3,2-d]pyrimidine-6-carbonitrile (3-4); 4-((2S,5R)-2,5-diethyl-4-(1-(4-(trifluoromethyl)phenyl)propyl) piperazin-1-yl)-1-methyl-2-oxo-1,2-dihydropyrido[3,2-d]pyrimidine-6-carbonitrile (5-6); 4-((2 S, 5R)-5-ethyl-2-methyl-4-(1-(4-(trifluoromethyl)phenyl)ethyl)piperazin-1-yl)-1-methyl-2-oxo-1,2-dihydropyrido[3,2-d]pyrimidine-6-carbonitrile (7-8); 4-((2S, 5R)-2,5-diethyl-4-(1-(4-(trifluoromethoxy)phenyl)ethyl) piperazin-1-yl)-1-methyl-2-oxo-1,2-dihydropyrido[3,2-d] pyrimidine-6-carbonitrile (9-10); 4-((2S,5R)-2,5-diethyl-4-(1-(2-fluoro-4-methoxyphenyl)propyl)piperazin-1-yl)-1-methyl-2-oxo-1,2-dihydropyrido[3,2-d]pyrimidine-6-carbonitrile (11-12); 4-((2S,5R)-4-(1-(2,2-difluorobenzo[d][1,3]dioxol-5-yl)ethyl)-2,5-diethylpiperazin-1-yl)-1-methyl-2-oxo-1,2-dihydropyrido[3,2-d]pyrimidine-6-carbonitrile (14-15); 4-((2S,5R)-2,5-diethyl-4-(1-(4-methoxyphenyl)ethyl)piperazin-1-yl)-1-methyl-2-oxo-1,2- dihydropyrido[3,2-d]pyrimidine-6-carbonitrile (16-17); 4-((2S,5R)-2,5-diethyl-4-(1-(4-isopropoxyphenyl)ethyl)piperazin-1-yl)-1-methyl-2-oxo-1,2-dihydropyrido[3,2-d]pyrimidine-6-carbonitrile (18-19); 4-((2S,5R)-2,5-diethyl-4-(1-(4-(trifluoromethyl)phenyl)ethyl)piperazin-1-yl)-1-methyl-2-oxo-1,2-dihydropyrido[3,2-d] pyrimidine-6-carbonitrile (20-21); 4-((2S,5R)-2,5-diethyl-4-(4-(trifluoromethoxy)benzyl) piperazin-1-yl)-1-methyl-2-oxo-1,2-dihydropyrido[3,2-d]pyrimidine-6-carbonitrile (22); 4-((2S,5R)-4-(1-(4-(cyclopropylmethoxy)phenyl)ethyl)-2,5-diethylpiperazin-1-yl)-1-methyl-2-oxo-1,2-dihydropyrido[3,2-d]pyrimidine-6-carbonitrile (23-24); 4-((2 S,5R)-2,5-diethyl-4-(1-(2-fluoro-4-(trifluoromethyl)phenyl)ethyl) piperazin-1-yl)-1-methyl-2-oxo-1,2-dihydropyrido[3,2-d] pyrimidine-6-carbonitrile (25-26); 4-((2S,5R)-4-(1-(4-cyclopropylphenyl)ethyl)-2,5-diethylpiperazin-1-yl)-1-methyl-2-oxo-1,2-dihydropyrido[3,2-d]pyrimidine-6-carbonitrile (28-29); 4-((2S,5R)-2,5-diethyl-4-(1-(3-fluoro-4-(trifluoromethoxy)phenyl)ethyl)piperazin-1-yl)-1-methyl-2-oxo-1,2-dihydropyrido[3,2-d]pyrimidine-6-carbonitrile (30-31); 4-((2S,5R)-4-(1-(4-(cyclopropylmethoxy)-2-fluorophenyl)ethyl)-2,5-diethylpiperazin-1-yl)-1-methyl-2-oxo-1,2-dihydropyrido[3,2-d]pyrimidine-6-carbonitrile (32-33); 4-((2 S,5R)-2,5-diethyl-4-(1-(4-(trifluoromethoxy)phenyl) propyl)piperazin-1-yl)-1-methyl-2-oxo-1,2-dihydropyrido [3,2-d]pyrimidine-6-carbonitrile (36-37); 4-((2S,5R)-2,5-diethyl-4-(1-(2-fluoro-4-(trifluoromethoxy)phenyl)ethyl) piperazin-1-yl)-1-methyl-2-oxo-1,2-dihydropyrido[3,2-d] pyrimidine-6-carbonitrile (38-39); 4-((2S,5R)-4-(1-(4-cyclopropyl-2-fluorophenyl)ethyl)-2,5-diethylpiperazin-1-yl)-1-methyl-2-oxo-1,2-dihydropyrido[3,2-d]pyrimidine-6-carbonitrile (40-41); 4-((2S,5R)-2,5-diethyl-4-(1-(6-(trifluoromethyl) pyridin-3-yl)ethyl)piperazin-1-yl)-1-methyl-2-oxo-1,2-dihydropyrido[3,2-d]pyrimidine-6-carbonitrile (44-45); 4-((2S,5R)-5-ethyl-2-methyl-4-(1-(4-(trifluoromethoxy)phenyl) ethyl)piperazin-1-yl)-1-methyl-2-oxo-1,2-dihydropyrido[3,2-d]pyrimidine-6-carbonitrile (48-49); 4-((2S,5R)-5-ethyl-4-(1-(4-isopropoxyphenyl)ethyl)-2-methylpiperazin-1-yl)-1-methyl-2-oxo-1,2-dihydropyrido[3,2-d]pyrimidine-6-carbonitrile (52-53); 4-((2S, 5R)-5-ethyl-4-(1-(4-methoxyphenyl)ethyl)-2-methylpiperazin-1-yl)-1-methyl-2-oxo-1,2-dihydropyrido [3,2-d]pyrimidine-6-carbonitrile (56-57); 4-((2S,5R)-5-ethyl-4-(1-(2-fluoro-4-(trifluoromethyl)phenyl)ethyl)-2-methylpiperazin-1-yl)-1-methyl-2-oxo-1,2-dihydropyrido [3,2-d]pyrimidine-6-carbonitrile (58-59); 4-((2S,5R)-4-(1-(4-cyanophenyl) ethyl)-5-ethyl-2-methylpiperazin-1-yl)-1-methyl-2-oxo-1,2-dihydropyrido[3,2-d] pyrimidine-6-carbonitrile (60-61); 4-((2S,5R)-4-(1-(4-cyclopropylphenyl) ethyl)-5-ethyl-2-methylpiperazin-1-yl)-1-methyl-2-oxo-1,2-dihydropyrido[3,2-d]pyrimidine-6-carbonitrile (63-64); 4-((2S,5R)-4-(1-(4-(cyclopropylmethoxy)phenyl)ethyl)-5-ethyl-2-methylpiperazin-1-yl)-1-methyl-2-oxo-1,2-dihydropyrido[3,2-d]pyrimidine-6-carbonitrile (67-68); 4-((2S,5R)-4-(1-(4-(cyclopropylmethoxy)-2-fluorophenyl)ethyl)-5-ethyl-2-methylpiperazin-1-yl)-1-methyl-2-oxo-1,2-dihydropyrido[3,2-d]pyrimidine-6-carbonitrile (69-70); 4-((2S,5R)-4-(1-(2,2-difluorobenzo[d][1,3]dioxol-5-yl) ethyl)-5-ethyl-2-methylpiperazin-1-yl)-1-methyl-2-oxo-1,2-dihydropyrido[3,2-d]pyrimidine-6-carbonitrile (71-72); 4-((2S,5R)-4-(1-(4-(difluoromethoxy)phenyl)propyl)-5-ethyl-2-methylpiperazin-1-yl)-1-methyl-2-oxo-1,2-dihydropyrido[3,2-d]pyrimidine-6-carbonitrile (77-78); 4-((2S,5R)-4-(1-(2,2-difluorobenzo[d][1,3]dioxol-5-yl)propyl)-5-ethyl-2-methylpiperazin-1-yl)-1-methyl-2-oxo-1,2-dihydropyrido[3,2-d]pyrimidine-6-carbonitrile (79-80); 4-((2S,5R)-5-ethyl-4-(1-(2-fluoro-4-(trifluoromethoxy)phenyl)ethyl)-2-methylpiperazin-1-yl)-1-methyl-2-oxo-1,2-dihydropyrido [3,2-d]pyrimidine-6-carbonitrile (81-82); 4-((2S,5R)-5-ethyl-2-methyl-4-(1-(4-(trifluoromethoxy)phenyl)propyl) piperazin-1-yl)-1-methyl-2-oxo-1,2-dihydropyrido[3,2-d] pyrimidine-6-carbonitrile (83-84); 4-((2S,5R)-5-ethyl-4-(1-(2-fluoro-4-(trifluoromethoxy)phenyl)propyl)-2-methylpiperazin-1-yl)-1-methyl-2-oxo-1,2-dihydropyrido [3,2-d]pyrimidine-6-carbonitrile (85-86); 4-((2S,5R)-5-ethyl-2-methyl-4-(1-(4-(trifluoromethyl)phenyl)propyl) piperazin-1-yl)-1-methyl-2-oxo-1,2-dihydropyrido[3,2-d] pyrimidine-6-carbonitrile (89-90); 4-((2S,5R)-4-(1-(4-cyclopropyl-2-fluorophenyl)ethyl)-5-ethyl-2-methylpiperazin-1-yl)-1-methyl-2-oxo-1,2-dihydropyrido [3,2-d]pyrimidine-6-carbonitrile (91-92); 4-((2S,5R)-2-ethyl-5-methyl-4-(1-(4-(trifluoromethyl)phenyl)ethyl) piperazin-1-yl)-1-methyl-2-oxo-1,2-dihydropyrido[3,2-d] pyrimidine-6-carbonitrile (116-117); 4-((2S,5R)-2-ethyl-4-(1-(2-fluoro-4-(trifluoromethyl)phenyl)ethyl)-5-methylpiperazin-1-yl)-1-methyl-2-oxo-1,2-dihydropyrido [3,2-d]pyrimidine-6-carbonitrile (118-119); 4-((2S,5R)-2-ethyl-5-methyl-4-(1-(4-(trifluoromethoxy)phenyl)ethyl) piperazin-1-yl)-1-methyl-2-oxo-1,2-dihydropyrido[3,2-d] pyrimidine-6-carbonitrile (122-123); 4-((2S,5R)-4-(1-(4-fluorophenyl)ethyl)-2,5-dimethylpiperazin-1-yl)-1-methyl-2-oxo-1,2-dihydropyrido[3,2-d]pyrimidine-6-carbonitrile (128-129); 4-((2S,5R)-2,5-dimethyl-4-(1-(4-(trifluoromethoxy)phenyl)ethyl)piperazin-1-yl)-1-methyl-2-oxo-1,2-dihydropyrido[3,2-d]pyrimidine-6-carbonitrile (131-132); 4-((2S,5R)-2,5-dimethyl-4-(1-(3,4,5-trifluorophenyl)ethyl) piperazin-1-yl)-1-methyl-2-oxo-1,2-dihydropyrido[3,2-d] pyrimidine-6-carbonitrile (138-139); 4-((2S,5R)-2,5-dimethyl-4-(1-(4-(trifluoromethyl) phenyl)ethyl)piperazin-1-yl)-1-methyl-2-oxo-1,2-dihydropyrido[3,2-d]pyrimidine-6-carbonitrile (140-141); 4-((2S,5R)-4-(1-(2-fluoro-4-(trifluoromethoxy)phenyl)ethyl)-2,5-dimethylpiperazin-1-yl)-1-methyl-2-oxo-1,2-dihydropyrido[3,2-d]pyrimidine-6-carbonitrile (142-143); 4-((2S,5R)-4-(1-(2,4-difluorophenyl)ethyl)-2,5-dimethylpiperazin-1-yl)-1-methyl-2-oxo-1,2-dihydropyrido[3,2-d]pyrimidine-6-carbonitrile (144-145); 4-((2S,5R)-4-(1-(4-chloro-2-fluorophenyl)ethyl)-2,5-dimethylpiperazin-1-yl)-1-methyl-2-oxo-1,2-dihydropyrido[3,2-d]pyrimidine-6-carbonitrile (146-147); 4-((2 S,5R)-4-(1-(3,4-difluorophenyl)ethyl)-2,5-dimethylpiperazin-1-yl)-1-methyl-2-oxo-1,2-dihydropyrido [3,2-d]pyrimidine-6-carbonitrile (148-149); 4-((2S,5R)-4-(1-(2-fluoro-4-(trifluoromethyl)phenyl)ethyl)-2,5-dimethylpiperazin-1-yl)-1-methyl-2-oxo-1,2-dihydropyrido [3,2-d]pyrimidine-6-carbonitrile (150-151); 4-((2S,5R)-4-(1-(2-fluoro-4-(trifluoromethoxy)phenyl)propyl)-2,5-dimethylpiperazin-1-yl)-1-methyl-2-oxo-1,2-dihydropyrido [3,2-d]pyrimidine-6-carbonitrile (152-153); 4-((2 S,5R)-2,5-dimethyl-4-(1-(4-(trifluoromethoxy)phenyl)propyl) piperazin-1-yl)-1-methyl-2-oxo-1,2-dihydropyrido[3,2-d] pyrimidine-6-carbonitrile (154-155); 4-((2S,5R)-4-(1-(4-(difluoromethoxy)phenyl)ethyl)-2,5-dimethylpiperazin-1-yl)-1-methyl-2-oxo-1,2-dihydropyrido[3,2-d]pyrimidine-6-carbonitrile (156-157); 4-((2 S,5R)-4-(1-(3-fluoro-4-(trifluoromethoxy)phenyl)ethyl)-2,5-dimethylpiperazin-1-yl)-1-methyl-2-oxo-1,2-dihydropyrido[3,2-d]pyrimidine-6-carbonitrile (160-161); 4-((2S,5R)-4-(1-(2,2-difluorobenzo [d][1,3]dioxol-5-yl)ethyl)-2,5-dimethylpiperazin-1-yl)-1-methyl-2-oxo-1,2-dihydropyrido[3,2-d]pyrimidine-6-carbonitrile (166-167); 4-((2S,5R)-4-(1-(4-cyclopropyl-2-fluorophenyl)ethyl)-2,5-dimethylpiperazin-1-yl)-1-methyl-2-oxo-1,2-dihydropyrido[3,2-d]pyrimidine-6-carbonitrile (168-169); 6-chloro-4-((2 S,5 S)-5-(hydroxymethyl)-2-methyl-4-(1-(4-(trifluoromethyl)phenyl)ethyl) piperazin-1- yl)-1-methylpyrido[3,2-d]pyrimidin-2(1H)-one (172); 6-chloro-4-((2S,5 S)-5-(methoxymethyl)-2-methyl-4-(1-(4-(trifluoromethyl)phenyl)ethyl) piperazin-1-yl)-1-methylpyrido[3,2-d]pyrimidin-2(1H)-one (173); 4-((2S,5S)-5-(methoxymethyl)-2-methyl-4-(1-(4-(trifluoromethyl) phenyl)ethyl)piperazin-1-yl)-1-methyl-2-oxo-1,2-dihydropyrido[3,2-d]pyrimidine-6-carbonitrile (174-175); 4-((2S,5 S)-5-(methoxymethyl)-2-methyl-4-(1-(4-(trifluoromethoxy)phenyl)ethyl)piperazin-1-yl)-1-methyl-2-oxo-1,2-dihydropyrido[3,2-d]pyrimidine-6-carbonitrile (176-177); 4-((2S,5 S)-5-(hydroxymethyl)-2-methyl-4-(1-(4-(trifluoromethoxy)phenyl)ethyl)piperazin-1-yl)-1-methyl-2-oxo-1,2-dihydropyrido[3,2-d]pyrimidine-6-carbonitrile (183-184); 6-chloro-4-((2S,5R)-2,5-diethyl-4-(1-(4-((1-hydroxy-2-methylpropan-2-yl)oxy)phenyl)ethyl)piperazin-1-yl)-1-methylpyrido[3,2-d]pyrimidin-2(1H)-one (186); 6-chloro-4-((2S,5R)-2,5-diethyl-4-(1-(4-((1-methoxy-2-methylpropan-2-yl)oxy)phenyl)ethyl)piperazin-1-yl)-1-methylpyrido[3,2-d]pyrimidin-2(1H)-one (187); 6-chloro-4-((2S,5R)-2,5-diethyl-4-(1-(4-((1-methoxy-2-methylpropan-2- yl)oxy) phenyl)ethyl)piperazin-1-yl)-1-methylpyrido[3,2-d] pyrimidin-2(1H)-one (188-189); 4-((2S,5R)-2,5-diethyl-4-(1-(4-(methoxy-$d_3$)phenyl)ethyl)piperazin-1-yl)-1-methyl-2-oxo-1,2-dihydropyrido[3,2-d]pyrimidine-6-carbonitrile (190-191); 4-((2 S,5R)-4-(1-(6-cyclopropylpyridin-3-yl) ethyl)-2,5-diethylpiperazin-1-yl)-1-methyl-2-oxo-1,2-dihydropyrido[3,2-d]pyrimidine-6-carbonitrile (192-193); 4-((2S,5R)-2,5-diethyl-4-(1-(2-morpholino-4-(trifluoromethyl)phenyl)ethyl)piperazin-1-yl)-1-methyl-2-oxo-1,2-dihydropyrido[3,2-d]pyrimidine-6-carbonitrile (194-195); 4-((2S,5R)-4-(1-(4-(2-cyanopropan-2-yl)phenyl)ethyl)-2,5-diethylpiperazin-1-yl)-1-methyl-2-oxo-1,2-dihydropyrido[3,2-d]pyrimidine-6-carbonitrile (196-197); 4-((2S,5R)-4-(1-(4-(cyclopropylmethoxy)-2-fluorophenyl)propyl)-2,5-diethylpiperazin-1-yl)-1-methyl-2-oxo-1,2-dihydropyrido[3,2-d]pyrimidine-6-carbonitrile (198-199); 4-((2S,5R)-4-(1-(4-cyclopropylphenyl)propyl)-2,5-diethylpiperazin-1-yl)-1-methyl-2-oxo-1,2-dihydropyrido[3,2-d]pyrimidine-6-carbonitrile (200-201); 4-((2S,5R)-2,5-diethyl-4-(1-(3-methyl-2-oxo-2,3-dihydrobenzo[d]oxazol-5-yl)ethyl) piperazin-1-yl)-1-methyl-2-oxo-1,2-dihydropyrido[3,2-d] pyrimidine-6-carbonitrile (202-203); 4-((2S,5R)-2,5-diethyl-4-(1-(2-morpholinopyrimidin-5-yl)ethyl)piperazin-1-yl)-1-methyl-2-oxo-1,2-dihydropyrido[3,2-d] pyrimidine-6-carbonitrile (206-207); 4-((2S,5R)-2,5-diethyl-4-(1-(4-(methoxy-$d_3$) phenyl)propyl)piperazin-1-yl)-1-methyl-2-oxo-1,2-dihydropyrido[3,2-d]pyrimidine-6-carbonitrile (208-209); 4-((2S,5R)-2,5-diethyl-4-(1-(4-methoxyphenyl) propyl)piperazin-1-yl)-1-methyl-2-oxo-1,2-dihydropyrido [3,2-d]pyrimidine-6-carbonitrile (212-213); 4-((2S,5R)-2,5-diethyl-4-(1-(6-methoxypyridin-2-yl)ethyl)piperazin-1-yl)-1-methyl-2-oxo-1,2-dihydropyrido[3,2-d]pyrimidine-6-carbonitrile (214-215); 4-((2S,5R)-4-(1-(4-(cyclopropylmethoxy)phenyl)propyl)-2,5-diethylpiperazin-1-yl)-1-methyl-2-oxo-1,2-dihydropyrido[3,2-d]pyrimidine-6-carbonitrile (216-217); 4-((2S,5R)-2,5-diethyl-4-(1-(4-(1-methylcyclopropyl)phenyl)ethyl)piperazin-1-yl)-1-methyl-2-oxo-1,2-dihydropyrido[3,2-d]pyrimidine-6-carbonitrile (218-219); 4-((2S,5R)-4-(1-(4-cyanophenyl)propyl)-2,5-diethylpiperazin-1-yl)-1-methyl-2-oxo-1,2-dihydropyrido[3,2-d] pyrimidine-6-carbonitrile (220-221); 4-((2S,5R)-4-(1-(4-(difluoromethoxy)phenyl) propyl)-2,5-diethylpiperazin-1-yl)-1-methyl-2-oxo-1,2-dihydropyrido[3,2-d]pyrimidine-6-carbonitrile (222-223); 4-((2S,5R)-2,5-diethyl-4-(1-(6-(trifluoromethyl)pyridin-3-yl) propyl)piperazin-1-yl)-1-methyl-2-oxo-1,2-dihydropyrido[3,2-d]pyrimidine-6-carbonitrile (224-225); 4-((2S,5R)-2,5-diethyl-4-(1-(2-(trifluoromethyl)pyrimidin-5-yl)ethyl) piperazin-1-yl)-1-methyl-2-oxo-1,2-dihydropyrido[3,2-d]pyrimidine-6-carbonitrile (226-227); 4-((2S,5R)-2,5-diethyl-4-(1-(6-methylpyrimidin-3-yl)ethyl)piperazin-1-yl)-1-methyl-2-oxo-1,2-dihydropyrido[3,2-d]pyrimidine-6-carbonitrile (228-229); 4-((2S,5R)-2,5-diethyl-4-(1-(4-(2-oxopyrrolidin-1-yl)phenyl)ethyl)piperazin-1-yl)-1-methyl-2-oxo-1,2-dihydropyrido[3,2-d]pyrimidine-6-carbonitrile (230-231); 4-((2S,5R)-4-(1-(4-(difluoromethoxy)-2-fluorophenyl)propyl)-2,5-diethylpiperazin-1-yl)-1-methyl-2-oxo-1,2-dihydropyrido[3,2-d]pyrimidine-6-carbonitrile (232-233); 4-((2S,5R)-2,5-diethyl-4-(1-(4-isopropoxyphenyl)propyl)piperazin-1-yl)-1-methyl-2-oxo-1,2-dihydropyrido[3,2-d] pyrimidine-6-carbonitrile (234-235); 4-((2S,5R)-2,5-diethyl-4-(1-(p-tolyl) propyl) piperazin-1-yl)-1-methyl-2-oxo-1,2-dihydropyrido [3,2-d]pyrimidine-6-carbonitrile (236-237); 4-((2S,5R)-4-(1-(4-chloro-2-fluorophenyl)propyl)-2,5-diethylpiperazin-1-yl)-1-methyl-2-oxo-1,2-dihydropyrido[3,2-d]pyrimidine-6-carbonitrile (238-239); 4-((2S,5R)-4-(1-(6-(difluoromethoxy)pyridin-2-yl)ethyl)-2,5-diethylpiperazin-1-yl)-1-methyl-2-oxo-1,2-dihydropyrido[3,2-d]pyrimidine-6-carbonitrile (240-241); 4-((2S,5R)-2,5-diethyl-4-(1-(4-(trifluoromethyl)phenyl)butyl)piperazin-1-yl)-1-methyl-2-oxo-1,2-dihydropyrido[3,2-d]pyrimidine-6-carbonitrile (243-244); 4-((2S,5R)-2,5-diethyl-4-(1-(6-(trifluoromethoxy)pyridin-2-yl)ethyl)piperazin-1-yl)-1-methyl-2-oxo-1,2-dihydropyrido[3,2-d]pyrimidine-6-carbonitrile (245-246); 4-((2S,5R)-2,5-diethyl-4-(1-(4-(2-morpholinopropan-2-yl)phenyl)ethyl)piperazin-1-yl)-1-methyl-2-oxo-1,2-dihydropyrido[3,2-d]pyrimidine-6-carbonitrile (247-248); 4-((2S,5R)-2,5-diethyl-4-(1-(4-methoxyphenyl)-2-methylpropyl)piperazin-1-yl)-1-methyl-2-oxo-1,2-dihydropyrido[3,2-d]pyrimidine-6-carbonitrile (249-250); 4-((2S,5R)-4-(1-(4-(2-cyanopropan-2-yl)phenyl) propyl)-2,5-diethylpiperazin-1-yl)-1-methyl-2-oxo-1,2-dihydropyrido [3,2-d]pyrimidine-6-carbonitrile (251-252); 4-((2S,5R)-4-(1-(2-cyclopropylbenzo[d]oxazol-5-yl)ethyl)-2,5-diethylpiperazin-1-yl)-1-methyl-2-oxo-1,2-dihydropyrido [3,2-d]pyrimidine-6-carbonitrile (253-254); 4-((2S,5R)-4-(1-(4-cyclopropoxyphenyl)propyl)-2,5-diethylpiperazin-1-yl)-1-methyl-2-oxo-1,2-dihydropyrido[3,2-d]pyrimidine-6-carbonitrile (255-256); ethyl (1S,2S)-2-(4-(1-((2R,5S)-4-(6-cyano-1-methyl-2-oxo-1,2-dihydropyrido[3,2-d]pyrimidin-4-yl)-2,5-diethylpiperazin-1-yl)ethyl)phenoxy) cyclopropane-1-carboxylate (259-260); 4-((2S,5R)-2,5-diethyl-4-(1-(4-isopropoxyphenyl)-2-methylpropyl) piperazin-1-yl)-1-methyl-2-oxo-1,2-dihydropyrido[3,2-d] pyrimidine-6-carbonitrile (261-262); 4-((2S,5R)-4-(1-(4-(1-cyanocyclopropyl)phenyl)ethyl)-2,5-diethylpiperazin-1-yl)-1-methyl-2-oxo-1,2-dihydropyrido[3,2-d]pyrimidine-6-carbonitrile (263-264); methyl 4-(1-((2R,5S)-4-(6-cyano-1-methyl-2-oxo-1,2-dihydropyrido[3,2-d]pyrimidin-4-yl)-2,5-diethylpiperazin-1-yl)ethyl)benzoate (265-266); 4-((2S,5R)-2,5-diethyl-4-(1-(4-(morpholinomethyl)phenyl) propyl) piperazin-1-yl)-1-methyl-2-oxo-1,2-dihydropyrido[3,2-d] pyrimidine-6-carbonitrile (267-268); 4-((2S,5R)-2,5-diethyl-4-(1-(4-(hydroxymethyl)phenyl)ethyl)piperazin-1-yl)-1-methyl-2-oxo-1,2-dihydropyrido[3,2-d]pyrimidine-6-carbonitrile (270-271); 4-((2S,5R)-4-(1-(4-(bromomethyl) phenyl)ethyl)-2,5-diethylpiperazin-1-yl)-1-methyl-2-oxo-1, 2-dihydropyrido[3,2-d]pyrimidine-6-carbonitrile (272); 4-((2S,5R)-2,5-diethyl-4-(1-(4-((4-methoxypiperidin-1-yl) methyl)phenyl)ethyl)piperazin-1-yl)-1-methyl-2-oxo-1,2-dihydropyrido[3,2-d]pyrimidine-6-carbonitrile (273-274); 4-((2S,5R)-4-(1-(4-((2,2-dimethylmorpholino)methyl)phenyl)ethyl)-2,5-diethylpiperazin-1-yl)-1-methyl-2-oxo-1,2-dihydropyrido[3,2-d]pyrimidine-6-carbonitrile (275-276);

4-((2S,5R)-4-(1-(4-((4,4-difluoropiperidin-1-yl)methyl) phenyl)ethyl)-2,5-diethylpiperazin-1-yl)-1-methyl-2-oxo-1, 2-dihydropyrido[3,2-d]pyrimidine-6-carbonitrile (277-278); 4-((2S,5R)-4-(1-(4-((2-oxa-6-azaspiro[3.3]heptan-6-yl) methyl)phenyl)ethyl)-2,5-diethylpiperazin-1-yl)-1-methyl-2-oxo-1,2-dihydropyrido[3,2-d]pyrimidine-6-carbonitrile (279-280); 4-((2S,5R)-2,5-diethyl-4-(1-(4-(piperidin-1-ylmethyl)phenyl)ethyl)piperazin-1-yl)-1-methyl-2-oxo-1,2-dihydropyrido[3,2-d]pyrimidine-6-carbonitrile (281-282); 4-((2S,5R)-4-(1-(4-((4-acetylpiperazin-1-yl)methyl)phenyl) ethyl)-2,5-diethylpiperazin-1-yl)-1-methyl-2-oxo-1,2-dihydropyrido[3,2-d]pyrimidine-6-carbonitrile (283-284); 4-((2S,5R)-2,5-diethyl-4-(1-(4-((4-hydroxypiperidin-1-yl) methyl)phenyl)ethyl)piperazin-1-yl)-1-methyl-2-oxo-1,2-dihydropyrido[3,2-d]pyrimidine-6-carbonitrile (285-286); 4-((2S,5R)-2,5-diethyl-4-(1-(4-((4-methyl-3-oxopiperazin-1-yl)methyl)phenyl)ethyl)piperazin-1-yl)-1-methyl-2-oxo-1,2-dihydropyrido[3,2-d]pyrimidine-6-carbonitrile (287-288); 4-((2S,5R)-2,5-diethyl-4-(1-(4-(((R)-3-hydroxypiperidin-1-yl)methyl)phenyl)ethyl)piperazin-1-yl)-1-methyl-2-oxo-1,2-dihydropyrido[3,2-d]pyrimidine-6-carbonitrile (289-290); 4-((2S,5R)-4-(1-(4-(((2S,6R)-2,6-dimethylmorpholino)methyl)phenyl)ethyl)-2,5-diethylpiperazin-1-yl)-1-methyl-2-oxo-1,2-dihydropyrido [3,2-d]pyrimidine-6-carbonitrile (291-292); 4-((2S,5R)-5-ethyl-2-methyl-4-(1-(3-methyl-2-oxo-2,3-dihydrobenzo[d] oxazol-5-yl)ethyl)piperazin-1-yl)-1-methyl-2-oxo-1,2-dihydropyrido[3,2-d]pyrimidine-6-carbonitrile (298-299); 4-((2S,5R)-4-(1-(4-cyclopropylphenyl)propyl)-5-ethyl-2-methylpiperazin-1-yl)-1-methyl-2-oxo-1,2-dihydropyrido [3,2-d]pyrimidine-6-carbonitrile (300-301); 4-((2S,5R)-4-(1-(4-cyclopropyl-2-fluorophenyl)propyl)-5-ethyl-2-methylpiperazin-1-yl)-1-methyl-2-oxo-1,2-dihydropyrido [3,2-d]pyrimidine-6-carbonitrile (302-303); 4-((2S,5R)-5-ethyl-4-(1-(4-methoxyphenyl)propyl)-2-methylpiperazin-1-yl)-1-methyl-2-oxo-1,2-dihydropyrido[3,2-d]pyrimidine-6-carbonitrile (304-305); 4-((2S,5R)-4-(1-(4-ethoxyphenyl) propyl)-5-ethyl-2-methylpiperazin-1-yl)-1-methyl-2-oxo-1, 2-dihydropyrido[3,2-d]pyrimidine-6-carbonitrile (306-307); 4-((2S,5R)-4-(1-(4-(cyclopropylmethoxy)phenyl)propyl)-5-ethyl-2-methylpiperazin-1-yl)-1-methyl-2-oxo-1,2-dihydropyrido[3,2-d]pyrimidine-6-carbonitrile (308-309); 4-((2S, 5R)-4-(1-(4-cyclopropoxyphenyl)propyl)-5-ethyl-2-methylpiperazin-1-yl)-1-methyl-2-oxo-1,2-dihydropyrido [3,2-d]pyrimidine-6-carbonitrile (311-312); 4-((2S,5R)-5-ethyl-4-(1-(4-methoxyphenyl)-2-methylpropyl)-2-methylpiperazin-1-yl)-1-methyl-2-oxo-1,2-dihydropyrido [3,2-d]pyrimidine-6-carbonitrile (313-314); 4-((2S,5R)-4-(1-(4-(2-cyanopropan-2-yl)phenyl)propyl)-5-ethyl-2-methylpiperazin-1-yl)-1-methyl-2-oxo-1,2-dihydropyrido [3,2-d]pyrimidine-6-carbonitrile (317-318); 4-((2S,5R)-4-(1-(3,4-difluorophenyl)propyl)-5-ethyl-2-methylpiperazin-1-yl)-1-methyl-2-oxo-1,2-dihydropyrido[3,2-d]pyrimidine-6-carbonitrile (319-320); 4-((2 S,5R)-4-(1-(4-bromophenyl) propyl)-5-ethyl-2-methylpiperazin-1-yl)-1-methyl-2-oxo-1, 2-dihydropyrido[3,2-d]pyrimidine-6-carbonitrile (321-322); 4-((2S,5R)-5-ethyl-4-(1-(4-isopropoxyphenyl)-2-methylpropyl)-2-methylpiperazin-1-yl)-1-methyl-2-oxo-1,2-dihydropyrido[3,2-d]pyrimidine-6-carbonitrile (323-324); 4-((2S,5R)-4-(1-(4-(1-cyanocyclopropyl)phenyl)ethyl)-5-ethyl-2-methylpiperazin-1-yl)-1-methyl-2-oxo-1,2-dihydropyrido[3,2-d]pyrimidine-6-carbonitrile (325-326); 4-((2S, 5R)-4-(1-(4-(cyclopropylmethoxy)-2,6-difluorophenyl) propyl)-5-ethyl-2-methylpiperazin-1-yl)-1-methyl-2-oxo-1, 2-dihydropyrido[3,2-d]pyrimidine-6-carbonitrile (327-328); 4-((2 S,5R)-5-ethyl-2-methyl-4-(1-(4-(tetrahydro-2H-pyran-4-yl)phenyl)piperazin-1-yl)-1-methyl-2-oxo-1, 2-dihydropyrido[3,2-d]pyrimidine-6-carbonitrile (329-330); 4-((2S,5R)-4-(1-(4-(1,3-dioxolan-2-yl)phenyl)propyl)-5-ethyl-2-methylpiperazin-1-yl)-1-methyl-2-oxo-1,2-dihydropyrido[3,2-d]pyrimidine-6-carbonitrile (331-332); 4-((2 S,5R)-5-ethyl-4-(1-(4-isopropoxyphenyl)propyl)-2-methylpiperazin-1-yl)-1-methyl-2-oxo-1,2-dihydropyrido[3,2-d] pyrimidine-6-carbonitrile (330-334); 4-((2S,5R)-5-ethyl-2-methyl-4-(1-(4-(3,3,3-trifluoropropoxy)phenyl)propyl) piperazin-1-yl)-1-methyl-2-oxo-1,2-dihydropyrido[3,2-d] pyrimidine-6-carbonitrile (335-336); 4-((2S,5R)-5-ethyl-2-methyl-4-(1-(4-((tetrahydro-2H-pyran-4-yl)methoxy) phenyl)propyl)piperazin-1-yl)-1-methyl-2-oxo-1,2-dihydropyrido[3,2-d]pyrimidine-6-carbonitrile (337-338); 4-((2S,5R)-4-(1-(4-(2-cyclopropylethoxy)phenyl)propyl)-5-ethyl-2-methylpiperazin-1-yl)-1-methyl-2-oxo-1,2-dihydropyrido[3,2-d]pyrimidine-6-carbonitrile (339-340); 4-((2S, 5R)-5-ethyl-2-methyl-4-(1-(4-(oxetan-3-ylmethoxy)phenyl) propyl)piperazin-1-yl)-1-methyl-2-oxo-1,2-dihydropyrido [3,2-d]pyrimidine-6-carbonitrile (341-342); 4-((2 S, 5R)-5-ethyl-2-methyl-4-(1-(4-((1-methylazetidin-3-yl)methoxy) phenyl)propyl)piperazin-1-yl)-1-methyl-2-oxo-1,2-dihydropyrido[3,2-d]pyrimidine-6-carbonitrile (343-344); 4-((2S,5R)-5-ethyl-2-methyl-4-(1-(4-((1-methylcyclopropyl)methoxy)phenyl)propyl)piperazin-1-yl)-1-methyl-2-oxo-1,2-dihydropyrido[3,2-d]pyrimidine-6-carbonitrile (345-346); 4-((2S,5R)-5-ethyl-2-methyl-4-(1-(4-(thiazol-2-ylmethoxy)phenyl)propyl)piperazin-1-yl)-1-methyl-2-oxo-1,2-dihydropyrido[3,2-d]pyrimidine-6-carbonitrile (347-348); 4-(2S,5R)-4-(1-(3-bromo-4-(trifluoromethyl)phenyl) ethyl)-5-ethyl-2-methylpiperazin-1-yl)-1-methyl-2-oxo-1,2-dihydropyrido[3,2-d]pyrimidine-6-carbonitrile (349); 4-((2S,5R)-5-ethyl-2-methyl-4-(1-(3-(morpholinomethyl)-4-(trifluoromethyl)phenyl)ethyl)piperazin-1-yl)-1-methyl-2-oxo-1,2-dihydropyrido[3,2-d]pyrimidine-6-carbonitrile (350-351); 4-((2S,5R)-4-(1-(3-((dimethylamino)methyl)-4-(tri fluoromethyl)phenyl)ethyl)-5-ethyl-2-methylpiperazin-1-yl)-1-methyl-2-oxo-1,2-dihydropyrido[3,2-d]pyrimidine-6-carbonitrile (352-353); 4-((2S,5R)-5-ethyl-2-methyl-4-(1-(3-(piperidin-1-ylmethyl)-4-(trifluoromethyl)phenyl) ethyl) piperazin-1-yl)-1-methyl-2-oxo-1,2-dihydropyrido[3,2-d] pyrimidine-6-carbonitrile (354-355); 4-((2S,5R)-4-(1-(3-cyano-4-(trifluoromethyl)phenyl)ethyl)-5-ethyl-2-methylpiperazin-1-yl)-1-methyl-2-oxo-1,2-dihydropyrido [3,2-d]pyrimidine-6-carbonitrile (356-357); 4-((2S,5R)-4-(1-(4-(aminomethyl)phenyl)ethyl)-5-ethyl-2-methylpiperazin-1-yl)-1-methyl-2-oxo-1,2-dihydropyrido [3,2-d]pyrimidine-6-carbonitrile (358); methyl (4-(1-((2R, 5S)-4-(6-cyano-1-methyl-2-oxo-1,2-dihydropyrido[3,2-d] pyrimidin-4-yl)-2-ethyl-5-methylpiperazin-1-yl)ethyl) benzyl)carbamate (359-360); 4-((2S,5R)-4-(1-(3-cyclopropyl-1,2,4-oxadiazol-5-yl)ethyl)-2,5-diethylpiperazin-1-yl)-1-methyl-2-oxo-1,2-dihydropyrido [3,2-d]pyrimidine-6-carbonitrile (361-362); 4-((2S,5R)-4-(1-(3-cyclopropyl-1,2,4-oxadiazol-5-yl)propyl)-2,5-diethylpiperazin-1-yl)-1-methyl-2-oxo-1,2-dihydropyrido [3,2-d]pyrimidine-6-carbonitrile (363-364); 4-((2S,5R)-4-(1-(3-cyclopropyl-1,2,4-oxadiazol-5-yl)-2-methylpropyl)-5-ethyl-2-methylpiperazin-1-yl)-1-methyl-2-oxo-1,2-dihydropyrido[3,2-d]pyrimidine-6-carbonitrile (365-366); 4-((2S,5R)-4-(1-(5-cyclopropyl-1,3,4-oxadiazol-2-yl)-2-methylpropyl)-5-ethyl-2-methylpiperazin-1-yl)-1-methyl-2-oxo-1,2-dihydropyrido[3,2-d]pyrimidine-6-carbonitrile (367-368); 2-((2R,5S)-4-(6-chloro-1-methyl-2-oxo-1,2-dihydropyrido[3,2-d]pyrimidin-4-yl)-2,5-diethylpiperazin-1-yl)-2-(4-fluorophenyl)acetonitrile (369); 4-((2S,5R)-4-(1-(4-((2-cyanopropan-2-yl)oxy)phenyl)ethyl)-2,5-dimethylpiperazin-1-yl)-1-methyl-2-oxo-1,2-dihydropyrido

[3,2-d]pyrimidine-6-carbonitrile (376-377); 4-((2S,5R)-4-(1-(4-cyclopropylphenyl)propyl)-2,5-dimethylpiperazin-1-yl)-1-methyl-2-oxo-1,2-dihydropyrido[3,2-d]pyrimidine-6-carbonitrile (378-379); 4-((2S,5R)-4-(1-(4-cyclopropyl-2-fluorophenyl)propyl)-2,5-dimethylpiperazin-1-yl)-1-methyl-2-oxo-1,2-dihydropyrido[3,2-d]pyrimidine-6-carbonitrile (380-381); 6-chloro-4-((2S,5R)-4-(1-(4-(hydroxymethyl)phenyl)ethyl)-2,5-dimethylpiperazin-1-yl)-1-methylpyrido[3,2-d]pyrimidin-2(1H)-one (382); 4-((2S,5R)-4-(1-(4-(hydroxymethyl)phenyl)ethyl)-2,5-dimethylpiperazin-1-yl)-1-methyl-2-oxo-1,2-dihydropyrido[3,2-d]pyrimidine-6-carbonitrile (383); 4-((2S,5R)-4-(1-(4-(bromomethyl)phenyl)ethyl)-2,5-dimethylpiperazin-1-yl)-1-methyl-2-oxo-1,2-dihydropyrido[3,2-d]pyrimidine-6-carbonitrile (384); 4-((2S,5R)-4-(1-(4-((2,2-dimethylmorpholino)methyl)phenyl)ethyl)-2,5-dimethylpiperazin-1-yl)-1-methyl-2-oxo-1,2-dihydropyrido[3,2-d]pyrimidine-6-carbonitrile (385-386); 4-((2S,5R)-4-(1-(4-(((1S,4S)-2-oxa-5-azabicyclo[2.2.1]heptan-5-yl)methyl)phenyl)ethyl)-2,5-dimethylpiperazin-1-yl)-1-methyl-2-oxo-1,2-dihydropyrido[3,2-d]pyrimidine-6-carbonitrile (387-388); 4-((2S,5R)-4-(1-(4-(((2S,6R)-2,6-dimethylmorpholino)methyl)phenyl)ethyl)-2,5-dimethylpiperazin-1-yl)-1-methyl-2-oxo-1,2-dihydropyrido[3,2-d]pyrimidine-6-carbonitrile (389); 4-((2S,5R)-4-(1-(4-((4,4-difluoropiperidin-1-yl)methyl)phenyl)ethyl)-2,5-dimethylpiperazin-1-yl)-1-methyl-2-oxo-1,2-dihydropyrido[3,2-d]pyrimidine-6-carbonitrile (390-391); 4-((2S,5R)-4-(1-(4-((2-oxa-6-azaspiro[3.3]heptan-6-yl)methyl)phenyl)ethyl)-2,5-dimethylpiperazin-1-yl)-1-methyl-2-oxo-1,2-dihydropyrido[3,2-d]pyrimidine-6-carbonitrile (392-393); 6-chloro-1-methyl-4-((2S,5R)-2-methyl-5-propyl-4-(1-(4-(trifluoromethyl)phenyl)ethyl)piperazin-1-yl) pyrido[3,2-d]pyrimidin-2(1H)-one (394); 1-methyl-4-((2S,5R)-2-methyl-5-propyl-4-(1-(4- (trifluoromethyl)phenyl)ethyl)piperazin-1-yl)-2-oxo-1,2-dihydropyrido[3,2-d]pyrimidine-6-carbonitrile (395-396); 6-chloro-4-((2S,5S)-5-(methoxymethyl)-2-methyl-4-(1-(4-(trifluoromethyl) phenyl) propyl)piperazin-1-yl)-1-methylpyrido[3,2-d]pyrimidin-2(1H)-one (397); 4-((2S,5S)-5-(methoxymethyl)-2-methyl-4-(1-(4-(trifluoromethyl) phenyl)propyl) piperazin-1-yl)-1-methyl-2-oxo-1,2-dihydropyrido[3,2-d]pyrimidine-6-carbonitrile (398-399); 4-((2S,5S)-5-(ethoxymethyl)-2-methyl-4-(1-(4-(trifluoromethyl) phenyl) propyl)piperazin-1-yl)-1-methyl-2-oxo-1,2-dihydropyrido[3,2-d]pyrimidine-6-carbonitrile (400-401); 4-((2S,5S)-5-(azidomethyl)-2-methyl-4-(1-(4-(trifluoromethyl) phenyl) ethyl)piperazin-1-yl)-6-chloro-1-methylpyrido[3,2-d]pyrimidin-2(1H)-one (402); 4-((2S,5R)-5-(aminomethyl)-2-methyl-4-(1-(4-(trifluoromethyl)phenyl)ethyl)piperazin-1-yl)-6-chloro-1-methylpyrido[3,2-d]pyrimidin-2(1H)-one (403); 4-((2S,5S)-5-(methoxymethyl)-2-methyl-4-(1-(4-(trifluoromethyl)phenyl)ethyl)piperazin-1-yl)-1-methyl-2-oxo-1,2-dihydropyrido[3,2-d]pyrimidine-6-carbonitrile (404-405); 4-((2R,5R)-2-(hydroxymethyl)-5-methyl-4-(1-(4-(trifluoromethyl)phenyl)ethyl) piperazin-1-yl)-1-methyl-2-oxo-1,2-dihydropyrido[3,2-d]pyrimidine-6-carbonitrile (406-407); 6-chloro-4-((2R,5R)-2-(methoxymethyl)-5-methyl-4-(1-(4-(trifluoromethyl)phenyl)ethyl) piperazin-1-yl)-1-methylpyrido[3,2-d]pyrimidin-2(1H)-one (408); 4-((2R,5R)-2-(methoxymethyl)-5-methyl-4-(1-(4-(trifluoromethyl)phenyl)ethyl) piperazin-1-yl)-1-methyl-2-oxo-1,2-dihydropyrido[3,2-d]pyrimidine-6-carbonitrile (409-410); 4-((2R,5R)-5-ethyl-2-(hydroxymethyl)-4-(1-(4-(trifluoromethyl)phenyl)ethyl)piperazin-1-yl)-1-methyl-2-oxo-1,2-dihydropyrido[3,2-d]pyrimidine-6-carbonitrile (411-412); 4-((2S,5R)-5-ethyl-2-methyl-4-(1-(4-(trifluoromethyl)phenyl)ethyl)piperazin-1-yl)-2-oxo-1,2-dihydropyrido[3,2-d]pyrimidine-6-carbonitrile (413-414); 4-((2S,5R)-2,5-diethyl-4-(1-(4-(trifluoromethyl)phenyl)propyl)piperazin-1-yl)-2-oxo-1,2-dihydropyrido[3,2-d]pyrimidine-6-carbonitrile (415-416); 6-chloro-4-((2S,5R)-5-ethyl-2-methyl-4-(1-(4-(trifluoromethyl)phenyl)ethyl)piperazin-1-yl)-1-(methyl-d$_3$)pyrido[3,2-d]pyrimidin-2(1H)-one (417-418); 4-((2S,5R)-5-ethyl-2-methyl-4-(1-(4-(trifluoromethyl) phenyl) ethyl)piperazin-1-yl)-1-(methyl-d$_3$)-2-oxo-1,2-dihydropyrido[3,2-d]pyrimidine-6-carbonitrile (419-420); 6-chloro-4-((2S,5R)-2,5-diethyl-4-(1-(4-(trifluoromethyl) phenyl) propyl)piperazin-1-yl)-1-methylpyrido[3,2-d]pyrimidin-2(1H)-one (421-422); 4-((2S,5R)-2,5-diethyl-4-(1-(4-(trifluoromethyl)phenyl)ethyl)piperazin-1-yl)-6-(hydroxymethyl)-1-methylpyrido[3,2-d]pyrimidin-2(1H)-one (423); 4-((2S,5R)-2,5-diethyl-4-(1-(4-(trifluoromethyl)phenyl)ethyl)piperazin-1-yl)-6-(methoxymethyl)-1-methylpyrido[3,2-d]pyrimidin-2(1H)-one (424-425); 6-chloro-4-((2S,5R)-2,5-diethyl-4-(1-(4-(trifluoromethyl) phenyl)ethyl)piperazin-1-yl)-1-methylpyrido[3,2-d]pyrimidin-2(1H)-one (426); 4-((2S,5R)-2,5-diethyl-4-(1-(4-(trifluoromethyl)phenyl)ethyl)piperazin-1-yl)-6-methoxy-1-methylpyrido[3,2-d]pyrimidin-2(1H)-one (427-428); 4-((2S,5R)-2,5-diethyl-4-(1-(4-(trifluoromethyl)phenyl) ethyl)piperazin-1-yl)-6-ethoxy-1-methylpyrido[3,2-d]pyrimidin-2(1H)-one (429-430); 4-((2S,5R)-2,5-diethyl-4-(1-(4-(trifluoromethyl)phenyl)ethyl) piperazin-1-yl)-6-(2-(dimethylamino)ethoxy)-1-methylpyrido[3,2-d]pyrimidin-2(1H)-one (431-432); 4-((2S,5R)-2,5-diethyl-4-(1-(4-(trifluoromethyl)phenyl)ethyl)piperazin-1-yl)-6-(2-methoxyethoxy)-1-methylpyrido[3,2-d]pyrimidin-2(1H)-one (433-434); 4-((2S,5R)-2,5-diethyl-4-(1-(4-(trifluoromethyl)phenyl)propyl)piperazin-1-yl)-6-methoxy-1-methylpyrido[3,2-d]pyrimidin-2(1H)-one (435-436); 4-((2S,5R)-2,5-diethyl-4-(1-(4-(trifluoromethyl)phenyl)propyl)piperazin-1-yl)-6-ethoxy-1-methylpyrido[3,2-d]pyrimidin-2(1H)-one (437-438); 4-(2S,5R)-2,5-diethyl-4-(1-(4-(trifluoromethyl)phenyl) ethyl)piperazin-1-yl)-6-(difluoromethyl)-1-methylpyrido[3,2-d]pyrimidin-2(1H)-one (439-440); 6-(difluoromethyl)-4-((2S,5R)-5-ethyl-2-methyl-4-(1-(4-(trifluoromethyl) phenyl)ethyl)piperazin-1-yl)-1-methylpyrido[3,2-d]pyrimidin-2(1H)-one (441-442); 4-((2S,5R)-2,5-diethyl-4-(1-(4-(trifluoromethyl)phenyl) ethyl)piperazin-1-yl)-6-hydroxy-1-methylpyrido[3,2-d]pyrimidin-2(1H)-one (443); 4-(2S,5R)-2,5-diethyl-4-(1-(4-(trifluoromethyl)phenyl)ethyl)piperazin-1-yl)-6-(difluoromethoxy)-1-methylpyrido[3,2-d]pyrimidin-2(1H)-one (444-445); 6-chloro-4-((2S,5R)-2,5-dimethyl-4-(1-(3-(trifluoromethyl)bicyclo[1.1.1]pentan-1-yl)propyl) piperazin-1-yl)-1-methylpyrido[3,2-d]pyrimidin-2(1H)-one (Diastereomeric Mixture) (446); 4-((2S,5R)-2,5-dimethyl-4-(1-(3-(trifluoromethyl)bicyclo[1.1.1]pentan-1-yl)propyl) piperazin-1-yl)-1-methyl-2-oxo-1,2-dihydropyrido[3,2-d]pyrimidine-6-carbonitrile (447-449); 4-((2S,5R)-4-(1-cyclopropylpropyl)-2,5-dimethylpiperazin-1-yl)-1-methyl-2-oxo-1,2-dihydropyrido[3,2-d]pyrimidine-6-carbonitrile (453-455); 4-((2S,5R)-4-(1-(3,3-difluorocyclobutyl)propyl)-2,5-dimethylpiperazin-1-yl)-1-methyl-2-oxo-1,2-dihydropyrido[3,2-d]pyrimidine-6-carbonitrile (456-458); or 4-((2S,5R)-4-(1-(4,4-difluorocyclohexyl)propyl)-2,5-dimethylpiperazin-1-yl)-1-methyl-2-oxo-1,2-dihydropyrido[3,2-d]pyrimidine-6-carbonitrile (459-460).

In one embodiment, a compound of Formula (I) or a salt thereof is provided wherein said compound is:

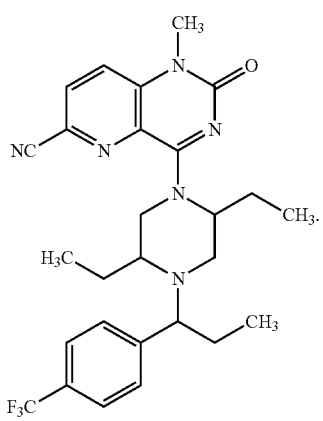 [SMILES: CCC1CN(C(CC)c2ccc(C(F)(F)F)cc2)C(CC)CN1c1nc(=O)n(C)c2ccc(C#N)nc12]

In one embodiment, a compound of Formula (I) or a salt thereof is provided wherein said compound is 4-((2S,5R)-2,5-diethyl-4-(1-(4-(trifluoromethyl)phenyl)propyl) piperazin-1-yl)-1-methyl-2-oxo-1,2-dihydropyrido[3,2-d]pyrimidine-6-carbonitrile (5-6).

In one embodiment, a compound of Formula (I) or a salt thereof is provided wherein said compound is 4-((2S,5R)-2,5-diethyl-4-((S)-1-(4-(trifluoromethyl)phenyl) propyl)piperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is 4-((2S,5R)-2,5-diethyl-4-((R)-1-(4-(trifluoromethyl)phenyl) propyl) piperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is:

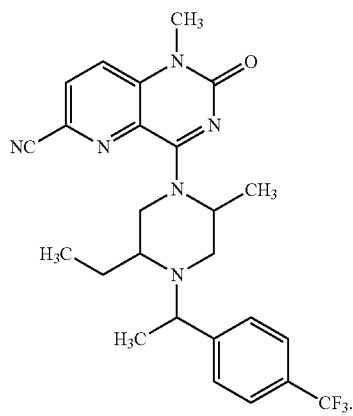 [SMILES: CCC1CN(c2nc(=O)n(C)c3ccc(C#N)nc23)C(C)CN1C(C)c1ccc(C(F)(F)F)cc1]

In one embodiment, a compound of Formula (I) or a salt thereof is provided wherein said compound is 4-((2S,5R)-5-ethyl-2-methyl-4-(1-(4-(trifluoromethyl)phenyl) ethyl) piperazin-1-yl)-1-methyl-2-oxo-1,2-dihydropyrido[3,2-d]pyrimidine-6-carbonitrile (7-8).

In one embodiment, a compound of Formula (I) or a salt thereof is provided wherein said compound is 4-((2S,5R)-5-ethyl-2-methyl-4-((S)-1-(4-(trifluoromethyl) phenyl) ethyl)piperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is 4-((2S,5R)-5-ethyl-2-m ethyl-4-((R)-1-(4-(trifluoromethyl) phenyl) ethyl)piperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is:

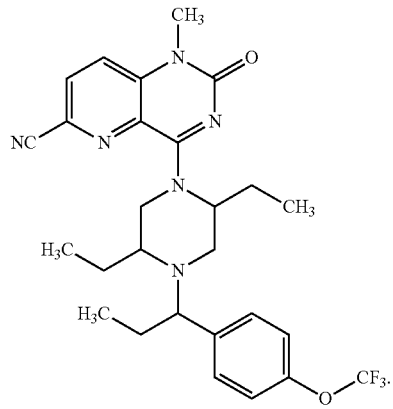 [SMILES: CCC1CN(C(CC)c2ccc(OC(F)(F)F)cc2)C(CC)CN1c1nc(=O)n(C)c2ccc(C#N)nc12]

In one embodiment, a compound of Formula (I) or a salt thereof is provided wherein said compound is 4-((2S,5R)-2,5-diethyl-4-(1-(4-(trifluoromethoxy)phenyl) propyl)piperazin-1-yl)-1-methyl-2-oxo-1,2-dihydropyrido[3,2-d]pyrimidine-6-carbonitrile (36-37).

In one embodiment, a compound of Formula (I) or a salt thereof is provided wherein said compound is 4-((2S,5R)-2,5-diethyl-4-((S)-1-(4-(trifluoromethoxy)phenyl) propyl) piperazin-1-yl)-1-methyl-2-oxo-1,2-dihydropyrido[3,2-d] pyrimidine-6-carbonitrile.

In one embodiment, a compound of Formula (I) or a salt thereof is provided wherein said compound is 4-((2S,5R)-2,5-diethyl-4-((R)-1-(4-(trifluoromethoxy)phenyl) propyl) piperazin-1-yl)-1-methyl-2-oxo-1,2-dihydropyrido[3,2-d] pyrimidine-6-carbonitrile.

In one embodiment, a compound of Formula (I) or a salt thereof is provided wherein said compound is:

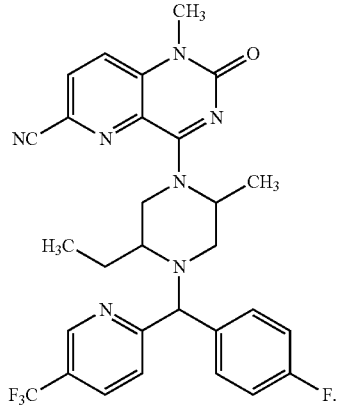

In one embodiment, a compound of Formula (I) or a salt thereof is provided wherein said compound is 4-((2S,5R)-5-ethyl-4((4-fluorophenyl)(5-(trifluoromethyl) pyridin-2-yl) methyl)-2-methylpiperazin-1-yl)-1-methyl-2-oxo-1,2-dihydropyrido[3,2-d]pyrimidine-6-carbonitrile (46-47).

In one embodiment, a compound of Formula (I) or a salt thereof is provided wherein said compound is 4-((2S,5R)-5-ethyl-4((S)-(4-fluorophenyl)(5-(trifluoromethyl) pyridin- 2-yl)methyl)-2-methylpiperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is 4-((2S,5R)-5-ethyl-4-((R)-(4-fluorophenyl)(5-(trifluoromethyl) pyridin-2-yl)methyl)-2-methylpiperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is:

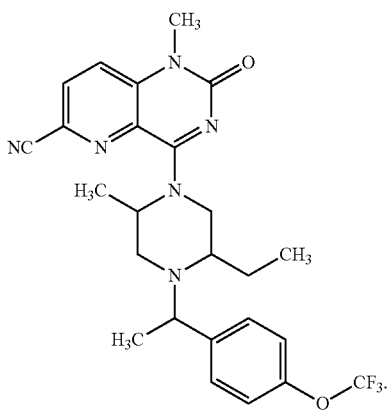 [SMILES: CCC1CN(c2nc(=O)n(C)c3ccc(C#N)nc23)C(C)CN1C(C)c1ccc(OC(F)(F)F)cc1]

In one embodiment, a compound of Formula (I) or a salt thereof is provided wherein said compound is 4-((2S,5R)-5-ethyl-2-methyl-4-(1-(4-(trifluoromethoxy) phenyl)ethyl)piperazin-1-yl)-1-methyl-2-oxo-1,2-dihydropyrido[3,2-d]pyrimidine-6-carbonitrile (48-49).

In one embodiment, a compound of Formula (I) or a salt thereof is provided wherein said compound is 4-((2S,5R)-5-ethyl-2-methyl-4-((S)-1-(4-(trifluoromethoxy) phenyl)ethyl)piperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is 4-((2S,5R)-5-ethyl-2-methyl-4-((R)-1-(4-(trifluoromethoxy) phenyl)ethyl)piperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is:

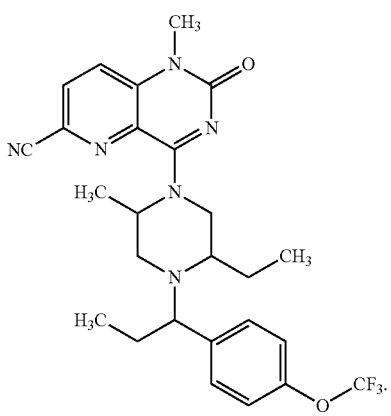 [SMILES: CCC1CN(c2nc(=O)n(C)c3ccc(C#N)nc23)C(C)CN1C(CC)c1ccc(OC(F)(F)F)cc1]

In one embodiment, a compound of Formula (I) or a salt thereof is provided wherein said compound is 4-((2S,5R)-5-ethyl-2-methyl-4-(1-(4-(trifluoromethoxy) phenyl)propyl)piperazin-1-yl)-1-methyl-2-oxo-1,2-dihydropyrido[3,2-d]pyrimidine-6-carbonitrile (83-84).

In one embodiment, a compound of Formula (I) or a salt thereof is provided wherein said compound is 4-((2S,5R)-5-ethyl-2-methyl-4-((S)-1-(4-(trifluoromethoxy) phenyl)propyl)piperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is 4-((2S,5R)-5-ethyl-2-methyl-4-((R)-1-(4-(trifluoromethoxy) phenyl)propyl)piperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is:

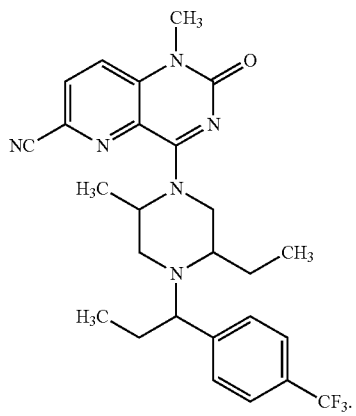 [SMILES: CCC1CN(c2nc(=O)n(C)c3ccc(C#N)nc23)C(C)CN1C(CC)c1ccc(C(F)(F)F)cc1]

In one embodiment, a compound of Formula (I) or a salt thereof is provided wherein said compound is 4-((2S,5R)-5-ethyl-2-methyl-4-(1-(4-(trifluoromethyl)phenyl) propyl)piperazin-1-yl)-1-methyl-2-oxo-1,2-dihydropyrido[3,2-d]pyrimidine-6-carbonitrile (89-90).

In one embodiment, a compound of Formula (I) or a salt thereof is provided wherein said compound is 4-((2S,5R)-5-ethyl-2-methyl-4-((S)-1-(4-(trifluoromethyl) phenyl)propyl)piperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is 4-((2S,5R)-5-ethyl-2-methyl-4-((R)-1-(4-(trifluoromethyl) phenyl)propyl)piperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is:

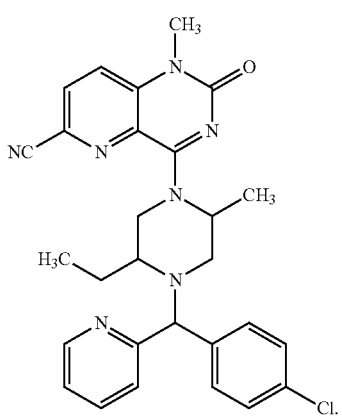 [SMILES: CCC1CN(c2nc(=O)n(C)c3ccc(C#N)nc23)C(C)CN1C(c1ccc(Cl)cc1)c1ccccn1]

In one embodiment, a compound of Formula (I) or a salt thereof is provided wherein said compound is 4-((2S,5R)-4-((4-chlorophenyl)(pyridin-2-yl)methyl)-5-ethyl-2-methylpiperazin-1-yl)-1-methyl-2-oxo-1,2-dihydropyrido[3,2-d]pyrimidine-6-carbonitrile (95-96).

In one embodiment, a compound of Formula (I) or a salt thereof is provided wherein said compound is 4-((2S,5R)-4-((R)-(4-chlorophenyl)(pyridin-2-yl)methyl)-5-ethyl-2-methylpiperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is 4-((2S,5R)-4-((S)-(4-chlorophenyl)(pyridin-2-yl)methyl)-5-ethyl-2-methylpiperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is:

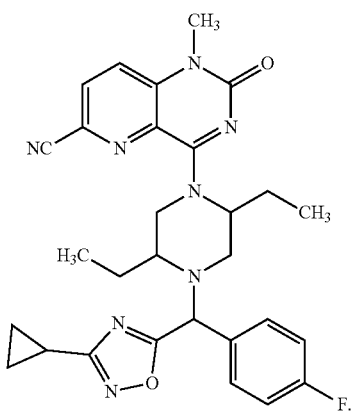 [SMILES: CCC1CN(C(c2ccc(F)cc2)c2nc(C3CC3)no2)C(CC)CN1c1nc(=O)n(C)c2ccc(C#N)nc12]

In one embodiment, a compound of Formula (I) or a salt thereof is provided wherein said compound is 4-((2S,5R)-4-(3-cyclopropyl-1,2,4-oxadiazol-5-yl)(4-fluorophenyl)methyl)-2,5-dimethylpiperazin-1-yl)-1-methyl-2-oxo-1,2-dihydropyrido[3,2-d]pyrimidine-6-carbonitrile (110-111).

In one embodiment, a compound of Formula (I) or a salt thereof is provided wherein said compound is 4-((2S,5R)-4-((R)-(3-cyclopropyl-1,2,4-oxadiazol-5-yl)(4-fluorophenyl)methyl)-2,5-diethylpiperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is 4-((2S,5R)-4-((S)-(3-cyclopropyl-1,2,4-oxadiazol-5-yl)(4-fluorophenyl)methyl)-2,5-diethylpiperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is:

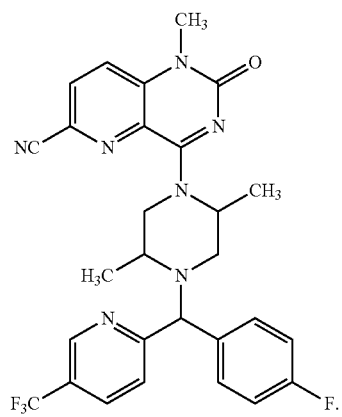 [SMILES: CC1CN(C(c2ccc(F)cc2)c2ccc(C(F)(F)F)cn2)C(C)CN1c1nc(=O)n(C)c2ccc(C#N)nc12]

In one embodiment, a compound of Formula (I) or a salt thereof is provided wherein said compound is 4-((2S,5R)-4-((4-fluorophenyl)(5-(trifluoromethyl)pyridin-2-yl)methyl)-2,5-dimethylpiperazin-1-yl)-1-methyl-2-oxo-1,2-dihydropyrido[3,2-d]pyrimidine-6-carbonitrile (126-127).

In one embodiment, a compound of Formula (I) or a salt thereof is provided wherein said compound is 4-((2S,5R)-4-((S)-(4-fluorophenyl)(5-(trifluoromethyl)pyridin-2-yl)methyl)-2,5-dimethylpiperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is 4-((2S,5R)-4-((R)-(4-fluorophenyl)(5-(trifluoromethyl)pyridin-2-yl)methyl)-2,5-dimethylpiperazin-1-yl)-1-methyl-2-oxo-1,2-dihydropyrido[3,2-d] pyrimidine-6-carbonitrile.

In one embodiment, a compound of Formula (I) or a salt thereof is provided wherein said compound is:

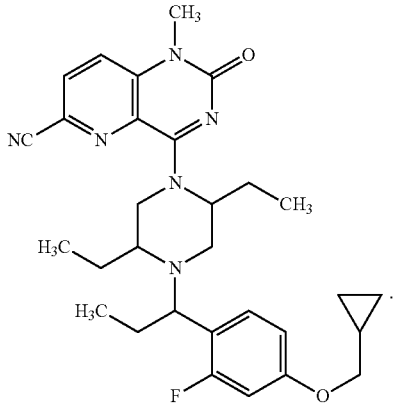 [SMILES: CCC1CN(C(CC)c2ccc(OCC3CC3)cc2F)C(CC)CN1c1nc(=O)n(C)c2ccc(C#N)nc12]

In one embodiment, a compound of Formula (I) or a salt thereof is provided wherein said compound is 4-((2S,5R)-4-(1-(4-(cyclopropylmethoxy)-2-fluorophenyl) propyl)-2,5-diethylpiperazin-1-yl)-1-methyl-2-oxo-1,2-dihydropyrido[3,2-d]pyrimidine-6-carbonitrile (198-199).

In one embodiment, a compound of Formula (I) or a salt thereof is provided wherein said compound is 4-((2S,5R)-4-((S)-1-(4-(cyclopropylmethoxy)-2-fluorophenyl) propyl)-

2,5-diethylpiperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is 4-((2S,5R)-4-((R)-1-(4-(cyclopropylmethoxy)-2-fluorophenyl) propyl)-2,5-diethylpiperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is:

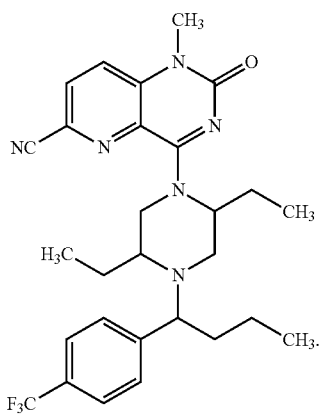 [SMILES: CCCC(c1ccc(C(F)(F)F)cc1)N1CC(CC)N(c2nc(=O)n(C)c3ccc(C#N)nc23)CC1CC]

In one embodiment, a compound of Formula (I) or a salt thereof is provided wherein said compound is 4-((2S,5R)-2,5-diethyl-4-(1-(4-(trifluoromethyl)phenyl) butyl)piperazin-1-yl)-1-methyl-2-oxo-1,2-dihydropyrido[3,2-d]pyrimidine-6-carbonitrile (243-244).

In one embodiment, a compound of Formula (I) or a salt thereof is provided wherein said compound is 4-((2S,5R)-2,5-diethyl-4-((S)-1-(4-(trifluoromethyl)phenyl) butyl)piperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is 4-((2S,5R)-2,5-diethyl-4-((R)-1-(4-(trifluoromethyl)phenyl) butyl)piperazin-1-yl)-1-methyl-2-oxo-1,2-dihydropyrido[3,2-d]pyrimidine-6-carbonitrile.

In one embodiment, a compound of Formula (I) or a salt thereof is provided wherein said compound is:

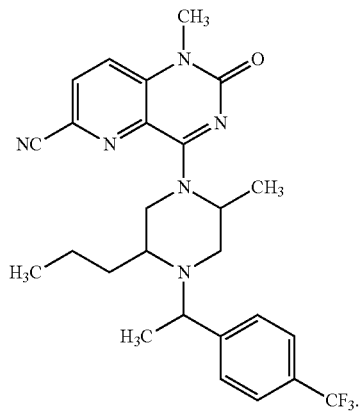

In one embodiment, a compound of Formula (I) or a salt thereof is provided wherein said compound is 1-methyl-4-((2S,5R)-2-methyl-5-propyl-4-(1-(4-(trifluoromethyl)phenyl)ethyl)piperazin-1-yl)-2-oxo-1,2-dihydropyrido[3,2-d]pyrimidine-6-carbonitrile (395-396).

In one embodiment, a compound of Formula (I) or a salt thereof is provided wherein said compound is 1-methyl-4-((2S,5R)-2-methyl-5-propyl-4-((S)-1-(4-(trifluoromethyl)phenyl)ethyl)piperazin-1-yl)-2-oxo-1,2-dihydropyrido[3,2-d]pyrimidine-6-carbonitrile.

In one embodiment, a compound of Formula (I) or a salt thereof is provided wherein said compound is 1-methyl-4-((2S,5R)-2-methyl-5-propyl-4-((R)-1-(4-(trifluoromethyl)phenyl)ethyl)piperazin-1-yl)-2-oxo-1,2-dihydropyrido[3,2-d]pyrimidine-6-carbonitrile.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —$NH_2$.

The term "azido" refers to the group $N_3$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "bromoalkyl" as used herein is intended to include both branched and straight-chain saturated aliphatic hydrocarbon groups substituted with one or more bromine atoms. For example, "$C_{1-4}$ bromoalkyl" is intended to include $C_1$, $C_2$, $C_3$, and $C_4$ alkyl groups substituted with one or more bromine atoms. Representative examples of fluoroalkyl groups include, but are not limited to, —$CH_2Br$ and —$CH_2CH_2Br$.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "cyanoalkyl" includes both branched and straight-chain saturated alkyl groups substituted with one or more cyano groups. For example, "cyanoalkyl" includes —$CH_2CN$, —$CH_2CH_2CN$, and $C_{1-3}$ cyanoalkyl.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "cycloalkyl" as used herein, refers to a group derived from a non-aromatic monocyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "fluorocycloalkyl" as used herein is intended to include a cycloalkyl group substituted with one or more fluorine atoms.

The term "carbocyclyl" as used herein, refers to a group derived from a non-aromatic monocyclic or polycyclic hydrocarbon molecule by removal of one hydrogen atom from a saturated ring carbon atom. Representative examples of carbocyclyl groups include, but are not limited to, cycloalkyls and bicycloalkyls such as bicyclo[1.1.1]pentanyl, bicyclohexanes, bicycloheptanes, and bicyclooctanes.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The terms "cyanoalkoxy" and "—O(cyanoalkyl)" represent a cyanoalkyl group as defined above attached through an oxygen linkage (—O—). For example, "$C_{1-3}$ cyanoalkoxy" is intended to include $C_1$, $C_2$, and $C_3$ cyanoalkoxy groups.

The terms "carbocyclo", "carbocyclic" or "carbocyclyl" may be used interchangeably and refer to cyclic groups having at least one saturated or partially saturated non-aromatic ring wherein all atoms of all rings are carbon. The carbocyclyl ring may be unsubstituted or may contain one or more substituents as valence allows. Thus, the term includes nonaromatic rings such as for example, cycloalkyl, cycloalkenyl, and cycloalkynyl rings. Exemplary bicyclic carbocyclyl groups include, indanyl, indenyl, dihydronaphthalenyl, tetrahydronaphthenyl, hexahydronaphthalenyl, octahydronaphthalenyl, decahydronaphthalenyl, bicycloheptanyl, bicyclooctanyl, and bicyclononanyl.

The term "aryl" as used herein, refers to a group of atoms derived from a molecule containing aromatic carbon ring(s) by removing one hydrogen that is bonded to the aromatic ring(s). Bicyclic aryl groups include aryl groups with two aromatic carbon rings and aryl groups with one aromatic carbon ring and one non-aromatic carbon ring. Representative examples of aryl groups include monocyclic aryl groups such as phenyl, and bicyclic aryl groups such as naphthalenyl, dihydronaphthalenyl, tetrahydronaphthalenyl, indenyl, and indanyl. The aryl ring may be unsubstituted or may contain one or more substituents as valence allows.

The term "benzyl," as used herein, refers to a methyl group in which one of the hydrogen atoms is replaced by a phenyl group. The phenyl ring may be unsubstituted or may contain one or more substituents as valence allows.

The term "heteroatom" refers to oxygen (O), sulfur (S), and nitrogen (N).

The terms "heterocyclo", "heterocyclic", or "heterocyclyl" may be used interchangeably and refer to cyclic groups having saturated or partially saturated non-aromatic ring(s) and wherein one or more of the rings have at least one heteroatom (O, S or N), said heteroatom containing ring preferably having 1 to 4 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include azetidinyl, pyrrolidinyl, imidazolinyl, oxazolidinyl, isoxazolinyl, thiazolidinyl, isothiazolidinyl, tetrahydrofuranyl, piperidinyl, piperazinyl, piperazinonyl, piperidinonyl, pyrrolidinonyl, azepinyl, azepinonyl, tetrahydropyranyl, morpholinyl, thiamorpholinyl, thiamorpholinyl sulfoxide, thiamorpholinyl sulfone, dioxolanyl, and tetrahydro-1,1-dioxothienyl.

The term "heteroaryl" refers to substituted and unsubstituted aromatic 5- or 6-membered monocyclic groups and 9- or 10-membered bicyclic groups that have at least one heteroatom (O, S or N) in at least one of the rings, said heteroatom-containing ring preferably having 1, 2, 3, or 4 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Bicyclic heteroaryl groups include heteroaryl groups with two aromatic rings in which one or both of the rings include at least one heteroatom; and heteroaryl groups with one aromatic ring and one non-aromatic ring in which one or both of the rings include at least one heteroatom. The nitrogen and sulfur atoms may optionally be oxidized and the nitrogen atoms may optionally be quaternized. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemi sulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are known in the art and are described in Rautio, J. et al., *Nature Review Drug Discovery*, 17, 559-587 (2018).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor of DGKα and/or DGKζ, or effective to treat or prevent viral infections and proliferative disorders, such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) and/or pharmaceutically acceptable salts thereof can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one pharmaceutically acceptable salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Utility

The compounds of Formula (I) are useful for the treatment of cancer.

In another embodiment, the present invention provides a combined preparation of a compound of Formula (I), and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with DGK target inhibition in T cells.

In another aspect, the invention provides a method of treating a patient suffering from or susceptible to a medical condition that is associated with DGK target inhibition in T cells. A number of medical conditions can be treated. The method comprises administering to the patient a therapeutically effective amount of a composition comprising a compound of Formula (I) and/or a pharmaceutically acceptable salt thereof, a stereoisomer thereof or a tautomer thereof. For example, the compounds described herein may be used to treat or prevent viral infections and proliferative diseases such as cancer.

The compounds for Formula (I) and pharmaceutical compositions comprising at least one compound of Formula (I) are useful in treating or preventing any disease or conditions that are associated with DGK target inhibition in T cells. These include viral and other infections (e.g., skin infections, GI infection, urinary tract infections, genito-urinary infections, systemic infections), and proliferative diseases (e.g., cancer). The compounds of Formula (I) and pharmaceutical compositions comprising in at least one compound of Formula (I) may be administered to animals, preferably mammals (e.g., domesticated animals, cats, dogs, mice, rats), and more preferably humans. Any method of administration may be used to deliver the compound or pharmaceutical composition to the patient. In certain embodiments, the compound of Formula (I) or pharmaceutical composition comprising at least compound of Formula (I) is administered orally. In other embodiments, the Formula (I) or pharmaceutical composition comprising at least compound of Formula (I) is administered parenterally.

The compounds of Formula (I) can inhibit activity of the diacylglycerol kinase alpha and zeta (DGKα/ζ). For example, the compounds of Formula (I) can be used to inhibit activity of DGKα and DGKζ in a cell or in an individual in need of modulation of DGKα and DGKζ by administering an inhibiting amount of a compound of Formula (I) or a salt thereof.

The present invention further provides methods of treating diseases associated with activity or expression, including abnormal activity and/or overexpression, of DGKα and DGKζ in an individual (e.g., patient) by administering to the individual in need of such treatment a therapeutically effective amount or dose of a compound of Formula (I) or a pharmaceutical composition thereof. Example diseases can include any disease, disorder or condition that is directly or indirectly linked to expression or activity of DGKα and DGKζ enzyme, such as over expression or abnormal activity. A DGKα and DGKζ-associated disease can also include any disease, disorder or condition that can be prevented, ameliorated, or cured by modulating DGKα and DGKζ enzyme activity. Examples of DGKα and DGKζ associated diseases include cancer and viral infections such as HIV infection, hepatitis B, and hepatitis C.

In one aspect, the compound(s) of Formula (I) are sequentially administered prior to administration of the immuno-oncology agent. In another aspect, compound(s) of Formula (I) are administered concurrently with the immuno-oncology agent. In yet another aspect, compound(s) of Formula (I) are sequentially administered after administration of the immuno-oncology agent.

In another aspect, compounds of Formula (I) may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In one aspect, T cell responses can be stimulated by a combination of a compound of Formula (I) and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of Formula (I) for the treatment of cancer include antagonists of inhibitory receptors on NK cells or agonists of activating receptors on NK cells. For example, compounds of Formula (I) can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of Formula (I) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, BMS-986205, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the DGKα and DGKζ enzyme with a compound of Formula (I) includes the administration of a compound of the present invention to an individual or patient, such as a human, having DGKα and DGKζ, as well as, for example, introducing a compound of Formula (I) into a sample containing a cellular or purified preparation containing DGKα and DGKζ enzyme.

The term "DGKα and DGKζ inhibitor" refers to an agent capable of inhibiting the activity of diacylglycerol kinase alpha and/or diacylglycerol kinase zeta (DGKα and DGKζ) in T cells resulting in T cell stimulation. The DGKα and DGKζ inhibitor may be a reversible or irreversible DGKα and DGKζ inhibitor. "A reversible DGKα and DGKζ inhibitor" is a compound that reversibly inhibits DGKα and DGKζ enzyme activity either at the catalytic site or at a non-catalytic site and "an irreversible DGKα and DGKζ inhibitor" is a compound that irreversibly destroys DGKα and DGKζ enzyme activity by forming a covalent bond with the enzyme.

Types of cancers that may be treated with the compound of Formula (I) include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of Formula (I) for treatment of DGKα and DGKζ associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of Formula (I) include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds of Formula (I) may also be combined with immunotherapy drugs, including cytokines such as interferon alpha, interleukin 2, and tumor necrosis factor (TNF) in the treatment of melanoma.

Compounds of Formula (I) may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of Formula (I), using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 38.9° C. to 40° C. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors ORES SA®, SSI-774) and antibodies (Imclone: C225 [Goldstein et al., $Clin.$ $Cancer$ $Res.,$ 1:1311-1318 (1995)], and Abgenix: ABX-EGF); (iii) her-2/neu receptor inhibitors such as farnesyl transferase inhibitors (FTI) such as, for example, L-744,832 (Kohl et al., $Nat.$ $Med.,$ 1(8):792-797 (1995)); (iv) inhibitors of Akt family kinases or the Akt pathway, such as, for example, rapamycin (see, for example, Sekulic et al., $Cancer$ $Res.,$ 60:3504-3513 (2000)); (v) cell cycle kinase inhibitors such as, for example, flavopiridol and UCN-01 (see, for example, Sausville, $Curr.$ $Med.$ $Chem.$ $Anti-Canc.$ $Agents,$ 3:47-56 (2003)); and (vi) phosphatidyl inositol kinase inhibitors such as, for example, LY294002 (see, for example, Vlahos et al., $J.$ $Biol.$ $Chem.,$ 269:5241-5248 (1994)). Alternatively, at least one STI and at least one compound of Formula (I) may be in separate pharmaceutical compositions. In a specific embodiment of the present invention, at least one compound of Formula (I) and at least one STI may be administered to the patient concurrently or sequentially. In other words, at least one compound of Formula (I) may be administered first, at least one STI may be administered first, or at least one compound of Formula (I) and at least one STI may be administered at the same time. Additionally, when more than one compound of Formula (I) and/or STI is used, the compounds may be administered in any order.

The present invention further provides a pharmaceutical composition for the treatment of a chronic viral infection in a patient comprising at least one compound of Formula (I), optionally, at least one chemotherapeutic drug, and, optionally, at least one antiviral agent, in a pharmaceutically acceptable carrier.

Also provided is a method for treating a chronic viral infection in a patient by administering an effective amount of the above pharmaceutical composition.

In a specific embodiment of the present invention, at least one compound of Formula (I) and at least one chemotherapeutic agent are administered to the patient concurrently or sequentially. In other words, at least one compound of Formula (I) may be administered first, at least one chemotherapeutic agent may be administered first, or at least one compound of Formula (I) and the at least one STI may be administered at the same time. Additionally, when more than one compound of Formula (I) and/or chemotherapeutic agent is used, the compounds may be administered in any order. Similarly, any antiviral agent or STI may also be administered at any point in comparison to the administration of the compound of Formula (I).

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

Suitable antiviral agents contemplated for use in combination with the compound of Formula (I) can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir; BCH-I0652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir; DMP-450; BMS-2322623; ABT-378; and AG-1549. Other antiviral agents include hydroxyurea, ribavirin, IL-2, IL-12, pentafuside and Yissum Project No. 11607.

The present invention also includes pharmaceutical kits useful, for example, in the treatment or prevention of DGKα and DGKζ-associated diseases or disorders, and other diseases referred to herein which include one or more containers containing a pharmaceutical composition comprising a therapeutically effective amount of a compound of Formula (I). Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The invention also provides pharmaceutically acceptable compositions which comprise a therapeutically effective amount of one or more of the compounds of Formula (I), formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms; and not injurious to the patient.

The term "pharmaceutical composition" means a composition comprising a compound of the invention in combination with at least one additional pharmaceutically acceptable carrier.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 Volumes), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. L gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the therapeutic effect and gradually increase the dosage until the effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined below. Common intermediates are generally useful for the preparation of more than one Example and are identified sequentially (e.g., Intermediate 1, Intermediate 2, etc.) and are abbreviated as Int. 1 or I1, Int. 2 or I2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well-known bioisosteric replacements known in the art, for example, replacement of a carboxylic acid group with a tetrazole or a phosphate moiety. $^1$H NMR data collected in deuterated dimethyl sulfoxide used water suppression in the data processing. The reported spectra are uncorrected for the effects of water suppression. Protons adjacent to the water suppression frequency of 3.35 ppm exhibit diminished signal intensity.

Abbreviations

Ac acetyl
anhyd. anhydrous
aq. aqueous
Bn benzyl
Boc-anhydride di-tert-butyl dicarbonate
BOC-D-ABU-OH N-(tert-butoxycarbonyl)-D-alanine
BOP benzotriazol-1-yloxytris-(dimethylamino)-phosphonium hexafluorophosphate
Bu butyl
CDI carbonyldiimidazole
DCM dichloromethane
DEA diethylamine
DIEA or DIPEA diisopropylethylamine
DMAP dimethylamino pyridine
DMF dimethylformamide
DMSO dimethyl sulfoxide
dppf 1,1'-bis(diphenylphosphino)ferrocene
EDC 1-ethyl-3-(3-dimethylaminopropyl)carbodiimide
Et ethyl
EtOAc ethyl acetate
EtOH ethanol
h, hours or hrs hour(s)
H homochiral
H-ABU-OME HCl methyl (2S)-2-aminobutanoate, HCl
HATU (1-[bis(dimethylamino)methylene]-1H-1,2,3-triazolo[4,5-b]pyridinium 3-oxide hexafluorophosphate)
HCl hydrochloric acid
HPLC high pressure liquid chromatography
LC liquid chromatography
LCMS liquid chromatography-mass spectrometry
M molar
mM millimolar
Me methyl
MeOH methanol
Mesyl-Cl methanesulfonyl chloride
MHz megahertz
mins minute(s)
$M^{+1}$ $(M+H)^+$
MS mass spectrometry
n or N normal
$NH_4OAc$ ammonium acetate
nM nanomolar
NMP N-methylpyrrolidinone
$Pd_2(dba)_3$ tris-(dibenzylideneacetone)dipalladium
$PdCl_2$(dppf) [1,1'-Bis(diphenylphosphino)ferrocene]dichloropalladium(II)
pet ether petroleum ether
Ph phenyl
PMB para-methoxy benzyl
$POCl_3$ phosphorous oxychloride
rt or Ret time retention time
sat. saturated TBAF tetrabutylammonium fluoride
t-BuXphos 2-Di-tert-butylphosphino-2',4',6'-triisopropylbiphenyl
t-BuXphos-Rd-G1 chloro[2-(di-tert-butylphosphino)-2',4',6'-triisopropyl-1,1'-biphenyl][2-(2-aminoethyl)phenyl)] palladium(II)
TEA triethylamine
TFA trifluoroacetic acid
THF tetrahydrofuran
Xphos 2-dicyclohexylphosphino-2',4',6'-triisopropylbiphenyl LCMS Conditions:

Method A: Column: XBridge BEH XP C18 (50×2.1 mm, 2.5 μm); mobile phase A: 10 mM NH$_4$OAc in water: acetonitrile (95:5); mobile phase B: 10 mM NH$_4$OAc: acetonitrile (5:95); Gradient=0-100% B over 3 minutes; Temperature: 50° C.; Flow rate: 1.1 mL/min; Detection: UV at 220 nm.

Method B: Column: XBridge BEH XP C18 (50×2 mm, 2.5 μm); mobile phase A: 0.1% TFA in water: acetonitrile (95:5); mobile phase B: 0.1% TFA in water: acetonitrile (5:95); Gradient=0-100% B over 3 minutes; Temperature: 50° C.; Flow rate: 1.1 mL/min; Detection: UV at 220 nm.

Intermediate 1

6-Chloro-3-(methylamino)picolinamide

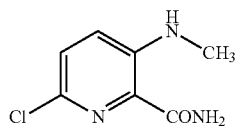

Intermediate 1 was prepared according to the method described in Adams et al., Bioorganic & Medicinal Chemistry Letters 26 (2016) 1086-1089.

Intermediate 2

6-Chloro-4-hydroxy-1-methylpyrido[3,2-d]pyrimidin-2(1H)-one

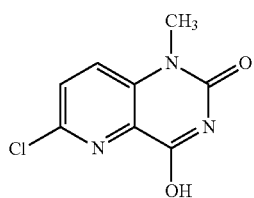

To a solution of 6-chloro-3-(methylamino)picolinamide (3 g, 16.16 mmol) in N,N-dimethylformamide (40 mL) was added NaH (1.29 g, 32.3 mmol, 60% w/w) at 0° C. The reaction mixture was stirred for 1 hour at room temperature. A solution of CDI (3.93 g, 24.24 mmol) in dimethylformamide (5 mL) was added and the reaction mixture was heated at 70° C. for 2 h. The reaction mixture was cooled to room temperature. The solid product separated was filtered, washed with water and dried under reduced pressure to afford 6-chloro-4-hydroxy-1-methylpyrido[3,2-d]pyrimidin-2(1H)-one (3.4 g, 85% yield). LCMS: m/z=212.1 (M+H); retention time 0.53 min. (Column: AQUITY UPLC BEH C18 (3.0×50 mm) 1.7 μm M. phase A: 10 mM NH$_4$OAc:ACN (95:5) M. phase B: 10 mM NH$_4$OAc:ACN (5:95) Description: Method: % B: 0 min-20:2 min-100:2.3 min-100, Flow: 0.7 mL/min). $^1$H NMR (300 Mhz, DMSO-d$_6$) δ 11.89 (br s, 1H), 8.00 (br d, J=8.4 Hz, 1H), 7.85 (br d, J=8.3 Hz, 1H), 3.42 (br s, 3H).

Intermediate 3

4,6-Dichloro-1-methylpyrido[3,2-d]pyrimidin-2(1H)-one

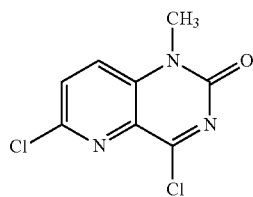

To a suspension of 6-chloro-4-hydroxy-1-methylpyrido[3,2-d]pyrimidin-2(1H)-one (2.0 g, 9.45 mmol) in dry toluene (20 mL) were added POCl$_3$ (4.40 mL, 47.3 mmol) and DIPEA (4.13 mL, 23.63 mmol) at room temperature. The reaction mixture was heated at 110° C. for 16 h. The reaction mixture was cooled to room temperature and the solvent was removed under reduced pressure. The crude product was dissolved in ethyl acetate and added K$_2$CO$_3$ (1.0 g), stirred for 5 min, diluted with water and extracted with ethyl acetate. The aqueous layer was basified and re-extracted with ethyl acetate (3×500 mL). The combined organic layer was dried over anhydrous Na$_2$SO$_4$, filtered and evaporated under reduced pressure to afford 4,6-dichloro-1-methylpyrido[3,2-d]pyrimidin-2(1H)-one (1.9 g, 32% yield) as a light brown semi-solid. LCMS: m/z=229.9 (M+H); rt 0.81 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20% B over 1.1 minute, then a 2.2 minute hold at 100% B; Temperature: 50° C.; Flow rate: 0.7 mL/min; Detection: UV at 110 nm).

Intermediate 4 tert-Butyl (2R,5S)-4-(6-chloro-1-methyl-2-oxo-1,2-dihydropyrido[3,2-d]pyrimidin-4-yl)-2,5-diethylpiperazine-1-carboxylate

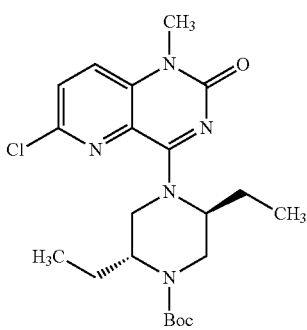 [SMILES: CC[C@@H]1CN(c2nc(=O)n(C)c3ccc(Cl)nc23)[C@@H](CC)CN1C(=O)OC(C)(C)C]

To a stirred solution of tert-butyl (2R,5S)-2,5-diethylpiperazine-1-carboxylate (1.37 g, 5.65 mmol) in acetonitrile (10 mL) were added DIPEA (2.3 mL, 13.04 mmol) and 4,6-dichloro-1-methylpyrido[3,2-d]pyrimidin-2(1H)-one (1.0 g, 4.35 mmol) at room temperature. The reaction mixture was heated at 85° C. for 6 h. The reaction mixture was cooled to room temperature and concentrated under reduced pressure to obtain the crude product, which was purified using silica gel column chromatography (60-70% EtOAc/petroleum ether; 40 g column) to afford tert-butyl (2R,5S)-4-(6-chloro-1-methyl-2-oxo-1,2-dihydropyrido[3,2-d]pyrimidin-4-yl)-2,5-diethylpiperazine-1-carboxylate (1.00 g, 47% yield). LCMS: m/z=436.2 (M+H); rt 1.82 min. LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20% B over 1.1 minute, then a 2.2 minute hold at 100% B; Temperature: 50° C.; Flow rate: 0.7 mL/min; Detection: UV at 110 nm).

Intermediate 5 tert-Butyl (2R,5S)-4-(6-cyano-1-methyl-2-oxo-1,2-dihydropyrido[3,2-d]pyrimidin-4-yl)-2,5-diethylpiperazine-1-carboxylate

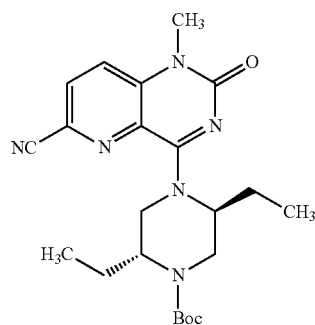 [SMILES: CC[C@@H]1CN(c2nc(=O)n(C)c3ccc(C#N)nc23)[C@@H](CC)CN1C(=O)OC(C)(C)C]

To a stirred solution of tert-butyl (2R,5S)-4-(6-chloro-1-methyl-2-oxo-1,2-dihydropyrido[3,2-d]pyrimidin-4-yl)-2,5-diethylpiperazine-1-carboxylate (1 g, 2.29 mmol) in NMP (5 mL) were added dppf (0.254 g, 0.459 mmol), zinc (0.15 g, 2.29 mmol) and zinc cyanide (0.54 g, 4.59 mmol). The reaction mixture was degassed for 5 min. and Pd$_2$(dba)$_3$ (0.21 g, 0.23 mmol) was added. The reaction mixture was heated at 90° C. overnight. The reaction mixture was cooled to room temperature, diluted with ethyl acetate and filtered through Celite pad. The filtrate was washed with water, brine and the organic layer was dried over anhydrous Na$_2$SO$_4$, filtered and evaporated under reduced pressure to obtain crude compound. The crude residue was purified using silica gel chromatography (70-80% EtOAc/petroleum ether; 40 g column) to afford the tert-butyl (2R,5S)-4-(6-chloro-1-methyl-2-oxo-1,2-dihydropyrido[3,2-d]pyrimidin-4-yl)-2,5-diethylpiperazine-1-carboxylate (0.8 g, 75% yield). LCMS: m/z=427.2 (M+H); rt 1.56 min. LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20% B over 1.1 minute, then a 2.2 minute hold at 100% B; Temperature: 50° C.; Flow rate: 0.7 mL/min; Detection: UV at 110 nm).

Intermediate 6

4-((2S,5R)-2,5-Diethylpiperazin-1-yl)-1-methyl-2-oxo-1,2-dihydropyrido[3,2-d]pyrimidine-6-carbonitrile, TFA

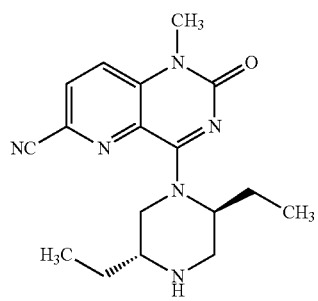 [SMILES: CC[C@@H]1CN(c2nc(=O)n(C)c3ccc(C#N)nc23)[C@@H](CC)CN1]

To a stirred solution of tert-butyl (2R,5S)-4-(6-cyano-1-methyl-2-oxo-1,2-dihydropyrido[3,2-d]pyrimidin-4-yl)-2,5-diethylpiperazine-1-carboxylate (0.46 g, 1.08 mmol) in dry DCM (10 mL) was added TFA (3.5 mL, 45.4 mmol) at room temperature. The reaction mixture was stirred for 2 h. The solvent was removed under reduced pressure to afford 4-((2S,5R)-2,5-diethylpiperazin-1-yl)-1-methyl-2-oxo-1,2-dihydropyrido[3,2-d]pyrimidine-6-carbonitrile, TFA (0.46 g, 55% yield). LCMS: m/z=327.2 (M+H); rt 0.61 min. LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate: acetonitrile (5:95), Gradient=20% B over 1.1 minute, then a 2.2 minute hold at 100% B; Temperature: 50° C.; Flow rate: 0.7 mL/min; Detection: UV at 110 nm).

Examples 1 and 2

4-((2S,5R)-2,5-Diethyl-4((4-fluorophenyl)(5-(trifluoromethyl)pyridin-2-yl)methyl) piperazin-1-yl)-1-methyl-2-oxo-1,2-dihydropyrido[3,2-d]pyrimidine-6-carbonitrile (1-2)

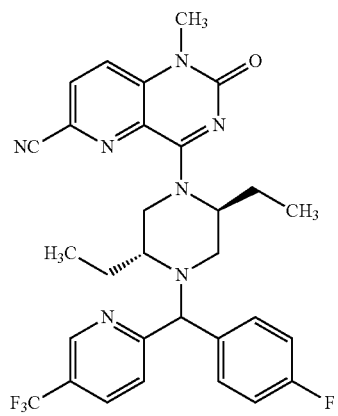

Coupling Method A: To a stirred solution of 4-((2S,5R)-2,5-diethylpiperazin-1-yl)-1-methyl-2-oxo-1,2-dihydropyrido[3,2-d]pyrimidine-6-carbonitrile, TFA (100 mg, 0.23 mmol) in acetonitrile (10 mL) was added DIPEA (0.12 mL, 0.68 mmol), followed by 2-(bromo(4-fluorophenyl)methyl)-5-(trifluoromethyl)pyridine (0.23 g, 0.68 mmol). The reaction mixture was heated at 85° C. overnight. The reaction mixture was cooled to room temperature and the solvent was removed under reduced pressure to yield the crude product, which was purified by preparative HPLC (HPLC Method: Column: Sunfire C18, 150×19 mm ID, 5 μm; Mobile Phase A: 10 mM ammonium acetate in water; Mobile Phase B: acetonitrile; Gradient: 0-100% B over 18 minutes, then a 5 minute hold at 100% B; Flow: 17 mL/min), fractions were concentrated under reduced pressure and lyophilized from (EtOH/H$_2$O, 1:5) to yield Example 1 and Example 2.

Example 1: 23 mg, 17% yield; LCMS: m/z=580.3 (M+H); rt 3.46 min; (LCMS method: Column: Column-Kinetex XB-C18 (75×3 mm-2.6 μm), Mobile phase A: 98% water: 2% acetonitrile; 10 mM ammonium formate; Mobile phase B: 2% Water: 98% acetonitrile; 10 mM ammonium formate; Flow: 1.0 mL/min; Temp: 50° C.; Time (min): 0-4; % B: 0-100%). $^1$H NMR (400 MHz, DMSO-d$_6$): δ ppm 8.91 (s, 1H), 8.29-8.15 (m, 2H), 8.02-7.91 (m, 2H), 7.68-7.60 (m, 2H), 7.23-7.13 (m, 2H), 5.95-5.85 (m, 0.5H), 5.42-5.32 (m, 0.5H), 5.05-5.01 (m, 1H), 4.97-4.89 (m, 1H), 3.70-3.63 (m, 1H), 3.46-3.40 (m, 4H), 2.71-2.65 (m, 2H), 2.36-2.29 (m, 1H), 2.09-1.89 (m, 1H), 1.68-1.38 (m, 2H), 0.84-0.73 (m, 3H), 0.70-0.48 (m, 3H).

Example 2: 11 mg, 8% yield; LCMS: m/z=580.3 (M+H); rt 3.46 min; (LCMS method: Column: Column-Kinetex XB-C18 (75×3 mm-2.6 μm), Mobile phase A: 98% water: 2% acetonitrile; 10 mM ammonium formate; Mobile phase B: 2% Water: 98% acetonitrile; 10 mM ammonium formate; Flow: 1.0 mL/min; Temp: 50° C.; Time (min): 0-4; % B: 0-100%). $^1$H NMR (400 MHz, DMSO-d$_6$): δ ppm 8.91 (s, 1H), 8.31-8.11 (m, 2H), 8.05-7.86 (m, 2H), 7.63-7.574 (m, 2H), 7.27-7.06 (m, 2H), 5.91-5.36 (m, 1H), 5.02 (s, 1H), 4.98-4.90 (m, 1H), 3.70-3.61 (m, 1H), 3.43-3.89 (m, 4H), 2.70-2.62 (m, 2H), 2.33-2.37 (m, 1H), 2.09-1.93 (m, 1H), 1.68-1.42 (m, 2H), 0.79 (q, J=7.2 Hz, 3H), 0.70-0.48 (m, 3H)

Examples 3 and 4

4-((2S,5R)-4-(1-(4-Cyclopropylphenyl)ethyl)-2,5-dimethylpiperazin-1-yl)-1-methyl-2-oxo-1,2-dihydropyrido[3,2-d]pyrimidine-6-carbonitrile (3-4)

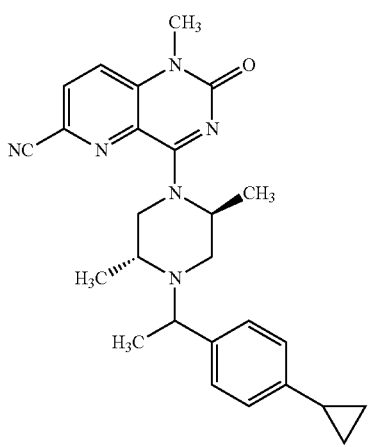

Coupling Method B: To a stirred solution of 4-((2S,5R)-2,5-dimethylpiperazin-1-yl)-1-methyl-2-oxo-1,2-dihydropyrido[3,2-d]pyrimidine-6-carbonitrile (60 mg, 0.20 mmol) in acetonitrile (8 mL) were added DIPEA (0.11 mL, 0.60 mmol), 1-(1-chloroethyl)-4-cyclopropylbenzene (43.6 mg, 0.24 mmol) and sodium iodide (15.1 mg, 0.10 mmol). The reaction mixture was heated at 85° C. for 16 h. The reaction mixture was cooled to room temperature and the solvent was removed under reduced pressure and the residue was dissolved in ethyl acetate, washed with brine, dried over Na$_2$SO$_4$ and concentrated under reduced pressure to yield the crude product, which was purified by preparative HPLC (HPLC Method: Column: Gemini NX (250 mm×21.2 mm ID, 5 μm) Mobile phase A=10 mM ammonium acetate in water Mobile phase B=acetonitrile: MeOH (1:1) Gradient: 0-100% B over 16 minutes, then a 5 minute hold at 100% B; Flow: 19 mL/min) to yield a diastereomeric mixture of product, which was purified by preparative chiral HPLC (Chiral HPLC Method: Column: Cellulose-5 (250×19 ID) 5 micron Mobile Phase A: 10 mM NH$_4$OAc in MeOH Flow: 25 mL/min). The fractions were concentrated under reduced pressure and lyophilized from EtOH/H$_2$O (1:5) to yield Example 3 and Example 4.

Example 3 (1.5 mg, 2% yield). LCMS: m/z=443.3 (M+H); rt 2.25 min; (LCMS method: Column: XBridge BEH XP C18 (50×2.1 mm), 2.5 μm; Mobile phase A: 95% water: 5% acetonitrile; 10 mM ammonium acetate; Mobile phase B: 5% Water: 95% acetonitrile; 10 mM ammonium acetate; Flow: 1.1 mL/min; Temp: 50° C.; Time (min): 0-3; % B: 0-100%). $^1$H NMR; (400 MHz, DMSO-d$_6$) δ ppm 8.22 (br d, J=8.6 Hz, 1H), 8.00-7.94 (m, 1H), 7.28-7.22 (m, 2H), 7.07-7.02 (m, 2H), 5.79-4.12 (m, 2H), 3.57-3.52 (m, 2H), 3.44-3.41 (s, 3H), 2.89-2.76 (m, 3H), 1.94-1.84 (m, 1H), 1.52-1.37 (m, 3H), 1.25-1.19 (m, 3H), 0.95-0.84 (m, 5H), 0.70-0.62 (m, 2H).

Example 4 (2.0 mg, 2% yield). LCMS: m/z=443.3 (M+H); rt 2.26 min; (LCMS method: Column: XBridge BEH XP C18 (50×2.1 mm), 2.5 μm; Mobile phase A: 95% water: 5% acetonitrile; 10 mM ammonium acetate; Mobile phase B: 5% water: 95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.23 (d, J=8.6 Hz, 1H), 7.99 (d, J=8.8 Hz, 1H), 7.24 (d, J=8.1 Hz, 2H), 7.03 (d, J=8.3 Hz, 2H), 5.75-5.38 (m, 0.5H), 5.06-4.68 (m, 0.5H), 3.58-3.53 (m, 1H), 3.44 (s, 3H), 3.42-3.38 (m, 1H), 2.59-2.54 (m, 3H), 2.25-2.16 (m, 1H), 1.94-1.84 (m, 1H), 1.37-1.19 (m, 6H), 1.12-0.98 (m, 3H), 0.96-0.89 (m, 2H), 0.69-0.62 (m, 2H).

Examples 5 and 6

4-((2S,5R)-2,5-Diethyl-4-(1-(4-(trifluoromethyl)phenyl)propyl)piperazin-1-yl)-1-methyl-2-oxo-1,2-dihydropyrido[3,2-d]pyrimidine-6-carbonitrile

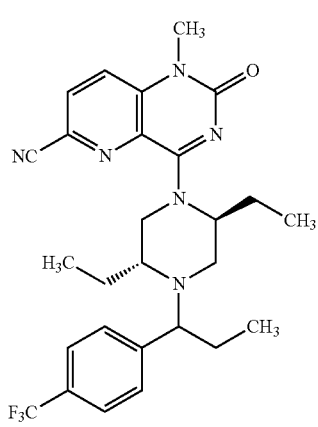

(5-6)

To a stirred solution of 4-((2S,5R)-2,5-diethylpiperazin-1-yl)-1-methyl-2-oxo-1,2-dihydropyrido[3,2-d]pyrimidine-6-carbonitrile, TFA (0.12 g, 0.27 mmol) in acetonitrile (10 mL) were added DIPEA (0.14 mL, 0.82 mmol), 1-(1-chloropropyl)-4-(trifluoromethyl)benzene (0.12 g, 0.55 mmol), and sodium iodide (0.04 g, 0.27 mmol). The reaction mixture was heated at 85° C. for 16 h. The reaction mixture was cooled to room temperature and the solvent was removed under reduced pressure to yield the crude product, which was purified by preparative HPLC [HPLC Method: Column: Sunfire C18, 150×19 mm ID, 5 µm; Mobile Phase A: 10 mM ammonium acetate in water; Mobile Phase B: acetonitrile; Gradient: 0-100% B over 18 minutes, then a 5 minute hold at 100% B; Flow: 17 mL/min]. The fractions were concentrated under reduced pressure and lyophilized from EtOH/H$_2$O (1:5) to yield Examples 5 and 6.

Example 5: (10 mg, 7% yield); LCMS: m/z=513.3 (M+H); rt 2.52 min; (LCMS method: Column: XBridge BEH XP C18 (50×2.1) mm, 2.5 µm Mobile phase A: 95% water: 5% acetonitrile; 10 mM ammonium formate; Mobile phase B: 5% Water: 95% acetonitrile; 10 mM ammonium formate; Flow: 1.1 mL/min; Temp: 50° C.; Time (min): 0-4; % B: 0-100; $^1$H NMR (400 MHz, DMSO-d$_6$) δ 8.24 (d, J=6.6 Hz, 1H), 7.98 (d, J=9.0 Hz, 1H), 7.73 (d, J=8.1 Hz, 2H), 7.56 (d, J=7.1 Hz, 2H), 5.83-5.48 (m, 1H), 4.98-4.86 (m, 1H), 3.64 (br. s., 1H), 3.43 (s, 3H), 3.08 (d, J=9.8 Hz, 1H), 2.93-2.82 (m, 2H), 2.42-2.26 (m, 1H), 2.13-2.08 (m, 1H), 1.98-1.82 (m, 3H), 1.66-1.54 (m, 1H), 1.44-1.31 (m, 1H), 0.98-0.91 (br. s., 3H), 0.69-0.53 (m, 6H).

Example 6: (3 mg, 2% yield); LCMS: m/z=513.3 (M+H); rt 2.54 min; (LCMS method: Column: XBridge BEH XP C18 (50×2.1) mm, 2.5 µm Mobile phase A: 95% water: 5% acetonitrile; 10 mM ammonium formate; Mobile phase B: 5% Water: 95% acetonitrile; 10 mM ammonium formate; Flow: 1.1 mL/min; Temp: 50° C.; Time (min): 0-4; % B: 0-100; $^1$H NMR (400 MHz, DMSO-d$_6$) δ 8.28-8.19 (m, 1H), 8.01-7.95 (m, 1H), 7.72 (d, J=7.8 Hz, 2H), 7.58 (d, J=8.6 Hz, 2H), 6.06-5.28 (m, 1H), 5.08-4.76 (m, 1H), 3.64-3.50 (m, 2H), 3.43 (s, 3H), 3.16-3.08 (m, 1H), 2.25-2.14 (m, 2H), 2.00-1.83 (m, 3H), 1.57-1.53 (m, 3H), 1.03-0.89 (m, 3H), 0.65-0.54 (m, 6H).

Examples 7 and 8

4-((2S,5R)-5-Ethyl-2-methyl-4-(1-(4-(trifluoromethyl)phenyl)ethyl)piperazin-1-yl)-1-methyl-2-oxo-1,2-dihydropyrido[3,2-d]pyrimidine-6-carbonitrile

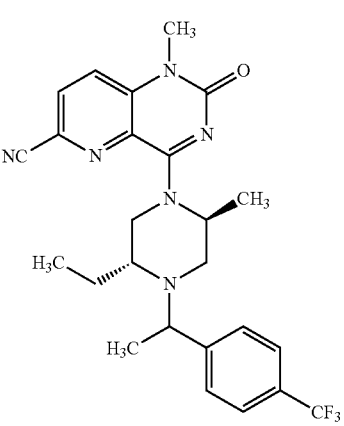

(7-8)

To a stirred solution of 4-((2S,5R)-5-ethyl-2-methylpiperazin-1-yl)-1-methyl-2-oxo-1,2-dihydropyrido[3,2-d]pyrimidine-6-carbonitrile, TFA (70 mg, 0.22 mmol) in acetonitrile (2 mL) at room temperature were added DIPEA (0.12 mL, 0.67 mmol), 1-(1-chloroethyl)-4-(trifluoromethyl)benzene (93 mg, 0.45 mmol), sodium iodide (33.6 mg, 0.22 mmol) and heated at 85° C. for 16 h. The reaction mixture cooled to room temperature and the solvent was removed under reduced pressure, the residue was dissolved in ethyl acetate (100 mL). The organic layer was washed with brine, dried over Na$_2$SO$_4$ and concentrated under reduced pressure to yield the crude product, which was purified by preparative HPLC [HPLC Method: Column: Sunfire C18 (150 mm×19.2 mm ID, 5 µm), Mobile phase A=10 mM ammonium acetate in water, Mobile phase B=acetonitrile, Flow: 19 mL/min], fractions were concentrated under reduced pressure, diluted with EtOH/H$_2$O (1:5), and lyophilized to yield Examples 7 and 8.

Example 7: (9 mg, 8% yield); LCMS: m/z=485.1 (M+H); rt 2.34 min; (LCMS method: Column: XBridge BEH XP C18 (50×2.1 mm), 2.5 µm; Mobile phase A: 95% water: 5% acetonitrile; 10 mM ammonium acetate; Mobile phase B: 5% Water: 95% acetonitrile; 10 mM ammonium acetate; Flow: 1.1 mL/min; Temp: 50° C.; Time (min): 0-3; % B: 0-100. $^1$H NMR (400 MHz, DMSO-d$_6$) δ ppm 8.32-8.17 (m, 1H), 8.05-7.94 (m, 1H), 7.76-7.66 (m, 2H), 7.66-7.55 (m, 2H), 6.11-5.42 (m, 1H), 5.10-4.79 (m, 1H), 3.78-3.59 (m, 2H), 3.44 (s, 3H), 3.17-3.05 (m, 1H), 2.64-2.55 (m, 1H), 2.26-2.09 (m, 1H), 1.65-1.34 (m, 3H), 1.31-1.16 (m, 5H), 1.01 (br t, J=7.1 Hz, 3H)

Example 8: (9 mg, 8% yield); LCMS: m/z=485.1 (M+H); rt 2.29 min; (LCMS Method: Column: XBridge BEH XP C18 (50×2.1 mm), 2.5 µm; Mobile phase A: 95% water: 5% acetonitrile; 10 mM ammonium acetate; Mobile phase B: 5% Water: 95% acetonitrile; 10 mM ammonium acetate; Flow: 1.1 mL/min; Temp: 50° C.; Time (min): 0-3; % B: 0-100%). $^1$H NMR (400 MHz, DMSO-d$_6$) δ ppm 8.24 (br d, J=8.6 Hz, 1H), 7.99 (d, J=9.0 Hz, 1H), 7.73 (d, J=8.3 Hz, 2H), 7.61 (br d, J=8.3 Hz, 2H), 5.87-5.63 (m, 1H), 5.10-4.79 (m, 1H), 3.90-3.80 (m, 1H), 3.44 (s, 3H), 3.46-3.15 (m, 1H), 2.89-2.73 (m, 2H), 2.41-2.34 (m, 1H), 1.63-1.34 (m, 5H), 1.29 (br d, J=6.1 Hz, 3H), 0.79-0.64 (m, 3H)

The examples in the Table 1 were prepared according to the general procedure described in Examples 1 to 4, using the appropriate benzhydryl/α-substituted benzyl/benzyl halide. When the reaction provided a mixture of diastereomers, the mixture was separated at the final stage using either preparative chromatography or preparative chiral chromatography. The absolute stereochemistry was not assigned at the newly formed carbon-nitrogen bond. Coupling Method A is described in the general procedure for the preparation of Examples 1 and 2. Coupling Method B is described in the general procedure for the preparation of Examples 3 and 4.

TABLE 1

| Ex. No. | Structure | Stereo Chem. | LCMS Method | LCMS RT | M + H | Coupling Method |
| --- | --- | --- | --- | --- | --- | --- |
| 9 | 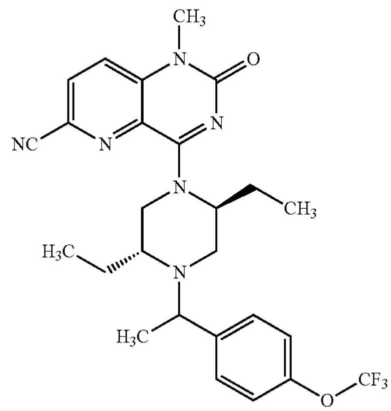 [SMILES: CC[C@H]1CN(C(C)c2ccc(OC(F)(F)F)cc2)[C@H](CC)CN1c1nc(=O)n(C)c2ccc(C#N)nc12] | H | A | 2.45 | 515.2 | B |
| 10 | 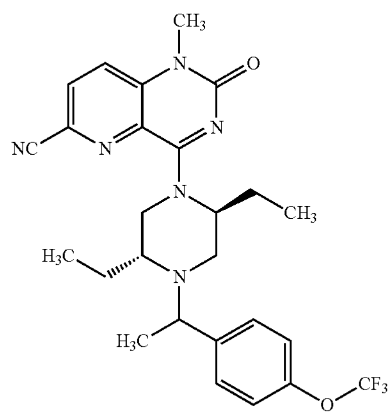 [SMILES: CC[C@H]1CN(C(C)c2ccc(OC(F)(F)F)cc2)[C@H](CC)CN1c1nc(=O)n(C)c2ccc(C#N)nc12] | H | A | 2.47 | 515.3 | B |
| 11 | 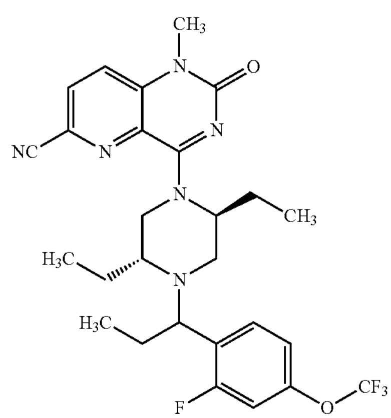 [SMILES: CCC(c1ccc(OC(F)(F)F)cc1F)N1C[C@H](CC)N(c2nc(=O)n(C)c3ccc(C#N)nc23)C[C@H]1CC] | H | A | 2.56 | 547.2 | B |

TABLE 1-continued

| Ex. No. | Structure | Stereo Chem. | LCMS Method | LCMS RT | M + H | Coupling Method |
|---|---|---|---|---|---|---|
| 12 | 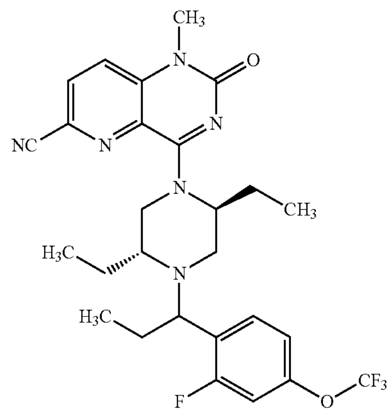 [SMILES: CCC(c1ccc(OC(F)(F)F)cc1F)N1C[C@H](CC)N(c2nc(=O)n(C)c3ccc(C#N)nc23)C[C@H]1CC] | H | A | 2.59 | 547.2 | B |
| 13 | 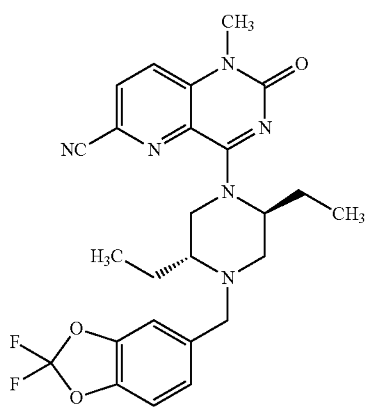 [SMILES: CC[C@@H]1CN(c2nc(=O)n(C)c3ccc(C#N)nc23)[C@@H](CC)CN1Cc1ccc2c(c1)OC(F)(F)O2] | H | A | 2.33 | 497.2 | A |
| 14 | 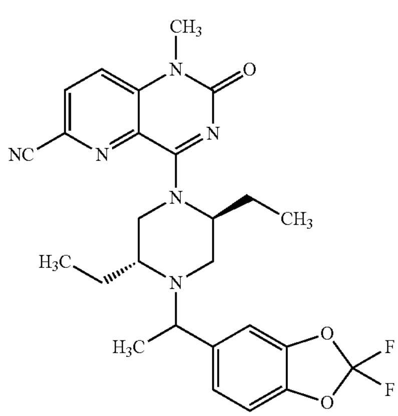 [SMILES: CC[C@H]1CN(C(C)c2ccc3c(c2)OC(F)(F)O3)[C@H](CC)CN1c1nc(=O)n(C)c2ccc(C#N)nc12] | H | A | 2.43 | 511.3 | B |

TABLE 1-continued
| Ex. No. | Structure | Stereo Chem. | LCMS Method | LCMS RT | M + H | Coupling Method |
|---|---|---|---|---|---|---|
| 15 | 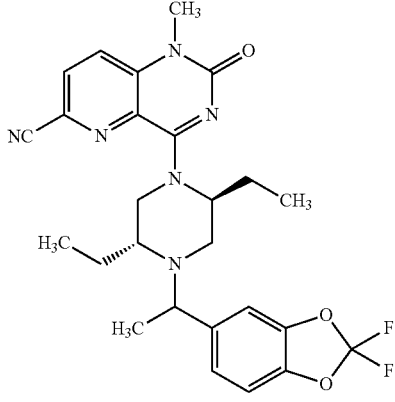 [SMILES: CC[C@H]1CN(C(C)c2ccc3c(c2)OC(F)(F)O3)[C@H](CC)CN1c1nc(=O)n(C)c2ccc(C#N)nc12] | H | A | 2.44 | 511.3 | B |
| 16 | 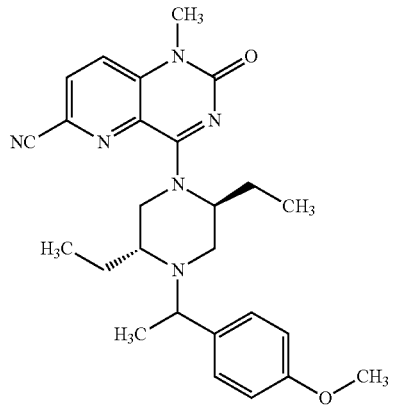 [SMILES: CC[C@H]1CN(C(C)c2ccc(OC)cc2)[C@H](CC)CN1c1nc(=O)n(C)c2ccc(C#N)nc12] | H | A | 2.16 | 461.3 | B |
| 17 | 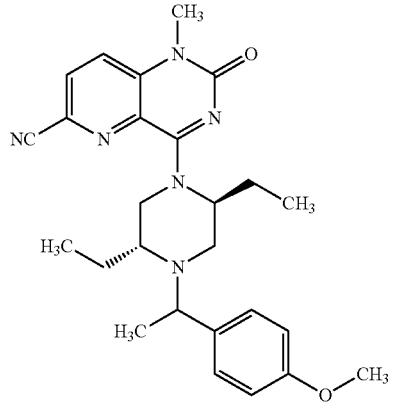 [SMILES: CC[C@H]1CN(C(C)c2ccc(OC)cc2)[C@H](CC)CN1c1nc(=O)n(C)c2ccc(C#N)nc12] | H | A | 2.19 | 461.3 | B |

TABLE 1-continued

| Ex. No. | Structure | Stereo Chem. | LCMS Method | LCMS RT | M + H | Coupling Method |
|---|---|---|---|---|---|---|
| 18 | 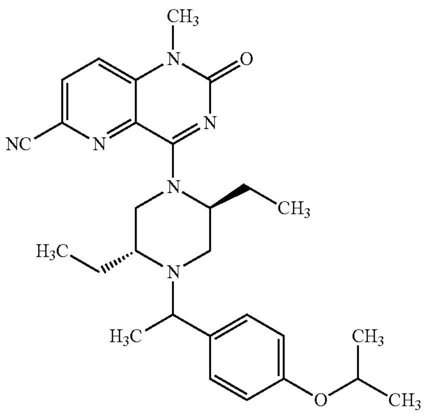 [SMILES: CC[C@H]1CN(C(C)c2ccc(OC(C)C)cc2)[C@H](CC)CN1c1nc(=O)n(C)c2ccc(C#N)nc12] | H | A | 2.43 | 489.3 | B |
| 19 | 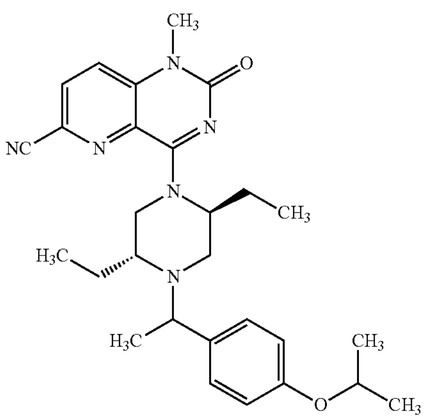 [SMILES: CC[C@H]1CN(C(C)c2ccc(OC(C)C)cc2)[C@H](CC)CN1c1nc(=O)n(C)c2ccc(C#N)nc12] | H | A | 2.41 | 489.3 | B |
| 20 | 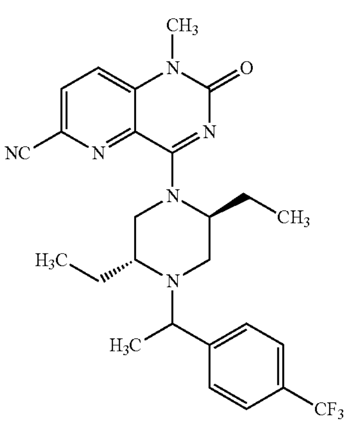 [SMILES: CC[C@H]1CN(C(C)c2ccc(C(F)(F)F)cc2)[C@H](CC)CN1c1nc(=O)n(C)c2ccc(C#N)nc12] | H | A | 2.42 | 499.1 | B |

TABLE 1-continued

| Ex. No. | Structure | Stereo Chem. | LCMS Method | LCMS RT | M + H | Coupling Method |
|---|---|---|---|---|---|---|
| 21 | 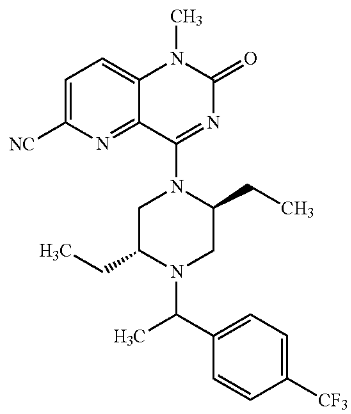 [SMILES: CC[C@H]1CN(C(C)c2ccc(C(F)(F)F)cc2)[C@H](CC)CN1c1nc(=O)n(C)c2ccc(C#N)nc12] | H | A | 1.45 | 499.3 | B |
| 22 | 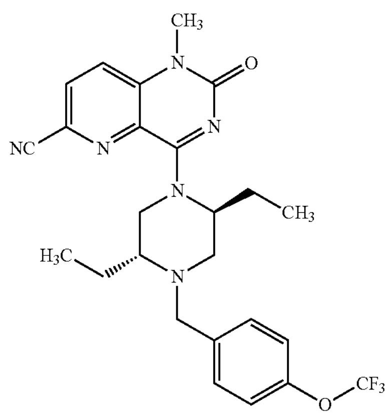 [SMILES: CC[C@@H]1CN(c2nc(=O)n(C)c3ccc(C#N)nc23)[C@@H](CC)CN1Cc1ccc(OC(F)(F)F)cc1] | H | A | 2.37 | 501.1 | A |
| 23 | 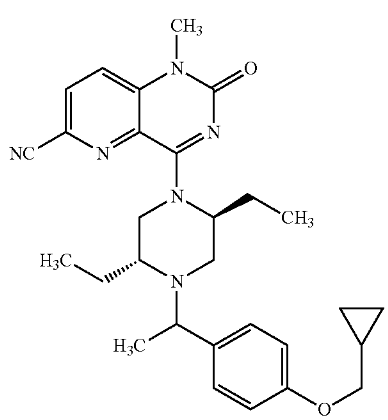 [SMILES: CC[C@H]1CN(C(C)c2ccc(OCC3CC3)cc2)[C@H](CC)CN1c1nc(=O)n(C)c2ccc(C#N)nc12] | H | A | 2.41 | 501.1 | B |

TABLE 1-continued

| Ex. No. | Structure | Stereo Chem. | LCMS Method | LCMS RT | M + H | Coupling Method |
|---|---|---|---|---|---|---|
| 24 | 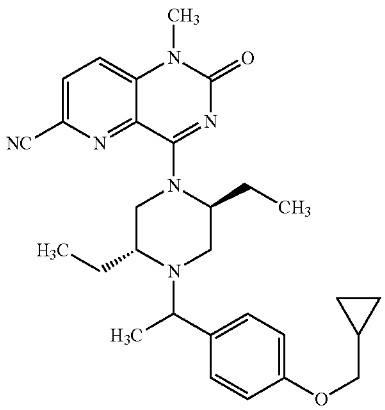 [SMILES: CC[C@H]1CN(C(C)c2ccc(OCC3CC3)cc2)[C@H](CC)CN1c1nc(=O)n(C)c2ccc(C#N)nc12] | H | A | 2.43 | 501.2 | B |
| 25 | 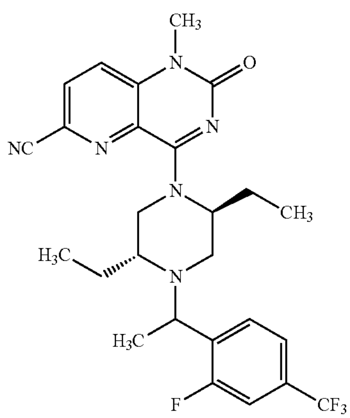 [SMILES: CC[C@H]1CN(C(C)c2ccc(C(F)(F)F)cc2F)[C@H](CC)CN1c1nc(=O)n(C)c2ccc(C#N)nc12] | H | A | 2.47 | 517.3 | B |
| 26 | 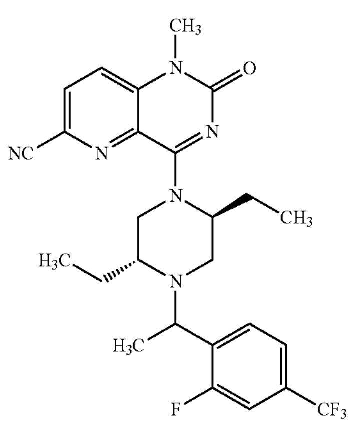 [SMILES: CC[C@H]1CN(C(C)c2ccc(C(F)(F)F)cc2F)[C@H](CC)CN1c1nc(=O)n(C)c2ccc(C#N)nc12] | H | A | 2.45 | 517.3 | B |

TABLE 1-continued

| Ex. No. | Structure | Stereo Chem. | LCMS Method | LCMS RT | M + H | Coupling Method |
|---|---|---|---|---|---|---|
| 27 | 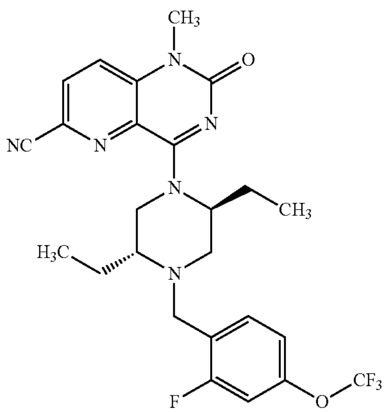 [SMILES: CC[C@@H]1CN(c2nc(=O)n(C)c3ccc(C#N)nc23)[C@@H](CC)CN1Cc1ccc(OC(F)(F)F)cc1F] | H | A | 2.41 | 519.3 | A |
| 28 | 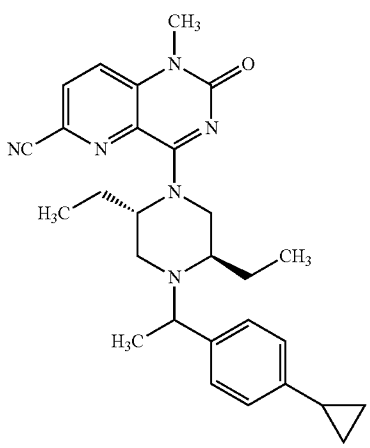 [SMILES: CC[C@H]1CN(C(C)c2ccc(C3CC3)cc2)[C@H](CC)CN1c1nc(=O)n(C)c2ccc(C#N)nc12] | H | A | 2.5 | 471.3 | B |
| 29 | 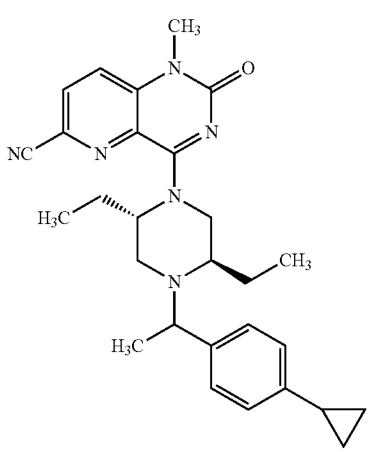 [SMILES: CC[C@H]1CN(C(C)c2ccc(C3CC3)cc2)[C@H](CC)CN1c1nc(=O)n(C)c2ccc(C#N)nc12] | H | A | 2.48 | 471.3 | B |

TABLE 1-continued
| Ex. No. | Structure | Stereo Chem. | LCMS Method | LCMS RT | M + H | Coupling Method |
|---|---|---|---|---|---|---|
| 30 | 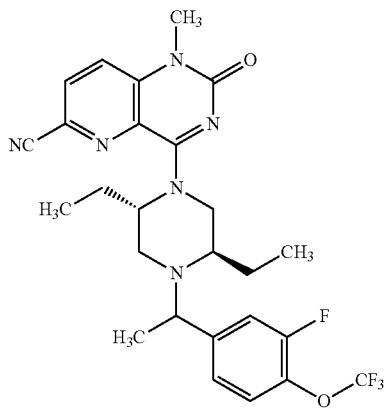 [SMILES: CC[C@H]1CN(C(C)c2ccc(OC(F)(F)F)c(F)c2)[C@H](CC)CN1c1nc(=O)n(C)c2ccc(C#N)nc12] | H | A | 2.47 | 533.3 | B |
| 31 | 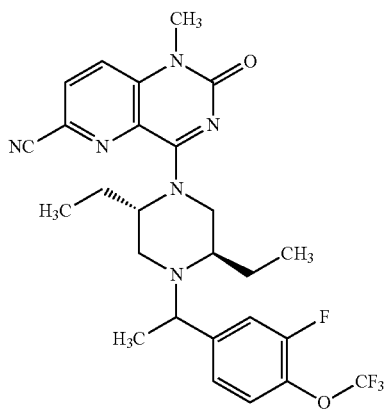 [SMILES: CC[C@H]1CN(C(C)c2ccc(OC(F)(F)F)c(F)c2)[C@H](CC)CN1c1nc(=O)n(C)c2ccc(C#N)nc12] | H | A | 2.49 | 533.3 | B |
| 32 | 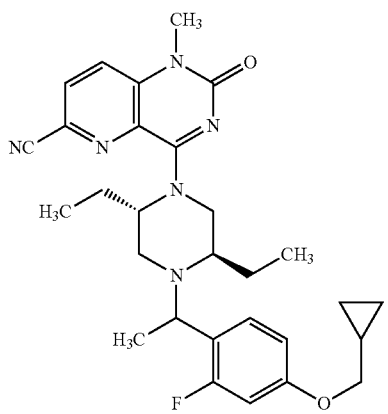 [SMILES: CC[C@H]1CN(C(C)c2ccc(OCC3CC3)cc2F)[C@H](CC)CN1c1nc(=O)n(C)c2ccc(C#N)nc12] | H | A | 2.46 | 519.3 | B |

TABLE 1-continued

| Ex. No. | Structure | Stereo Chem. | LCMS Method | LCMS RT | M + H | Coupling Method |
|---|---|---|---|---|---|---|
| 33 | 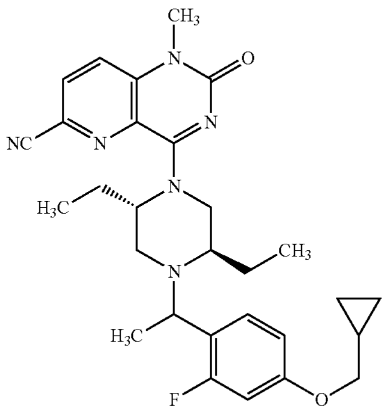 [SMILES: CC[C@H]1CN(C(C)c2ccc(OCC3CC3)cc2F)[C@H](CC)CN1c1nc(=O)n(C)c2ccc(C#N)nc12] | H | A | 2.48 | 519.4 | B |
| 34 | 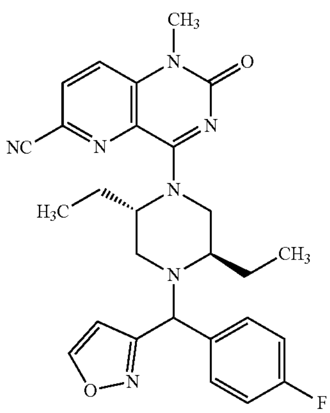 [SMILES: CC[C@H]1CN(C(c2ccc(F)cc2)c2ccon2)[C@H](CC)CN1c1nc(=O)n(C)c2ccc(C#N)nc12] | H | A | 1.98 | 502.3 | A |
| 35 | 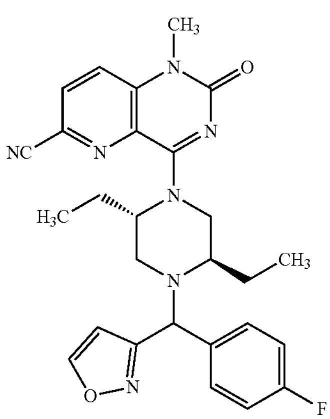 [SMILES: CC[C@H]1CN(C(c2ccc(F)cc2)c2ccon2)[C@H](CC)CN1c1nc(=O)n(C)c2ccc(C#N)nc12] | H | A | 1.96 | 502.3 | A |

TABLE 1-continued

| Ex. No. | Structure | Stereo Chem. | LCMS Method | LCMS RT | M + H | Coupling Method |
|---|---|---|---|---|---|---|
| 36 | 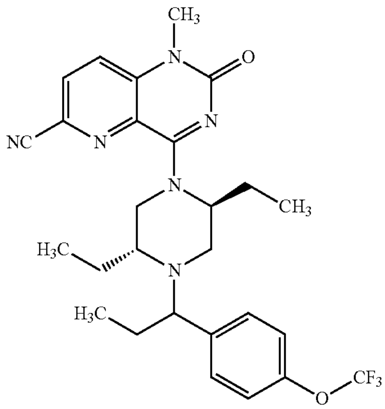 [SMILES: CCC(c1ccc(OC(F)(F)F)cc1)N1C[C@H](CC)N(c2nc(=O)n(C)c3ccc(C#N)nc23)C[C@H]1CC] | H | A | 2.57 | 529.3 | B |
| 37 | 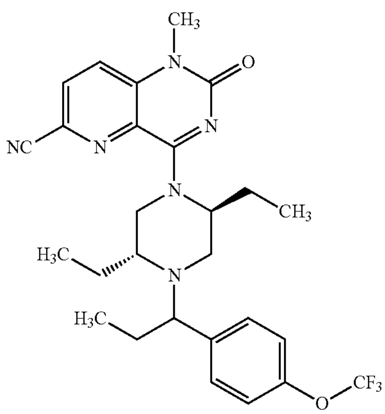 [SMILES: CCC(c1ccc(OC(F)(F)F)cc1)N1C[C@H](CC)N(c2nc(=O)n(C)c3ccc(C#N)nc23)C[C@H]1CC] | H | A | 2.59 | 529.3 | B |
| 38 | 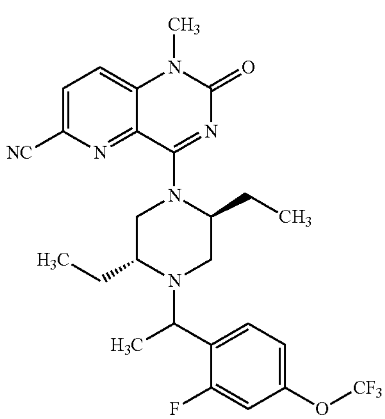 [SMILES: CC[C@H]1CN(C(C)c2ccc(OC(F)(F)F)cc2F)[C@H](CC)CN1c1nc(=O)n(C)c2ccc(C#N)nc12] | H | A | 2.49 | 533.3 | B |

TABLE 1-continued

| Ex. No. | Structure | Stereo Chem. | LCMS Method | LCMS RT | M + H | Coupling Method |
|---|---|---|---|---|---|---|
| 39 | 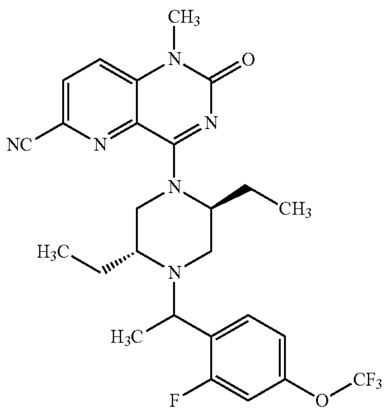 [SMILES: CC[C@H]1CN(C(C)c2ccc(OC(F)(F)F)cc2F)[C@H](CC)CN1c1nc(=O)n(C)c2ccc(C#N)nc12] | H | A | 2.52 | 533.3 | B |
| 40 | 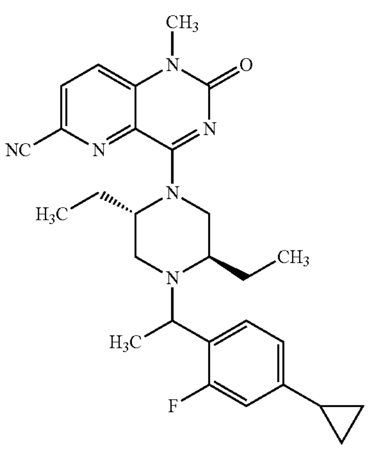 [SMILES: CC[C@H]1CN(C(C)c2ccc(C3CC3)cc2F)[C@H](CC)CN1c1nc(=O)n(C)c2ccc(C#N)nc12] | H | A | 2.47 | 489.4 | B |
| 41 | 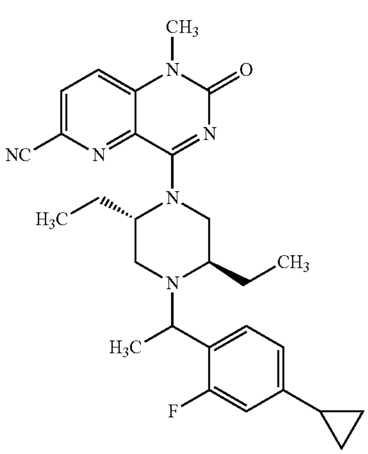 [SMILES: CC[C@H]1CN(C(C)c2ccc(C3CC3)cc2F)[C@H](CC)CN1c1nc(=O)n(C)c2ccc(C#N)nc12] | H | A | 2.49 | 489.3 | B |

TABLE 1-continued
| Ex. No. | Structure | Stereo Chem. | LCMS Method | LCMS RT | M + H | Coupling Method |
|---|---|---|---|---|---|---|
| 42 | 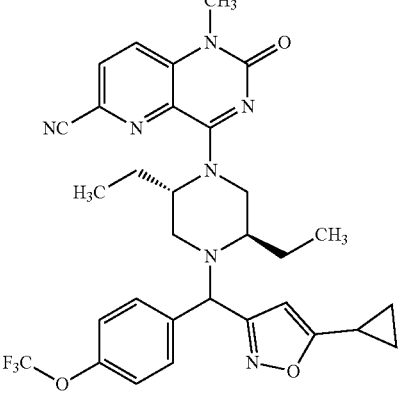 | H | A | 2.38 | 608.3 | A |
| 43 | 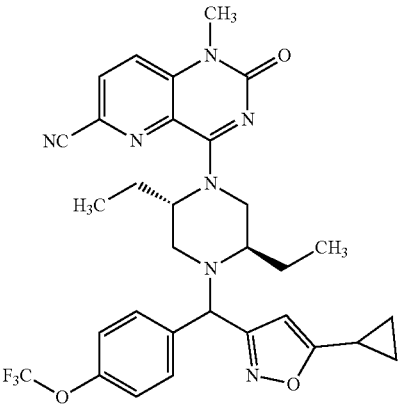 [SMILES: CC[C@H]1CN(C(c2ccc(OC(F)(F)F)cc2)c2cc(C3CC3)on2)[C@H](CC)CN1c1nc(=O)n(C)c2ccc(C#N)nc12] | H | A | 2.39 | 608.3 | A |
| 44 | 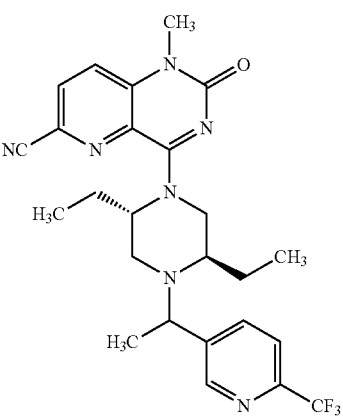 [SMILES: CC[C@H]1CN(C(C)c2ccc(C(F)(F)F)nc2)[C@H](CC)CN1c1nc(=O)n(C)c2ccc(C#N)nc12] | H | A | 3.07 | 500.2 | B |

TABLE 1-continued

| Ex. No. | Structure | Stereo Chem. | LCMS Method | LCMS RT | M + H | Coupling Method |
|---|---|---|---|---|---|---|
| 45 | 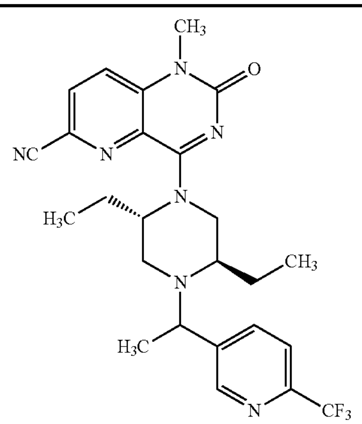 | H | A | 3.05 | 500.2 | B |

Examples 46 and 47

4-((2S,5R)-5-Ethyl-4-((4-fluorophenyl)(5-(trifluoromethyl)pyridin-2-yl)methyl)-2-methylpiperazin-1-yl)-1-methyl-2-oxo-1,2-dihydropyrido[3,2-d]pyrimidine-6-carbonitrile

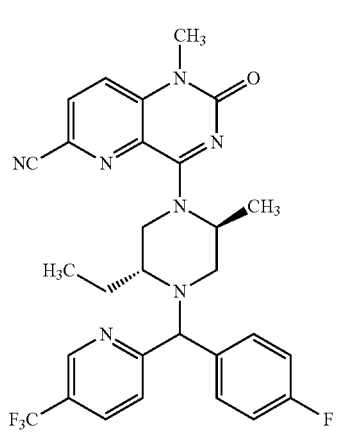

(46-47)

To a stirred solution of 4-((2S,5R)-5-ethyl-2-methylpiperazin-1-yl)-1-methyl-2-oxo-1,2-dihydropyrido[3,2-d]pyrimidine-6-carbonitrile, TFA (0.5 g, 1.17 mmol) in acetonitrile (10 mL) was added DIPEA (1.02 mL, 5.86 mmol), followed by 2-(bromo(4-fluorophenyl)methyl)-5-(trifluoromethyl)pyridine (0.78 mg, 2.35 mmol). The reaction mixture was heated at 80° C. for 3 h. The reaction mixture was cooled to room temperature and the solvent was removed under reduced pressure to yield the crude product, which was purified by preparative HPLC (HPLC Method: Column: INERTSIL ODS 21.2×250 mm, 5 µm; Mobile Phase A: 0.1% TFA in water; Mobile Phase B: acetonitrile; Gradient: 30-80% B over 14 minutes, then a 5 minute hold at 100% B; Flow: 17 mL/min), fractions were concentrated under reduced pressure and lyophilized from (EtOH/H$_2$O, 1:5) to yield Example 46 and Example 47.

Example 46: 140 mg, 21% yield; LCMS: m/z=566.2 (M+H); rt 3.26 min; (LCMS method: Column: Column-Kinetex XB-C18 (75×3 mm-2.6 µm), Mobile phase A: 98% water: 2% acetonitrile; 10 mM ammonium formate; Mobile phase B: 2% Water: 98% acetonitrile; 10 mM ammonium formate; Flow: 1.0 mL/min; Temp: 50° C.; Time (min): 0-4; % B: 0-100%). $^1$H NMR (400 MHz, DMSO-d$_6$) δ ppm 8.83 (br s, 1H), 8.19-8.31 (m, 2 H), 7.95-8.12 (m, 2H), 7.53-7.63 (m, 2H), 7.12-7.26 (m, 2H), 5.41-6.26 (m, 1H), 4.79-5.20 (m, 2H), 3.60-3.74 (m, 1H), 3.44 (s, 3H), 2.73-2.87 (m, 1H), 2.22-2.42 (m, 2H), 1.40-1.68 (m, 5H), 0.53-0.71 (m, 3H).

Example 47: 155 mg, 23% yield; LCMS: m/z=566.2 (M+H); rt 3.25 min; (LCMS method: Column: Column-Kinetex XB-C18 (75×3 mm-2.6 µm), Mobile phase A: 98% water: 2% acetonitrile; 10 mM ammonium formate; Mobile phase B: 2% Water: 98% acetonitrile; 10 mM ammonium formate; Flow: 1.0 mL/min; Temp: 50° C.; Time (min): 0-4; % B: 0-100%). $^1$H NMR (400 MHz, DMSO-d$_6$) δ ppm 8.92 (s, 1H), 8.17-8.27 (m, 2H), 7.90-8.02 (m, 2H), 7.60-7.67 (m, 2H), 7.14-7.22 (m, 2H), 5.52-6.07 (m, 1H), 4.87-5.08 (m, 2H), 3.39-3.71 (m, 4H), 2.69-2.78 (m, 1H), 2.37-2.45 (m, 1H), 1.37-1.69 (m, 5H), 0.58-0.77 (m, 3H).

Examples 96 and 97

4-((2S,5R)-4-((4-chlorophenyl)(pyridin-2-yl)methyl)-5-ethyl-2-methylpiperazin-1-yl)-1-methyl-2-oxo-1,2-dihydropyrido[3,2-d]pyrimidine-6-carbonitrile

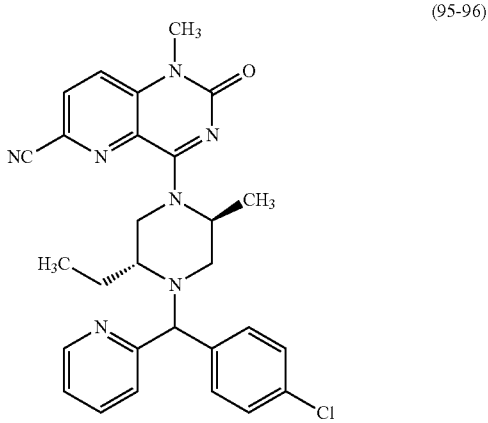 [SMILES: CC[C@@H]1CN(c2nc(=O)n(C)c3ccc(C#N)nc23)[C@@H](C)CN1C(c1ccc(Cl)cc1)c1ccccn1]

(95-96)

To a stirred solution of 4-((2S,5R)-5-ethyl-2-methylpiperazin-1-yl)-1-methyl-2-oxo-1,2-dihydropyrido[3,2-d]pyrimidine-6-carbonitrile (100 mg, 0.32 mmol) in acetonitrile (5 mL) was added DIPEA (0.3 mL, 1.60 mmol), followed by 2-(bromo(4-chlorophenyl)methyl)pyridine (181 mg, 0.64 mmol). The reaction mixture was heated at 80° C. for 3 h. The reaction mixture was cooled to room temperature and the solvent was removed under reduced pressure to yield the crude product, which was purified by preparative HPLC (HPLC Method: Column: Cellulose-5 (250*20 ID) 5 micron; Mobile Phase A: 0.1% DEA in IPA; Mobile Phase B: 0.1% DEA in ACN; Gradient: 90% of B, then a 5 minute hold at 100% B; Flow: 18 mL/min), fractions were concentrated under reduced pressure and lyophilized from (EtOH/H$_2$O, 1:5) to yield Example 95 and Example 96.

Example 95: 24 mg, 14% yield; LCMS: m/z=514.2 (M+H); rt 2.94 min; (LCMS method: Column: Column-Kinetex XB-C18 (75×3 mm-2.6 μm), Mobile phase A: 98% water: 2% acetonitrile; 10 mM ammonium formate; Mobile phase B: 2% Water: 98% acetonitrile; 10 mM ammonium formate; Flow: 1.0 mL/min; Temp: 50° C.; Time (min): 0-4; % B: 0-100%). $^1$H NMR (400 MHz, DMSO-d6): δ ppm 8.52 (d, J=4.5 Hz, 1H), 8.23 (d, J=9.0 Hz, 1H), 7.96-8.02 (m, 1H), 7.75-7.81 (m, 1H), 7.59-7.68 (m, 3H), 7.39 (d, J=8.5 Hz, 2H), 7.22-7.29 (m, 1H), 5.54-5.95 (m, 1H), 4.81-5.07 (m, 2H), 3.39-3.68 (m, 5H), 2.69-2.76 (m, 1H), 2.35-2.44 (m, 1H), 1.37-1.67 (m, 5H), 0.58-0.67 (m, 3H).

Example 96: 22 mg, 13% yield; LCMS: m/z=514.2 (M+H); rt 2.94 min; (LCMS method: Column: Column-Kinetex XB-C18 (75×3 mm-2.6 μm), Mobile phase A: 98% water: 2% acetonitrile; 10 mM ammonium formate; Mobile phase B: 2% Water: 98% acetonitrile; 10 mM ammonium formate; Flow: 1.0 mL/min; Temp: 50° C.; Time (min): 0-4; % B: 0-100%). $^1$H NMR (400 MHz, DMSO-d6): δ ppm 8.41-8.45 (m, 1H), 8.23 (d, J=9.0 Hz, 1H), 7.96-8.02 (m, 1H), 7.78-7.85 (m, 2H), 7.53-7.61 (m, 2H), 7.40 (d, J=8.5 Hz, 2H), 7.20-7.26 (m, 1H), 5.52-5.97 (m, 1H), 4.87-5.04 (m, 1H), 4.78-4.86 (m, 1H), 3.37-3.71 (m, 4H), 2.72-2.78 (m, 1H), 2.54-2.63 (m, 1H), 2.35-2.46 (m, 1H), 1.40-1.64 (m, 5H), 0.58-0.70 (m, 3H).

The examples in the Table 2 were prepared according to the general procedures described in Examples 1 to 4, using the appropriate benzhydryl/α-substituted benzyl/benzyl halide. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 2

| Ex. No. | Structure | Stereo chem. | LCMS Method | LCMS RT | M + H | Coupling Method |
|---|---|---|---|---|---|---|
| 48 | 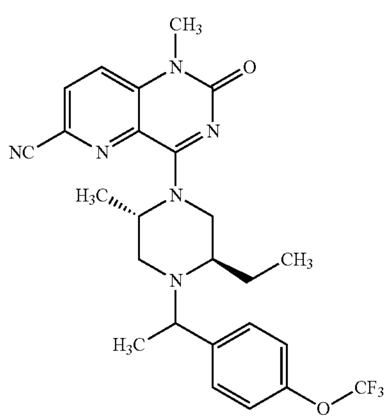 [SMILES: CC[C@@H]1CN(c2nc(=O)n(C)c3ccc(C#N)nc23)[C@@H](C)CN1C(C)c1ccc(OC(F)(F)F)cc1] | H | A | 2.34 | 501.2 | B |

TABLE 2-continued
| Ex. No. | Structure | Stereo chem. | LCMS Method | LCMS RT | M + H | Coupling Method |
|---|---|---|---|---|---|---|
| 49 | 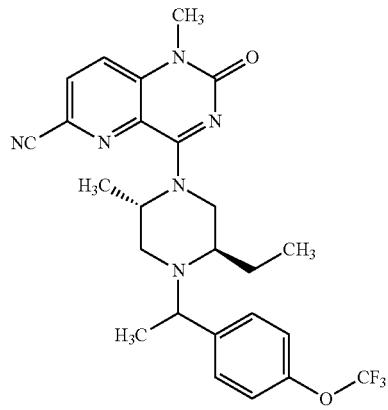 [SMILES: CC[C@@H]1CN(c2nc(=O)n(C)c3ccc(C#N)nc23)[C@@H](C)CN1C(C)c1ccc(OC(F)(F)F)cc1] | H | A | 2.39 | 501.2 | B |
| 50 | 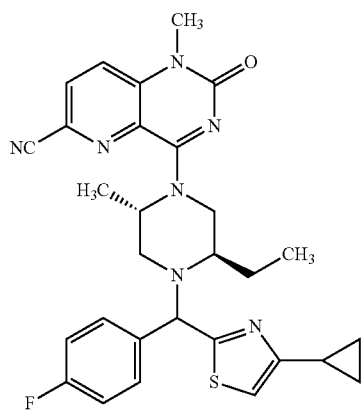 [SMILES: CC[C@@H]1CN(c2nc(=O)n(C)c3ccc(C#N)nc23)[C@@H](C)CN1C(c1ccc(F)cc1)c1nc(C2CC2)cs1] | H | A | 2.19 | 544.3 | A |
| 51 | 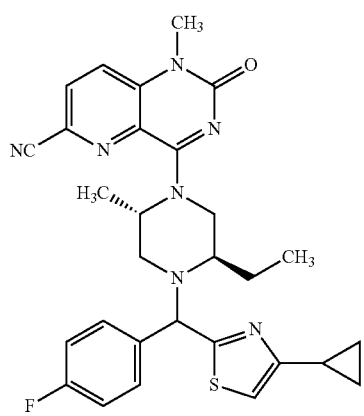 [SMILES: CC[C@@H]1CN(c2nc(=O)n(C)c3ccc(C#N)nc23)[C@@H](C)CN1C(c1ccc(F)cc1)c1nc(C2CC2)cs1] | H | A | 2.24 | 544.3 | A |

TABLE 2-continued

| Ex. No. | Structure | Stereo chem. | LCMS Method | LCMS RT | M + H | Coupling Method |
|---|---|---|---|---|---|---|
| 52 | 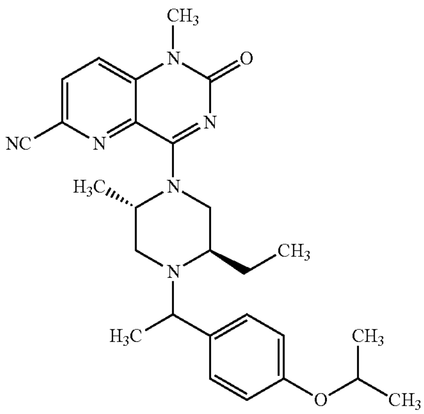 [SMILES: CC[C@@H]1CN(c2nc(=O)n(C)c3ccc(C#N)nc23)[C@@H](C)CN1C(C)c1ccc(OC(C)C)cc1] | H | A | 2.27 | 475.3 | B |
| 53 | 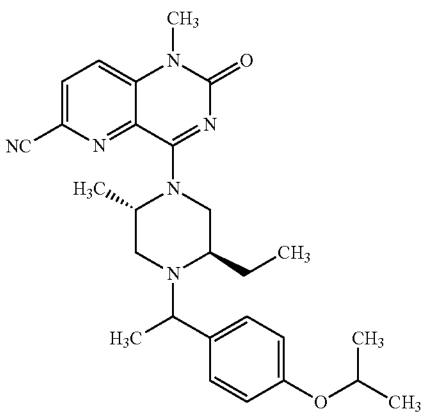 [SMILES: CC[C@@H]1CN(c2nc(=O)n(C)c3ccc(C#N)nc23)[C@@H](C)CN1C(C)c1ccc(OC(C)C)cc1] | H | A | 2.35 | 475.3 | B |
| 54 | 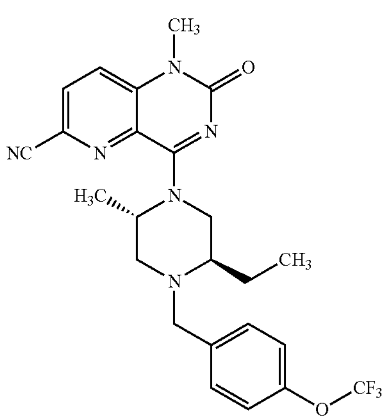 [SMILES: CC[C@@H]1CN(c2nc(=O)n(C)c3ccc(C#N)nc23)[C@@H](C)CN1Cc1ccc(OC(F)(F)F)cc1] | H | A | 2.29 | 487.2 | A |

TABLE 2-continued
| Ex. No. | Structure | Stereo chem. | LCMS Method | LCMS RT | M + H | Coupling Method |
|---|---|---|---|---|---|---|
| 55 | 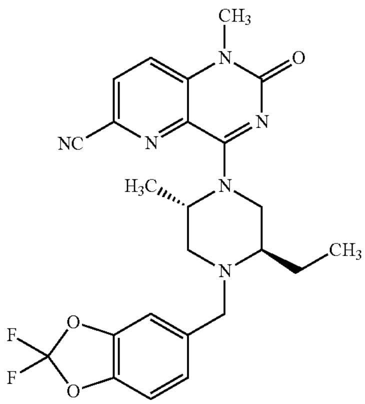 [SMILES: CC[C@@H]1CN(c2nc(=O)n(C)c3ccc(C#N)nc23)[C@@H](C)CN1Cc1ccc2c(c1)OC(F)(F)O2] | H | A | 2.24 | 483.2 | A |
| 56 | 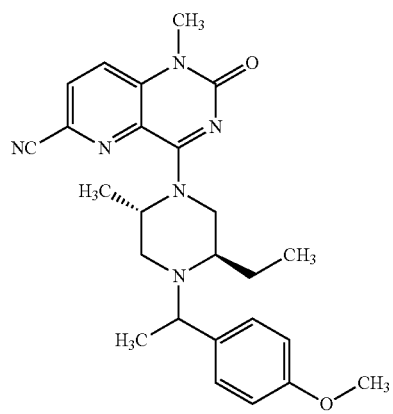 [SMILES: CC[C@@H]1CN(c2nc(=O)n(C)c3ccc(C#N)nc23)[C@@H](C)CN1C(C)c1ccc(OC)cc1] | H | A | 2.01 | 447.3 | B |
| 57 | 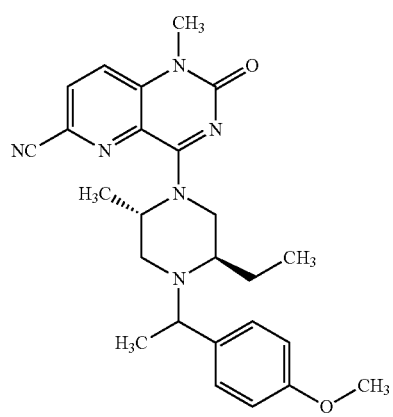 [SMILES: CC[C@@H]1CN(c2nc(=O)n(C)c3ccc(C#N)nc23)[C@@H](C)CN1C(C)c1ccc(OC)cc1] | H | A | 2.09 | 447.3 | B |

TABLE 2-continued

| Ex. No. | Structure | Stereo chem. | LCMS Method | LCMS RT | M + H | Coupling Method |
|---|---|---|---|---|---|---|
| 58 | 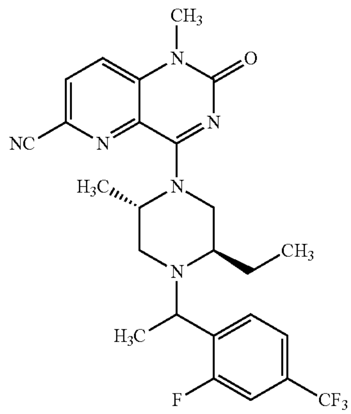 [SMILES: CC[C@@H]1CN(c2nc(=O)n(C)c3ccc(C#N)nc23)[C@@H](C)CN1C(C)c1ccc(C(F)(F)F)cc1F] | H | A | 2.34 | 503.3 | B |
| 59 | 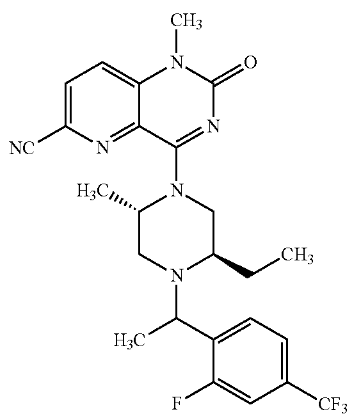 [SMILES: CC[C@@H]1CN(c2nc(=O)n(C)c3ccc(C#N)nc23)[C@@H](C)CN1C(C)c1ccc(C(F)(F)F)cc1F] | H | A | 2.39 | 503.2 | B |
| 60 | 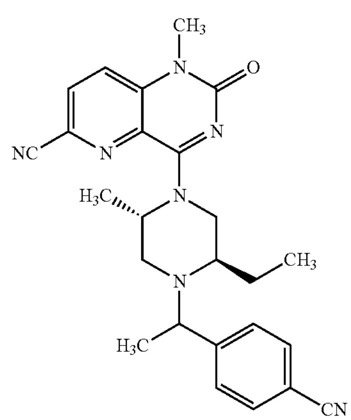 [SMILES: CC[C@@H]1CN(c2nc(=O)n(C)c3ccc(C#N)nc23)[C@@H](C)CN1C(C)c1ccc(C#N)cc1] | H | A | 1.89 | 442.3 | B |

TABLE 2-continued

| Ex. No. | Structure | Stereo chem. | LCMS Method | LCMS RT | M + H | Coupling Method |
|---|---|---|---|---|---|---|
| 61 | 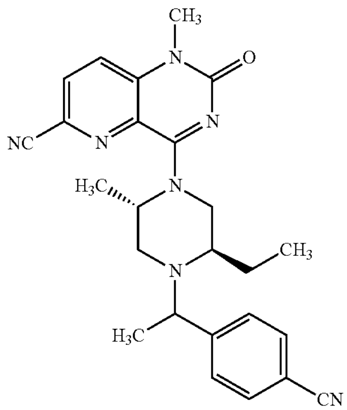 [SMILES: CC[C@@H]1CN(c2nc(=O)n(C)c3ccc(C#N)nc23)[C@@H](C)CN1C(C)c1ccc(C#N)cc1] | H | A | 1.96 | 442.3 | B |
| 62 | 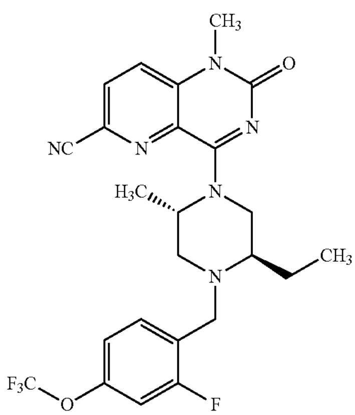 [SMILES: CC[C@@H]1CN(c2nc(=O)n(C)c3ccc(C#N)nc23)[C@@H](C)CN1Cc1ccc(OC(F)(F)F)cc1F] | H | A | 2.29 | 505.3 | A |
| 63 | 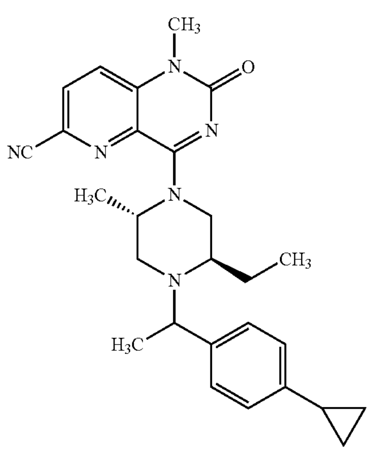 [SMILES: CC[C@@H]1CN(c2nc(=O)n(C)c3ccc(C#N)nc23)[C@@H](C)CN1C(C)c1ccc(C2CC2)cc1] | H | A | 2.34 | 457.3 | B |

TABLE 2-continued

| Ex. No. | Structure | Stereo chem. | LCMS Method | LCMS RT | M + H | Coupling Method |
|---|---|---|---|---|---|---|
| 64 | 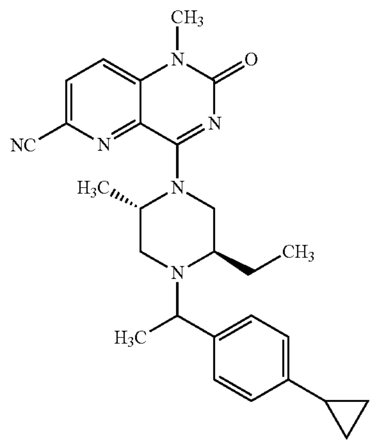 [SMILES: CC[C@@H]1CN(c2nc(=O)n(C)c3ccc(C#N)nc23)[C@@H](C)CN1C(C)c1ccc(C2CC2)cc1] | H | A | 2.41 | 457.3 | B |
| 65 | 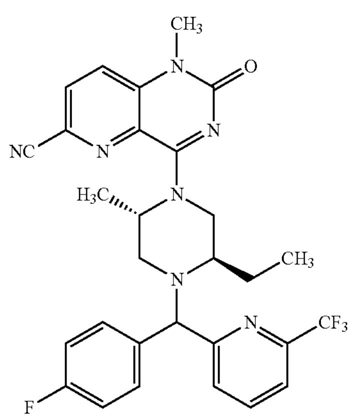 [SMILES: CC[C@@H]1CN(c2nc(=O)n(C)c3ccc(C#N)nc23)[C@@H](C)CN1C(c1ccc(F)cc1)c1cccc(C(F)(F)F)n1] | H | A | 2.24 | 566.2 | A |
| 66 | 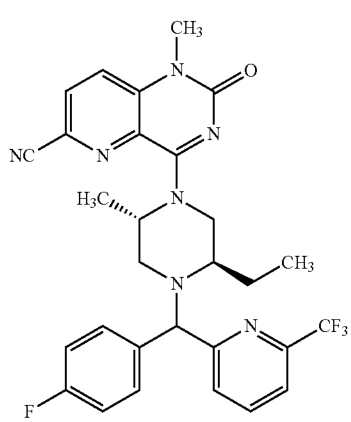 [SMILES: CC[C@@H]1CN(c2nc(=O)n(C)c3ccc(C#N)nc23)[C@@H](C)CN1C(c1ccc(F)cc1)c1cccc(C(F)(F)F)n1] | H | A | 2.25 | 566.2 | A |

TABLE 2-continued

| Ex. No. | Structure | Stereo chem. | LCMS Method | LCMS RT | M + H | Coupling Method |
|---|---|---|---|---|---|---|
| 67 | 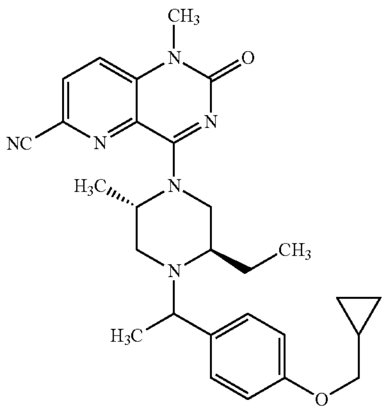 [SMILES: CC[C@@H]1CN(c2nc(=O)n(C)c3ccc(C#N)nc23)[C@@H](C)CN1C(C)c1ccc(OCC2CC2)cc1] | H | A | 1.42 | 487.3 | B |
| 68 | 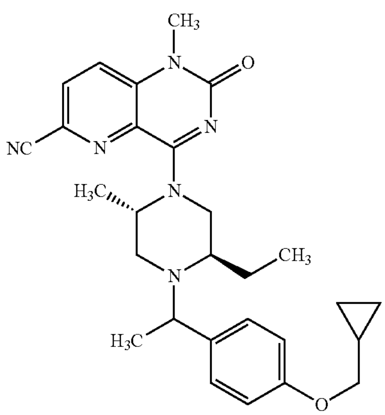 [SMILES: CC[C@@H]1CN(c2nc(=O)n(C)c3ccc(C#N)nc23)[C@@H](C)CN1C(C)c1ccc(OCC2CC2)cc1] | H | A | 2.36 | 487.3 | B |
| 69 | 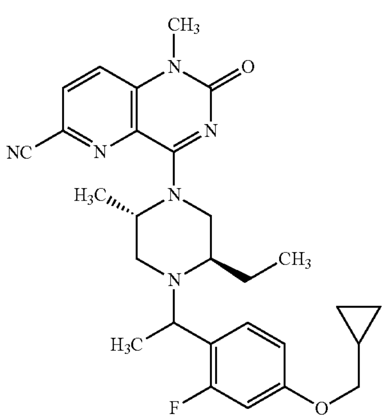 [SMILES: CC[C@@H]1CN(c2nc(=O)n(C)c3ccc(C#N)nc23)[C@@H](C)CN1C(C)c1ccc(OCC2CC2)cc1F] | H | A | 2.33 | 505.3 | B |

TABLE 2-continued
| Ex. No. | Structure | Stereo chem. | LCMS Method | LCMS RT | M + H | Coupling Method |
|---|---|---|---|---|---|---|
| 70 | 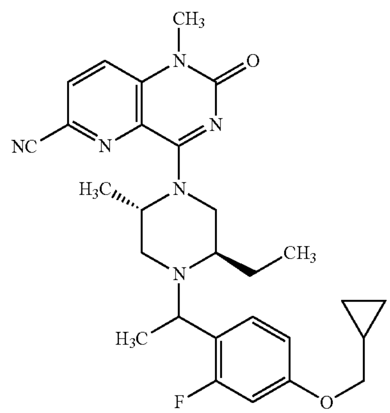 [SMILES: CC[C@@H]1CN(c2nc(=O)n(C)c3ccc(C#N)nc23)[C@@H](C)CN1C(C)c1ccc(OCC2CC2)cc1F] | H | A | 2.41 | 505.3 | B |
| 71 | 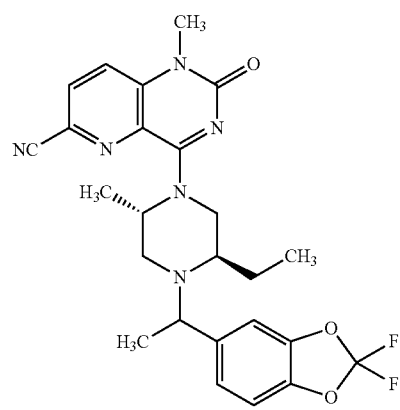 [SMILES: CC[C@@H]1CN(c2nc(=O)n(C)c3ccc(C#N)nc23)[C@@H](C)CN1C(C)c1ccc2c(c1)OC(F)(F)O2] | H | A | 2.32 | 497.3 | B |
| 72 | 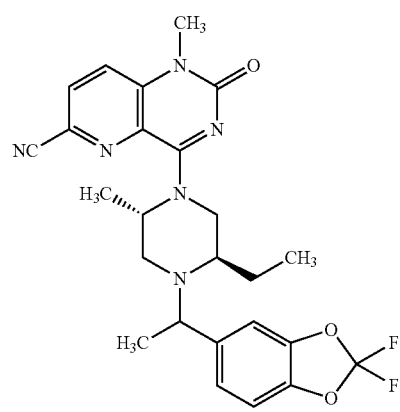 [SMILES: CC[C@@H]1CN(c2nc(=O)n(C)c3ccc(C#N)nc23)[C@@H](C)CN1C(C)c1ccc2c(c1)OC(F)(F)O2] | H | A | 2.37 | 497.3 | B |

TABLE 2-continued
| Ex. No. | Structure | Stereo chem. | LCMS Method | LCMS RT | M + H | Coupling Method |
|---|---|---|---|---|---|---|
| 73 | 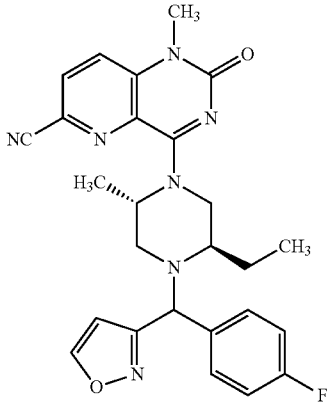 [SMILES: CC[C@@H]1CN(c2nc(=O)n(C)c3ccc(C#N)nc23)[C@@H](C)CN1C(c1ccc(F)cc1)c1ccon1] | H | A | 1.88 | 488.3 | A |
| 74 | 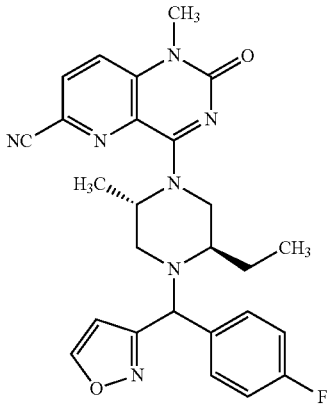 [SMILES: CC[C@@H]1CN(c2nc(=O)n(C)c3ccc(C#N)nc23)[C@@H](C)CN1C(c1ccc(F)cc1)c1ccon1] | H | A | 1.89 | 488.3 | A |
| 75 | 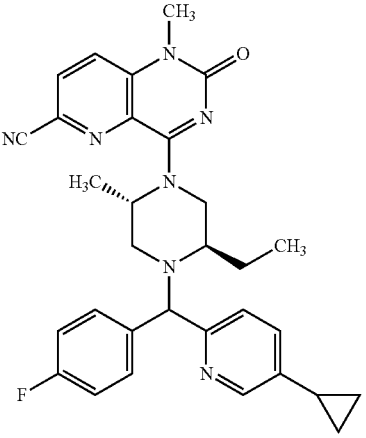 [SMILES: CC[C@@H]1CN(c2nc(=O)n(C)c3ccc(C#N)nc23)[C@@H](C)CN1C(c1ccc(F)cc1)c1ccc(C2CC2)cn1] | H | A | 2.12 | 538.3 | A |

TABLE 2-continued
| Ex. No. | Structure | Stereo chem. | LCMS Method | LCMS RT | M + H | Coupling Method |
|---|---|---|---|---|---|---|
| 76 | 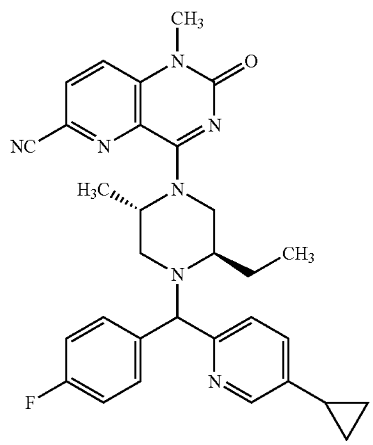 [SMILES: CC[C@@H]1CN(c2nc(=O)n(C)c3ccc(C#N)nc23)[C@@H](C)CN1C(c1ccc(F)cc1)c1ccc(C2CC2)cn1] | H | A | 2.12 | 538.3 | A |
| 77 | 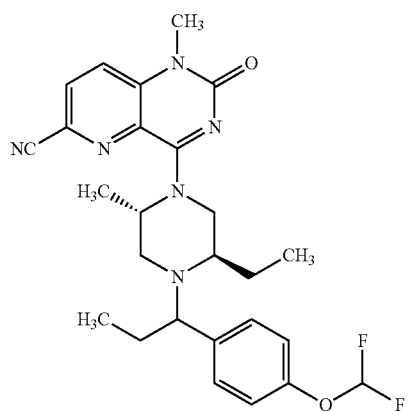 [SMILES: CCC(c1ccc(OC(F)F)cc1)N1C[C@H](C)N(c2nc(=O)n(C)c3ccc(C#N)nc23)C[C@H]1CC] | H | A | 2.28 | 497.3 | B |
| 78 | 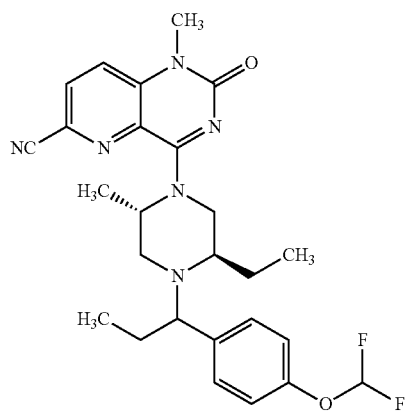 [SMILES: CCC(c1ccc(OC(F)F)cc1)N1C[C@H](C)N(c2nc(=O)n(C)c3ccc(C#N)nc23)C[C@H]1CC] | H | A | 2.27 | 497.3 | B |

TABLE 2-continued

| Ex. No. | Structure | Stereo chem. | LCMS Method | LCMS RT | M + H | Coupling Method |
|---------|-----------|--------------|-------------|---------|-------|-----------------|
| 79 | 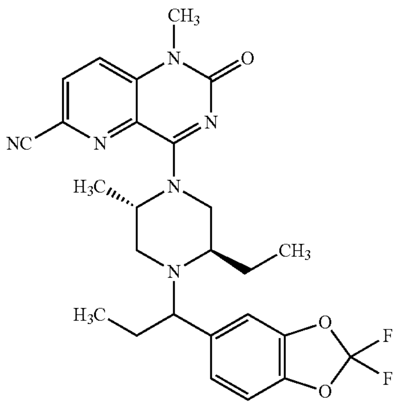 [SMILES: CCC(c1ccc2c(c1)OC(F)(F)O2)N1C[C@H](C)N(c2nc(=O)n(C)c3ccc(C#N)nc23)C[C@H]1CC] | H | A | 2.41 | 511.3 | B |
| 80 | 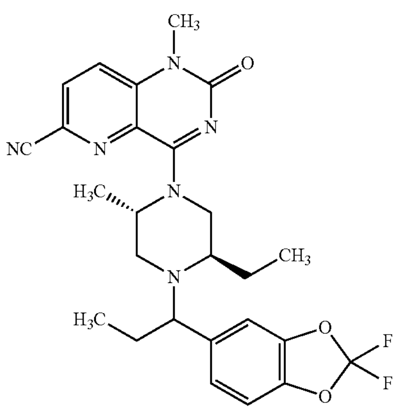 [SMILES: CCC(c1ccc2c(c1)OC(F)(F)O2)N1C[C@H](C)N(c2nc(=O)n(C)c3ccc(C#N)nc23)C[C@H]1CC] | H | A | 2.47 | 511.3 | B |
| 81 | 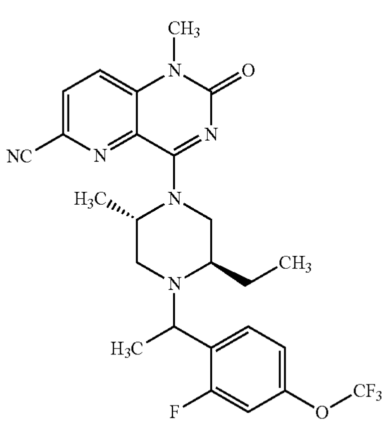 [SMILES: CC[C@@H]1CN(c2nc(=O)n(C)c3ccc(C#N)nc23)[C@@H](C)CN1C(C)c1ccc(OC(F)(F)F)cc1F] | H | A | 2.37 | 519.3 | B |

TABLE 2-continued

| Ex. No. | Structure | Stereo chem. | LCMS Method | LCMS RT | M + H | Coupling Method |
|---|---|---|---|---|---|---|
| 82 | 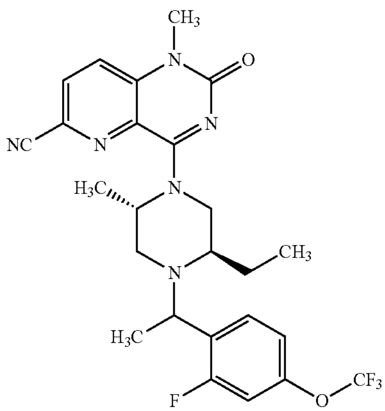 [SMILES: CC[C@@H]1CN(c2nc(=O)n(C)c3ccc(C#N)nc23)[C@@H](C)CN1C(C)c1ccc(OC(F)(F)F)cc1F] | H | A | 2.43 | 519.3 | B |
| 83 | 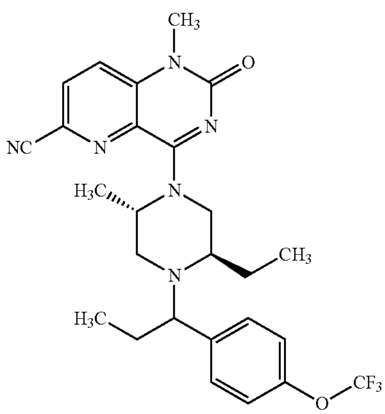 [SMILES: CCC(c1ccc(OC(F)(F)F)cc1)N1C[C@H](C)N(c2nc(=O)n(C)c3ccc(C#N)nc23)C[C@H]1CC] | H | A | 2.45 | 515.3 | B |
| 84 | 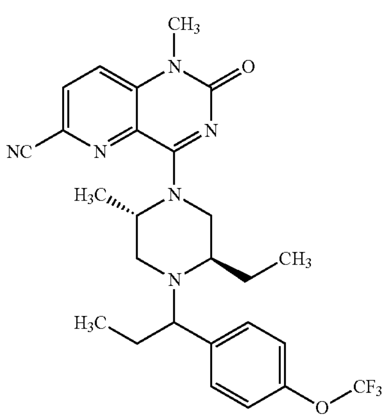 [SMILES: CCC(c1ccc(OC(F)(F)F)cc1)N1C[C@H](C)N(c2nc(=O)n(C)c3ccc(C#N)nc23)C[C@H]1CC] | H | A | 2.51 | 515.3 | B |

| Ex. No. | Structure | Stereo chem. | LCMS Method | LCMS RT | M + H | Coupling Method |
|---|---|---|---|---|---|---|
| 85 | 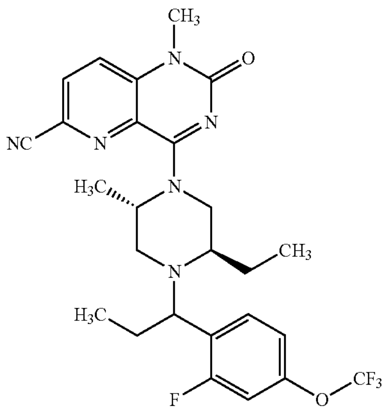 [SMILES: CCC(c1ccc(OC(F)(F)F)cc1F)N1C[C@H](C)N(c2nc(=O)n(C)c3ccc(C#N)nc23)C[C@H]1CC] | H | A | 2.47 | 533.3 | B |
| 86 | 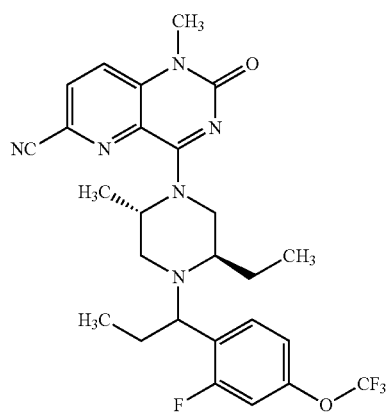 [SMILES: CCC(c1ccc(OC(F)(F)F)cc1F)N1C[C@H](C)N(c2nc(=O)n(C)c3ccc(C#N)nc23)C[C@H]1CC] | H | A | 2.53 | 533.3 | B |
| 87 | 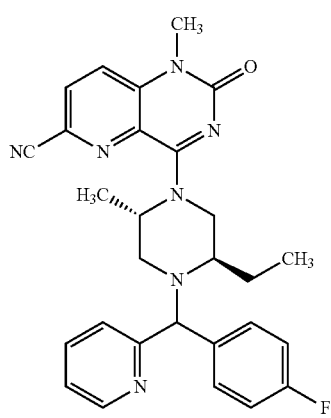 [SMILES: CC[C@@H]1CN(c2nc(=O)n(C)c3ccc(C#N)nc23)[C@@H](C)CN1C(c1ccc(F)cc1)c1ccccn1] | H | A | 1.88 | 498.3 | A |

TABLE 2-continued
| Ex. No. | Structure | Stereo chem. | LCMS Method | LCMS RT | M + H | Coupling Method |
|---|---|---|---|---|---|---|
| 88 | 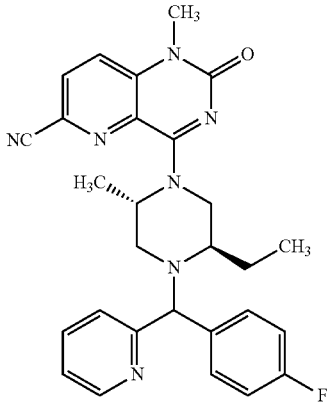 [SMILES: CC[C@@H]1CN(c2nc(=O)n(C)c3ccc(C#N)nc23)[C@@H](C)CN1C(c1ccc(F)cc1)c1ccccn1] | H | A | 1.87 | 498.3 | A |
| 89 | 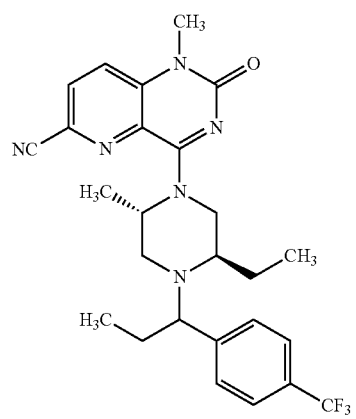 [SMILES: CCC(c1ccc(C(F)(F)F)cc1)N1C[C@H](C)N(c2nc(=O)n(C)c3ccc(C#N)nc23)C[C@H]1CC] | H | A | 2.41 | 499.3 | B |
| 90 | 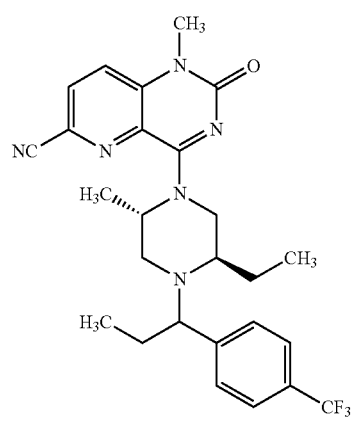 [SMILES: CCC(c1ccc(C(F)(F)F)cc1)N1C[C@H](C)N(c2nc(=O)n(C)c3ccc(C#N)nc23)C[C@H]1CC] | H | A | 2.47 | 499.3 | B |

TABLE 2-continued

| Ex. No. | Structure | Stereo chem. | LCMS Method | LCMS RT | M + H | Coupling Method |
|---|---|---|---|---|---|---|
| 91 | 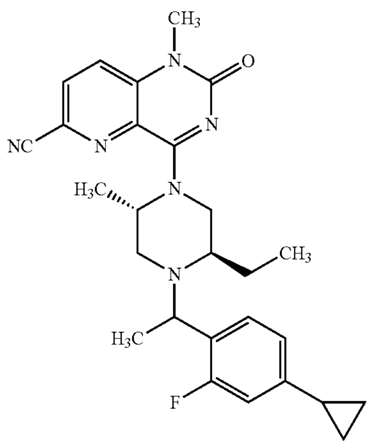 [SMILES: CC[C@@H]1CN(c2nc(=O)n(C)c3ccc(C#N)nc23)[C@@H](C)CN1C(C)c1ccc(C2CC2)cc1F] | H | A | 2.35 | 475.3 | B |
| 92 | 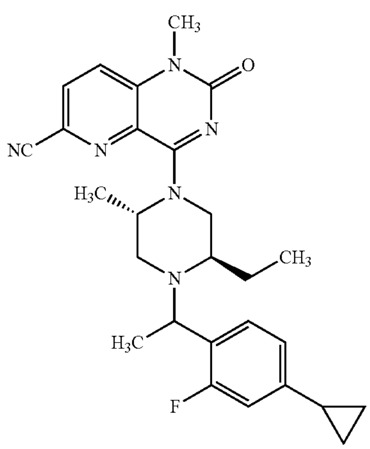 [SMILES: CC[C@@H]1CN(c2nc(=O)n(C)c3ccc(C#N)nc23)[C@@H](C)CN1C(C)c1ccc(C2CC2)cc1F] | H | A | 2.41 | 475.3 | B |
| 93 | 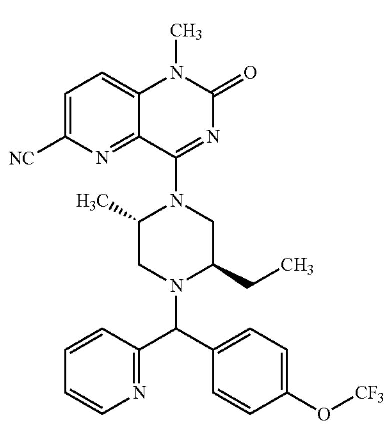 [SMILES: CC[C@@H]1CN(c2nc(=O)n(C)c3ccc(C#N)nc23)[C@@H](C)CN1C(c1ccc(OC(F)(F)F)cc1)c1ccccn1] | H | A | 2.1 | 564.3 | A |

TABLE 2-continued
| Ex. No. | Structure | Stereo chem. | LCMS Method | LCMS RT | M + H | Coupling Method |
|---|---|---|---|---|---|---|
| 94 | 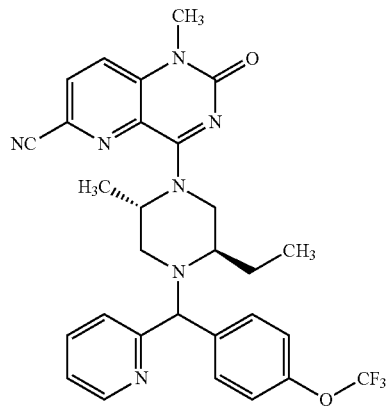 [SMILES: CC[C@@H]1CN(c2nc(=O)n(C)c3ccc(C#N)nc23)[C@@H](C)CN1C(c1ccc(OC(F)(F)F)cc1)c1ccccn1] | H | A | 2.1 | 564.3 | A |
| 97 | 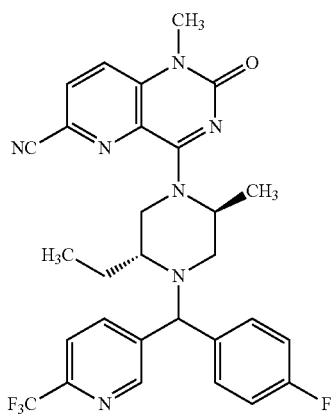 [SMILES: CC[C@@H]1CN(c2nc(=O)n(C)c3ccc(C#N)nc23)[C@@H](C)CN1C(c1ccc(F)cc1)c1ccc(C(F)(F)F)nc1] | H | A | 2.16 | 566.2 | A |
| 98 | 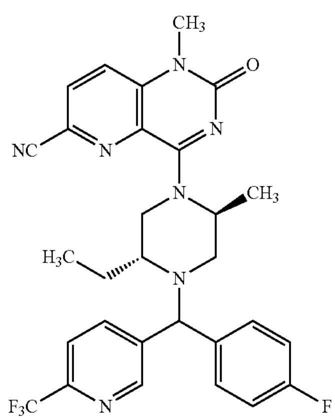 [SMILES: CC[C@@H]1CN(c2nc(=O)n(C)c3ccc(C#N)nc23)[C@@H](C)CN1C(c1ccc(F)cc1)c1ccc(C(F)(F)F)nc1] | H | A | 2.17 | 566.2 | A |

TABLE 2-continued
| Ex. No. | Structure | Stereo chem. | LCMS Method | LCMS RT | M + H | Coupling Method |
|---|---|---|---|---|---|---|
| 99 | 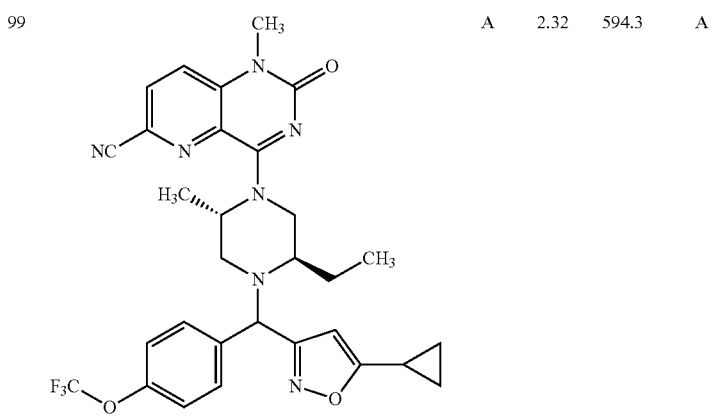 | | A | 2.32 | 594.3 | A |
| 100 | 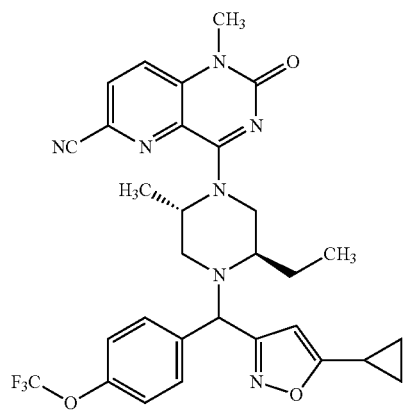 [SMILES: CC[C@@H]1CN(c2nc(=O)n(C)c3ccc(C#N)nc23)[C@@H](C)CN1C(c1ccc(OC(F)(F)F)cc1)c1cc(C2CC2)on1] | H | A | 2.31 | 594.3 | A |
| 101 | 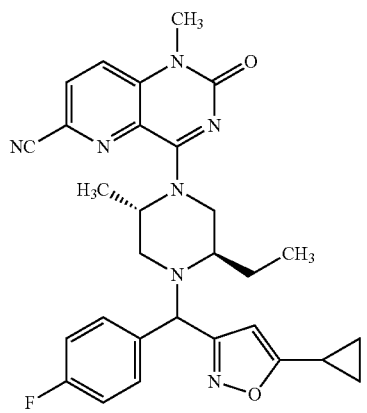 [SMILES: CC[C@@H]1CN(c2nc(=O)n(C)c3ccc(C#N)nc23)[C@@H](C)CN1C(c1ccc(F)cc1)c1cc(C2CC2)on1] | H | A | 2.10 | 528.3 | A |

TABLE 2-continued
| Ex. No. | Structure | Stereo chem. | LCMS Method | LCMS RT | M + H | Coupling Method |
|---|---|---|---|---|---|---|
| 102 | 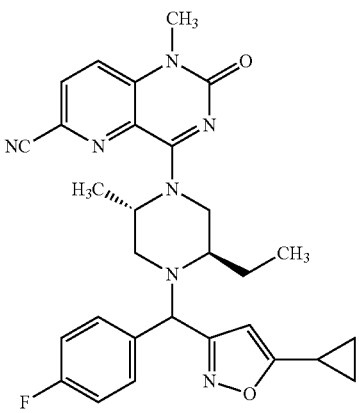 [SMILES: CC[C@@H]1CN(c2nc(=O)n(C)c3ccc(C#N)nc23)[C@@H](C)CN1C(c1ccc(F)cc1)c1cc(C2CC2)on1] | H | A | 2.09 | 528.3 | A |
| 103 | 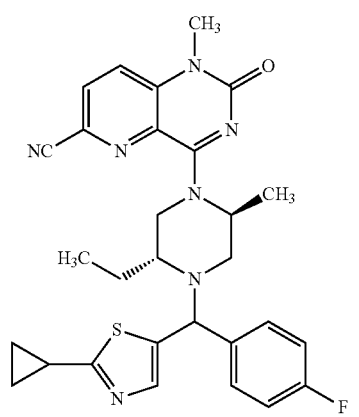 [SMILES: CC[C@@H]1CN(c2nc(=O)n(C)c3ccc(C#N)nc23)[C@@H](C)CN1C(c1ccc(F)cc1)c1cnc(C2CC2)s1] | H | A | 3.15 | 544.2 | A |
| 104 | 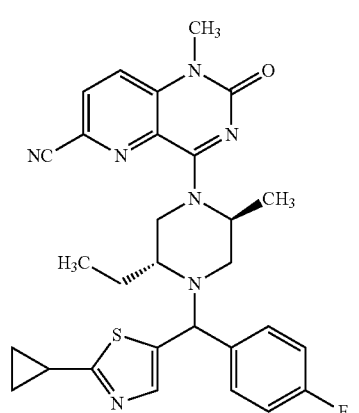 | H | A | 3.14 | 544.2 | A |

Example 105

6-Chloro-4-((2S,5R)-4-((3-cyclopropyl-1,2,4-oxadiazol-5-yl)(4-fluorophenyl)methyl)-2,5-dimethylpiperazin-1-yl)-1-methylpyrido[3,2-d]pyrimidin-2(1H)-one

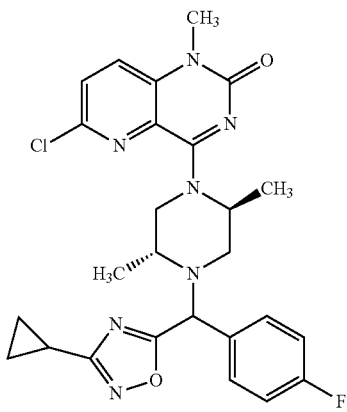

(105)

To a stirred solution of 4,6-dichloro-1-methylpyrido[3,2-d]pyrimidin-2(1H)-one (100 mg, 0.44 mmol), 3-cyclopropyl-5-(((2R,5S)-2,5-dimethylpiperazin-1-yl)(4-fluorophenyl)methyl)-1,2,4-oxadiazole, TFA (213 mg, 0.48 mmol) in acetonitrile (2 mL) was added DIPEA (0.23 mL, 1.30 mmol). The reaction mixture was heated to 85° C. for 3 h. The reaction mixture was cooled to room temperature and concentrated under reduced pressure to give the crude product, which was purified by flash chromatography (24 g silica gel) by eluting with 10% MeOH in DCM to yield 6-chloro-4-((2S,5R)-4-((3-cyclopropyl-1,2,4-oxadiazol-5-yl)(4-fluorophenyl)methyl)-2,5-dimethylpiperazin-1-yl)-1-methylpyrido[3,2-d]pyrimidin-2(1H)-one (255 mg, 56% yield). LCMS: m/z, 524.3 (M+H); retention time 2.0 min; LCMS Method: Column: AQUITY UPLC BEH C18 (3.0× 50 mm) 1.7 μm; Mobile phase A: 10 mM ammonium acetate: acetonitrile (98:2), Mobile phase B: 10 mM ammonium acetate: acetonitrile (2:98), Gradient=20-100% B over 4 minutes, then a 0.6 minute hold at 100% B; Temperature: 27° C.; Flow rate: 0.7 mL/min; Detection: UV at 220 nm).

Examples 106 and 107

4-((2S,5R)-4-((3-Cyclopropyl-1,2,4-oxadiazol-5-yl)(4-fluorophenyl)methyl)-2,5-dimethylpiperazin-1-yl)-1-methyl-2-oxo-1,2-dihydropyrido[3,2-d]pyrimidine-6-carbonitrile

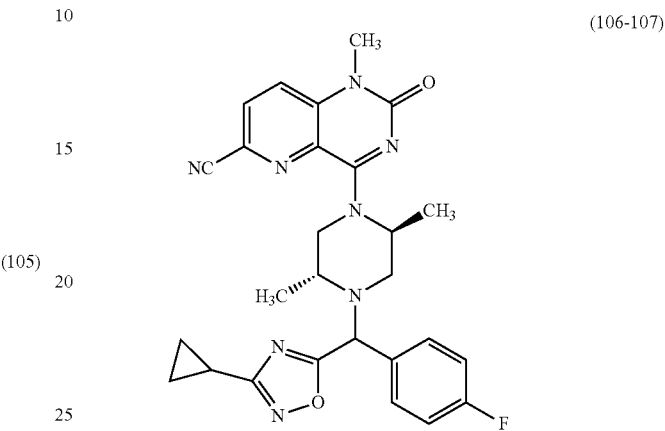

(106-107)

To a stirred solution of 6-chloro-4-((2S,5R)-4-((3-cyclopropyl-1,2,4-oxadiazol-5-yl)(4-fluorophenyl)methyl)-2,5-dimethylpiperazin-1-yl)-1-methylpyrido[3,2-d]pyrimidin-2(1H)-one (150 mg, 0.29 mmol) in DMF (2.0 mL) were added zinc (28.1 mg, 0.43 mmol) and TEA (0.12 mL, 0.86 mmol). The reaction mixture was degassed with argon gas for 5 min followed by the addition of zinc cyanide (101 mg, 0.86 mmol) and dichloro[9,9-dimethyl-4,5-bis(diphenylphosphino)xanthene]palladium(II) (87 mg, 0.12 mmol). The reaction mixture heated at 85° C. for 16 h. The reaction mixture was cooled to room temperature and concentrated under reduced pressure to afford a residue which was purified via preparative HPLC (Chiral Separation Method: COLUMN: Chiralpak-ADH (250×4.6 mm), 5 μm; % $CO_2$=70%; Co solvent: 30% of acetonitrile: methanol (50:50), Total Flow: 80.0 g/min. Back pressure: 100 bar; temperature: 30° C.; UV detection: 215 nm).

Example 106: (4.5 mg, 3% yield): LCMS: m/z, 515.2 (M+H); rt 2.90 min; (LCMS method: Column: Column-Kinetex XB-C18 (75×3 mm-2.6 μm), Mphase A: 10 mM ammonium formate in water: acetonitrile (98:2); Mphase B: 10 mM ammonium formate in water:acetonitrile (2:98); Flow: 1 mL/min; Gradient: 20-100% B over 4 minutes then 0.6 min hold at 100% B, Flow: 1.5 mL/min; Gradient: 100-20% B over 0.1 minutes then 0.3 min hold at 20% B, Flow: 1.5 mL/min. $^1$H NMR (400 MHz, DMSO-$d_6$) δ ppm 8.23-8.21 (m, 1H), 7.99-7.97 (m, 1H), 7.65-7.62 (m, 2H), 7.28-7.24 (m, 2H), 5.21 (s, 1H), 3.43 (s, 3H), 3.03-2.94 (m, 2H), 2.23-2.08 (m, 2H), 1.14-1.05 (m, 3H), 1.05-1.03 (m, 2H), 0.90-0.88 (m, 5H), 3 H obscured with moisture peak.

Example 107: (4.5 mg, 3% yield): LCMS: m/z, 515.2 (M+H); rt 2.90 min; (LCMS method: Column: Column-Kinetex XB-C18 (75×3 mm-2.6 μm), Mphase A: 10 mM ammonium formate in water: acetonitrile (98:2); Mphase B: 10 mM ammonium formate in water:acetonitrile (2:98); Flow: 1 mL/min; Gradient: 20-100% B over 4 minutes then 0.6 min hold at 100% B, Flow: 1.5 mL/min; Gradient: 100-20% B over 0.1 minutes then 0.3 min hold at 20% B, Flow: 1.5 mL/min. $^1$H NMR (400 MHz, DMSO-$d_6$) δ ppm 8.23-8.21 (m, 1H), 7.99-7.97 (m, 1H), 7.65-7.62 (m, 2H), 7.28-7.24 (m, 2H), 5.21 (s, 1H), 3.43 (s, 3H), 3.00-2.94 (m, 1H), 2.80-2.70 (m, 1H), 2.38-2.25 (m, 1H), 2.21-2.10 (m, 1H), 1.33-1.25 (m, 3H), 1.07-1.05 (m, 5H), 0.91-0.90 (m, 2H), 3H obscured with moisture peak.

The examples in the Table 3 were prepared according to the general procedure described in Examples 106 and 107, using the appropriate amidoxime. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 3

| Ex. No. | Structure | Stereo chem. | LCMS Method | LCMS RT | M + H |
|---|---|---|---|---|---|
| 108 | 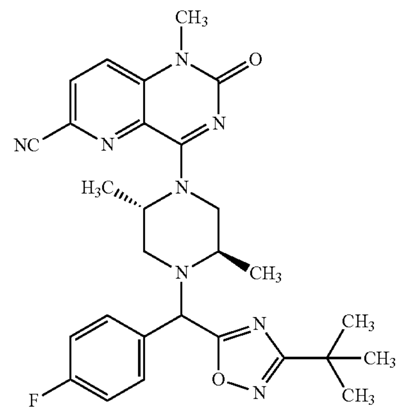 [SMILES: C[C@@H]1CN(c2nc(=O)n(C)c3ccc(C#N)nc23)[C@@H](C)CN1C(c1ccc(F)cc1)c1nc(C(C)(C)C)no1] | H | A | 2.25 | 531.2 |
| 109 | 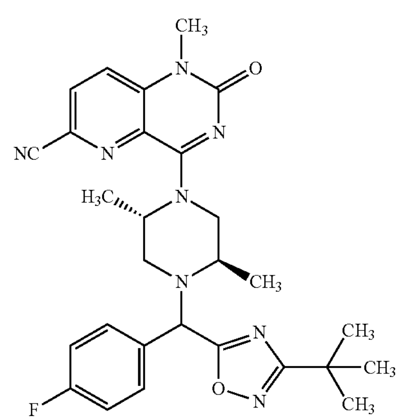 [SMILES: C[C@@H]1CN(c2nc(=O)n(C)c3ccc(C#N)nc23)[C@@H](C)CN1C(c1ccc(F)cc1)c1nc(C(C)(C)C)no1] | H | A | 2.24 | 531.2 |

147

Intermediate 13

2-((2R,5S)-4-(6-Cyano-1-methyl-2-oxo-1,2-dihydro-pyrido[3,2-d]pyrimidin-4-yl)-2,5-diethylpiperazin-1-yl)-2-(4-fluorophenyl)Acetic Acid

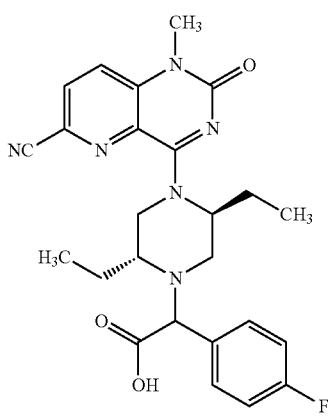 [SMILES: CC[C@H]1CN(C(C(=O)O)c2ccc(F)cc2)[C@H](CC)CN1c1nc(=O)n(C)c2ccc(C#N)nc12]

To a stirred solution of 4-((2S,5R)-2,5-diethylpiperazin-1-yl)-1-methyl-2-oxo-1,2-dihydropyrido[3,2-d]pyrimidine-6-carbonitrile (0.03 g, 0.09 mmol) in acetonitrile (2 mL) were added DIPEA (0.05 mL, 0.29 mmol) and 2-bromo-2-(4-fluorophenyl)acetic acid (0.03 g, 0.11 mmol). The reaction mixture was heated at 85° C. for 16 h. The reaction mixture cooled to room temperature and concentrated under reduced pressure to yield 2-((2R,5S)-4-(6-cyano-1-methyl-2-oxo-1,2-dihydropyrido[3,2-d]pyrimidin-4-yl)-2,5-diethylpiperazin-1-yl)-2-(4-fluorophenyl)acetic acid (44 mg, 17% yield) as a gummy liquid. LCMS: m/z=479.2 (M+H); retention time 0.80 min. LC-MS Method: Column-AQUITY UPLC BEH C18 (3.0×50 mm) 1.7 μm; Mobile phase A: Buffer: acetonitrile (95:5); Mobile phase B: Buffer: acetonitrile (5:95), Buffer: 10 mM ammonium acetate; Gradient: 20-100% B over 2.0 minutes, then a 0.2 minute hold at 100% B, flow rate 0.7 mL/min.

148

Examples 110 and 111

4-((2S,5R)-4-((3-Cyclopropyl-1,2,4-oxadiazol-5-yl)(4-fluorophenyl)methyl)-2,5-dimethylpiperazin-1-yl)-1-methyl-2-oxo-1,2-dihydropyrido[3,2-d]pyrimidine-6-carbonitrile

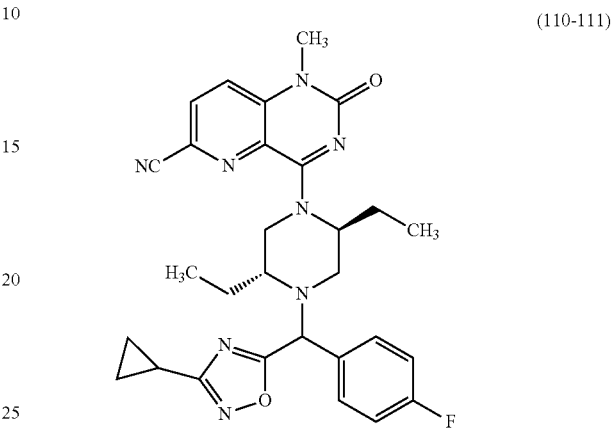

(110-111)

To a stirred solution of 2-((2R,5S)-4-(6-cyano-1-methyl-2-oxo-1,2-dihydropyrido[3,2-d]pyrimidin-4-yl)-2,5-diethylpiperazin-1-yl)-2-(4-fluorophenyl)acetic acid, (0.045 g, 0.09 mmol), N-hydroxycyclopropanecarboximidamide (9.4 mg, 0.09 mmol) in DMF (2 mL), BOP (0.01 g, 0.23 mmol) and triethylamine (0.04 mL, 0.23 mmol) were added at room temperature. After 2 hours, the reaction mixture was heated at 110° C. for 3 h. The reaction mixture was cooled to room temperature and evaporated under reduced pressure to yield crude product, which was purified via preparative HPLC. Chiral Separation Method: Column: DAD-1-Cellulose-2 (250×4.6 mm), 5 micron. Mobile Phase: 0.1% DEA in acetonitrile, Flow:2.0 mL\min.

Example 110: (1.9 mg, 6% yield): LCMS: m/z, 543.3 (M+H); rt 2.21 min; LCMS method: Column: XBridge BEH XP C18 (50×2.1) mm, 2.5 μm; Mobile phase A: 95% water: 5% acetonitrile; 10 mM ammonium acetate; Mobile phase B: 5% water: 95% acetonitrile; 10 mM ammonium acetate; Flow: 1.1 mL/min; Temp: 50° C.; Time (min) Time (min): 0-3; % B: 0-100%). $^1$H NMR (400 MHz, DMSO-$d_6$) δ ppm 8.29-8.16 (m, 1H), 8.06-7.92 (m, 1H), 7.75-7.58 (m, 2H), 7.26 (m, 2H), 6.01-5.32 (m, 1H), 5.28 (br s, 1H), 5.00-4.79 (m, 1H), 3.66-3.56 (m, 1H), 3.43 (s, 3H), 2.65-2.57 (m, 1H), 2.44-2.34 (m, 2H), 2.18-2.00 (m, 1H), 1.95-1.74 (m, 2H), 1.68-1.34 (m, 2H), 1.15-1.02 (m, 2H), 0.93-0.83 (m, 2H), 0.81-0.62 (m, 6H).

Example 111: (1.0 mg, 3% yield): LCMS: m/z, 543.3 (M+H); rt 2.20 min; LCMS method: Column: XBridge BEH XP C18 (50×2.1) mm, 2.5 μm; Mobile phase A: 95% water: 5% acetonitrile; 10 mM ammonium acetate; Mobile phase B: 5% water: 95% acetonitrile; 10 mM ammonium acetate; Flow: 1.1 mL/min; Temp: 50° C.; Time (min) Time (min): 0-3; % B: 0-100%). $^1$H NMR (400 MHz, DMSO-$d_6$) δ ppm 8.23 (d, J=8.8 Hz, 1H), 8.06-7.91 (m, 1H), 7.62 (dd, J=6.2, 7.5 Hz, 2H), 7.26 (t, J=8.8 Hz, 2H), 5.92-5.31 (m, 1H), 5.29 (s, 1H), 4.96-4.78 (m, 1H), 3.60-3.50 (m, 1H), 3.43 (s, 3H), 3.25-3.10 (m, 1H), 2.97-2.75 (m, 2H), 2.27-1.65 (m, 3H), 1.49-1.24 (m, 2H), 1.11-0.97 (m, 2H), 0.94-0.75 (m, 5H), 0.74-0.50 (m, 3H).

The examples in the Table 4 were prepared according to the general procedure described in Examples 110 and 111, using the appropriate piperazine. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 4

| Ex. No. | Structure | LCMS Method | LCMS RT | M + H |
|---|---|---|---|---|
| 112 | (structure) | A | 2.75 | 529.2 |
| 113 | (structure) | A | 2.75 | 529.2 |

The examples in the Table 5 were prepared according to the general procedure described in Examples 1 and 2, using appropriate benzhydryl/α-substituted benzyl/benzyl halide. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 5

| Ex. No. | Structure | LCMS Method | LCMS RT | M + H | Coupling Method |
|---|---|---|---|---|---|
| 114 | (structure) | A | 2.21 | 566.3 | A |
| 115 | (structure) | A | 2.22 | 566.3 | A |

TABLE 5-continued

| Ex. No. | Structure | LCMS Method | LCMS RT | M + H | Coupling Method |
|---|---|---|---|---|---|
| 116 | 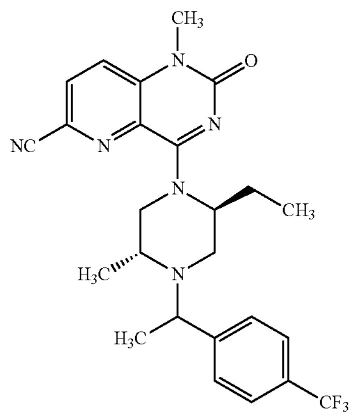 [SMILES: CC[C@H]1CN(C(C)c2ccc(C(F)(F)F)cc2)[C@H](C)CN1c1nc(=O)n(C)c2ccc(C#N)nc12] | A | 2.32 | 485.3 | B |
| 117 | 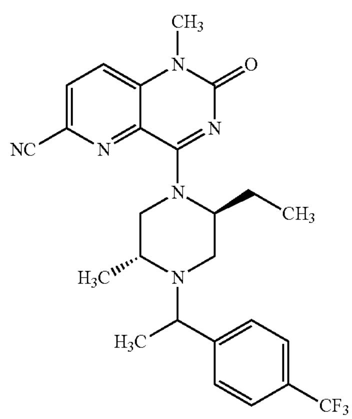 [SMILES: CC[C@H]1CN(C(C)c2ccc(C(F)(F)F)cc2)[C@H](C)CN1c1nc(=O)n(C)c2ccc(C#N)nc12] | A | 2.35 | 485.3 | B |
| 118 | 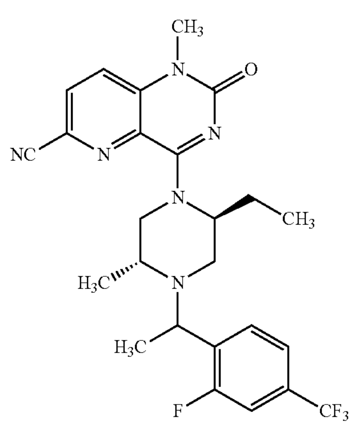 [SMILES: CC[C@H]1CN(C(C)c2ccc(C(F)(F)F)cc2F)[C@H](C)CN1c1nc(=O)n(C)c2ccc(C#N)nc12] | A | 2.37 | 503.3 | A |

TABLE 5-continued
| Ex. No. | Structure | LCMS Method | LCMS RT | M + H | Coupling Method |
|---|---|---|---|---|---|
| 119 | 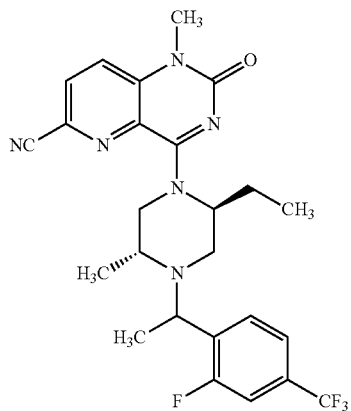 | A | 2.34 | 503.2 | A |
| 120 | 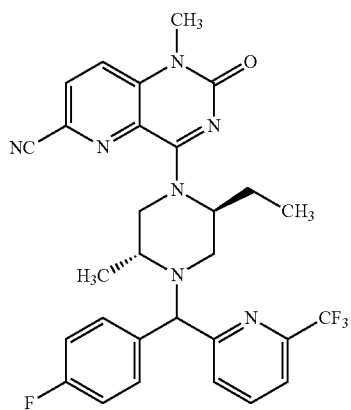 [SMILES: CC[C@H]1CN(C(c2ccc(F)cc2)c2cccc(C(F)(F)F)n2)[C@H](C)CN1c1nc(=O)n(C)c2ccc(C#N)nc12] | A | 2.24 | 566.3 | A |
| 121 | 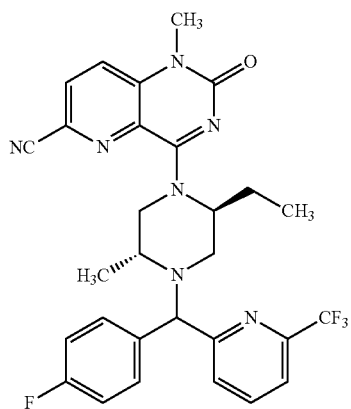 [SMILES: CC[C@H]1CN(C(c2ccc(F)cc2)c2cccc(C(F)(F)F)n2)[C@H](C)CN1c1nc(=O)n(C)c2ccc(C#N)nc12] | A | 2.23 | 566.2 | A |

TABLE 5-continued

| Ex. No. | Structure | LCMS Method | LCMS RT | M + H | Coupling Method |
|---|---|---|---|---|---|
| 122 | 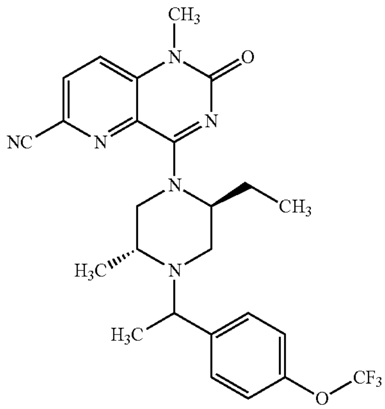 [SMILES: CC[C@H]1CN(C(C)c2ccc(OC(F)(F)F)cc2)[C@H](C)CN1c1nc(=O)n(C)c2ccc(C#N)nc12] | A | 2.39 | 501.3 | A |
| 123 | 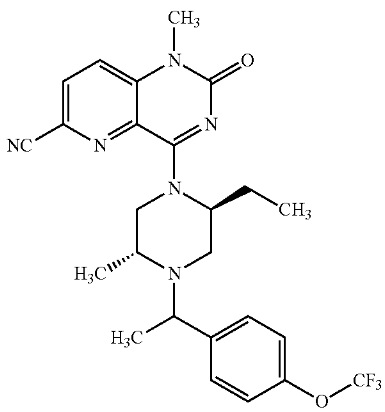 [SMILES: CC[C@H]1CN(C(C)c2ccc(OC(F)(F)F)cc2)[C@H](C)CN1c1nc(=O)n(C)c2ccc(C#N)nc12] | A | 2.36 | 501.3 | A |

Examples 126 and 127

4-((2S,5R)-4-(4-fluorophenyl)(5-(trifluoromethyl) pyridin-2-yl)methyl)-2,5-dimethylpiperazin-1-yl)-1-methyl-2-oxo-1,2-dihydropyrido[3,2-d]pyrimidine-6-carbonitrile

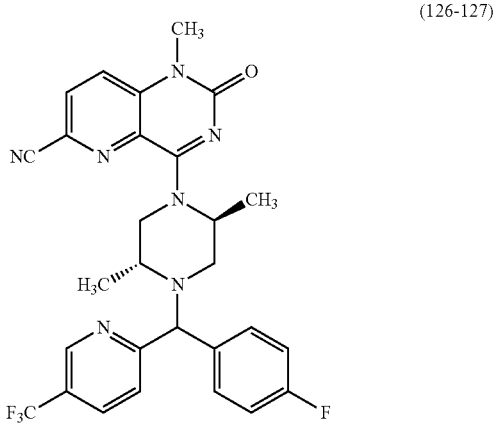 [SMILES: C[C@@H]1CN(c2nc(=O)n(C)c3ccc(C#N)nc23)[C@@H](C)CN1C(c1ccc(F)cc1)c1ccc(C(F)(F)F)cn1]

(126-127)

To a stirred solution of 4-((2S,5R)-2,5-dimethylpiperazin-1-yl)-1-methyl-2-oxo-1,2-dihydropyrido[3,2-d]pyrimidine-6-carbonitrile (1 g, 3.35 mmol) in acetonitrile (10 mL) was added DIPEA (5.9 mL, 33.5 mmol), followed by 2-(bromo (4-fluorophenyl) methyl)-5-(trifluoromethyl)pyridine (2.24 g, 6.70 mmol). The reaction mixture was heated at 80° C. for 4 h. The reaction mixture was cooled to room temperature and the solvent was removed under reduced pressure to yield the crude product, which was purified by preparative HPLC (HPLC Method: Column: Sunfire C18, 150×19 mm ID, 5 µm; Mobile Phase A: 0.1% TFA in water; Mobile Phase B: Acetonitrile:MeOH (1:1); Gradient: 50-100% B over 20 minutes, then a 5 minute hold at 100% B; Flow: 19 mL/min), fractions were concentrated under reduced pressure and lyophilized from (EtOH/H$_2$O, 1:5) to yield Example 126 and Example 127.

Example 126: 110 mg, 6% yield; LCMS: m/z=552.2 (M+H); rt 3.09 min; (LCMS method: Column: Column-Kinetex XB-C18 (75×3 mm-2.6 µm), Mobile phase A: 98% water: 2% acetonitrile; 10 mM ammonium formate; Mobile phase B: 2% Water: 98% acetonitrile; 10 mM ammonium formate; Flow: 1.0 mL/min; Temp: 50° C.; Time (min): 0-4; % B: 20-100%). $^1$H NMR (400 MHz, DMSO-d$_6$) δ ppm 8.83 (s, 1H), 8.22 (d, J=9.0 Hz, 2H), 8.11-7.95 (m, 2H), 7.71-7.58 (m, 2H), 7.25-7.13 (m, 2H), 5.76-5.44 (m, 1H), 5.13-4.67 (m, 2H), 3.86-3.49 (m, 1H), 3.44 (s, 3H), 3.19-3.08 (m, 1H), 2.84 (dd, J=3.8, 12.3 Hz, 1H), 2.38-2.26 (m, 1H), 1.67-1.39 (m, 3H), 1.11-0.86 (m, 3H).

Example 127: 145 mg, 8% yield; LCMS: m/z=552.2 (M+H); rt 3.09 min; (LCMS method: Column: Column-Kinetex XB-C18 (75×3 mm-2.6 µm), Mobile phase A: 98% water: 2% acetonitrile; 10 mM ammonium formate; Mobile phase B: 2% Water: 98% acetonitrile; 10 mM ammonium formate; Flow: 1.0 mL/min; Temp: 50° C.; Time (min): 0-4; % B: 0-100%). $^1$H NMR (400 MHz, DMSO-d$_6$) δ ppm 8.91 (s, 1H), 8.27-8.16 (m, 2H), 7.99 (d, J=9.0 Hz, 2H), 7.69-7.57 (m, 2H), 7.23-7.13 (m, 2H), 5.77-5.41 (m, 1H), 5.09-4.62 (m, 2H), 3.90-3.65 (m, 1H), 3.44 (s, 3H), 3.14-3.02 (m, 1H), 2.80-2.74 (m, 1H), 1.61-1.40 (m, 3H), 1.10-0.93 (m, 3H) [1H obscured with solvent peak].

The examples in the Table 6 were prepared from general procedure described in Examples 1 and 2, using appropriate benzhydryl/α-substituted benzyl/benzyl halide. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 6

| Ex. No. | Structure | Stereo chem. | LCMS Method | LCMS RT | M + H | Coupling Method |
|---|---|---|---|---|---|---|
| 124 | 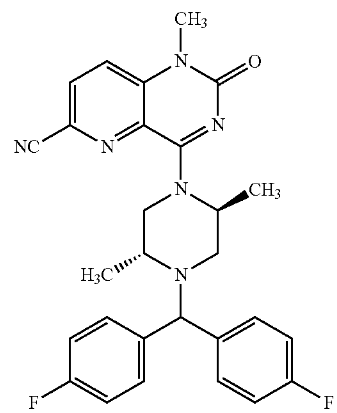 [SMILES: C[C@@H]1CN(c2nc(=O)n(C)c3ccc(C#N)nc23)[C@@H](C)CN1C(c1ccc(F)cc1)c1ccc(F)cc1] | H | B | 3.39 | 501.2 | A |
| 125 | 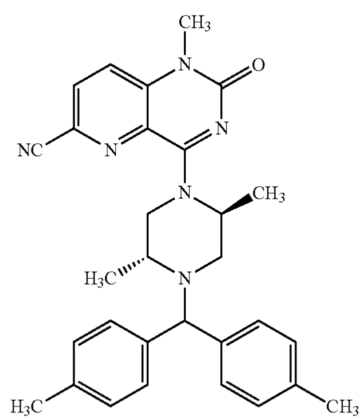 | H | B | 2.93 | 493.2 | A |
| 128 | 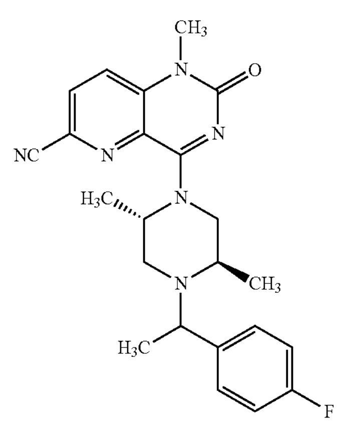 [SMILES: CC(c1ccc(F)cc1)N1C[C@H](C)N(c2nc(=O)n(C)c3ccc(C#N)nc23)C[C@H]1C] | H | A | 2.01 | 421.1 | A |

TABLE 6-continued
| Ex. No. | Structure | Stereo chem. | LCMS Method | LCMS RT | M + H | Coupling Method |
|---|---|---|---|---|---|---|
| 129 | 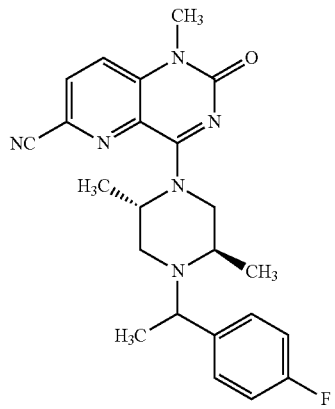 [SMILES: CC(c1ccc(F)cc1)N1C[C@H](C)N(c2nc(=O)n(C)c3ccc(C#N)nc23)C[C@H]1C] | H | A | 1.99 | 421.1 | A |
| 130 | 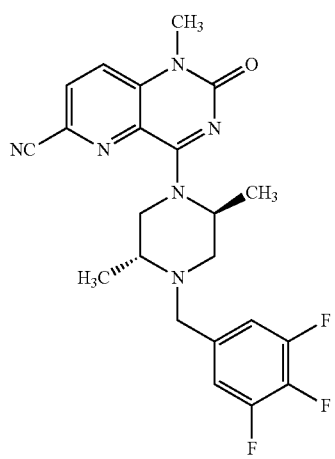 [SMILES: C[C@@H]1CN(c2nc(=O)n(C)c3ccc(C#N)nc23)[C@@H](C)CN1Cc1cc(F)c(F)c(F)c1] | H | A | 2.05 | 443.2 | A |
| 131 | 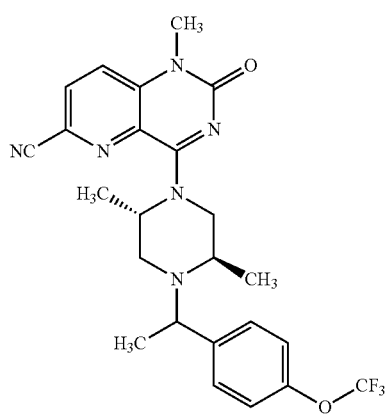 [SMILES: CC(c1ccc(OC(F)(F)F)cc1)N1C[C@H](C)N(c2nc(=O)n(C)c3ccc(C#N)nc23)C[C@H]1C] | H | A | 1.35 | 487.2 | B |

TABLE 6-continued
| Ex. No. | Structure | Stereo chem. | LCMS Method | LCMS RT | M + H | Coupling Method |
|---|---|---|---|---|---|---|
| 132 | 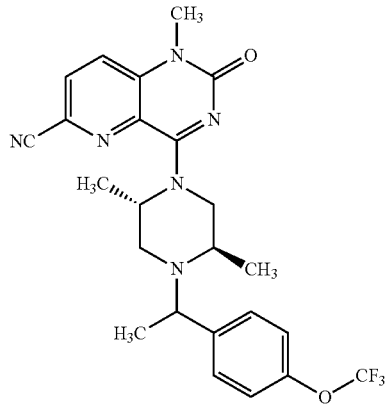 [SMILES: CC(c1ccc(OC(F)(F)F)cc1)N1C[C@H](C)N(c2nc(=O)n(C)c3ccc(C#N)nc23)C[C@H]1C] | H | A | 2.28 | 487.2 | B |
| 133 | 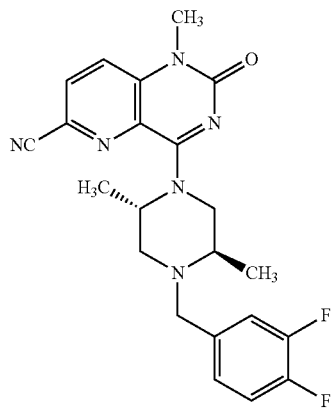 [SMILES: C[C@@H]1CN(c2nc(=O)n(C)c3ccc(C#N)nc23)[C@@H](C)CN1Cc1ccc(F)c(F)c1] | H | A | 1.97 | 425.2 | A |
| 134 | 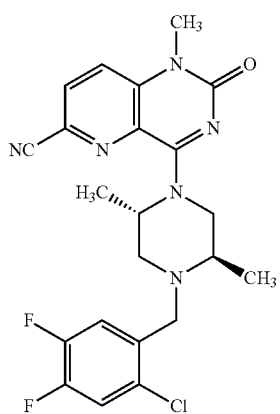 [SMILES: C[C@@H]1CN(c2nc(=O)n(C)c3ccc(C#N)nc23)[C@@H](C)CN1Cc1cc(F)c(F)cc1Cl] | H | A | 2.13 | 459.1 | A |

TABLE 6-continued
| Ex. No. | Structure | Stereo chem. | LCMS Method | LCMS RT | M + H | Coupling Method |
|---|---|---|---|---|---|---|
| 135 | 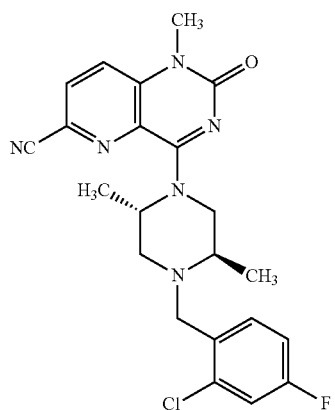 [SMILES: C[C@@H]1CN(c2nc(=O)n(C)c3ccc(C#N)nc23)[C@@H](C)CN1Cc1ccc(F)cc1Cl] | H | A | 2.13 | 469.2 | A |
| 136 | 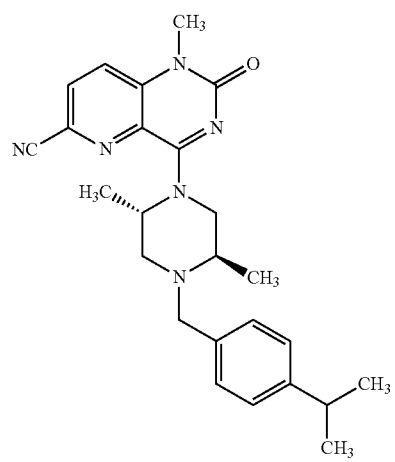 | H | A | 1.07 | 441.2 | A |
| 137 | 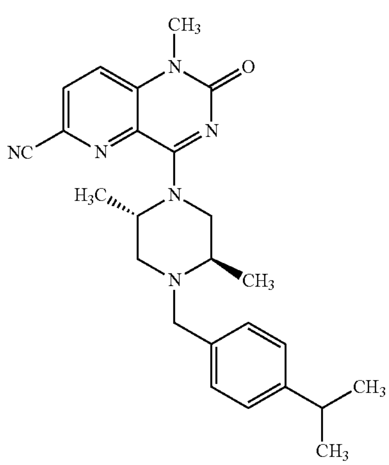 [SMILES: CC(C)c1ccc(CN2C[C@H](C)N(c3nc(=O)n(C)c4ccc(C#N)nc34)C[C@H]2C)cc1] | H | A | 2.29 | 431.2 | A |

TABLE 6-continued
| Ex. No. | Structure | Stereo chem. | LCMS Method | LCMS RT | M + H | Coupling Method |
|---|---|---|---|---|---|---|
| 138 | 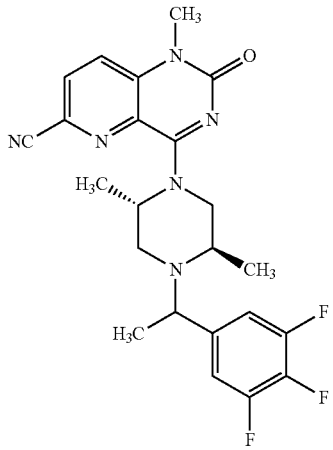 [SMILES: CC(c1cc(F)c(F)c(F)c1)N1C[C@H](C)N(c2nc(=O)n(C)c3ccc(C#N)nc23)C[C@H]1C] | H | A | 2.14 | 457.2 | A |
| 139 | 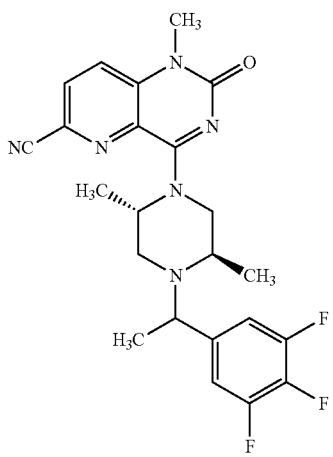 [SMILES: CC(c1cc(F)c(F)c(F)c1)N1C[C@H](C)N(c2nc(=O)n(C)c3ccc(C#N)nc23)C[C@H]1C] | H | A | 2.15 | 457.2 | A |
| 140 | 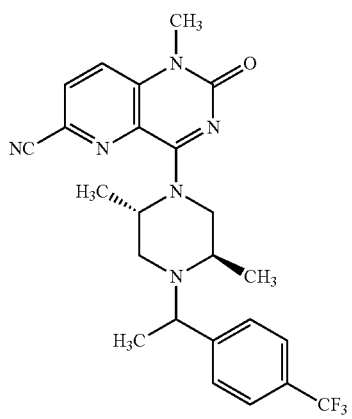 [SMILES: CC(c1ccc(C(F)(F)F)cc1)N1C[C@H](C)N(c2nc(=O)n(C)c3ccc(C#N)nc23)C[C@H]1C] | H | A | 2.23 | 471.2 | A |

TABLE 6-continued

| Ex. No. | Structure | Stereo chem. | LCMS Method | LCMS RT | M + H | Coupling Method |
|---|---|---|---|---|---|---|
| 141 | 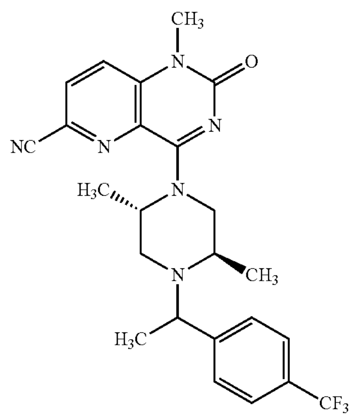 [SMILES: CC(c1ccc(C(F)(F)F)cc1)N1C[C@H](C)N(c2nc(=O)n(C)c3ccc(C#N)nc23)C[C@H]1C] | H | A | 2.23 | 471.2 | A |
| 142 | 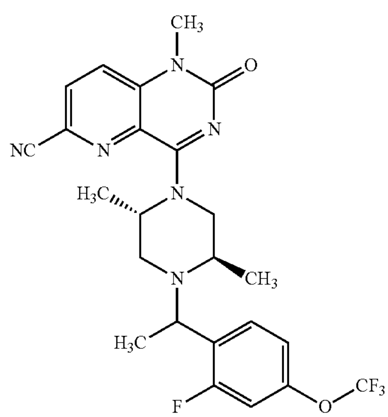 [SMILES: CC(c1ccc(OC(F)(F)F)cc1F)N1C[C@H](C)N(c2nc(=O)n(C)c3ccc(C#N)nc23)C[C@H]1C] | H | A | 2.3 | 505.2 | B |
| 143 | 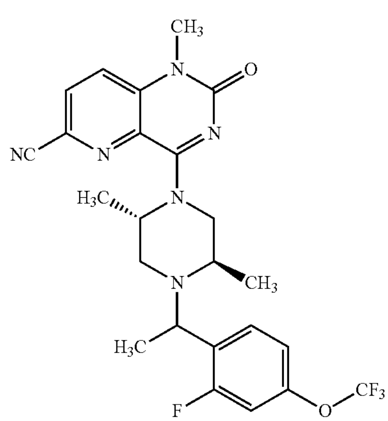 [SMILES: CC(c1ccc(OC(F)(F)F)cc1F)N1C[C@H](C)N(c2nc(=O)n(C)c3ccc(C#N)nc23)C[C@H]1C] | H | A | 2.3 | 505.2 | B |

| Ex. No. | Structure | Stereo chem. | LCMS Method | LCMS RT | M + H | Coupling Method |
|---|---|---|---|---|---|---|
| 144 | 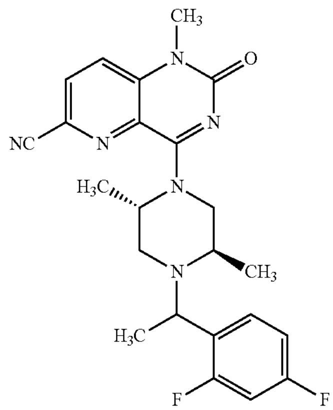 [SMILES: CC(c1ccc(F)cc1F)N1C[C@H](C)N(c2nc(=O)n(C)c3ccc(C#N)nc23)C[C@H]1C] | H | A | 2.06 | 439.2 | A |
| 145 | 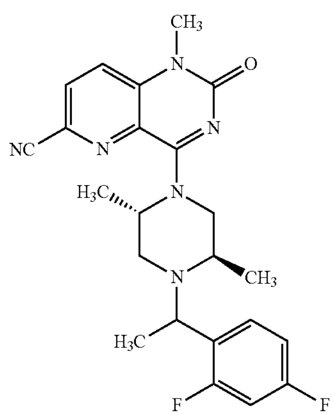 [SMILES: CC(c1ccc(F)cc1F)N1C[C@H](C)N(c2nc(=O)n(C)c3ccc(C#N)nc23)C[C@H]1C] | H | A | 2.06 | 439.1 | A |
| 146 | 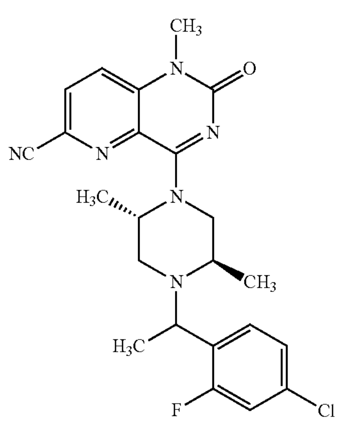 [SMILES: CC(c1ccc(Cl)cc1F)N1C[C@H](C)N(c2nc(=O)n(C)c3ccc(C#N)nc23)C[C@H]1C] | H | A | 2.23 | 455.1 | A |

TABLE 6-continued
| Ex. No. | Structure | Stereo chem. | LCMS Method | LCMS RT | M + H | Coupling Method |
|---|---|---|---|---|---|---|
| 147 | 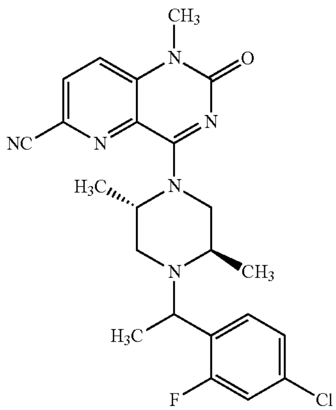 [SMILES: CC(c1ccc(Cl)cc1F)N1C[C@H](C)N(c2nc(=O)n(C)c3ccc(C#N)nc23)C[C@H]1C] | H | A | 2.23 | 455.2 | A |
| 148 | 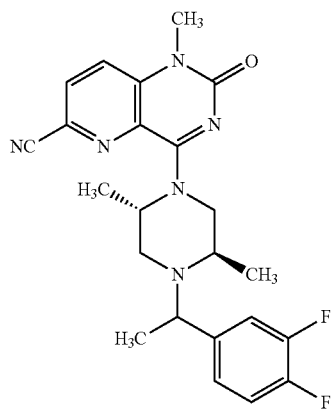 | H | A | 2.07 | 439.2 | A |
| 149 | 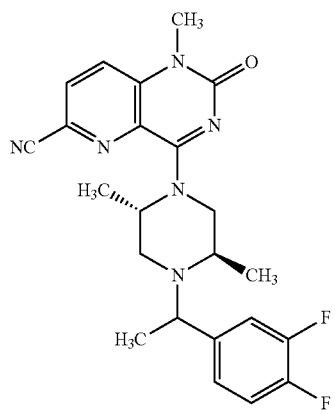 [SMILES: CC(c1ccc(F)c(F)c1)N1C[C@H](C)N(c2nc(=O)n(C)c3ccc(C#N)nc23)C[C@H]1C] | H | A | 2.08 | 439.2 | A |

TABLE 6-continued

| Ex. No. | Structure | Stereo chem. | LCMS Method | LCMS RT | M + H | Coupling Method |
|---|---|---|---|---|---|---|
| 150 | 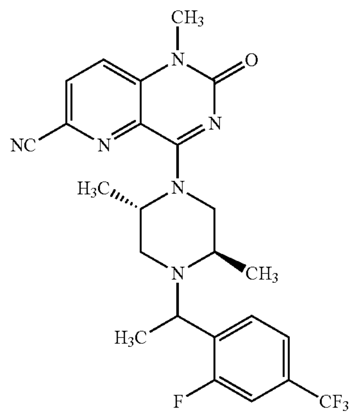 [SMILES: CC(c1ccc(C(F)(F)F)cc1F)N1C[C@H](C)N(c2nc(=O)n(C)c3ccc(C#N)nc23)C[C@H]1C] | H | A | 2.26 | 489.2 | A |
| 151 | 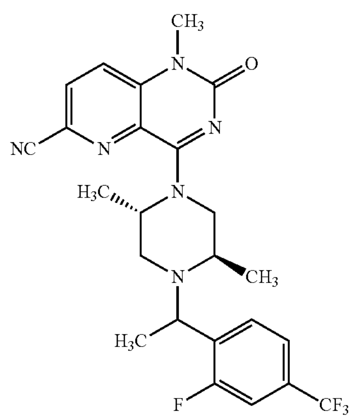 [SMILES: CC(c1ccc(C(F)(F)F)cc1F)N1C[C@H](C)N(c2nc(=O)n(C)c3ccc(C#N)nc23)C[C@H]1C] | H | A | 2.26 | 489.2 | A |
| 152 | 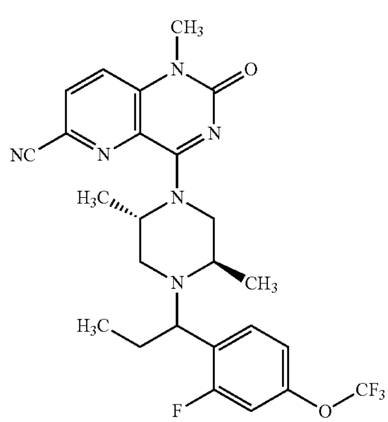 [SMILES: CCC(c1ccc(OC(F)(F)F)cc1F)N1C[C@H](C)N(c2nc(=O)n(C)c3ccc(C#N)nc23)C[C@H]1C] | H | A | 2.45 | 519.2 | A |

TABLE 6-continued
| Ex. No. | Structure | Stereo chem. | LCMS Method | LCMS RT | M + H | Coupling Method |
|---|---|---|---|---|---|---|
| 153 | 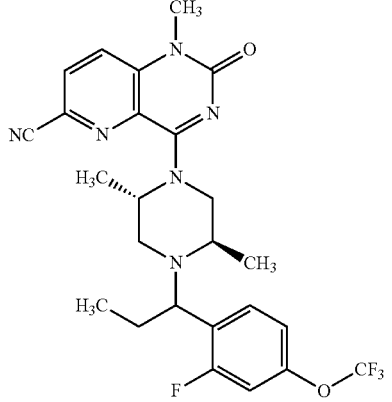 [SMILES: CCC(c1ccc(OC(F)(F)F)cc1F)N1C[C@H](C)N(c2nc(=O)n(C)c3ccc(C#N)nc23)C[C@H]1C] | H | A | 2.47 | 519.2 | A |
| 154 | 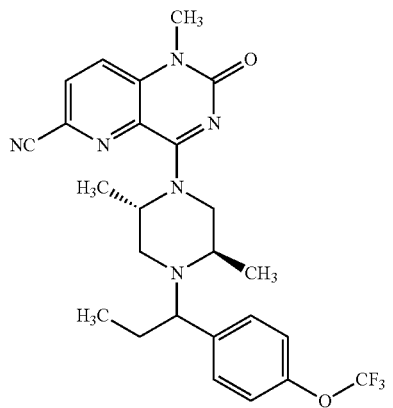 [SMILES: CCC(c1ccc(OC(F)(F)F)cc1)N1C[C@H](C)N(c2nc(=O)n(C)c3ccc(C#N)nc23)C[C@H]1C] | H | A | 2.36 | 501.2 | A |
| 155 | 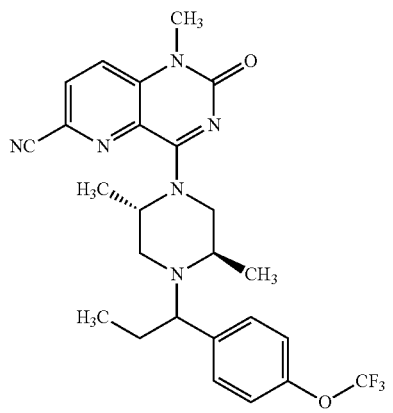 [SMILES: CCC(c1ccc(OC(F)(F)F)cc1)N1C[C@H](C)N(c2nc(=O)n(C)c3ccc(C#N)nc23)C[C@H]1C] | H | A | 2.38 | 501.2 | A |

TABLE 6-continued

| Ex. No. | Structure | Stereo chem. | LCMS Method | LCMS RT | M + H | Coupling Method |
|---|---|---|---|---|---|---|
| 156 | 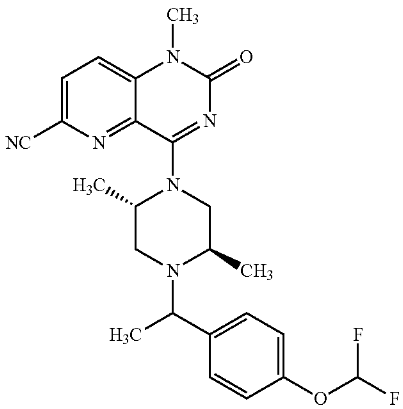 [SMILES: CC(c1ccc(OC(F)F)cc1)N1C[C@H](C)N(c2nc(=O)n(C)c3ccc(C#N)nc23)C[C@H]1C] | H | A | 2.02 | 469.2 | A |
| 157 | 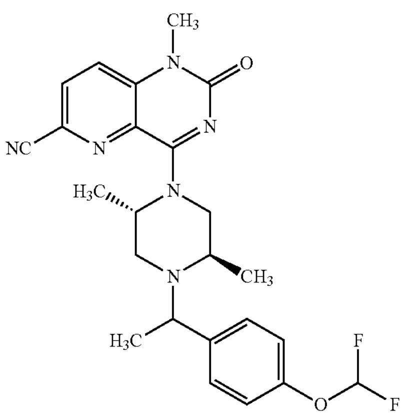 [SMILES: CC(c1ccc(OC(F)F)cc1)N1C[C@H](C)N(c2nc(=O)n(C)c3ccc(C#N)nc23)C[C@H]1C] | H | A | 2.05 | 469.2 | A |
| 158 | 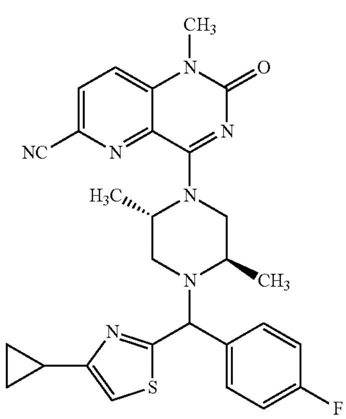 [SMILES: C[C@@H]1CN(c2nc(=O)n(C)c3ccc(C#N)nc23)[C@@H](C)CN1C(c1ccc(F)cc1)c1nc(C2CC2)cs1] | H | A | 2.11 | 530.3 | A |

TABLE 6-continued

| Ex. No. | Structure | Stereo chem. | LCMS Method | LCMS RT | M + H | Coupling Method |
|---|---|---|---|---|---|---|
| 159 | 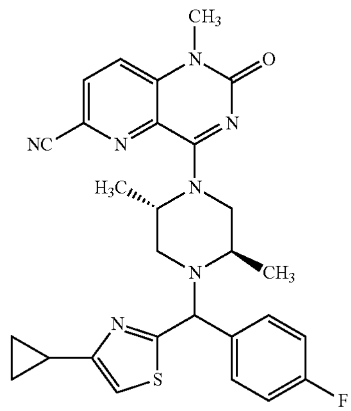 [SMILES: C[C@@H]1CN(c2nc(=O)n(C)c3ccc(C#N)nc23)[C@@H](C)CN1C(c1ccc(F)cc1)c1nc(C2CC2)cs1] | H | A | 2.14 | 530.3 | A |
| 160 | 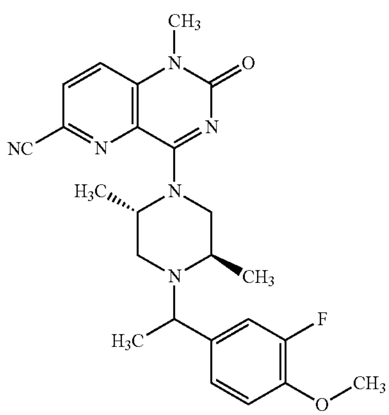 [SMILES: COc1ccc(C(C)N2C[C@H](C)N(c3nc(=O)n(C)c4ccc(C#N)nc34)C[C@H]2C)cc1F] | H | A | 2.28 | 505.2 | A |
| 161 | 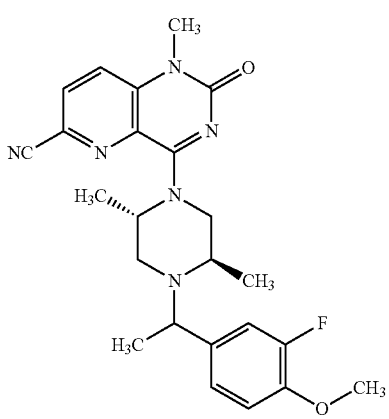 [SMILES: COc1ccc(C(C)N2C[C@H](C)N(c3nc(=O)n(C)c4ccc(C#N)nc34)C[C@H]2C)cc1F] | H | A | 2.29 | 505.2 | A |

TABLE 6-continued

| Ex. No. | Structure | Stereo chem. | LCMS Method | LCMS RT | M + H | Coupling Method |
|---|---|---|---|---|---|---|
| 162 | 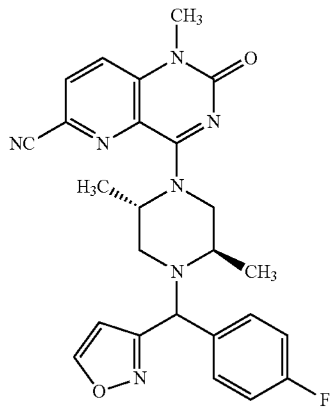 [SMILES: C[C@@H]1CN(c2nc(=O)n(C)c3ccc(C#N)nc23)[C@@H](C)CN1C(c1ccc(F)cc1)c1ccon1] | H | A | 1.80 | 474.2 | A |
| 163 | 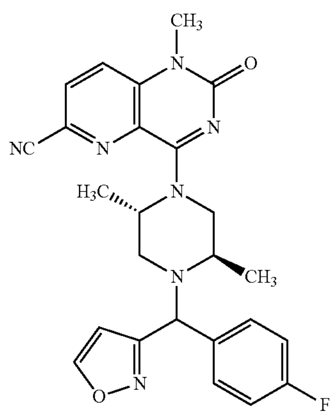 [SMILES: C[C@@H]1CN(c2nc(=O)n(C)c3ccc(C#N)nc23)[C@@H](C)CN1C(c1ccc(F)cc1)c1ccon1] | H | A | 1.79 | 474.2 | A |
| 164 | 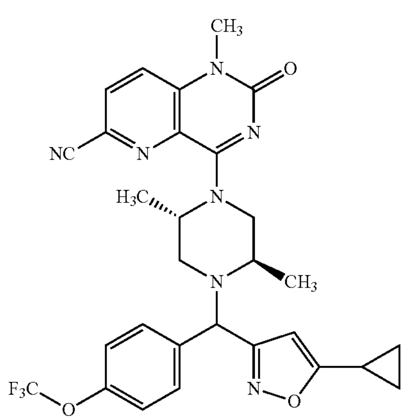 [SMILES: C[C@@H]1CN(c2nc(=O)n(C)c3ccc(C#N)nc23)[C@@H](C)CN1C(c1ccc(OC(F)(F)F)cc1)c1cc(C2CC2)on1] | H | A | 2.25 | 580.3 | A |

TABLE 6-continued
| Ex. No. | Structure | Stereo chem. | LCMS Method | LCMS RT | M + H | Coupling Method |
|---|---|---|---|---|---|---|
| 165 | 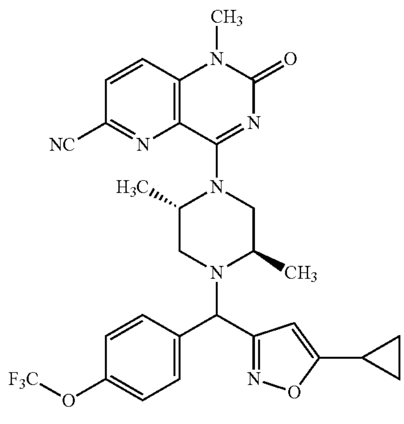 [SMILES: C[C@@H]1CN(c2nc(=O)n(C)c3ccc(C#N)nc23)[C@@H](C)CN1C(c1ccc(OC(F)(F)F)cc1)c1cc(C2CC2)on1] | H | A | 2.24 | 580.3 | A |
| 166 | 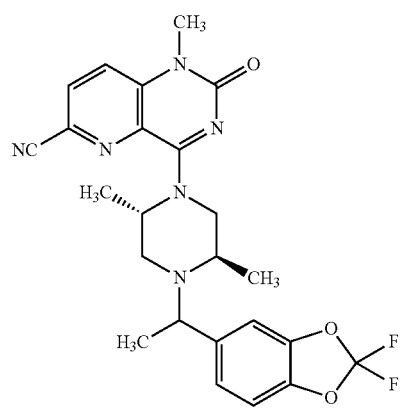 [SMILES: CC(c1ccc2c(c1)OC(F)(F)O2)N1C[C@H](C)N(c2nc(=O)n(C)c3ccc(C#N)nc23)C[C@H]1C] | H | A | 2.24 | 483.2 | A |
| 167 | 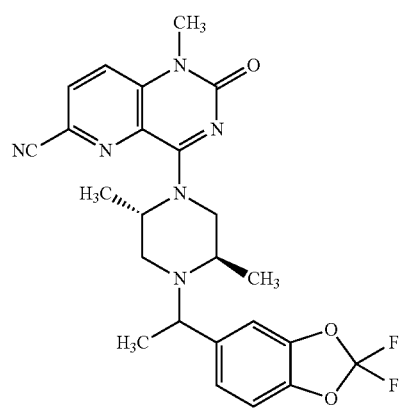 [SMILES: CC(c1ccc2c(c1)OC(F)(F)O2)N1C[C@H](C)N(c2nc(=O)n(C)c3ccc(C#N)nc23)C[C@H]1C] | H | A | 2.24 | 483.3 | A |

TABLE 6-continued

| Ex. No. | Structure | Stereo chem. | LCMS Method | LCMS RT | M + H | Coupling Method |
|---|---|---|---|---|---|---|
| 168 | 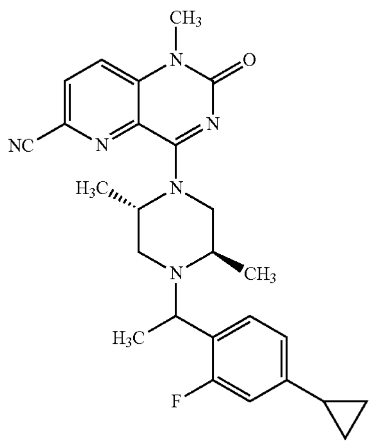 [SMILES: CC(c1ccc(C2CC2)cc1F)N1C[C@H](C)N(c2nc(=O)n(C)c3ccc(C#N)nc23)C[C@H]1C] | H | A | 2.27 | 461.3 | B |
| 169 | 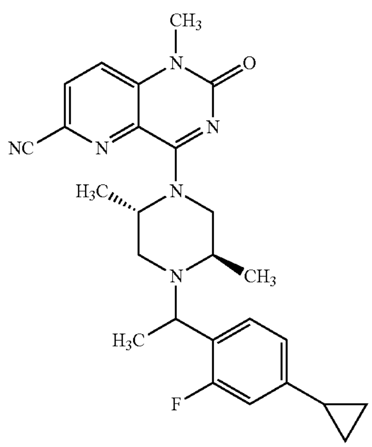 [SMILES: CC(c1ccc(C2CC2)cc1F)N1C[C@H](C)N(c2nc(=O)n(C)c3ccc(C#N)nc23)C[C@H]1C] | H | A | 2.27 | 461.3 | B |
| 170 | 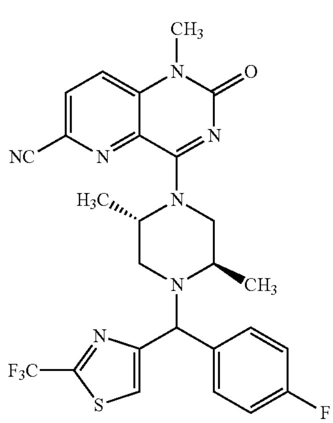 [SMILES: C[C@@H]1CN(c2nc(=O)n(C)c3ccc(C#N)nc23)[C@@H](C)CN1C(c1ccc(F)cc1)c1csc(C(F)(F)F)n1] | H | A | 2.19 | 558.2 | A |

TABLE 6-continued

| Ex. No. | Structure | Stereo chem. | LCMS Method | LCMS RT | M + H | Coupling Method |
|---|---|---|---|---|---|---|
| 171 | ![structure] | H | A | 2.2 | 558.2 | A |

Intermediate 14 tert-Butyl (2S,5S)-5-(hydroxymethyl)-2-methyl-4-(1-(4-(trifluoromethyl)phenyl)ethyl)piperazine-1-carboxylate (Diastereomeric Mixture)

Intermediate 15

((2S,5S)-5-methyl-1-(1-(4-(trifluoromethyl)phenyl)ethyl)piperazin-2-yl)methanol.HCl salt (Diastereomeric Mixture)

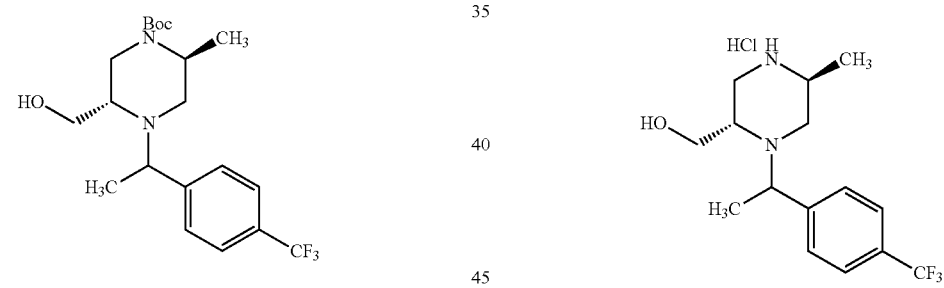

To a stirred solution of tert-butyl (2S,5S)-5-(hydroxymethyl)-2-methylpiperazine-1-carboxylate (2 g, 8.68 mmol) in acetonitrile (20 mL), DIPEA (7.6 mL, 43.4 mmol) and 1-(1-chloroethyl)-4-(trifluoromethyl)benzene (1.8 g, 8.68 mmol) were added sequentially at room temperature, followed by heating at 80° C. for 3 h. The reaction mixture was cooled to room temperature and solvent was removed under reduced pressure to give the crude product, which was purified by silica gel column chromatography using a 24 g silica gel flash column, eluting with 40-60% EtOAc in hexane to afford tert-butyl (2S,5S)-5-(hydroxymethyl)-2-methyl-4-(1-(4-(trifluoromethyl)phenyl)ethyl)piperazine-1-carboxylate (2.5 g, 61% yield) as an off-white solid. LCMS: m/z, 403.2 (M+H); rt 3.48 min. (LCMS Method: Column-Kinetex XB-C18 (75×3 mm-2.6 µm), Mphase A: 10 mM ammonium formate in water: acetonitrile (98:2); Mphase B: 10 mM ammonium formate in water:acetonitrile (2:98); Flow: 1 mL/min; Gradient: 20-100% B over 4 minutes then 0.6 min hold at 100% B, Detection: UV at 220 nm).

To a stirred solution of tert-butyl (2S,5S)-5-(hydroxymethyl)-2-methyl-4-(1-(4-(trifluoromethyl)phenyl)ethyl)piperazine-1-carboxylate (0.7 g, 1.74 mmol) in DCM (10 mL), HCl (4 N in dioxane) (0.53 mL, 17.4 mmol) was added drop wise at room temperature. The reaction mixture was stirred for 3 h. Solvent was removed under reduced pressure, the solids were co-distilled with acetonitrile (3×10 mL), and dried to afford ((2S,5S)-5-methyl-1-(1-(4-(trifluoromethyl)phenyl)ethyl)piperazin-2-yl)methanol, HCl salt (0.5 g, 86% yield) as an off-white solid. LCMS: m/z, 303.2 (M+H); rt 1.77 & 2.07 min. (LCMS Method: Column-Kinetex XB-C18 (75×3 mm-2.6 µm), Mphase A: 10 mM ammonium formate in water: acetonitrile (98:2); Mphase B: 10 mM ammonium formate in water:acetonitrile (2:98); Flow: 1 mL/min; Gradient: 20-100% B over 4 minutes then 0.6 min hold at 100% B, Detection: UV at 220 nm).

Example 172

6-chloro-4-((2S,5S)-5-(hydroxymethyl)-2-methyl-4-(1-(4-(trifluoromethyl)phenyl)ethyl) piperazin-1-yl)-1-methylpyrido[3,2-d]pyrimidin-2(1H)-one (Diastereomeric Mixture)

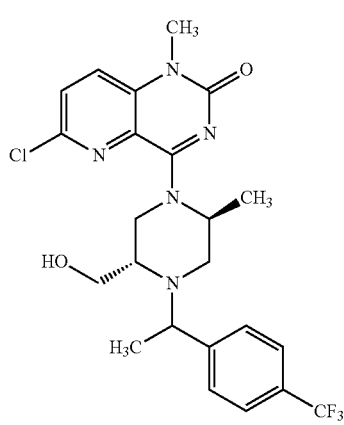

(172)

To a stirred solution of ((2S,5S)-5-methyl-1-(1-(4-(trifluoromethyl)phenyl)ethyl) piperazin-2-yl)methanol, HCl salt (150 mg, 0.50 mmol) in acetonitrile (5 mL), DIPEA (0.44 mL, 2.48 mmol) and 4,6-dichloro-1-methylpyrido[3,2-d]pyrimidin-2(1H)-one (114 mg, 0.50 mmol) were added sequentially at room temperature followed by heating at 80° C. for 12 h. The reaction mixture was cooled to room temperature and solvent was removed under reduced pressure to give the crude product, which was purified by silica gel column chromatography using 12 g flash column, eluting with 0-10% MeOH in CHCl$_3$ to afford 6-chloro-4-((2S,5S)-5-(hydroxymethyl)-2-methyl-4-(1-(4-(trifluoromethyl)phenyl)ethyl)piperazin-1-yl)-1-methylpyrido[3,2-d]pyrimidin-2(1H)-one (150 mg, 57% yield). LCMS: m/z, 496.2 (M+H); rt 1.99 min. (LCMS Method: Column: Waters Acquity UPLC BEH C18 (3.0×50 mm) 1.7 µm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Example 173

6-Chloro-4-(2S,5S)-5-(methoxymethyl)-2-methyl-4-(1-(4-(trifluoromethyl)phenyl)ethyl) piperazin-1-yl)-1-methylpyrido[3,2-d]pyrimidin-2(1H)-one (Diastereomeric Mixture)

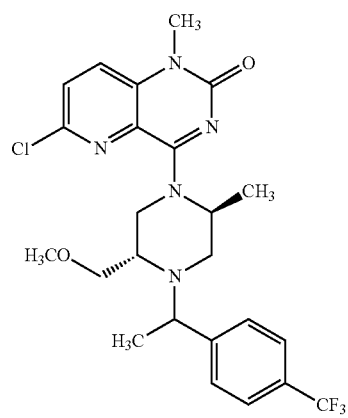

(173)

To a stirred suspension of NaH (40.3 mg, 1.01 mmol, 60% w/w) in THF (5 mL) was added 6-chloro-4-(2S,5S)-5-(hydroxymethyl)-2-methyl-4-(1-(4-(trifluoromethyl) phenyl)ethyl)piperazin-1-yl)-1-methylpyrido[3,2-d]pyrimidin-2(1H)-one (250 mg, 0.50 mmol) at 0° C. After 5 minutes, a solution of methyl iodide (0.06 mL, 1.01 mmol) in THF (2 mL) was added and the reaction mixture was stirred for 2 h at room temperature. The reaction mixture was cooled to 0° C., quenched with ice cold water and extracted with EtOAc (2×50 mL). The combined organic extracts were washed with brine, dried over Na$_2$SO$_4$ and concentrated to give the crude product, which was purified by silica gel flash column chromatography (5-10% MeOH in DCM; 12 g column) to afford 6-chloro-4-((2S,5S)-5-(methoxymethyl)-2-methyl-4-(1-(4-(trifluoromethyl)phenyl)ethyl)piperazin-1-yl)-1-methylpyrido[3,2-d]pyrimidin-2(1H)-one (200 mg, 78% yield). LCMS: m/z, 510.1 (M+H); rt 1.08 and 1.11 min. (LCMS Method: Column: AQUITY UPLC BEH C18 (3.0×50 mm) 1.7 µm; Mobile phase A: 10 mM ammonium acetate:acetonitrile (95:5), Mobile phase B: 10 mM ammonium acetate:acetonitrile (5:95), Method:% B: 0 min-20:2 min-100:2.3 min-100, Temperature: 27° C.; Flow rate: 0.7 mL/min; Detection: UV at 220 nm).

Examples 174 and 175

4-((2S,5S)-5-(Methoxymethyl)-2-methyl-4-(1-(4-(trifluoromethyl)phenyl)ethyl)piperazin-1-yl)-1-methyl-2-oxo-1,2-dihydropyrido[3,2-d]pyrimidine-6-carbonitrile

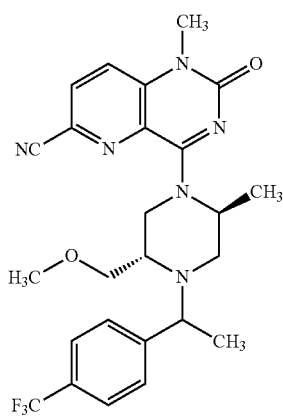

(174-175)

To a stirred solution of 6-chloro-4-((2S,5S)-5-(methoxymethyl)-2-methyl-4-(1-(4-(trifluoromethyl)phenyl)ethyl)piperazin-1-yl)-1-methylpyrido[3,2-d]pyrimidin-2(1H)-one (140 mg, 0.27 mmol) in DMF (5 mL) were added zinc (27 mg, 0.41 mmol) and TEA (0.15 mL, 1.08 mmol). The reaction mixture was degassed with argon gas for 5 min., followed by the addition of zinc cyanide (97 mg, 0.82 mmol) and dichloro[9,9-dimethyl-4,5-bis(diphenylphosphino)xanthene]palladium(II) (21 mg, 0.03 mmol). The reaction mixture was heated at 90° C. for 12 h. The reaction mixture was cooled to room temperature and concentrated under reduced pressure to afford a residue which was purified via preparative HPLC. (Chiral Separation Method: Column: Cellulose-5 (250*19 ID) 5 micron; Mobile Phase A: 10 mM NH$_4$OAc in MeOH; Flow: 20 mL/min; UV detection: 215 nm).

Example 174: (5 mg, 4% yield): LCMS: m/z, 501.3 (M+H); rt 2.11 min; (LCMS Method: Column: XBridge BEH XP C18 (2.1×50 mm), 2.5 µm; Mobile phase A: 10 mM ammonium acetate: acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm). $^1$H NMR (400 MHz, DMSO-d$_6$) δ ppm 8.15-8.28 (m, 1H), 7.97-8.02 (m, 1H), 7.73 (d, J=8.1 Hz, 2H), 7.59 (br d, J=8.1 Hz, 2H), 5.57-6.01 (m, 1H), 4.80-5.08 (m, 1H), 3.92-4.11 (m, 1H), 3.37-3.75 (m, 6H), 3.07-3.23 (m, 2H), 2.86-3.01 (m, 2H), 2.76-2.83 (m, 1H), 2.61-2.72 (m, 1H), 1.05-1.68 (m, 6H).

Example 175: (14 mg, 10% yield): LCMS: m/z, 501.3 (M+H); rt 2.14 min; (LCMS Method: Column: XBridge BEH XP C18 (2.1×50 mm), 2.5 µm; Mobile phase A: 10 mM ammonium acetate: acetonitrile (95:5), Mobile phase B: 10 mM ammonium acetate: acetonitrile (5:95), Gradient=0-100% B over 3 minutes; Temperature: 50° C.; Flow rate: 1.1 mL/min; Detection: UV at 220 nm). $^1$H NMR (400 MHz, DMSO-d6) δ ppm 8.25 (br d, J=9.0 Hz, 1H), 8.00 (d, J=9.0 Hz, 1H), 7.70 (m, J=8.1 Hz, 2H), 7.59-7.65 (m, 2H), 6.00-6.16 (m, 1H), 4.72-4.88 (m, 1H), 3.89-3.95 (m, 1H), 3.70-3.83 (m, 1H), 3.49-3.65 (m, 1H), 3.45 (s, 3H), 3.37-3.41 (m, 1H), 3.23-3.32 (m, 2H), 3.00-3.13 (m, 2H), 2.53-2.65 (m, 1H), 2.35-2.46 (m, 1H), 1.36 (d, J=6.4 Hz, 3H), 1.16-1.28 (m, 3H).

The examples in the Table 7 were prepared according to the general procedure described in Examples 174 and 175, using the appropriate benzhydryl/α-substituted benzyl/benzyl halide. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 7

| Ex. No. | Structure | LCMS Method | LCMS RT | M + H | Stereo Chem. |
|---|---|---|---|---|---|
| 176 | 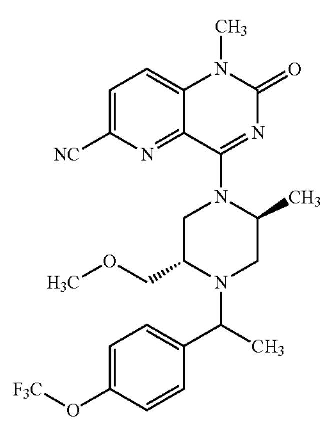 [SMILES: COC[C@@H]1CN(c2nc(=O)n(C)c3ccc(C#N)nc23)[C@@H](C)CN1C(C)c1ccc(OC(F)(F)F)cc1] | A | 2.15 | 517.3 | H |

TABLE 7-continued

| Ex. No. | Structure | LCMS Method | LCMS RT | M + H | Stereo Chem. |
|---|---|---|---|---|---|
| 177 | 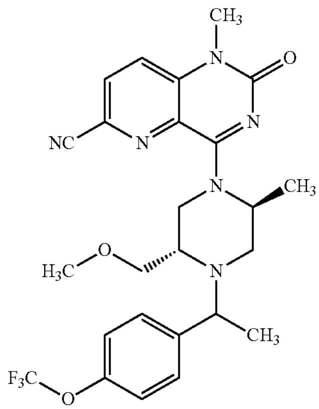 [SMILES: COC[C@@H]1CN(c2nc(=O)n(C)c3ccc(C#N)nc23)[C@@H](C)CN1C(C)c1ccc(OC(F)(F)F)cc1] | A | 2.19 | 517.3 | H |
| 178 | 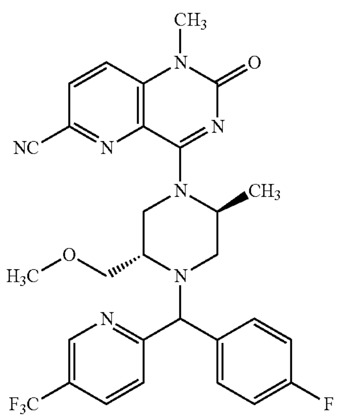 [SMILES: COC[C@@H]1CN(c2nc(=O)n(C)c3ccc(C#N)nc23)[C@@H](C)CN1C(c1ccc(F)cc1)c1ccc(C(F)(F)F)cn1] | A | 2.08 | 582.2 | H |
| 179 | 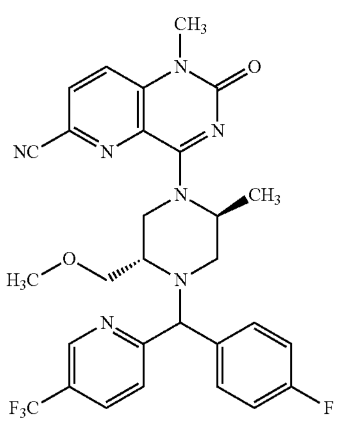 [SMILES: COC[C@@H]1CN(c2nc(=O)n(C)c3ccc(C#N)nc23)[C@@H](C)CN1C(c1ccc(F)cc1)c1ccc(C(F)(F)F)cn1] | A | 2.07 | 582.1 | H |

Intermediate 18 tert-Butyl(2S,5S)-4-((4-fluorophenyl)(5-(trifluoromethyl)pyridin-2-yl)methyl)-5-(hydroxymethyl)-2-methylpiperazine-1-carboxylate (Diastereomeric Mixture)

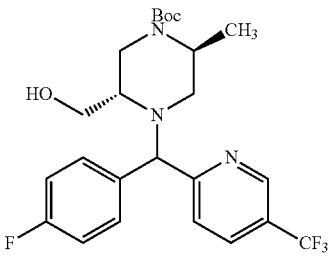 [SMILES: C[C@H]1CN(C(c2ccc(F)cc2)c2ccc(C(F)(F)F)cn2)[C@H](CO)CN1C(=O)OC(C)(C)C]

To a stirred solution of tert-butyl (2S,5S)-5-(hydroxymethyl)-2-methylpiperazine-1-carboxylate (1 g, 4.34 mmol) in acetonitrile (20 mL), DIPEA (3.0 mL, 17.4 mmol) and 2-(bromo(4-fluorophenyl)methyl)-5-(trifluoromethyl)pyridine (1.75 g, 5.21 mmol) were added sequentially at room temperature. The reaction mixture was heated at 80° C. for 3 h. The reaction mixture was cooled to room temperature and solvent was removed under reduced pressure to give the crude product, which was purified by silica gel column chromatography using a 24 g silica gel flash column, eluting with 3% MeOH in CHCl₃ to afford tert-butyl (2S,5S)-4-((4-fluorophenyl)(5-(trifluoromethyl)pyridin-2-yl)methyl)-5-(hydroxymethyl)-2-methylpiperazine-1-carboxylate (1.4 g, 67% yield). LCMS: m/z, 484.2 (M+H); rt 1.97 and 1.99 min. (LCMS Method: Column: Waters Acquity UPLC BEH C18 (3.0×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 19

((2S,5S)-1-((4-Fluorophenyl)(5-(trifluoromethyl)pyridin-2-yl)methyl)-5-methylpiperazin-2-yl)methanol, HCl (Diastereomeric Mixture)

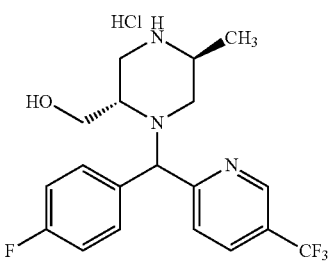 [SMILES: Cl ; C[C@H]1CN(C(c2ccc(F)cc2)c2ccc(C(F)(F)F)cn2)[C@H](CO)CN1]

To a stirred solution of tert-butyl (2S,5S)-4-((4-fluorophenyl)(5-(trifluoromethyl) pyridin-2-yl)methyl)-5-(hydroxymethyl)-2-methylpiperazine-1-carboxylate (1 g, 2.07 mmol) in DCM (20 mL), HCl (4 N in dioxane) (2.6 mL, 10.4 mmol) was added drop wise at room temperature. The reaction mixture was stirred for 3 h. Solvent was removed under reduced pressure, the solids were co-distilled with acetonitrile (3×10 mL), and dried to afford ((2S,5S)-1-((4-fluorophenyl)(5-(trifluoromethyl)pyridin-2-yl) methyl)-5-methylpiperazin-2-yl)methanol, HCl (800 mg, 92% yield) as an off-white solid. LCMS: m/z, 384.2 (M+H); rt 1.05 & 1.11 min. (LCMS Method: Column: Waters Acquity UPLC BEH C18 (3.0×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Example 180

6-Chloro-4-((2S,5S)-4-((4-fluorophenyl)(5-(trifluoromethyl)pyridin-2-yl)methyl)-5-(hydroxymethyl)-2-methylpiperazin-1-yl)-1-methylpyrido[3,2-d]pyrimidin-2(1H)-one (Diastereomeric Mixture)

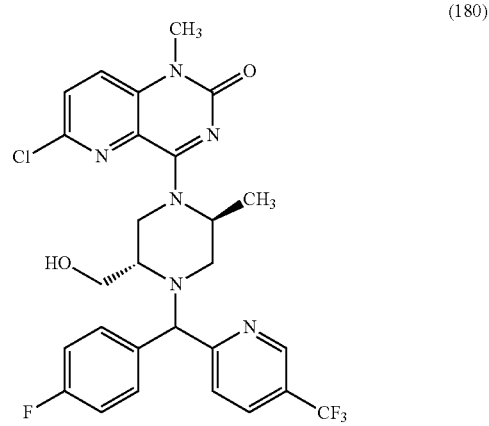 [SMILES: C[C@H]1CN(C(c2ccc(F)cc2)c2ccc(C(F)(F)F)cn2)[C@H](CO)CN1c1nc(=O)n(C)c2ccc(Cl)nc12]

(180)

To a stirred solution of ((2S,5S)-1-((4-fluorophenyl)(5-(trifluoromethyl)pyridin-2-yl)methyl)-5-methylpiperazin-2-yl)methanol, HCl (400 mg, 0.95 mmol) in acetonitrile (15 mL), DIPEA (0.8 mL, 4.8 mmol) and 4,6-dichloro-1-methylpyrido[3,2-d]pyrimidin-2(1H)-one (292 mg, 0.95 mmol) were added sequentially at room temperature followed by heating at 80° C. for 12 h. The reaction mixture was cooled to room temperature and solvent was removed under reduced pressure to give crude residue, which was purified by silica gel column chromatography using 12 g flash column, eluting with 3-7% MeOH in CHCl₃ to afford 6-chloro-4-((2S,5S)-4-((4-fluorophenyl)(5-(trifluoromethyl)pyridin-2-yl) methyl)-5-(hydroxymethyl)-2-methylpiperazin-1-yl)-1-methylpyrido[3,2-d]pyrimidin-2(1H)-one (450 mg, 82% yield). LCMS: m/z, 577.2 (M+H); rt 1.92 and 1.94 min. (LCMS Method: Column: Waters Acquity UPLC BEH C18 3.0×50 mm 1.7 μm, Mobile phase A: 10 mM ammonium acetate: acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 181 and 182

4-((2S,5S)-4-((4-Fluorophenyl)(5-(trifluoromethyl)pyridin-2-yl)methyl)-5-(hydroxymethyl)-2-methylpiperazin-1-yl)-1-methyl-2-oxo-1,2-dihydropyrido[3,2-d]pyrimidine-6-carbonitrile

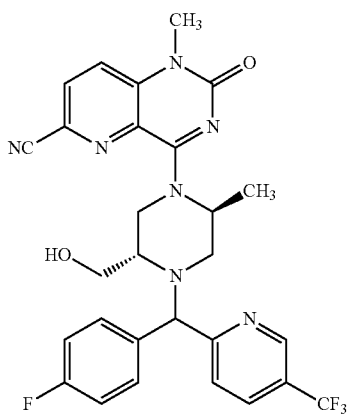

(181-182)

To a stirred solution of 6-chloro-4-((2S,5S)-4-((4-fluorophenyl)(5-(trifluoromethyl)pyridin-2-yl)methyl)-5-(hydroxymethyl)-2-methylpiperazin-1-yl)-1-methylpyrido[3,2-d]pyrimidin-2(1H)-one (150 mg, 0.26 mmol) in DMF (5 mL) were added zinc (26 mg, 0.39 mmol) and TEA (0.15 mL, 1.08 mmol). The reaction mixture was degassed with argon gas for 5 min., followed by the addition of zinc cyanide (92 mg, 0.78 mmol) and dichloro[9,9-dimethyl-4,5-bis(diphenylphosphino)xanthene] palladium(II) (20 mg, 0.03 mmol). The reaction mixture heated at 90° C. for 12 h. The reaction mixture was cooled to room temperature and concentrated under reduced pressure to afford a residue which was purified via preparative HPLC (Chiral Separation Method: Column: Cellulose-5 (250*19 ID) 5 micron; Mobile Phase A: 10 mM $NH_4OAc$ in MeOH; Flow: 20 mL/min; UV detection: 215 nm).

Example 181: (15 mg, 10% yield): LCMS: m/z, 568.2 (M+H); rt 2.74 min; (LCMS Method: Column-Kinetex XB-C18 (75×3 mm-2.6 μm), Mphase A: 10 mM ammonium formate in water: acetonitrile (98:2); Mphase B: 10 mM ammonium formate in water: acetonitrile (2:98); Flow: 1 mL/min; Gradient: 20-100% B over 4 minutes then 0.6 min hold at 100% B, Detection: UV at 220 nm). $^1$H NMR (400 MHz, DMSO-$d_6$) δ ppm 8.92 (s, 1H), 8.16-8.26 (m, 2H), 8.00 (br d, J=9.5 Hz, 1H), 7.86-7.96 (m, 1H), 7.53-7.60 (m, 2H), 7.10-7.22 (m, 2H), 5.50-5.86 (m, 1H), 5.24 (s, 1H), 5.02-5.15 (m, 1H), 4.65-4.89 (m, 1H), 4.17-4.54 (m, 1H), 3.56-3.92 (m, 2H), 3.45 (s, 3H), 2.77-2.92 (m, 2H), 2.52-2.61 (m, 1H), 1.31-1.59 (m, 3H).

Example 182: (17 mg, 11% yield): LCMS: m/z, 568.2 (M+H); rt 2.72 min; (LCMS Method: Column-Kinetex XB-C18 (75×3 mm-2.6 μm), Mphase A: 10 mM ammonium formate in water: acetonitrile (98:2); Mphase B: 10 mM ammonium formate in water: acetonitrile (2:98); Flow: 1 mL/min; Gradient: 20-100% B over 4 minutes then 0.6 min hold at 100% B, Detection: UV at 220 nm). $^1$H NMR (400 MHz, DMSO-$d_6$) δ ppm 8.83 (br s, 1H), 8.23 (br d, J=5.5 Hz, 2H), 7.99 (br d, J=8.0 Hz, 2H), 7.50-7.68 (m, 2H), 7.18 (br t, J=8.8 Hz, 2H), 5.48-5.84 (m, 1H), 5.04-5.27 (m, 2H), 4.69-4.84 (m, 1H), 4.20-4.55 (m, 1H), 3.75-3.87 (m, 1H), 3.52-3.64 (m, 2H), 3.45 (s, 3H), 2.85-2.98 (m, 2H), 1.37-1.62 (m, 3H).

The examples in the Table 8 were prepared according to the general procedure described in Examples 181 and 182, using the appropriate benzhydryl/α-substituted benzyl/benzyl halide. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 8

| Ex. No. | Structure | LCMS Method | LCMS RT | M + H | Stereo chem. |
|---|---|---|---|---|---|
| 183 | 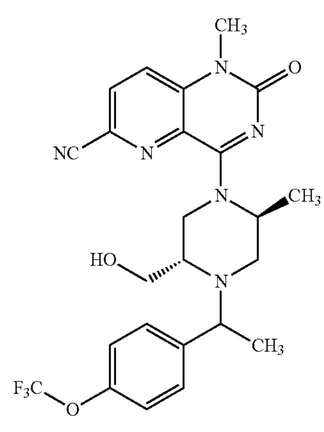 [SMILES: CC(c1ccc(OC(F)(F)F)cc1)N1C[C@H](C)N(c2nc(=O)n(C)c3ccc(C#N)nc23)C[C@H]1CO] | A | 1.98 | 503.3 | H |

TABLE 8-continued

| 184 | 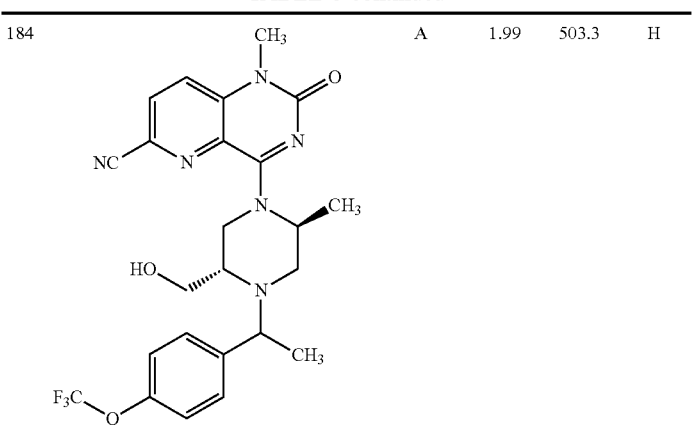 | A | 1.99 | 503.3 | H |

LCMS Conditions:

Method C: Column: XBridge BEH XP C18 (50×2.1 mm, 2.5 μm); mobile phase A: 10 mM NH$_4$OAc in water: acetonitrile (95:5); mobile phase B: 10 mM NH$_4$OAc in water:acetonitrile (5:95); Gradient=0-100% B over 3 minutes; Temperature: 50° C.; Flow rate: 1.1 mL/min; Detection: UV at 220 nm.

Method D: Column: XBridge BEH XP C18 (50×2 mm, 2.5 μm); mobile phase A: 0.1% TFA in water:acetonitrile (95:5); mobile phase B: 0.1% TFA in water:acetonitrile (5:95); Gradient=0-100% B over 3 minutes; Temperature: 50° C.; Flow rate: 1.1 mL/min; Detection: UV at 220 nm.

Method E: Column-KINETEX-XB-C18 (75×3 mm, 2.6 μm); mobile phase A: 10 mM NH$_4$OAc in water:acetonitrile (98:2); mobile phase B: 10 mM NH$_4$OAc in water:acetonitrile (02:98); Gradient=20-100% B over 4 minutes; Temperature: 50° C.; Flow rate: 1.1 mL/min; Detection: UV at 254 nm.

Method F: Column:)(Bridge C18 (50×2.1 mm, 1.7 μm); mobile phase A: 0.1% TFA in water:acetonitrile (95:5); mobile phase B: 0.1% TFA in water, acetonitrile (5:95); Gradient=0-100% B over 3 minutes; Temperature: 50° C.; Flow rate: 1.0 mL/min; Detection: UV at 220 nm.

Intermediate 20

Methyl (S)-2-(benzylamino)butanoate

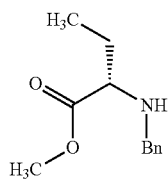

To a stirred solution of H-ABU-OME HCl (5 g, 32.6 mmol) in dry DCM (50 mL) was added benzaldehyde (4.3 mL, 42.3 mmol). The reaction mixture was stirred at room temperature for 16 h. The reaction mixture was cooled with an ice water bath and solid sodium triacetoxyborohydride (10.35 g, 48.8 mmol) was added in portion wise over 15 min. The cooling bath was removed and the milky white solution was stirred at room temperature for 16 h. The solvent was removed under reduced pressure and the resulting crude product was partitioned between EtOAc (~100 mL) and 1 N HCl (~200 mL). The layers were separated and the aqueous layer was extracted with EtOAc (2×500 mL). The aqueous layer was adjusted to pH ~10 with 1 N NaOH (450 mL) and the milky aqueous layer was extracted immediately with EtOAc (3×150 mL). The combined organic layer was washed with brine (250 mL), dried over anhydrous MgSO$_4$, filtered and concentrated under reduced pressure to afford methyl (S)-2-(benzylamino)butanoate (4 g, 56% yield). LCMS: m/z=208.2 [M+H]$^+$; retention time 2.28 min, LCMS Method: Kinetex XB-C18 (3×75 mm, 2.6 μm); mobile phase A: 10 mM ammonium formate in water: acetonitrile (98:2), mobile phase B: 10 mM ammonium formate in water: acetonitrile (2:98), Gradient=20-100% B over 4 minutes, then a 0.6 minute hold at 100% B; Temperature: 27° C.; Flow rate: 1.0 mL/min.

Intermediate 21

Methyl (S)-2-((R)—N-benzyl-2-((tert-butoxycarbonyl)amino)butanamido)butanoate

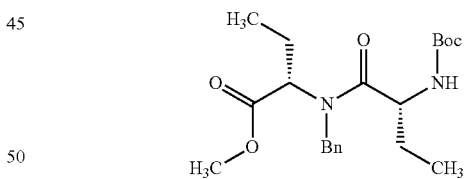

To a stirred solution of BOC-D-ABU-OH (1 g, 4.92 mmol) in dry DMF (8 mL) was added HATU (3.74 g, 9.84 mmol) and DIPEA (2.1 mL, 12.3 mmol). The reaction mixture was stirred for 5 min. and methyl (S)-2-(benzylamino)butanoate (1.43 g, 6.89 mmol) was added. The reaction mixture was stirred at room temperature for 16 h. The reaction mixture was diluted with ethyl acetate and washed with water. The organic layer was dried over anhydrous Na$_2$SO$_4$, filtered and evaporated under reduced pressure to yield the crude compound, which was purified by silica gel chromatography (eluted with 20-30% ethyl acetate/pet ether) to yield methyl (S)-2-((R)—N-benzyl-2-((tert-butoxycarbonyl)amino)butanamido)butanoate (1 g, 52% yield). LCMS: m/z=393.2 [M+H]$^+$; retention time 3.26 min, LCMS Method: Column: Kinetex XB-C18 (3×75 mm, Intermediate 22

Methyl (S)-2-((R)-2-amino-N-benzylbutanamido)butanoate

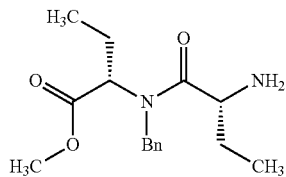 [SMILES: CC[C@@H](N)C(=O)N(Cc1ccccc1)[C@@H](CC)C(=O)OC]

To a stirred solution of methyl (S)-2-((R)—N-benzyl-2-((tert-butoxycarbonyl) amino)butanamido)butanoate (1 g, 2.55 mmol) in dry DCM (10 mL) was added TFA (5 mL, 64.9 mmol) at room temperature. The reaction mixture was stirred for 2 h. The solvent was removed under reduced pressure to yield methyl (S)-2-((R)-2-amino-N-benzylbutanamido)butanoate, TFA (1 g, 58% yield). LCMS: m/z=293.2 [M+H]$^+$; retention time 1.08 min, LCMS Method; Column: AQUITY UPLC BEH C18 (3.0×50 mm, 1.7 μm); mobile phase A: 10 mM NH$_4$OAc in water:acetonitrile (95:5); mobile phase B: 10 mM NH$_4$OAc in water:acetonitrile (5:95); gradient=20-100% B over 1.1 min, then a 0.6 minute hold at 100% B, flow: 0.7 mL/min, temperature: 27° C.; detection: UV at 220 nm.

Intermediate 23

(3R,6S)-1-Benzyl-3,6-diethylpiperazine-2,5-dione

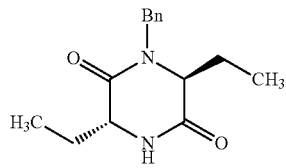 [SMILES: CC[C@H]1NC(=O)[C@H](CC)N(Cc2ccccc2)C1=O]

Methyl (S)-2-((R)-2-amino-N-benzylbutanamido)butanoate TFA (1 g, 3.42 mmol) was dissolved in MeOH (15 mL) and the reaction mixture was heated at 70° C. for 16 h. The reaction mixture was cooled to room temperature and the solvent was removed under reduced pressure to yield the crude compound, which was dissolved in DCM and washed with saturated aqueous NaHCO$_3$ solution. The combined organic layer was dried over anhydrous Na$_2$SO$_4$, filtered and evaporated under reduced pressure to yield (3R,6S)-1-benzyl-3,6-diethylpiperazine-2,5-dione (0.6 g, 46.0% yield). LCMS: m/z=261.2 [M+H]$^+$; retention time 1.08 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 1.1 min, then a 0.6 minute hold at 100% B, flow: 0.7 mL/min, temperature: 27° C.; detection: UV at 220 nm.

Intermediate 24

(2S,5R)-1-Benzyl-2,5-diethylpiperazine

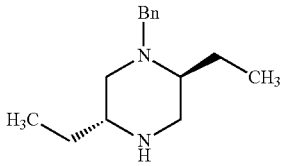 [SMILES: CC[C@@H]1CN(Cc2ccccc2)[C@@H](CC)CN1]

To a stirred solution of (3R,6S)-1-benzyl-3,6-diethylpiperazine-2,5-dione (0.63 g, 2.42 mmol) in dry tetrahydrofuran (15 mL) was slowly added BH$_3$. THF (1 M, 12.1 mL, 12.1 mmol) at 0° C. The reaction mixture heated at 70° C. for 16 h. The reaction mixture was cooled to room temperature. The reaction was quenched with the addition of methanol (20 mL) and aqueous 1.5 N HCl (1 mL, 32.9 mmol). The mixture was heated at 70° C. for 2 h, then cooled to room temperature and the solvent was removed under reduced pressure to yield the crude product, which was dissolved in DCM and washed with saturated aqueous NaHCO$_3$ solution. The organic layer was dried over anhydrous Na$_2$SO$_4$, filtered and evaporated under reduced pressure to yield (2S,5R)-1-benzyl-2,5-diethylpiperazine (0.51 g, 86% yield). LCMS: m/z=233.0 [M+H]$^+$; retention time 0.454 min, LCMS Method: Kinetex XB-C18 (3×75 mm, 2.6 μm); mobile phase A: 0.1% TFA in water, mobile phase B: 0.1% TFA in acetonitrile, Gradient=20-100% B over 4 minutes, then a 0.6 minute hold at 100% B; Flow rate: 1.5 mL/min.

Intermediate 25 tert-Butyl (2R,5S)-4-benzyl-2,5-diethylpiperazine-1-carboxylate

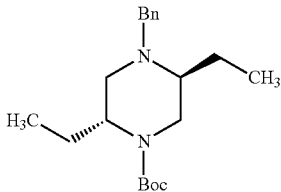

To a stirred solution of (2S,5R)-1-benzyl-2,5-diethylpiperazine (0.51 g, 2.19 mmol) in dry DCM (10 mL) was added TEA (0.8 mL, 5.49 mmol) and Boc-anhydride (0.8 mL, 3.29 mmol). The reaction mixture was stirred at room temperature for 2 h. The reaction mixture was diluted with DCM and washed with water, brine and dried over anhydrous Na$_2$SO$_4$. Evaporation of the solvent under reduced pressure provided the crude compound, which was purified by silica gel column chromatography (eluted with 5-10% ethyl acetate/pet ether) to yield tert-butyl (2R,5S)-4-benzyl-2,5-diethylpiperazine-1-carboxylate (0.45 g, 60% yield). LCMS: m/z=333.2 [M+H]$^+$; retention time 2.02 min, LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Flow rate: 1.0 mL/min.

Intermediate 26 tert-Butyl (2R,5S)-2,5-diethylpiperazine-1-carboxylate

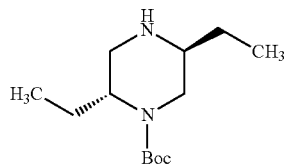 [SMILES: CC[C@H]1CN(C(=O)OC(C)(C)C)[C@H](CC)CN1]

tert-Butyl (2R,5S)-4-benzyl-2,5-diethylpiperazine-1-carboxylate (450 mg, 1.35 mmol) was dissolved in MeOH (10 mL) and to this solution was added acetic acid (0.1 mL, 1.35 mmol), followed by Pd/C (10% w/w) (100 mg, 0.026 mmol). The reaction mixture was stirred under $H_2$ at 70 psi for 16 hours. The reaction mixture was filtered through a Celite® pad, washed with methanol and evaporated under reduced pressure to yield tert-butyl (2R,5S)-2,5-diethylpiperazine-1-carboxylate, AcO-(0.32 g, 69% yield). LCMS: m/z=243.2 [M+H]$^+$; retention time 0.78 min, LCMS Method: Column-Luna 3.0 C18 (2) 100 Å LC column (20×4.0 mm); mobile phase A: 0.1% TFA in water; mobile phase B: 0.1% TFA in acetonitrile, Gradient=20-100% B over 4 minutes, then a 0.6 minute hold at 100% B; Temperature: 27° C.; Flow rate: 1.0 mL/min; Detection: UV at 220 nm.

Experimental Method C:

Example 185

4-((2S,5R)-4-(4-(Cyclopropylmethoxy)benzyl)-2,5-diethylpiperazin-1-yl)-1-methyl-2-oxo-1,2-dihydropyrido[3,2-d]pyrimidine-6-carbonitrile

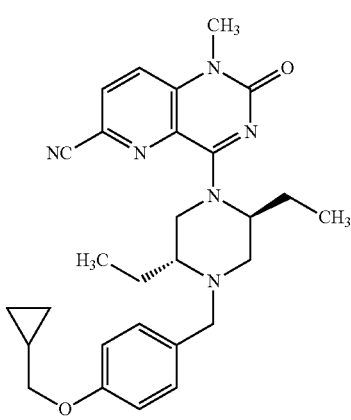

(185)

To a solution of 4-((2S,5R)-2,5-diethylpiperazin-1-yl)-1-methyl-2-oxo-1,2-dihydropyrido[3,2-d]pyrimidine-6-carbonitrile (0.05 g, 0.15 mmol) in methanol (2 mL) were added 4-(cyclopropylmethoxy)benzaldehyde (0.040 g, 0.23 mmol), acetic acid (4.38 µL, 0.08 mmol) and magnesium sulfate (0.018 g, 0.15 mmol). The reaction mixture was stirred at room temperature for 16 h. Sodium cyanoborohydride (9.6 mg, 0.15 mmol) was added to the reaction mixture. The reaction mixture was stirred for 3 h. The reaction was quenched with the addition of water. The mixture was extracted with ethyl acetate (2×100 mL), the combined organic layer was washed with water, brine and dried over sodium sulfate. The solvent was evaporated under reduced pressure to yield the crude product, which was purified by preparative HPLC. HPLC Method: Column:) (Bridge C18 (19×50 mm, 5 µm); mobile phase A: 10 mM ammonium acetate in water; mobile phase B: acetonitrile; Gradient: 20-70% B over 20 minutes, then a 5 minute hold at 100% B; Flow: 15 mL/min), fractions were concentrated under reduced pressure and lyophilized from (EtOH/H$_2$O, 1:5) to yield Example 185 (6 mg, 8% yield); LCMS: m/z=487.3 [M+H]$^+$; rt 2.310 min; LCMS method: Column: XBridge BEH XP C18 (50×2.1 mm, 2.5 µm); mobile phase A: 10 mM NH$_4$OAc in water:acetonitrile (95:5); mobile phase B: 10 mM NH$_4$OAc in water:acetonitrile (5:95); Gradient=0-100% B over 3 minutes; Temperature: 50° C.; Flow rate: 1.1 mL/min; Detection: UV at 220 nm. $^1$H NMR (400 MHz, DMSO-d$_6$) δ (ppm)=8.23 (br d, J=8.6 Hz, 1H), 7.98 (br d, J=8.8 Hz, 1H), 7.23-7.25 (m, 2H), 6.99-6.74 (m, 2H), 6.01-5.29 (m, 1H), 4.92 (br s, 1H), 3.79 (d, J=7.1 Hz, 2H), 3.65-3.46 (m, 3H), 3.43 (s, 3H), 2.67-2.68 (m, 2H), 2.46-2.42 (m, 1H), 2.12-1.75 (m, 2H), 1.58-1.28 (m, 2H), 1.27-1.13 (m, 1H), 0.99-0.65 (m, 6H), 0.60-0.46 (m, 2H), 0.37-0.25 (m, 2H).

Experimental Method D:

Intermediate 27

6-Chloro-4-((2S,5R)-2,5-diethylpiperazin-1-yl)-1-methylpyrido[3,2-d]pyrimidin-2(1H)-one

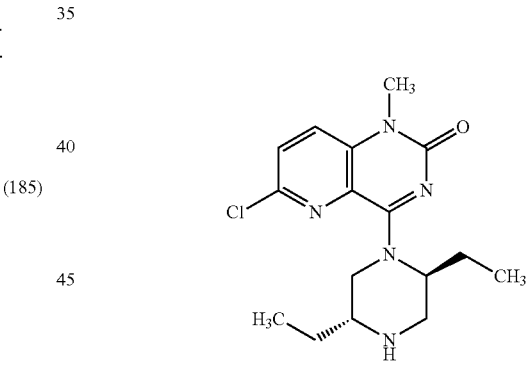

To a stirred solution tert-butyl (2R,5S)-4-(6-chloro-1-methyl-2-oxo-1,2-dihydropyrido[3,2-d]pyrimidin-4-yl)-2,5-diethylpiperazine-1-carboxylate (2.30 g, 5.28 mmol) in DCM (50 mL) was added TFA (8 mL, 104 mmol). The reaction mixture was stirred at room temperature for 4 hours, concentrated under reduced pressure to yield the TFA salt of 6-chloro-4-((2S,5R)-2,5-diethylpiperazin-1-yl)-1-methylpyrido[3,2-d]pyrimidin-2(1H)-one (1.55 g, 87% yield). LCMS: m/z=336.2 [M+H]$^+$; rt=0.41 min, LCMS Method; Column: AQUITY UPLC BEH C18 (3.0×50 mm, 1.7 µm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min, temperature: 27° C.; detection: UV at 220 nm.

205

Intermediate 28

Ethyl 2-(4-(1-((2R,5S)-4-(6-chloro-1-methyl-2-oxo-1,2-dihydropyrido[3,2-d]pyrimidin-4-yl)-2,5-diethylpiperazin-1-yl)ethyl)phenoxy)-2-methylpropanoate

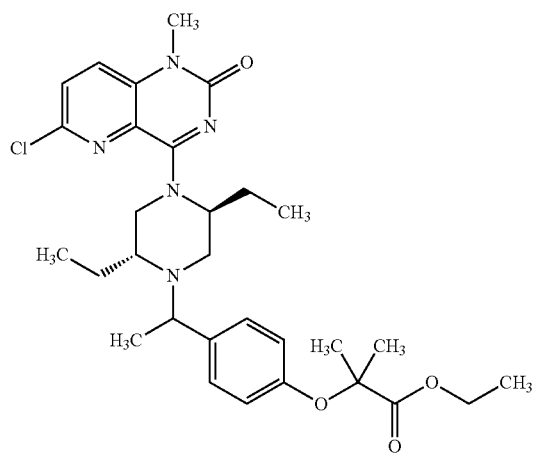 [SMILES: CCOC(=O)C(C)(C)Oc1ccc(C(C)N2C[C@H](CC)N(c3nc(=O)n(C)c4ccc(Cl)nc34)C[C@H]2CC)cc1]

206

Example 186

6-Chloro-4-((2S,5R)-2,5-diethyl-4-(1-(4-((1-hydroxy-2-methylpropan-2-yl)oxy)phenyl)ethyl)piperazin-1-yl)-1-methylpyrido[3,2-d]pyrimidin-2(1H)-one

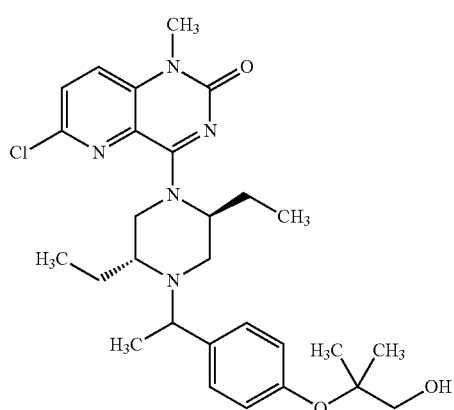

(186)

To a stirred solution of 6-chloro-4-((2S,5R)-2,5-diethylpiperazin-1-yl)-1-methylpyrido[3,2-d]pyrimidin-2(1H)-one, HCl (500 mg, 1.34 mmol) in acetonitrile (20 mL) were added DIPEA (0.71 mL, 4.03 mmol) and ethyl 2-(4-(1-chloroethyl)phenoxy)-2-methylpropanoate (436 mg, 1.61 mmol). The reaction mixture was stirred at 80° C. overnight. The reaction mixture was diluted with ethyl acetate (100 mL) and washed with water, the organic layer was dried over anhydrous $Na_2SO_4$ and filtered. The volatiles were removed under reduced pressure to yield the crude product, which was purified by flash column chromatography on silica gel (Hexane:EtOAc=45:55) to give ethyl 2-(4-(1-((2R,5S)-4-(6-chloro-1-methyl-2-oxo-1,2-dihydropyrido[3,2-d]pyrimidin-4-yl)-2,5-diethylpiperazin-1-yl)ethyl)phenoxy)-2-methylpropanoate (0.35 g, 45% yield). LCMS: m/z=556.2 (M−Et+ Me−+H); rt 2.38 min. LCMS Method: Column-Luna 3.0 C18 (2) 100 Å LC column (20×4.0 mm); mobile phase A: 10 mM $NH_4OAc$ in water:acetonitrile (95:5); mobile phase B: 10 mM $NH_4OAc$ in water:acetonitrile (5:95); Gradient=0-100% B over 3 minutes; Temperature: 50° C.; Flow rate: 1.1 mL/min; Detection: UV at 220 nm.

To a stirred solution of ethyl 2-(4-(1-((2R,5S)-4-(6-chloro-1-methyl-2-oxo-1,2-dihydropyrido[3,2-d]pyrimidin-4-yl)-2,5-diethylpiperazin-1-yl)ethyl)phenoxy)-2-methylpropanoate (180 mg, 0.32 mmol) in tetrahydrofuran (5 mL) was added $LiBH_4$ (2 M, 0.8 mL, 1.6 mmol) at 0° C. The reaction mixture was stirred at room temperature for 3 h. The reaction mixture was dissolved in ethyl acetate and washed with saturated aqueous $NH_4Cl$ solution, the organic layer was dried over anhydrous $Na_2SO_4$ filtered and evaporated under reduced pressure to afford 6-chloro-4-((2S,5R)-2,5-diethyl-4-(1-(4-((1-hydroxy-2-methylpropan-2-yl)oxy)phenyl)ethyl)piperazin-1-yl)-1-methylpyrido[3,2-d]pyrimidin-2(1H)-one (0.16 g, 97% yield). LCMS: m/z=528.2 [M+H]$^+$; rt 1.98 min. LCMS Method: Column-Luna C18 (20×4.0 mm, 100 Å); mobile phase A: 10 mM $NH_4OAc$ in water:acetonitrile (95:5); mobile phase B: 10 mM $NH_4OAc$ in water:acetonitrile (5:95); Gradient=0-100% B over 3 minutes; Temperature: 50° C.; Flow rate: 1.1 mL/min; Detection: UV at 220 nm.

Example 187

6-Chloro-4-((2S,5R)-2,5-diethyl-4-(1-(4-((1-methoxy-2-methylpropan-2-yl)oxy)phenyl)ethyl)piperazin-1-yl)-1-methylpyrido[3,2-d]pyrimidin-2(1H)-one

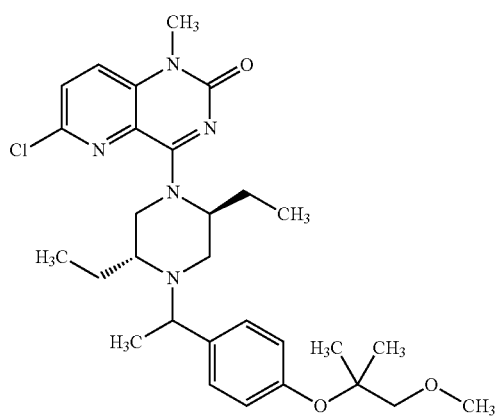

(187)

To a stirred solution of 6-chloro-4-((2S,5R)-2,5-diethyl-4-(1-(4-((1-hydroxy-2-methylpropan-2-yl)oxy)phenyl)ethyl)piperazin-1-yl)-1-methylpyrido[3,2-d]pyrimidin-2(1H)-one (200 mg, 0.379 mmol) in tetrahydrofuran (5 mL) was added NaH (22.72 mg, 0.57 mmol, 60% w/w) at 0° C. After 10 minutes, methyl iodide (0.03 mL, 0.45 mmol) was added dropwise and the reaction mixture was stirred at room temperature for 16 h. The reaction quenched with water (4 mL). The reaction mixture was extracted with EtOAc (25 mL), dried over anhydrous $Na_2SO_4$, filtered and evaporated under reduced pressure to afford 6-chloro-4-((2S,5R)-2,5-diethyl-4-(1-(4-((1-methoxy-2-methylpropan-2-yl)oxy)phenyl)ethyl)piperazin-1-yl)-1-methylpyrido[3,2-d]pyrimidin-2(1H)-one (0.16 g, 17% yield). LCMS: m/z=542.5 [M+H]$^+$; rt 1.43 min, LCMS Method; Column: AQUITY UPLC BEH C18 (3.0×50 mm, 1.7 µm); mobile phase A:2.5 mM $NH_4OAc$ in water:acetonitrile (95:5); mobile phase B: 2.5 mM $NH_4OAc$ in water:acetonitrile (5:95); gradient=20-100% B over 2 min, then a 1 minute hold at 100% B, flow: 0.7 mL/min, temperature: 27° C.; detection: UV at 220 nm.

Examples 188 and 189

6-Chloro-4-((2S,5R)-2,5-diethyl-4-(1-(4-((1-methoxy-2-methylpropan-2-yl)oxy)phenyl) ethyl)piperazin-1-yl)-1-methylpyrido[3,2-d]pyrimidin-2(1H)-one

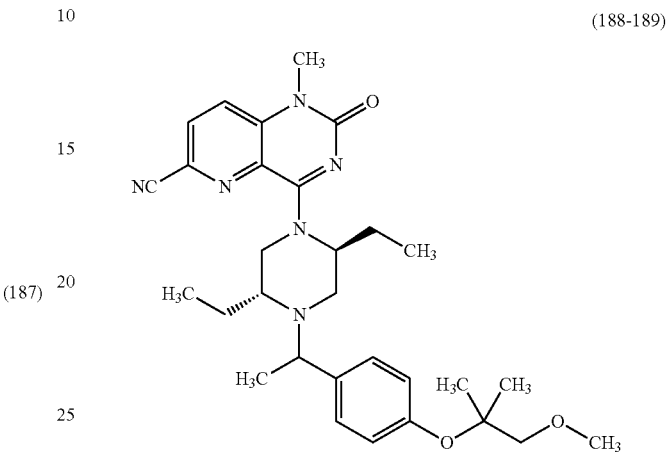

(188-189)

To a stirred solution of 6-chloro-4-((2S,5R)-2,5-diethyl-4-(1-(4-((1-methoxy-2-methylpropan-2-yl)oxy)phenyl)ethyl)piperazin-1-yl)-1-methylpyrido[3,2-d]pyrimidin-2(1H)-one (80 mg, 0.15 mmol) in DMF (1.5 mL) was added zinc (9.7 mg, 0.15 mmol), zinc cyanide (35 mg, 0.295 mmol) and triethylamine (0.062 mL, 0.443 mmol). Next, dichloro[9,9-dimethyl-4,5-bis(diphenylphosphino)xanthene] palladium(II) (11.16 mg, 0.015 mmol) was added under argon. The reaction mixture was heated to 90° C. for 16 h, cooled, diluted with ethyl acetate and filtered through the Celite® pad, and washed with ethyl acetate. The filtrate was removed under reduced pressure to yield the crude product which was purified by preparative HPLC method: Column: Sunfire OBD (250×30 mm, 5 µm), mobile phase A: 10 mM ammonium acetate in water, mobile phase B: acetonitrile, Flow 19 mL/min. to yield Examples 188 and 189.

EXAMPLE 188: Fraction 1 was concentrated under reduced pressure and the product was diluted with (EtOH/$H_2O$, 1:5) and lyophilized to yield Example 188 (6.1 mg, 7.14% yield); LCMS: m/z, 533.3 [M+H]$^+$; rt 2.312 min; (LCMS method: Column: XBridge BEH C18 XP (50×2.1 mm, 2.5 µm); mobile phase A: 5:95 acetonitrile:water with 10 mM $NH_4OAc$ in water; mobile phase B: 95:5 acetonitrile:water with 10 mM $NH_4OAc$ in water; Temperature: 50° C.; Gradient: 0-100% B over 3 minutes. $^1$H NMR (400 MHz, DMSO-d$_6$) δ (ppm)=8.29-8.16 (m, 1H), 7.98 (d, J=9.0 Hz, 1H), 7.28-7.21 (m, 2H), 6.91-6.96 (m, 2H), 5.82-5.41 (m, 1H), 5.00-4.76 (m, 1H), 3.43-3.66 (m, 1H), 3.42 (s, 3H), 3.31-3.29 (m, 4H), 3.10-3.03 (m, 1H), 2.93-2.86 (m, 1H), 2.74-2.67 (m, 1H), 2.15-2.33 (m, 1H), 1.95 (s, 2H), 1.22-1.28 (m, 11H), 0.96-0.84 (m, 3H), 0.71-0.51 (m, 3H).

EXAMPLE 189: Fraction 2 was concentrated under reduced pressure and the product was diluted with (EtOH/$H_2O$, 1:5) and lyophilized to yield Example 189 (6.0 mg, 6.95% yield); LCMS: m/z, 533.3 [M+H]$^+$; rt 2.339 min; (LCMS Method: Column: XBridge BEH C18 XP (50×2.1 mm, 2.5 µm); mobile phase A: 5:95 acetonitrile:water with 10 mM $NH_4OAc$ in water mobile phase B: 95:5 acetonitrile:water with 10 mM $NH_4OAc$ in water; Temperature: 50° C.;

Gradient: 0-100% B over 3 minutes. $^1$H NMR (400 MHz, DMSO-d$_6$) δ (ppm)=8.28-8.16 (m, 1H), 8.02-7.91 (m, 1H), 7.28 (d, J=8.3 Hz, 2H), 6.92 (d, J=8.6 Hz, 2H), 5.21-5.05 (m, 1H), 4.70-4.64 (m, 1H), 3.63-3.47 (m, 1H), 3.43 (s, 3H), 3.31 (s, 5H), 3.16-3.04 (m, 1H), 2.45-2.41 (m, 1H), 2.30-2.20 (m, 1H), 2.13-2.05 (m, 1H), 1.73-1.39 (m, 3H), 1.23-1.25 (m, 3H), 1.20 (s, 7H), 1.03-0.90 (m, 3H), 0.62-0.53 (m, 3H).

Intermediate 135

4-(Cyclopropylmethoxy)-2-fluorobenzaldehyde

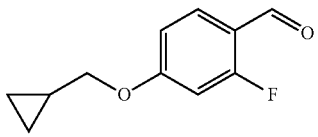 [SMILES: O=Cc1ccc(OCC2CC2)cc1F]

To a stirred solution of 2-fluoro-4-hydroxybenzaldehyde (5 g, 7.14 mmol) in acetonitrile (50 mL) were added K$_2$CO$_3$ (2.96 g, 21.41 mmol) and (bromomethyl) cyclopropane (0.832 mL, 8.56 mmol). The reaction mixture was heated to 60° C. for 16 h. The reaction mixture cooled to room temperature, the solvent was removed under reduced pressure and the residue was dissolved in water (150 mL) and extracted twice with ethyl acetate (2×40 mL). The organic layer was dried over Na$_2$SO$_4$, concentrated under reduced pressure to yield the crude product, which was purified by column chromatography (using 10-35% EtOAc in pet ether) to yield 4-(cyclopropylmethoxy)-2-fluorobenzaldehyde (4.2 g, 60.6% yield). $^1$H NMR (DMSO-d$_6$, 400MHz) δ (ppm) 10.07 (s, 1H), 7.77 (m, 1H), 6.81-7.08 (m, 2H), 3.96 (d, J=7.0 Hz, 2H), 1.21-1.29 (m, 1H), 0.53-0.69 (m, 2H), 0.23-0.44 (m, 2H).

Intermediate 136

1-(4-(Cyclopropylmethoxy)-2-fluorophenyl)propan-1-ol

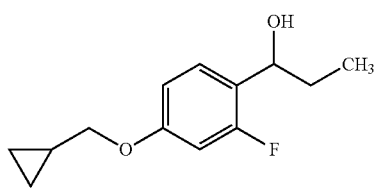 [SMILES: CCC(O)c1ccc(OCC2CC2)cc1F]

To a stirred solution of 4-(cyclopropylmethoxy)-2-fluorobenzaldehyde (4 g, 20.60 mmol) in THF (40 mL) was added ethylmagnesium bromide (13.73 mL, 41.2 mmol) at 0° C. The reaction mixture was stirred at room temperature for 4 h. The reaction was slowly quenched with the addition of saturated NH$_4$Cl solution (100 mL). The reaction mixture was extracted twice with ethyl acetate (2×30 mL). The organic layer was dried over Na$_2$SO$_4$, concentrated under reduced pressure to yield the crude product. The crude was purified by column chromatography (using 10-45% EtOAc in pet ether) to yield 1-(4-(cyclopropylmethoxy)-2-fluorophenyl)propan-1-ol (4.0 g, 85% yield). $^1$H NMR (DMSO-d$_6$, 400 MHz) δ (ppm) 7.34 (m, 1H), 6.59-6.82 (m, 2H), 5.09 (d, J=4.5 Hz, 1H), 4.66 (m, 1H), 3.80 (d, J=7.0 Hz, 2H), 1.52-1.69 (m, 2H), 1.13-1.28 (m, 1H), 0.81 (t, J=7.5 Hz, 3H), 0.57 (m, 2H), 0.31 (m, 2H).

Intermediate 137

1-(1-Chloropropyl)-4-(cyclopropylmethoxy)-2-fluorobenzene

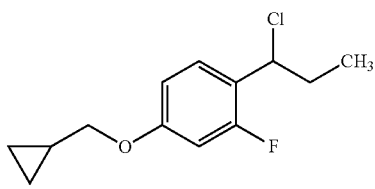

To a stirred solution of 1-(4-(cyclopropylmethoxy)-2-fluorophenyl)propan-1-ol (1 g, 4.46 mmol) in dichloromethane (10 mL) was added thionyl chloride (1.627 mL, 22.29 mmol). The reaction mixture was stirred at room temperature for 4 h. Evaporation the volatiles under reduced pressure gave the crude 1-(1-chloropropyl)-4-(cyclopropylmethoxy)-2-fluorobenzene (1 g, crude). $^1$H NMR (DMSO-d$_6$, 400MHz) δ (ppm) 7.44 (m, 1H), 6.73-6.89 (m, 2H), 5.17 (m, 1H), 3.84 (d, J=7.0 Hz, 2H), 1.99-2.24 (m, 2H), 1.14-1.28 (m, 1H), 0.93 (t, J=7.3 Hz, 3H), 0.51-0.63 (m, 2H), 0.24-0.37 (m, 2H).

The examples in Table 9 were prepared according to the general procedures described in Examples 1 to 4 and 185-186 (using the appropriate method A through D depending on the substrate used (benzhydryl/α-substituted benzyl/benzyl halides/benzaldehyde). When the reaction provided a mixture of diastereomers, the mixture was separated at the final stage using either preparative chromatography or preparative chiral chromatography. The absolute stereochemistry was not assigned at the newly formed carbon-nitrogen bond.

Example 198 and 199

4-((2S,5R)-4-(1-(4-(cyclopropylmethoxy)-2-fluorophenyl)propyl)-2,5-diethylpiperazin-1-yl)-1-methyl-2-oxo-1,2-dihydropyrido[3,2-d]pyrimidine-6-carbonitrile (198-199)

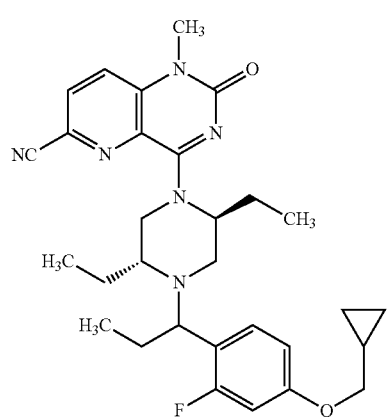

To a stirred solution of 4-((2S,5R)-2,5-diethylpiperazin-1-yl)-1-methyl-2-oxo-1,2-dihydropyrido[3,2-d]pyrimidine-6-carbonitrile, HCl (200 mg, 0.55 mmol) in acetonitrile (5 mL) were added DIPEA (0.3 mL, 1.65 mmol), sodium iodide (83 mg, 0.55 mmol) and 1-(1-chloropropyl)-4-(cyclopropylmethoxy)-2-fluorobenzene (268 mg, 1.1 mmol). The reaction mixture was heated at 80° C. for 16 h. The reaction mixture was allowed to cool to room temperature. Another lot of 1-(1-chloropropyl)-4-(cyclopropylmethoxy)-2-fluorobenzene (268 mg, 1.102 mmol) was added and continued heating for another 16 h. The reaction mixture was cooled, the solvent was removed under reduced pressure and the residue was dissolved in ethyl acetate (10×20 mL). The organic layer was washed with brine, dried over Na$_2$SO$_4$, concentrated under reduced pressure to yield the crude product which was purified by preparative HPLC. HPLC method: Column: EXRS (20×250 mm, 5 µm), mobile phase A-10 mM ammonium acetate in water R, mobile phase A-B: acetonitrile, FLOW: 20 mL/min.

Fraction 1 was concentrated under reduced pressure and the product was diluted with (EtOH/H$_2$O, 1:5) and lyophilized to yield Example 198 (35 mg, 11.6% yield); LCMS: m/z, 533.4 [M+H]$^+$, rt 1.57 min; (LCMS method: Column: KINETIX XB C18 (75×3 mm, 2.6 µm); mobile phase A: 10 mM ammonium acetate in water (pH 3.3), mobile phase B: acetonitrile. $^1$H NMR (DMSO-d$_6$, 400MHz) δ (ppm) 8.23 (d, J=9.0 Hz, 1H), 7.97 (d, J=9.0 Hz, 1H), 7.33 (m, 1H), 6.62-6.92 (m, 2H), 5.29-6.06 (m, 1H), 4.70-5.05 (m, 1H), 3.82 (m, 3H), 3.43 (s, 3H), 2.99-3.10 (m, 1H), 2.80-2.87 (m, 1H), 2.63-2.78 (m, 1H), 2.33 (s, 1H), 1.74-2.11 (m, 3H), 1.51-1.66 (m, 1H), 1.17-1.46 (m, 3H), 0.84-1.01 (m, 3H), 0.61-0.78 (m, 6H), 0.53-0.61 (m, 2H), 0.29-0.35 (m, 2H).

Fraction 2 was concentrated under reduced pressure and the product was diluted with (EtOH/H$_2$O, 1:5) and lyophilized to yield Example 199 (37 mg, 12.35% yield); LCMS: m/z, 533.4 [M+H]$^+$, rt 2.72 min; [(LCMS Method: Column: KINETIX XB C18 (75×3 mm, 2.6 µm); mobile phase A: 10 mM ammonium acetate in water (pH 3.3), mobile phase B: acetonitrile. $^1$H NMR (DMSO-d$_6$, 400MHz): δ (ppm) 8.13-8.35 (m, 1H), 7.98 (m, 1H), 7.38 (m, 1H), 6.61-6.89 (m, 2H), 5.18-6.15 (m, 1H), 4.66-5.13 (m, 1H), 3.63-3.90 (m, 3H), 3.43 (s, 3H), 3.25 (m, 1H), 3.00-3.15 (m, 1H), 2.63-2.70 (m, 1H), 2.26-2.38 (m, 1H), 1.81 (m, 3H), 1.35-1.61 (m, 2H), 1.15-1.26 (m, 2H), 0.88-1.00 (m, 3H), 0.61-0.71 (m, 6H), 0.51-0.59 (m, 2H), 0.32 (m, 2H).

Example 243 and 244

4-((2S,5R)-2,5-Diethyl-4-(1-(4-(trifluoromethyl)phenyl)butyl)piperazin-1-yl)-1-methyl-2-oxo-1,2-dihydropyrido[3,2-d]pyrimidine-6-carbonitrile (243-244)

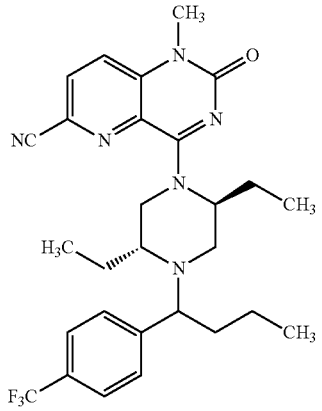

To a stirred solution of 4-((2S,5R)-2,5-diethylpiperazin-1-yl)-1-methyl-2-oxo-1,2-dihydropyrido[3,2-d]pyrimidine-6-carbonitrile, HCl (0.4 g, 1.1 mmol) in acetonitrile (10 mL) was added DIPEA (0.6 mL, 3.31 mmol), followed by 1-(1-chlorobutyl)-4-trifluoromethyl)benzene (0.783 g, 3.31 mmol) and sodium iodide (0.165 g, 1.102 mmol). The reaction mixture was heated at 85° C. for 16 h. The reaction mixture was filtered through a Celite pad, washed with ethyl acetate and the filtrate was concentrated under reduced pressure to give the crude compound, which was purified by preparative HPLC [HPLC Method: Column: YMC ExRS (250 mm×21.2 mm, 5 µm) Mobile phase A=10 mM ammonium acetate pH 4.5 in water. Mobile phase B=acetonitrile Gradient: 80% B over 2 minutes, then a 16 minute hold at 100% B; Flow: 19 mL/min) to yield Examples 243 and 244.

Example 243: (10 mg, 1.7% yield), LCMS: m/z=527.4 (M+H); rt 2.626 min; [LCMS Method: Column: XBridge BEH XP C18 (50×2.1 mm), 2.5 µm; Mobile phase A: 95% Water: 5% Acetonitrile; 10 mM NH$_4$OAC; Mobile phase B: 5% Water: 95% Acetonitrile; 10 mM NH$_4$OAC; Flow: 1.1 mL/min; Temp:50° C.; Time (min)]. $^1$H NMR (400 MHz, DMSO-d$_6$) δ 8.30-8.16 (m, 1H), 7.98 (d, J=9.0 Hz, 1H), 7.72 (d, J=8.3 Hz, 2H), 7.56 (br d, J=7.8 Hz, 2H), 5.86-5.44 (m, 1H),5.01-4.77 (m, 1H), 3.730-3.718(m, 1H), 3.46 (s, 3H), 3.43-3.35(m, 1H) 3.13-3.01 (m, 1H), 2.93-2.75 (m, 2H), 2.38-2.26 (m, 1H), 2.17-1.74 (m, 3H), 1.63-1.22 (m, 3H), 1.01-0.86 (m, 4H), 0.84-0.75 (m, 3H), 0.73-0.54 (m, 3H).

Example 244: (7.2 mg, 1.23% yield), LCMS: m/z=527.3 (M+H); rt 2.654 min; [LCMS Method: Column: XBridge BEH XP C18 (50×2.1) mm, 2.5 µm; Mobile phase A: 95% Water: 5% Acetonitrile; 10 mM NH$_4$OAC; Mobile phase B: 5% Water:95% Acetonitrile; 10 mM NH$_4$OAC; Flow: 1.1 mL/min; Temp:50° C.; Time (min)]. $^1$H NMR (400 MHz, DMSO-d$_6$) δ=8.29-8.15 (m, 1H), 7.96-8.02 (m, 1H), 7.70 (d, J=8.1 Hz, 2H), 7.58 (br d, J=8.1 Hz, 2H), 6.09-5.22 (m, 1H), 5.13-4.66 (m, 1H), 3.68-3.52 (m, 2H), 3.43 (s, 3H), 3.28-3.04 (m, 2H), 2.60-2.53 (m, 1H), 2.25-2.12 (m, 1H), 2.04-1.68 (m, 3H), 1.60-1.29 (m,3H), 1.05-0.74 (m, 7H), 0.59 (t, J=7.5 Hz, 3H).

TABLE 9

| Ex. No. | Structure | Stereo chem | LCMS Method | LCMS rt | [M + H]+ | Coupling Method |
|---|---|---|---|---|---|---|
| 190 | | H | C | 2.16 | 464.3 | B |
| 191 | | H | C | 2.18 | 464.3 | B |
| 192 | | H | C | 2.01 | 472.3 | B |
| 193 | | H | C | 2.02 | 472.3 | B |
| 194 | | H | C | 2.41 | 584.4 | B |
| 195 | | H | C | 2.40 | 584.3 | B |

TABLE 9-continued

| Ex. No. | Structure | Stereo chem | LCMS Method | LCMS rt | [M + H]+ | Coupling Method |
|---|---|---|---|---|---|---|
| 196 | | H | C | 2.13 | 498.4 | B |
| 197 | | H | C | 2.15 | 498.3 | B |
| 200 | | H | C | 2.59 | 485.4 | B |
| 201 | | H | C | 2.62 | 485.3 | B |
| 202 | | H | C | 1.90 | 502.3 | B |
| 203 | | H | C | 1.91 | 502.3 | B |

| Ex. No. | Structure | Stereo chem | LCMS Method | LCMS rt | [M + H]+ | Coupling Method |
|---|---|---|---|---|---|---|
| 204 | 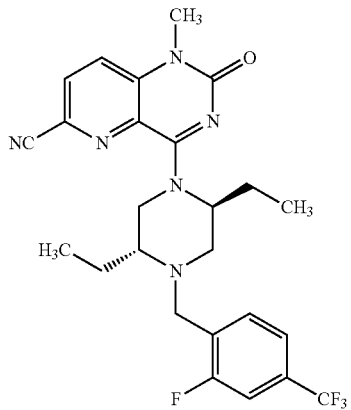 [SMILES: CC[C@@H]1CN(c2nc(=O)n(C)c3ccc(C#N)nc23)[C@@H](CC)CN1Cc1ccc(C(F)(F)F)cc1F] | H | C | 2.35 | 503.2 | A |
| 205 | 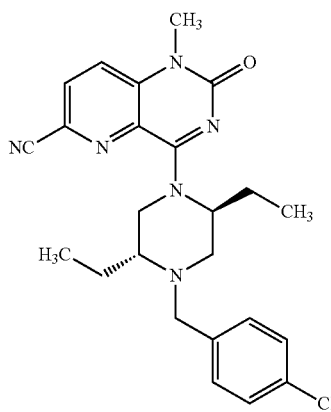 | H | C | 2.33 | 485.3 | A |
| 206 | | H | C | 1.83 | 518.3 | B |
| 207 | 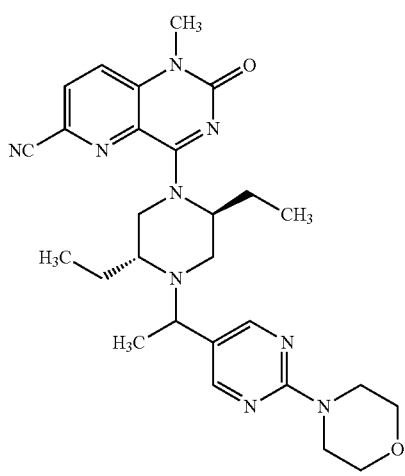 [SMILES: CC[C@H]1CN(C(C)c2cnc(N3CCOCC3)nc2)[C@H](CC)CN1c1nc(=O)n(C)c2ccc(C#N)nc12] | H | D | 1.11 | 518.5 | B |

TABLE 9-continued

| Ex. No. | Structure | Stereo chem | LCMS Method | LCMS rt | [M + H]+ | Coupling Method |
|---|---|---|---|---|---|---|
| 208 | | H | C | 2.29 | 478.3 | B |
| 209 | | H | C | 2.32 | 478.4 | B |
| 210 | | H | C | 2.35 | 586.3 | A |
| 211 | | H | C | 2.36 | 586.3 | A |
| 212 | | H | C | 2.29 | 475.3 | B |
| 213 | | H | C | 2.32 | 475.4 | B |

TABLE 9-continued

| Ex. No. | Structure | Stereo chem | LCMS Method | LCMS rt | [M + H]+ | Coupling Method |
|---|---|---|---|---|---|---|
| 214 | | H | C | 2.07 | 462.3 | B |
| 215 | | H | C | 2.08 | 462.3 | B |
| 216 | | H | D | 1.57 | 515.4 | B |
| 217 | | H | C | 2.57 | 515.3 | B |
| 218 | | H | C | 2.62 | 485.3 | B |
| 219 | | H | C | 2.64 | 485.3 | B |

TABLE 9-continued

| Ex. No. | Structure | Stereo chem | LCMS Method | LCMS rt | [M + H]+ | Coupling Method |
|---|---|---|---|---|---|---|
| 220 | | H | C | 2.13 | 470.3 | B |
| 221 | | H | C | 2.15 | 470.3 | B |
| 222 | | H | C | 2.32 | 511.3 | B |
| 223 | | H | C | 2.35 | 511.3 | B |
| 224 | | H | E | 3.24 | 514.2 | B |
| 225 | | H | E | 3.26 | 514.2 | B |

TABLE 9-continued
| Ex. No. | Structure | Stereo chem | LCMS Method | LCMS rt | [M + H]+ | Coupling Method |
|---|---|---|---|---|---|---|
| 226 | 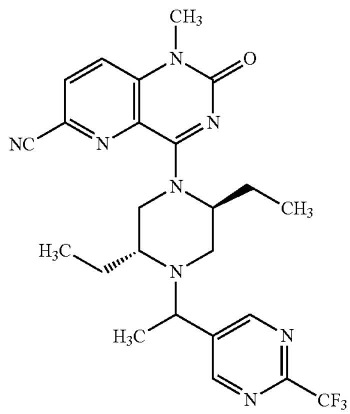 [SMILES: CC[C@H]1CN(C(C)c2cnc(C(F)(F)F)nc2)[C@H](CC)CN1c1nc(=O)n(C)c2ccc(C#N)nc12] | H | E | 2.87 | 501.2 | B |
| 227 | | H | E | 2.86 | 501.2 | B |
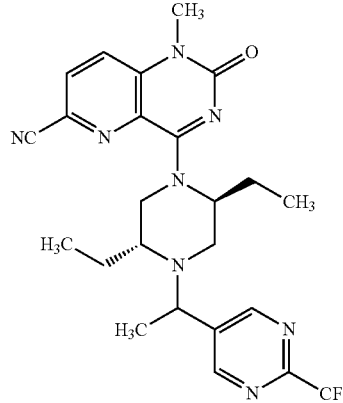
| 228 | | H | C | 1.73 | 446.3 | B |
| 229 | | H | C | 1.75 | 446.3 | B |
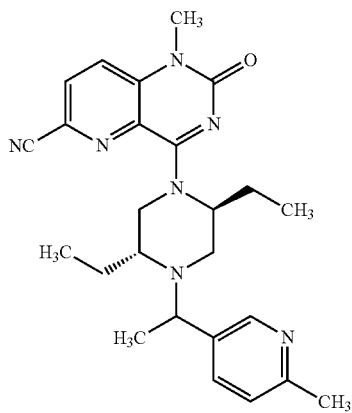 [SMILES: CC[C@H]1CN(C(C)c2ccc(C)nc2)[C@H](CC)CN1c1nc(=O)n(C)c2ccc(C#N)nc12]
| 230 | | H | C | 1.85 | 514.3 | B |
| 231 | | H | C | 1.85 | 514.3 | B |
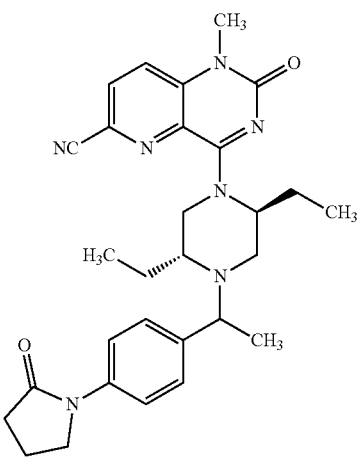 [SMILES: CC[C@H]1CN(C(C)c2ccc(N3CCCC3=O)cc2)[C@H](CC)CN1c1nc(=O)n(C)c2ccc(C#N)nc12]

TABLE 9-continued

| Ex. No. | Structure | Stereo chem | LCMS Method | LCMS rt | [M + H]+ | Coupling Method |
|---|---|---|---|---|---|---|
| 232 | | H | C | 2.34 | 529.3 | B |
| 233 | | H | C | 2.37 | 529.3 | B |
| 234 | | H | F | 1.72 | 503.25 | B |
| 235 | | H | F | 1.70 | 503.27 | B |
| 236 | | H | E | 3.86 | 459.4 | B |
| 237 | | H | E | 3.95 | 459.4 | B |

TABLE 9-continued
| Ex. No. | Structure | Stereo chem | LCMS Method | LCMS rt | [M + H]+ | Coupling Method |
| --- | --- | --- | --- | --- | --- | --- |
| 238 | | H | E | 3.92 | 497.2 | B |
| 239 | | H | E | 3.98 | 497.2 | B |
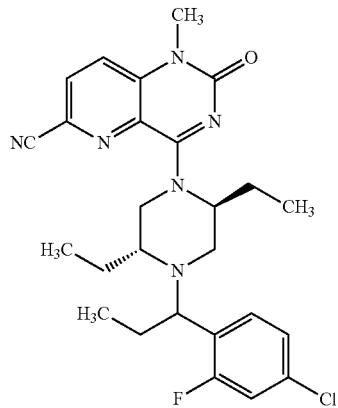 [SMILES: CCC(c1ccc(Cl)cc1F)N1C[C@H](CC)N(c2nc(=O)n(C)c3ccc(C#N)nc23)C[C@H]1CC]
| 240 | | H | C | 2.14 | 498.3 | B |
| 241 | | H | C | 2.15 | 498.3 | B |
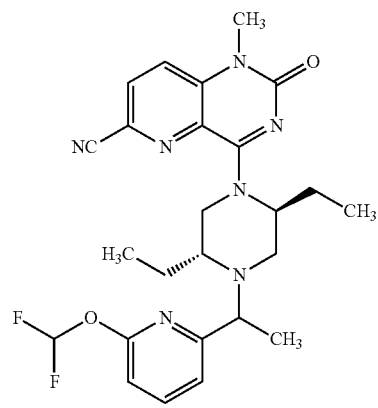 [SMILES: CC[C@H]1CN(C(C)c2cccc(OC(F)F)n2)[C@H](CC)CN1c1nc(=O)n(C)c2ccc(C#N)nc12]
| 242 | | H | C | 2.37 | 475.3 | B |
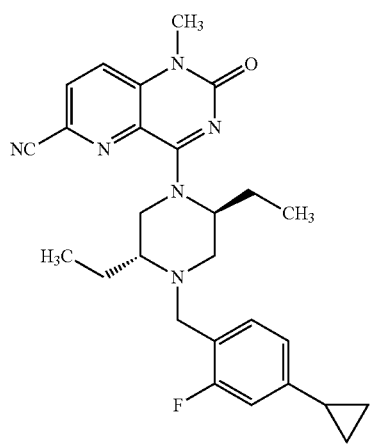 [SMILES: CC[C@@H]1CN(c2nc(=O)n(C)c3ccc(C#N)nc23)[C@@H](CC)CN1Cc1ccc(C2CC2)cc1F]

TABLE 9-continued

| Ex. No. | Structure | Stereo chem | LCMS Method | LCMS rt | [M + H]+ | Coupling Method |
|---|---|---|---|---|---|---|
| 245 | | H | C | 2.24 | 516.3 | B |
| 246 | | H | C | 2.24 | 516.3 | B |
| 247 | | H | E | 3.18 | 558.5 | B |
| 248 | | H | E | 3.02 | 558.5 | B |
| 249 | | H | C | 2.40 | 489.3 | B |
| 250 | | H | C | 2.45 | 489.3 | B |

TABLE 9-continued

| Ex. No. | Structure | Stereo chem | LCMS Method | LCMS rt | [M + H]+ | Coupling Method |
|---|---|---|---|---|---|---|
| 251 | | H | C | 2.3 | 512.3 | B |
| 252 | | H | C | 2.33 | 512.3 | B |
| 253 | | H | E | 1.88 | 512.4 | B |
| 254 | | H | E | 1.96 | 513.4 | B |
| 255 | | H | C | 2.47 | 501.3 | B |
| 256 | | H | C | 2.50 | 501.3 | B |

TABLE 9-continued

| Ex. No. | Structure | Stereo chem | LCMS Method | LCMS rt | [M + H]⁺ | Coupling Method |
|---|---|---|---|---|---|---|
| 257 | | H | C | 2.21 | 562.3 | A |
| 258 | | H | D | 1.72 | 562.3 | A |
| 259 | | H | C | 1.87 | 559.3 | B |
| 260 | | H | C | 1.87 | 559.3 | B |
| 261 | | H | C | 2.72 | 517.4 | B |
| 262 | | H | C | 2.76 | 517.4 | B |

TABLE 9-continued

| Ex. No. | Structure | Stereo chem | LCMS Method | LCMS rt | [M + H]+ | Coupling Method |
|---|---|---|---|---|---|---|
| 263 | | H | D | 1.29 | 496.4 | B |
| 264 | | H | C | 2.23 | 496.4 | B |
| 265 | | H | C | 2.13 | 489.4 | B |
| 266 | | H | C | 2.12 | 489.4 | B |
| 267 | | H | C | 2.13 | 544.4 | B |
| 268 | | H | C | 2.18 | 544.4 | B |

TABLE 9-continued

| Ex. No. | Structure | Stereo chem | LCMS Method | LCMS rt | [M + H]+ | Coupling Method |
|---|---|---|---|---|---|---|
| 269 | 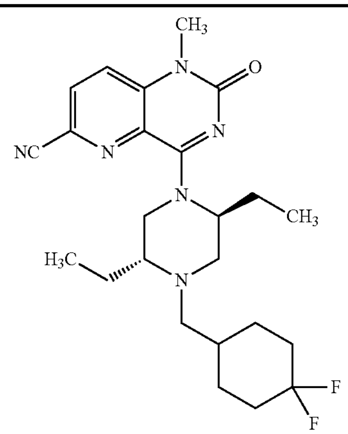 | H | C | 2.19 | 459.3 | C |

Intermediate 29

Methyl 4-(1-chloroethyl)benzoate

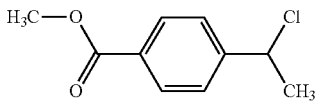

To a stirred solution of methyl 4-(1-hydroxyethyl)benzoate (2.3 g, 12.76 mmol) in DCM (20 mL) was added thionyl chloride (4.7 mL, 63.8 mmol) at 0° C. under nitrogen. The reaction mixture was allowed to warm to room temperature and stirring was continued for 2 h. The solvent was removed under reduced pressure, co-distilled with acetonitrile (2×10 mL) and dried to afford methyl 4-(1-chloroethyl)benzoate (2 g, 79% yield). ¹H NMR (300 MHz, DMSO-d₆) δ (ppm)=7.97 (d, J=8.3 Hz, 2H), 7.64 (d, J=8.3 Hz, 2H), 5.48-5.37 (m, 1H), 3.86 (s, 3H), 1.80 (d, J=6.8 Hz, 3H).

Intermediate 30

4-(1-Chloroethyl)phenyl)methanol

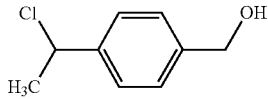

A stirred solution of methyl 4-(1-chloroethyl)benzoate (2.5 g, 12.6 mmol) in THF (25 mL) was cooled to 0° C. and lithium borohydride (2M in THF) (12.6 mL, 25.2 mmol) was added drop wise under nitrogen. The reaction mixture was allowed to warm room temperature and stirred for 12 h. The reaction mixture was cooled to 0° C. The reaction was quenched with the addition of saturated aqueous NH₄Cl solution. The reaction mixture was extracted with EtOAc (3×50 mL). The combined organic extract was washed with water, brine solution, dried over sodium sulphate and the solvent was removed under reduced pressure to afford (4-(1-chloroethyl)phenyl)methanol (1.5 g, 49% yield). LCMS: m/z, 135.1 [M-Cl]; rt 1.89 min, LCMS Method; Column: AQUITY UPLC BEH C18 (3.0×50 mm, 1.7 μm); mobile phase A:10 mM NH₄OAc in water:acetonitrile (95:5); mobile phase B: 10 mM NH₄OAc in water:acetonitrile (5:95); gradient=20-100% B over 2 min, then a 0.3 minute hold at 100% B, flow: 0.7 mL/min, temperature: 27° C.; detection: UV at 220 nm.

Examples 270 and 271

4-((2S,5R)-2,5-Diethyl-4-(1-(4-(hydroxymethyl)phenyl)ethyl)piperazin-1-yl)-1-methyl-2-oxo-1,2-dihydropyrido[3,2-d]pyrimidine-6-carbonitrile (270-271)

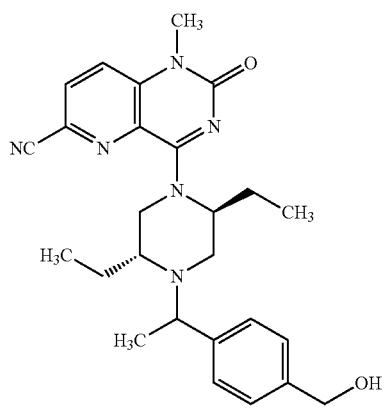

To a stirred solution of 4-((2S,5R)-2,5-diethylpiperazin-1-yl)-1-methyl-2-oxo-1,2-dihydropyrido[3,2-d]pyrimidine-6-carbonitrile hydrochloride (80 mg, 0.22 mmol) in acetonitrile (2 mL), DIPEA (0.12 mL, 0.66 mmol), (4-(1-chloroethyl)phenyl)methanol (56.4 mg, 0.33 mmol) and sodium iodide (33.0 mg, 0.22 mmol) were added sequentially at room temperature followed by heating at 80° C. for 12 h. The reaction mixture was cooled to room temperature and solvent was removed under reduced pressure to give the crude product, which was purified using preparative SFC. SFC Method: Column: Chiralpak IG (250×30 mm, 5 μm); mobile phase: 50% CO₂/50% of co-solvent: acetonitrile:MeOH; Flow: 95 g/min; Detector Wavelength: 220 nm; Temperature: 40° C.

EXAMPLE 270 (6.7 mg, 7% yield). LCMS: m/z=461.3 [M+H]⁺; rt 1.71 min; LCMS method: Column: XBridge BEH XP C18 (50×2.1 mm, 2.5 μm); mobile phase A: 10 mM NH₄OAc in water:acetonitrile (95:5); mobile phase B: 10 mM NH₄OAc in water:acetonitrile (5:95); Gradient=0-100% B over 3 minutes; Temperature: 50° C.; Flow rate: 1.1 mL/min; Detection: UV at 220 nm. ¹H NMR (400 MHz, DMSO-d₆) δ (ppm)=8.27-8.19 (m, 1H), 7.98 (d, J=9.0 Hz, 1H), 7.35-7.27 (m, 4H), 5.86-5.46 (m, 1H), 5.17-5.09 (m, 1H), 5.05-4.81 (m, 1H), 4.53-4.47 (m, 2H), 3.73-3.65 (m, 1H), 3.44 (s, 3H), 3.12-2.88 (m, 2H), 2.79-2.70 (m, 1H), 2.47-2.35 (m, 1H), 2.27-1.84 (m, 2H), 1.53-1.31 (m, 2H), 1.30-1.25 (m, 3H), 1.03-0.86 (m, 3H), 0.73-0.54 (m, 3H).

EXAMPLE 271 (8 mg, 8% yield). LCMS: m/z=461.3 [M+H]⁺; rt 1.73 min; LCMS method: Column: XBridge BEH XP C18 (50×2.1 mm, 2.5 μm); mobile phase A: 10 mM NH₄OAc in water:acetonitrile (95:5); mobile phase B: 10 mM NH₄OAc in water:acetonitrile (5:95); Gradient=0-100% B over 3 minutes; Temperature: 50° C.; Flow rate: 1.1 mL/min; Detection: UV at 220 nm. ¹H NMR (400 MHz, DMSO-d₆) δ (ppm)=8.29-8.13 (m, 1H), 8.05-7.89 (m, 1H), 7.39-7.16 (m, 4H), 6.10-5.19 (m, 1H), 5.14-4.71 (m, 2H), 4.47 (br d, J=5.6 Hz, 2H), 3.67-3.50 (m, 2H), 3.43, 3.41 (s, 3H), 3.18-3.04 (m, 1H), 2.45-2.24 (m, 2H), 2.10-1.66 (m, 2H), 1.54-1.38 (m, 2H), 1.25-1.21 (m, 3H), 1.00-0.85 (m, 3H), 0.69-0.55 (m, 3H).

Example 272

4-((2S,5R)-4-(1-(4-(Bromomethyl)phenyl)ethyl)-2,5-diethylpiperazin-1-yl)-1-methyl-2-oxo-1,2-dihydropyrido[3,2-d]pyrimidine-6-carbonitrile (Diastereomeric Mixture)

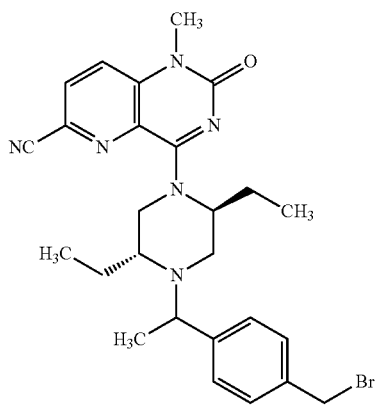

(272)

A stirred solution of 4-((2S,5R)-2,5-diethyl-4-(1-(4-(hydroxymethyl)phenyl) ethyl)piperazin-1-yl)-1-methyl-2-oxo-1,2-dihydropyrido[3,2-d]pyrimidine-6-carbonitrile (1.2 g, 2.61 mmol) in DCM (20 mL) was cooled to 0° C. Triphenylphosphine polymer bound (1.3 mmol/g) (0.820 g, 3.13 mmol) was added followed by the addition of CBR₄ (1.73 g, 5.21 mmol) in DCM (10 mL). The reaction mixture was allowed to warm to room temperature and stirred for 2 h. The solvent was removed under reduced pressure to give the crude product, which was purified by silica gel column chromatography using 10-12% MeOH in CHCl₃ to afford 4-((2S,5R)-4-(1-(4-(bromomethyl)phenyl)ethyl)-2,5-diethylpiperazin-1-yl)-1-methyl-2-oxo-1,2-dihydropyrido[3,2-d]pyrimidine-6-carbonitrile (1 g, 0.955 mmol, 36.7% yield). LCMS: m/z, 525.1 [M+2]; rt 1.99 and 2.01 min, LCMS Method; Column: AQUITY UPLC BEH C18 (3.0×50 mm, 1.7 μm); mobile phase A:10 mM NH₄OAc in water:acetonitrile (95:5); mobile phase B: 10 mM NH₄OAc in water:acetonitrile (5:95); gradient=20-100% B over 2 min, then a 1 minute hold at 100% B, flow: 0.7 mL/min, temperature: 27° C.; detection: UV at 220 nm.

Examples 273 and 274

4-((2S,5R)-2,5-Diethyl-4-(1-(4-((4-methoxypiperidin-1-yl)methyl)phenyl)ethyl)piperazin-1-yl)-1-methyl-2-oxo-1,2-dihydropyrido[3,2-d]pyrimidine-6-carbonitrile

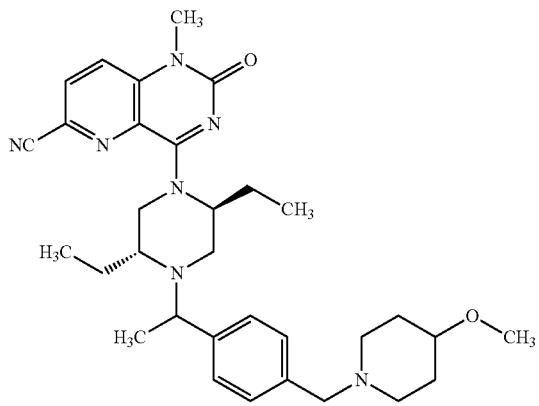 [SMILES: CC[C@H]1CN(C(C)c2ccc(CN3CCN(C(C)=O)CC3)cc2)[C@H](CC)CN1c1nc(=O)n(C)c2ccc(C#N)nc12]

(273-274)

To a stirred solution of 4-((2S,5R)-4-(1-(4-(bromomethyl) phenyl)ethyl)-2,5-diethylpiperazin-1-yl)-1-methyl-2-oxo-1, 2-dihydropyrido[3,2-d]pyrimidine-6-carbonitrile (100 mg, 0.19 mmol) in acetonitrile (2 mL) were added DIPEA (0.1 mL, 0.57 mmol) and 4-methoxypiperidine (44.0 mg, 0.38 mmol) at room temperature. The reaction mixture was heated at 80° C. for 1 h. The reaction mixture was cooled to room temperature and the solvent was removed under reduced pressure to give the crude product, which was purified using preparative SFC. SFC Method: Column: Chiralpak IG (250×30 mm, 5 μm); mobile phase: 50% CO₂/50% of co-solvent: 0.2% ammonia in MeOH, Flow: 95 g/min; Detector Wavelength: 220 nm; Temperature: 40° C.

EXAMPLE 273: (5.4 mg, 5% yield). LCMS: m/z=558.2 [M+H]⁺; rt 1.91 min; LCMS method: Column: XBridge BEH XP C18 (50×2.1 mm, 2.5 μm); mobile phase A: 10 mM NH₄OAc in water:acetonitrile (95:5); mobile phase B: 10 mM NH₄OAc in water:acetonitrile (5:95); Gradient=0-100% B over 3 minutes; Temperature: 50° C.; Flow rate: 1.1 mL/min; Detection: UV at 220 nm. ¹H NMR (400 MHz, DMSO-d₆) δ (ppm)=8.24-8.18 (m, 1H), 7.96 (d, J=9.0 Hz, 1H), 7.32-7.21 (m, 4H), 5.82-5.44 (m, 1H), 5.03-4.78 (m, 1H), 3.66 (q, J=6.2 Hz, 1H), 3.42 (s, 5H), 3.20 (s, 3H), 3.19-3.03 (m, 2H), 2.93-2.86 (m, 1H), 2.76-2.68 (m, 1H), 2.65-2.58 (m, 2H), 2.45-2.33 (m, 1H), 2.24-2.01 (m, 3H), 1.85-1.75 (m, 2H), 1.48-1.18 (m, 8H), 0.98-0.86 (m, 3H), 0.71-0.51 (m, 3H).

EXAMPLE 274: (3.7 mg, 4% yield). LCMS: m/z=558.4 [M+H]+; rt 1.93 min; LCMS method: Column: XBridge BEH XP C18 (50×2.1 mm, 2.5 μm); mobile phase A: 10 mM NH4OAc in water:acetonitrile (95:5); mobile phase B: 10 mM NH4OAc in water:acetonitrile (5:95); Gradient=0-100% B over 3 minutes; Temperature: 50° C.; Flow rate: 1.1 mL/min; Detection: UV at 220 nm. $^1$H NMR (400 MHz, DMSO-d6) δ (ppm)=8.29-8.16 (m, 1H), 8.03-7.91 (m, 1H), 7.36-7.21 (m, 4H), 6.12-5.16 (m, 1H), 5.14-4.67 (m, 1H), 3.67-3.49 (m, 2H), 3.45-3.40 (m, 5H), 3.20 (s, 3H), 3.18-3.05 (m, 2H), 2.62-2.60 (m, 2H), 2.47-2.41 (m, 1H), 2.30-2.21 (m, 1H), 2.09-2.01 (m, 2H), 1.86-1.76 (m, 2H), 1.54-1.33 (m, 4H), 1.33-1.15 (m, 5H), 1.03-0.90 (m, 3H), 0.58 (t, J=7.3 Hz, 3H).

The examples in the Table 10 were prepared according to the general procedure described in Examples 273 and 274, using the appropriate amine and ((2S,5R)-4-(1-(4-(bromomethyl)phenyl)ethyl)-2,5-diethylpiperazin-1-yl)-1-methyl-2-oxo-1,2-dihydropyrido[3,2-d]pyrimidine-6-carbonitrile.

When the reaction provided a mixture of diastereomers, the mixture was separated at the final stage using either preparative chromatography or preparative chiral chromatography. The absolute stereochemistry was not assigned at the benzylic position.

TABLE 10

| Ex. No. | Structure | Stereo Chem. | LCMS Method | LCMS rt | [M + H]+ |
|---|---|---|---|---|---|
| 275 | | H | E | 3.76 | 558.4 |
| 276 | | H | E | 3.87 | 558.4 |
| 277 | | H | E | 3.76 | 564.4 |
| 278 | | H | E | 3.68 | 564.4 |
| 279 | | H | C | 1.67 | 542.4 |
| 280 | | H | C | 1.68 | 542.4 |

TABLE 10-continued

| Ex. No. | Structure | Stereo Chem. | LCMS Method | LCMS rt | [M + H]+ |
|---|---|---|---|---|---|
| 281 | | H | E | 2.68 | 528.4 |
| 282 | | H | E | 2.25 | 528.4 |
| 283 | | H | C | 1.8 | 571.4 |
| 284 | | H | C | 1.83 | 571.4 |
| 285 | | H | C | 1.52 | 544.4 |
| 286 | | H | C | 1.54 | 544.4 |

TABLE 10-continued

| Ex. No. | Structure | Stereo Chem. | LCMS Method | LCMS rt | [M + H]+ |
|---|---|---|---|---|---|
| 287 | | H | C | 1.76 | 557.4 |
| 288 | | H | C | 1.77 | 557.3 |
| 289 | | H | C | 1.68 | 544.4 |
| 290 | | H | C | 1.69 | 544.4 |
| 291 | | H | C | 2.27 | 558.4 |
| 292 | | H | C | 2.3 | 558.4 |

249

Intermediate 31

(3-Bromo-1-methyl-1H-1,2,4-triazol-5-yl)(4-fluorophenyl)methanol

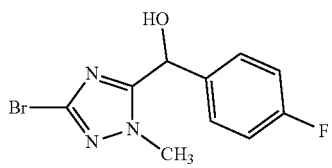 [SMILES: Cn1nc(Br)nc1C(O)c1ccc(F)cc1]

To a solution of 3,5-dibromo-1-methyl-1H-1,2,4-triazole (1.0 g, 4.15 mmol) in THF (15 mL) at −78° C. was added n-butyl lithium (2.5 M, 1.66 mL, 4.15 mmol). The reaction mixture was stirred for 20 minutes, 4-fluorobenzaldehyde (0.515 g, 4.15 mmol) was added at −78° C. and stirred for 30 minutes at room temperature. The reaction was quenched with the addition of saturated aqueous ammonium chloride solution (25 mL). The reaction mixture was extracted with ethyl acetate (2×50 mL) and the combined organic layer was dried over anhydrous sodium sulphate and filtered. Evaporation of the solvent under reduced pressure furnished the crude product, which was purified using silica gel chromatography (0-40% ethyl acetate/pet ether) to afford 3-bromo-1-methyl-1H-1,2,4-triazol-5-yl)(4-fluorophenyl)methanol (950 mg, 80% yield). LCMS: m/z, 286.0 [M+2]$^+$; retention time 1.09 min; LCMS Method; Column: AQUITY UPLC BEH C18 (3.0×50 mm, 1.7 μm); mobile phase A: 10 mM NH$_4$OAc in water:acetonitrile (95:5); mobile phase B: 10 mM NH$_4$OAc in water:acetonitrile (5:95); gradient=20-100% B over 4 min, then a 0.6 minute hold at 100% B, flow: 0.7 mL/min, temperature: 27° C.; detection: UV at 220 nm.

Intermediate 32

3-Bromo-5-(chloro(4-fluorophenyl)methyl)-1-methyl-1H-1,2,4-triazole

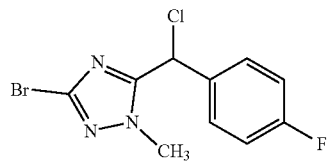 [SMILES: Cn1nc(Br)nc1C(Cl)c1ccc(F)cc1]

To a stirred solution of (3-bromo-1-methyl-1H-1,2,4-triazol-5-yl)(4-fluorophenyl) methanol (200 mg, 0.7 mmol) in dry DCM (3.0 mL) were added DIPEA (0.37 mL, 2.1 mmol) and mesyl chloride (0.07 mL, 0.84 mmol) at 0° C. The reaction mixture was stirred at room temperature for 2 h. The reaction was quenched with the addition of water (5 mL). The crude material was extracted with DCM (1×100 mL), washed with water, brine, and dried over sodium sulphate. Evaporation of the solvent under reduced pressure furnished 3-bromo-5-(chloro(4-fluorophenyl)methyl)-1-methyl-1H-1,2,4-triazole (200 mg, 94% yield) as a brown semi solid. LCMS: m/z, 304.0 [M+2]; retention time 1.56 min; LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 4 min, then a 0.6 minute hold at 100% B, flow: 0.7 mL/min, temperature: 27° C.; detection: UV at 220 nm.

Example 293

4-((2S,5R)-4-((3-Bromo-1-methyl-1H-1,2,4-triazol-5-yl)(4-fluorophenyl)methyl)-2,5-diethylpiperazin-1-yl)-1-methyl-2-oxo-1,2-dihydropyrido[3,2-d]pyrimidine-6-carbonitrile

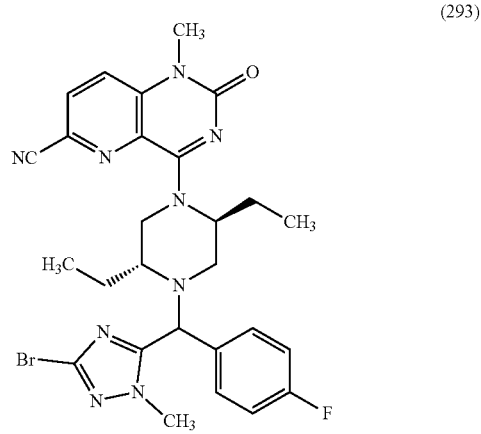 [SMILES: CC[C@H]1CN(C(c2ccc(F)cc2)c2nc(Br)nn2C)[C@H](CC)CN1c1nc(=O)n(C)c2ccc(C#N)nc12]

(293)

To a stirred solution of 3-bromo-5-(chloro(4-fluorophenyl)methyl)-1-methyl-1H-1,2,4-triazole (120 mg, 0.39 mmol), 4-((2S,5R)-2,5-diethylpiperazin-1-yl)-1-methyl-2-oxo-1,2-dihydropyrido[3,2-d]pyrimidine-6-carbonitrile, TFA (208 mg, 0.473 mmol) in acetonitrile (6.0 mL) was added DIPEA (0.21 mL, 1.18 mmol). The reaction mixture was heated at 85° C. for 3 h and then cooled to room temperature. The volatiles were removed under reduced pressure to obtain the crude product, which was purified by silica gel (12 g) chromatography by using 0-10% methanol in chloroform as eluent. The fractions were concentrated under reduced pressure to obtain 4-((2S,5R)-4-((3-bromo-1-methyl-1H-1,2,4-triazol-5-yl)(4-fluorophenyl)methyl)-2,5-diethylpiperazin-1-yl)-1-methyl-2-oxo-1,2-dihydropyrido[3,2-d]pyrimidine-6-carbonitrile (120 mg, 51% yield). LCMS: m/z, 594.3 [M+H]$^+$; retention time 1.70 min; LCMS Method; Column: AQUITY UPLC BEH C18 (3.0×50 mm, 1.7 μm); mobile phase A: 10 mM NH$_4$OAc in water:acetonitrile (95:5); mobile phase B: 10 mM NH$_4$OAc in water:acetonitrile (5:95); gradient=20-100% B over 2 min, then a 0.2 minute hold at 100% B, flow: 0.7 mL/min, temperature: 27° C.; detection: UV at 220 nm.

Examples 294 and 295

4-((2S,5R)-4-((3-Cyclopropyl-1-methyl-1H-1,2,4-triazol-5-yl)(4-fluorophenyl)methyl)-2,5-diethylpiperazin-1-yl)-1-methyl-2-oxo-1,2-dihydropyrido[3,2-d]pyrimidine-6-carbonitrile

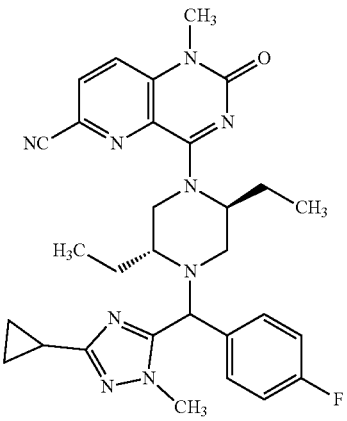

(294-295)

A solution of 4-((2S,5R)-4-((3-bromo-1-methyl-1H-1,2,4-triazol-5-yl)(4-fluorophenyl)methyl)-2,5-diethylpiperazin-1-yl)-1-methyl-2-oxo-1,2-dihydropyrido[3,2-d]pyrimidine-6-carbonitrile (70 mg, 0.12 mmol), cyclopropylboronic acid (10.11 mg, 0.118 mmol) and $Cs_2CO_3$ (115 mg, 0.35 mmol) in dry dioxane (2.0 mL) was purged with argon for 10 minutes. $PdCl_2(dppf)$-$CH_2Cl_2$ adduct (9.62 mg, 0.01 mmol) was added. The reaction mixture was purged with argon for another 5 minutes and heated at 120° C. for 6 h. The reaction mixture was cooled to room temperature and the volatiles were removed under reduced pressure to obtain the crude product, which was purified using preparative chiral LCMS. HPLC Method: Column:)(Bridge C18 (19× 150 mm, 5 μm); mobile phase A: water:acetonitrile (95:5); mobile phase B: water:acetonitrile (5:95); 15-47% over 25 minutes, then a 5 minute hold at 100% B; Flow: 15 mL/min; fractions were concentrated under reduced pressure and lyophilized from (EtOH/$H_2O$, 1:5) to yield Examples 294 and 295.

EXAMPLE 294: (13 mg, 19% yield); LCMS: m/z, 556.6 $[M+H]^+$; rt 1.85 min; LCMS method: Column: XBridge BEH XP C18 (50×2.1 mm, 2.5 μm); mobile phase A: 10 mM $NH_4OAc$ in water:acetonitrile (95:5); mobile phase B: 10 mM $NH_4OAc$ in water:acetonitrile (5:95); Gradient=0-100% B over 3 minutes; Temperature: 50° C.; Flow rate: 1.1 mL/min; Detection: UV at 220 nm. $^1H$ NMR (400 MHz, DMSO-$d_6$) δ (ppm)=8.31-8.18 (m, 1H), 8.06-7.93 (m, 1H), 7.69-7.54 (m, 2H), 7.21 (t, J=8.8 Hz, 2H), 5.97-5.35 (m, 1H), 5.1 (s, 1H), 4.99-4.82 (m, 1H), 3.85 (s, 3H), 3.66-3.55 (m, 1H), 3.43 (s, 3H), 2.62 (ddd, J=1.3, 2.0, 14.2 Hz, 2H), 2.22-1.75 (m, 3H), 1.52-1.30 (m, 2H), 0.87 (dd, J=2.9, 8.3 Hz, 2H), 0.80-0.57 (m, 9H).

EXAMPLE 295: (21 mg, 30% yield); LCMS: m/z, 556.4 $[M+H]^+$; rt 1.85 min; LCMS method: Column: XBridge BEH XP C18 (50×2.1 mm, 2.5 μm); mobile phase A: 10 mM $NH_4OAc$ in water:acetonitrile (95:5); mobile phase B: 10 mM $NH_4OAc$ in water:acetonitrile (5:95); Gradient=0-100% B over 3 minutes; Temperature: 50° C.; Flow rate: 1.1 mL/min; Detection: UV at 220 nm. $^1H$ NMR (400 MHz, DMSO-$d_6$) δ (ppm)=8.24 (d, J=8.8 Hz, 1H), 8.03-7.95 (m, 1H), 7.76-7.62 (m, 2H), 7.31-7.17 (m, 2H), 5.96-5.32 (m, 1H), 5.29-4.81 (m, 2H), 3.99-3.89 (m, 1H), 3.77 (br s, 3H), 3.69-3.58 (m, 1H), 3.32-3.24 (m, 1H), 2.90-2.73 (m, 1H), 2.62-2.55 (m, 1H), 2.31-2.00 (m, 3H), 1.95-1.69 (m, 2H), 1.62-1.33 (m, 2H), 0.94-0.58 (m, 10H).

Intermediate 33 methyl N-benzyl-N—((R)-2-((tert-butoxycarbonyl)amino)butanoyl)-L-alaninate

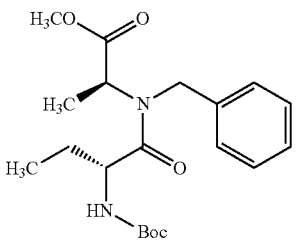 [SMILES: CC[C@@H](NC(=O)OC(C)(C)C)C(=O)N(Cc1ccccc1)[C@@H](C)C(=O)OC]

To a solution of (R)-2-((tert-butoxycarbonyl)amino)butanoic acid (6.31 g, 31.0 mmol) in DMF (2 mL) at room temperature was added HATU (8.85 g, 23.29 mmol), DIPEA (8.13 mL, 46.6 mmol), and methyl benzyl-L-alaninate (3 g, 15.52 mmol). The reaction mixture was stirred at room temperature for 2 h. The reaction was quenched with water. The reaction mixture was extracted with ethyl acetate (2×100 mL), the combined organic layer was washed with water, brine and dried over sodium sulfate. The solvent was evaporated under reduced pressure to obtain the crude product, which was purified by silica gel column chromatography using 30% EtOAc in pet ether. The fractions were concentrated under reduced pressure to obtain the purified methyl N-benzyl-N—((R)-2-((tert-butoxycarbonyl)amino) butanoyl)-L-alaninate (5 g, 13.21 mmol, 85% yield). LCMS: m/z=379.4 $[M-41]^+$; retention time 1.80 min. LCMS Method; Column: AQUITY UPLC BEH C18 (3.0×50 mm, 1.7 μm); mobile phase A:10 mM $NH_4OAc$ in water:acetonitrile (95:5); mobile phase B: 10 mM $NH_4OAc$ in water:acetonitrile (5:95); gradient=20-100% B over 2 min, then a 1 minute hold at 100% B, flow: 0.7 mL/min, temperature: 27° C.; detection: UV at 220 nm.

Intermediate 34

Methyl N—((R)-2-aminobutanoyl)-N-benzyl-L-alaninate

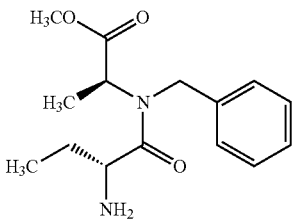 [SMILES: CC[C@@H](N)C(=O)N(Cc1ccccc1)[C@@H](C)C(=O)OC]

To a solution of methyl N-benzyl-N—((R)-2-((tert-butoxycarbonyl)amino) butanoyl)-L-alaninate (5 g, 13.21 mmol) in DCM (10 mL) at 0° C. was added TFA (15.27 mL, 198 mmol). The reaction mixture was stirred at room temperature for 3 h. The reaction mixture was concentrated under reduced pressure and the crude product was washed with 1:1 diethyl ether and pet ether and dried under high vacuum to yield the methyl N—((R)-2-aminobutanoyl)-N-benzyl-L-alaninate, TFA (5 g, 10.96 mmol, 83% yield)). LCMS: m/z=279.3 [M+H]$^+$; retention time 0.96 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min, temperature: 27° C.; detection: UV at 220 nm.

Intermediate 35

(3R,6S)-1-Benzyl-3-ethyl-6-methylpiperazine-2,5-dione

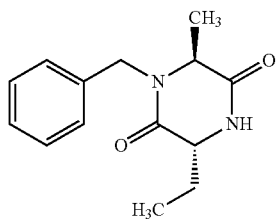 [SMILES: CC[C@H]1NC(=O)[C@H](C)N(Cc2ccccc2)C1=O]

A solution of methyl N—((R)-2-aminobutanoyl)-N-benzyl-L-alaninate, TFA (5 g, 12.74 mmol) in methanol (5 mL) was refluxed at 65° C. overnight. The reaction mixture was concentrated under reduced pressure and dried under high vacuum to afford the (3R,6S)-1-benzyl-3-ethyl-6-methylpiperazine-2,5-dione (2.5 g, 10.15 mmol, 80% yield). LCMS: m/z=247.3 [M+H]$^+$; retention time 0.46 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min, temperature: 27° C.; detection: UV at 220 nm.

Intermediate 36

(2S,5R)-1-Benzyl-5-ethyl-2-methylpiperazine

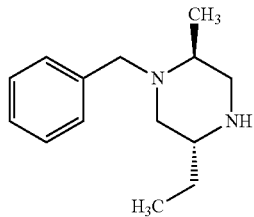

To a stirred solution of (3R,6S)-1-benzyl-3-ethyl-6-methylpiperazine-2,5-dione (2.5 g, 10.15 mmol) in THF (10 mL) at 0° C. was added dropwise 1 M solution of borane tetrahydrofuran complex (50.7 mL, 50.7 mmol) in THF. The mixture was refluxed overnight and cooled. The reaction was quenched slowly with the addition of methanol. To this reaction mixture was added concentrated HCl (0.5 mL) and refluxed for 3 h, cooled, and concentrated under reduced pressure. The crude product was dissolved in DCM and washed with saturated aqueous NaHCO$_3$ solution, brine, dried over anhydrous Na$_2$SO$_4$, filtered and evaporated under reduced pressure to yield (2S,5R)-1-benzyl-5-ethyl-2-methylpiperazine (2.0 g, 7.33 mmol, 72.2% yield). LCMS: m/z=219.2 [M+H]$^+$; retention time 0.33 min. Column: Kinetex XB-C18 (75×3 mm, 2.6 μm) mobile phase A: 10 mM NH$_4$OAc in water:acetonitrile (98:2) mobile phase B: 10 mM NH$_4$OAc in water:acetonitrile (2:98).

Intermediate 37 tert-Butyl (2R,5S)-4-benzyl-2-ethyl-5-methylpiperazine-1-carboxylate

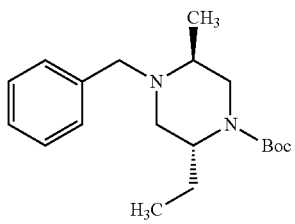 [SMILES: CC[C@@H]1CN(Cc2ccccc2)[C@@H](C)CN1C(=O)OC(C)(C)C]

To a solution of (2S,5R)-1-benzyl-5-ethyl-2-methylpiperazine (2.3 g, 10.53 mmol) in DCM (5 mL) was added TEA (2.202 mL, 15.80 mmol), Boc-anhydride (2.446 mL, 10.53 mmol) at room temperature. The reaction mixture was stirred for 3 h. The reaction was quenched with water. The reaction mixture was extracted with ethyl acetate (2×100 mL), the combined organic layer was washed with water, brine and dried over sodium sulfate. The solvent was evaporated under reduced pressure to obtain the crude product which was purified by silica gel column chromatography using 40% EtOAc in pet ether. The fractions were concentrated under reduced pressure to yield purified tert-butyl (2R,5S)-4-benzyl-2-ethyl-5-methylpiperazine-1-carboxylate (2 g, 5.53 mmol, 52.5% yield). LCMS: m/z=319.4 [M+H]$^+$; retention time 1.69 min, LCMS Method; Column: AQUITY UPLC BEH C18 (3.0×50 mm, 1.7 μm); mobile phase A: 10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min, temperature: 27° C.; detection: UV at 220 nm.

Intermediate 38 tert-Butyl (2R,5S)-2-ethyl-5-methylpiperazine-1-carboxylate

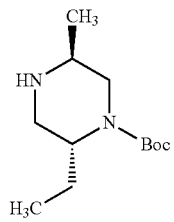

In a 100 mL autoclave, a solution of tert-butyl (2R,5S)-4-benzyl-2-ethyl-5-methylpiperazine-1-carboxylate (2.1 g, 6.59 mmol) in methanol (5 mL) and acetic acid (0.413 mL, 7.22 mmol) at room temperature was purged with nitrogen. Palladium on carbon (0.211 g, 1.978 mmol, 10% w/w) was added and the reaction mixture was evacuated. The reaction mixture was placed under hydrogen and stirred under hydrogen overnight. The reaction mixture was filtered through a Celite® bed, and the filtrate was concentrated under reduced pressure. The product was dried under high vacuum to yield the tert-butyl (2R,5S)-2-ethyl-5-methylpiperazine-1-carboxylate, AcOH (1.5 g, 5.20 mmol, 79% yield). LCMS: m/z=229.2 [M+H]$^+$; retention time 0.90 min. Column: Kinetex XB-C18 (75×3 mm, 2.6 μm); mobile phase A: 10 mM NH$_4$OAc in water:acetonitrile (98:2) mobile phase B: 10 mM NH$_4$OAc in water:acetonitrile (2:98).

Intermediate 39 tert-Butyl (2R,5S)-4-(6-cyano-1-methyl-2-oxo-1,2-dihydro-1,5-naphthyridin-4-yl)-2-ethyl-5-methylpiperazine-1-carboxylate

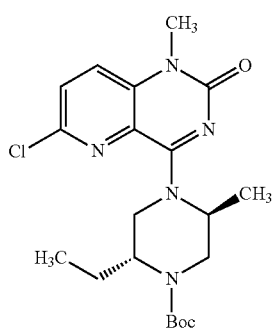 [SMILES: CC[C@@H]1CN(c2nc(=O)n(C)c3ccc(Cl)nc23)[C@@H](C)CN1C(=O)OC(C)(C)C]

To a stirred solution of tert-butyl (2R,5S)-2-ethyl-5-methylpiperazine-1-carboxylate (0.6 g, 2.63 mmol) in acetonitrile (2 mL) were added DIPEA (1.37 mL, 7.88 mmol) and 4,6-dichloro-1-methylpyrido[3,2-d]pyrimidin-2(1H)-one (0.907 g, 3.94 mmol) at room temperature. The reaction mixture was heated at 85° C. for 6 h. The reaction mixture was cooled to room temperature and concentrated under reduced pressure to obtain the crude product, which was purified using silica gel column chromatography (60-70% EtOAc/petroleum ether) to afford tert-butyl (2R,5S)-4-(6-cyano-1-methyl-2-oxo-1,2-dihydro-1,5-naphthyridin-4-yl)-2-ethyl-5-methylpiperazine-1-carboxylate (0.5 g, 0.797 mmol, 30.3% yield). LCMS: m/z=422.3 [M+H]$^+$; rt 1.76 min. LCMS Method: Column: Acquity UPLC BEH C18 (2.1×50 mm, 1.7 μm); mobile phase A: 10 mM ammonium acetate:acetonitrile (95:5); mobile phase B: 10 mM ammonium acetate:acetonitrile (5:95), Gradient=20% B over 1.1 minute, then a 2.2 minute hold at 100% B; Temperature: 50° C.; Flow rate: 0.7 mL/min; Detection: UV at 2200 nm.

Intermediate 40 tert-Butyl (2R,5S)-4-(6-cyano-1-methyl-2-oxo-1,2-dihydropyrido[3,2-d]pyrimidin-4-yl)-2-ethyl-5-methylpiperazine-1-carboxylate

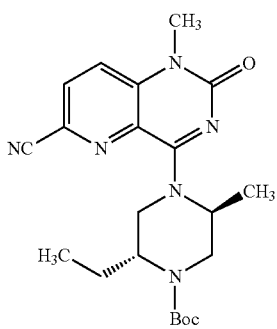 [SMILES: CC[C@@H]1CN(c2nc(=O)n(C)c3ccc(C#N)nc23)[C@@H](C)CN1C(=O)OC(C)(C)C]

To a stirred solution of tert-butyl (2R,5S)-4-(6-cyano-1-methyl-2-oxo-1,2-dihydro-1,5-naphthyridin-4-yl)-2-ethyl-5-methylpiperazine-1-carboxylate (0.55 g, 1.304 mmol) in NMP (2 mL) were added dppf (0.145 g, 0.261 mmol), zinc (0.085 g, 1.304 mmol) and zinc cyanide (0.306 g, 2.61 mmol). The reaction mixture was degassed for 5 min, followed by the addition of Pd$_2$(dba)$_3$ (0.119 g, 0.130 mmol) and heating at 90° C. for overnight. The reaction mixture was cooled to room temperature, diluted with ethyl acetate and filtered through a Celite® pad. The filtrate was washed with water, brine and the organic layer was dried over anhydrous Na$_2$SO$_4$, filtered and evaporated under reduced pressure to obtain the crude compound which was purified using silica gel chromatography (70-80% EtOAc/petroleum ether) to afford the tert-butyl (2R,5S)-4-(6-cyano-1-methyl-2-oxo-1,2-dihydropyrido[3,2-d]pyrimidin-4-yl)-2-ethyl-5-methylpiperazine-1-carboxylate (0.3 g, 0.473 mmol, 36.3% yield). LCMS: m/z=413.1 [M+H]$^+$; rt 1.50 min. LCMS Method: Column: Acquity UPLC BEH C18 (2.1×50 mm, 1.7 μm); mobile phase A: 10 mM ammonium acetate: acetonitrile (95:5); mobile phase B: 10 mM ammonium acetate: acetonitrile (5:95), Gradient=20% B over 1.1 minute, then a 2.2 minute hold at 100% B; Temperature: 50° C.; Flow rate: 0.7 mL/min; Detection: UV at 110 nm).

Intermediate 41

4-((2S,5R)-5-Ethyl-2-methylpiperazin-1-yl)-1-methyl-2-oxo-1,2-dihydropyrido[3,2-d]pyrimidine-6-carbonitrile

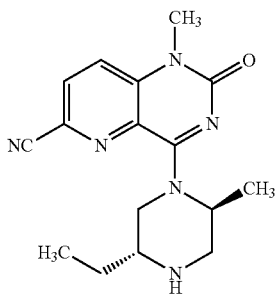

To a stirred solution of tert-butyl (2R,5S)-4-(6-cyano-1-methyl-2-oxo-1,2-dihydropyrido[3,2-d]pyrimidin-4-yl)-2-ethyl-5-methylpiperazine-1-carboxylate (0.2 g, 0.485 mmol) in dry DCM (5 mL) was added TFA (0.560 mL, 7.27 mmol) at room temperature. The reaction mixture was stirred for 3 h. The solvent was removed under reduced pressure to afford 4-((2S,5R)-5-ethyl-2-methylpiperazin-1-yl)-1-methyl-2-oxo-1,2-dihydropyrido[3,2-d]pyrimidine-6-carbonitrile (0.15 g, 0.392 mmol, 81% yield) as a TFA salt. LCMS: m/z=313.1 [M+H]$^+$; rt 0.63 min. LCMS Method: Column: Acquity UPLC BEH C18 (2.1×50 mm, 1.7 μm); mobile phase A: 10 mM ammonium acetate:acetonitrile (95:5); mobile phase B: 10 mM ammonium acetate: acetonitrile (5:95), Gradient=20% B over 1.1 minute, then a 2.2 minute hold at 100% B; Temperature: 50° C.; Flow rate: 0.7 mL/min; Detection: UV at 110 nm).

The examples in the Table 11 were prepared according to the general procedures described in Examples 152 and 153, using the appropriate benzhydryl/α-substituted benzyl/benzyl halide. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 11

| Ex. No. | Structure | Stereo chem. | LCMS Method | LCMS rt | [M + H]$^+$ | Coupling Method |
|---|---|---|---|---|---|---|
| 296 | | H | C | 2.27 | 572.3 | A |
| 297 | | H | C | 2.28 | 572.3 | |
| 298 | | H | C | 1.753 | 488.3 | B |
| 299 | | H | C | 1.833 | 488.3 | B |
| 300 | | H | C | 2.46 | 471.3 | B |
| 301 | | H | C | 2.53 | 471.3 | B |

TABLE 11-continued

| Ex. No. | Structure | Stereo chem. | LCMS Method | LCMS rt | [M + H]+ | Coupling Method |
|---|---|---|---|---|---|---|
| 302 | 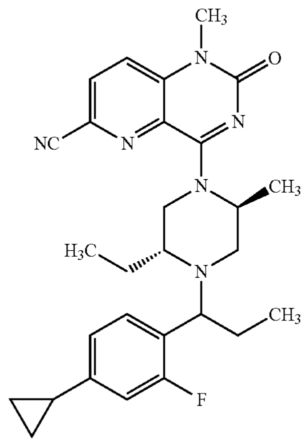 [SMILES: CCC(c1ccc(C2CC2)cc1F)N1C[C@H](C)N(c2nc(=O)n(C)c3ccc(C#N)nc23)C[C@H]1CC] | H | C | 2.45 | 489.3 | B |
| 303 | | H | C | 2.52 | 489.3 | B |
| 304 | 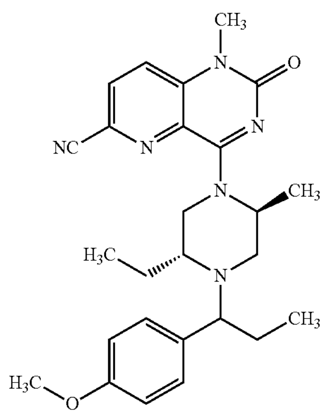 [SMILES: CCC(c1ccc(OC)cc1)N1C[C@H](C)N(c2nc(=O)n(C)c3ccc(C#N)nc23)C[C@H]1CC] | H | C | 2.146 | 461.3 | B |
| 305 | | H | C | 2.23 | 461.3 | B |
| 306 | 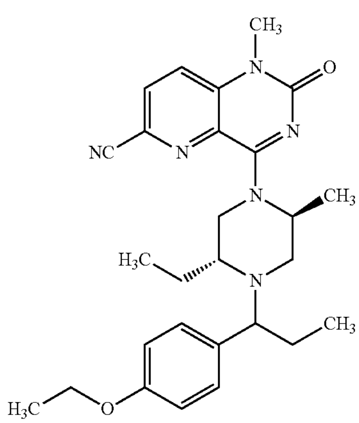 [SMILES: CCOc1ccc(C(CC)N2C[C@H](C)N(c3nc(=O)n(C)c4ccc(C#N)nc34)C[C@H]2CC)cc1] | H | C | 2.29 | 475.3 | B |
| 307 | | H | C | 2.36 | 475.3 | B |

TABLE 11-continued
| Ex. No. | Structure | Stereo chem. | LCMS Method | LCMS rt | [M + H]+ | Coupling Method |
|---|---|---|---|---|---|---|
| 308 | | H | F | 1.73 | 500.9 | B |
| 309 | 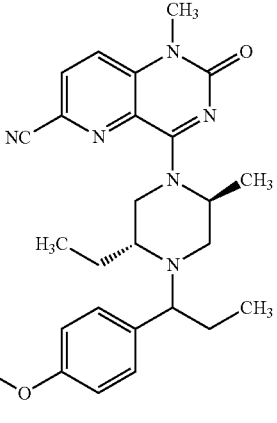 | H | F | 1.6 | 500.9 | B |
| 310 | 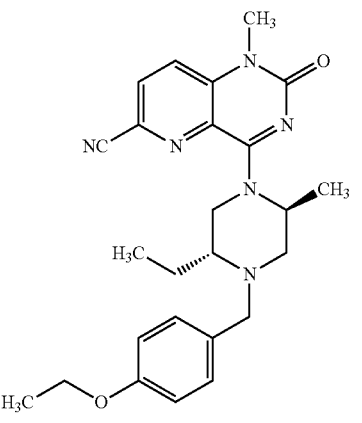 [SMILES: CCOc1ccc(CN2C[C@H](C)N(c3nc(=O)n(C)c4ccc(C#N)nc34)C[C@H]2CC)cc1] | H | C | 2.07 | 447.3 | B |
| 311 | | H | C | 2.33 | 487.2 | B |
| 312 | 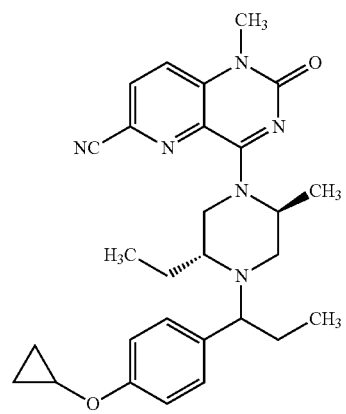 [SMILES: CCC(c1ccc(OC2CC2)cc1)N1C[C@H](C)N(c2nc(=O)n(C)c3ccc(C#N)nc23)C[C@H]1CC] | H | C | 2.40 | 487.2 | B |

TABLE 11-continued
| Ex. No. | Structure | Stereo chem. | LCMS Method | LCMS rt | [M + H]+ | Coupling Method |
|---|---|---|---|---|---|---|
| 313 | | H | C | 2.35 | 475.3 | B |
| 314 | | H | C | 2.26 | 475.4 | B |
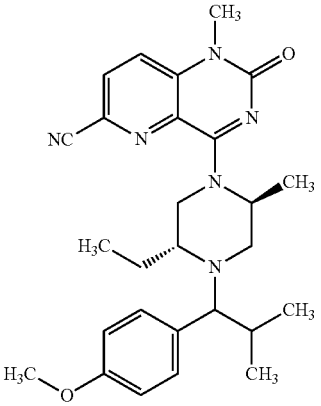 [SMILES: CC[C@@H]1CN(c2nc(=O)n(C)c3ccc(C#N)nc23)[C@@H](C)CN1C(c1ccc(OC)cc1)C(C)C]
| 315 | | H | C | 2.092 | 548.3 | A |
| 316 | | H | C | 2.087 | 548.3 | A |
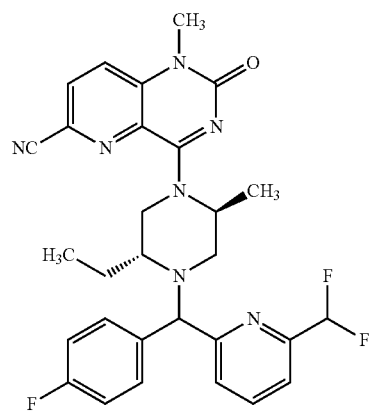 [SMILES: CC[C@@H]1CN(c2nc(=O)n(C)c3ccc(C#N)nc23)[C@@H](C)CN1C(c1ccc(F)cc1)c1cccc(C(F)F)n1]
| 317 | | H | C | 2.145 | 498.3 | B |
| 318 | | H | C | 2.22 | 498.3 | B |
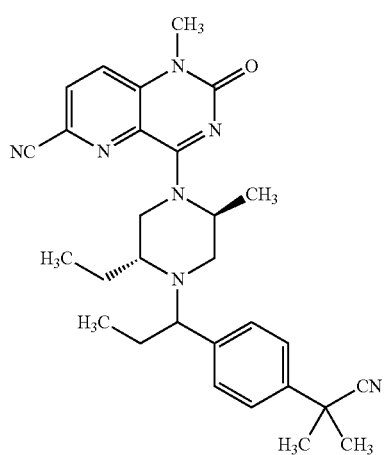 [SMILES: CCC(c1ccc(C(C)(C)C#N)cc1)N1C[C@H](C)N(c2nc(=O)n(C)c3ccc(C#N)nc23)C[C@H]1CC]

TABLE 11-continued
| Ex. No. | Structure | Stereo chem. | LCMS Method | LCMS rt | [M + H]+ | Coupling Method |
|---|---|---|---|---|---|---|
| 319 | 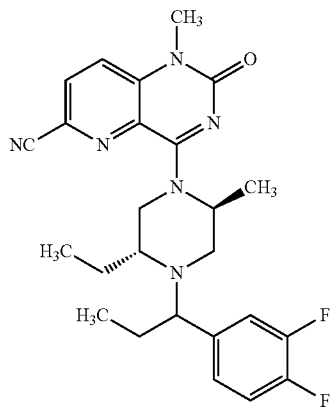 [SMILES: CCC(c1ccc(F)c(F)c1)N1C[C@H](C)N(c2nc(=O)n(C)c3ccc(C#N)nc23)C[C@H]1CC] | H | C | 2.28 | 467.3 | B |
| 320 | | H | C | 2.34 | 467.3 | B |
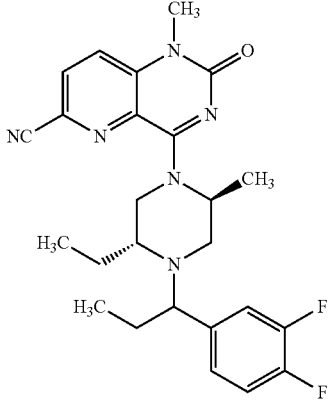
| 321 | | H | C | 2.464 | 511.2 | B |
| 322 | | H | C | 2.521 | 511.2 | B |
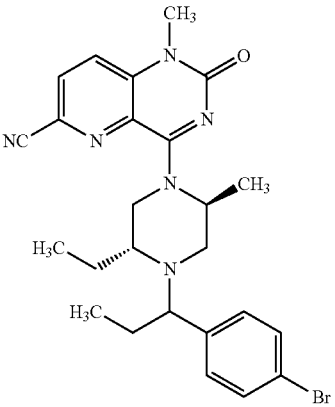 [SMILES: CCC(c1ccc(Br)cc1)N1C[C@H](C)N(c2nc(=O)n(C)c3ccc(C#N)nc23)C[C@H]1CC]
| 323 | | H | C | 2.60 | 503.4 | B |
| 324 | | H | C | 2.64 | 503.3 | B |
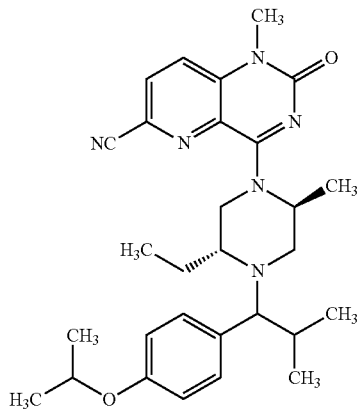 [SMILES: CC[C@@H]1CN(c2nc(=O)n(C)c3ccc(C#N)nc23)[C@@H](C)CN1C(c1ccc(OC(C)C)cc1)C(C)C]

TABLE 11-continued

| Ex. No. | Structure | Stereo chem. | LCMS Method | LCMS rt | [M + H]+ | Coupling Method |
|---|---|---|---|---|---|---|
| 325 | | H | C | 2.085 | 482.3 | B |
| 326 | | H | C | 2.159 | 482.4 | B |
| 327 | | H | C | 2.54 | 537.3 | B |
| 328 | | H | C | 2.59 | 537.3 | B |
| 329 | | H | C | 2.17 | 501.3 | B |
| 330 | | H | C | 2.09 | 501.3 | B |

TABLE 11-continued

| Ex. No. | Structure | Stereo chem. | LCMS Method | LCMS rt | [M + H]+ | Coupling Method |
|---|---|---|---|---|---|---|
| 331 | 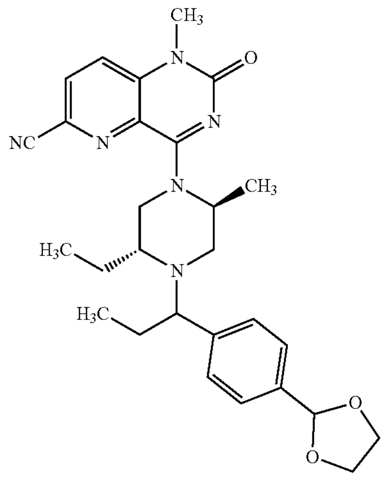 | H | F | 1.37 | 503.21 | B |
| 332 | | H | F | 1.36 | 503.15 | B |
| 333 | 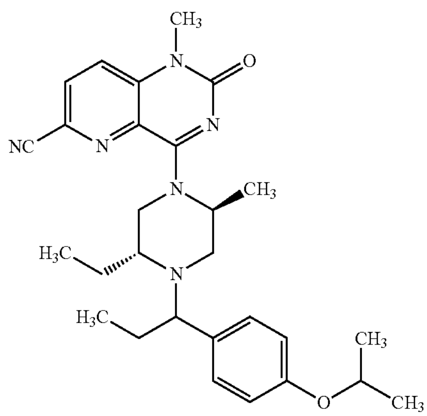 | H | F | 1.65 | 489.16 | B |
| 334 | | H | F | 1.57 | 489.22 | B |

Examples 335 and 336

4-((2S,5R)-5-Ethyl-2-methyl-4-(1-(4-(3,3,3-trifluoropropoxy)phenyl)propyl)piperazin-1-yl)-1-methyl-2-oxo-1,2-dihydropyrido[3,2-d]pyrimidine-6-carbonitrile (335-336)

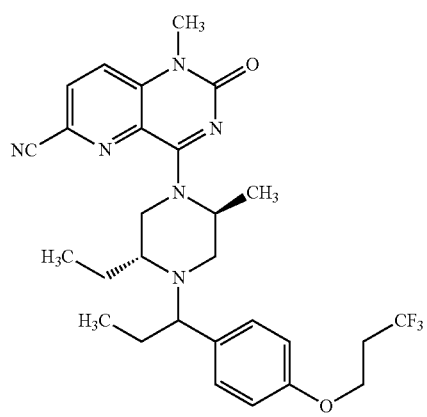 [SMILES: CCC(c1ccc(OCC2(C)CC2)cc1)N1C[C@H](C)N(c2nc(=O)n(C)c3ccc(C#N)nc23)C[C@H]1CC]

To a stirred solution of 4-((2S,5R)-4-(1-(4-bromophenyl)propyl)-5-ethyl-2-methylpiperazin-1-yl)-1-methyl-2-oxo-1,2-dihydropyrido[3,2-d]pyrimidine-6-carbonitrile (100 mg, 0.20 mmol), 3,3,3-trifluoropropan-1-ol (45 mg, 0.39 mmol), Cs$_2$CO$_3$ (192 mg, 0.59 mmol), 2-di-tert-butylphosphino-3-methoxy-6-methyl-2',4',6'-triisopropyl-1,1'-biphenyl, 97% (9.20 mg, 0.02 mmol) in toluene (5 mL) was flushed with argon for 10 min. Then, Pd$_2$(dba)$_3$ (9 mg, 9.81 μmol) was added. The reaction vessel was sealed and heated at 110° C. overnight. The reaction mixture was cooled to room temperature, filtered through a Celite® pad, washed with excess 10% MeOH in DCM (20 mL) and the filtrate was concentrated under reduced pressure to give the crude product, which was purified by flash chromatography (3% MeOH in CHCl$_3$) to afford the diastereomeric mixture of 4-((2S,5R)-5-ethyl-2-methyl-4-(1-(4-(3,3,3-trifluoropropoxy)phenyl)propyl) piperazin-1-yl)-1-methyl-2-oxo-1,2-dihydropyrido [3,2-d]pyrimidine-6-carbonitrile. The diastereomeric mixture was further purified using preparative HPLC (Chiral Separation Method: Column: Gemini NX (250×21.2 mm, 5 μm); mobile phase A=10 mM ammonium acetate in MeOH; mobile phase B=acetonitrile; Flow 20 mL/min. Gradient: 10-90% B over 20 minutes). Fractions were concentrated under reduced pressure and lyophilized from (EtOH/H$_2$O, 1:5) to yield Examples 335 and 336.

EXAMPLE 335 (18 mg, 16% yield). LCMS: m/z, 543.3 [M+H]+; rt 2.03 min. (LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm). $^1$H NMR (400 MHz, DMSO-$d_6$) δ (ppm)=8.26-8.16 (m, 1H), 7.98 (d, J=9.0 Hz, 1H), 7.28-7.15 (m, 2H), 6.98-6.91 (m, 2H), 5.95-5.55 (m, 1H), 5.04-4.81 (m, 1H), 4.26-4.13 (m, 2H), 3.51-3.41 (m, 5H), 2.91-2.69 (m, 3H), 1.91-1.20 (m, 9H), 0.76-0.56 (m, 6H).

EXAMPLE 336 (14 mg, 13% yield). LCMS: m/z, 543.3 [M+H]$^+$; rt 2.09 min. (LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm). $^1$H NMR (400 MHz, DMSO-$d_6$) δ (ppm)=8.31-8.17 (m, 1H), 8.08-7.91 (m, 1H), 7.26 (br d, J=8.5 Hz, 2H), 6.93 (d, J=8.8 Hz, 2H), 6.16-5.36 (m, 1H), 5.04-4.75 (m, 1H), 4.24-4.16 (m, 2H), 3.67-3.58 (m, 1H), 3.44 (s, 3H), 3.16-3.04 (m, 1H), 2.85-2.68 (m, 2H), 2.61-2.53 (m, 2H), 2.28-2.16 (m, 1H), 1.88-1.76 (m, 1H), 1.61-1.41 (m, 3H), 1.40-1.32 (m, 1H), 1.29-1.18 (m, 2H), 1.04-0.95 (m, 3H), 0.61 (t, J=7.3 Hz, 3H).

The examples in the Table 12 were prepared according to the general procedures described in Examples 335 and 336, using the appropriate alcohol and 4-((2S,5R)-4-(1-(4-bromophenyl)propyl)-5-ethyl-2-methylpiperazin-1-yl)-1-methyl-2-oxo-1,2-dihydropyrido[3,2-d]pyrimidine-6-carbonitrile. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 12

| Ex. No. | Structure | Stereo-chemistry | LCMS Method | LCMS rt | [M + H]$^+$ |
|---|---|---|---|---|---|
| 337 | | H | E | 1.74 | 545.4 |
| 338 | | H | E | 1.83 | 545.4 |
| 339 | | H | E | 2.22 | 515.4 |
| 340 | | H | E | 2.28 | 515.4 |

TABLE 12-continued

| Ex. No. | Structure | Stereo-chemistry | LCMS Method | LCMS rt | [M + H]+ |
|---|---|---|---|---|---|
| 341 | | H | E | 1.38 | 517.4 |
| 342 | | H | E | 1.38 | 518.4 |
| 343 | | H | E | 2.5 | 530.4 |
| 344 | | H | E | 2.68 | 530.4 |
| 345 | | H | E | 2.27 | 515.4 |
| 346 | | H | E | 2.27 | 515.3 |

TABLE 12-continued

| Ex. No. | Structure | Stereo- chemistry | LCMS Method | LCMS rt | [M + H]⁺ |
|---|---|---|---|---|---|
| 347 | 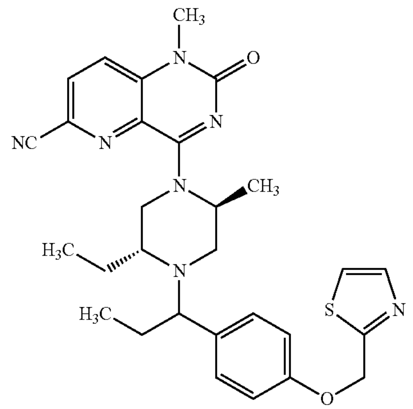 [SMILES: CCC(c1ccc(OCc2nccs2)cc1)N1C[C@H](C)N(c2nc(=O)n(C)c3ccc(C#N)nc23)C[C@H]1CC] | H | E | 1.65 | 544.3 |
| 348 | | H | E | 1.61 | 544.3 |

Intermediate 42

2-Bromo-4-(1-chloroethyl)-1-(trifluoromethyl)benzene

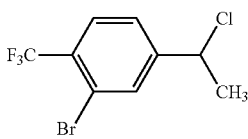

To a solution of 1-(3-bromo-4-(trifluoromethyl)phenyl)ethan-1-ol (600 mg, 2.23 mmol) in DCM (10 mL) was added thionyl chloride (0.16 mL, 2.23 mmol) slowly at 0° C. The reaction mixture was stirred for 10 minutes and then allowed it reach room temperature over 16 h. The reaction mixture was concentrated under reduced pressure to yield 2-bromo-4-(1-chloroethyl)-1-(trifluoromethyl)benzene (640 mg, 100% yield). ¹H NMR (400 MHz, CDCl₃) δ (ppm)=7.78 (s, 1H), 7.19-7.16 (m, 1H), 6.64-6.61 (m, 1H), 4.42-4.38 (m, 1H), 1.36 (d, J=6.4 Hz, 3H).

Example 349

4-((2S,5R)-4-(1-(3-bromo-4-(trifluoromethyl)phenyl)ethyl)-5-ethyl-2-methylpiperazin-1-yl)-1-methyl-2-oxo-1,2-dihydropyrido[3,2-d]pyrimidine-6-carbonitrile (349)

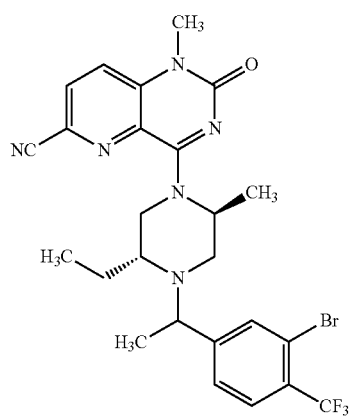

To a stirred suspension of 4-((2S,5R)-5-ethyl-2-methylpiperazin-1-yl)-1-methyl-2-oxo-1,2-dihydropyrido[3,2-d]pyrimidine-6-carbonitrile, TFA (600 mg, 1.41 mmol), 2-bromo-4-(1-chloroethyl)-1-(trifluoromethyl)benzene (809 mg, 2.81 mmol), sodium iodide (211 mg, 1.41 mmol) in acetonitrile (6.0 mL) was added DIPEA (0.74 mL, 4.22 mmol). The reaction mixture was stirred for 5 minutes. The reaction mixture was heated to 85° C. and maintained for 3 h. The reaction mixture concentrated under reduced pressure to obtain the crude product, which was purified by silica gel (24 g) column chromatography by using 0-10% methanol in chloroform as eluent. The fractions were concentrated under reduced pressure to obtain 4-(2S,5R)-4-(1-(3-bromo-4-(trifluoromethyl)phenyl)ethyl)-5-ethyl-2-methylpiperazin-1-yl)-1-methyl-2-oxo-1,2-dihydropyrido[3,2-d]pyrimidine-6-carbonitrile (750 mg, 80% yield). LCMS: m/z, 563.2 [M+H]⁺; retention time 2.12 min; LCMS Method; Column: AQUITY UPLC BEH C18 (3.0×50 mm, 1.7 μm); mobile phase A:10 mM NH₄OAc in water:acetonitrile (95:5); mobile phase B: 10 mM NH₄OAc in water:acetonitrile (5:95); gradient=20-100% B over 2 min, then a 0.2 minute hold at 100% B, flow: 0.7 mL/min.

Examples 350 and 351

4-((2S,5R)-5-ethyl-2-methyl-4-(1-(3-(morpholinomethyl)-4-(trifluoromethyl)phenyl) ethyl)piperazin-1-yl)-1-methyl-2-oxo-1,2-dihydropyrido[3,2-d]pyrimidine-6-carbonitrile

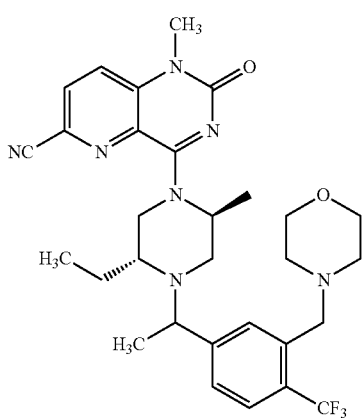

(350-351)

A suspension of 4-((2S,5R)-4-(1-(3-bromo-4-(trifluoromethyl)phenyl)ethyl)-5-ethyl-2-methylpiperazin-1-yl)-1-methyl-2-oxo-1,2-dihydropyrido[3,2-d]pyrimidine-6-carbonitrile (50 mg, 0.09 mmol), trifluoro(morpholinomethyl) borate (17.88 mg, 0.106 mmol), Cs₂CO₃ (87 mg, 0.27 mmol) in THF (1.0 mL) and water (0.1 mL) was purged with argon gas for 10 minutes, followed by addition of XPhos (8.46 mg, 0.02 mmol) and Pd(OAc)₂ (1.992 mg, 8.87 μmol). The reaction mixture was purged argon for another 5 minutes. The reaction mixture was heated to 85° C. and was maintained for 16 h. The reaction mixture was concentrated under reduced pressure to obtain crude product, which was purified by preparative SFC. SFC Method: Column: ChiralCel OJ-H (250×21 mm, 5 μm); mobile phase: 90% CO₂/10% of co-solvent 0.2% DEA in methanol, Flow: 100 g/min; Detector Wavelength: 230 nm. Example 350: Isolate 1: First eluting peak, rt=2.69 min. Example 351: Isolate 2: Second eluting peak, rt=4.03 min.

EXAMPLE 350: (20.6 mg, 39% yield); LCMS: m/z, 584.2 [M+H]⁺; rt 2.32 min; LCMS method: Column: XBridge BEH XP C18 (50×2.1 mm, 2.5 μm); mobile phase A: 10 mM NH₄OAc in water:acetonitrile (95:5); mobile phase B: 10 mM NH₄OAc in water:acetonitrile (5:95); Gradient=0-100% B over 3 minutes; Temperature: 50° C.; Flow rate: 1.1 mL/min; Detection: UV at 220 nm. ¹H NMR (400 MHz, DMSO-d₆) δ (ppm)=8.38-8.13 (m, 2H), 7.98 (d, J=9.0 Hz, 1H), 7.82 (br d, J=0.7 Hz, 1H), 7.73-7.62 (m, 1H), 7.51-7.37 (m, 1H), 5.86-5.61 (m, 1H), 5.10-4.78 (m, 1H), 3.83 (ddd, J=1.7, 5.6, 6.9 Hz, 1H), 3.68-3.56 (m, 2H), 3.43 (s, 3H), 2.98-2.87 (m, 3H), 2.85-2.73 (m, 2H), 2.45-2.31 (m, 2H), 1.64-1.34 (m, 3H), 1.29 (br dd, J=1.8, 4.8 Hz, 3H), 1.16 (t, J=7.3 Hz, 7H), 0.69 (br t, J=5.5 Hz, 3H).

EXAMPLE 351: (18.4 mg, 35% yield); LCMS: m/z, 584.2 [M+H]⁺; rt 2.32 min; LCMS method: Column: XBridge BEH XP C18 (50×2.1 mm, 2.5 μm); mobile phase A: 10 mM NH₄OAc in water:acetonitrile (95:5); mobile phase B: 10 mM NH₄OAc in water:acetonitrile (5:95); Gradient=0-100% B over 3 minutes; Temperature: 50° C.; Flow rate: 1.1 mL/min; Detection: UV at 220 nm. ¹H NMR (400 MHz, DMSO-d₆) δ (ppm)=8.43-8.15 (m, 3H), 8.05-7.95 (m, 1H), 7.83 (br d, J=1.5 Hz, 1H), 7.70-7.61 (m, 1H), 7.52-7.42 (m, 1H), 6.08-5.52 (m, 1H), 5.08-4.83 (m, 1H), 3.75-3.55 (m, 2H), 3.44 (s, 3H), 3.18-3.03 (m, 1H), 2.99-2.88 (m, 4H), 2.63-2.55 (m, 1H), 2.46-2.13 (m, 3H), 1.62-1.36 (m, 3H), 1.32-1.21 (m, 3H), 1.16 (t, J=7.2 Hz, 6H), 1.07-0.91 (m, 3H).

The examples in the Table 13 were prepared according to the general procedure described in Examples 350 and 351, substituting ammonia with the appropriate trifluoroborate in the synthetic sequence. When the synthesis provided a mixture of diastereomer, the mixture was separated at the final stage using either preparative chromatography or preparative chiral chromatography.

TABLE 13

| Ex. No. | Structure | Stereo-chemistry | LCMS Method | LCMS rt | [M + H]⁺ |
|---|---|---|---|---|---|
| 352 | | H | C | 2.32 | 542.4 |
| 353 | | H | C | 2.37 | 542.4 |

TABLE 13-continued

| Ex. No. | Structure | Stereo-chemistry | LCMS Method | LCMS rt | [M + H]+ |
|---|---|---|---|---|---|
| 354 | 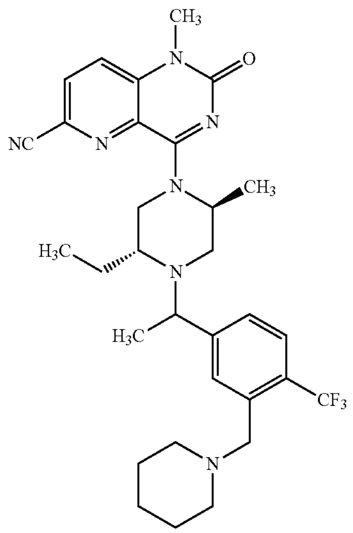 [SMILES: CC[C@@H]1CN(c2nc(=O)n(C)c3ccc(C#N)nc23)[C@@H](C)CN1C(C)c1ccc(C(F)(F)F)c(CN2CCCCC2)c1] | H | C | 2.73 | 582.3 |
| 355 | | H | C | 2.77 | 582.3 |

Examples 356 and 357

4-((2S,5R)-4-(1-(3-Cyano-4-(trifluoromethyl)phenyl)ethyl)-5-ethyl-2-methylpiperazin-1-yl)-1-methyl-2-oxo-1,2-dihydropyrido[3,2-d]pyrimidine-6-carbonitrile

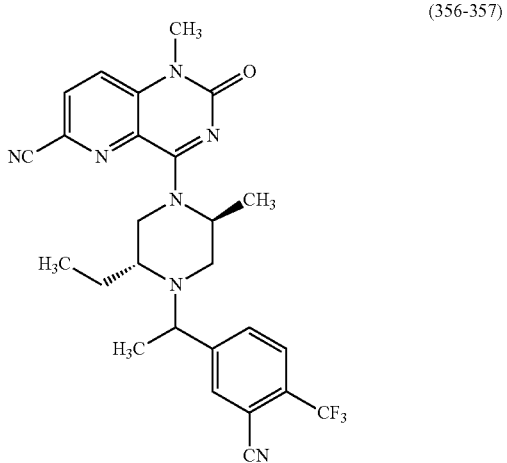 [SMILES: CC[C@@H]1CN(c2nc(=O)n(C)c3ccc(C#N)nc23)[C@@H](C)CN1C(C)c1ccc(C(F)(F)F)c(C#N)c1]

(356-357)

To a stirred solution of 4-((2S,5R)-4-(1-(3-bromo-4-(trifluoromethyl)phenyl) ethyl)-5-ethyl-2-methylpiperazin-1-yl)-1-methyl-2-oxo-1,2-dihydropyrido[3,2-d]pyrimidine-6-carbonitrile (50 mg, 0.089 mmol) in DMF (2.0 mL) was added copper (I) cyanide (15.90 mg, 0.177 mmol) at room temperature. The reaction mixture was heated at 130° C. for 16 h, cooled, and filtered through a Celite® pad, which was then washed with DCM. The filtrate was washed with water, brine, dried over sodium sulfate, and concentrated under reduced pressure to obtain the crude product, which was purified by using preparative SFC. SFC Method: Column: Chiralpak IG (250×30 mm, 5 μm); mobile phase: 65% $CO_2$/35% Methanol, 80 g/min; Detector Wavelength: 230 nm. Example 356: Isolate 1: First eluting peak, rt=7.5 min, Example 357: Isolate 2: Second eluting peak, rt=8.8 min.

EXAMPLE 356: (1.7 mg, 4% yield); LCMS: m/z, 510.3 [M-41]+; rt 2.14 min; LCMS method: Column: XBridge BEH XP C18 (50×2.1 mm, 2.5 μm); mobile phase A: 10 mM $NH_4OAc$ in water:acetonitrile (95:5); mobile phase B: 10 mM $NH_4OAc$ in water:acetonitrile (5:95); Gradient=0-100% B over 3 minutes; Temperature: 50° C.; Flow rate: 1.1 mL/min; Detection: UV at 220 nm. $^1$H NMR (400 MHz, DMSO-$d_6$) δ (ppm)=8.26-8.20 (m, 1H), 8.18 (d, J=0.7 Hz, 1H), 8.03-7.93 (m, 3H), 6.54 (s, 1H), 3.97 (br d, J=5.9 Hz, 2H), 3.44 (s, 1H), 2.87-2.83 (m, 1H), 2.77-2.72 (m, 1H), 1.59-1.35 (m, 6H), 1.33-1.28 (m, 4H), 1.24 (m, 2H), 0.80-0.68 (m, 3H).

EXAMPLE 357: (2.0 mg, 4% yield); LCMS: m/z, 510.3 [M+H]+; rt 2.14 min; LCMS method: Column: XBridge BEH XP C18 (50×2.1 mm, 2.5 μm); mobile phase A: 10 mM $NH_4OAc$ in water:acetonitrile (95:5); mobile phase B: 10 mM $NH_4OAc$ in water:acetonitrile (5:95); Gradient=0-100% B over 3 minutes; Temperature: 50° C.; Flow rate: 1.1 mL/min; Detection: UV at 220 nm. $^1$H NMR (400MHz, DMSO-$d_6$) δ (ppm)=8.32-8.21 (m, 1H), 8.18 (d, J=0.7 Hz, 1H), 8.03-7.93 (m, 3H), 6.54 (s, 1H), 3.97 (br d, J=5.9 Hz, 2H), 3.44 (s, 1H), 2.87-2.83 (m, 1H), 2.77-2.72 (m, 1H), 1.59-1.35 (m, 6H), 1.33-1.28 (m, 4H), 1.24 (m, 2H), 01.00-0.98 (m, 3H).

Intermediate 43

1-(4-(Azidomethyl)phenyl)ethan-1-one

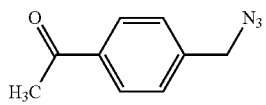

To a stirred solution of 1-(4-(bromomethyl)phenyl)ethan-1-one (2 g, 9.39 mmol) in DMF (20 mL) was added sodium azide (0.91 g, 14.08 mmol) at room temperature and the reaction mixture was heated at 80° C. for 12 h. The reaction mixture was cooled to room temperature, extracted with EtOAc (2×50 mL), washed with cold water (2×100 mL), brine, dried over sodium sulphate and concentrated under reduced pressure to give the crude product, which was purified by silica gel column chromatography using 20-30% EtOAc in n-hexane to afford 1-(4-(azidomethyl)phenyl)ethan-1-one (1.4 g, 51% yield). LCMS: m/z, 176.1 [M+H]$^+$; rt 1.35 min. (LCMS Method: Column: Acquity UPLC BEH C18 (3.0×50 mm, 1.7 μm); mobile phase A: 10 mM ammonium acetate:acetonitrile (95:5); mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm). $^1$H NMR (300 MHz, DMSO-d$_6$) δ (ppm)=7.99 (d, J=8.3 Hz, 2H), 7.52 (d, J=7.9 Hz, 2H), 4.57 (s, 2H), 2.59 (s, 3H).

Intermediate 44

1-(4-(Azidomethyl)phenyl)ethan-1-ol (racemate)

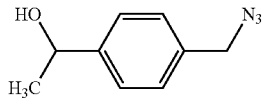

To a solution of 1-(4-(azidomethyl)phenyl)ethan-1-one (1.3 g, 7.42 mmol) in methanol (20 mL) was added NaBH$_4$ (0.56 g, 14.84 mmol) in two equal portions at 0° C. under nitrogen. The reaction mixture was allowed to warm to room temperature and stirred for 2 h. The reaction was quenched with the addition of saturated aqueous NH$_4$Cl solution, extracted with ethyl acetate (2×20 mL) and washed with water. The combined organic layer was dried over anhydrous Na$_2$SO$_4$, evaporated under reduced pressure to obtain 1-(4-(azidomethyl)phenyl)ethan-1-ol (1 g, 62% yield). $^1$H NMR (300 MHz, DMSO-d$_6$) δ (ppm)=7.34 (d, J=10.6 Hz, 4H), 5.27-5.12 (m, 1H), 4.77-4.64 (m, 1H), 4.41 (s, 2H), 1.31 (d, J=6.4 Hz, 3H).

Intermediate 45

1-(Azidomethyl)-4-(1-chloroethyl)benzene (racemate)

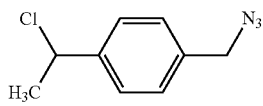

To a solution of 1-(4-(azidomethyl)phenyl)ethan-1-ol (0.6 g, 3.39 mmol) in dichloromethane (10.0 mL) was added SOCl$_2$ (1.25 mL, 16.93 mmol) at 0° C. The reaction mixture was stirred at room temperature for 2 h. The volatiles were removed from the reaction mixture under reduced pressure, co-distilled with acetonitrile (2×10 mL) and dried to obtain 1-(azidomethyl)-4-(1-chloroethyl)benzene (0.5 g, 75% yield). $^1$H NMR (300 MHz, DMSO-d$_6$) δ (ppm)=7.52 (d, J=8.3 Hz, 2H), 7.41-7.35 (m, 2H), 5.46-5.29 (m, 1H), 4.46 (s, 2H), 1.79 (d, J=6.8 Hz, 3H).

Intermediate 46

4-((2S,5R)-4-(1-(4-(Azidomethyl)phenyl)ethyl)-5-ethyl-2-methylpiperazin-1-yl)-1-methyl-2-oxo-1,2-dihydropyrido[3,2-d]pyrimidine-6-carbonitrile (diastereomeric mixture)

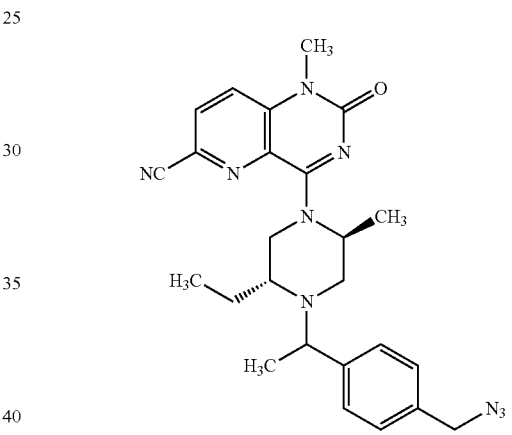

To a stirred solution of 4-((2S,5R)-5-ethyl-2-methylpiperazin-1-yl)-1-methyl-2-oxo-1,2-dihydropyrido[3,2-d]pyrimidine-6-carbonitrile (0.6 g, 1.921 mmol) in acetonitrile (10 mL), DIPEA (1 mL, 5.76 mmol), 1-(azidomethyl)-4-(1-chloroethyl)benzene (0.56 g, 2.88 mmol) and sodium iodide (0.29 g, 1.92 mmol) were added at room temperature. The reaction mixture was heated at 80° C. for 12 h. and then cooled to room temperature. The solvent was removed under reduced pressure to give the crude product, which was purified by silica gel column chromatography using 10-15% MeOH in DCM to afford 4-((2S,5R)-4-(1-(4-(azidomethyl) phenyl)ethyl)-5-ethyl-2-methylpiperazin-1-yl)-1-methyl-2-oxo-1,2-dihydropyrido[3,2-d]pyrimidine-6-carbonitrile (0.5 g, 0.944 mmol, 49.1% yield). LCMS: m/z, 472.2 [M+H]$^+$; rt: 3.21 and 3.35 min. (LCMS Method: Column: Kinetex XB-C18 (3×75 mm) 2.6 μm; mobile phase A: 10 mM ammonium formate in 0.1% formic acid, mobile phase B: acetonitrile, Gradient=20-100% B over 4 minutes, then a 0.6 minute hold at 100% B; Temperature: 27° C.; Flow rate: 1.0 mL/min; Detection: UV at 220 nm).

Example 358

4-((2S,5R)-4-(1-(4-(Aminomethyl)phenyl)ethyl)-5-ethyl-2-methylpiperazin-1-yl)-1-methyl-2-oxo-1,2-dihydropyrido[3,2-d]pyrimidine-6-carbonitrile (diastereomeric mixture)

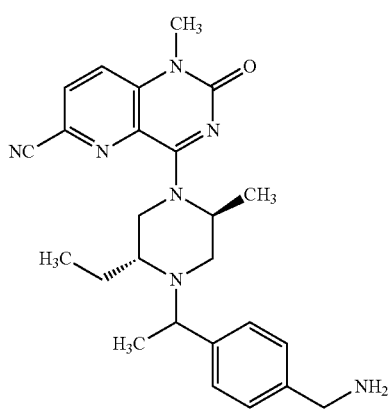

(358)

To a stirred solution of 4-((2S,5R)-4-(1-(4-(azidomethyl)phenyl)ethyl)-5-ethyl-2-methylpiperazin-1-yl)-1-methyl-2-oxo-1,2-dihydropyrido[3,2-d]pyrimidine-6-carbonitrile (500 mg, 1.060 mmol) in THF (6 mL) and water (3 mL) was added triphenylphosphine (556 mg, 2.121 mmol) at room temperature. The reaction mixture was heated at 70° C. for 12 h. and then cooled to room temperature. The solvent was removed under reduced pressure to give the crude product which was purified by silica gel column chromatography using 8-10% MeOH in DCM to afford 4-((2S,5R)-4-(1-(4-(aminomethyl) phenyl)ethyl)-5-ethyl-2-methylpiperazin-1-yl)-1-methyl-2-oxo-1,2-dihydropyrido[3,2-d]pyrimidine-6-carbonitrile (0.3 g, 50% yield). LCMS: m/z, 446.4 [M+H]+; rt: 1.22 and 1.31 min. (LCMS Method: Column: Acquity UPLC BEH C18 (3.0×50 mm, 1.7 µm); mobile phase A: 10 mM ammonium acetate:acetonitrile (95:5); mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 359 and 360

Methyl (4-(1-((2R,5S)-4-(6-cyano-1-methyl-2-oxo-1,2-dihydropyrido[3,2-d]pyrimidin-4-yl)-2-ethyl-5-methylpiperazin-1-yl)ethyl)benzyl)carbamate

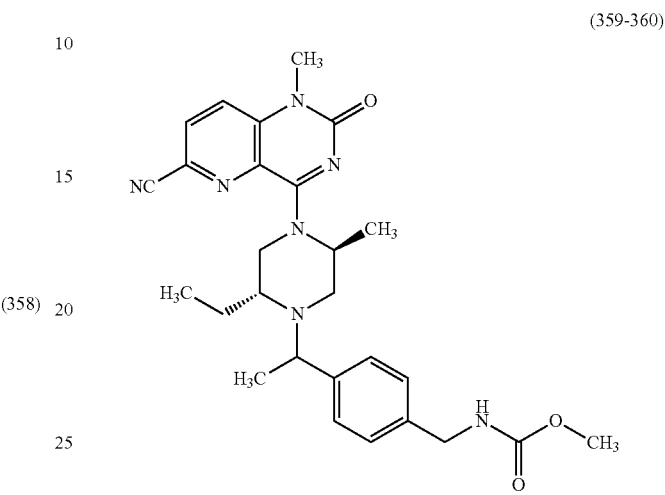

(359-360)

To a stirred solution of 4-((2S,5R)-4-(1-(4-(aminomethyl)phenyl)ethyl)-5-ethyl-2-methylpiperazin-1-yl)-1-methyl-2-oxo-1,2-dihydropyrido[3,2-d]pyrimidine-6-carbonitrile (60 mg, 0.14 mmol) in dichloromethane (5 mL) was cooled to 0° C. and added TEA (0.04 mL, 0.269 mmol) followed by methyl chloroformate (0.02 mL, 0.269 mmol) under nitrogen. The reaction mixture was allowed to warm to room temperature and stirred for 2 h. The volatiles were removed under reduced pressure to give the crude product, which was purified by prep-HPLC [Method: Column: Sunfire C18 (150×19 mm, 5 µm); mobile phase A=10 mM ammonium acetate in water pH ~4.5; mobile phase B=MeOH; Gradient: 50-80% B over 22 minutes, then a 5 minute hold at 100% B; Flow rate: 19 mL/min] fractions were concentrated under reduced pressure and lyophilized from (EtOH/H$_2$O, 1:5) to yield Examples 359 and 360.

EXAMPLE 359: (5 mg, 7% yield), LCMS: m/z, 504.2 (([M+H]+; rt 1.14 min. (LCMS Method: Column: Kinetex XB-C18 (3×75 mm) 2.6 µm; mobile phase A: 10 mM ammonium formate in water (pH 3.3), mobile phase B: acetonitrile, Gradient=20-100% B over 4 minutes, then a 0.6 minute hold at 100% B; Temperature: 27° C.; Flow rate: 1.0 mL/min; Detection: UV at 220 nm). $^1$H NMR (400 MHz, DMSO-d6) δ (ppm)=8.23 (d, J=8.5 Hz, 1H), 7.98 (d, J=9.0 Hz, 1H), 7.70-7.64 (m, 1H), 7.29 (s, 2H), 7.25-7.19 (m, 2H), 5.91-5.57 (m, 1H), 5.12-4.72 (m, 1H), 4.19 (d, J=6.0 Hz, 2H), 3.74-3.66 (m, 1H), 3.56 (s, 3H), 3.45-3.41 (m, 4H), 2.85-2.78 (m, 1H), 2.77-2.70 (m, 1H), 2.42-2.35 (m, 1H), 1.58-1.30 (m, 5H), 1.30-1.23 (m, 3H), 0.73-0.66 (m, 3H).

EXAMPLE 360: (5 mg, 7% yield), LCMS: m/z, 504.2 [M+H]+; rt 1.22 min. (LCMS Method: Column: Kinetex XB-C18 (3×75 mm, 2.6 µm); mobile phase A: 10 mM ammonium formate in water (pH 3.3), mobile phase B: acetonitrile, Gradient=20-100% B over 4 minutes, then a 0.6 minute hold at 100% B; Temperature: 27° C.; Flow rate: 1.0 mL/min; Detection: UV at 220 nm). $^1$H NMR (400 MHz, DMSO-d$_6$) δ (ppm)=8.31-8.17 (m, 1H), 8.04-7.92 (m, 1H), 7.64 (br s, 1H), 7.34 (br d, J=7.5 Hz, 2H), 7.20 (d, J=8.0 Hz, 2H), 6.13-5.35 (m, 1H), 5.16-4.75 (m, 1H), 4.17 (d, J=6.0

Hz, 2H), 3.74-3.53 (m, 5H), 3.46-3.39 (m, 4H), 3.14-3.03 (m, 1H), 2.27-2.17 (m, 1H), 1.59-1.42 (m, 2H), 1.41-1.32 (m, 1H), 1.29-1.18 (m, 5H), 0.99 (br t, J=7.3 Hz, 3H).

The examples in the Table 14 were prepared according to the general procedure described in Examples 110 and 111, using the appropriate piperazine. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 14

| Ex. No. | STRUCTURE | Stereo chemistry | LCMS Method | LCMS rt | [M + H]+ |
|---|---|---|---|---|---|
| 361 | | H | C | 1.86 | 463.3 |
| 362 | | H | C | 1.84 | 463.3 |
| 363 | | H | C | 2.01 | 477.3 |
| 364 | | H | C | 2.02 | 477.3 |
| 365 | | H | C | 2.02 | 477.3 |
| 366 | | H | C | 2.06 | 477.3 |

287

Intermediate 46

N-(2-((2R,5S)-4-(6-Cyano-1-methyl-2-oxo-1,2-dihydropyrido[3,2-d]pyrimidin-4-yl)-2-ethyl-5-methylpiperazin-1-yl)-3-methylbutanoyl)cyclopropanecarbohydrazide

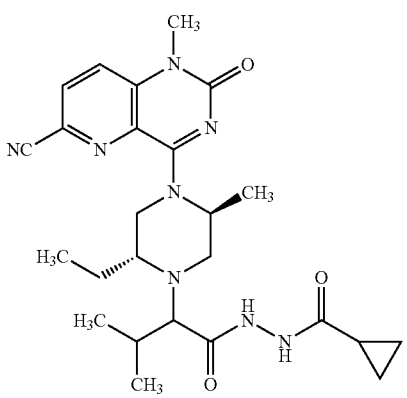 [SMILES: CC[C@@H]1CN(c2nc(=O)n(C)c3ccc(C#N)nc23)[C@@H](C)CN1C(C(=O)NNC(=O)C1CC1)C(C)C]

To a solution of 2-((2R,5S)-4-(6-cyano-1-methyl-2-oxo-1,2-dihydropyrido[3,2-d]pyrimidin-4-yl)-2-ethyl-5-methylpiperazin-1-yl)-3-methylbutanoic acid (500 mg, 1.21 mmol) in DMF (3 mL) were added HATU (922 mg, 2.42 mmol) and DIPEA (0.42 mL, 2.42 mmol). The reaction mixture was stirred for 10 minutes. Next, cyclopropanecarbohydrazide (182 mg, 1.82 mmol) was added and stirring was continued for 16 h. The reaction was quenched with cold water. The reaction mixture was diluted with EtOAc (100 mL), washed with water (20 mL), brine (20 mL), dried over $Na_2SO_4$ and concentrated under reduced pressure to obtain the crude compound, which was purified by silica gel chromatography (12 g) by using 0-10% MeOH/$CHCl_3$ as eluent. Pure fractions were collected and concentrated to obtain N'-(2-((2R,5S)-4-(6-cyano-1-methyl-2-oxo-1,2-dihydropyrido[3,2-d]pyrimidin-4-yl)-2-ethyl-5-methylpiperazin-1-yl)-3-methylbutanoyl)cyclopropanecarbohydrazide (350 mg, 58% yield). LCMS: m/z=495.3 [M+H]$^+$; retention time 1.05 and 1.11 min, LCMS Method; Column: AQUITY UPLC BEH C18 (3.0×50 mm, 1.7 μm); mobile phase A:10 mM $NH_4OAc$ in water:acetonitrile (95:5); mobile phase B: 10 mM $NH_4OAc$ in water:acetonitrile (5:95); gradient=20-100% B over 2 min, then a 1 minute hold at 100% B, flow: 0.7 mL/min.

288

Examples 367 and 368

4-((2S,5R)-4-(1-(5-Cyclopropyl-1,3,4-oxadiazol-2-yl)-2-methylpropyl)-5-ethyl-2-methylpiperazin-1-yl)-1-methyl-2-oxo-1,2-dihydropyrido[3,2-d]pyrimidine-6-carbonitrile (367-368)

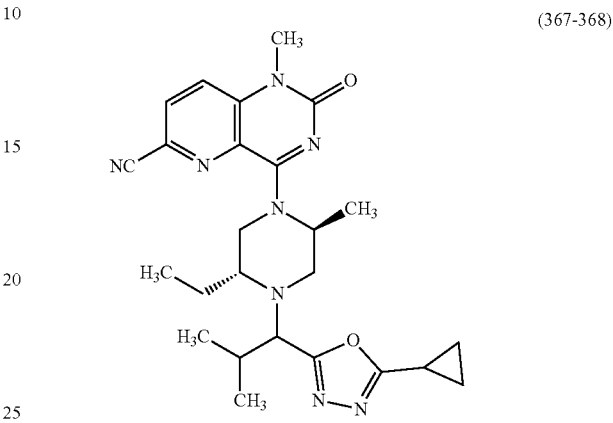

To a solution of N'-(2-((2R,5S)-4-(6-cyano-1-methyl-2-oxo-1,2-dihydropyrido[3,2-d]pyrimidin-4-yl)-2-ethyl-5-methylpiperazin-1-yl)-3-ethylbutanoyl) cyclopropanecarbohydrazide (50 mg, 0.1 mmol) in acetonitrile (3 mL) was added $POCl_3$ (0.02 mL, 0.20 mmol). The reaction mixture was heated at 80° C. for 16 h, cooled, concentrated under reduced pressure. The reaction was quenched with saturated $NaHCO_3$ solution. The reaction mixture was diluted with EtOAc (100 mL), washed with water (20 mL), brine (20 mL), dried over $Na_2SO_4$ and concentrated under reduced pressure to obtain the crude compound, which was purified by preparative HPLC. HPLC Method: Column:)(Bridge C18 (19×50 mm, 5 μm); mobile phase A: 10 mM ammonium acetate in water; mobile phase B: acetonitrile; gradient 15-50% B over 23 minutes, then 5 minutes hold at 100 B, flow 20 mL/min.

EXAMPLE 367: (First eluting isomer, 2 mg, 2% yield); LCMS: m/z, 477.3 [M+H]$^+$; rt 1.82 min; LCMS method: Column: XBridge BEH XP C18 (50×2.1 mm, 2.5 μm); mobile phase A: 10 mM $NH_4OAc$ in water:acetonitrile (95:5); mobile phase B: 10 mM $NH_4OAc$ in water:acetonitrile (5:95); Gradient=0-100% B over 3 minutes; Temperature: 50° C.; Flow rate: 1.1 mL/min; Detection: UV at 220 nm. $^1$H NMR (400 MHz, DMSO-$d_6$) δ (ppm)=8.25 (d, J=9.0 Hz, 1H), 7.99 (d, J=9.0 Hz, 1H), 6.12-5.79 (m, 1H), 5.01-4.76 (m, 1H), 3.56 (d, J=10.5 Hz, 2H), 3.44 (s, 3H), 3.00 (dd, J=12.5, 6.0 Hz, 1H), 2.37 (br d, J=10.5 Hz, 1H), 2.30-2.20 (m, 2H), 1.44-1.33 (m, 1H), 1.28-1.10 (m, 6H), 1.06-0.88 (m, 6H), 0.84-0.70 (m, 6H).

EXAMPLE 368: (Second eluting isomer, 1.8 mg, 2% yield); LCMS: m/z, 477.3 [M+H]$^+$; rt 2.02 min; LCMS method: Column: XBridge BEH XP C18 (50×2.1 mm, 2.5 μm); mobile phase A: 10 mM $NH_4OAc$ in water:acetonitrile (95:5); mobile phase B: 10 mM $NH_4OAc$ in water:acetonitrile (5:95); Gradient=0-100% B over 3 minutes; Temperature: 50° C.; Flow rate: 1.1 mL/min; Detection: UV at 220 nm. $^1$H NMR (400 MHz, DMSO-$d_6$) δ (ppm)=8.24 (br d, J=9.0 Hz, 1H), 8.05-7.90 (m, 1H), 5.94-5.56 (m, 1H), 5.05-4.86 (m, 1H), 3.76-3.56 (m, 2H), 3.46-3.41 (m, 3H), 2.99-2.86 (m, 1H), 2.74 (dd, J=12.3, 3.8 Hz, 1H), 2.22 (br dd, J=4.5, 3.0 Hz, 1H), 2.14-2.04 (m, 1H), 1.58-1.25 (m, 4H), 1.20-1.02 (m, 6H), 1.00-0.81 (m, 6H), 0.72 (br d, J=5.5 Hz, 3H).

Example 369

2-((2R,5S)-4-(6-chloro-1-methyl-2-oxo-1,2-dihydropyrido[3,2-d]pyrimidin-4-yl)-2,5-diethylpiperazin-1-yl)-2-(4-fluorophenyl)acetonitrile

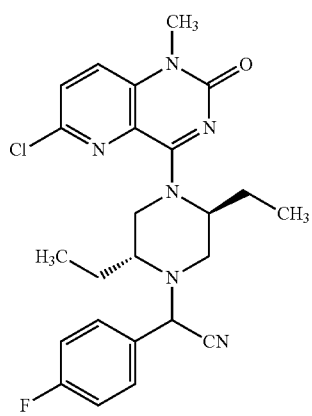

(369)

To a solution of 6-chloro-4-((2S,5R)-2,5-diethylpiperazin-1-yl)-1-methylpyrido[3,2-d]pyrimidin-2(1H)-one (0.85 g, 2.53 mmol) in acetonitrile (2 mL) were added DIPEA (1.33 mL, 7.59 mmol) and 2-bromo-2-(4-fluorophenyl)acetonitrile (1.27 g, 5.06 mmol) at room temperature. The mixture was heated at 85° C. for 16 h. and then was allowed to cool to room temperature. The reaction mixture was concentrated under reduced pressure to obtain the crude product, which was purified by silica gel chromatography (0-100% ethyl acetate in pet ether) to obtain 2-((2R,5S)-4-(6-chloro-1-methyl-2-oxo-1,2-dihydropyrido[3,2-d]pyrimidin-4-yl)-2,5-diethylpiperazin-1-yl)-2-(4-fluorophenyl) acetonitrile (550 mg, 29% yield). LCMS: m/z=469.4 [M+H]$^+$; retention time 0.92 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 0.2 minute hold at 100% B, flow: 0.7 mL/min.

Intermediate 47

(Z)-2-((2R,5S)-4-(6-Chloro-1-methyl-2-oxo-1,2-dihydropyrido[3,2-d]pyrimidin-4-yl)-2,5-diethylpiperazin-1-yl)-2-(4-fluorophenyl)-N'-hydroxyacetimidamide

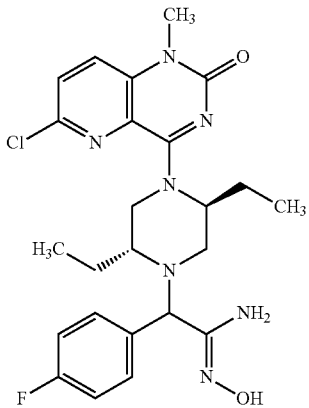 [SMILES: CC[C@H]1CN(C(/C(N)=N/O)c2ccc(F)cc2)[C@H](CC)CN1c1nc(=O)n(C)c2ccc(Cl)nc12]

To a solution of 2-((2R,5S)-4-(6-chloro-1-methyl-2-oxo-1,2-dihydropyrido[3,2-d]pyrimidin-4-yl)-2,5-diethylpiperazin-1-yl)-2-(4-fluorophenyl)acetonitrile (0.320 g, 0.68 mmol) in ethanol (5 mL), hydroxylamine solution (0.046 mL, 0.751 mmol) was added at room temperature and was stirred for 16 h. The reaction mixture was concentrated under reduced pressure, suspended in water (10 mL) and extracted with EtOAc (2×10 mL). The combined organic layer was dried over Na$_2$SO$_4$ and concentrated to obtain the crude product, which was purified by silica gel chromatography (0-10% MeOH in DCM) to afford 2-((2R,5S)-4-(6-chloro-1-methyl-2-oxo-1,2-dihydropyrido[3,2-d]pyrimidin-4-yl)-2,5-diethylpiperazin-1-yl)-2-(4-fluorophenyl)-N-hydroxyacetimidamide (200 mg, 43% yield). LCMS: m/z=502.2 [M+H]$^+$; retention time 1.41 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min.

291

Intermediate 48

(Z)-2-((2R,5S)-4-(6-Chloro-1-methyl-2-oxo-1,2-dihydropyrido[3,2-d]pyrimidin-4-yl)-2,5-diethylpiperazin-1-yl)-N-((cyclopropanecarbonyl)oxy)-2-(4-fluorophenyl)acetimidamide

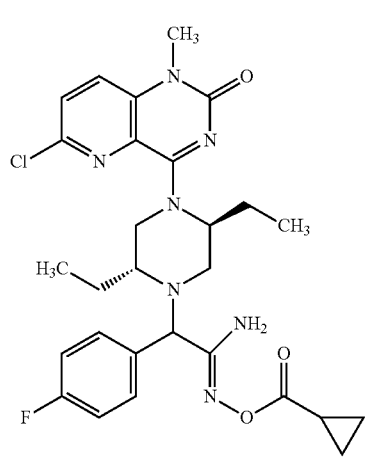 [SMILES: CC[C@H]1CN(C(/C(N)=N/OC(=O)C2CC2)c2ccc(F)cc2)[C@H](CC)CN1c1nc(=O)n(C)c2ccc(Cl)nc12]

To a stirred solution of 2-((2R,5S)-4-(6-chloro-1-methyl-2-oxo-1,2-dihydropyrido[3,2-d]pyrimidin-4-yl)-2,5-diethylpiperazin-1-yl)-2-(4-fluorophenyl)-N-hydroxyacetimidamide (0.200 g, 0.32 mmol) in DMF (2 mL), triethylamine (0.14 mL, 0.97 mmol), BOP (0.36 g, 0.81 mmol) and cyclopropanecarboxylic acid (0.034 g, 0.39 mmol) were added at room temperature. After stirring for 2 h, the reaction mixture was washed with saturated ammonium chloride (5 mL) and extracted with ethyl acetate (3×10 mL). The combined organic layer was dried over anhydrous sodium sulphate and then concentrated under reduced pressure to obtain the crude compound N—((E)-2-((2R,5S)-4-(6-chloro-1-methyl-2-oxo-1,2-dihydropyrido[3,2-d]pyrimidin-4-yl)-2,5-diethylpiperazin-1-yl)-2-(4-fluorophenyl)-1-(hydroxyimino)ethyl)cyclopropanecarboxamide (180 mg, 69% yield). LCMS: m/z=570.2 [M+H]$^+$; retention time 1.59 and 1.61 min, LCMS Method; Column: AQUITY UPLC BEH C18 (3.0×50 mm, 1.7 µm); mobile phase A:10 mM NH$_4$OAc in water:acetonitrile (95:5); mobile phase B: 10 mM NH$_4$OAc in water:acetonitrile (5:95); gradient=20-100% B over 2 min, then a 0.2 minute hold at 100% B, flow: 0.7 mL/min.

292

Example 370

6-Chloro-4-((2S,5R)-4-((5-cyclopropyl-1,2,4-oxadiazol-3-yl)(4-fluorophenyl)methyl)-2,5-diethylpiperazin-1-yl)-1-methylpyrido[3,2-d]pyrimidin-2(1H)-one (370)

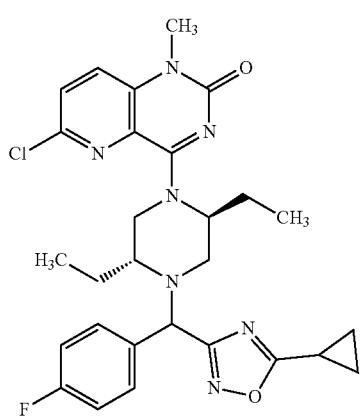

To a stirred solution of N—((E)-2-((2R,5S)-4-(6-chloro-1-methyl-2-oxo-1,2-dihydropyrido[3,2-d]pyrimidin-4-yl)-2,5-diethylpiperazin-1-yl)-2-(4-fluorophenyl)-1-(hydroxyimino)ethyl)cyclopropanecarboxamide, TFA (0.180 g, 0.263 mmol) in THF (3 mL), TBAF (1.316 mL, 1.316 mmol) was added at room temperature. The reaction mixture was heated at 65° C. for 16 h. The reaction mixture was allowed to reach room temperature, washed with water (10 mL) and extracted with ethyl acetate (2×10 mL). The organic layer was washed with brine solution, dried over anhydrous sodium sulphate and then concentrated under reduced pressure to give the crude product, which was purified by silica gel chromatography (10% MeOH in DCM as eluent) to obtain 6-chloro-4-((2S,5R)-4-((5-cyclopropyl-1,2,4-oxadiazol-3-yl)(4-fluorophenyl)methyl)-2,5-diethylpiperazin-1-yl)-1-methylpyrido[3,2-d]pyrimidin-2(1H)-one (130 mg, 58% yield) LCMS: m/z=552.2 [M+H]$^+$; retention time 2.04 and 2.06 min, LCMS Method; Column: AQUITY UPLC BEH C18 (3.0×50 mm, 1.7 µm); mobile phase A:10 mM NH$_4$OAc in water:acetonitrile (95:5); mobile phase B: 10 mM NH$_4$OAc in water:acetonitrile (5:95); gradient=20-100% B over 2 min, then a 0.2 minute hold at 100% B, flow: 0.7 mL/min.

Examples 371 and 372

4-((2S,5R)-4-((5-Cyclopropyl-1,2,4-oxadiazol-3-yl)(4-fluorophenyl)methyl)-2,5-diethylpiperazin-1-yl)-1-methyl-2-oxo-1,2-dihydropyrido[3,2-d]pyrimidine-6-carbonitrile

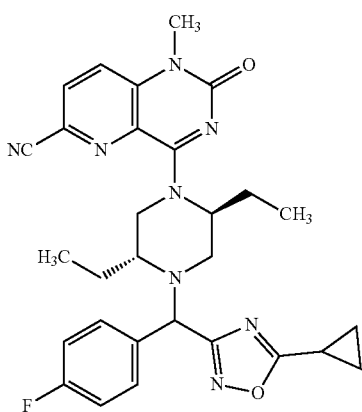

(371-372)

To a solution of 6-chloro-4-((2S,5R)-4-((5-cyclopropyl-1,2,4-oxadiazol-3-yl)(4-fluorophenyl)methyl)-2,5-diethylpiperazin-1-yl)-1-methylpyrido[3,2-d]pyrimidin-2(1H)-one (0.06 g, 0.11 mmol) in THF (3 mL) and water (3 mL) were added zinc cyanide (0.03 g, 0.22 mmol), t-BuXPhos (4.62 mg, 10.87 mmol). The reaction mixture was flushed with nitrogen followed by the addition of t-BuXPhos-Pd-G1 (0.043 mg, 1.087 μmol) and again flushed with nitrogen for 1 min. The reaction mixture was heated at 40° C. for 16 h. The reaction mixture was treated with saturated aqueous NaHCO$_3$ (2 mL) and EtOAc (3 mL). The biphasic mixture was stirred for 5 min. The aqueous layer was further extracted with EtOAc (3×3 mL). The combined organic layer was dried over MgSO$_4$, filtered, and concentrated in vacuo to obtain the crude product, which was purified by preparative HPLC. HPLC Method: Column: Cellulose-2 (250×21 mm, 5 μm); mobile phase 0.1% DEA in acetonitrile; Flow: 19 mL/min). Example 371: Isolate 1: First eluting peak, rt=9.54 min. Example 372: Isolate 2: Second eluting peak, rt=12.04 min.

EXAMPLE 371: (2.3 mg, 4% yield); LCMS: m/z, 543.3 [M+H]$^+$; rt 2.13 min; LCMS method: Column: XBridge BEH XP C18 (50×2.1 mm, 2.5 μm); mobile phase A: 10 mM NH$_4$OAc in water:acetonitrile (95:5); mobile phase B: 10 mM NH$_4$OAc in water:acetonitrile (5:95); Gradient=0-100% B over 3 minutes; Temperature: 50° C.; Flow rate: 1.1 mL/min; Detection: UV at 220 nm. $^1$H NMR (400MHz, DMSO-d$_6$) δ (ppm)=8.29-8.16 (m, 1H), 8.04-7.92 (m, 1H), 7.70-7.56 (m, 2H), 7.20 (t, J=8.9 Hz, 2H), 5.99-5.25 (m, 1H), 5.02-4.80 (m, 2H), 3.64-3.53 (m, 1H), 3.43 (s, 3H), 2.65-2.60 (m, 1H), 2.41-2.35 (m, 1H), 2.12-1.40 (m, 3H), 1.23 (br s, 3H), 1.12-1.05 (m, 2H), 0.81-0.64 (m, 6H), (2H are buried under solvent peak).

EXAMPLE 372: (2.2 mg, 4% yield); LCMS: m/z, 543.3 [M+H]$^+$; rt 2.15 min; LCMS method: Column: XBridge BEH XP C18 (50×2.1 mm, 2.5 μm); mobile phase A: 10 mM NH$_4$OAc in water:acetonitrile (95:5); mobile phase B: 10 mM NH$_4$OAc in water:acetonitrile (5:95); Gradient=0-100% B over 3 minutes; Temperature: 50° C.; Flow rate: 1.1 mL/min; Detection: UV at 220 nm. $^1$H NMR (400MHz, DMSO-d$_6$) δ (ppm)=8.23 (d, J=9.0 Hz, 1H), 8.05-7.91 (m, 1H), 7.66 (br dd, J=5.8, 8.3 Hz, 2H), 7.22 (t, J=9.0 Hz, 2H), 5.92-5.31 (m, 1H), 5.01 (s, 1H), 4.97-4.81 (m, 1H), 3.43 (s, 3H), 3.20 3.16 (m, 1H), 2.80-2.71 (m, 1H), 2.46-2.31 (m, 2H), 2.08-1.70 (m, 1H), 1.57-1.35 (m, 2H), 1.31-1.18 (m, 2H), 1.17-0.98 (m, 3H), 0.92-0.76 (m, 4H), 0.74-0.55 (m, 3H).

The examples in the Table 15 were prepared from general procedure described in Examples 371 and 372, using appropriate benzhydryl/α-substituted benzyl/benzyl halide. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 15

| Ex. No. | STRUCTURE | Stereochem. | LCMS Method | LCMS rt | [M + H]$^+$ | Synthetic Route (A or B) |
|---|---|---|---|---|---|---|
| 373 | (structure shown) | H | D | 1.53 | 533.25 | D |

TABLE 15-continued

| Ex. No. | STRUCTURE | Stereo chem. | LCMS Method | LCMS rt | [M + H]+ | Synthetic Route (A or B) |
|---|---|---|---|---|---|---|
| 374 | | H | F | 1.89 | 508.33 | B |
| 375 | | H | F | 1.87 | 508.08 | B |
| 376 | | H | E | 2.83 | 486.2 | D |
| 377 | | H | E | 3.02 | 486.2 | D |
| 378 | | H | C | 2.38 | 457.3 | B |
| 379 | | H | C | 2.4 | 457.3 | B |

TABLE 15-continued

| Ex. No. | STRUCTURE | Stereo chem. | LCMS Method | LCMS rt | [M + H]+ | Synthetic Route (A or B) |
|---|---|---|---|---|---|---|
| 380 | 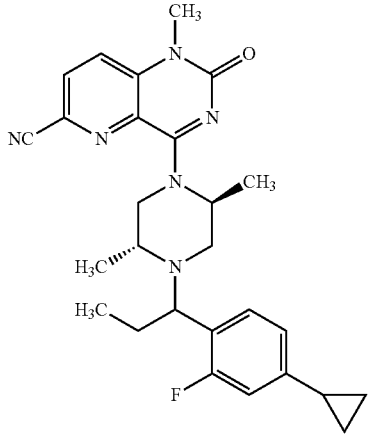 [SMILES: CCC(c1ccc(C2CC2)cc1F)N1C[C@H](C)N(c2nc(=O)n(C)c3ccc(C#N)nc23)C[C@H]1C] | H | C | 2.39 | 475.3 | B |
| 381 | | H | C | 2.4 | 475.3 | B |

Intermediate 49 tert-Butyl (2S,5R)-4-(1-(4-(methoxycarbonyl)phenyl)ethyl)-2,5-dimethylpiperazine-1-carboxylate

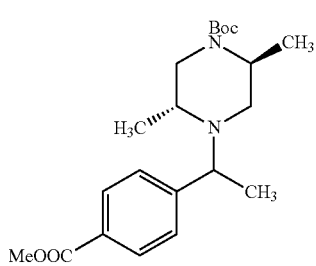 [SMILES: COC(=O)c1ccc(C(C)N2C[C@H](C)N(C(=O)OC(C)(C)C)C[C@H]2C)cc1]

To a stirred solution of tert-butyl (2S,5R)-2,5-dimethylpiperazine-1-carboxylate (2.5 g, 11.67 mmol) in acetonitrile (30 mL), DIPEA (6.1 mL, 35.0 mmol), potassium iodide (1.94 g, 11.67 mmol) and methyl 4-(1-chloroethyl)benzoate (2.32 g, 11.67 mmol) were added sequentially at room temperature. The reaction mixture was heated at 80° C. for 24 h, then it was cooled to room temperature and the solvent was removed under reduced pressure to give the crude product, which was purified by silica gel column chromatography using 20-30% EtOAc in n-hexane to afford tert-butyl (2S,5R)-4-(1-(4-(methoxycarbonyl)phenyl)ethyl)-2,5-dimethylpiperazine-1-carboxylate (3.5 g, 62% yield). LCMS: m/z, 377.3 [M+H]+; rt 1.39 min rt (LCMS Method: Column: Acquity UPLC BEH C18 (3.0×50 mm, 1.7 µm); mobile phase A: 10 mM ammonium acetate:acetonitrile (95:5); mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 50 tert-Butyl (2S,5R)-4-(1-(4-(hydroxymethyl)phenyl)ethyl)-2,5-dimethylpiperazine-1-carboxylate

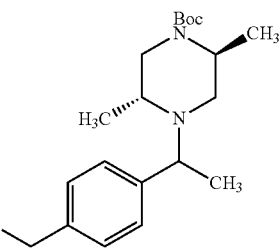

To a stirred solution of tert-butyl (2S,5R)-4-(1-(4-(methoxycarbonyl)phenyl) ethyl)-2,5-dimethylpiperazine-1-carboxylate (1.8 g, 4.78 mmol) in THF (20 mL) was cooled to 0° C. and lithium borohydride (2 M in THF) (24 mL, 47.8 mmol) was added drop wise under nitrogen. The reaction mixture was allowed to warm room temperature and stirred for 2 h. The reaction mixture was cooled to 0° C. The reaction was quenched with the addition of saturated aqueous NH4Cl solution. The reaction mixture was extracted with EtOAc (3×50 mL). The combined organic extract was washed with water, brine, dried over sodium sulphate and the solvent was removed under reduced pressure to afford tert-butyl (2S,5R)-4-(1-(4-(hydroxymethyl)phenyl)ethyl)-2,5-dimethylpiperazine-1-carboxylate (1.3 g, 76% yield). LCMS: m/z, 349.3 [M+H]+; rt 3.05 min. (LCMS Method: Column-Kinetex XB-C18 (75×3 mm-2.6 µm); Mobile phase A: 10 mM ammonium formate in water:acetonitrile (98:2); Mobile phase B: 10 mM ammonium formate in water:acetonitrile (2:98); Flow: 1 mL/min; Gradient: 20-100% B over 4 minutes then 0.6 min hold at 100% B, Detection: UV at 220 nm).

Intermediate 51

(4-(1-((2R,5S)-2,5-Dimethylpiperazin-1-yl)ethyl)phenyl)methanol, HCl salt (Diastereomeric Mixture)

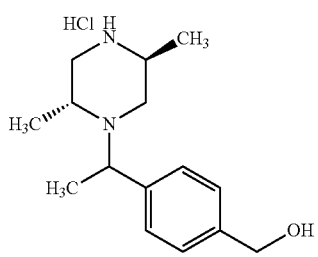 [SMILES: Cl ; CC(c1ccc(CO)cc1)N1C[C@H](C)NC[C@H]1C]

To a stirred solution of tert-butyl (2S,5R)-4-(1-(4-(hydroxymethyl)phenyl)ethyl)-2,5-dimethylpiperazine-1-carboxylate (0.8 g, 2.30 mmol) in DCM (15 mL), HCl (4 N in dioxane) (2.9 mL, 11.5 mmol) was added drop wise at room temperature. The reaction mixture was stirred for 3 h, solvent was removed under reduced pressure, the solids were co-distilled with acetonitrile (3×10 mL), and dried to afford (4-(1-((2R,5S)-2,5-dimethylpiperazin-1-yl)ethyl)phenyl)methanol HCl salt (0.4 g, 45% yield) as an off-white solid. LCMS: m/z, 249.2 [M+H]$^+$; rt 0.51 and 0.55 min. (LCMS Method: Column: Acquity UPLC BEH C18 (3.0×50 mm, 1.7 μm); mobile phase A: 10 mM ammonium acetate:acetonitrile (95:5); mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Example 382

6-Chloro-4-((2S,5R)-4-(1-(4-(hydroxymethyl)phenyl)ethyl)-2,5-dimethylpiperazin-1-yl)-1-methylpyrido[3,2-d]pyrimidin-2(1H)-one (Diastereomeric Mixture)

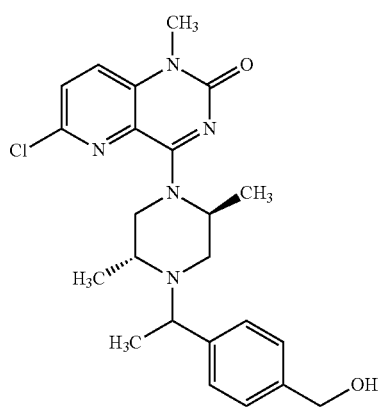

(382)

To a stirred solution of (4-(1-((2R,5S)-2,5-dimethylpiperazin-1-yl)ethyl)phenyl) methanol HCl salt (600 mg, 2.416 mmol) in acetonitrile (10 mL), DIPEA (2.1 mL, 12.1 mmol) and 4,6-dichloro-1-methylpyrido[3,2-d]pyrimidin-2(1H)-one (560 mg, 2.42 mmol) were added sequentially at room temperature. The reaction mixture was heated at 80° C. for 12 h. The reaction mixture was cooled to room temperature and the solvent was removed under reduced pressure to give the crude product, which was purified by silica gel column chromatography using 0-10% MeOH in CHCl$_3$ to afford 6-chloro-4-((2S,5R)-4-(1-(4-(hydroxymethyl)phenyl)ethyl)-2,5-dimethylpiperazin-1-yl)-1-methylpyrido[3,2-d]pyrimidin-2(1H)-one (0.6 g, 51% yield). LCMS: m/z, 442.3 [M+H]$^+$; rt 1.48 min. (LCMS Method: Column: Acquity UPLC BEH C18 (3.0×50 mm, 1.7 μm); mobile phase A: 10 mM ammonium acetate:acetonitrile (95:5); mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Example 383

4-((2S,5R)-4-(1-(4-(Hydroxymethyl)phenyl)ethyl)-2,5-dimethylpiperazin-1-yl)-1-methyl-2-oxo-1,2-dihydropyrido[3,2-d]pyrimidine-6-carbonitrile (Diastereomeric Mixture)

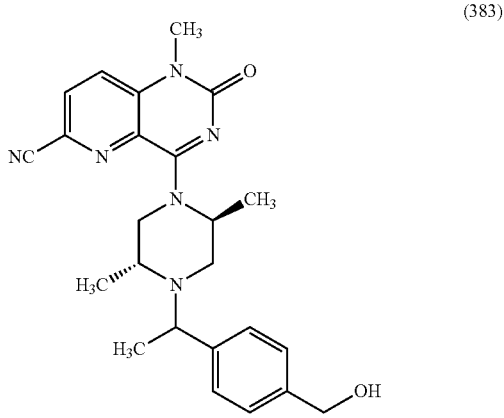 [SMILES: CC(c1ccc(CO)cc1)N1C[C@H](C)N(c2nc(=O)n(C)c3ccc(C#N)nc23)C[C@H]1C]

(383)

To a stirred solution of 6-chloro-4-((2S,5R)-4-(1-(4-(hydroxymethyl)phenyl) ethyl)-2,5-dimethylpiperazin-1-yl)-1-methylpyrido[3,2-d]pyrimidin-2(1H)-one (400 mg, 0.905 mmol) in DMF (10.0 mL) were added zinc (89 mg, 1.36 mmol) and TEA (0.5 mL, 3.62 mmol). The reaction mixture was flushed with argon for 5 min followed by the addition of zinc cyanide (320 mg, 2.72 mmol) and dichloro[9,9-dimethyl-4,5-bis(diphenylphosphino)xanthene]palladium (II) (68.4 mg, 0.091 mmol). The reaction mixture heated at 90° C. for 16 h, then cooled to room temperature, filtered through Celite® pad, washed with excess EtOAc (40 mL) and the filtrate was concentrated under reduced pressure to give the crude product, which was purified by silica gel column chromatography using 0-10% MeOH in CHCl$_3$ to afford 4-((2S,5R)-4-(1-(4-(hydroxymethyl)phenyl)ethyl)-2,5-dimethylpiperazin-1-yl)-1-methyl-2-oxo-1,2-dihydropyrido[3,2-d]pyrimidine-6-carbonitrile (260 mg, 57% yield). LCMS: m/z, 433.2 [M+H]$^+$; rt 1.22 and 1.23 min. (LCMS Method: Column: Acquity UPLC BEH C18 (3.0×50 mm, 1.7 μm); mobile phase A: 10 mM ammonium acetate:acetonitrile (95:5); mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Example 384

4-((2S,5R)-4-(1-(4-(Bromomethyl)phenyl)ethyl)-2,5-dimethylpiperazin-1-yl)-1-methyl-2-oxo-1,2-dihydropyrido[3,2-d]pyrimidine-6-carbonitrile (Diastereomeric Mixture)

Examples 385 and 386

4-((2S,5R)-4-(1-(4-((2,2-Dimethylmorpholino)methyl)phenyl)ethyl)-2,5-dimethylpiperazin-1-yl)-1-methyl-2-oxo-1,2-dihydropyrido[3,2-d]pyrimidine-6-carbonitrile (385-386)

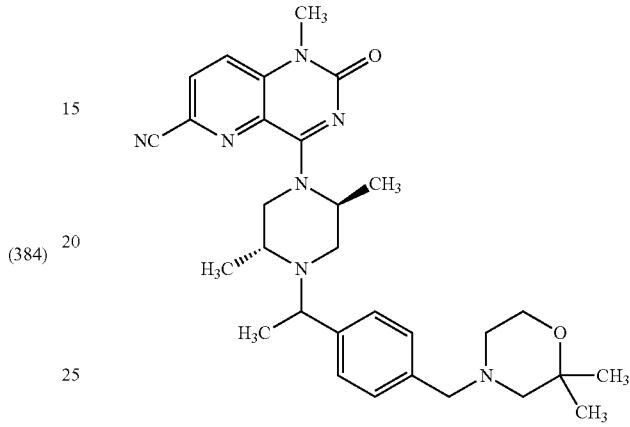

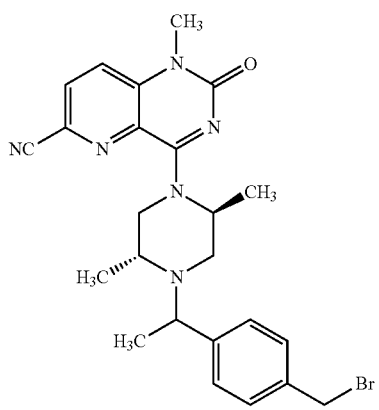

(384)

To a stirred solution of 4-((2S,5R)-4-(1-(4-(hydroxymethyl)phenyl)ethyl)-2,5-dimethylpiperazin-1-yl)-1-methyl-2-oxo-1,2-dihydropyrido[3,2-d]pyrimidine-6-carbonitrile (300 mg, 0.69 mmol) in DCM (10 mL) was cooled 0° C., added triphenylphosphine polymer bound (1.3 mmol/g) (1.5 g, 5.55 mmol) followed by CBR$_4$ (460 mg, 1.40 mmol) in DCM (5 mL). The reaction mixture was allowed to warm to room temperature and stirred for 2 h. The solvent was removed under reduced pressure to give the crude product, which was purified by silica gel column chromatography using 80-100% EtOAc in n-hexane to afford 4-((2S,5R)-4-(1-(4-(bromomethyl)phenyl) ethyl)-2,5-dimethylpiperazin-1-yl)-1-methyl-2-oxo-1,2-dihydropyrido[3,2-d]pyrimidine-6-carbonitrile (360 mg, 49% yield). LCMS: m/z, 495.2 [M+H]$^+$; rt 1.89 min. LCMS Method: Column: Acquity UPLC BEH C18 (3.0×50 mm, 1.7 μm); mobile phase A: 10 mM ammonium acetate:acetonitrile (95:5); mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm.

To a stirred solution of 4-((2S,5R)-4-(1-(4-(bromomethyl)phenyl)ethyl)-2,5-dimethylpiperazin-1-yl)-1-methyl-2-oxo-1,2-dihydropyrido[3,2-d]pyrimidine-6-carbonitrile (80 mg, 0.16 mmol) in acetonitrile (2 mL), potassium carbonate (89 mg, 0.65 mmol) and 2,2-dimethylmorpholine (37.2 mg, 0.32 mmol) were added sequentially at room temperature and heated at 60° C. for 1 h. The reaction mixture cooled to room temperature, filtered through a Celite® pad, washed with excess acetonitrile (10 mL) and the filtrate was concentrated under reduced pressure to give the crude product, which was purified using preparative HPLC (Chiral Separation Method: Column: Cellulose-5 (250×21.2 mm, 5 μm); mobile phase: 0.3% DEA in MeOH; Flow: 20 mL/min; UV detection: 215 nm).

EXAMPLE 385: (2 mg, 2% yield). LCMS: m/z=530.4 [M+H]$^+$; rt 2.19 min; LCMS method: Column: XBridge BEH XP C18 (50×2.1 mm, 2.5 μm); mobile phase A: 10 mM NH$_4$OAc in water:acetonitrile (95:5); mobile phase B: 10 mM NH$_4$OAc in water:acetonitrile (5:95); Gradient=0-100% B over 3 minutes; Temperature: 50° C.; Flow rate: 1.1 mL/min; Detection: UV at 220 nm. $^1$H NMR (400 MHz, DMSO-d$_6$) δ (ppm)=8.22 (br d, J=9.0 Hz, 1H), 7.98 (d, J=9.0 Hz, 1H), 7.36-7.26 (m, 4H), 5.81-5.32 (m, 1H), 5.19-4.53 (m, 1H), 3.63-3.57 (m, 3H), 3.45-3.40 (m, 5H), 2.88-2.75 (m, 3H), 2.28 (br s, 2H), 2.16 (s, 2H), 1.57-1.36 (m, 3H), 1.24 (br d, J=6.4 Hz, 3H), 1.16 (s, 6H), 0.93-0.86 (m, 3H), (1H might be obscured with solvent peak).

EXAMPLE 386: (2.0 mg, 2% yield). LCMS: m/z=530.4 [M+H]$^+$; rt 2.15 min; LCMS method: Column: XBridge BEH XP C18 (50×2.1 mm, 2.5 μm); mobile phase A: 10 mM NH$_4$OAc in water:acetonitrile (95:5); mobile phase B: 10 mM NH$_4$OAc in water:acetonitrile (5:95); Gradient=0-100% B over 3 minutes; Temperature: 50° C.; Flow rate: 1.1 mL/min; Detection: UV at 220 nm. $^1$H NMR (400 MHz, DMSO-d$_6$) δ (ppm)=8.23 (br d, J=8.8 Hz, 1H), 7.98 (d, J=9.0 Hz, 1H), 7.36-7.22 (m, 4H), 5.78-5.46 (m, 1H), 4.97-4.72 (m, 1H), 3.75-3.53 (m, 4H), 3.48-3.39 (m, 6H), 2.61-2.55 (m, 1H), 2.28 (br d, J=3.4 Hz, 2H), 2.21-2.12 (m, 3H), 1.35-1.19 (m, 6H), 1.15 (s, 6H), 1.10-0.99 (m, 3H).

The examples in the Table 16 were prepared from general procedure described in Examples 385 and 386, using appropriate amine and 4-((2S,5R)-4-(1-(4-(bromomethyl) phenyl) ethyl)-2,5-dimethylpiperazin-1-yl)-1-methyl-2-oxo-1,2-dihydropyrido[3,2-d]pyrimidine-6-carbonitrile (Diastereomeric Mixture). Diastereomers was separated at the final stage using either preparative chromatography or preparative chiral chromatography. The absolute stereochemistry was not assigned at the newly formed carbon-nitrogen bond.

TABLE 16

| Ex. No. | Structure | Stereo chemistry | LCMS Method | LCMS rt | [M + H]+ |
|---|---|---|---|---|---|
| 387 | | H | C | 1.53 | 514.3 |
| 388 | | H | C | 1.55 | 514.3 |
| 389 | | H | C | 2.04 | 530.4 |
| 390 | | H | C | 2.18 | 536.3 |
| 391 | | H | C | 2.2 | 536.3 |

TABLE 16-continued

| Ex. No. | Structure | Stereo chemistry | LCMS Method | LCMS rt | [M + H]+ |
|---|---|---|---|---|---|
| 392 | 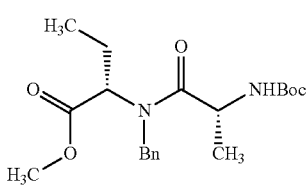 | H | C | 1.43 | 514.3 |
| 393 | | H | C | 1.43 | 514.4 |

Intermediate 52

Methyl (S)-2-((R)—N-benzyl-2-((tert-butoxycarbonyl)amino)propanamido)butanoate

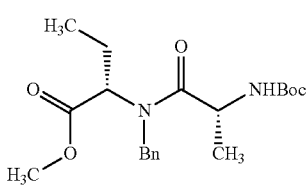

To a solution of methyl (S)-2-(benzylamino) butanoate (3.0 g, 14.47 mmol) and (tert-butoxycarbonyl)-D-alanine (4.11 g, 21.71 mmol) in DMF (30 mL) were added DIPEA (7.58 mL, 43.4 mmol) and HATU (11.01 g, 28.9 mmol) at room temperature. The reaction mixture was stirred at room temperature for 16 h. The reaction was quenched with the addition of water. The reaction mixture was extracted with ethyl acetate (2×100 mL), the combined organic layer was washed 0.5 N aqueous HCl, water, brine and dried over sodium sulfate. Evaporation of the solvent yielded methyl (S)-2-((R)—N-benzyl-2-((tert-butoxycarbonyl)amino)propanamido)butanoate (4.0 g, 10.57 mmol, 73.0% yield). LCMS: m/z=379.2 [M+H]+; retention time 2.95 min. (Column: Kinetex XB-C18 (75×3 mm, 2.6 µm); mobile phase A: 10 mM NH4OAc in water:acetonitrile (98:2) mobile phase B: 10 mM NH4OAc in water:acetonitrile (2:98). Gradient=20-100% B over 4 minutes, then a 0.6 minute hold at 100% B; Flow rate: 1.5 mL/min; Detection: UV at 220 nm.

Intermediate 53

Methyl (S)-2-((R)-2-amino-n-benzylpropanamido)butanoate, TFA

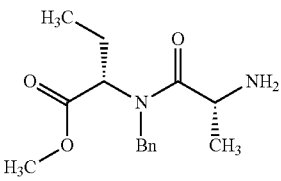

To a solution of methyl (S)-2-((R)—N-benzyl-2-((tert-butoxycarbonyl)amino) propanamido)butanoate (4.0 g, 10.57 mmol) in DCM (30 mL) was added TFA (10 mL, 130 mmol) at 0° C. The reaction mixture was stirred at room temperature for 4 h. The reaction mixture was concentrated under reduced pressure to afford methyl (S)-2-((R)-2-amino-N-benzylpropanamido)butanoate, TFA (4.15 g, 10.58 mmol, 100% yield). LCMS: m/z=279.3 [M+H]+; retention time 0.75 min, LCMS Method: Column-Luna 3.0 C18 (2) 100 Å LC column (20×4.0 mm); mobile phase A: 0.1% TFA in water, mobile phase B: 0.1% TFA in acetonitrile. Gradient=20-100% B over 2.5 minutes, then a 0.8 minute hold at 100% B; Flow rate: 1.5 mL/min; Detection: UV at 220 nm.

Intermediate 54

(3R,6S)-1-Benzyl-6-ethyl-3-methylpiperazine-2,5-dione

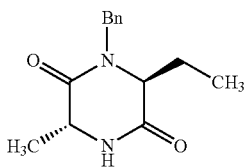 [SMILES: CC[C@H]1C(=O)N[C@H](C)C(=O)N1Cc1ccccc1]

A solution of methyl (S)-2-((R)-2-amino-N-benzylpropanamido)butanoate, TFA (4.0 g, 10.19 mmol) in methanol (5 mL) was refluxed at 65° C. for 24 h. The reaction mixture was concentrated under reduced pressure and dried under high vacuum to afford (3R,6S)-1-benzyl-6-ethyl-3-methylpiperazine-2,5-dione (2.2 g, 8.93 mmol, 88% yield). LCMS: m/z=247.2 [M+H]$^+$; retention time 1.41 min. Column: Kinetex XB-C18 (3×75 mm, 2.6 μm); mobile phase A: 10 mM ammonium acetate: acetonitrile (98:2), mobile phase B: 10 mM ammonium acetate: acetonitrile (2:98), Gradient=20-100% B over 4 minutes, then a 0.6 minute hold at 100% B; Flow rate: 1.0 mL/min; Detection: UV at 220 nm.

Intermediate 55

(2S,5R)-1-Benzyl-2-ethyl-5-methylpiperazine

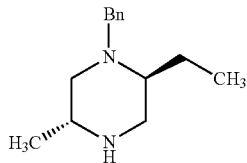 [SMILES: CC[C@H]1CN[C@H](C)CN1Cc1ccccc1]

To a solution of (3R,6S)-1-benzyl-6-ethyl-3-methylpiperazine-2,5-dione (2.2 g, 8.93 mmol) in THF (30 mL) at 0° C. was added 1 M solution of borane tetrahydrofuran complex (26.8 mL, 26.8 mmol) in THF. The reaction mixture was stirred at reflux for 24 h. The reaction mixture was cooled. The reaction was quenched with the addition of methanol. To the mixture was added concentrated HCl (5.0 mL). The mixture was refluxed for 3 h and cooled to room temperature. The mixture was concentrated under reduced pressure and the resultant residue was dissolved in DCM and washed with water, brine and dried over sodium sulphate and concentrated under reduced pressure to afford (2S,5R)-1-benzyl-2-ethyl-5-methylpiperazine (1.90 g, 8.70 mmol, 97% yield). LCMS: m/z=219.2 [M+H]$^+$; retention time 0.43 min, LCMS Method: Column-Luna 3.0 C18 (2) 100 Å LC column (20×4.0 mm); mobile phase A: 0.1% TFA in water mobile phase B: 0.1% TFA in acetonitrile. Gradient=20-100% B over 2.5 minutes, then a 0.3 minute hold at 100% B; Flow rate: 1.5 mL/min; Detection: UV at 220 nm.

Intermediate 56 tert-Butyl (2R,5S)-4-benzyl-5-ethyl-2-methylpiperazine-1-carboxylate

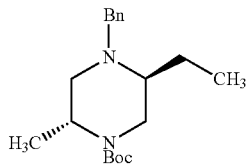 [SMILES: CC[C@H]1CN(C(=O)OC(C)(C)C)[C@H](C)CN1Cc1ccccc1]

To a solution of (2S,5R)-1-benzyl-2-ethyl-5-methylpiperazine (1.9 g, 8.70 mmol) in DCM (20 mL) was added TEA (2.43 mL, 17.40 mmol) and Boc-anhydride (4.04 mL, 17.40 mmol). The reaction mixture was stirred at room temperature for 2 h. The reaction mixture was concentrated under reduced pressure to obtain the crude product which was purified by silica gel column chromatography using 20% EtOAc in pet ether. The fractions were concentrated under reduced pressure to yield the pure product tert-butyl (2R,5S)-4-benzyl-5-ethyl-2-methylpiperazine-1-carboxylate (2.0 g, 6.28 mmol, 72.2% yield). LCMS: m/z=319.2 [M+H]$^+$; retention time 4.2 min. Column: Kinetex XB-C18 (3×75 mm, 2.6 μm); mobile phase A: 10 mM ammonium acetate: acetonitrile (98:2), mobile phase B: 10 mM ammonium acetate: acetonitrile (2:98), Gradient=20-100% B over 4 minutes, then a 0.6 minute hold at 100% B; Flow rate: 1.5 mL/min; Detection: UV at 220 nm.

Intermediate 57 tert-Butyl (2R,5S)-5-ethyl-2-methylpiperazine-1-carboxylate

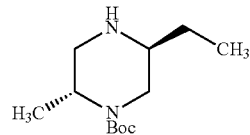

In a 100 mL autoclave, to a solution of tert-butyl (2R,5S)-4-benzyl-5-ethyl-2-methylpiperazine-1-carboxylate (2.0 g, 6.28 mmol) in methanol (40 mL) was added acetic acid (0.360 mL, 6.28 mmol) at room temperature. The reaction mixture was purged with $N_2$ and 10% palladium on carbon (200 mg, 0.188 mmol) was added. The reaction mixture was evacuated and stirred overnight under hydrogen (70 psi) atmosphere. The reaction mixture was filtered through a Celite® pad. The filtrate was concentrated under reduced pressure and dried under high vacuum to yield tert-butyl (2R,5S)-5-ethyl-2-methylpiperazine-1-carboxylate, AcOH (1.4 g, 4.85 mmol, 77% yield). $^1$H NMR (400 MHz, DMSO-$d_6$) δ (ppm)=0.79-0.91 (m, 3H) 1.13 (d, J=6.53 Hz, 3H) 1.23-1.35 (m, 9H) 1.37-1.40 (m, 2H), 2.28-2.45 (m, 2H) 2.90 (m, 1H), 3.07 (m, 1H), 3.52 (m, 1H), 3.59 (m, 1H) 3.91-4.13 (m, 1H).

Intermediate 58

Methyl N-benzyl-N—((R)-2-((tert-butoxycarbonyl)amino)pentanoyl)-L-alaninate

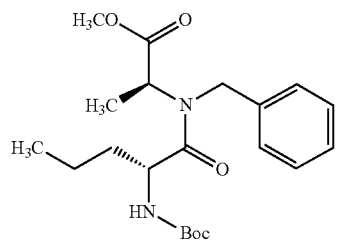 [SMILES: CCC[C@@H](NC(=O)OC(C)(C)C)C(=O)N(Cc1ccccc1)[C@@H](C)C(=O)OC]

To a solution of (R)-2-((tert-butoxycarbonyl)amino)pentanoic acid (13.49 g, 62.1 mmol) in DMF (50 mL) at room temperature was added HATU (18.89 g, 49.7 mmol) and DIPEA (21.7 mL, 124 mmol), followed by methyl benzyl-L-alaninate (8 g, 41.4 mmol). The reaction mixture was stirred at room temperature for 16 h. Water was added to quench the reaction. The mixture was extracted with ethyl acetate (2×100 mL), the combined organic layer was washed with water, brine and dried over sodium sulfate. The solvent was evaporated under reduced pressure to yield the crude product, which was purified by silica gel column chromatography using 30% EtOAc in pet ether as eluent. The fractions were concentrated under reduced pressure to yield methyl N-benzyl-N—((R)-2-((tert-butoxycarbonyl)amino) pentanoyl)-L-alaninate (11 g, 68% yield). LCMS: m/z=393.2 [M+H]$^+$; retention time 1.84 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min.

Intermediate 59

Methyl N—((R)-2-aminopentanoyl)-N-benzyl-L-alaninate

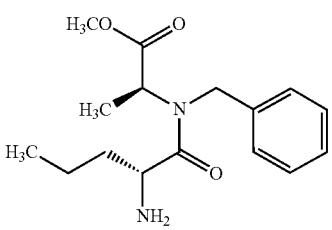 [SMILES: CCC[C@@H](N)C(=O)N(Cc1ccccc1)[C@@H](C)C(=O)OC]

To a solution of methyl N-benzyl-N—((R)-2-((tert-butoxycarbonyl)amino) pentanoyl)-L-alaninate (3.5 g, 8.92 mmol) in DCM (15 mL) at 0° C. was added TFA (0.7 mL, 8.92 mmol). The reaction mixture was stirred at room temperature for 16 h. The reaction mixture was concentrated under reduced pressure and washed with 1:1 diethyl ether: pet ether and dried under high vacuum to yield methyl N—((R)-2-aminopentanoyl)-N-benzyl-L-alaninate, TFA (3 g, 7.38 mmol, 83% yield). LCMS: m/z=293.2 [M+H]$^+$; retention time 1.08 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min.

Intermediate 60

(3R,6S)-1-Benzyl-6-methyl-3-propylpiperazine-2,5-Dione

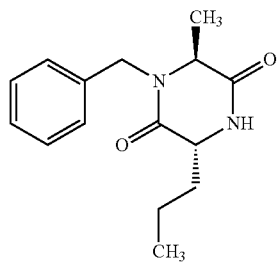 [SMILES: CCC[C@H]1NC(=O)[C@H](C)N(Cc2ccccc2)C1=O]

A stirred solution of methyl N—((R)-2-aminopentanoyl)-N-benzyl-L-alaninate, TFA (3 g, 10.26 mmol) in methanol (15 mL) was heated at 70° C. for 16 h. The reaction mixture was concentrated and dried under reduced pressure to afford (3R,6S)-1-benzyl-6-methyl-3-propylpiperazine-2,5-dione (2 g, 23% yield). LCMS: m/z=261.2 [M+H]$^+$; retention time 1.06 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min.

Intermediate 61

(2S, 5R)-1-Benzyl-2-methyl-5-propylpiperazine

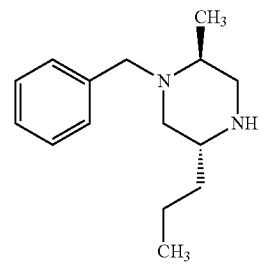 [SMILES: CCC[C@@H]1CN(Cc2ccccc2)[C@@H](C)CN1]

To a stirred solution of (3R,6S)-1-benzyl-6-methyl-3-propylpiperazine-2,5-dione (0.5 g, 1.92 mmol) in THF (25 mL) at 0° C. was added borane tetrahydrofuran complex (9.6 mL, 9.6 mmol). The reaction mixture was heated at reflux overnight. The reaction was quenched with the addition of methanol. To the reaction mixture was added aqueous concentrated HCl (0.5 mL). The reaction mixture was refluxed for 3 h. Then the reaction mixture was concentrated under reduced pressure and the residue was dissolved in DCM, washed with saturated aqueous NaHCO$_3$ solution, water, brine and dried with anhydrous sodium sulphate and concentrated under reduced pressure to yield (2S,5R)-1-benzyl-2-methyl-5-propylpiperazine (0.3 g, 59% yield). LCMS: m/z=233.2 [M+H]$^+$; retention time 1.7 min. LCMS Method: Column-Kinetex XB-C18 (75×3 mm, 2.6 μm); mobile phase A: 0.1% TFA in water, mobile phase B: 0.1% TFA in acetonitrile.

Intermediate 62 tert-Butyl (2R,5S)-4-benzyl-5-methyl-2-propylpiperazine-1-carboxylate

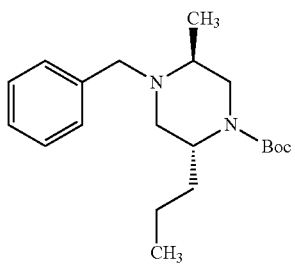 [SMILES: CCC[C@@H]1CN(Cc2ccccc2)[C@@H](C)CN1C(=O)OC(C)(C)C]

To a solution of (2S,5R)-1-benzyl-2-methyl-5-propylpiperazine (0.35 g, 1.51 mmol) in DCM (10 mL) was added triethylamine (0.6 mL, 4.52 mmol), followed by Boc-anhydride (0.5 mL, 2.26 mmol) at room temperature. The reaction mixture was stirred for 3 h. The reaction was quenched with the addition of water. The mixture was extracted with ethyl acetate (2×100 mL). The combined organic layer was washed with water, brine and dried over sodium sulfate. The solvent was evaporated under reduced pressure to yield the crude product, which was purified by silica gel column chromatography using 40% EtOAc in pet ether as eluent. The homogenous fractions were concentrated under reduced pressure to yield the product tert-butyl (2R,5S)-4-benzyl-5-methyl-2-propylpiperazine-1-carboxylate (0.3 g, 60% yield). LCMS: m/z=333.2 [M+H]$^+$; retention time 4.26 min LCMS Method: Column-Kinetex XB-C18 (75×3 mm, 2.6 µm); mobile phase A: 10 mM NH$_4$OAc in water: acetonitrile (98:2) Mobile phase B: 10 mM NH$_4$OAc in water:acetonitrile (2:98).

Intermediate 63 tert-Butyl (2R,5S)-5-methyl-2-propylpiperazine-1-carboxylate

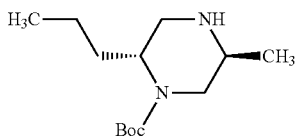 [SMILES: CCC[C@@H]1CN[C@@H](C)CN1C(=O)OC(C)(C)C]

To a solution of tert-butyl (2R,5S)-4-benzyl-5-methyl-2-propylpiperazine-1-carboxylate (0.4 g, 1.2 mmol) in methanol (5 mL) was added acetic acid (0.07 mL, 1.2 mmol) and 10% Pd on carbon (0.333 g, 1.564 mmol) at room temperature. The reaction mixture was stirred overnight under a hydrogen atmosphere. The reaction mixture was filtered through a Celite® pad, and the filtrate was concentrated and dried under reduced pressure to yield tert-butyl (2R,5S)-5-methyl-2-propylpiperazine-1-carboxylate AcO-(0.2 g, 0.584 mmol, 48.5% yield). LCMS: m/z=243.2 [M+H]$^+$; retention time 2.50 min. (Column: Kinetex XB-C18 (75×3 mm, 2.6 µm); mobile phase A: 10 mM NH$_4$OAc in water:acetonitrile (98:2) mobile phase B: 10 mM NH$_4$OAc in water:acetonitrile (2:98).

Intermediate 64 tert-Butyl (2R,5S)-4-(6-chloro-1-methyl-2-oxo-1,2-dihydropyrido[3,2-d]pyrimidin-4-yl)-5-methyl-2-propylpiperazine-1-carboxylate

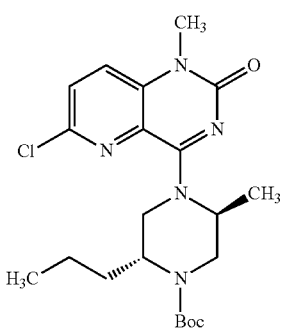

To a stirred solution of tert-butyl (2R,5S)-5-methyl-2-propylpiperazine-1-carboxylate AcO— (0.45 g, 1.493 mmol) in acetonitrile (10 mL) were added DIPEA (0.97 mL, 5.6 mmol) and 4,6-dichloro-1-methylpyrido[3,2-d]pyrimidin-2(1H)-one (0.427 g, 1.86 mmol) sequentially at room temperature. The reaction mixture was heated at 85° C. for 16 h. The reaction mixture was concentrated under reduced pressure to yield the crude product, which was purified by silica gel column chromatography (eluted with 50% EtOAc in pet ether) to yield tert-butyl (2R,5S)-4-(6-chloro-1-methyl-2-oxo-1,2-dihydropyrido[3,2-d]pyrimidin-4-yl)-5-methyl-2-propylpiperazine-1-carboxylate (0.3 g, 25% yield). LCMS: m/z=436.2 [M+H]$^+$; retention time 1.87 min, LCMS Method; Column: AQUITY UPLC BEH C18 (3.0× 50 mm, 1.7 µm); mobile phase A:10 mM NH$_4$OAc in water:acetonitrile (95:5); mobile phase B: 10 mM NH$_4$OAc in water:acetonitrile (5:95); gradient=20-100% B over 1.1 min, then a 0.6 minute hold at 100% B, flow: 0.7 mL/min.

Intermediate 65

6-Chloro-1-methyl-4-((2S,5R)-2-methyl-5-propylpiperazin-1-yl)pyrido[3,2-d]pyrimidin-2(1H)-one

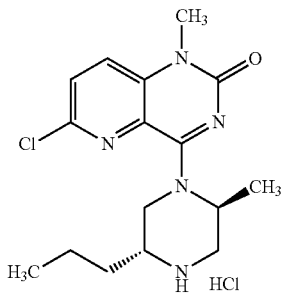 [SMILES: CCC[C@@H]1CN(c2nc(=O)n(C)c3ccc(Cl)nc23)[C@@H](C)CN1 ; Cl]

To a solution of tert-butyl (2R,5S)-4-(6-chloro-1-methyl-2-oxo-1,2-dihydropyrido[3,2-d]pyrimidin-4-yl)-5-methyl-2-propylpiperazine-1-carboxylate (0.15 g, 0.34 mmol) in dioxane (5 mL) was added 4 N HCl in 1,4-dioxane (4, M, 0.9 mL, 3.4 mmol) at 0° C. The reaction mixture was stirred at room temperature for 3 h. The reaction mixture was concentrated under reduced pressure yield 6-chloro-1-methyl-4-((2S,5R)-2-methyl-5-propylpiperazin-1-yl)pyrido[3,2-d] pyrimidin-2(1H)-one HCl salt (yield: 0.12 g, 79%). LCMS: m/z=336.2 [M+H]$^+$; retention time 0.88 min, LCMS Method; Column: AQUITY UPLC BEH C18 (3.0×50 mm, 1.7 µm); mobile phase A:10 mM NH$_4$OAc in water:acetonitrile (95:5); mobile phase B: 10 mM NH$_4$OAc in water: acetonitrile (5:95); gradient=20-100% B over 1.1 min, then a 0.6 minute hold at 100% B, flow: 0.7 mL/min.

Example 394

6-Chloro-1-methyl-4-((2S,5R)-2-methyl-5-propyl-4-(1-(4-(trifluoromethyl)phenyl)ethyl)piperazin-1-yl)pyrido[3,2-d]pyrimidin-2(1H)-one

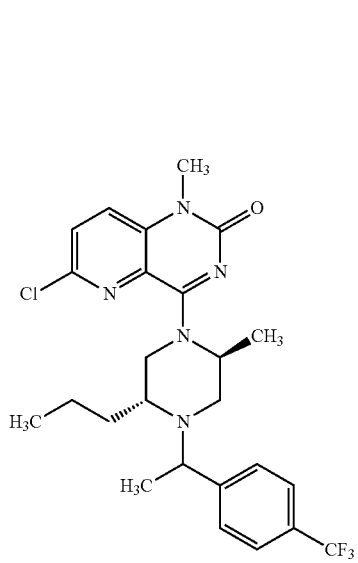

(394)

To a stirred solution of 6-chloro-1-methyl-4-((2S,5R)-2-methyl-5-propylpiperazin-1-yl)pyrido[3,2-d]pyrimidin-2(1H)-one HCl salt (0.15 g, 0.333 mmol) in acetonitrile (5 mL) were added DIPEA (0.2 mL, 1.0 mmol), 1-(1-chloroethyl)-4-(trifluoromethyl) benzene (0.139 g, 0.67 mmol) and sodium iodide (0.05 g, 0.33 mmol) at room temperature. The reaction mixture was heated at 85° C. for 16 h. The reaction was quenched with the addition of water. The reaction mixture was extracted with ethyl acetate (2×100 mL), the combined organic layer was washed with water, brine and dried over sodium sulfate. The solvent was evaporated under reduced pressure to yield the crude product, which was purified by silica gel column chromatography (eluted with 30% EtOAc in pet ether). The fractions were concentrated under reduced pressure to yield 6-chloro-1-methyl-4-((2S, 5R)-2-methyl-5-propyl-4-(1-(4-(trifluoromethyl)phenyl)ethyl) piperazin-1-yl)pyrido[3,2-d]pyrimidin-2(1H)-one (0.1 g, 22% yield). LCMS: m/z=508.3 [M+H]$^+$; retention time 1.59 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 1.1 min, then a 0.6 minute hold at 100% B, flow: 0.7 mL/min.

Examples 395 and 396

1-Methyl-4-((2S,5R)-2-methyl-5-propyl-4-(1-(4-(trifluoromethyl)phenyl)ethyl)piperazin-1-yl)-2-oxo-1,2-dihydropyrido[3,2-d]pyrimidine-6-carbonitrile

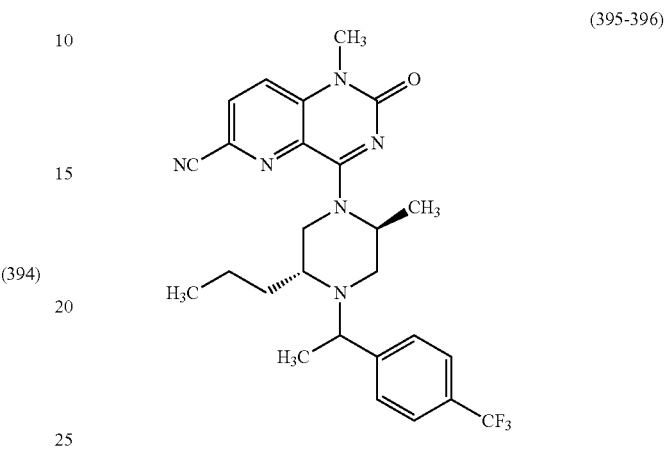

(395-396)

To a solution of 6-chloro-1-methyl-4-((2S,5R)-2-methyl-5-propyl-4-(1-(4-(trifluoromethyl)phenyl)ethyl)piperazin-1-yl)pyrido[3,2-d]pyrimidin-2(1H)-one (0.1 g, 0.19 mmol) in DMF (2 mL) were added zinc cyanide (0.046 g, 0.39 mmol), zinc (0.7 mg, 9.8 μmol) and triethylamine (0.1 mL, 0.59 mmol) followed by dichloro[9,9-dimethyl-4,5-bis(diphenylphosphino)xanthene]palladium(II) (0.015 g, 0.02 mmol) at room temperature under argon atmosphere. The reaction mixture was heated at 90° C. overnight. The reaction mixture was diluted with EtOAc (50 mL) and filtered through Celite® pad, washed with additional ethyl acetate (2×50 mL). The filtrate was washed with water (50 mL), brine, dried over Na$_2$SO$_4$ and concentrated under reduced pressure to yield the crude product, which was purified by preparative HPLC (HPLC method: Column: YMC EXRS (250×19 mm, 5 μm); mobile phase A:10 mM ammonium acetate in water pH~4.5; mobile phase B: acetonitrile Flow: 20 mL/min) to yield Example 395 and Example 396.

EXAMPLE 395: (13 mg, 14% yield). LCMS: m/z=499.3 [M+H]$^+$; rt 2.376 min; (LCMS Method: Column: XBridge BEH XP C18 (50×2.1 mm, 2.5 μm); mobile phase A: 95% water: 5% acetonitrile; 10 mM NH$_4$OAc; mobile phase B: 5% water:95% acetonitrile; 10 mM NH$_4$OAC; Flow: 1.1 mL/min; Temp: 50° C.). $^1$H NMR (400 MHz, DMSO-d$_6$) δ (ppm)=8.22 (br d, J=8.8 Hz, 1H), 7.98 (d, J=8.8 Hz, 1H), 7.70-7.72 (m, 2H), 7.59-7.61 (m, 2H), 5.84-5.59 (m, 1H), 5.10-4.67 (m, 1H), 3.91-3.75 (m, 1H), 3.38-3.43 (m, 4H), 2.86-2.70 (m, 2H), 2.47-2.36 (m, 1H), 1.63-1.51 (m, 1H), 1.47-1.18 (m, 8H), 0.9-0.99 (m, 1H), 0.75-0.59 (m, 3H).

EXAMPLE 396: (13 mg, 13% yield); LCMS: m/z=499.3 [M-41]$^+$; rt 2.436 min; (LCMS Method: Column: XBridge BEH XP C18 (50×2.1 mm, 2.5 μm); mobile phase A: 95% water: 5% acetonitrile; 10 mM NH$_4$OAc; mobile phase B: 5% water: 95% acetonitrile; 10 mM NH$_4$OAC; Flow: 1.1 mL/min; Temp:50° C.). $^1$H NMR (400 MHz, DMSO-d$_6$) δ (ppm)=8.25 (br d, J=2.4 Hz, 1H), 8.06-7.92 (m, 1H), 7.77-7.65 (m, 2H), 7.65-7.54 (m, 2H), 6.09-5.44 (m, 1H), 5.04-4.68 (m, 1H), 3.81-3.59 (m, 2H), 3.44 (s, 3H), 3.28-3.13 (m, 1H), 2.52-2.61 (m, 1H), 2.24-2.05 (m, 1H), 1.72-1.48 (m, 2H), 1.47-1.15 (m, 8H), 0.98-0.75 (m, 3H).

Intermediate 66 tert-Butyl (2S,5S)-5-(hydroxymethyl)-2-methyl-4-(1-(4-(trifluoromethyl)phenyl)propyl)piperazine-1-carboxylate (diasteromeric mixture)

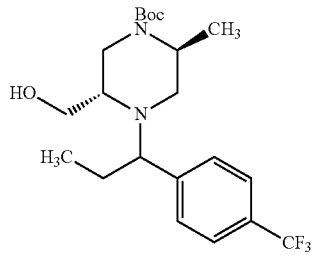 [SMILES: CCC(c1ccc(C(F)(F)F)cc1)N1C[C@H](C)N(C(=O)OC(C)(C)C)C[C@H]1CO]

To a stirred solution of tert-butyl (2S,5S)-5-(hydroxymethyl)-2-methylpiperazine-1-carboxylate (1.0 g, 4.34 mmol) in acetonitrile (8 mL), 2,2,6,6-tetramethylpiperidine (3.7 mL, 21.7 mmol), 1-(4-(trifluoromethyl)phenyl)propyl methanesulfonate (1.84 g, 6.51 mmol) and sodium iodide (0.65 g, 4.34 mmol) were added sequentially at room temperature. The reaction mixture was heated at 60° C. for 14 h. and cooled to room temperature. The solvent was removed under reduced pressure to give the crude product, which was purified by silica gel flash column chromatography (30-50% EtOAc in n-hexane) to afford tert-butyl (2S,5S)-5-(hydroxymethyl)-2-methyl-4-(1-(4-(trifluoromethyl)phenyl)propyl)piperazine-1-carboxylate (800 mg, 44% yield). LCMS: m/z, 417.3 [M+H]$^+$; rt 3.68 min. (LCMS Method: Column: Kinetex XB-C18 (3×75 mm, 2.6 µm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 67 tert-Butyl (2S,5S)-5-(methoxymethyl)-2-methyl-4-(1-(4-(trifluoromethyl)phenyl)propyl)piperazine-1-carboxylate (diasteromeric mixture)

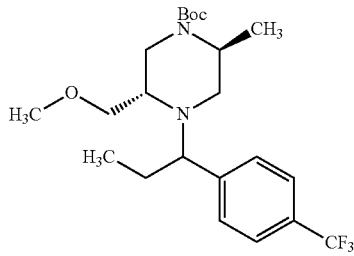 [SMILES: CCC(c1ccc(C(F)(F)F)cc1)N1C[C@H](C)N(C(=O)OC(C)(C)C)C[C@H]1COC]

To a stirred solution of tert-butyl (2S,5S)-5-(hydroxymethyl)-2-methyl-4-(1-(4-(trifluoromethyl)phenyl)propyl)piperazine-1-carboxylate (200 mg, 0.480 mmol) in THF (5 mL) was added NaH (58 mg, 1.44 mmol, 60% w/w) at 0° C. under nitrogen. The reaction mixture was stirred for 10 min. Iodomethane (0.15 mL, 2.40 mmol) was added. The reaction mixture was allowed to warm to room temperature and stirred for 2 h. The reaction mixture was then cooled to 0° C. The reaction was quenched with ice-cold water. The reaction mixture was extracted with EtOAc (2×50 mL). The combined organic extract was washed with brine, dried over Na$_2$SO$_4$ and concentrated to give the crude product, which was purified by silica gel flash column chromatography (15-20% EtOAc in n-hexane) to afford a tert-butyl (2S,5S)-5-(methoxymethyl)-2-methyl-4-(1-(4-(trifluoromethyl)phenyl)propyl) piperazine-1-carboxylate (130 mg, 63% yield). LCMS: m/z, 431.3 [M+H]$^+$; rt 1.55 and 1.59 min, LCMS Method; Column: AQUITY UPLC BEH C18 (3.0×50 mm, 1.7 µm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min.

Intermediate 68

(2S,5S)-2-(Methoxymethyl)-5-methyl-1-(1-(4-(trifluoromethyl)phenyl)propyl)piperazine, TFA (Diastereomeric Mixture)

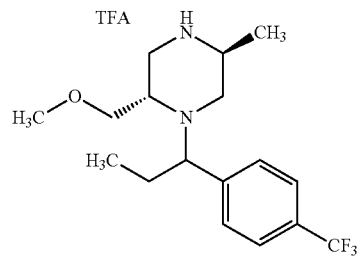 [SMILES: CCC(c1ccc(C(F)(F)F)cc1)N1C[C@H](C)NC[C@H]1COC]

To a stirred solution of tert-butyl (2S,5S)-5-(methoxymethyl)-2-methyl-4-(1-(4-(trifluoromethyl)phenyl)propyl) piperazine-1-carboxylate (150 mg, 0.35 mmol) in dry DCM (4 mL) was added TFA (0.3 mL, 3.50 mmol) at 0° C. The reaction mixture was allowed to warm to room temperature and stirred for 2 h. The solvent was removed under reduced pressure to afford (2S,5S)-2-(methoxymethyl)-5-methyl-1-(1-(4-(trifluoromethyl) phenyl)propyl)piperazine, TFA (120 mg, 77% yield). LCMS: m/z=331.3 [M+H]$^+$; rt 1.36 and 1.38 min, LCMS Method; Column: AQUITY UPLC BEH C18 (3.0×50 mm, 1.7 µm); mobile phase A:10 mM NH$_4$OAc in water: acetonitrile (95:5); mobile phase B: 10 mM NH$_4$OAc in water:acetonitrile (5:95); gradient=20-100% B over 2 min, then a 1 minute hold at 100% B, flow: 0.7 mL/min.

Example 397

6-Chloro-4-((2S,5S)-5-(methoxymethyl)-2-methyl-4-(1-(4-(trifluoromethyl)phenyl) propyl)piperazin-1-yl)-1-methylpyrido[3,2-d]pyrimidin-2(1H)-one (diastereomeric mixture)

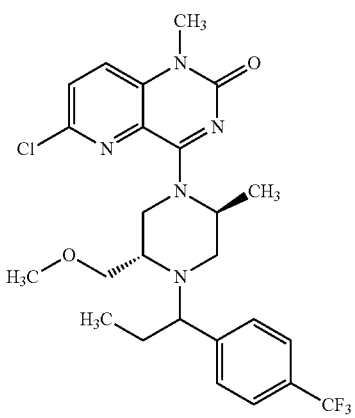

(397)

To a stirred solution of (2S,5S)-2-(methoxymethyl)-5-methyl-1-(1-(4-(trifluoromethyl)phenyl)propyl)piperazine, TFA (130 mg, 0.29 mmol) in acetonitrile (5 mL), DIPEA (0.5 mL, 2.93 mmol) and 4,6-dichloro-1-methylpyrido[3,2-d]pyrimidin-2(1H)-one (101 mg, 0.44 mmol) were added sequentially at room temperature followed by heating the mixture at 80° C. for 12 h. The reaction mixture was then cooled to room temperature and the solvent was removed under reduced pressure to give the crude product, which was purified by silica gel column chromatography using 0-10% MeOH in CHCl₃ to afford 6-chloro-4-((2S,5S)-5-(methoxymethyl)-2-methyl-4-(1-(4-(trifluoromethyl)phenyl)propyl)piperazin-1-yl)-1-methylpyrido[3,2-d]pyrimidin-2(1H)-one (120 mg, 78% yield). LCMS: m/z, 524.3 [M+H]⁺; rt 1.28 and 1.34 min, LCMS Method; Column: AQUITY UPLC BEH C18 (3.0×50 mm, 1.7 μm); mobile phase A:10 mM NH₄OAc in water:acetonitrile (95:5); mobile phase B: 10 mM NH₄OAc in water:acetonitrile (5:95); gradient=20-100% B over 2 min, then a 0.3 minute hold at 100% B, flow: 0.7 mL/min.

Examples 398 and 399

4-((2S,5S)-5-(Methoxymethyl)-2-methyl-4-(1-(4-(trifluoromethyl)phenyl)propyl) piperazin-1-yl)-1-methyl-2-oxo-1,2-dihydropyrido[3,2-d]pyrimidine-6-carbonitrile

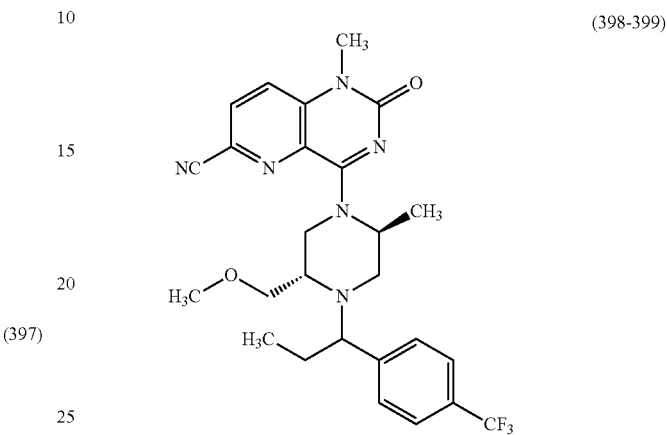

(398-399)

To a stirred solution of 6-chloro-4-((2S,5S)-5-(methoxymethyl)-2-methyl-4-(1-(4-(trifluoromethyl)phenyl)propyl)piperazin-1-yl)-1-methylpyrido[3,2-d]pyrimidin-2(1H)-one (120 mg, 0.23 mmol) in DMF (5 mL) were added zinc (20 mg, 0.30 mmol) and TEA (0.16 mL, 1.14 mmol). The reaction mixture was then flushed with argon for 5 minutes, followed by the addition of zinc cyanide (81 mg, 0.69 mmol) and dichloro[9,9-dimethyl-4,5-bis(diphenylphosphino)xanthene]palladium(II) (17.3 mg, 0.02 mmol). The reaction mixture was heated at 90° C. for 12 h, cooled to room temperature and concentrated under reduced pressure to afford the product, which was purified using preparative HPLC (HPLC Method: Column: Sunfire C18 (150×19 mm, 5 μm); mobile phase A: 10 mM ammonium acetate in water; mobile phase B: acetonitrile; Gradient: 0-100% B over 18 minutes, then a 5 minute hold at 100% B; Flow: 19 mL/min).

EXAMPLE 398: (11.6 mg, 10% yield): LCMS: m/z, 515.3 [M+H]⁺; rt 2.22 min; LCMS method: Column: XBridge BEH XP C18 (50×2.1 mm, 2.5 μm); mobile phase A: 10 mM NH₄OAc in water:acetonitrile (95:5); mobile phase B: 10 mM NH₄OAc in water:acetonitrile (5:95); Gradient=0-100% B over 3 minutes; Temperature: 50° C.; Flow rate: 1.1 mL/min; Detection: UV at 220 nm. ¹H NMR (400 MHz, DMSO-d₆) δ (ppm)=8.23 (d, J=9.0 Hz, 1H), 7.98 (d, J=9.0 Hz, 1H), 7.74 (d, J=8.1 Hz, 2H), 7.53 (d, J=7.8 Hz, 2H), 6.10-5.37 (m, 1H), 5.01-4.75 (m, 1H), 3.86-3.70 (m, 1H), 3.58-3.38 (m, 5H), 3.23-2.86 (m, 6H), 2.82-2.72 (m, 1H), 1.98-1.82 (m, 1H), 1.74-1.59 (m, 1H), 1.44-1.11 (m, 3H), 0.83-0.61 (m, 3H).

EXAMPLE 399: (10.5 mg, 9% yield): LCMS: m/z, 515.3 [M+H]⁺; rt 2.26 min; LCMS method: Column: XBridge BEH XP C18 (50×2.1 mm, 2.5 μm); mobile phase A: 10 mM NH₄OAc in water:acetonitrile (95:5); mobile phase B: 10 mM NH₄OAc in water:acetonitrile (5:95); Gradient=0-100% B over 3 minutes; Temperature: 50° C.; Flow rate: 1.1 mL/min; Detection: UV at 220 nm. ¹H NMR (400 MHz, DMSO-d₆) δ (ppm)=8.24 (d, J=8.8 Hz, 1H), 7.99 (d, J=8.8 Hz, 1H), 7.70 (d, J=8.1 Hz, 2H), 7.56 (d, J=8.1 Hz, 2H), 6.05-5.40 (m, 1H), 5.05-4.74 (m, 1H), 3.79-3.49 (m, 3H), 3.44 (s, 3H), 3.39-3.35 (m, 2H), 3.28-3.18 (m, 1H), 3.15-3.00 (m, 2H), 2.71-2.58 (m, 1H), 2.40-2.16 (m, 1H), 2.06-1.89 (m, 1H), 1.78-1.60 (m, 1H), 1.40-1.17 (m, 3H), 0.66-0.63 (m, 3H).

The examples in the Table 17 were prepared according to the general procedure described in Examples 398 and 399, using ethyl iodide instead of methyl iodide in the synthetic sequence. Mixture of diastereomers were separated at the final stage using either preparative chromatography or preparative chiral chromatography. The absolute stereochemistry was not assigned at the carbon-nitrogen bond.

washed with water, brine and dried over anhydrous sodium sulphate. Evaporation of the solvent under reduced pressure furnished tert-butyl (2S,5S)-5-(chloromethyl)-2-methyl-4-(1-(4-(trifluoromethyl)phenyl)ethyl) piperazine-1-carboxylate (2 g, 81% yield). LCMS: m/z, 421.2 [M+H]$^+$; retention time 4.17 and 4.26 min. [LCMS Method: Column: Kinetex-18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm].

TABLE 17

| Ex. No. | Structure | Stereo Chem. | LCMS Method | LCMS rt | [M + H]$^+$ |
|---|---|---|---|---|---|
| 400 | 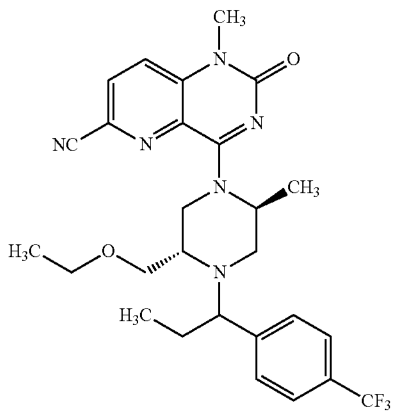 [SMILES: CCOC[C@@H]1CN(c2nc(=O)n(C)c3ccc(C#N)nc23)[C@@H](C)CN1C(CC)c1ccc(C(F)(F)F)cc1] | H | C | 2.32 | 529.3 |
| 401 | | H | C | 2.36 | 529.3 |

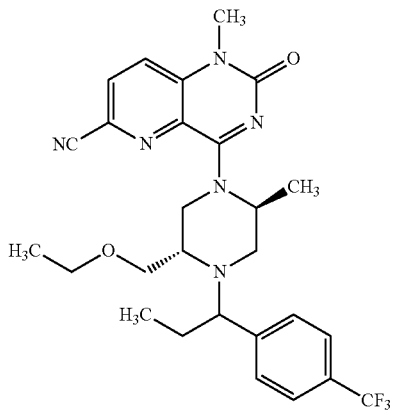

Intermediate 69 tert-Butyl (2S,5S)-5-(chloromethyl)-2-methyl-4-(1-(4-(trifluoromethyl)phenyl)ethyl)piperazine-1-carboxylate

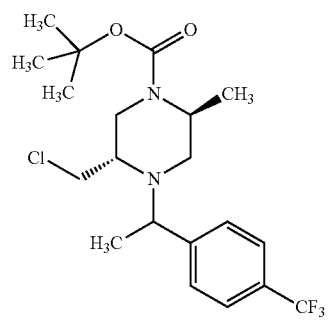 [SMILES: CC(c1ccc(C(F)(F)F)cc1)N1C[C@H](C)N(C(=O)OC(C)(C)C)C[C@H]1CCl]

To a stirred solution of tert-butyl (2S,5S)-5-(hydroxymethyl)-2-methyl-4-(1-(4-(trifluoromethyl)phenyl)ethyl)piperazine-1-carboxylate (2.3 g, 5.71 mmol) in DCM (25 mL) were added Et$_3$N (2.4 mL, 17.14 mmol) and DMAP (0.035 g, 0.286 mmol) followed by methanesulfonyl chloride (0.9 mL, 11.43 mmol) at 0° C. The reaction mixture was stirred at room temperature for 16 h. Water was added to quench the reaction. The mixture was extracted with DCM (2×50 mL), Intermediate 70 tert-Butyl (2S,5S)-5-(azidomethyl)-2-methyl-4-(1-(4-(trifluoromethyl)phenyl)ethyl)piperazine-1-carboxylate

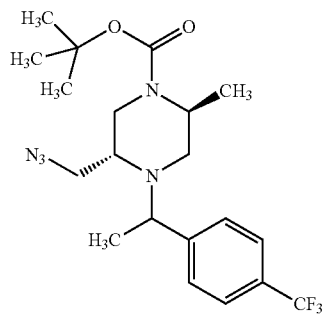 [SMILES: CC(c1ccc(C(F)(F)F)cc1)N1C[C@H](C)N(C(=O)OC(C)(C)C)C[C@H]1CN=[N+]=[N-]]

To a stirred solution of tert-butyl (2S,5S)-5-(chloromethyl)-2-methyl-4-(1-(4-(trifluoromethyl)phenyl)ethyl)piperazine-1-carboxylate (1.5 g, 3.56 mmol) in DMF (40 mL) were added tetrabutylammonium iodide (0.13 g, 0.36 mmol) and sodium azide (0.7 g, 10.7 mmol) at room temperature. The reaction mixture was heated at 80° C. for 16 h, cooled to room temperature, diluted with water, extracted with EtOAc (2×50 mL), washed with water and brine solution. The combined organic extract was dried over sodium sulphate and the solvent was concentrated under reduced pressure to obtain the crude product, which was purified by silica gel flash column chromatography (50-60% EtOAc in n-hexane) to afford tert-butyl (2S,5S)-5-(azidomethyl)-2-methyl-4-(1-(4-(trifluoromethyl)phenyl)ethyl) piperazine-1-carboxylate (1.2 g, 73% yield). LCMS: m/z, 428.2 [M+H]$^+$; rt 4.16 & 4.23 min. [LCMS Method: Column: Kinetex-18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm].

Intermediate 71

(2S,5S)-2-(Azidomethyl)-5-methyl-1-(1-(4-(trifluoromethyl)phenyl)ethyl)piperazine.HCl salt (Diastereomeric Mixture)

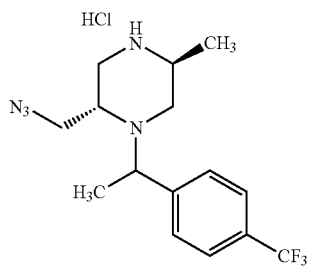 [SMILES: Cl ; CC(c1ccc(C(F)(F)F)cc1)N1C[C@H](C)NC[C@H]1CN=[N+]=[N-]]

To a stirred solution of tert-butyl (2S,5S)-5-(azidomethyl)-2-methyl-4-(1-(4-(trifluoromethyl)phenyl)ethyl) piperazine-1-carboxylate (0.6 g, 1.40 mmol) in DCM (15 mL), HCl (4 N in dioxane) (0.43 mL, 14.0 mmol) was added dropwise at room temperature. The reaction mixture was stirred for 3 h. The solvent was removed under reduced pressure, co-distilled with acetonitrile (3×10 mL), and dried to afford (2S,5S)-2-(azidomethyl)-5-methyl-1-(1-(4-(trifluoromethyl)phenyl)ethyl) piperazine, HCl salt (0.42 g, 81% yield) as an off-white solid. LCMS: m/z, 328.2 [M+H]$^+$; rt 2.07 and 2.19 min. (LCMS Method: Column: Kinetex-18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Example 402

4-((2S,5S)-5-(Azidomethyl)-2-methyl-4-(1-(4-(trifluoromethyl)phenyl)ethyl)piperazin-1-yl)-6-chloro-1-methylpyrido[3,2-d]pyrimidin-2(1H)-one (Diastereomeric Mixture)

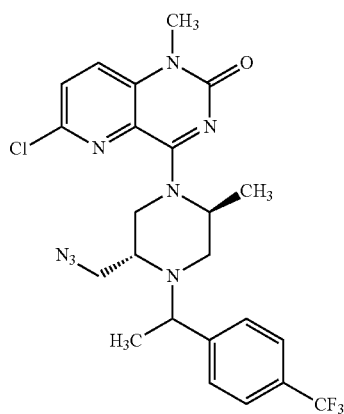

(402)

To a stirred solution of (2S,5S)-2-(azidomethyl)-5-methyl-1-(1-(4-(trifluoromethyl)phenyl)ethyl) piperazine.HCl salt (400 mg, 1.22 mmol) in acetonitrile (10 mL), DIPEA (1.1 mL, 6.11 mmol) and 4,6-dichloro-1-methylpyrido[3,2-d]pyrimidin-2(1H)-one (281 mg, 1.22 mmol) were added sequentially at room temperature followed by heating at 80° C. for 12 h. The reaction mixture was cooled to room temperature and the solvent was removed under reduced pressure to give the crude product, which was purified by silica gel column chromatography using 0-10% MeOH in CHCl$_3$ to afford 4-((2S,5S)-5-(azidomethyl)-2-methyl-4-(1-(4-(trifluoromethyl)phenyl)ethyl)piperazin-1-yl)-6-chloro-1-methylpyrido[3,2-d]pyrimidin-2(1H)-one (420 mg, 43% yield). LCMS: m/z, 521.3 [M+H]$^+$; rt 3.59 and 3.66 min. (LCMS Method: Column: Kinetex-18 (3×75 mm, 2.6 μm); mobile phase A: 10 mM ammonium formate: acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Example 403

4-((2S,5R)-5-(Aminomethyl)-2-methyl-4-(1-(4-(trifluoromethyl)phenyl)ethyl)piperazin-1-yl)-6-chloro-1-methylpyrido[3,2-d]pyrimidin-2(1H)-one (Diastereomeric Mixture)

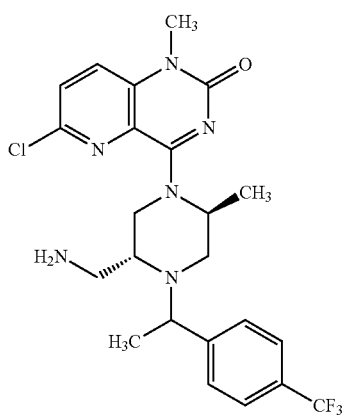

(403)

To a stirred solution of 4-(2S,5S)-5-(azidomethyl)-2-methyl-4-(1-(4-(trifluoromethyl)phenyl)ethyl)piperazin-1-yl)-6-chloro-1-methylpyrido[3,2-d]pyrimidin-2(1H)-one (200 mg, 0.38 mmol) in THF (7 mL) and water (3 mL) was added polymer bound triphenylphosphine (1.4 mmol to 2 mmol per gram) (302 mg, 1.15 mmol) at room temperature. The reaction mixture was heated at 65° C. for 16 h. The reaction mixture was cooled to room temperature, filtered through Celite® pad and washed with excess EtOAc (20 mL). The filtrate was dried over sodium sulphate and concentrated under reduced pressure to give 4-((2S,5R)-5-(aminomethyl)-2-methyl-4-(1-(4-(trifluoromethyl) phenyl) ethyl)piperazin-1-yl)-6-chloro-1-methylpyrido[3,2-d]pyrimidin-2(1H)-one (150 mg, 41% yield). LCMS: m/z, 495.1 [M+H]$^+$; rt 1.38 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 0.3 minute hold at 100% B, flow: 0.7 mL/min.

Examples 404 and 405

4-((2S,5S)-5-(Methoxymethyl)-2-methyl-4-(1-(4-(trifluoromethyl)phenyl)ethyl)piperazin-1-yl)-1-methyl-2-oxo-1,2-dihydropyrido[3,2-d]pyrimidine-6-carbonitrile

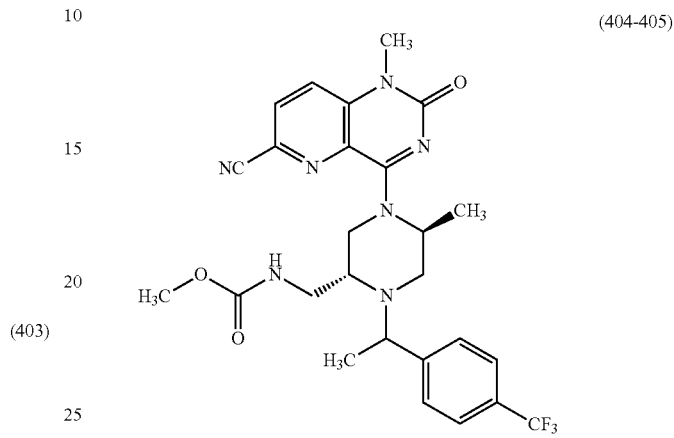

(404-405)

To a stirred solution of 4-((2S,5R)-5-(aminomethyl)-2-methyl-4-(1-(4-(trifluoromethyl)phenyl)ethyl)piperazin-1-yl)-6-chloro-1-methylpyrido[3,2-d]pyrimidin-2(1H)-one (200 mg, 0.40 mmol) in DCM (5 mL) were added DIPEA (0.11 mL, 0.61 mmol) and methyl chloroformate (0.1 mL, 1.21 mmol) at room temperature. The reaction mixture was stirred for 3 h. The solvent was removed under reduced pressure and co-distilled with acetonitrile (2×5 mL) to afford methyl (((2R,5S)-4-(6-chloro-1-methyl-2-oxo-1,2-dihydropyrido[3,2-d]pyrimidin-4-yl)-5-methyl-1-(1-(4-(trifluoromethyl)phenyl) ethyl)piperazin-2-yl)methyl)carbamate (170 mg, 76% yield).

To a stirred solution of methyl (((2R,5S)-4-(6-chloro-1-methyl-2-oxo-1,2-dihydropyrido[3,2-d]pyrimidin-4-yl)-5-methyl-1-(1-(4-(trifluoromethyl)phenyl)ethyl) piperazin-2-yl)methyl)carbamate (140 mg, 0.25 mmol) in DMF (5 mL) were added zinc (25 mg, 0.38 mmol) and TEA (0.15 mL, 1.08 mmol). The reaction mixture was flushed with argon for 5 minutes, followed by the addition of zinc cyanide (89 mg, 0.76 mmol) and dichloro[9,9-dimethyl-4,5-bis(diphenylphosphino)xanthene] palladium(II) (19 mg, 0.025 mmol). The reaction mixture was heated at 90° C. for 12 h, cooled to room temperature and concentrated under reduced pressure to afford the crude product, which was purified using preparative HPLC. (Column: Sunfire C18 (150 mm×19 mm, 5 μm); mobile phase A: 10 mM NH$_4$OAc in water; mobile phase B: acetonitrile; Gradient: 50-75% B over 20 minutes, then a 5 minute hold at 100% B; Flow: 19 mL/min; UV detection: 220 nm).

EXAMPLE 404: (40 mg, 28% yield): LCMS: m/z, 544.3 [M+H]$^+$; rt 3.08 min; (LCMS Method: Column: Kinetex –18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm). $^1$H NMR (400 MHz, DMSO-d$_6$) δ (ppm)=8.25 (d, J=8.5 Hz, 1H), 8.00 (br d, J=9.0 Hz, 1H), 7.75-7.68 (m, J=8.0 Hz, 2H), 7.62 (br d, J=8.0 Hz, 2H), 7.01-6.76 (m, 1H), 5.96-5.27 (m, 1H), 5.12-4.65 (m, 1H), 3.91-3.51 (m, 3H), 3.49-3.36 (m, 4H), 3.30-3.20 (m, 3H), 3.04-2.92 (m, 1H), 2.65-2.53 (m, 1H), 2.46-2.35 (m, 1H), 1.43-1.33 (m, 4H), 1.27-1.17 (m, 2H).

EXAMPLE 405: (50 mg, 35% yield): LCMS: m/z, 544.4 [M+H]$^+$; rt 3.01 min; (LCMS Method: Column: Kinetex-18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm). $^1$H NMR (400 MHz, DMSO-d$_6$) δ (ppm)=8.30-8.19 (m, 1H), 8.00 (br s, 1H), 7.72 (d, J=8.0 Hz, 2H), 7.61 (d, J=8.0 Hz, 2H), 6.80 (br s, 1H), 5.72-5.46 (m, 1H), 5.13-4.54 (m, 1H), 4.03-3.90 (m, 1H), 3.73-3.58 (m, 1H), 3.52-3.41 (m, 4H), 3.24-3.13 (m, 2H), 3.08-2.83 (m, 3H), 2.83-2.77 (m, 1H), 2.75-2.69 (m, 1H), 1.56-1.26 (m, 6H).

Intermediate 72 tert-Butyl (2R,5R)-4-(6-chloro-1-methyl-2-oxo-1,2-dihydropyrido[3,2-d]pyrimidin-4-yl)-5-(hydroxymethyl)-2-methylpiperazine-1-carboxylate (homochiral)

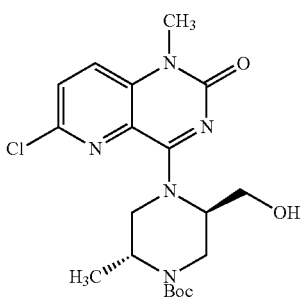 [SMILES: C[C@@H]1CN(c2nc(=O)n(C)c3ccc(Cl)nc23)[C@@H](CO)CN1C(=O)OC(C)(C)C]

To a stirred solution of tert-butyl (2R,5R)-5-(hydroxymethyl)-2-methylpiperazine-1-carboxylate (0.60 g, 2.61 mmol) in acetonitrile (8 mL), DIPEA (3.8 mL, 21.7 mmol) and 4,6-dichloro-1-methylpyrido[3,2-d]pyrimidin-2(1H)-one (0.5 g, 2.17 mmol) were added at room temperature followed by heating at 80° C. for 12 h. The reaction mixture was cooled to room temperature. Solvent was removed under reduced pressure to give the crude product, which was purified by silica gel column chromatography using 7-10% MeOH in CHCl$_3$ to afford tert-butyl (2R,5R)-4-(6-chloro-1-methyl-2-oxo-1,2-dihydropyrido[3,2-d]pyrimidin-4-yl)-5-(hydroxymethyl)-2-methylpiperazine-1-carboxylate (0.7 g, 76% yield). LCMS: m/z, 424.2 [M+H]$^+$; rt 2.08 min. (LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 73 tert-Butyl (2R,5R)-4-(6-cyano-1-methyl-2-oxo-1,2-dihydropyrido[3,2-d]pyrimidin-4-yl)-5-(hydroxymethyl)-2-methylpiperazine-1-carboxylate (homochiral)

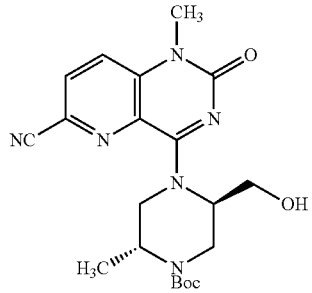 [SMILES: C[C@@H]1CN(c2nc(=O)n(C)c3ccc(C#N)nc23)[C@@H](CO)CN1C(=O)OC(C)(C)C]

To a stirred solution of tert-butyl (2R,5R)-4-(6-chloro-1-methyl-2-oxo-1,2-dihydropyrido[3,2-d]pyrimidin-4-yl)-5-(hydroxymethyl)-2-methylpiperazine-1-carboxylate (300 mg, 0.71 mmol) in DMF (10 mL) were added zinc (5 mg, 0.07 mmol) and TEA (0.5 mL, 3.54 mmol). The reaction mixture was flushed with argon for 5 minutes, followed by the addition of zinc cyanide (250 mg, 2.12 mmol) and dichloro[9,9-dimethyl-4,5-bis(diphenylphosphino)xanthene]palladium(II) (53.5 mg, 0.07 mmol). The reaction mixture was heated at 95° C. for 6 h, cooled to room temperature, filtered through a Celite® pad and washed with DCM (50 mL). The filtrate was concentrated under reduced pressure to afford the crude product, which was purified by silica gel column chromatography using 0-10% MeOH in CHCl$_3$ to afford tert-butyl (2R,5R)-4-(6-cyano-1-methyl-2-oxo-1,2-dihydropyrido[3,2-d]pyrimidin-4-yl)-5-(hydroxymethyl)-2-methylpiperazine-1-carboxylate (220 mg, 75% yield). LCMS: m/z, 415.2 [M-41]$^+$; rt 1.84 min. (LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 74

4-((2R,5R)-2-(Hydroxymethyl)-5-methylpiperazin-1-yl)-1-methyl-2-oxo-1,2-dihydropyrido[3,2-d]pyrimidine-6-carbonitrile, TFA

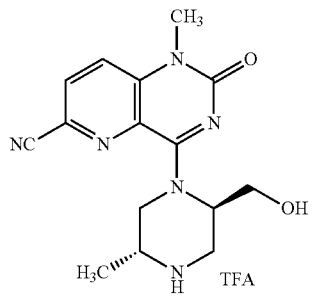 [SMILES: C[C@@H]1CN(c2nc(=O)n(C)c3ccc(C#N)nc23)[C@@H](CO)CN1]

To a stirred solution of tert-butyl (2R,5R)-4-(6-cyano-1-methyl-2-oxo-1,2-dihydropyrido[3,2-d]pyrimidin-4-yl)-5-(hydroxymethyl)-2-methylpiperazine-1-carboxylate (250 mg, 0.60 mmol) in dry DCM (8 mL) was added TFA (0.2 mL, 3.02 mmol) at 0° C. The reaction mixture was allowed to warm to room temperature and stirred for 2 h. The solvent was removed under reduced pressure to afford 4-((2R,5R)-2-(hydroxymethyl)-5-methylpiperazin-1-yl)-1-methyl-2-oxo-1,2-dihydropyrido[3,2-d]pyrimidine-6-carbonitrile, TFA (200 mg, 77% yield). LCMS: m/z=315.2 [M+H]$^+$; rt 0.47 min, LCMS Method; Column: AQUITY UPLC BEH C18 (3.0×50 mm, 1.7 μm); mobile phase A: 10 mM NH$_4$OAc in water:acetonitrile (95:5); mobile phase B: 10 mM NH$_4$OAc in water:acetonitrile (5:95); gradient=20-100% B over 1.1 min, then a 2.2 minute hold at 100% B, flow: 0.7 mL/min.

Examples 406 and 407

4-((2R,5R)-2-(Hydroxymethyl)-5-methyl-4-(1-(4-(trifluoromethyl)phenyl)ethyl) piperazin-1-yl)-1-methyl-2-oxo-1,2-dihydropyrido[3,2-d]pyrimidine-6-carbonitrile

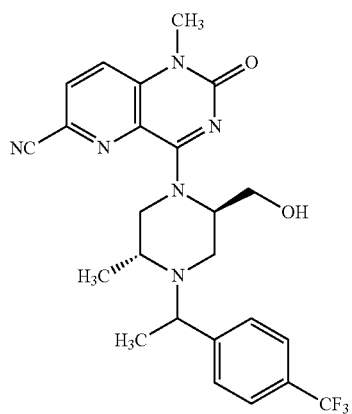

(406-407)

To a stirred solution of 4-((2R,5R)-2-(hydroxymethyl)-5-methylpiperazin-1-yl)-1-methyl-2-oxo-1,2-dihydropyrido[3,2-d]pyrimidine-6-carbonitrile, TFA (80 mg, 0.19 mmol) in acetonitrile (4 mL) were added DIPEA (0.33 mL, 1.87 mmol) and potassium iodide (31 mg, 0.19 mmol) followed by 1-(1-chloroethyl)-4-(trifluoromethyl)benzene (78 mg, 0.37 mmol). The reaction mixture was heated at 85° C. for 4 h. and then cooled to room temperature. The solvent was removed under reduced pressure to yield the crude product, which was purified by preparative HPLC (HPLC Method: Sunfire OBD (250×30 mm, 5 μm); mobile phase A: 10 mM ammonium acetate in water; mobile phase B: acetonitrile; Gradient: 65-100% B over 16 minutes, then a 5 minute hold at 100% B; Flow: 25 mL/min).

EXAMPLE 406 (18.6 mg, 20% yield); LCMS: m/z=487.2 [M+H]$^+$; rt 2.76 min; (LCMS Method: Column: Kinetex XB-C18 (3×75 mm) 2.6 μm; mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm). $^1$H NMR (400 MHz, DMSO-d$_6$) δ (ppm)=8.29-8.19 (m, 1H), 7.99 (d, J=9.0 Hz, 1H), 7.72 (d, J=8.5 Hz, 2H), 7.62 (d, J=8.0 Hz, 2H), 6.06-5.28 (m, 1H), 5.14-4.87 (m, 1H), 4.03-3.90 (m, 1H), 3.78-3.70 (m, 2H), 3.57-3.42 (m, 5H), 3.20-3.08 (m, 1H), 2.99-2.71 (m, 2H), 1.27 (br d, J=6.5 Hz, 3H), 0.90 (br d, J=6.0 Hz, 3H).

EXAMPLE 407 (23 mg, 25% yield); LCMS: m/z=487.2 [M+H]$^+$; rt 2.81 min; (LCMS Method: Column: Kinetex XB-C18 (3×75 mm) 2.6 μm; mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm). $^1$H NMR (400 MHz, DMSO-d$_6$) δ (ppm)=8.28-8.19 (m, 1H), 8.00 (br d, J=9.0 Hz, 1H), 7.69 (d, J=8.0 Hz, 2H), 7.63-7.57 (m, 2H), 5.85-5.60 (m, 1H), 4.93-4.78 (m, 1H), 4.70-4.45 (m, 2H), 3.80-3.67 (m, 2H), 3.65-3.58 (m, 2H), 3.45 (s, 3H), 3.06-2.70 (m, 1H), 2.61-2.55 (m, 1H), 1.27 (d, J=6.5 Hz, 3H), 1.04 (d, J=6.5 Hz, 3H).

Intermediate 75 tert-Butyl (2R,5R)-4-(6-chloro-1-methyl-2-oxo-1,2-dihydropyrido[3,2-d]pyrimidin-4-yl)-5-(methoxymethyl)-2-methylpiperazine-1-carboxylate (homochiral)

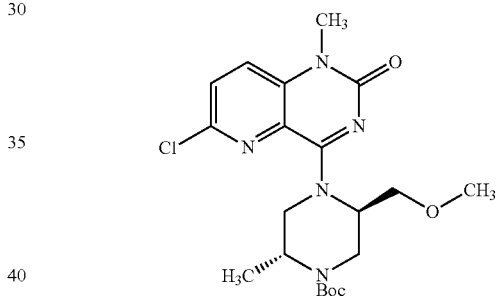

To a stirred solution of tert-butyl (2R,5R)-4-(6-chloro-1-methyl-2-oxo-1,2-dihydropyrido[3,2-d]pyrimidin-4-yl)-5-(hydroxymethyl)-2-methylpiperazine-1-carboxylate (200 mg, 0.47 mmol) in THF (5 mL) was added NaH (57 mg, 1.42 mmol, 60% w/w) at 0° C. under nitrogen. The reaction mixture was stirred for 10 min. Next, iodomethane (0.06 mL, 0.94 mmol) was added. The reaction mixture was allowed to warm to room temperature and stirred for 2 h. The reaction mixture was cooled to 0° C. The reaction was quenched with the addition of ice cold water. The mixture was extracted with EtOAc (2×50 mL). The combined organic extract was washed with brine, dried over Na$_2$SO$_4$ and concentrated to give the crude product, which was purified by silica gel flash column chromatography (5-10% MeOH in DCM) to afford a tert-butyl (2R,5R)-4-(6-chloro-1-methyl-2-oxo-1,2-dihydropyrido[3,2-d]pyrimidin-4-yl)-5-(methoxymethyl)-2-methylpiperazine-1-carboxylate (140 mg, 68% yield). LCMS: m/z, 438.2 [M+H]$^+$; rt 2.56 min. (LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 76

6-Chloro-4-((2R,5R)-2-(methoxymethyl)-5-methylpiperazin-1-yl)-1-methylpyrido[3,2-d]pyrimidin-2(1H)-one, TFA

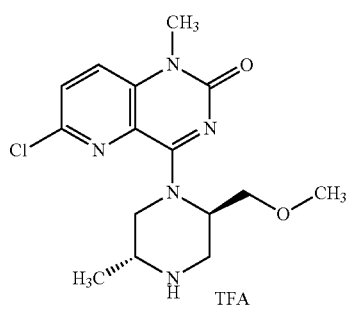 [SMILES: COC[C@H]1CN[C@H](C)CN1c1nc(=O)n(C)c2ccc(Cl)nc12]

To a stirred solution of tert-butyl (2R,5R)-4-(6-chloro-1-methyl-2-oxo-1,2-dihydropyrido[3,2-d]pyrimidin-4-yl)-5-(methoxymethyl)-2-methylpiperazine-1-carboxylate (190 mg, 0.43 mmol) in dry DCM (4 mL) was added TFA (0.17 mL, 2.17 mmol) at 0° C. The reaction mixture was allowed to warm to room temperature and stirred for 2 h. The solvent was removed under reduced pressure to afford 6-chloro-4-((2R,5R)-2-(methoxymethyl)-5-methylpiperazin-1-yl)-1-methylpyrido[3,2-d]pyrimidin-2(1H)-one, TFA (150 mg, 77% yield). LCMS: m/z=338.2 [M+H]$^+$; rt 0.57 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 1.1 min, then a 2.2 minute hold at 100% B, flow: 0.7 mL/min.

Example 408

6-Chloro-4-((2R,5R)-2-(methoxymethyl)-5-methyl-4-(1-(4-(trifluoromethyl)phenyl)ethyl) piperazin-1-yl)-1-methylpyrido[3,2-d]pyrimidin-2(1H)-one (408)

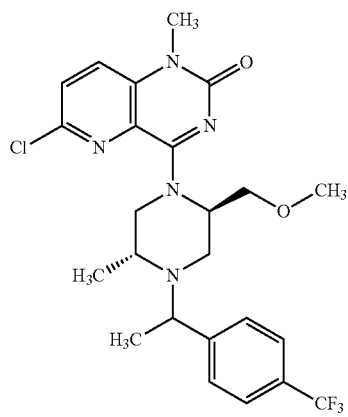

To a stirred solution of 6-chloro-4-((2R,5R)-2-(methoxymethyl)-5-methylpiperazin-1-yl)-1-methylpyrido[3,2-d]pyrimidin-2(1H)-one, TFA (100 mg, 0.22 mmol) in acetonitrile (4 mL) was added DIPEA (0.4 mL, 2.21 mmol), followed by 1-(1-chloroethyl)-4-(trifluoromethyl)benzene (92 mg, 0.44 mmol) and NaI (33.2 mg, 0.21 mmol). The reaction mixture was heated at 85° C. for 4 h. The reaction mixture was cooled to room temperature and the solvent was removed under reduced pressure to yield the crude product, which was purified by silica gel flash column chromatography (5-10% MeOH in DCM) to afford a 6-chloro-4-((2R,5R)-2-(methoxymethyl)-5-methyl-4-(1-(4-(trifluoromethyl)phenyl)ethyl)piperazin-1-yl)-1-methylpyrido[3,2-d]pyrimidin-2(1H)-one (65 mg, 58% yield). LCMS: m/z=510.2 [M+H]$^+$; rt 2.11 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 1.1 min, then a 2.2 minute hold at 100% B, flow: 0.7 mL/min.

Examples 409 and 410

4-((2R,5R)-2-(Methoxymethyl)-5-methyl-4-(1-(4-(trifluoromethyl)phenyl)ethyl) piperazin-1-yl)-1-methyl-2-oxo-1,2-dihydropyrido[3,2-d]pyrimidine-6-carbonitrile (409-410)

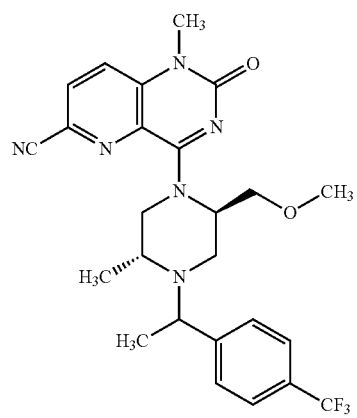

To a stirred solution of 6-chloro-4-((2R,5R)-2-(methoxymethyl)-5-methyl-4-(1-(4-(trifluoromethyl)phenyl)ethyl)piperazin-1-yl)-1-methylpyrido[3,2-d]pyrimidin-2(1H)-one (80 mg, 0.16 mmol) in DMF (10 mL) were added zinc (10 mg, 0.16 mmol) and TEA (0.11 mL, 0.78 mmol). The reaction mixture was degassed with argon gas for 5 minutes, followed by the addition of zinc cyanide (92 mg, 0.78 mmol) and dichloro[9,9-dimethyl-4,5-bis(diphenylphosphino)xanthene]palladium(II) (12 mg, 0.02 mmol). The reaction mixture was heated at 95° C. for 6 h. The reaction mixture was cooled to room temperature, filtered through Celite® pad and washed with excess DCM (50 mL). The filtrate was concentrated under reduced pressure to afford the crude product, which was purified by SFC. SFC Method: Column: Chiralpak IC (250×4.6 mm, 5 μm); mobile phase: % CO$_2$=80%; co-solvent: 20% of NH$_4$OAc in acetonitrile: methanol (50:50), total flow: 80.0 g/min. back pressure: 100 bar; temperature: 30° C.; UV detection: 215 nm. Example 409; Isolate 1: First eluting peak, rt=3.09 min; Example 410 Isolate 2: Second eluting peak, rt=3.62 min.

EXAMPLE 409: (10.2 mg, 13% yield); LCMS: m/z=501.3 [M+H]$^+$; rt 3.28 min; (LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm). $^1$H NMR (400 MHz, DMSO-$d_6$) δ (ppm)=8.29-8.20 (m, 1H), 8.01 (d, J=8.5 Hz, 1H), 7.74-7.70 (m, 2H), 7.65-7.61 (m, 2H), 5.61-5.10 (m, 1H), 4.56-4.39 (m, 1H), 3.92-3.86 (m, 2H), 3.78-3.71 (m, 3H), 3.13-3.05 (m, 3H), 2.88-2.77 (m, 1H), 1.26 (br d, J=6.5 Hz, 3H), 0.90 (br d, J=6.5 Hz, 3H).

EXAMPLE 410: (9.1 mg, 12% yield); LCMS: m/z=501.3 [M+H]$^+$; rt 3.26 min; (LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm). $^1$H NMR (400 MHz, DMSO-$d_6$) δ (ppm)=8.29-8.21 (m, 1H), 8.01 (d, J=8.5 Hz, 1H), 7.70 (d, J=8.0 Hz, 2H), 7.60 (d, J=8.0 Hz, 2H), 5.85-5.60 (m, 1H), 5.05-4.64 (m, 1H), 3.77-3.57 (m, 5H), 3.45 (s, 3H), 3.21-3.17 (m, 1H), 3.13-3.06 (m, 2H), 2.62-2.58 (m, 1H), 2.39 (br dd, J=3.3, 8.3 Hz, 1H), 1.28 (d, J=6.5 Hz, 3H), 1.04 (br d, J=6.0 Hz, 3H).

Intermediate 77

Methyl (R)-2-((S)-2-(((benzyloxy)carbonyl)amino)-3-hydroxypropanamido)butanoate

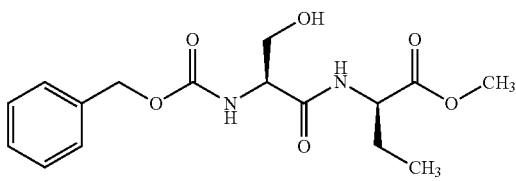 [SMILES: CC[C@@H](NC(=O)[C@H](CO)NC(=O)OCc1ccccc1)C(=O)OC]

To a stirred solution of (R)-2-aminobutanoate hydrochloride (4.82 g, 31.4 mmol), EDC (4.81 g, 25.1 mmol) and ((benzyloxy)carbonyl)-L-serine (5.0 g, 21.0 mmol) in dichloromethane (50 mL) was added DIPEA (11 mL, 62.7 mmol) dropwise. The resulting mixture was stirred under nitrogen at ambient temperature for 16 h. After removing solvent in vacuo at 40° C., the crude product was diluted with saturated sodium carbonate (20 mL), water (20 mL) and extracted with EtOAc (2×100 mL). The combined organic phase was washed with 1.5 M hydrochloric acid, brine, dried over sodium sulfate and concentrated under reduced pressure to yield methyl (R)-2-((S)-2-(((benzyloxy)carbonyl)amino)-3-hydroxypropanamido)butanoate (5.0 g, 71% yield) as an off-white solid. LCMS: m/z, 339.2 [M+H]$^+$; rt 1.12 min. (LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm). $^1$H NMR (400 MHz, DMSO-$d_6$) δ (ppm)=8.20 (br d, J=7.5 Hz, 1H), 7.41-7.27 (m, 5H), 7.13 (br d, J=8.5 Hz, 1H), 5.03 (s, 2H), 4.90-4.79 (m, 1H), 4.24-4.07 (m, 2H), 3.63-3.49 (m, 5H), 1.76-1.55 (m, 2H), 0.83 (t, J=7.3 Hz, 3H).

Intermediate 78

Methyl (R)-2-((S)-2-amino-3-hydroxypropanamido)butanoate

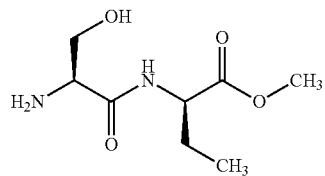

To a stirred solution of methyl (R)-2-((S)-2-(((benzyloxy)carbonyl)amino)-3-hydroxypropanamido)butanoate (4.0 g, 11.8 mmol) in MeOH (40 mL) was added 10% palladium on carbon (1.26 g, 1.18 mmol). The reaction mixture was stirred under a hydrogen atmosphere at 1 atm for 16 h. The reaction mixture was filtered through Celite® pad, washed with excess MeOH (50 mL) and the filtrate was removed under reduced pressure to give methyl (R)-2-((S)-2-amino-3-hydroxypropanamido)butanoate (2.3 g, 95% yield). LCMS: m/z, 205.2 [M+H]$^+$; rt 1.19 min. LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: ELSD detector.

Intermediate 79

(3R,6S)-3-Ethyl-6-(hydroxymethyl)piperazine-2,5-dione

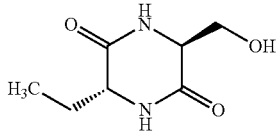

Methyl (R)-2-((S)-2-amino-3-hydroxypropanamido)butanoate (1.0 g, 4.90 mmol) was added to MeOH (8 mL). The reaction mixture was heated at 70° C. for 14 h. The reaction mixture was cooled to room temperature and concentrated under reduced pressure to give (3R,6S)-3-ethyl-6-(hydroxymethyl)piperazine-2,5-dione (0.7 g, 83% yield). 41 NMR (400 MHz, DMSO-$d_6$) δ (ppm)=8.05 (s, 1H), 7.93 (s, 1H), 5.08 (br s, 1H), 3.86 (t, J=4.5 Hz, 1H), 3.77-3.67 (m, 2H), 3.56-3.49 (m, 1H), 1.85-1.56 (m, 2H), 0.81 (t, J=7.3 Hz, 3H).

Intermediate 80

((2R,5R)-5-Ethylpiperazin-2-yl)methanol, 2 HCl

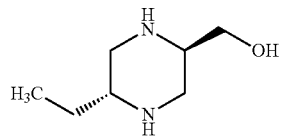

333

To (3R,6S)-3-ethyl-6-(hydroxymethyl)piperazine-2,5-dione (0.8 g, 4.65 mmol) was added a solution of 1 M borane in THF (35 mL, 34.8 mmol). The mixture was heated at 70° C. for 18 h. and then cooled to 0° C. Next, MeOH (10 mL) was gradually added, followed by the addition of 5 M hydrochloric acid (5 mL). The mixture was refluxed for 2 h at 70° C. and then cooled to ambient temperature. The resulting solid was filtered, triturated with THF (20 mL) and dried to give ((2R,5R)-5-ethylpiperazin-2-yl) methanol, 2 HCl (700 mg, 69% yield). $^1$H NMR (400 MHz, DMSO-d$_6$) δ (ppm)=10.19-9.87 (m, 1H), 9.84-9.60 (m, 1H), 3.76-3.55 (m, 3H), 3.52-3.45 (m, 2H), 3.42-3.35 (m, 2H), 3.17-3.04 (m, 2H), 1.83-1.60 (m, 2H), 0.97 (t, J=7.5 Hz, 3H).

Intermediate 81 tert-Butyl (2R,5R)-2-ethyl-5-(hydroxymethyl)piperazine-1-carboxylate

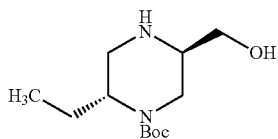 [SMILES: CC[C@@H]1CN[C@@H](CO)CN1C(=O)OC(C)(C)C]

To an ice cooled stirred solution of ((2R,5R)-5-ethylpiperazin-2-yl)methanol, 2 HCl (2.0 g, 9.21 mmol) in MeOH (10 mL), TEA (12.8 mL, 92 mmol) was added. The reaction mixture was stirred for 5 min. and Boc-anhydride (8.6 mL, 36.8 mmol) in MeOH (10 mL) was added dropwise over a period of 15 min. The reaction mixture was allowed to reach to room temperature, stirred for 1 h followed by heating at 50° C. for 16 h. The reaction mixture was concentrated and dissolved in EtOH (10 mL). A solution of NaOH (1.0 g, 25.0 mmol) in water (5 mL) was added and the reaction mixture was heated at 100° C. for 16 h, then cooled to room temperature, pH was adjusted to ~9 by aqueous 1.5 N HCl and extracted with chloroform (3×80 mL). The combined organic extract was dried over sodium sulfate, filtered and concentrated to give tert-butyl (2R,5R)-2-ethyl-5-(hydroxymethyl)piperazine-1-carboxylate (1.8 g, 80% yield). $^1$H NMR (400 MHz, METHANOL-d$_4$) δ (ppm)=3.97-3.90 (m, 1H), 3.89-3.82 (m, 1H), 3.71-3.63 (m, 1H), 3.58-3.52 (m, 1H), 3.15 (dd, J=4.5, 14.1 Hz, 1H), 3.02 (dd, J=5.0, 13.1 Hz, 1H), 2.92-2.85 (m, 1H), 2.60 (dd, J=2.8, 12.8 Hz, 1H), 1.97-1.82 (m, 1H), 1.68-1.57 (m, 1H), 1.48 (s, 9H), 0.90 (t, J=7.5 Hz, 3H).

334

Intermediate 82 tert-Butyl (2R,5R)-4-(6-chloro-1-methyl-2-oxo-1,2-dihydropyrido[3,2-d]pyrimidin-4-yl)-2-ethyl-5-(hydroxymethyl)piperazine-1-carboxylate (homochiral)

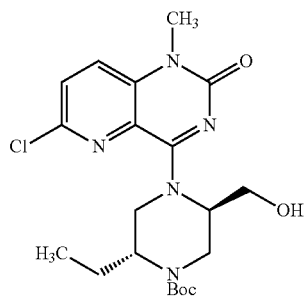 [SMILES: CC[C@@H]1CN(c2nc(=O)n(C)c3ccc(Cl)nc23)[C@@H](CO)CN1C(=O)OC(C)(C)C]

To a stirred solution of 4,6-dichloro-1-methylpyrido[3,2-d]pyrimidin-2(1H)-one (300 mg, 1.30 mmol) in acetonitrile (8 mL), DIPEA (2.3 mL, 13.04 mmol) and 4 tert-butyl (2R,5R)-2-ethyl-5-(hydroxymethyl)piperazine-1-carboxylate (382 mg, 1.57 mmol) were added sequentially at room temperature followed by heating at 80° C. for 12 h. The reaction mixture was cooled to room temperature and the solvent was removed under reduced pressure to give the crude product, which was purified by silica gel column chromatography using 7-10% MeOH in CHCl$_3$ to afford tert-butyl (2R,5R)-4-(6-chloro-1-methyl-2-oxo-1,2-dihydropyrido[3,2-d]pyrimidin-4-yl)-2-ethyl-5-(hydroxymethyl) piperazine-1-carboxylate (200 mg, 35% yield). LCMS: m/z, 438.3 [M+H]$^+$; rt 1.43 min, LCMS Method; Column: AQUITY UPLC BEH C18 (3.0×50 mm, 1.7 μm); mobile phase A:10 mM NH$_4$OAc in water:acetonitrile (95: 5); mobile phase B: 10 mM NH$_4$OAc in water:acetonitrile (5:95); gradient=20-100% B over 2 min, then a 1 minute hold at 100% B, flow: 0.7 mL/min.

Intermediate 83 tert-Butyl (2R,5R)-4-(6-cyano-1-methyl-2-oxo-1,2-dihydropyrido[3,2-d]pyrimidin-4-yl)-2-ethyl-5-(hydroxymethyl)piperazine-1-carboxylate (homochiral)

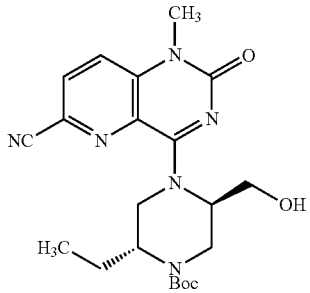 [SMILES: CC[C@@H]1CN(c2nc(=O)n(C)c3ccc(C#N)nc23)[C@@H](CO)CN1C(=O)OC(C)(C)C]

To a stirred solution of tert-butyl (2R,5R)-4-(6-chloro-1-methyl-2-oxo-1,2-dihydropyrido[3,2-d]pyrimidin-4-yl)-2-ethyl-5-(hydroxymethyl)piperazine-1-carboxylate (200 mg, 0.46 mmol) in DMF (10 mL) were added zinc (30 mg, 0.46 mmol) and TEA (0.32 mL, 2.28 mmol). The reaction mixture was flushed with argon for 5 minutes, followed by the addition of zinc cyanide (161 mg, 1.37 mmol) and dichloro [9,9-dimethyl-4,5-bis(diphenylphosphino)xanthene]palladium(II) (35 mg, 0.05 mmol). The reaction mixture was heated at 95° C. for 6 h, cooled to room temperature, filtered through Celite® pad and washed with excess DCM (50 mL). The filtrate was concentrated under reduced pressure to afford the crude product, which was purified by silica gel column chromatography using 7-10% MeOH in CHCl$_3$ to afford a tert-butyl (2R,5R)-4-(6-cyano-1-methyl-2-oxo-1,2-dihydropyrido[3,2-d]pyrimidin-4-yl)-2-ethyl-5-(hydroxymethyl) piperazine-1-carboxylate (150 mg, 77% yield). LCMS: m/z, 429.3 [M+H]$^+$; rt 1.25 min, LCMS Method; Column: AQUITY UPLC BEH C18 (3.0×50 mm, 1.7 μm); mobile phase A:10 mM NH$_4$OAc in water:acetonitrile (95: 5); mobile phase B: 10 mM NH$_4$OAc in water:acetonitrile (5:95); gradient=20-100% B over 2 min, then a 1 minute hold at 100% B, flow: 0.7 mL/min.

Intermediate 84

4-((2R,5R)-5-ethyl-2-(hydroxymethyl)piperazin-1-yl)-1-methyl-2-oxo-1,2-dihydropyrido[3,2-d]pyrimidine-6-carbonitrile, TFA

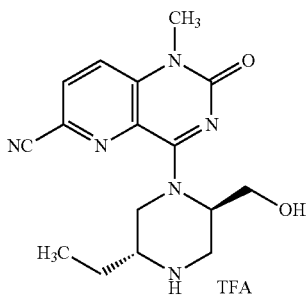 [SMILES: CC[C@@H]1CN(c2nc(=O)n(C)c3ccc(C#N)nc23)[C@@H](CO)CN1]

To a stirred solution of tert-butyl (2R,5R)-4-(6-cyano-1-methyl-2-oxo-1,2-dihydropyrido[3,2-d]pyrimidin-4-yl)-2-ethyl-5-(hydroxymethyl)piperazine-1-carboxylate (150 mg, 0.35 mmol) in dry DCM (4 mL) was added TFA (0.3 mL, 3.50 mmol) at 0° C. The reaction mixture was allowed to warm to room temperature and stirred for 2 h. The solvent was removed under reduced pressure to afford 4-((2R,5R)-5-ethyl-2-(hydroxymethyl)piperazin-1-yl)-1-methyl-2-oxo-1,2-dihydropyrido[3,2-d]pyrimidine-6-carbonitrile, TFA (120 mg, 77% yield). LCMS: m/z=329.2 [M+H]$^+$; rt 0.56 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 1.1 min, then a 2.2 minute hold at 100% B, flow: 0.7 mL/min.

Examples 411 and 412

4-((2R,5R)-5-Ethyl-2-(hydroxymethyl)-4-(1-(4-(trifluoromethyl)phenyl)ethyl)piperazin-1-yl)-1-methyl-2-oxo-1,2-dihydropyrido[3,2-d]pyrimidine-6-carbonitrile (411-412)

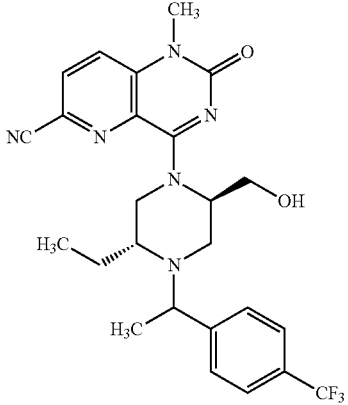

To a stirred solution of 4-((2R,5R)-5-ethyl-2-(hydroxymethyl)piperazin-1-yl)-1-methyl-2-oxo-1,2-dihydropyrido[3,2-d]pyrimidine-6-carbonitrile, TFA (80 mg, 0.18 mmol) in acetonitrile (4 mL) were added DIPEA (0.32 mL, 1.81 mmol) and sodium iodide (27.1 mg, 0.18 mmol) followed by the addition of 1-(1-chloroethyl)-4-(trifluoromethyl) benzene (45 mg, 0.22 mmol). The reaction mixture was heated at 85° C. for 4 h, cooled to room temperature and the solvent was removed under reduced pressure to yield the crude product, which was purified by preparative HPLC (HPLC Method: Column: GEMINI NX C18 (250×21.2 mm, 5 μm); mobile phase A: 10 mM ammonium acetate in water, pH 4.5; mobile phase B: acetonitrile; Gradient: 40-58% B over 20 minutes, then a 5 minute hold at 100% B; Flow: 20 mL/min.

EXAMPLE 411: (4.1 mg, 5% yield); LCMS: m/z=501.4 [M+H]$^+$; rt 1.98 min; (LCMS Method: Column: Kinetex XB-C18 (3×75 mm, 2.6 μm); mobile phase A: 10 mM ammonium formate in water (pH 3.3), mobile phase B: acetonitrile, Gradient=20-100% B over 4 minutes, then a 0.6 minute hold at 100% B; Temperature: 27° C.; Flow rate: 1.0 mL/min; Detection: UV at 220 nm).

EXAMPLE 412: (4.8 mg, 5% yield); LCMS: m/z=501.3 [M+H]$^+$; rt 2.13 min; LCMS Method: Column: Kinetex XB-C18 (3×75 mm, 2.6 μm); mobile phase A: 10 mM ammonium formate in water (pH 3.3), mobile phase B: acetonitrile, Gradient=20-100% B over 4 minutes, then a 0.6 minute hold at 100% B; Temperature: 27° C.; Flow rate: 1.0 mL/min; Detection: UV at 220 nm.

Intermediate 85

6-Chloro-3-((4-methoxybenzyl)amino)picolinonitrile

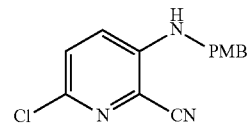

To a solution of 3-amino-6-chloropicolinonitrile (3 g, 19.54 mmol) in ethyl acetate (60 mL) at room temperature were added 4-methoxybenzaldehyde (2.66 g, 19.54 mmol) and TFA (1.505 mL, 19.54 mmol). The reaction mixture was stirred at room temperature for 1 h. Sodium triacetoxyborohydride (6.21 g, 29.3 mmol) was added and the reaction mixture was stirred at room temperature for 3 h. The reaction was quenched with the addition of water. The reaction mixture was extracted with ethyl acetate (2×100 mL), the combined organic layer was washed with water, brine and dried over sodium sulfate. The solvent was evaporated under reduced pressure to yield the crude product, which was purified by silica gel column chromatography using 30% EtOAc in pet ether. The fractions were concentrated under reduced pressure to yield the product 6-chloro-3-((4-methoxybenzyl)amino) picolinonitrile (2 g, 30% yield). LCMS: m/z=274.2 [M+H]$^+$; rt 2.69 min; LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Intermediate 86

6-Chloro-3-((4-methoxybenzyl)amino)picolinamide

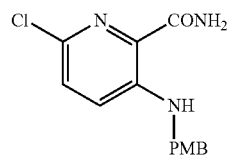

To a solution of 6-chloro-3-((4-methoxybenzyl)amino) picolinonitrile (2 g, 7.31 mmol) in DMSO (10 mL) and water (5 mL) were added K$_2$CO$_3$ (2.020 g, 14.61 mmol) and H$_2$O$_2$ (1.493 mL, 14.61 mmol, 30% water) at room temperature. The reaction mixture was stirred for 4 h. The reaction was quenched with the addition of water. The reaction mixture was extracted with ethyl acetate (2×100 mL), the combined organic layer was washed with water, brine and dried over sodium sulfate. The solvent was evaporated under reduced pressure to yield the crude product, which was purified by silica gel column chromatography using 30% EtOAc in pet ether. The fractions were concentrated under reduced pressure to yield 6-chloro-3-((4-methoxybenzyl)amino)picolinamide (1.5 g, 42. % yield). LCMS: m/z=292.1 [M+H]$^+$; rt 1.58 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 1.1 min, then a 0.6 minute hold at 100% B, flow: 0.7 mL/min.

Intermediate 87

6-Chloro-1-(4-methoxybenzyl)pyrido[3,2-d]pyrimidine-2,4(1H,3H)-dione

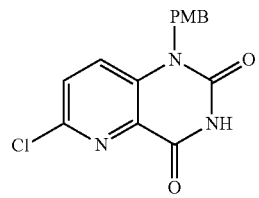

To a solution of 6-chloro-3-((4-methoxybenzyl)amino) picolinamide (1.3 g, 4.46 mmol) in DMF (15 mL) was added sodium hydride (0.356 g, 8.91 mmol, 60% w/w) at 0° C. The reaction mixture was stirred for 1 h. and CDI (1.084 g, 6.68 mmol) was added. The reaction mixture was heated at 70° C. for 2 h. Cold water was added to quench the reaction. The reaction mixture was acidified with 1 N HCl, filtered the yellow solid formed, dried under reduced pressure to yield 6-chloro-1-(4-methoxybenzyl)pyrido[3,2-d]pyrimidine-2,4 (1H,3H)-dione (0.8 g, 57% yield). LCMS: m/z=318.1 [M+H]$^+$; rt 1.06 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 1.1 min, then a 0.6 minute hold at 90% B, flow: 0.7 mL/min.

Intermediate 88

4,6-Dichloro-1-(4-methoxybenzyl)pyrido[3,2-d]pyrimidin-2(1H)-one

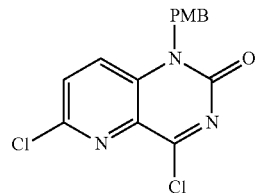

To a solution of 6-chloro-1-(4-methoxybenzyl)pyrido[3,2-d]pyrimidine-2,4(1H,3H)-dione (1.5 g, 4.72 mmol) in toluene (50 mL) at room temperature were added DIPEA (2.061 mL, 11.80 mmol) and phosphoryl chloride (2.2 mL, 23.61 mmol). The reaction mixture was heated at 110° C. for 16 h. The reaction mixture was concentrated under reduced pressure to yield 4,6-dichloro-1-(4-methoxybenzyl)pyrido [3,2-d]pyrimidin-2(1H)-one (1.5 g, 94% yield). LCMS: m/z=336.0 [M+H]$^+$; rt 2.2 min; LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Intermediate 89 tert-Butyl (2R,5S)-4-(6-chloro-1-(4-methoxybenzyl)-2-oxo-1,2-dihydropyrido[3,2-d]pyrimidin-4-yl)-2-ethyl-5-methylpiperazine-1-carboxylate

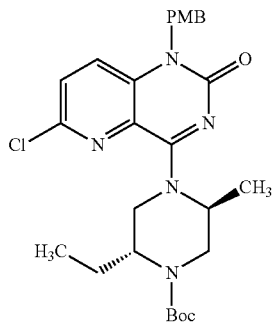

To a solution of tert-butyl (2R,5S)-2-ethyl-5-methylpiperazine-1-carboxylate (0.5 g, 1.74 mmol) in acetonitrile (20 mL) was added DIPEA (3.04 mL, 17.40 mmol) at room temperature. The reaction mixture was stirred for 15 mins. and 4,6-dichloro-1-(4-methoxybenzyl)pyrido[3,2-d]pyrimidin-2(1H)-one (0.585 g, 1.74 mmol) was added. The reaction mixture was heated at 85° C. for 16 h. The reaction was quenched with the addition of water. The mixture was extracted with ethyl acetate (2×100 mL). The combined organic layer was washed with water, brine and dried over sodium sulfate, concentrated under reduced pressure to yield the crude product, which was purified by silica gel column chromatography using 30% EtOAc in pet ether. The fractions were concentrated under reduced pressure to yield tert-butyl (2R,5S)-4-(6-chloro-1-(4-methoxybenzyl)-2-oxo-1,2-dihydropyrido[3,2-d]pyrimidin-4-yl)-2-ethyl-5-methylpiperazine-1-carboxylate (0.55 g, 51% yield). LCMS: m/z=528.2 [M+H]$^+$; rt 3.4 min; LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Intermediate 90 tert-Butyl (2R,5S)-4-(6-cyano-1-(4-methoxybenzyl)-2-oxo-1,2-dihydropyrido[3,2-d]pyrimidin-4-yl)-2-ethyl-5-methylpiperazine-1-carboxylate

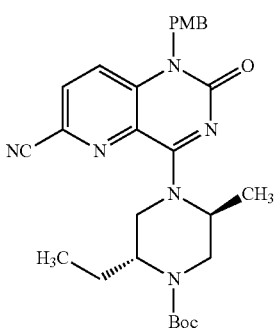

To a stirred solution of tert-butyl (2R,5S)-4-(6-chloro-1-(4-methoxybenzyl)-2-oxo-1,2-dihydropyrido[3,2-d]pyrimidin-4-yl)-2-ethyl-5-methylpiperazine-1-carboxylate (0.5 g, 0.95 mmol) in NMP (2 mL) at room temperature were added zinc cyanide (0.222 g, 1.89 mmol), zinc (0.062 g, 0.95 mmol), and Pd$_2$(dba)$_3$ (0.087 g, 0.1 mmol), dppf (0.105 g, 0.19 mmol). The reaction mixture was heated at 90° C. for overnight. The reaction mixture was diluted with EtOAc, filtered through Celite® pad and the filtrate was concentrated under reduced pressure to yield the crude product, which was purified by silica gel column chromatography using 80% EtOAc in pet ether. The fractions were concentrated under reduced pressure to yield tert-butyl (2R,5S)-4-(6-cyano-1-(4-methoxybenzyl)-2-oxo-1,2-dihydropyrido[3,2-d]pyrimidin-4-yl)-2-ethyl-5-methylpiperazine-1-carboxylate (0.43 g, 28% yield). LCMS: m/z=519.4 [M+H]$^+$; rt 1.83 min LCMS Method: Column: Acquity UPLC BEH C18 (2.1×50 mm, 1.7 μm); mobile phase A: 10 mM NH$_4$OAc in water:acetonitrile (95:5); mobile phase B: 10 mM NH$_4$OAc in water:acetonitrile (5:95), Gradient=20-90% B over 1.1 minute, then a 0.6 minute hold at 90% B; Temperature: 50° C.; Flow rate: 0.7 mL/min; Detection: UV at 220 nm.

Intermediate 91

4-((2S,5R)-5-Ethyl-2-methylpiperazin-1-yl)-1-(4-methoxybenzyl)-2-oxo-1,2-dihydropyrido[3,2-d]pyrimidine-6-carbonitrile.HCl

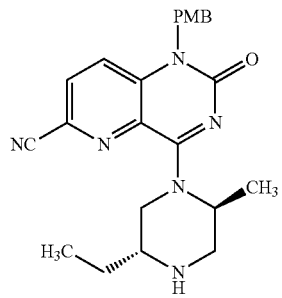

To a solution of tert-butyl (2R,5S)-4-(6-cyano-1-(4-methoxybenzyl)-2-oxo-1,2-dihydropyrido[3,2-d]pyrimidin-4-yl)-2-ethyl-5-methylpiperazine-1-carboxylate (400 mg, 0.77 mmol) in ethyl acetate (5 mL) was added HCl in 1,4-Dioxane (4M, 1.9 mL, 7.71 mmol) at 0° C. The reaction mixture was stirred at room temperature for 6 h. The reaction mixture was evaporated under reduced pressure to yield 4-((2S,5R)-5-ethyl-2-methylpiperazin-1-yl)-1-(4-methoxybenzyl)-2-oxo-1,2-dihydropyrido[3,2-d]pyrimidine-6-carbonitrile, HCl (250 mg, yield 77%). LCMS: m/z=419.2 [M+H]$^+$; rt 1.76 min; LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

341

Intermediate 92

4-((2S,5R)-5-Ethyl-2-methyl-4-(1-(4-(trifluoromethyl)phenyl)ethyl)piperazin-1-yl)-1-(4-methoxybenzyl)-2-oxo-1,2-dihydropyrido[3,2-d]pyrimidine-6-carbonitrile

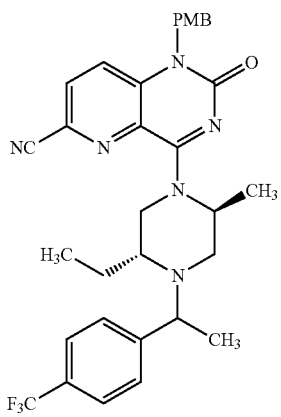

To a solution of 4-((2S,5R)-5-ethyl-2-methylpiperazin-1-yl)-1-(4-methoxybenzyl)-2-oxo-1,2-dihydropyrido[3,2-d]pyrimidine-6-carbonitrile, HCl (0.4 g, 0.879 mmol) in acetonitrile (20 mL) were added DIPEA (0.768 mL, 4.4 mmol), 1-(1-chloroethyl)-4-(trifluoromethyl)benzene (0.55 g, 2.64 mmol) and sodium iodide (0.132 g, 0.879 mmol) at room temperature. The reaction mixture was heated at 85° C. for 16 h. The reaction was quenched with saturated aqueous NH$_4$Cl solution. The reaction mixture was extracted with ethyl acetate (2×100 mL), the combined organic layer was washed with water, brine and dried over sodium sulfate, and concentrated under reduced pressure to yield the crude product, which was purified by silica gel column chromatography using 30% EtOAc in pet ether. The fractions were concentrated under reduced pressure to yield 4-((2S,5R)-5-ethyl-2-methyl-4-(1-(4-(trifluoromethyl)phenyl)ethyl) piperazin-1-yl)-1-(4-methoxybenzyl)-2-oxo-1,2-dihydropyrido[3,2-d]pyrimidine-6-carbonitrile (0.2 g, 35% yield). LCMS: m/z=591.2 [M+H]$^+$; rt 3.77 min; LCMS Method: Column: Kinetex XB-C18 (3×75 mm, 2.6 μm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

342

Examples 413 and 414

4-((2S,5R)-5-Ethyl-2-methyl-4-(1-(4-(trifluoromethyl)phenyl)ethyl)piperazin-1-yl)-2-oxo-1,2-dihydropyrido[3,2-d]pyrimidine-6-carbonitrile (413-414)

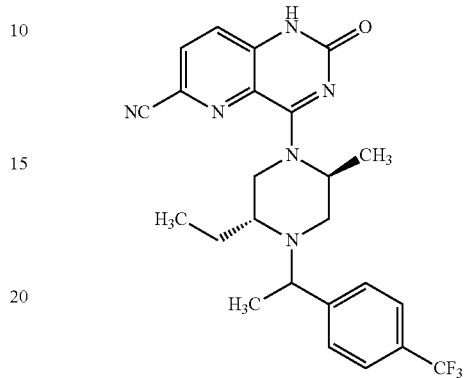

To a solution of 4-((2S,5R)-5-ethyl-2-methyl-4-(1-(4-(trifluoromethyl)phenyl) ethyl)piperazin-1-yl)-1-(4-methoxybenzyl)-2-oxo-1,2-dihydropyrido[3,2-d]pyrimidine-6-carbonitrile (150 mg, 0.25 mmol) in TFA (1.5 mL, 19.47 mmol) at 0° C. was added trifluoromethane sulfonic acid (0.75 mL, 8.45 mmol). The reaction mixture was stirred at room temperature for 4 h. The reaction mixture was basified with NaHCO$_3$ solution and extracted with EtOAc. The organic layer was washed with water, brine and dried over sodium sulfate. The solvent was evaporated under reduced pressure to yield crude product, which was purified by preparative HPLC Method: Column: YMC TRIART C18 EXRS (250× 20 mm, 5 μm); mobile phase A:10 mM ammonium acetate in water; mobile phase B: acetonitrile; Flow: 20 mL/min] to yield Examples 413 and 414.

EXAMPLE 413: (30 mg, 25% yield), LCMS: m/z=469.2 [M−H]; rt 3.19 min; LCMS Method: Column: Kinetex XB-C18 (3×75 mm, 2.6 μm); mobile phase A: 10 mM ammonium formate in water (pH 3.3); mobile phase B: acetonitrile, Gradient=20-100% B over 4 minutes, then a 0.6 minute hold at 100% B; Temperature: 27° C.; Flow rate: 1.0 mL/min; Detection: UV at 220 nm. $^1$H NMR (DMSO-d$_6$, 400 MHz) δ (ppm)=10.9-11.2 (m, 1H), 8.06 (d, J=8.5 Hz, 1H), 7.71-7.73 (m, 2H), 7.6-7.7 (m, 3H), 5.62-5.97(m, 1H), 4.86-5.29(m, 1H), 3.82-3.85(m, 1H), 2.7-2.9 (m, 2H), 2.6-2.7 (m, 1H), 2.2-2.5 (m, 1H), 1.4-1.6 (m, 5H), 1.29 (d, J=6.5 Hz, 3H), 0.70 (t, J=7.3 Hz, 3H).

EXAMPLE 414: (30 mg, 25% yield), LCMS: m/z=471.2 [M+H]$^+$; rt 3.33 min; LCMS Method: Column: Kinetex XB-C18 (3×75 mm, 2.6 μm); mobile phase A: 10 mM ammonium formate in water (pH 3.3); mobile phase B: acetonitrile, Gradient=20-100% B over 4 minutes, then a 0.6 minute hold at 100% B; Temperature: 27° C.; Flow rate: 1.0 mL/min; Detection: UV at 220 nm. $^1$H NMR (DMSO-d$_6$, 400 MHz) δ (ppm)=10.8-11.7(m, 1H), (8.08 (d, 1H, J=8.8 Hz), 7.7-7.7 (m, 2H), 7.6-7.7 (m, 3H), 4.6-6.3(m, 2H), 3.70-3.76 (m, 1H), 3.09-3.11 (m, 1H), 3.1-3.1 (m, 1H), 2.58-2.62 (m, 1H), 2.15-2.18 (m, 1H), 1.4-1.6 (m, 2H), 1.2-1.3 (m, 6H), 1.01 (t, 3H, J=7.4 Hz).

The example in the Table 18 were prepared according to the general procedure described in Examples 413 and 414. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 18

| Ex. No. | Structure | Stereo chem. | LCMS Method | LCMS rt | [M + H]+ |
|---|---|---|---|---|---|
| 415 | 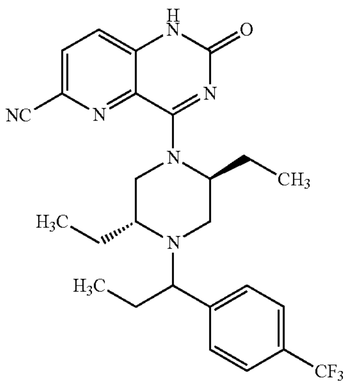 [SMILES: CCC(c1ccc(C(F)(F)F)cc1)N1C[C@H](CC)N(c2nc(=O)[nH]c3ccc(C#N)nc23)C[C@H]1CC] | H | E | 3.19 | 499.3 |
| 416 | | H | E | 2.70 | 499.2 |

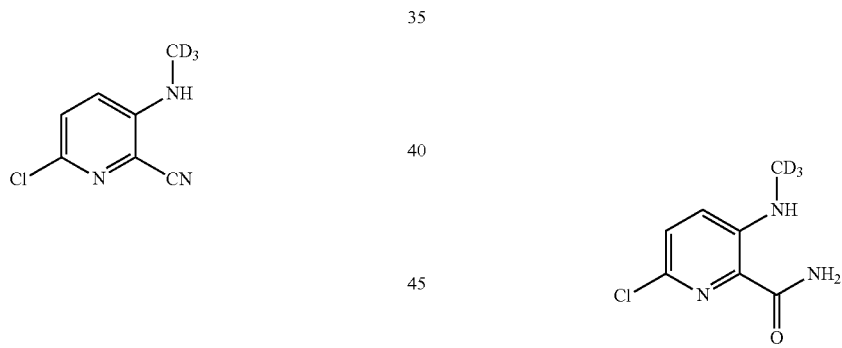

Intermediate 93

6-Chloro-3-((methyl-d$_3$)amino)picolinonitrile

To a solution of N-(6-chloro-2-cyanopyridin-3-yl)-2,2,2-trifluoroacetamide (3 g, 12.02 mmol) in DMF (15 mL) at room temperature was added potassium carbonate (4.15 g, 30.1 mmol), followed by iodomethane-d3 (3.9 mL, 60.1 mmol). The reaction mixture was stirred for 16 h. The reaction was quenched with the addition of water. The mixture was extracted with ethyl acetate (2×100 mL), the combined organic layer was washed with water, brine and dried over sodium sulfate. The solvent was evaporated under reduced pressure to yield the crude product, which was purified by silica gel column chromatography using 30% EtOAc in pet ether. The fractions were concentrated under reduced pressure to yield N-(6-chloro-2-cyanopyridin-3-yl)-2,2,2-trifluoro-N-(methyl-d$_3$) acetamide (1.5 g, 47% yield). LCMS: m/z=171.1 [M+H]+; rt 1.19 min, LCMS Method; Column: AQUITY UPLC BEH C18 (3.0×50 mm, 1.7 µm); mobile phase A:10 mM NH$_4$OAc in water:acetonitrile (95: 5); mobile phase B: 10 mM NH$_4$OAc in water:acetonitrile (5:95); gradient=20-100% B over 1.1 min, then a 2.2 minute hold at 100% B, flow: 0.7 mL/min.

Intermediate 94

6-Chloro-3-((methyl-d$_3$)amino)picolinamide

To a solution of 6-chloro-3-((methyl-d$_3$)amino)picolinonitrile (2 g, 11.72 mmol) in DMSO (100 mL) and water (50 mL) were added potassium carbonate (3.24 g, 23.44 mmol) and hydrogen peroxide (2.4 mL, 23.44 mmol, 30% in water) at 0° C. The reaction mixture was stirred at room temperature for 3 h. The reaction mixture was diluted with water and the precipitate formed was filtered, dried under reduced pressure to yield 6-chloro-3-((methyl-d$_3$)amino)picolinamide (1 g, 45% yield). LCMS: m/z=189.1 [M+H]+; rt 1.06 min, LCMS Method; Column: AQUITY UPLC BEH C18 (3.0×50 mm, 1.7 µm); mobile phase A:10 mM NH$_4$OAc in water: acetonitrile (95:5); mobile phase B: 10 mM NH$_4$OAc in water:acetonitrile (5:95); gradient=20-100% B over 2 min, then a 1 minute hold at 100% B, flow: 0.7 mL/min.

Intermediate 95

6-Chloro-4-hydroxy-1-(methyl-d₃)pyrido[3,2-d]pyrimidin-2(1H)-one

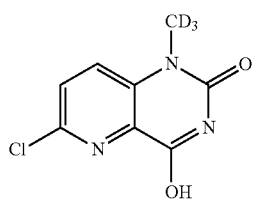 [SMILES: [2H]C([2H])([2H])n1c(=O)nc(O)c2nc(Cl)ccc21]

To a solution of 6-chloro-3-((methyl-d₃)amino)picolinamide (1.4 g, 7.42 mmol) in DMF (10 mL) at 0° C. were added sodium hydride (0.594 g, 14.84 mmol, 60% w/w) and CDI (1.805 g, 11.13 mmol). The reaction mixture was stirred at room temperature for 3 h. The reaction was quenched with the addition of ice water. The mixture was acidified with 1.5 N HCl. The mixture was filtered to separate a yellow solid, which was dried under reduced pressure to yield 6-chloro-1-(methyl-d₃) pyrido[3,2-d]pyrimidine-2,4(1H,3H)-dione (1.0 g, 62% yield). LCMS: m/z=215.1 [M+H]⁺; rt 0.50 min, LCMS Method; Column: AQUITY UPLC BEH C18 (3.0× 50 mm, 1.7 µm); mobile phase A:10 mM NH₄OAc in water:acetonitrile (95:5); mobile phase B: 10 mM NH₄OAc in water:acetonitrile (5:95); gradient=20-100% B over 2 min, then a 1 minute hold at 100% B, flow: 0.7 mL/min.

Intermediate 96

4,6-Dichloro-1-(methyl-d₃)pyrido[3,2-d]pyrimidin-2(1H)-one

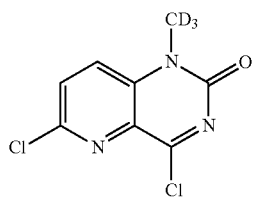 [SMILES: [2H]C([2H])([2H])n1c(=O)nc(Cl)c2nc(Cl)ccc21]

To a solution of 6-chloro-4-hydroxy-1-(methyl-d₃)pyrido[3,2-d]pyrimidin-2(1H)-one (0.5 g, 2.33 mmol) in toluene (30 mL) at room temperature were added DIPEA (1.0 mL, 5.82 mmol) and phosphoryl chloride (1.1 mL, 11.65 mmol). The reaction mixture was heated at 110° C. for 16 h. The reaction mixture was concentrated under reduced pressure to yield 4,6-dichloro-1-(methyl-d₃)pyrido[3,2-d]pyrimidin-2(1H)-one (0.4 g, 74% yield). LCMS: m/z=232.9 (M+H); retention time 0.84 min. (Column: AQUITY UPLC BEH C18 (3.0×50 mm, 1.7 µm), mobile phase A:10 mM NH₄OAc in water:acetonitrile (95:5); mobile phase B: 10 mM NH₄OAc in water:acetonitrile (5:95); gradient=20-100% B over 2 min, then a 1 minute hold at 100% B, flow: 0.7 mL/min.

Intermediate 97 tert-Butyl (2R,5S)-4-(6-chloro-1-(methyl-d₃)-2-oxo-1,2-dihydropyrido[3,2-d]pyrimidin-4-yl)-2-ethyl-5-methylpiperazine-1-carboxylate

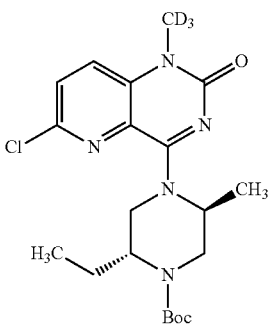

To a solution of tert-butyl (2R,5S)-2-ethyl-5-methylpiperazine-1-carboxylate (0.5 g, 2.190 mmol) in acetonitrile (20 mL) at room temperature was added DIPEA (3.8 mL, 21.90 mmol), followed by 4,6-dichloro-1-(methyl-d₃)pyrido[3,2-d]pyrimidin-2(1H)-one (0.510 g, 2.19 mmol). The reaction mixture was heated at 85° C. for 16 h. The reaction was quenched with the addition of water. The mixture was extracted with ethyl acetate (2×100 mL), the combined organic layer was washed with water, brine and dried over sodium sulfate. The solvent was evaporated under reduced pressure to yield the crude product, which was purified by silica gel column chromatography using 90% EtOAc in pet ether. The fractions were concentrated under reduced pressure to yield tert-butyl (2R,5S)-4-(6-chloro-1-(methyl-d₃)-2-oxo-1,2-dihydropyrido[3,2-d]pyrimidin-4-yl)-2-ethyl-5-methylpiperazine-1-carboxylate (0.4 g, 41% yield). LCMS: m/z=425.2 [M+H]⁺; rt 2.77 min; LCMS method: Column: Kinetex XB-C18 (3×75 mm, 2.6 µm); mobile phase A: 10 mM ammonium formate:acetonitrile (98:2), mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Intermediate 98

6-Chloro-4-((2S,5R)-5-ethyl-2-methylpiperazin-1-yl)-1-(methyl-d₃)pyrido[3,2-d]pyrimidin-2(1H)-one.TFA

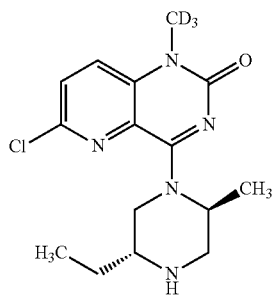 [SMILES: [2H]C([2H])([2H])n1c(=O)nc(N2C[C@@H](CC)NC[C@@H]2C)c2nc(Cl)ccc21]

To a solution of tert-butyl (2R,5S)-4-(6-chloro-1-(methyl-d$_3$)-2-oxo-1,2-dihydropyrido[3,2-d]pyrimidin-4-yl)-2-ethyl-5-methylpiperazine-1-carboxylate (0.42 g, 0.988 mmol) in DCM (5 mL) at 0° C. was added TFA (1.2 mL, 14.8 mmol). The reaction mixture was stirred at room temperature for 3 h. The volatiles were removed under reduced pressure to yield 6-chloro-4-((2S,5R)-5-ethyl-2-methylpiperazin-1-yl)-1-(methyl-d$_3$)pyrido[3,2-d]pyrimidin-2(1H)-one, TFA (0.4 g, 76% yield). LCMS: m/z=325.2 [M+H]$^+$; rt 0.67 min, LCMS Method; Column: AQUITY UPLC BEH C18 (3.0× 50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min.

Examples 417 and 418

6-Chloro-4-((2S,5R)-5-ethyl-2-methyl-4-(1-(4-(trifluoromethyl)phenyl)ethyl)piperazin-1-yl)-1-(methyl-d$_3$)pyrido[3,2-d]pyrimidin-2(1H)-one

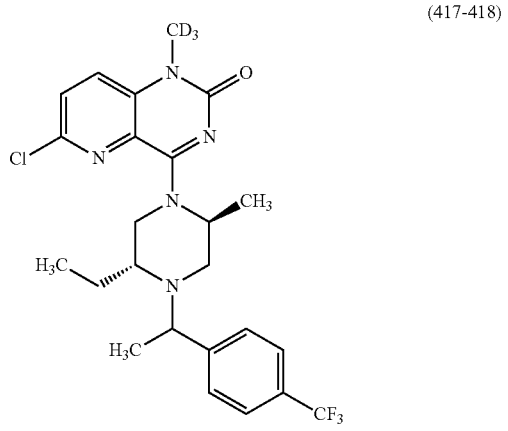 [SMILES: [2H]C([2H])([2H])n1c(=O)nc(N2C[C@@H](CC)N(C(C)c3ccc(C(F)(F)F)cc3)C[C@@H]2C)c2nc(Cl)ccc21]

(417-418)

To a solution of 6-chloro-4-((2S,5R)-5-ethyl-2-methylpiperazin-1-yl)-1-(methyl-d$_3$)pyrido[3,2-d]pyrimidin-2 (1H)-one, TFA (0.4 g, 0.911 mmol) in acetonitrile (5 mL) at room temperature was added DIPEA (0.5 mL, 2.73 mmol), followed by 1-(1-chloroethyl)-4-(trifluoromethyl)benzene (0.570 g, 2.73 mmol), sodium iodide (0.137 g, 0.911 mmol). The reaction mixture was heated at 85° C. for 16 h. The reaction mixture was diluted with EtOAc (50 mL) and filtered through Celite® pad, washed with additional ethyl acetate (2×50 mL). The filtrate was washed with water (50 mL), brine (50 mL), dried over Na$_2$SO$_4$ and concentrated under reduced pressure to yield the crude product, which was purified by preparative HPLC to yield Examples 414 and 415. HPLC method: column: HPLC Method: Column: YMC TRIART C18 EXRS (250×4.6 mm, 5 μm); mobile phase A=10 mM ammonium acetate in water; mobile phase B=acetonitrile, Gradient: 0-20% B over 20 minutes: 20.0 mL/min.

Example 417: (13 mg, 3% yield), LCMS: m/z=497.3 [M+H]$^+$; rt 2.52 min, LCMS Method; Column: AQUITY UPLC BEH C18 (3.0×50 mm, 1.7 μm); mobile phase A: 10 mM NH$_4$OAc in water:acetonitrile (95:5); mobile phase B: 10 mM NH$_4$OAc in water:acetonitrile (5:95); gradient=20-90% B over 1.1 min, then a 0.6 minute hold at 90% B, flow: 0.7 mL/min. $^1$H NMR (400 MHz, DMSO-d$_6$) δ (ppm)=7.91 (d, J=9.0 Hz, 1H), 7.78 (d, J=9.0 Hz, 1H), 7.72-7.74 (m, 2H), 7.60-7.62 (m, 2H), 5.99-5.73 (m, 1H), 5.17-4.70 (m, 1H), 3.84 (q, J=6.4 Hz, 1H), 3.53-3.36 (m, 1H), 2.89-2.68 (m, 2H), 2.37-2.25 (m, 1H), 1.61-1.22 (m, 8H), 0.69 (t, J=6.8 Hz, 3H).

EXAMPLE 418: (13 mg, 3% yield), LCMS: m/z=497.3 [M+H]$^+$; rt 2.58 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-90% B over 1.1 min, then a 0.6 minute hold at 90% B, flow: 0.7 mL/min. $^1$H NMR (400 MHz, DMSO-d$_6$) δ (ppm)=7.93 (d, J=9.0 Hz, 1H), 7.79 (br d, J=9.0 Hz, 1H), 7.73-7.66 (m, 2H), 7.66-7.54 (m, 2H), 6.23-5.47 (m, 1H), 5.06-4.73 (m, 1H), 3.77-3.54 (m, 2H), 3.19-2.95 (m, 1H), 2.64-2.54 (m, 1H), 2.24-2.01 (m, 1H), 1.60-1.40 (m, 2H), 1.36-1.08 (m, 5H), 0.99 (t, J=7.3 Hz 3H).

Examples 419 And 420

4-((2S,5R)-5-Ethyl-2-methyl-4-(1-(4-(trifluoromethyl)phenyl)ethyl)piperazin-1-yl)-1-(methyl-d$_3$)-2-oxo-1,2-dihydropyrido[3,2-d]pyrimidine-6-carbonitrile

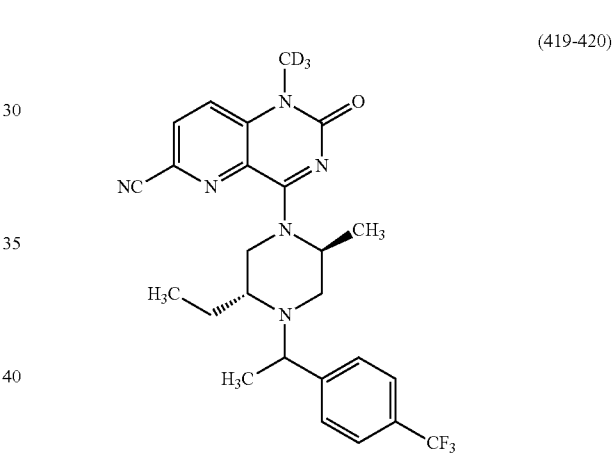

(419-420)

To a stirred solution of 6-chloro-4-(2S,5R)-5-ethyl-2-methyl-4-(1-(4-(trifluoromethyl)phenyl)ethyl)piperazin-1-yl)-1-(methyl-d$_3$)pyrido[3,2-d]pyrimidin-2(1H)-one (150 mg, 0.30 mmol) in NMP (2 mL) at room temperature were added zinc cyanide (70.9 mg, 0.604 mmol), zinc (19.73 mg, 0.30 mmol), Pd$_2$(dba)$_3$ (27.6 mg, 0.030 mmol) and dppf (33.5 mg, 0.060 mmol) under an argon atmosphere. The reaction mixture was heated at 90° C. for overnight. The reaction mixture was diluted with EtOAc (50 mL) and filtered through a Celite® pad, washed with additional ethyl acetate (2×50 mL). The filtrate was washed with water (50 mL), brine (50 mL), dried over Na$_2$SO$_4$ and concentrated under reduced pressure to yield the crude product, which was purified by preparative HPLC method: Column: Sunfire C18 (150×19 mm, 5 μm); mobile phase A=10 mM ammonium acetate in water; mobile phase B=acetonitrile; Flow 19 mL/min; Gradient: 10-85% B, over 0-22 min] to yield Examples 419 and 420.

EXAMPLE 419: (25 mg, 17% yield), LCMS: m/z=488.3 [M+H]$^+$; rt 2.31 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-

90% B over 1.1 min, then a 0.6 minute hold at 90% B, flow: 0.7 mL/min. $^1$H NMR (400 MHz, DMSO-$d_6$) δ (ppm)=8.22 (d, J=9.0 Hz, 1H), 7.97 (d, J=8.8 Hz, 1H), 7.72-7.74 (m, 2H), 7.60-7.62 (m, 2H), 5.85-5.63 (m, 1H), 5.10-4.77 (m, 1H), 3.83-3.88 (m, 1H), 3.51-3.39 (m, 1H), 2.89-2.71 (m, 2H), 2.41-2.32 (m, 1H), 1.68-1.00 (m, 8H), 0.79-0.59 (m, 3H).

EXAMPLE 420: (30 mg, 20% yield), LCMS: m/z=488.3 [M+H]$^+$; rt 2.36 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-90% B over 1.1 min, then a 0.6 minute hold at 90% B, flow: 0.7 mL/min. $^1$H NMR (400 MHz, DMSO-$d_6$) δ (ppm)=8.33-8.15 (m, 1H), 8.06-7.90 (m, 1H), 7.77-7.51 (m, 4H), 6.06-5.43 (m, 1H), 5.10-4.71 (m, 1H), 3.79-3.55 (m, 2H), 3.17-2.99 (m, 1H), 2.64-2.55 (m, 1H), 2.26-2.02 (m, 1H), 1.61-1.11 (m, 8H), 1.00 (br t, J=7.2 Hz, 3H).

Examples 421 and 422

6-Chloro-4-((2S,5R)-2,5-diethyl-4-(1-(4-(trifluoromethyl)phenyl)propyl)piperazin-1-yl)-1-methylpyrido[3,2-d]pyrimidin-2(1H)-one

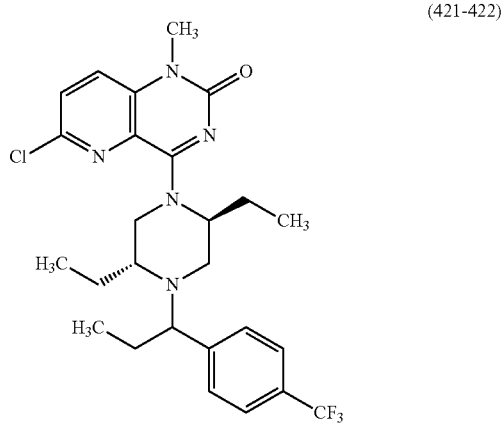 [SMILES: CCC(c1ccc(C(F)(F)F)cc1)N1C[C@H](CC)N(c2nc(=O)n(C)c3ccc(Cl)nc23)C[C@H]1CC]

(421-422)

To a stirred suspension of 6-chloro-4-((2S,5R)-2,5-diethylpiperazin-1-yl)-1-methylpyrido[3,2-d]pyrimidin-2(1H)-one, TFA (500 mg, 1.111 mmol), 1-(1-chloropropyl)-4-(trifluoromethyl)benzene (297 mg, 1.334 mmol) in acetonitrile (15 mL) were added sodium iodide (333 mg, 2.223 mmol) and DIPEA (1.165 mL, 6.67 mmol). The reaction mixture was heated at 85° C. and stirred for 16 h. The reaction mixture was cooled to room temperature and was concentrated under reduced pressure to obtain the crude product, which was purified using silica gel (24 g) chromatography by using 0-10% methanol in chloroform as eluent. The fractions were concentrated under reduced pressure to obtain 6-chloro-4-((2S,5R)-2,5-diethyl-4-(1-(4-(trifluoromethyl)phenyl) propyl)piperazin-1-yl)-1-methylpyrido[3,2-d]pyrimidin-2(1H)-one (255 mg, 38% yield) as diasteromeric mixture. LCMS: m/z=522.3 [M+H]$^+$; rt 1.59 and 1.62 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 0.2 minute hold at 100% B, flow: 0.7 mL/min.

The diasteromeric mixture was purified by preparative SFC. SFC Method: Column: Chiralpak IG (250×30 mm, 5 μm); mobile phase: 80% CO$_2$/20% of 4 M methanolic ammonia; Flow: 90 g/min; Detector Wavelength: 260 nm; Temperature: 40° C. Example 421; Isolate 1: First eluting peak, rt=3.09 min; Example 422 Isolate 2: Second eluting peak, rt=3.62 min.

EXAMPLE 421: LCMS: m/z, 522.3 [M+H]$^+$; rt 2.77 min; LCMS method: Column: XBridge BEH XP C18 (50×2.1 mm, 2.5 μm); mobile phase A: 10 mM NH$_4$OAc in water:acetonitrile (95:5); mobile phase B: 10 mM NH$_4$OAc in water:acetonitrile (5:95); Gradient=0-100% B over 3 minutes; Temperature: 50° C.; Flow rate: 1.1 mL/min; Detection: UV at 220 nm. $^1$H NMR (400MHz, DMSO-$d_6$) δ (ppm)=7.92 (d, J=9.0 Hz, 1H), 7.78 (br d, J=8.6 Hz, 1H), 7.72 (d, J=8.3 Hz, 2H), 7.55 (br d, J=8.3 Hz, 2H), 5.99 5.56 (s, 1H), 5.06-4.78 (m, 1H), 3.67-3.60 (m, 1H), 3.42 (s, 3H), 3.08-2.74 (m, 3H), 2.37-2.27 (m, 1H), 1.96-1.80 (m, 2H), 1.67-1.53 (m, 2H), 1.50-1.18 (m, 2H), 1.03-0.86 (m, 3H), 0.71-0.47 (m, 6H).

EXAMPLE 422: LCMS: m/z, 522.3 [M+H]$^+$; rt 2.78 min; LCMS method: Column:)(Bridge BEH XP C18 (50×2.1 mm, 2.5 μm); mobile phase A: 10 mM NH$_4$OAc in water:acetonitrile (95:5); mobile phase B: 10 mM NH$_4$OAc in water:acetonitrile (5:95); Gradient=0-100% B over 3 minutes; Temperature: 50° C.; Flow rate: 1.1 mL/min; Detection: UV at 220 nm. $^1$H NMR (400MHz, DMSO-$d_6$) δ (ppm)=7.98-7.86 (m, 1H), 7.85-7.65 (m, 3H), 7.57 (d, J=8.1 Hz, 2H), 6.20-5.32 (m, 1H), 5.11-4.66 (m, 1H), 3.66-3.46 (m, 2H), 3.42 (s, 3H), 3.28-3.00 (m, 2H), 2.25-2.11 (m, 1H), 1.99-1.69 (m, 3H), 1.59-1.35 (m, 3H), 1.02-0.86 (m, 3H), 0.61-0.57 (m, 6H).

Intermediate 99

4-((2S,5R)-2,5-Diethyl-4-(1-(4-(trifluoromethyl)phenyl)ethyl)piperazin-1-yl)-1-methyl-2-oxo-1,2-dihydropyrido[3,2-d]pyrimidine-6-carboxylic acid

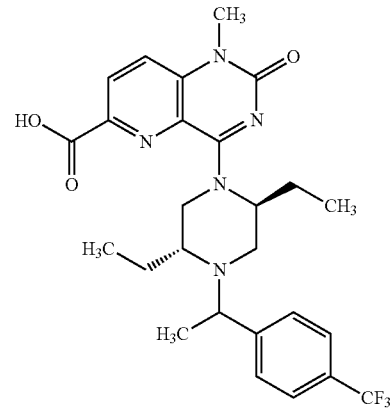 [SMILES: CC[C@H]1CN(C(C)c2ccc(C(F)(F)F)cc2)[C@H](CC)CN1c1nc(=O)n(C)c2ccc(C(=O)O)nc12]

To a solution of 4-((2S,5R)-2,5-diethyl-4-(1-(4-(trifluoromethyl)phenyl)ethyl) piperazin-1-yl)-1-methyl-2-oxo-1,2-dihydropyrido[3,2-d]pyrimidine-6-carbonitrile (350 mg, 0.70 mmol) in ethanol (2.5 mL) was added NaOH (281 mg, 7.02 mmol) in H$_2$O (2.5 mL). The reaction mixture was heated at 90° C. and stirred overnight. The reaction mixture was cooled to room temperature and concentrated under reduced pressure. The residue was acidified with 1.5 N HCl to pH 3 and was extracted with EtOAc (100 mL). The organic layer was washed with water (20 mL), brine (20 mL), dried over Na$_2$SO$_4$ and concentrated under reduced pressure to yield 4-((2S,5R)-2,5-diethyl-4-(1-(4-(trifluoromethyl)phenyl)ethyl) piperazin-1-yl)-1-methyl-2-oxo-1,2-dihydropyrido[3,2-d]pyrimidine-6-carboxylic acid (300 mg, 83% yield). LCMS: m/z=518.3 [M+H]⁺; retention time 1.13 and 1.14 min, LCMS Method; Column: AQUITY UPLC BEH C18 (3.0×50 mm, 1.7 μm); mobile phase A:10 mM NH₄OAc in water:acetonitrile (95:5); mobile phase B: 10 mM NH₄OAc in water:acetonitrile (5:95); gradient=20-90% B over 1.1 min, then a 2.2 minute hold at 90% B, flow: 0.7 mL/min.

Example 423

4-((2S,5R)-2,5-Diethyl-4-(1-(4-(trifluoromethyl)phenyl)ethyl)piperazin-1-yl)-6-(hydroxymethyl)-1-methylpyrido[3,2-d]pyrimidin-2(1H)-one

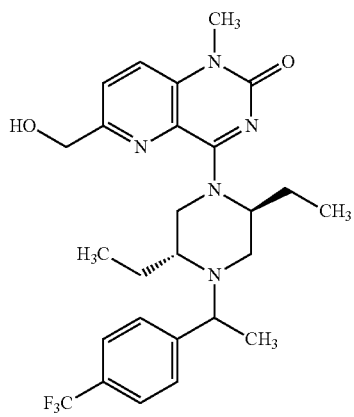

(423)

To a solution of 4-((2S,5R)-2,5-diethyl-4-(1-(4-(trifluoromethyl)phenyl)ethyl) piperazin-1-yl)-1-methyl-2-oxo-1,2-dihydropyrido[3,2-d]pyrimidine-6-carboxylic acid (150 mg, 0.29 mmol) in THF (5 mL) was added drop wise BH₃.dimethyl sulfide (0.08 mL, 0.87 mmol) at 0° C. After warming-up to ambient temperature, stirring was continued for additional 24 h. The solution was cooled again to 0° C. The reaction was quenched with MeOH. The reaction mixture was refluxed for 1 h. The volatiles removed under the reduced pressure and reaction mixture was diluted with water. The aqueous phase was extracted with ethyl acetate (50 mL) and the organic layer was washed with water, brine, dried, filtered and concentrated under reduced pressure to afford 4-((2S,5R)-2,5-diethyl-4-(1-(4-(trifluoromethyl)phenyl)ethyl)piperazin-1-yl)-6-(hydroxymethyl)-1-methylpyrido[3,2-d]pyrimidin-2(1H)-one (100 mg, 69% yield). LCMS: m/z=504.3 [M+H]⁺; retention time 1.78 min, LCMS Method; Column: AQUITY UPLC BEH C18 (3.0×50 mm, 1.7 μm); mobile phase A:10 mM NH₄OAc in water:acetonitrile (95:5); mobile phase B: 10 mM NH₄OAc in water:acetonitrile (5:95); gradient=20-90% B over 1.1 min, then a 2.2 minute hold at 90% B, flow: 0.7 mL/min.

Examples 424 and 425

4-((2S,5R)-2,5-Diethyl-4-(1-(4-(trifluoromethyl)phenyl)ethyl)piperazin-1-yl)-6-(methoxymethyl)-1-methylpyrido[3,2-d]pyrimidin-2(1H)-one

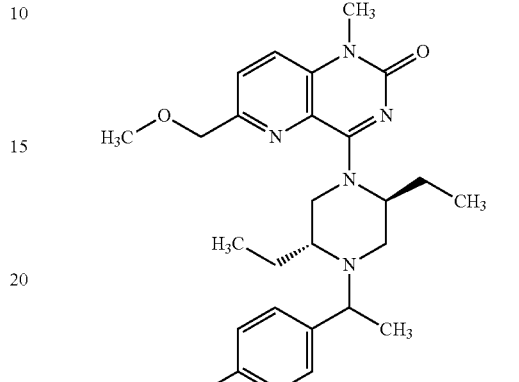

(424-425)

To a stirred suspension of NaH (17 mg, 0.42 mmol, 60% w/w) in DMF (3 mL) was added 4-((2S,5R)-2,5-diethyl-4-(1-(4-(trifluoromethyl)phenyl)ethyl) piperazin-1-yl)-6-(hydroxymethyl)-1-methylpyrido[3,2-d]pyrimidin-2(1H)-one (70 mg, 0.14 mmol) at 0° C. After 5 minutes, a solution of methyl iodide (0.02 mL, 0.28 mmol) in DMF (1 mL) was added and stirred for 2 h at room temperature. The reaction mixture was cooled to 0° C. The reaction was quenched with the addition of ice cold water. The reaction mixture was extracted with EtOAc (2×50 mL). The combined organic extract was washed with brine, dried over Na₂SO₄ and concentrated under reduced pressure to give the crude product, which was purified using preparative SFC. SFC Method: Column: Chiralpak IG (250×30 mm, 5 μm); mobile phase: 70% CO₂/30% of MeOH; Flow: 80 g/min; Detector Wavelength: 220 nm; Temperature: 35° C. Example 424: Isolate 1: First eluting peak, rt=2.96 min. Example 425: Isolate 2: Second eluting peak, rt=4.01 min.

EXAMPLE 424: (5.1 mg, 7% yield): LCMS: m/z, 518.3 [M+H]⁺; retention time 2.48 min; LCMS method: Column: XBridge BEH XP C18 (50×2.1 mm, 2.5 μm); mobile phase A: 10 mM NH₄OAc in water:acetonitrile (95:5); mobile phase B: 10 mM NH₄OAc in water:acetonitrile (5:95); Gradient=0-100% B over 3 minutes; Temperature: 50° C.; Flow rate: 1.1 mL/min; Detection: UV at 220 nm. ¹H NMR (400 MHz, DMSO-d₆) δ (ppm)=7.86 (d, J=8.8 Hz, 1H), 7.77-7.64 (m, 3H), 7.60 (br d, J=8.3 Hz, 2H), 6.28-5.87 (m, 1H), 5.18-4.80 (m, 1H), 4.60-4.34 (m, 2H), 3.91-3.68 (m, 1H), 3.42 (s, 3H), 3.28 (br s, 2H), 3.11-2.85 (m, 2H), 2.79-2.69 (m, 1H), 2.40-2.18 (m, 1H), 2.14-1.83 (m, 2H), 1.32-1.18 (m, 3H), 0.89 (br t, J=7.2 Hz, 3H), 0.75-0.36 (m, 3H).

EXAMPLE 425: (2.2 mg, 3% yield)): LCMS: m/z, 518.3 [M+H]⁺; retention time 2.49 min; LCMS method: Column: XBridge BEH XP C18 (50×2.1 mm, 2.5 μm); mobile phase A: 10 mM NH₄OAc in water:acetonitrile (95:5); mobile phase B: 10 mM NH₄OAc in water:acetonitrile (5:95); Gradient=0-100% B over 3 minutes; Temperature: 50° C.; Flow rate: 1.1 mL/min; Detection: UV at 220 nm. ¹H NMR (400 MHz, DMSO-d₆) δ (ppm)=7.92-7.83 (m, 1H), 7.75-7.64 (m, 3H), 7.64-7.56 (m, 2H), 5.91-5.73 (m, 1H), 5.15-

4.84 (m, 1H), 4.60-4.35 (m, 2H), 3.72-3.60 (m, 1H), 3.42 (s, 3H), 3.19-2.96 (m, 2H), 2.26-2.08 (m, 2H), 1.94-1.74 (m, 2H), 1.52-1.38 (m, 2H), 1.25 (br d, J=6.1 Hz, 3H), 1.03-0.73 (m, 3H), 0.67-0.47 (m, 3H).

Example 426

6-Chloro-4-((2S,5R)-2,5-diethyl-4-(1-(4-(trifluoromethyl)phenyl)ethyl)piperazin-1-yl)-1-methylpyrido[3,2-d]pyrimidin-2(1H)-one

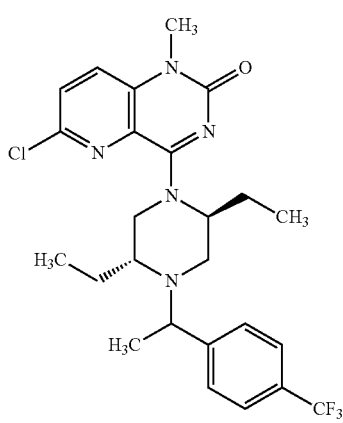

(426)

To a stirred solution of 6-chloro-4-((2S,5R)-2,5-diethylpiperazin-1-yl)-1-methylpyrido[3,2-d]pyrimidin-2(1H)-one, TFA (1.0 g, 2.22 mmol) in acetonitrile (15 mL) was added DIPEA (1.165 mL, 6.67 mmol). The reaction mixture was stirred for 5 min and then 1-(1-chloroethyl)-4-(trifluoromethyl)benzene (0.556 g, 2.67 mmol) was added at room temperature. The reaction mixture was heated at 85° C. and was stirred for 20 h. The reaction mixture was cooled to room temperature and concentrated under reduced pressure to obtain the crude product, which was purified using silica gel (24 g) chromatography by using 0-10% methanol in chloroform as eluent. The fractions were concentrated under reduced pressure to obtain 6-chloro-4-((2S,5R)-2,5-diethyl-4-(1-(4-(trifluoromethyl)phenyl)ethyl)piperazin-1-yl)-1-methylpyrido[3,2-d]pyrimidin-2(1H)-one (750 mg, 58% yield) as a diasteromeric mixture. LCMS: m/z=508.3 [M+H]+; rt 1.50 and 1.53 min, LCMS Method; Column: AQUITY UPLC BEH C18 (3.0×50 mm, 1.7 μm); mobile phase A:10 mM NH4OAc in water:acetonitrile (95:5); mobile phase B: 10 mM NH4OAc in water:acetonitrile (5:95); gradient=20-100% B over 2 min, then a 0.2 minute hold at 100% B, flow: 0.7 mL/min.

Examples 427 and 428

4-((2S,5R)-2,5-Diethyl-4-(1-(4-(trifluoromethyl)phenyl)ethyl)piperazin-1-yl)-6-methoxy-1-methylpyrido[3,2-d]pyrimidin-2(1H)-one

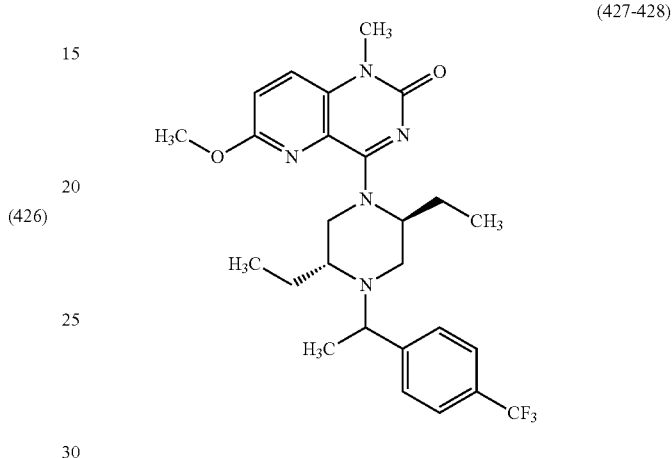

(427-428)

To a solution of 6-chloro-4-((2S,5R)-2,5-diethyl-4-(1-(4-(trifluoromethyl)phenyl) ethyl)piperazin-1-yl)-1-methylpyrido[3,2-d]pyrimidin-2(1H)-one (100 mg, 0.2 mmol) in MeOH (2.0 mL) was added sodium methoxide (0.23 mL, 0.98 mmol). The reaction mixture was stirred at 60° C. for 48 h. The reaction mixture was concentrated under reduced pressure, dissolved in ethyl acetate (50 mL), washed with water, brine, dried over Na2SO4, concentrated under reduced pressure to give the crude product which was purified by chiral preparative HPLC. HPLC Method: Column: Cellulose-5 (150×19 mm, 5 μm); mobile phase: 10 mM ammonium acetate in MeOH, Flow: 22 mL/min). Peak 1 (Diastereomer 1): rt=10.04 min and Peak 2 (Diastereomer 2), rt=11.53 min.

EXAMPLE 427: (17 mg, 23% yield); LCMS: m/z, 504.3 [M+H]+; rt 2.48 min; LCMS method: Column:)(Bridge BEH XP C18 (50×2.1 mm, 2.5 μm); mobile phase A: 10 mM NH4OAc in water:acetonitrile (95:5); mobile phase B: 10 mM NH4OAc in water:acetonitrile (5:95); Gradient=0-100% B over 3 minutes; Temperature: 50° C.; Flow rate: 1.1 mL/min; Detection: UV at 220 nm. 1H NMR (400 MHz, DMSO-d6) δ (ppm)=7.88 (d, J=9.3 Hz, 1H), 7.71 (d, J=8.3 Hz, 2H), 7.61 (d, J=7.8 Hz, 2H), 7.24 (br d, J=8.8 Hz, 1H), 6.31-5.91 (m, 1H), 5.23-4.69 (m, 1H), 3.87-3.75 (m, 3H), 3.42 (s, 3H), 3.13 2.71 (m, 3H), 2.98-2.73 (m, 2H), 2.39-2.29 (m, 1H), 2.16-1.88 (m, 2H), 1.54-1.34 (m, 1H), 1.49-1.16 (m, 3H), 0.93-0.71 (m, 3H), 0.68-0.36 (m, 3H).

EXAMPLE 428: (14 mg, 18% yield); LCMS: m/z, 504.3 [M+H]+; rt 2.49 min; LCMS method: Column:)(Bridge BEH XP C18 (50×2.1 mm, 2.5 μm); mobile phase A: 10 mM NH$_4$OAc in water:acetonitrile (95:5); mobile phase B: 10 mM NH$_4$OAc in water:acetonitrile (5:95); Gradient=0-100% B over 3 minutes; Temperature: 50° C.; Flow rate: 1.1 mL/min; Detection: UV at 220 nm. $^1$H NMR (400 MHz, DMSO-d$_6$) δ (ppm)=7.88 (d, J=9.3 Hz, 1H), 7.76-7.67 (m, 2H), 7.64-7.53 (m, 2H), 7.31-7.14 (m, 1H), 6.32-6.01 (m, 1H), 5.00 (br s, 1H), 3.97-3.62 (m, 4H), 3.43 (s, 3H), 3.20-2.97 (m, 2H), 2.76-2.57 (m, 1H), 2.27-2.15 (m, 1H), 2.05-1.83 (m, 1H), 1.76-1.63 (m, 1H), 1.58-1.32 (m, 2H), 1.24 (d, J=6.6 Hz, 3H), 1.00-0.43 (m, 6H).

The examples in the Table 19 were prepared according to the general procedure described in Examples 427 and 428, using the appropriate alcohol and chloro derivative in the synthetic sequence. When the synthesis provided a mixture of diastereomers, the mixture was separated at the final stage using either preparative chromatography or preparative chiral chromatography.

TABLE 19

| Ex. No. | Structure | Stereochemistry | LCMS Method | LCMS rt | [M + H]$^+$ |
|---|---|---|---|---|---|
| 429 | | H | C | 2.60 | 518.3 |
| 430 | | H | C | 2.61 | 518.3 |
| 431 | | H | C | 2.08 | 561.4 |
| 432 | | H | C | 2.10 | 561.4 |
| 433 | | H | C | 2.37 | 548.4 |
| 434 | | H | C | 2.38 | 548.4 |

TABLE 19-continued

| Ex. No. | Structure | Stereo-chemistry | LCMS Method | LCMS rt | [M + H]⁺ |
|---|---|---|---|---|---|
| 435 | | H | C | 2.61 | 518.3 |
| 436 | | H | C | 2.61 | 518.3 |
| 437 | | H | C | 2.72 | 532.4 |
| 438 | | H | C | 2.72 | 532.4 |

Examples 439 and 440

4-((2S,5R)-2,5-Diethyl-4-(1-(4-(trifluoromethyl)phenyl)ethyl)piperazin-1-yl)-6-(difluoromethyl)-1-methylpyrido[3,2-d]pyrimidin-2(1H)-one

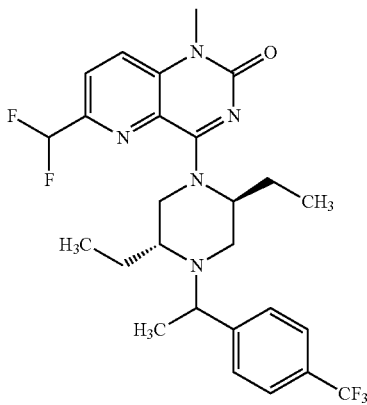

(439-440)

To a stirred solution of 6-chloro-4-((2S,5R)-2,5-diethyl-4-(1-(4-(trifluoromethyl) phenyl)ethyl)piperazin-1-yl)-1-methylpyrido[3,2-d]pyrimidin-2(1H)-one (80 mg, 0.16 mmol) in toluene (5 mL) were added (1,3-bis(2,6-diisopropylphenyl)imidazolidin-2-ylidene)(difluoromethyl)silver (87 mg, 0.16 mmol), bis(2-diphenylphosphinophenyl) ether (9.0 mg, 0.016 mmol) and bis(dibenzylideneacetone)palladium(0) (4.53 mg, 7.87 μmol). The reaction mixture was purged with argon over 5 min and was heated at 80° C. for 16 h. The reaction was quenched with the addition of water (20 mL). The reaction mixture was extracted with ethyl acetate (3×20 mL). The combined organic layer was dried over anhydrous sodium sulphate, filtered and evaporated under reduced pressure to yield crude product, which was purified by preparative HPLC. HPLC Method: Column: Gemini NX (250×21.2 mm, 5 μm); mobile phase A=10 mM ammonium acetate in water, pH 4.5, mobile phase B=acetonitrile, Flow 20 mL/min to yield Example 439 and Example 440.

EXAMPLE 439: (2 mg, 3.0% yield). LCMS: m/z=524.3 [M+H]⁺; rt 2.67 min; LCMS Method: Column: Ascentis Express C18 (50×2.1 mm, 2.7 μm); mobile phase A: 10 mM NH₄OAc in water:acetonitrile (95:5); mobile phase B: 10 mM NH₄OAc in water:acetonitrile (5:95); Gradient=0-100% B over 3 minutes; Temperature: 50° C.; Flow rate: 1.1 mL/min; Detection: UV at 220 nm. ¹H NMR:(400 MHz, DMSO-d₆) δ (ppm)=8.03-7.92 (m, 2H), 7.71-7.71 (m, 2H), 7.60-7.62 (m, 2H), 7.19-6.80 (m, 1H), 6.18-5.87 (m, 1H), 5.21-4.80 (m, 1H), 3.90-3.79 (m, 1H), 3.51-3.40 (m, 3H), 3.14-3.04 (m, 1H), 2.99-2.87 (m, 1H), 2.84-2.70 (m, 1H), 2.34-2.38 (m, 1H), 2.29-1.84, (m, 2H), 1.52-1.36 (m, 2H), 1.29 (d, J=6.5 Hz, 3H), 0.99-0.82 (m, 3H), 0.77-0.31 (m, 3H).

EXAMPLE 440: (2.3 mg, 4.39 µmol, 2.79% yield). LCMS: m/z=524.3 [M+H]+; rt 2.68 min; LCMS Method: Column: Ascentis Express C18 (50×2.1 mm, 2.7 µm); mobile phase A: 10 mM $NH_4OAc$ in water:acetonitrile (95:5); mobile phase B: 10 mM $NH_4OAc$ in water:acetonitrile (5:95); Gradient=0-100% B over 3 minutes; Temperature: 50° C.; Flow rate: 1.1 mL/min; Detection: UV at 220 nm. $^1$H NMR: (400 MHz, DMSO-$d_6$) δ (ppm)=7.95-7.95 (m, 1H), 8.09-7.86 (m, 1H), 7.78-7.65 (m, 2H), 7.65-7.51 (m, 2H), 7.25-6.75 (m, 1H), 6.42-5.72 (m, 1H), 5.21-4.80 (m, 1H), 3.66-3.70 (m, 2H), 3.45 (s, 3H), 3.29-2.92 (m, 1H), 2.60-2.54 (m, 1H), 2.14-2.18 (m, 1H), 1.94-1.72 (m, 2H), 1.61-1.34 (m, 2H), 1.26 (d, J=6.5 Hz, 3H), 1.04-0.71 (m, 3H), 0.68-0.45 (m, 3H).

Water (50 mL) was added to quench the reaction. The reaction mixture was extracted with ethyl acetate (3×50 mL). The combined organic layer was dried over anhydrous sodium sulphate, filtered and evaporated under reduced pressure to yield 4-((2S,5R)-2,5-diethyl-4-(1-(4-(trifluoromethyl)phenyl)ethyl) piperazin-1-yl)-6-hydroxy-1-methylpyrido[3,2-d]pyrimidin-2(1H)-one (90 mg, 61.7% yield). LCMS: m/z=490.2 [M+H]+; retention time 0.79 min; LCMS Method; Column: AQUITY BEH C18 (2.1×50 mm, 1.7 µm); mobile phase A: 10 mM $NH_4OAc/HCO_2H$ (pH:5) in water:acetonitrile (95:5); mobile phase B: 10 mM $NH_4OAc/HCO_2H$ (pH:5) in water:acetonitrile (5:95); gradient=0-5% B over 1.1 min, then a 1.7 minute hold at 95% B, flow: 0.8 mL/min, temperature: 27° C.; detection: UV at 220 nm.

TABLE 20

| Ex. No. | Structure | Stereochemistry | LCMS Method | LCMS rt | [M + H]+ |
|---|---|---|---|---|---|
| 441 | 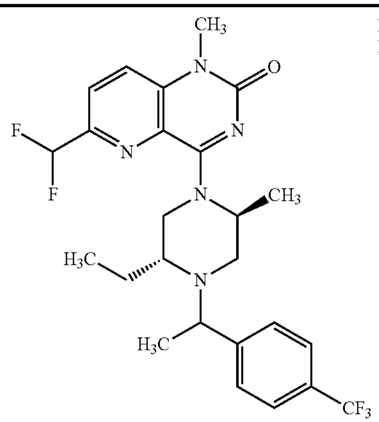 | H | C | 2.46 | 510.3 |
| 442 | | H | C | 2.42 | 510.3 |

Example 443

4-((2S,5R)-2,5-Diethyl-4-(1-(4-(trifluoromethyl)phenyl)ethyl)piperazin-1-yl)-6-hydroxy-1-methylpyrido[3,2-d]pyrimidin-2(1H)-one

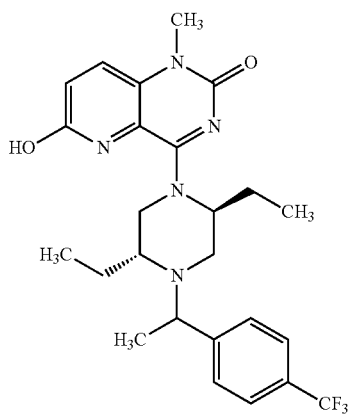

(443)

To a solution of 4-((2S,5R)-2,5-diethyl-4-(1-(4-(trifluoromethyl)phenyl)ethyl) piperazin-1-yl)-6-methoxy-1-methylpyrido[3,2-d]pyrimidin-2(1H)-one (150 mg, 0.3 mmol) in DMF (4 mL) was added lithium chloride (63.1 mg, 1.49 mmol). The reaction mixture was heated at 180° C. for 6 h.

Examples 444 and 445

4-((2S,5R)-2,5-Diethyl-4-(1-(4-(trifluoromethyl)phenyl)ethyl)piperazin-1-yl)-6-(difluoromethoxy)-1-methylpyrido[3,2-d]pyrimidin-2(1H)-one

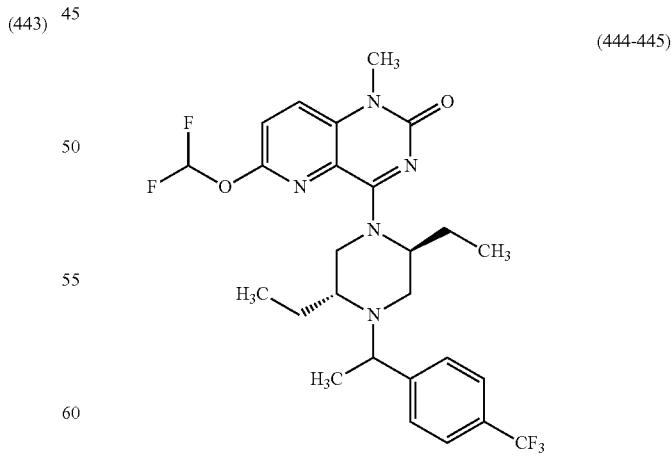

(444-445)

To a stirred solution of 4-((2S,5R)-2,5-diethyl-4-(1-(4-(trifluoromethyl)phenyl) ethyl)piperazin-1-yl)-6-hydroxy-1-methylpyrido[3,2-d]pyrimidin-2(1H)-one (90 mg, 0.18 mmol) in acetonitrile (5 mL) was added NaH (18 mg, 0.46 mmol, 60% w/w) at 0° C. The reaction mixture was stirred at room temperature for 20 min and 2 2-difluoro-2-(fluorosulfonyl)acetic acid (0.03 mL, 0.31 mmol) was added. The reaction mixture was stirred at room temperature for another 3 h. Water was added to quench the reaction. The mixture was concentrated under reduced pressure to obtain the crude product, which was suspended with water (20 mL) and was extracted with ethyl acetate (3×20 mL). The combined organic layer was dried over anhydrous sodium sulphate, filtered and evaporated under reduced pressure to obtain the crude product, which was purified by preparative HPLC [Method Info: Preparative Column: ACE C18 (250×21.2 mm, 5 μm), mobile phase A=10 mM ammonium acetate in water, mobile phase B=acetonitrile: MeOH (1:1), Flow 19 mL/min, Gradient: 70-100% B over 25 minutes, then a 5 minute hold at 100% B].

EXAMPLE 444: (1.0 mg, 1.853 μmol, 1.0% yield). LCMS: m/z=540.3 [M+H]+; rt 2.48 min; LCMS Method: Column: Ascentis Express C18 (50×2.1 mm, 2.7 μm); mobile phase A: 10 mM NH$_4$OAc in water:acetonitrile (95:5); mobile phase B: 10 mM NH$_4$OAc in water:acetonitrile (5:95); Gradient=0-100% B over 3 minutes; Temperature: 50° C.; Flow rate: 1.1 mL/min; Detection: UV at 220 nm. $^1$H NMR: (400 MHz, DMSO-d$_6$) δ (ppm)=8.03 (d, J=9.0 Hz, 1H), 7.71 (d, J=8.1 Hz, 2H), 7.60-7.62 (m, 2H), 7.36-7.55(m,2H), 6.00-5.34 (m, 1H), 5.25-4.64 (m, 1H), 3.91-3.75 (m, 1H), 3.62-3.41 (m, 1H), 3.38-3.44 (m, 4H), 3.16-2.98 (m, 1H), 2.98-2.72 (m, 2H), 2.39-2.28 (m, 1H), 2.14-1.84 (m, 2H), 1.32-1.20, (m, 3H), 1.54-1.11 (m, 2H), 0.92-0.71 (m, 3H), 0.94-0.25 (m, 1H).

EXAMPLE 445: (1.0 mg, 1.86 μmol, 1% yield). LCMS: m/z=540.3 [M+H]+; rt 2.49 min; LCMS Method: Column: Ascentis Express C18 (50×2.1 mm, 2.7 μm); mobile phase A: 10 mM NH$_4$OAc in water:acetonitrile (95:5); mobile phase B: 10 mM NH$_4$OAc in water:acetonitrile (5:95); Gradient=0-100% B over 3 minutes; Temperature: 50° C.; Flow rate: 1.1 mL/min; Detection: UV at 220 nm. $^1$H NMR: (400 MHz, DMSO-d$_6$) δ (ppm)=8.04 (d, J=9.3 Hz, 1H), 7.68-7.76 (m, 2H), 7.61-7.63 (m, 2H), 7.43-7.50 (m, 2H), 5.80-5.59 (m, 1H), 5.04-4.89 (m, 1H), 3.80-3.71 (m, 1H), 3.67-3.70 (m, 1H), 3.44 (s, 3H), 3.27-3.22 (m, 1H), 3.04-2.98 (m, 1H), 2.17-2.20 (m, 1H), 2.04-1.87 (m, 1H), 1.63-1.70 (m,1H), 1.42-1.46 (m, 2H), 1.24 (d, J=6.4 Hz, 3H), 1.01-0.78 (m, 2H), 0.73-0.39 (m, 4H).

Intermediate 100

(5-Cyclopropylisoxazol-3-yl)(4-(trifluoromethoxy)phenyl)methanone

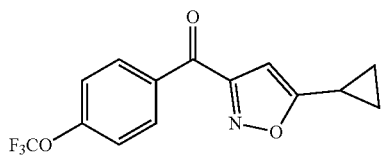 [SMILES: O=C(c1ccc(OC(F)(F)F)cc1)c1cc(C2CC2)on1]

To a stirred solution of 5-cyclopropyl-N-methoxy-N-methylisoxazole-3-carboxamide (250 mg, 1.27 mmol) in tetrahydrofuran (4 mL) was added (4-(trifluoromethoxy)phenyl)magnesium bromide (0.5 M, 12.7 mL, 6.37 mmol) at 0° C. The reaction mixture was stirred at room temperature for 16 h. The reaction was quenched with the addition of a saturated aqueous NH$_4$Cl solution. The mixture was extracted with ethyl acetate (2×20 mL). The organic layer was separated, dried over Na$_2$SO$_4$ and evaporated under reduced pressure to yield (5-cyclopropylisoxazol-3-yl)(4-(trifluoromethoxy)phenyl)methanone (250 mg, 66% yield). $^1$H NMR (CDCl$_3$, 400 MHz): δ (ppm)=8.38-8.43 (m, 2H), 7.33-7.38 (m, 2H), 6.46 (s, 1H), 1.67-1.78 (m, 1H), 1.15-1.21 (m, 2H), 1.04-1.10 (m, 2H).

Intermediate 101

(5-Cyclopropylisoxazol-3-yl)(4-fluorophenyl)methanol

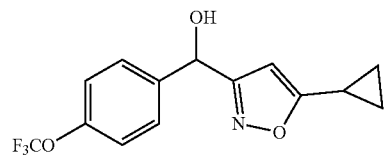 [SMILES: OC(c1ccc(OC(F)(F)F)cc1)c1cc(C2CC2)on1]

To a stirred solution of (5-cyclopropylisoxazol-3-yl)(4-(trifluoromethoxy)phenyl) methanone (800 mg, 2.69 mmol) in MeOH (10 mL) was added NaBH$_4$ (204 mg, 5.38 mmol) at 0° C. The reaction mixture was stirred at room temperature for 3 h. The reaction was quenched with the addition of saturated aqueous NH$_4$Cl. The mixture was diluted with water and extracted with ethyl acetate (20 mL). The organic layer was separated, dried over Na$_2$SO$_4$ and evaporated under reduced pressure to yield (5-cyclopropylisoxazol-3-yl)(4-fluorophenyl)methanol (710 mg, 88% yield). $^1$H NMR (CDCl$_3$, 400MHz): δ (ppm)=7.44-7.49 (m, 2H), 7.19-7.23 (m, 2H), 5.92 (d, J=4.0 Hz, 1H), 5.78 (s, 1H), 2.80 (d, J=4.0 Hz, 1H), 1.98 (tt, J=8.5, 5.0 Hz, 1H), 1.01-1.05 (m, 2H), 0.91-0.97 (m, 2H).

Intermediate 102

3-(Bromo(4-(trifluoromethoxy)phenyl)methyl)-5-cyclopropylisoxazole

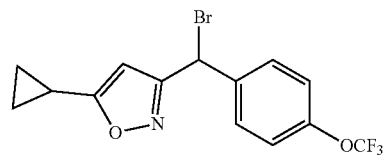 [SMILES: FC(F)(F)Oc1ccc(C(Br)c2cc(C3CC3)on2)cc1]

To a stirred solution of (5-cyclopropylisoxazol-3-yl)(4-(trifluoromethoxy)phenyl) methanol (300 mg, 1.00 mmol) in dichloromethane (5 mL) was added BBR$_3$ (2.005 mL, 2.005 mmol) at 0° C. and stirred at room temperature for 2 h. The reaction mixture evaporated under reduced pressure to yield 3-(bromo(4-(trifluoromethoxy)phenyl) methyl)-5-cyclopropylisoxazole (240 mg, 66% yield). $^1$H NMR (CDCl$_3$, 400MHz): δ (ppm)=7.54-7.59 (m, 2H), 7.23 (dd, J=8.8, 1.0 Hz, 2H), 6.15 (s, 1H), 6.10 (s, 1H), 2.05 (tt, J=8.5, 5.2 Hz, 1H), 1.07-1.13 (m, 2H), 0.99-1.05 (m, 2H).

Intermediate 103

2-Cyclopropyl-N-methoxy-N-methylthiazole-5-carboxamide

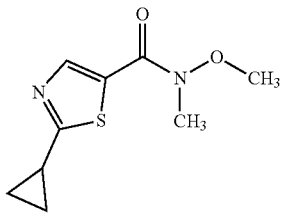

To a solution of 2-cyclopropylthiazole-5-carboxylic acid (0.4 g, 2.36 mmol) in DMF (5 mL) at room temperature was added HATU (1.348 g, 3.55 mmol), DIPEA (1.2 mL, 7.09 mmol) and N,O-dimethylhydroxylamine hydrochloride (0.346 g, 3.55 mmol). The reaction mixture was stirred at room temperature for 5 h. The reaction was quenched with the addition of water. The mixture was extracted with ethyl acetate (2×100 mL), the combined organic layer was washed with water, brine and dried over sodium sulfate. The solvent was evaporated under reduced pressure to yield the crude product (2-cyclopropylthiazol-5-yl)(4-fluorophenyl)methanol (0.15 g, 46% yield. LCMS: m/z=213.2 [M+H]$^+$; rt 0.91 min, LCMS Method; Column: AQUITY UPLC BEH C18 (3.0×50 mm, 1.7 µm); mobile phase A:10 mM NH$_4$OAc in water:acetonitrile (95:5); mobile phase B: 10 mM NH$_4$OAc in water:acetonitrile (5:95); gradient=20-90% B over 1.1 min, then a 0.6 minute hold at 90% B, flow: 0.7 mL/min.

Intermediate 104

(2-Cyclopropylthiazol-5-yl)(4-fluorophenyl)methanone

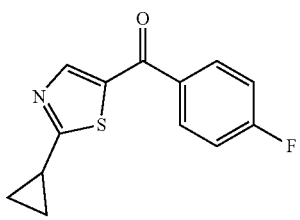 [SMILES: O=C(c1ccc(F)cc1)c1cnc(C2CC2)s1]

To a solution of 2-cyclopropyl-N-methoxy-N-methylthiazole-5-carboxamide (0.2 g, 0.94 mmol) in THF (10 mL) at 0° C. was added (4-fluorophenyl)magnesium bromide (1 M, 1.8 mL, 1.8 mmol). The reaction mixture was and stirred at 25° C. for 16 h. The reaction mixture was quenched with saturated ammonium chloride solution and extracted with ethylacetate (2×100 mL), the combined organic layer was washed with water, brine and dried over sodium sulfate. The solvent was evaporated under reduced pressure to yield the crude desired product (2-cyclopropylthiazol-5-yl)(4-fluorophenyl)methanol (0.15 g, 48% yield). LCMS: m/z=248.1 [M+H]$^+$; rt 1.56 min, LCMS Method; Column: AQUITY UPLC BEH C18 (3.0×50 mm, 1.7 µm); mobile phase A:10 mM NH$_4$OAc in water:acetonitrile (95:5); mobile phase B: 10 mM NH$_4$OAc in water:acetonitrile (5:95); gradient=20-90% B over 2 min, then a 1 minute hold at 90% B, flow: 0.7 mL/min.

Intermediate 105

(2-Cyclopropylthiazol-5-yl)(4-fluorophenyl)methanol

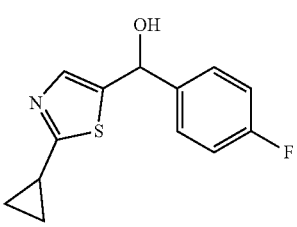 [SMILES: OC(c1ccc(F)cc1)c1cnc(C2CC2)s1]

To a solution of (2-cyclopropylthiazol-5-yl)(4-fluorophenyl)methanone (0.2 g, 0.81 mmol) in methanol (5 mL) at 0° C. was added sodium borohydride (0.046 g, 1.21 mmol). The reaction mixture was stirred at room temperature for 3 h. The reaction was quenched with the addition of saturated aqueous ammonium chloride solution. The mixture was extracted with ethyl acetate (2×100 mL), the combined organic layer was washed with water, brine and dried over sodium sulfate. The solvent was evaporated under reduced pressure to yield (2-cyclopropylthiazol-5-yl)(4-fluorophenyl)methanol (0.15 g, 48% yield). LCMS: m/z=250.2 [M+H]$^+$; rt 1.22 min, LCMS Method; Column: AQUITY UPLC BEH C18 (3.0×50 mm, 1.7 µm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min.

Intermediate 106

5-(Bromo(4-fluorophenyl)methyl)-2-cyclopropylthiazoles

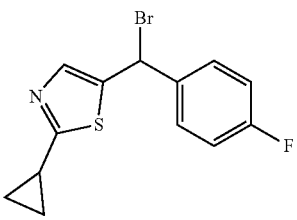 [SMILES: Fc1ccc(C(Br)c2cnc(C3CC3)s2)cc1]

To a solution of (2-cyclopropylthiazol-5-yl)(4-fluorophenyl)methanol (0.2 g, 0.8 mmol) in DCM (10 mL) at 0° C. was added boron tribromide (1.2 mL, 1.2 mmol). The reaction mixture was stirred at room temperature for 3 h. The reaction was quenched with the addition of water. The mixture was extracted with ethyl acetate (2×100 mL), the combined organic layer was washed with water, brine and dried over sodium sulfate. The solvent was evaporated under reduced pressure to yield 5-(bromo(4-fluorophenyl)methyl)-2-cyclopropylthiazole (0.18 g, 0.577 mmol, 71.9% yield).

Intermediate 107

Ethyl (1R,2R)-2-(4-formylphenoxy)cyclopropane-1-carboxylate

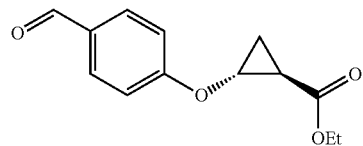 [SMILES: CCOC(=O)[C@@H]1C[C@H]1Oc1ccc(C=O)cc1]

To a stirred suspension of KOH (1.378 g, 24.57 mmol) in DMSO (12 mL) were added 4-hydroxybenzaldehyde (0.75 g, 6.14 mmol) and ethyl (1S,2R)-2-iodocyclopropane-1-carboxylate (1.769 g, 7.37 mmol). The reaction mixture was stirred at room temperature for 16 h. The reaction mixture was quenched with water (100 mL) and was extracted with ethyl acetate (3×100 mL). The combined organic layer was dried over anhydrous sodium sulfate, filtered and evaporated under reduced pressure to yield the crude product (350 mg, 24%). LCMS: m/z=235.1 [M+H]$^+$; retention time 1.49 & 1.51 min (Diastereomeric Mixture), LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-90% B over 1.1 min, then a 0.6 minute hold at 90% B, flow: 0.7 mL/min.

Intermediate 108

Ethyl (1R,2R)-2-(4-(1-hydroxyethyl)phenoxy)cyclopropane-1-carboxylate

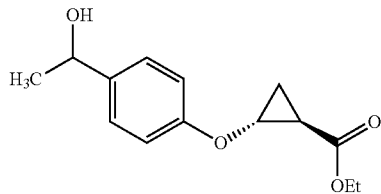

To a stirred solution of ethyl (1R,2R)-2-(4-formylphenoxy)cyclopropane-1-carboxylate (50 mg, 0.21 mmol) in tetrahydrofuran (3 mL) at 0° C. was added methylmagnesium bromide in diethyl ether (3 M, 0.1 mL, 0.3 mmol) drop wise. The reaction mixture stirred at room temperature for 2 h. The reaction was quenched with the addition of saturated aqueous ammonium chloride solution (10 mL). The mixture was extracted with ethyl acetate (3×10 mL). The combined organic layer was dried over anhydrous sodium sulfate, filtered and evaporated under reduced pressure to yield crude product. $^1$H NMR (300 MHz, CDCl$_3$) δ (ppm)=7.25-7.19 (m, 2H), 6.88 (d, J=9.1 Hz, 2H), 4.80 (q, J=6.4 Hz, 1H), 4.17-4.08 (m, 2H), 4.02-3.95 (m, 1H), 3.51-3.54 (m, 1H), 1.87-1.83 (m, 1H), 1.65-1.70 (m, 1H), 1.42-1.36 (m, 3H), 1.23-1.19 (m, 3H).

Intermediate 109

Ethyl (1S,2R)-2-(4-(1-chloroethyl)phenoxy)cyclopropane-1-carboxylate

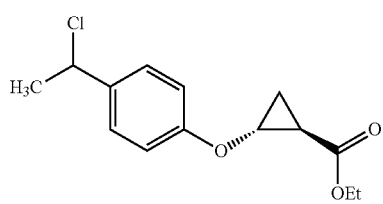 [SMILES: CCOC(=O)[C@@H]1C[C@H]1Oc1ccc(C(C)O)cc1]

To a stirred solution of ethyl (1R,2R)-2-(4-(1-hydroxyethyl)phenoxy) cyclopropane-1-carboxylate (70 mg, 0.28 mmol) in DCM (2 mL) was added SOCl$_2$ (0.16 mL, 2.24 mmol). The reaction mixture was heated at 40° C. for 5 h. The reaction mixture was concentrated under reduced pressure to yield ethyl (1R,2R)-2-(4-(1-chloroethyl) phenoxy) cyclopropane-1-carboxylate (68 mg, 0.25 mmol, 90% yield). $^1$H NMR (300MHz, CDCl$_3$) δ (ppm)=7.40-7.20 (m, 2H), 6.97-6.74 (m, 2H), 5.17-4.89 (m, 1H), 4.21-4.03 (m, 2H), 2.00-1.77, (m, 2H), 1.57-1.34 (m, 4H), 1.34-1.14 (m, 4H).

Intermediate 110

4-(2-(4-Bromophenyl)propan-2-yl)morpholine

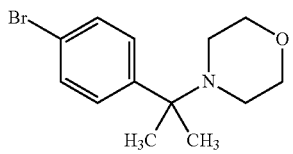

To a stirred solution of 2-(4-bromophenyl)propan-2-amine (1 g, 4.67 mmol) in acetonitrile (8 mL) were added K$_2$CO$_3$ (1.94 g, 14.01 mmol) and 2-bromoethyl ether (1.63 g, 7.01 mmol) at room temperature. The reaction mixture was stirred under microwave irradiation at 100° C. for 2 h. The reaction mixture was cooled to room temperature and solvent was removed under reduced pressure to give the crude product, which was purified by silica gel column chromatography using 70-80% EtOAc in n-hexane to afford 4-(2-(4-bromophenyl)propan-2-yl)morpholine (1 g, 62% yield). LCMS: m/z, 285.1 [M+2]; rt 2.05 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-90% B over 2 min, then a 0.3 minute hold at 90% B, flow: 0.7 mL/min.

Intermediate 111

1-(4-(2-Morpholinopropan-2-yl)phenyl)ethan-1-one

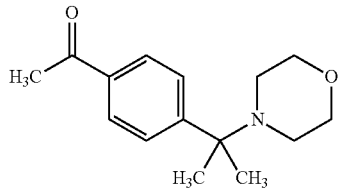

To a stirred solution of 4-(2-(4-bromophenyl)propan-2-yl)morpholine (0.5 g, 1.759 mmol) in DMF (5 mL) were added tributyl(1-ethoxyvinyl)tin (0.83 g, 2.29 mmol), bis(triphenylphosphine)palladium(II) dichloride (0.12 g, 0.176 mmol) at room temperature. The reaction mixture was flushed with nitrogen and heated at 70° C. for 16 h. The reaction mixture was cooled to room temperature and the volatiles were removed under reduced pressure to obtain the crude product. The residue was dissolved in 1 mL of aqueous 5 N HCl and stirred for 15 min. The solvent was removed under reduced pressure to yield the product, which was purified by silica gel column chromatography (eluting with 40-50% EtOAc in n-hexane) to afford 1-(4-(2-morpholinopropan-2-yl) phenyl)ethan-1-one (0.3 g, 69% yield). $^1$H NMR (300 MHz, DMSO-$d_6$) δ (ppm)=8.05 (d, J=8.3 Hz, 2H), 7.97-7.90 (m, 2H), 3.89 (br d, J=6.8 Hz, 4H), 3.20-3.10 (m, 2H), 3.05-2.91 (m, 2H), 2.62 (s, 3H), 1.84 (s, 6H).

Intermediate 112

1-(4-(2-Morpholinopropan-2-yl)phenyl)ethan-1-ol (racemate)

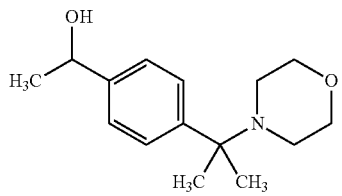

To a solution of 1-(4-(2-morpholinopropan-2-yl)phenyl)ethan-1-one (0.3 g, 1.21 mmol) in methanol (10 mL) was added NaBH$_4$ (0.09 g, 2.43 mmol) at 0° C. under a nitrogen atmosphere. The reaction mixture was stirred at room temperature for 2 h. The reaction was quenched with water (5 mL). The reaction mixture was extracted with ethyl acetate (2×20 mL). The combined organic layer was dried over anhydrous Na$_2$SO$_4$, evaporated under reduced pressure to obtain 1-(4-(2-morpholinopropan-2-yl)phenyl) ethan-1-ol (250 mg, 50% yield). LCMS: m/z, 250.2 [M+H]$^+$; rt 1.07 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min.

Intermediate 113

4-(2-(4-(1-chloroethyl)phenyl)propan-2-yl)morpholine (racemate)

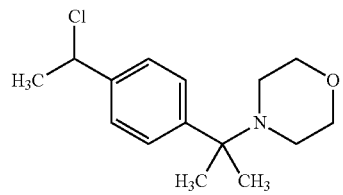 [SMILES: CC(Cl)c1ccc(C(C)(C)N2CCOCC2)cc1]

To a solution of 1-(4-(2-morpholinopropan-2-yl)phenyl)ethan-1-ol (0.1 g, 0.40 mmol) in dichloromethane (5.0 mL) was added SOCl$_2$ (0.15 mL, 2.00 mmol)) at 0° C. The reaction mixture was stirred at room temperature for 2 h. The volatiles were removed from the reaction mixture under reduced pressure to obtain 4-(2-(4-(1-chloroethyl)phenyl) propan-2-yl)morpholine (0.1 g, 0.273 mmol, 68% yield). LCMS: m/z, 268.1 [M+H]$^+$; rt 1.89 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min.

Intermediate 114

1-(4-(1-Hydroxyethyl)phenyl)pyrrolidin-2-one

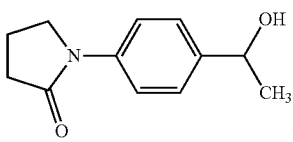

To a solution of 1-(4-acetylphenyl)pyrrolidin-2-one (250 mg, 1.23 mmol) in dry MeOH (5.0 mL) at 0° C., sodium borohydride (140 mg, 3.69 mmol) was added. The reaction mixture stirred for 2 h at room temperature. The reaction was quenched with saturated sodium bicarbonate solution. The reaction mixture was stirred for 10 minutes and was extracted with ethyl acetate (2×25 mL). The organic layer was separated, washed with water, brine, dried over sodium sulfate and concentrated under reduced pressure to yield 1-(4-(1-hydroxyethyl)phenyl)pyrrolidin-2-one (250 mg, 99% yield) as an off-white solid. LCMS: m/z=206.1 [M+H]$^+$; retention time 0.76 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 0.2 minute hold at 100% B, flow: 0.7 mL/min.

Intermediate 115

1-(4-(1-Chloroethyl)phenyl)pyrrolidin-2-one

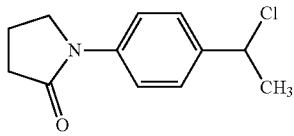

To a solution of 1-(4-(1-hydroxyethyl)phenyl)pyrrolidin-2-one (100 mg, 0.49 mmol) in DCM (2.0 mL), thionyl chloride (0.053 mL, 0.731 mmol) was added slowly at 0° C. The mixture was stirred for 1 h. and then diluted with DCM (50 mL). The mixture was washed with water, brine, dried over sodium sulfate and concentrated under reduced pressure to yield 1-(4-(1-chloroethyl)phenyl)pyrrolidin-2-one (100 mg, 92% yield). LCMS: m/z=242.1 [M+NH4$^+$]; retention time 1.11 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-100% B over 2 min, then a 1 minute hold at 100% B, flow: 0.7 mL/min.

Intermediate 116

5-(1-Chloroethyl)-3-methylbenzo[d]oxazole-2(3H)-one

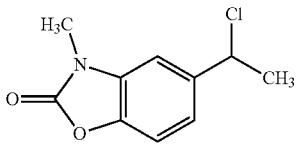

To a solution of 5-(1-hydroxyethyl)-3-methylbenzo[d]oxazol-2(3H)-one (0.2 g, 1.04 mmol) in DCM (5 mL) was added thionyl chloride (0.1 mL, 1.55 mmol) at 0° C. The reaction mixture was stirred at room temperature for 16 h. The volatiles were evaporated under reduced pressure to afford 5-(1-chloroethyl)-3-methylbenzo[d]oxazol-2(3H)-one (0.2 g, 59% yield). LCMS: m/z=212.1 [M+H]$^+$; retention time 0.60 min, LCMS Method; Column: AQUITY UPLC BEH C18 (3.0×50 mm, 1.7 μm); mobile phase A:10 mM NH$_4$OAc in water:acetonitrile (95:5); mobile phase B: 10 mM NH$_4$OAc in water:acetonitrile (5:95); gradient=20-90% B over 1.1 min, then a 0.6 minute hold at 90% B, flow: 0.7 mL/min.

Intermediate 117

1-(4-(Methoxy-d3)phenyl)propan-1-one

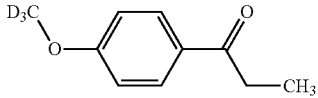

To a stirred solution of 1-(4-hydroxyphenyl)propan-1-one (0.5 g, 3.33 mmol) in DMF (10 mL) were added K$_2$CO$_3$ (0.92 g, 6.66 mmol) and iodomethane-d3 (0.579 g, 4.00 mmol) at room temperature. The reaction mixture was stirred for 16 h. The reaction mixture was diluted with ethyl acetate (200 mL) and washed with water. The organic layer was dried over anhydrous Na$_2$SO$_4$, filtered and evaporated under reduced pressure to afford 1-(4-(methoxy-d3)phenyl)propan-1-one (0.52 g, 92% yield). LCMS: m/z=168.2 [M+H]$^+$; rt 2.129 min. LCMS Method: (LCMS method: Column: Column-Kinetex XB-C18 (75×3 mm-2.6 μm), mobile phase A: 98% water: 2% acetonitrile; 10 mM ammonium formate; mobile phase B: 2% water: 98% acetonitrile; 10 mM ammonium Formate; Flow: 1.0 mL/min; Temp: 50° C.; Time (min): 0-4; % B: 0-100%).

Intermediate 118

1-(4-(Methoxy-d3)phenyl)propan-1-ol

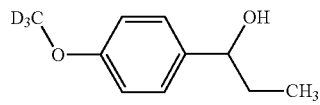

To a stirred solution of 1-(4-(methoxy-d$_3$)phenyl)propan-1-one (0.5 g, 2.99 mmol) in MeOH (1 mL) and THF (10 mL) was added NaBH$_4$ (0.283 g, 7.48 mmol) at 0° C. The reaction mixture was stirred at room temperature for 3 h. The solvent was removed under reduced pressure to yield the crude product, which was dissolved in ethyl acetate and washed with saturated aqueous NH$_4$Cl solution. The organic layer was dried over anhydrous Na$_2$SO$_4$, filtered and evaporated under reduced pressure to afford 1-(4-(methoxy-d$_3$)phenyl)propan-1-ol (0.38 g, 75% yield). $^1$H NMR (400 MHz, DMSO-d$_6$) δ (ppm)=7.21 (d, J=8.80 Hz, 2H) 6.86 (d, J=7.83 Hz, 2H) 4.98 (d, J=4.40 Hz, 1H) 4.34-4.40 (m, 1H) 1.49-1.66 (m, 2H) 0.79 (t, J=7.34 Hz, 3H).

Intermediate 119

1-(1-Chloropropyl)-4-(methoxy-d3)benzene

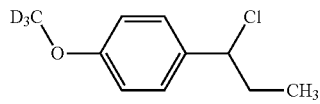

To a stirred solution of 1-(4-(methoxy-d$_3$)phenyl)propan-1-ol (0.35 g, 2.07 mmol) in dry DCM (10 mL) was added SOCl$_2$ (1 mL, 13.70 mmol) at room temperature. The reaction mixture was stirred for 2 h. The solvent was removed under reduced pressure to yield 1-(1-chloropropyl)-4-(methoxy-d3)benzene (0.380 g, 98% yield). $^1$H NMR (400 MHz, DMSO-d$_6$) δ (ppm)=7.24-7.39 (m, 2H) 6.84-6.98 (m, 2H) 5.03 (t, J=7.28 Hz, 1H) 1.96-2.14 (m, 2H) 0.91 (t, J=7.28 Hz, 3H).

Intermediate 120

1-(2-Morpholino-4-(trifluoromethyl)phenyl)ethan-1-one

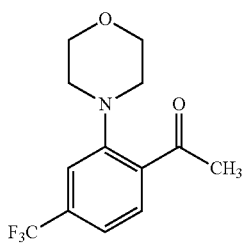

To a stirred solution of 1-(2-fluoro-4-(trifluoromethyl)phenyl)ethan-1-one (0.5 g, 2.43 mmol) in DMF (3 mL) was added morpholine (0.528 g, 6.06 mmol) and the reaction mixture was heated at 100° C. for 16 h. The reaction mixture was cooled to room temperature and diluted with ethyl acetate and washed with water, the organic layer was dried over anhydrous $Na_2SO_4$, filtered and evaporated under reduced pressure to yield the crude compound which was purified by column chromatography (eluted with 20-10% ethyl acetate/pet ether) to yield 1-(2-morpholino-4-(trifluoromethyl)phenyl) ethan-1-one (0.55 g, 82% yield)). LCMS: m/z=274.2 [M+H]$^+$; rt 2.502 min. LCMS Method: Method info: Column-Kinetex XB-C18 (75×3 mm-2.6 μm), Mobile phase A:10 mM $NH_4OAc$ in water: acetonitrile (98:02); mobile phase B: 10 mM $NH_4OAc$ in water:acetonitrile (02:98), Gradient: 20-100% B over 4 minutes, then a 16 minute hold at 100% B; Flow: 1.5 mL/min).

Intermediate 121

1-(2-Morpholino-4-(trifluoromethyl)phenyl)ethan-1-ol

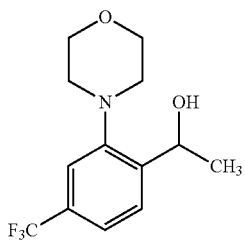

To a stirred solution of 1-(2-morpholino-4-(trifluoromethyl)phenyl)ethan-1-one (0.3 g, 1.1 mmol) in dry methanol (10 mL) was added $NaBH_4$ (0.104 g, 2.74 mmol) at 0° C. The reaction mixture was stirred at room temperature for 4 h. The solvent was removed under reduced pressure to yield the crude product, which was dissolved in ethyl acetate and washed with saturated aqueous ammonium chloride solution. The organic layer was dried over anhydrous $Na_2SO_4$, filtered and evaporated under reduced pressure to yield crude compound, which was purified by column chromatography (eluted with 40-30% ethyl acetate/pet ether) to afford 1-(2-morpholino-4-(trifluoromethyl)phenyl)ethan-1-ol (0.3 g, 98% yield. LCMS: m/z=276.2 [M+H]$^+$; rt 2.174 min. LCMS Method: Method info: Column-Kinetex XB-C18 (75×3 mm-2.6 μm), Mobile phase A: 10 mM $NH_4OAc$ in water: acetonitrile (98:02); mobile phase B: 10 mM $NH_4OAc$ in water:acetonitrile (02:98), Gradient: 20-100% B over 4 minutes, then a 16 minute hold at 100% B; Flow: 1.5 mL/min).

Intermediate 122

4-(2-(1-Chloroethyl)-5-(trifluoromethyl)phenyl)morpholine

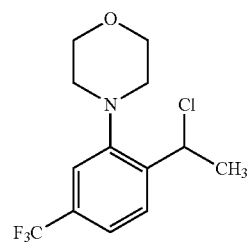

To a stirred solution of 1-(2-morpholino-4-(trifluoromethyl)phenyl)ethan-1-ol (0.3 g, 1.09 mmol) in dry DCM (5 mL) was added $SOCl_2$ (1 mL, 13.70 mmol) at room temperature. The reaction mixture was stirred at room temperature for 16 h. The solvent was removed under reduced pressure to yield 4-(2-(1-chloroethyl)-5-(trifluoromethyl)phenyl)morpholine (0.32 g, 100% yield).

Intermediate 123

1-(4-(3,6-Dihydro-2H-pyran-4-yl)phenyl)ethan-1-one

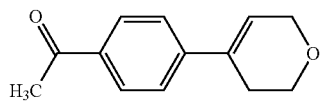

To a stirred solution of 2-(3,6-dihydro-2H-pyran-4-yl)-4,4,5,5-tetramethyl-1,3,2-dioxaborolane (1.15 g, 5.53 mmol) in 1,4-dioxane (15 mL) and $H_2O$ (1 mL) were added 1-(4-bromophenyl)ethan-1-one (1.0 g, 5.02 mmol) and $K_2CO_3$ (1.4 g, 10.05 mmol). The reaction mixture was degassed with argon for 10 min. and $PdCl_2(dppf)$ (0.37 g, 0.502 mmol) was added. The reaction mixture was heated at 100° C. for 16 h. The reaction mixture was cooled to room temperature, extracted with EtOAc (2×100 mL), washed with water, brine, dried over $Na_2SO_4$ and concentrated to give crude product, which was purified by flash chromatography using with 30%-40% EtOAc in pet. ether to afford 1-(4-(3,6-dihydro-2H-pyran-4-yl)phenyl)ethan-1-one (800 mg, 79% yield). $^1$H NMR (300 MHz, $CDCl_3$) δ (ppm)=7.96-7.73 (m, 2H), 7.41 (d, J=8.3 Hz, 2H), 6.26-6.11 (m, 1H), 4.37-4.22 (m, 2H), 3.94-3.81 (m, 2H), 2.51 (s, 3H), 2.50-2.44 (m, 2H).

Intermediate 124

1-(4-(Tetrahydro-2H-pyran-4-yl)phenyl)ethan-1-one

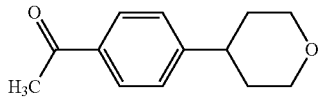

To a solution of 1-(4-(3,6-dihydro-2H-pyran-4-yl)phenyl) ethan-1-one (500 mg, 2.47 mmol) in EtOAc (50 mL) was added platinum (IV) oxide (56.1 mg, 0.247 mmol). The solution was stirred under $H_2$ for 16 h. The reaction mixture was filtered through a Celite® pad and washed with excess EtOAc (50 mL). The filtrate was concentrated under reduced pressure to give 1-(4-(tetrahydro-2H-pyran-4-yl)phenyl) ethan-1-one (400 mg, 79% yield). $^1$H NMR (300 MHz, $CDCl_3$) δ (ppm)=7.97-7.75 (m, 2H), 7.37-7.24 (m, 2H), 4.15-3.81 (m, 2H), 3.59-3.35 (m, 2H), 2.87-2.68 (m, 1H), 2.50 (s, 3H), 1.86-1.66 (m, 4H).

Intermediate 125

1-(4-(Tetrahydro-2H-pyran-4-yl)phenyl)ethan-1-one

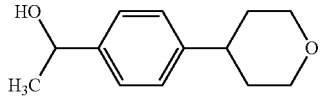

To a solution of 1-(4-(2-morpholinopropan-2-yl)phenyl) ethan-1-one (0.3 g, 1.21 mmol) in methanol (10 mL) was added $NaBH_4$ (0.09 g, 2.43 mmol) at 0° C. under nitrogen. The reaction mixture was allowed to warm to room temperature and stirred for 2 h. The reaction was quenched with the addition of water (5 mL). The reaction mixture was extracted with ethyl acetate (2×20 mL). The combined organic layer was dried over anhydrous $Na_2SO_4$, evaporated under reduced pressure to obtain 1-(4-(2-morpholinopropan-2-yl)phenyl)ethan-1-ol (250 mg, 50% yield). LCMS: m/z, 189.1 [M−OH]; rt 1.31 min, LCMS Method; Column: AQUITY UPLC BEH C18 (3.0×50 mm, 1.7 μm); mobile phase A:10 mM $NH_4OAc$ in water:acetonitrile (95:5); mobile phase B: 10 mM $NH_4OAc$ in water:acetonitrile (5:95); gradient=20-100% B over 2 min, then a 1 minute hold at 100% B, flow: 0.7 mL/min. $^1$H NMR (300 MHz, $CDCl_3$) δ (ppm)=7.30-7.24 (m, 2H), 7.17-7.12 (m, 2H), 4.90-4.75 (m, 1H), 4.08-3.94 (m, 2H), 3.50-3.40 (m, 2H), 2.75-2.60 (m, 1H), 1.78-1.67 (m, 4H), 1.43 (d, J=6.4 Hz, 3H).

Intermediate 126

4-(4-(1-Chloroethyl)phenyl)tetrahydro-2H-pyran

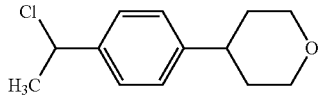

To a solution of 1-(4-(tetrahydro-2H-pyran-4-yl)phenyl) ethan-1-ol (100 mg, 0.49 mmol) in dichloromethane (5.0 mL) was added $SOCl_2$ (0.14 mL, 1.94 mmol)) at 0° C. The reaction mixture was stirred at room temperature for 3 h. The volatiles were removed from the reaction mixture under reduced pressure to give crude product, which was extracted with DCM (2×50 mL) and washed with saturate $NaHCO_3$ solution, water, brine, dried over sodium sulphate and concentrated under reduced pressure to obtain 4-(4-(1-chloroethyl)phenyl)tetrahydro-2H-pyran (90 mg, 83% yield). LCMS: m/z, 189.1 [M−Cl]; rt 1.96 min, LCMS Method; Column: AQUITY UPLC BEH C18 (3.0×50 mm, 1.7 μm); mobile phase A:10 mM $NH_4OAc$ in water:acetonitrile (95:5); mobile phase B: 10 mM $NH_4OAc$ in water:acetonitrile (5:95); gradient=20-100% B over 2 min, then a 0.3 minute hold at 100% B, flow: 0.7 mL/min. $^1$H NMR (300 MHz, $CDCl_3$) δ (ppm)=7.31 (d, J=8.3 Hz, 2H), 7.18-7.12 (m, 2H), 5.03 (q, J=6.9 Hz, 1H), 4.08-3.94 (m, 2H), 3.54-3.37 (m, 2H), 2.79-2.60 (m, 1H), 1.84-1.75 (m, 4H), 1.74-1.67 (m, 3H).

Intermediate 127

Ethyl 2-(4-acetylphenoxy)-2-methylpropanoate

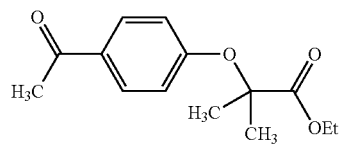 [SMILES: CCOC(=O)C(C)(C)Oc1ccc(C(C)=O)cc1]

To a stirred solution of 1-(4-hydroxyphenyl)ethan-1-one (5 g, 36.7 mmol) in acetonitrile (20 mL) was added $K_2CO_3$ (25.4 g, 184 mmol) and ethyl 2-bromo-2-methylpropanoate (10.9 mL, 73.4 mmol) at room temperature. The reaction mixture was heated at 80° C. for 16 h. The reaction mixture was diluted with ethyl acetate (100 mL) and washed with water, the organic layer was dried over anhydrous $Na_2SO_4$ and filtered. The volatiles were removed under reduced pressure to yield ethyl 2-(4-acetylphenoxy)-2-methylpropanoate (5.1 g, 56% yield). LCMS: m/z=251.3 [M+H]$^+$; rt 1.52 min, LCMS Method; Column: AQUITY UPLC BEH C18 (3.0×50 mm, 1.7 μm); mobile phase A:10 mM $NH_4OAc$ in water:acetonitrile (95:5); mobile phase B: 10 mM $NH_4OAc$ in water:acetonitrile (5:95); gradient=20-100% B over 2 min, then a 1 minute hold at 100% B, flow: 0.7 mL/min.

Intermediate 128

Ethyl 2-(4-(1-hydroxyethyl)phenoxy)-2-methylpropanoate

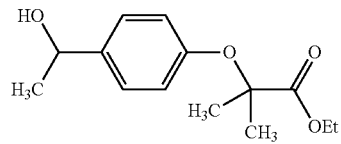 [SMILES: CCOC(=O)C(C)(C)Oc1ccc(C(C)O)cc1]

To a stirred solution of ethyl 2-(4-acetylphenoxy)-2-methylpropanoate (4 g, 15.98 mmol) in MeOH (1 mL) was added sodium borohydride (1.21 g, 32.0 mmol) at 0° C. The reaction mixture was stirred at room temperature for 3 h. The solvent was removed under reduced pressure to obtain the crude product, which was dissolved in ethyl acetate, washed with saturated aqueous NH$_4$Cl solution. The organic layer was dried over anhydrous, filtered, and evaporated under reduced pressure to yield ethyl 2-(4-(1-hydroxyethyl)phenoxy)-2-methylpropanoate (2.8 g, 69% yield). $^1$H NMR (CDCl$_3$, 400 MHz): δ (ppm)=7.20-7.31 (m, 2H), 6.74-6.86 (m, 2H), 4.81-4.87 (m, 1H), 4.01-4.37 (m, 2H), 3.77 (s, 3H), 1.59 (s, 6H), 1.47 (d, J=6.5 Hz, 3H).

Intermediate 129

Ethyl 2-(4-(1-chloroethyl)phenoxy)-2-methylpropanoate

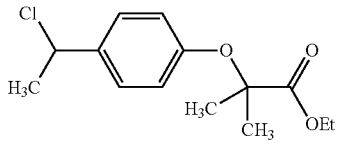

To a stirred solution of ethyl 2-(4-(1-hydroxyethyl)phenoxy)-2-methylpropanoate (1 g, 3.96 mmol) in dry DCM (10 mL) was added SOCl$_2$ (1.45 mL, 19.82 mmol) at room temperature. The reaction mixture was stirred for 2 h. The solvent was removed under reduced pressure to yield ethyl 2-(4-(1-chloroethyl)phenoxy)-2-methylpropanoate (0.92 g, 86% yield). $^1$H NMR (CDCl$_3$, 300 MHz): δ (ppm)=7.24-7.28 (m, 2H), 6.79-6.84 (m, 2H), 4.21-4.27 (m, 1H), 3.74-3.80 (m, 2H), 1.58 (s, 3H), 1.59 (s, 3H), 1.45-1.49 (m, 3H), 1.21-1.28 (m, 3H).

Intermediate 130

1-(4-(trifluoromethyl)phenyl)ethan-1-ol

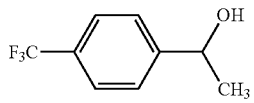

To a solution of 4-(trifluoromethyl)benzaldehyde (4.2 g, 24.12 mmol) in THF (10 mL) at 0° C. was added methylmagnesium bromide (3 M in Et$_2$O, 12.06 mL, 36.2 mmol). The reaction mixture was stirred at room temperature for 2 h. The reaction was quenched with the addition of saturated aqueous NH$_4$Cl solution. The reaction was extracted with EtOAc (2×100 mL), the combined organic layer was washed with water, brine and dried over sodium sulfate. The solvent was evaporated under reduced pressure to obtain the crude product, which was purified by silica gel column chromatography using 20% EtOAc in pet ether. The fractions were concentrated under reduced pressure to obtain 1-(4-(trifluoromethyl)phenyl)ethan-1-ol (4 g, 21.03 mmol, 87% yield). $^1$H NMR (400 MHz, CDCl$_3$) δ (ppm)=7.67-7.57 (m, 2H), 7.50 (d, J=8.0 Hz, 2H), 4.97 (dd, J=3.8, 6.3 Hz, 1H), 1.88 (d, J=3.5 Hz, 1H), 1.51 (d, J=6.5 Hz, 3H).

Intermediate 131

1-(1-Chloroethyl)-4-(trifluoromethyl)benzene

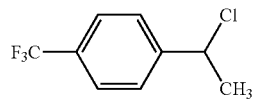

To a solution of 1-(4-(trifluoromethyl)phenyl)ethan-1-ol (1.1 g, 5.78 mmol) in DCM (10 mL) at 0° C. was added SOCl$_2$ (0.633 mL, 8.68 mmol). The reaction mixture was stirred at room temperature for 16 h. The volatiles were evaporated under reduced pressure to afford 1-(1-chloroethyl)-4-(trifluoromethyl)benzene (1 g, 4.79 mmol, 83% yield). $^1$H NMR (400 MHz, CDCl$_3$) δ (ppm)=7.65-7.60 (m, 2H), 7.56-7.52 (m, 2H), 5.11 (q, J=6.8 Hz, 1H), 1.86 (d, J=7.0 Hz, 3H).

Intermediate 132 tert-butyl (2S,5R)-2,5-dimethyl-4-(3-(trifluoromethyl)bicyclo[1.1.1]pentane-1-carbonyl)piperazine-1-carboxylate

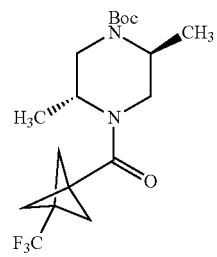 [SMILES: C[C@@H]1CN(C(=O)OC(C)(C)C)[C@@H](C)CN1C(=O)C12CC(C(F)(F)F)(C1)C2]

To a solution of tert-butyl (2S,5R)-2,5-dimethylpiperazine-1-carboxylate (74.4 mg, 0.347 mmol) and 3-(trifluoromethyl)bicyclo[1.1.1]pentane-1-carboxylic acid (50 mg, 0.278 mmol) in anhydrous DMF (2.776 mL), 1-methylimidazole (0.055 mL, 0.694 mmol) and chloro-N,N,N',N'-tetramethylformamidinium hexafluorophosphate (117 mg, 0.416 mmol) were added sequentially and the reaction mixture was stirred at room temperature for 17 h. The reaction was quenched with the addition of water (30 mL) and the mixture extracted with EtOAc (3×). The combined extracts were washed with brine, dried over Na$_2$SO$_4$, and the solvent was removed under reduced pressure, and the crude material was purified by silica gel column chromatography using 0-60% EtOAc in n-hexane to afford tert-butyl (2S,5R)-2,5-dimethyl-4-(3-(trifluoromethyl)bicyclo[1.1.1]pentane-1-carbonyl)piperazine-1-carboxylate (92 mg, 88% yield).

LCMS: m/z, 377.4 [M+H]$^+$; rt 1.45 mins (LCMS Method: Column: Acquity BEH C18 (2.1×50 mm, 1.7 μm); mobile phase A: 0.05% TFA in acetonitrile:water (5:95); mobile phase B: 0.05% TFA in acetonitrile:water (95:5), Gradient=0-100% B over 1.8 minute, then a 0.2 minute hold at 100% B; Temperature: 50° C.; Flow rate: 1.0 mL/min; Detection: UV at 220 nm). $^1$H NMR (500 MHz, CDCl$_3$) δ 4.79-4.67 (m, 1.2H), 4.54-4.40 (m, 1.2H), 4.34-4.21 (m, 1.5H), 4.17 (br dd, J=13.4, 3.0 Hz, 1.4H), 3.83 (br d, J=13.4 Hz, 0.5H), 3.74 (br dd, J=13.2, 9.5 Hz, 0.9H), 3.65 (br d, J=14.1 Hz, 0.7H), 3.60-3.54 (m, 1.3H), 3.53-3.42 (m, 1.3H), 3.26-3.15 (m, 1.2H), 3.10 (br d, J=13.5 Hz, 0.9H), 3.03 (dd, J=13.6, 4.4 Hz, 1.0H), 2.36-2.32 (m, J=3.1 Hz, 5.6H), 2.30 (s, 6.7H), 1.47 (br s, 7.8H), 1.46 (s, 10.1H), 1.28-1.23 (m, 3.0H), 1.15 (br t, J=6.3 Hz, 7.4H), 1.10 (t, J=7.0 Hz, 2.8H). Proton NMR shows characteristics of restricted rotation (rotamers).

Intermediate 133 tert-butyl (2S,5R)-2,5-dimethyl-4-(1-(3-(trifluoromethyl)bicyclo[1.1.1]pentan-1-yl)propyl)piperazine-1-carboxylate (Diastereomeric Mixture)

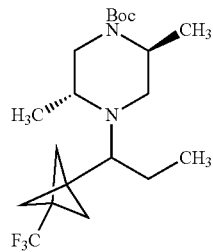

An oven-dried vial with stir bar was charged with tert-butyl (2S,5R)-2,5-dimethyl-4-(3-(trifluoromethyl)bicyclo[1.1.1]pentane-1-carbonyl)piperazine-1-carboxylate (90 mg, 0.239 mmol) and chlorocarbonylbis(triphenylphosphine)iridium(I) (Vaska's complex) (5.60 mg, 7.17 μmol) and purged with nitrogen for 5 mins. Anhydrous THF (2.657 mL), under nitrogen atmosphere was added and the solvent level marked on the vial. Additional anhydrous THF (3.5 mL), under nitrogen, was added, and the mixture continued to sparge with nitrogen for 15 mins at room temperature. The solvent level decreased during this time, approximately arriving at the marked 2.7 mL line once sparging was complete. Subsequently, 1,1,3,3-tetramethyldisiloxane (0.085 mL, 0.478 mmol) was added at room temperature and the mixture sparged with nitrogen for another 3 mins. The nitrogen sparge was stopped and the mixture further stirred at room temperature under nitrogen atmosphere for 1 h and 15 mins. Gradually, the bright yellow solution became colorless. The reaction mixture was cooled to −78° C. Ethylmagnesium bromide (0.159 mL, 0.478 mmol, 3 M in diethyl ether) was then added dropwise and the mixture stirred at −78° C. for 5 mins, and then warmed to room temperature and stirred for 17 h. The reaction was cooled to 0° C. and quenched with saturated aqueous NH$_4$Cl (10 mL). The mixture was stirred vigorously, warmed to room temperature and EtOAc and water were added. The aqueous layer was extracted with EtOAc (4×). The combined organic layers were washed with brine (1×) and the brine layer back-extracted with EtOAc (1×). The combined organic layers were dried over Na$_2$SO$_4$, filtered, and concentrated under reduced pressure to afford a yellow oil. The crude material was purified by silica gel column chromatography using 2-60% EtOAc in n-hexane to afford tert-butyl (2S,5R)-2,5-dimethyl-4-(1-(3-(trifluoromethyl)bicyclo[1.1.1]pentan-1-yl)propyl)piperazine-1-carboxylate (93 mg, 100% yield) as a diastereomeric mixture (1.3:1 dr).

LCMS: m/z, 391.0 [M+H]+; rt 1.16 mins (LCMS Method: Column: Acquity BEH C18 (2.1×50 mm, 1.7 μm); mobile phase A: 0.05% TFA in acetonitrile:water (5:95); mobile phase B: 0.05% TFA in acetonitrile:water (95:5), Gradient=0-100% B over 1.8 minute, then a 0.2 minute hold at 100% B; Temperature: 50° C.; Flow rate: 1.0 mL/min; Detection: UV at 220 nm, although product has no chromophore; peak detected by MS TIC). 41 NMR (500 MHz, CDCl$_3$) δ 4.10-3.98 (m, 1.9H), 3.59 (dd, J=13.2, 1.0 Hz, 1.9H), 3.26 (td, J=13.4, 4.2 Hz, 1.9H), 2.96-2.86 (m, 1.5H), 2.86-2.79 (m, 2.3H), 2.44-2.33 (m, 3.8H), 1.96-1.90 (m, 5.7H), 1.86 (td, J=9.6, 1.5 Hz, 5.9H), 1.46 (s, 9.2H), 1.46 (s, 7.6H), 1.44-1.38 (m, 1.3H), 1.38-1.34 (m, 1.9H), 1.34-1.26 (m, 1.6H), 1.17 (d, J=6.6 Hz, 2.5H), 1.14 (d, J=6.6 Hz, 3.3H), 1.02-0.94 (m, 8.9H), 0.90 (t, J=7.5 Hz, 3.0H). The proton signals of this 1.3:1 diastereomeric mixture are reported with fractional numbers to be reflective of the mixture.

Intermediate 134

(2R,5S)-2,5-dimethyl-1-(1-(3-(trifluoromethyl)bicyclo[1.1.1]pentan-1-yl)propyl)piperazine (Diastereomeric Mixture)

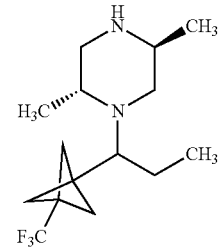 [SMILES: CCC(N1C[C@H](C)NC[C@H]1C)C12CC(C(F)(F)F)(C1)C2]

To a stirred solution of tert-butyl (2S,5R)-2,5-dimethyl-4-(1-(3-(trifluoromethyl) bicyclo[1.1.1]pentan-1-yl)propyl)piperazine-1-carboxylate (93 mg, 0.238 mmol, diastereomeric mixture) in anhydrous CH$_2$Cl$_2$ (2.382 mL) at room temperature was added TFA (0.183 mL, 2.382 mmol). The reaction mixture was stirred for 19 h, after which the solvent was removed under reduced pressure to afford the TFA salt of (2R,5S)-2,5-dimethyl-1-(1-(3-(trifluoromethyl)bicyclo[1.1.1]pentan-1-yl)propyl)piperazine (123 mg, 100% yield) after drying under high vacuum.

LCMS: m/z, 291.0 and 290.9 [M+H]$^+$; rt 0.97 and 0.99 min. (LCMS Method: Column: Acquity BEH C18 (2.1×50 mm, 1.7 μm); mobile phase A: 0.05% TFA in acetonitrile:water (5:95); mobile phase B: 0.05% TFA in acetonitrile:water (95:5), Gradient=0-100% B over 1.8 minute, then a 0.2 minute hold at 100% B; Temperature: 50° C.; Flow rate: 1.0 mL/min; Detection: UV at 220 nm, although product has no chromophore; peak detected by MS TIC). $^1$H NMR (500 MHz, methanol-d$_4$) δ 3.59-3.43 (m, 2.0H), 3.43-3.33 (m, 4.9H), 3.23 (dd, J=13.4, 2.9 Hz, 1.0H), 3.05 (t, J=11.9 Hz, 1.0H), 2.98-2.90 (m, 0.8H), 2.86-2.71 (m, 1.8H), 2.22-2.09 (m, 8.1H), 2.03 (dd, J=9.4, 1.5 Hz, 3.0H), 1.81-1.68 (m, 1.1H), 1.64-1.58 (m, 1.7H), 1.56-1.50 (m, 0.7H), 1.35 (d, J=2.3 Hz, 2.6H), 1.33 (d, J=2.4 Hz, 2.5H), 1.31-1.25 (m, 7.0H), 1.05 (t, J=7.5 Hz, 3.0H), 0.98 (t, J=7.4 Hz, 2.4H). The proton signals of this diastereomeric mixture are reported with fractional numbers to be reflective of the mixture.

Example 446

6-chloro-4-((2S,5R)-2,5-dimethyl-4-(1-(3-(trifluoromethyl)bicyclo[1.1.1]pentan-1-yl) propyl)piperazin-1-yl)-1-methylpyrido[3,2-d]pyrimidin-2(1H)-one (diastereomeric mixture)

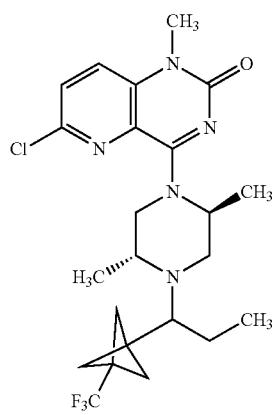

(446)

To a stirred solution of (2R,5S)-2,5-dimethyl-1-(1-(3-(trifluoromethyl) bicyclo[1.1.1]pentan-1-yl)propyl)piperazine TFA salt (96 mg, 0.238 mmol) in acetonitrile (2 mL), DIPEA (0.416 mL, 2.380 mmol) and 4,6-dichloro-1-methylpyrido[3,2-d]pyrimidin-2(1H)-one (65.7 mg, 0.286 mmol) were added sequentially at room temperature. The reaction mixture was heated at 80° C. for 2 h. The reaction mixture was cooled to room temperature and the solvent removed under reduced pressure. The crude material was dry-loaded onto Celite and purified by silica gel column chromatography using 0-15% MeOH in $CH_2Cl_2$ to afford 6-chloro-4-((2S,5R)-2,5-dimethyl-4-(1-(3-(trifluoromethyl)bicyclo[1.1.1]pentan-1-yl)propyl)piperazin-1-yl)-1-methylpyrido[3,2-d]pyrimidin-2(1H)-one (101.9 mg, 88% yield). LCMS: m/z, 484.05 [M+H]$^+$; rt 1.11 and 1.13 min. (LCMS Method: Column: Acquity BEH C18 (2.1×50 mm, 1.7 µm); mobile phase A: 0.05% TFA in acetonitrile:water (5:95); mobile phase B: 0.05% TFA in acetonitrile:water (95:5), Gradient=0-100% B over 1.8 minute, then a 0.2 minute hold at 100% B; Temperature: 50° C.; Flow rate: 1.0 mL/min; Detection: UV at 220 nm). $^1$H NMR (400 MHz, CDCl$_3$) δ 7.50 (s, 4.0H), 5.91-5.14 (bm, 2.2H), 3.69-3.59 (m, 1.5H), 3.56 (s, 3.2H), 3.55 (s, 3.0H), 3.25-3.07 (m, 2.2H), 3.03-2.87 (m, 2.0H), 2.65 (dt, J=12.1, 6.1 Hz, 2.0H), 2.52-2.36 (m, 2.2H), 2.05-1.96 (m, 2.9H), 1.96-1.88 (m, 6.9H), 1.87-1.78 (m, 3.9H), 1.52-1.38 (m, 3.6H), 1.37-1.28 (m, 8.3H), 1.04 (d, J=6.2 Hz, 6.1H), 1.02-0.96 (m, 4.2H), 0.88 (t, J=7.3 Hz, 3.4H). The proton signals of this diastereomeric mixture were reported with fractional numbers to be reflective of the mixture.

Examples 447-449

4-((2S,5R)-2,5-dimethyl-4-(1-(3-(trifluoromethyl)bicyclo[1.1.1]pentan-1-yl)propyl) piperazin-1-yl)-1-methyl-2-oxo-1,2-dihydropyrido[3,2-d]pyrimidine-6-carbonitrile (diastereomeric mixture and resolved homochiral samples)

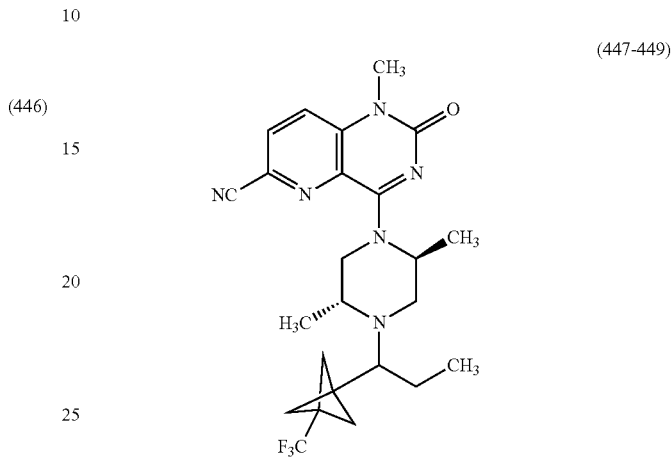

(447-449)

A solution of 6-chloro-4-((2S,5R)-2,5-dimethyl-4-(1-(3-(trifluoromethyl) bicyclo[1.1.1]pentan-1-yl)propyl)piperazin-1-yl)-1-methylpyrido[3,2-d]pyrimidin-2(1H)-one (101.9 mg, 0.211 mmol), PdCl$_2$(dppf)-CH$_2$Cl$_2$ adduct (17.2 mg, 0.021 mmol), zinc (11.0 mg, 0.168 mmol), and zinc cyanide (33 mg, 0.281 mmol) in anhydrous NMP (2.376 mL) was sparged with nitrogen for 15 min. The reaction mixture was heated at 80° C. for 19 h. The reaction was quenched with saturated aqueous sodium bicarbonate. EtOAc was added and the mixture stirred vigorously. The aqueous layer was extracted with EtOAc (4×). The combined organic layers were washed with brine (2×), dried over Na$_2$SO$_4$, filtered, and concentrated under reduced pressure to afford a red-brown oil. The crude material was purified via preparative LCMS with the following conditions: Column:) (Bridge C18, 200 mm×19 mm, 5-µm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 42% B, 42-82% B over 20 minutes, then a 0-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 60.5 mg (60.6% yield), and its estimated purity by LCMS analysis was 100%. Analytical LCMS was used to determine the final purity. Injection 1 conditions: Column: Waters)(Bridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100%; Observed Mass: 475.07, 475.07; Retention Time: 1.39, 1.42 min. Injection 2 conditions: Column: Waters Xbridge C18, 2.1 mm×50 mm, 1.7 µm particles; Mobile Phase A: 5:95 acetonitrile:water with 10 mM ammonium acetate; Mobile Phase B: 95:5 acetonitrile: water with 10 mM ammonium acetate; Temperature: 50° C.;

Gradient: 0% B to 100% B over 3 min, then a 0.50 min hold at 100% B; Flow: 1 mL/min; Detection: MS and UV (220 nm). Injection 2 results: Purity: 100%; Observed Mass: 475.06; Retention Time: 2.35 min. $^1$H NMR (500 MHz, DMSO-d$_6$) δ 8.22 (d, J=8.9 Hz, 2H), 7.97 (br d, J=9.2 Hz, 2H), 5.83-4.65 (m, 2H), 3.44 (s, 6H), 3.37-3.30 (m, 1H), 3.26-3.06 (m, 1H), 2.97-2.86 (m, 1H), 2.85-2.73 (m, 1H), 2.72-2.60 (m, 1H), 2.49-2.41 (m, 1H), 2.04 (br d, J=9.5 Hz, 2H), 1.98-1.82 (m, 10H), 1.48-1.30 (m, 4H), 1.30-1.20 (m, 6H), 1.01-0.89 (m, 9H), 0.82 (br t, J=7.2 Hz, 3H). Some peaks are obscured due to the water suppression technique employed. The multiplet between 2.49-2.41 ppm is obscured due to overlap with the DMSO-d6 NMR solvent peak.

The diastereomeric mixture of 4-((2S,5R)-2,5-dimethyl-4-(1-(3-(trifluoromethyl)bicyclo[1.1.1]pentan-1-yl)propyl)piperazin-1-yl)-1-methyl-2-oxo-1,2-dihydropyrido[3,2-d]pyrimidine-6-carbonitrile was resolved by the following chiral SFC separation method: Approximately 29 mg of sample were resolved into two peaks collected in IPA w/0.1% DEA. The chiral purity for the isolates were determined using the analytical chromatogram below.

| Isolate | Chiral Purity |
|---|---|
| 1st Eluting Peak | >95% |
| 2nd Eluting Peak | >95% |

Preparative Chromatographic Conditions:
  Instrument: Waters 100 Prep SFC
  Column: Chiral OD, 30×250 mm. 5 micron
  Mobile Phase: 80% CO$_2$/20% IPA w/0.1% DEA
  Flow Conditions: 100 mL/min
  Detector Wavelength: 220 nm
  Injection Details: 1000 μL 29 mg dissolved in 3 mL MeOH
Analytical Chromatographic Conditions (Before Prep):
  Instrument: Shimadzu Nexera UC SFC
  Column: Chiral OD, 4.6×100 mm, 5 micron
  Mobile Phase: 80% CO$_2$/20% IPA w/0.1% DEA
  Flow Conditions: 2 mL/min
  Detector Wavelength: 220 nm Example 448

Isolate 1: First Eluting Peak

Example 449

Isolate 2: Second Eluting Peak

EXAMPLE 448: The yield of the product was 6.7 mg (22.3%), and its purity was 100%. Analytical LCMS was used to determine the final purity. Injection 1 conditions: Column: Waters)(Bridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100%; Observed Mass: 475.09; Retention Time: 2.34 min. Injection 2 conditions: Column: Waters)(Bridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100%; Observed Mass: 474.90; Retention Time: 1.51 min. $^1$H NMR (500 MHz, DMSO-d$_6$) δ 8.22 (d, J=8.9 Hz, 1H), 7.96 (d, J=8.9 Hz, 1H), 5.88-4.58 (m, 1H), 4.36-4.28 (m, 1H), 3.43 (s, 3H), 3.39-3.28 (m, 1H), 3.25-3.13 (m, 1H), 2.94-2.84 (m, 1H), 2.83-2.70 (m, 1H), 2.49-2.45 (m, 1H), 2.11-1.90 (m, 6H), 1.46-1.30 (m, 2H), 1.26 (br s, 3H), 0.92 (br d, J=5.8 Hz, 3H), 0.82 (br t, J=7.2 Hz, 3H). Some peaks are obscured due to the water suppression technique employed. The multiplet between 2.49-2.45 ppm is obscured due to overlap with the DMSO-d6 NMR solvent peak.

EXAMPLE 449: The yield of the product was 10.0 mg (33.3%), and its purity was 100%. Analytical LCMS was used to determine the final purity. Injection 1 conditions: Column: Waters)(Bridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100%; Observed Mass: 475.30; Retention Time: 2.36 min. Injection 2 conditions: Column: Waters)(Bridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100%; Observed Mass: 474.92; Retention Time: 1.49 min. $^1$H NMR (500 MHz, DMSO-d$_6$) Shift 8.21 (d, J=8.9 Hz, 1H), 7.96 (d, J=8.9 Hz, 1H), 5.86-4.52 (m, 1H), 3.43 (s, 3H), 3.40-3.31 (m, 1H), 3.16-3.06 (m, 1H), 2.99-2.85 (m, 1H), 2.74-2.61 (m, 1H), 2.45 (br t, J=6.7 Hz, 1H), 1.95-1.79 (m, 6H), 1.48-1.32 (m, 2H), 1.26 (br d, J=2.4 Hz, 3H), 1.02-0.88 (m, 6H). Some peaks are obscured due to the water suppression technique employed.

The examples in the Table 21 were prepared from general procedure described in Examples 447-449, using appropriate carboxylic acid and Grignard reagent in the first and second steps, respectively. When the reaction provided a mixture of diastereomers, the mixture was separated at the final stage using either preparative chromatography or preparative chiral chromatography. The absolute stereochemistry was not assigned at the newly formed carbon-nitrogen bond.

TABLE 21

| Ex. No. | STRUCTURE | Stereo chem. | LCMS Method | LCMS rt | [M + H]+ |
|---|---|---|---|---|---|
| 450 | 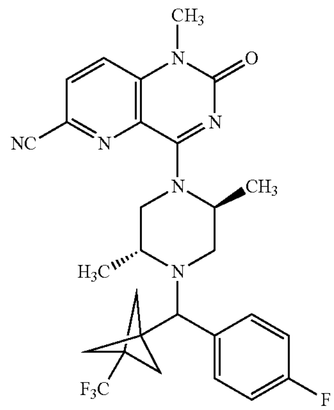 [SMILES: C[C@@H]1CN(c2nc(=O)n(C)c3ccc(C#N)nc23)[C@@H](C)CN1C(c1ccc(F)cc1)C12CC(C(F)(F)F)(C1)C2] | D | F | 1.80 | 540.9 |
| 451 | | H | F | 1.76 | 541.2 |
| 452 | | H | F | 1.79 | 541.0 |
| 453 | 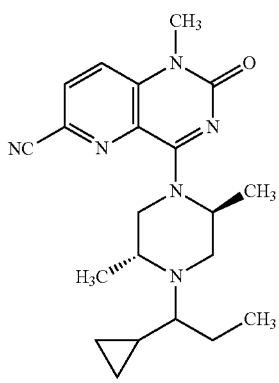 [SMILES: CCC(C1CC1)N1C[C@H](C)N(c2nc(=O)n(C)c3ccc(C#N)nc23)C[C@H]1C] | D | F | 1.04 | 381.0 |
| 454 | | H | F | 1.21 | 381.3 |
| 455 | | H | F | 1.20 | 381.3 |
| 456 | 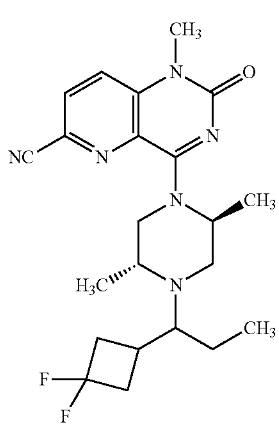 [SMILES: CCC(C1CC(F)(F)C1)N1C[C@H](C)N(c2nc(=O)n(C)c3ccc(C#N)nc23)C[C@H]1C] | D | F | 1.07 | 431.0 |
| 457 | | H | F | 1.23 | 431.2 |
| 458 | | H | F | 1.23 | 431.2 |

TABLE 21-continued

| Ex. No. | STRUCTURE | Stereo chem. | LCMS Method | LCMS rt | [M + H]+ |
|---|---|---|---|---|---|
| 459 | 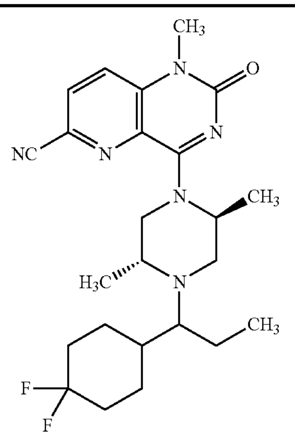 | H | F | 1.20 | 459.1 |
| 460 | | H | F | 1.23 | 459.1 |

Biological Assays

The pharmacological properties of the compounds of this invention may be confirmed by a number of biological assays. The exemplified biological assays, which follow, have been carried out with compounds of the invention.

DGK Alpha LIPGLO $IC_{50}$ (uM)

DGK Alpha ADPGLO (Truncated) $IC_{50}$ (uM)

1. In Vitro DGK Inhibition Assays

The DGKα and DGKζ reactions were performed using either extruded liposome (DGKα and DGKζ LIPGLO assays) or detergent/lipid micelle substrate (DGKα and DGKζ assays). The reactions were carried out in 50 mM MOPS pH 7.5, 100 mM NaCl, 10 mM $MgCl_2$, 1 μM $CaCl_2$, and 1 mM DTT (assay buffer). The reactions using a detergent/lipid micelle substrate also contained 50 mM octyl B-D-glucopyranoside. The lipid substrate concentrations were 11 mM PS and 1 mM DAG for the detergent/lipid micelle reactions. The lipid substrate concentrations were 2 mM PS, 0.25 mM DAG, and 2.75 mM PC for the extruded liposome reactions (5 mM total lipid). The reactions were carried out in 150 μM ATP. The enzyme concentrations for the DGKα and DGKζ were 5 nM The compound inhibition studies were carried out as follows: 25 nL (ADPGLO assay) or 50 nL (LIPGLO assay) droplets of each test compound (top concentration 10 mM with 11 point, 3-fold dilution series for each compound) solubilized in DMSO were transferred to wells of a white 1536 well plate (Corning 3725). A 5 mL enzyme/lipid substrate solution at 2× final reaction concentration was prepared by combining 2.5 mL 4× enzyme solution (20 nM DGKα or DGKζ (prepared as described below) in assay buffer) and 2.5 mL of either 4× liposome or 4× detergent/lipid micelle solution (compositions described below) and incubated at room temperature for 10 minutes. Next, 1 μL 2× enzyme/lipid substrate solution was added to wells containing the test compound and reactions were initiated with the addition of 1 μL 300 uM ATP. The reactions were allowed to proceed for 2 hr (ADPGLO assay) or 1 hr (LIPGLO assay), after which 2 μL Glo Reagent (Promega V9101) was added and incubated for 40 minutes. Next, 4 μL Kinase Detection Reagent was added and incubated for 30 minutes. Luminescence was recorded using an EnVision microplate reader. The percent inhibition was calculated from the ATP conversion generated by no enzyme control reactions for 100% inhibition and vehicle-only reactions for 0% inhibition. The compounds were evaluated at 11 concentrations to determine $IC_{50}$.

4× Detergent/lipid Micelle Preparation

The detergent/lipid micelle was prepared by combining 15 g phosphatidylserine (Avanti 840035P) and 1 g diacylglycerol (8008110) and dissolving into 150 mL chloroform in a 2 L round bottom flask. Chloroform was removed under high vacuum by rotary evaporation. The resulting colorless, tacky oil was resuspended in 400 mL 50 mM MOPS pH 7.5, 100 mM NaCl, 20 mM NaF, 10 mM $MgCl_2$, 1 μM $CaCl_2$, 1 mM DTT, and 200 mM octyl glucoside by vigorous mixing. The lipid/detergent solution was split into 5 mL aliquots and stored at −80° C.

2× Liposome Preparation

The lipid composition was 5 mol % DAG (Avanti 8008110), 40 mol % PS (Avanti 840035P), and 55 mol % PC (Avanti 850457) at a total lipid concentration of 7-8 mg/mL for the liposome solution. The PC, DAG, and PS were dissolved in chloroform, combined, and dried in vacuo to a thin film. The lipids were hydrated to 20 mM in 50 mM MOPS pH 7.5, 100 mM NaCl, 5 mM $MgCl_2$, and were freeze-thawed five times. The lipid suspension was extruded through a 100 nm polycarbonate filter 10-12 times. Dynamic light scattering was carried out to confirm liposome size (50-60 nm radius). The liposome preparation was stored at 4° C. for as long as four weeks.

4× Liposome Preparation

The lipid composition was 5 mol % DAG (Avanti 8008110), 40 mol % PS (Avanti 840035P), and 55 mol % PC (Avanti 850457) at a total lipid concentration of 15.2 mg/mL for the 4× liposome solution. The PC, DAG, and PS were dissolved in chloroform, combined, and dried in vacuo to a thin film. The lipids were hydrated to 20 mM in 50 mM MOPS pH 7.5, 100 mM NaCl, 5 mM $MgCl_2$, and were freeze-thawed five times. The lipid suspension was extruded through a 100 nm polycarbonate filter eleven times. Dynamic light scattering was carried out to confirm liposome size (50-60 nm radius). The liposome preparation was stored at 4° C. for as long as four weeks.

Baculovirus Expression of Human DGKα and DGKζ

Human DGK-alpha-TVMV-His-pFBgate and human DGK-zeta-transcript variant-2-TVMV-His-pFBgate baculovirus samples were generated using the Bac-to-Bac baculovirus expression system (Invitrogen) according to the manufacturer's protocol. The DNA used for expression of DGK-alpha and DGK-zeta have SEQ ID NOs: 1 and 3, respectively. Baculovirus amplification was achieved using infected Sf9 cells at 1:1500 virus/cell ratios, and grown for 65 hours at 27° C. post-transfection.

The expression scale up for each protein was carried out in the Cellbag 50 L WAVE-Bioreactor System 20/50 from GE Healthcare Bioscience. 12 L of $2 \times 10^6$ cells/mL Sf9 cells (Expression System, Davis, Calif.) grown in ESF921 insect medium (Expression System) were infected with virus stock at 1:200 virus/cell ratios, and grown for 66-68 hours at 27° C. post-infection. The infected cell culture was harvested by centrifugation at 2000 rpm for 20 min 4° C. in a SORVALL® RC12BP centrifuge. The cell pellets were stored at −70° C. until purification.

Purification of Human DGK-Alpha and DGK-Zeta

Full length human DGKα and DGKζ, each expressed containing a TVMV-cleavable C-terminal Hexa-His tag sequence (SEQ ID NOs: 2 and 4, respectively) and produced as described above, were purified from Sf9 baculovirus-infected insect cell paste. The cells were lysed using nitrogen cavitation method with a nitrogen bomb (Parr Instruments), and the lysates were clarified by centrifugation. The clarified lysates were purified to ~90% homogeneity, using three successive column chromatography steps on an ÄKTA Purifier Plus system. The three steps column chromatography included nickel affinity resin capture (i.e. HisTrap FF crude, GE Healthcare), followed by size exclusion chromatography (i.e. HiLoad 26/600 Superdex 200 prep grade, GE Healthcare for DGK-alpha, and HiPrep 26/600 Sephacryl S 300_HR, GE Healthcare for DGK-zeta). The third step was ion exchange chromatography, and differed for the two isoforms. DGKα was polished using Q-Sepharose anion exchange chromatography (GE Healthcare). DGKζ was polished using SP Sepharose cation exchange chromatography (GE Healthcare). The proteins were delivered at concentrations of ≥2 mg/mL. The formulation buffers were identical for both proteins: 50 mM Hepes, pH 7.2, 500 mM NaCl, 10% v/v glycerol, 1 mM TCEP, and 0.5 mM EDTA.

2. Raji CD4 T Cell IL2 Assay

A 1536-well IL-2 assay was performed in 4 μL volume using pre-activated CD4 T cells and Raji cells. Prior to the assay, CD4 T cells were pre-activated by treatment with α-CD3, α-CD28 and PHA at 1.5 μg/mL, 1 μg/mL, and 10 μg/mL, respectively. Raji cells were treated with Staphylococcal enterotoxin B (SEB) at 10,000 ng/mL. Serially diluted compounds were first transferred to 1536-well assay plate (Corning, #3727), followed by addition of 2 μL of pre-activated CD4 T cells (final density at 6000 cells/well) and 2 μL of SEB-treated Raji cells (2000 cells/well). After 24 hours incubation at a 37° C./5% $CO_2$ incubator, 4 μl of IL-2 detection reagents were added to the assay plate (Cisbio, #64IL2PEC). The assay plates were read on an Envision reader. To assess compound cytotoxicity, either Raji or CD4 T cells were incubated with the serially diluted compounds. After 24 hours incubation, 4 μL of Cell Titer Glo (Promega, #G7572) were added, and the plates were read on an Envision reader. The 50% effective concentration ($IC_{50}$) was calculated using the four-parameter logistic formula $y=A+((B-A)/(1+((C/x)^D)))$, where A and B denote minimal and maximal % activation or inhibition, respectively, C is the $IC_{50}$, D is hill slope and x represent compound concentration.

3. CellTiter-Glo CD8 T Cell Proliferation Assay

Frozen nave human CD8 T cells were thawed in RPMI+10% FBS, incubated for 2 h in 37° C., and counted. The 384-well tissue culture plate was coated overnight at 4° C. with 20 μl anti-human CD3 at 0.1 μg/mL in plain RPMI, which was removed off the plate before 20 k/40 μL CD8 T cells with 0.5 μg/ml soluble anti-human CD28 were added to each well. The compounds were echoed to the cell plate immediately after the cells were plated. After 72 h incubation at 37° C. incubator, 10 μL CellTiter-glo reagent (Promega catalog number G7570) was added to each well. The plate was vigorously shaken for 5 mins, incubated at room temperature for another 15 mins and read on Envision for CD8 T cell proliferation. In analysis, 0.1 μg/mL anti-CD3 and 0.5 μg/mL anti-CD28 stimulated CD8 T cell signal was background. The reference compound, 8-(4-(bis(4-fluorophenyl)methyl) piperazin-1-yl)-5-methyl-7-nitro-6-oxo-5,6-dihydro-1,5-naphthyridine-2-carbonitrile, at 3 μM was used to set the 100% range and $EC_{50}$ was at absolute 50% to normalize the data.

4. DGK AP1-Reporter Assay

The Jurkat AP1-luciferase Reporter was generated using the Cignal Lenti AP1 Reporter (luc) Kit from SABiosciences (CLS-011L).

The compounds were transferred from an Echo LDV plate to individual wells of a 384-well plate (white, solid-bottom, opaque PE CulturPlate 6007768) using an Echo550 instrument. The sample size was 30 nL per well; and one destination plate per source plate. The cell suspensions were prepared by transferring 40 mL cells (2×20 mL) to clean 50 mL conical tubes. The cells were concentrated by centrifugation (1200 rpm; 5 mins; ambient temperature). The supernatant was removed and all cells were suspended in RPMI (Gibco 11875)+10% FBS to make a $1.35 \times 10^6$ cells/ml concentration. The cells were added manually using a multichannel pipette, 30 μL/well of cell suspension to a 384-well TC plate containing the compounds, $4.0 \times 10^4$ cells per well. The cell plates were incubated for 20 minutes at 37° C. and 5% $CO_2$.

During the incubation, anti-CD3 antibody (αCD3) solutions were prepared by mixing 3 μL αCD3 (1.3 mg/mL) with 10 mL medium [final conc=0.4 μg/mL]. Next, 1.5 μl αCD3 (1.3 mg/mL) was mixed with 0.5 mL medium [final conc=4 μg/ml]. After 20 minutes, 10 μL medium was added to all wells in column 1, wells A to M, and 10 μL αCD3 (4 ug/mL) per well was added in column 1, rows N to P for reference. Then using a multi-channel pipette, 10 μL αCD3 (0.4 ug/mL) per well was added. The αCD3 stimulated +/− compound-treated cells were incubated at 37° C., 5% $CO_2$ for 6 hours.

During this incubation period, Steady-Glo (Promega E2520) reagent was slowly thawed to ambient temperature. Next, 20 μL Steady-Glo reagent per well was added using a multi-drop Combi-dispenser. Bubbles were removed by centrifugation (2000 rpm, ambient temperature, 10 secs). The cells were incubated at room temperature for 5 minutes. Samples were characterized by measuring the Relative Light Units (RLU) with an using Envision Plate Reader Instrument on a luminescence protocol. The data was analyzed using the reference compound, 8-(4-(bis(4-fluorophenyl)methyl)piperazin-1-yl)-5-methyl-7-nitro-6-oxo-5,6-dihydro-1,5-naphthyridine-2-carbonitrile, to normalize 100% inhibition.

5. Murine Cytotoxic T Lymphocyte Assay

An antigen-specific cytolytic T-cell (CTL) assay was developed to evaluate functionally the ability of DGKα and DGKζ inhibitors to enhance effector T cell mediated tumor cell killing activity. CD8+ T-cells isolated from the OT-1 transgenic mouse recognize antigen presenting cells, MC38, that present the ovalbumin derived peptide SIINFEKL. Recognition of the cognate antigen initiates the cytolytic activity of the OT-1 antigen-specific CD8+ T cells.

Functional CTL cells were generated as follows: OT-1 splenocytes from 8-12 week old mice were isolated and expanded in the presence of the SIINFEKL peptide at 1 µg/mL and mIL2 at 10 U/mL. After three days, fresh media with mIL2 U/ml was added. On day 5 of the expansion, the CD8+ T cells were isolated and ready for use. Activated CTL cells may be stored frozen for 6 months. Separately, one million MC38 tumor cells were pulsed with 1 µg/mL of SIINFEKL-OVA peptide for 3 hours at 37° C. The cells were washed (3×) with fresh media to remove excess peptide. Finally, CTL cells that were pretreated with DGK inhibitors for 1 hour in a 96-well U bottom plate were combined with the antigen loaded MC38 tumor cells at a 1:10 ratio. The cells were then spun at 700 rpm for 5 min and placed in an incubator overnight at 37° C. After 24 hours, the supernatant was collected for analysis of IFN-γ cytokine levels by AlphaLisa purchased from Perkin Elmer.

6. PHA Proliferation Assay

Phytohaemagglutinin (PHA)-stimulated blast cells from frozen stocks were incubated in RPMI medium (Gibco, ThermoFisher Scientific, Waltham, Mass.) supplemented with 10% fetal bovine serum (Sigma Aldrich, St. Louis, Mo.) for one hour prior to adding to individual wells of a 384-well plate (10,000 cells per well). The compounds were transferred to individual wells of a 384-well plate and the treated cells are maintained at 37° C., 5% $CO_2$ for 72 h in culture medium containing human IL2 (20 ng/mL) prior to measuring growth using MTS reagent [3-(4,5-dimethyl-2-yl)-5-(3-carboxymethoxyphenyl)-2-(4-sulfophenyl)-2H-tetrazolium] following manufacturer's instructions (Promega, Madison, Wis.). Percent inhibition was calculated comparing values between IL2 stimulated (0% inhibition) and unstimulated control (100% inhibition). Inhibition concentration ($IC_{50}$) determinations were calculated based on 50% inhibition on the fold-induction between IL2 stimulated and unstimulated treatments.

7. Human CD8 T cells IFN-γ Assay

Frozen naïve human CD8 T cells were thawed in AIM-V media, incubated for 2 h in 37° C., and counted. The 384-well tissue culture plate was coated overnight at 4° C. with 20 µL anti-human CD3 at 0.05 µg/mL in PBS, which was removed off the plate before 40,000 cells per 40 microliters CD8 T cells with 0.1 µg/mL soluble anti-human CD28 were added to each well. The compounds were transferred using an Echo liquid handler to the cell plate immediately after the cells were plated. After 20 h incubation at 37° C. incubator, 3 microliters per well supernatants transferred into a new 384-well white assay plate for cytokine measurement.

Interferon-γ (IFN-γ) was quantitated using the AlphLISA kit (Cat #AL217) as described by the manufacturer manual (Perkin Elmer). The counts from each well were converted to IFN-γ concentration (pg/mL). The compound $EC_{50}$ values were determined by setting 0.05 µg/mL anti-CD3 plus 0.1 µg/mL anti-CD28 as the baseline, and co-stimulation of 3 µM of the reference compound, 8-(4-(bis(4-fluorophenyl)methyl) piperazin-1-yl)-5-methyl-7-nitro-6-oxo-5,6-dihydro-1,5-naphthyridine-2-carbonitrile, with anti-CD3 plus anti-CD28 as 100% activation.

8. Human CD8 T Cells pERK Assay

Frozen naïve human CD8 T cells were thawed in AIM-V media, incubated for 2 h in 37° C., and counted. The CD8 positive T cells were added to 384-well tissue culture plate at 20,000 cells per well in AIM-V media. One compound was added to each well, then bead bound anti-human CD3 and anti-CD28 mAb were added at final concentration of 0.3 µg/mL. The cells were incubated at 37° C. for 10 minutes. The reaction was stopped by adding lysis buffer from the AlphaLISA Surefire kit. (Perkin Elmer, cat #ALSU-PERK-A). Lysate (5 µL per well) was transferred into a new 384-well white assay plate for pERK activation measurement.

Compound $EC_{50}$ was determined as setting anti-CD3 plus anti-CD28 as baseline, and co-stimulation of 3 µM 8-(4-(bis(4-fluorophenyl)methyl)piperazin-1-yl)-5-methyl-7-nitro-6-oxo-5,6-dihydro-1,5-naphthyridine-2-carbonitrile with anti-CD3 plus anti-CD28 as 100% activation.

9. Human Whole Blood IFN-γ Assay

Human venous whole blood (22.5 µL per well), obtained from healthy donors, was pre-treated with compounds for one hour at 37° C. in a humidified 95% air/5% $CO_2$ incubator. The blood was stimulated with 2.5 µL anti-human CD3 and anti-CD28 mAb at a final concentration of 1 µg/mL each for 24 hours at 37° C. IFN-γ in the supernatants was measured using AlphLISA kit (Cat #AL217).

Compound $EC_{50}$ determined as setting anti-CD3 plus anti-CD28 as baseline, and co-stimulation of 3 µM of the reference compound, 8-(4-(bis(4-fluorophenyl)methyl) piperazin-1-yl)-5-methyl-7-nitro-6-oxo-5,6-dihydro-1,5-naphthyridine-2-carbonitrile, with anti-CD3 plus anti-CD28 as 100% activation.

TABLE A

In vitro DGK Inhibition $IC_{50}$ Activity Values

| Ex. No. | DGK alpha LIPGLO $IC_{50}$ (uM) | DGK alpha ADPGLO (Truncated) $IC_{50}$ (uM) | DGK zeta LIPGLO $IC_{50}$ (uM) | IFN-γ Whole Blood Normalized $EC_{50}$ (uM) | pERK Whole Blood Normalized $IC_{50}$ (uM) |
|---|---|---|---|---|---|
| 1 | 0.016 | — | 0.036 | 0.027 | 1.04 |
| 2 | 0.032 | — | 0.047 | 0.076 | 0.15 |
| 3 | 0.19 | — | 0.11 | 0.031 | — |
| 4 | 1.33 | — | 0.76 | 0.97 | — |
| 5 | 0.16 | 0.064 | 0.13 | 0.02 | 0.13 |
| 6 | 4.66 | 0.058 | 2.44 | 3.75 | 6.98 |
| 7 | 0.39 | 0.18 | 0.81 | 0.52 | — |
| 8 | 0.12 | 0.14 | 0.044 | 0.032 | 0.18 |
| 9 | 0.007 | — | 0.048 | — | — |
| 10 | 0.37 | — | 0.97 | — | — |
| 11 | 0.005 | — | 0.060 | — | — |
| 12 | 0.41 | — | 0.60 | 4.15 | 0.60 |
| 13 | 0.70 | — | 0.23 | 2.12 | — |
| 14 | 0.35 | — | 0.036 | 0.094 | 0.90 |
| 15 | 0.49 | — | 1.22 | 1.74 | — |
| 16 | 0.045 | — | 0.037 | — | — |
| 17 | 0.32 | — | 2.14 | 2.89 | — |
| 18 | 0.030 | — | 0.025 | — | — |
| 19 | 4.05 | — | 3.10 | 2.06 | — |
| 20 | 0.14 | — | 0.036 | 0.06 | 0.13 |
| 21 | 0.386 | — | 1.01 | 2.85 | — |
| 22 | 0.002 | — | 0.18 | 0.38 | — |
| 23 | 0.058 | — | 0.029 | 0.011 | 0.086 |
| 24 | 0.68 | — | 0.63 | 0.45 | — |
| 25 | 1.23 | 0.33 | 1.34 | 1.25 | — |
| 26 | 0.081 | 0.029 | 0.21 | 0.18 | 0.24 |
| 27 | 0.002 | — | 0.23 | 0.62 | — |

TABLE A-continued

In vitro DGK Inhibition IC$_{50}$ Activity Values

| Ex. No. | DGK alpha LIPGLO IC$_{50}$ (uM) | DGK alpha ADPGLO (Truncated) IC$_{50}$ (uM) | DGK zeta LIPGLO IC$_{50}$ (uM) | IFN-γ Whole Blood Normalized EC$_{50}$ (uM) | pERK Whole Blood Normalized IC$_{50}$ (uM) |
|---|---|---|---|---|---|
| 28 | 1.57 | — | 2.65 | 2.04 | — |
| 29 | 0.040 | — | 0.010 | 0.027 | 0.10 |
| 30 | 0.076 | — | 0.004 | 0.023 | 0.059 |
| 31 | 1.70 | — | 0.96 | 0.27 | — |
| 32 | 0.50 | — | 0.031 | 0.019 | — |
| 33 | 2.56 | — | 5.93 | 3.83 | — |
| 34 | 0.62 | — | 0.31 | 0.42 | — |
| 35 | 0.030 | — | 0.12 | 0.12 | 0.15 |
| 36 | 0.016 | 0.19 | 0.075 | 0.082 | 0.25 |
| 37 | 0.069 | 0.12 | 0.47 | 20 | — |
| 38 | 0.066 | — | 0.12 | 0.072 | 0.22 |
| 39 | — | — | 0.77 | 2.73 | — |
| 40 | 0.32 | — | 0.041 | 0.021 | 0.010 |
| 41 | 2.27 | — | 1.08 | 0.47 | — |
| 42 | 0.078 | 0.007 | 0.11 | 0.081 | 0.35 |
| 43 | 0.022 | 0.082 | 0.13 | 0.12 | 0.34 |
| 44 | 0.085 | — | 0.021 | 0.26 | — |
| 45 | 0.31 | — | 0.51 | 1.04 | — |
| 46 | 0.094 | — | 0.060 | 0.073 | 0.043 |
| 47 | 0.099 | — | 0.054 | 0.032 | 0.020 |
| 48 | 0.016 | — | 0.048 | 0.018 | 0.025 |
| 49 | 0.39 | — | 0.85 | 2.34 | — |
| 50 | 0.11 | — | 0.037 | — | — |
| 51 | 0.037 | — | 0.027 | 0.006 | 0.009 |
| 52 | 0.23 | — | 0.052 | 0.053 | — |
| 53 | 0.63 | — | 0.079 | 0.20 | — |
| 54 | 0.24 | — | 0.35 | 0.31 | 0.91 |
| 55 | 0.41 | — | 0.038 | 0.79 | — |
| 56 | 0.037 | — | 0.011 | 0.039 | 0.20 |
| 57 | 0.96 | — | 0.93 | 1.90 | — |
| 58 | 0.27 | — | 0.054 | 0.022 | — |
| 59 | 0.30 | — | 0.26 | 0.50 | — |
| 60 | 0.030 | — | 0.028 | 0.023 | — |
| 61 | 0.052 | — | 0.38 | 4.50 | — |
| 62 | 0.058 | — | 0.22 | 0.20 | — |
| 63 | 0.040 | — | 0.021 | 0.070 | — |
| 64 | 0.34 | — | 0.76 | 0.69 | — |
| 65 | 1.19 | — | 0.10 | 0.36 | — |
| 66 | 0.23 | 0.002 | 0.11 | 0.075 | — |
| 67 | 0.21 | — | 0.033 | — | — |
| 68 | 1.63 | — | 0.48 | 1.90 | — |
| 69 | 0.21 | — | 0.014 | 0.033 | — |
| 70 | 0.84 | — | 1.41 | 1.44 | — |
| 71 | 0.67 | — | 0.022 | 0.066 | — |
| 72 | 1.50 | — | — | 0.79 | — |
| 73 | 0.029 | — | 0.14 | 0.022 | 0.08 |
| 74 | 0.25 | — | 0.96 | 0.43 | — |
| 75 | 0.039 | — | 0.033 | 0.030 | 0.10 |
| 76 | 0.079 | — | 0.023 | 0.18 | — |
| 77 | 0.036 | — | 0.014 | — | — |
| 78 | 0.47 | — | 1.13 | 0.075 | — |
| 79 | 0.30 | — | 0.023 | 0.30 | — |
| 80 | 2.16 | — | 1.18 | — | — |
| 81 | 0.30 | — | 0.13 | 0.057 | 0.099 |
| 82 | 1.54 | — | 2.45 | 0.53 | — |
| 83 | 0.097 | 0.015 | 0.16 | 0.017 | 0.087 |
| 84 | 3.22 | 0.054 | 2.09 | 0.67 | 0.78 |
| 85 | 0.21 | 0.066 | 0.091 | 0.022 | 0.066 |
| 86 | 2.94 | 0.42 | 2.37 | 1.54 | — |
| 87 | 0.028 | — | 0.31 | 0.44 | — |
| 88 | 0.11 | — | 0.076 | 0.048 | — |
| 89 | 0.055 | 0.060 | 0.11 | 0.035 | 0.26 |
| 90 | 0.12 | 0.14 | 0.59 | — | — |
| 91 | 0.33 | — | 0.044 | 0.19 | — |
| 92 | 0.46 | — | 0.12 | 0.35 | — |
| 93 | — | 0.018 | 0.52 | 0.17 | 0.67 |
| 94 | 0.20 | 0.016 | 0.086 | 0.043 | 0.22 |
| 95 | 0.15 | — | 0.29 | 0.37 | 10.48 |
| 96 | 0.32 | 0.096 | 0.13 | 0.057 | 0.20 |
| 97 | 0.63 | 0.21 | 0.045 | 0.099 | 0.38 |
| 98 | 0.31 | 0.026 | 0.055 | 0.088 | 0.14 |
| 99 | 0.13 | 0.004 | 0.12 | 0.12 | 0.14 |
| 100 | 0.25 | 0.011 | 0.11 | 0.044 | 0.32 |
| 101 | 0.14 | — | 0.066 | 0.10 | 0.25 |
| 102 | — | — | 0.094 | — | — |
| 103 | 0.17 | — | 0.036 | 0.094 | — |
| 104 | 0.47 | — | 0.11 | 0.21 | — |
| 106 | 0.039 | — | 0.13 | 0.24 | — |
| 107 | 0.13 | — | 0.040 | 0.049 | 0.12 |
| 108 | 0.40 | — | 0.050 | 0.057 | 0.028 |
| 109 | 0.034 | — | 0.19 | 0.11 | 0.048 |
| 110 | 0.067 | — | 0.029 | 0.009 | 0.015 |
| 111 | 0.014 | — | 0.033 | 0.021 | 0.090 |
| 112 | 0.043 | 0.011 | 0.022 | 0.011 | 0.015 |
| 113 | 0.047 | 0.010 | 0.046 | 0.057 | 0.17 |
| 114 | 0.16 | — | 0.44 | 0.47 | — |
| 115 | 0.16 | — | 2.47 | 0.23 | 0.52 |
| 116 | 1.00 | — | 2.11 | 1.43 | — |
| 117 | 0.002 | — | 0.002 | 0.16 | 0.78 |
| 118 | 0.095 | — | 0.016 | — | — |
| 119 | 0.65 | — | 0.73 | — | — |
| 120 | 1.71 | — | 0.74 | — | — |
| 121 | 1.94 | — | 1.65 | — | — |
| 122 | 0.032 | — | 1.96 | — | — |
| 123 | 1.38 | — | 1.33 | 2.57 | — |
| 124 | 0.56 | — | 2.56 | 0.50 | 0.27 |
| 125 | 0.74 | — | 0.99 | 0.50 | — |
| 126 | 0.19 | — | 0.44 | 0.68 | — |
| 127 | 0.18 | — | 0.56 | 0.41 | 0.24 |
| 128 | 0.026 | — | 0.11 | — | — |
| 129 | 0.82 | — | 1.55 | 13.2 | — |
| 130 | 12.4 | — | 0.96 | 4.07 | — |
| 131 | 0.010 | — | 0.13 | 0.36 | 0.17 |
| 132 | 0.70 | — | 5.95 | 2.65 | — |
| 133 | 0.53 | — | 0.24 | 0.71 | — |
| 134 | 4.26 | — | 0.78 | 3.67 | — |
| 135 | 4.50 | — | 1.41 | 10.7 | — |
| 136 | 0.92 | — | 0.22 | 0.65 | — |
| 137 | 0.083 | — | 0.19 | 2.65 | — |
| 138 | 2.41 | — | — | — | — |
| 139 | 25.6 | — | 2.88 | 20.0 | — |
| 140 | 0.18 | — | 0.36 | 0.43 | — |
| 141 | 1.27 | — | 1.76 | 3.55 | — |
| 142 | 0.052 | — | 0.23 | 3.65 | 0.10 |
| 143 | 1.33 | — | 2.12 | — | 1.14 |
| 144 | 0.028 | — | 0.046 | — | 0.065 |
| 145 | 1.13 | — | 1.89 | 20.0 | 0.75 |
| 146 | 0.047 | — | 0.044 | 0.71 | 0.25 |
| 147 | 1.46 | — | 1.13 | — | 1.00 |
| 148 | 0.26 | — | 0.10 | 0.57 | — |
| 149 | 4.56 | — | 1.18 | 8.06 | 1.95 |
| 150 | 0.35 | — | 0.20 | 0.48 | 0.14 |
| 151 | 3.46 | — | 0.83 | — | 1.87 |
| 152 | 0.029 | — | 0.092 | 0.20 | 0.11 |
| 153 | 0.69 | — | 1.98 | 2.31 | — |
| 154 | 0.016 | — | 0.37 | 1.43 | — |
| 155 | 0.25 | — | 0.75 | — | — |
| 156 | 0.010 | — | 0.12 | — | — |
| 157 | 0.33 | — | 1.38 | 1.42 | 4.36 |
| 158 | 0.66 | — | 0.57 | 1.58 | — |
| 159 | 0.094 | — | 0.038 | 0.25 | — |
| 160 | 0.11 | — | 0.25 | 0.24 | 0.86 |
| 161 | 2.10 | — | 1.21 | 4.01 | — |
| 162 | 0.056 | — | 1.15 | 1.85 | — |
| 163 | 0.038 | — | 0.46 | 0.25 | 0.49 |
| 164 | 0.12 | — | 0.34 | 0.65 | — |
| 165 | 0.38 | — | 0.37 | 0.63 | — |
| 166 | 5.39 | — | 0.33 | 0.50 | — |
| 167 | 17.8 | — | 2.38 | 3.85 | — |
| 168 | 0.23 | — | 0.15 | 0.11 | 0.22 |
| 169 | 4.62 | — | 2.18 | 1.33 | — |
| 170 | 1.61 | — | 0.33 | 0.096 | — |

TABLE A-continued

In vitro DGK Inhibition IC$_{50}$ Activity Values

| Ex. No. | DGK alpha LIPGLO IC$_{50}$ (uM) | DGK alpha ADPGLO (Truncated) IC$_{50}$ (uM) | DGK zeta LIPGLO IC$_{50}$ (uM) | IFN-γ Whole Blood Normalized EC$_{50}$ (uM) | pERK Whole Blood Normalized IC$_{50}$ (uM) |
|---|---|---|---|---|---|
| 171 | 1.56 | — | 0.56 | 0.22 | — |
| 174 | 0.59 | — | 0.14 | 0.14 | — |
| 175 | 0.98 | — | 0.83 | 1.69 | — |
| 176 | 0.18 | — | 0.11 | 0.19 | 0.21 |
| 177 | 0.61 | — | 0.77 | 1.71 | 0.52 |
| 178 | 0.29 | — | 0.13 | 0.091 | — |
| 179 | 0.081 | — | 0.022 | 0.055 | — |
| 181 | 4.92 | — | 12.4 | 0.73 | — |
| 182 | 0.43 | — | 2.03 | 2.53 | — |
| 183 | 0.083 | — | 2.69 | 2.33 | 0.27 |
| 184 | 2.66 | — | 45.0 | 20.0 | — |
| 185 | — | 0.27 | 0.61 | — | — |
| 188 | — | 0.014 | 0.31 | 0.073 | 0.27 |
| 189 | — | 0.85 | 17.0 | 0.45 | — |
| 190 | 0.029 | — | 0.017 | 0.009 | — |
| 191 | — | 0.46 | 0.26 | 0.29 | — |
| 192 | — | 0.061 | 0.052 | 0.11 | — |
| 193 | — | 0.65 | 1.77 | 1.15 | — |
| 194 | — | — | 5.25 | — | 0.27 |
| 195 | 125 | — | 5.07 | — | — |
| 196 | 0.12 | — | 0.012 | 0.031 | 0.049 |
| 197 | 1.47 | — | 0.22 | 0.31 | — |
| 198 | — | 0.037 | 0.038 | 0.015 | — |
| 199 | — | 0.63 | 0.92 | 2.06 | 11.3 |
| 200 | — | 0.012 | 0.013 | — | — |
| 201 | — | 0.16 | 0.90 | 0.23 | — |
| 202 | — | 0.36 | 0.42 | 0.16 | — |
| 203 | — | 0.78 | 2.71 | 2.21 | — |
| 204 | — | 0.12 | 1.41 | 0.41 | — |
| 205 | — | 0.061 | 3.74 | 0.83 | — |
| 206 | — | 3.98 | 51.0 | 20.0 | 0.080 |
| 207 | — | 0.62 | 0.97 | 1.06 | — |
| 208 | — | 0.025 | 0.078 | 0.017 | — |
| 209 | — | 0.091 | 1.03 | 1.28 | — |
| 210 | — | 0.046 | 0.97 | 0.031 | — |
| 211 | — | 0.046 | 0.10 | 0.018 | — |
| 212 | — | 0.018 | 0.070 | 0.022 | — |
| 213 | — | 0.059 | 0.95 | 0.19 | — |
| 214 | — | 2.01 | 6.62 | 20.0 | 0.066 |
| 215 | — | 0.077 | 0.11 | 0.17 | 20.0 |
| 216 | — | 0.087 | 0.088 | 0.012 | — |
| 217 | — | 1.66 | 4.26 | 0.87 | — |
| 218 | — | 0.078 | 0.018 | — | — |
| 220 | — | 0.11 | 0.046 | 0.081 | — |
| 221 | — | 0.002 | 0.25 | 0.48 | — |
| 222 | — | 0.002 | 0.017 | — | — |
| 223 | — | 0.13 | 2.08 | 0.90 | — |
| 224 | — | 0.081 | 0.14 | 0.12 | — |
| 225 | — | 0.46 | 4.13 | 0.61 | — |
| 226 | — | 1.21 | 2.65 | 5.60 | — |
| 227 | — | 2.45 | 1.79 | 0.64 | — |
| 228 | — | 0.19 | 0.30 | 0.60 | — |
| 229 | — | 0.68 | 3.56 | 1.61 | — |
| 230 | — | 0.042 | 0.13 | 1.29 | — |
| 231 | — | — | — | 9.74 | — |
| 232 | — | 0.002 | 0.013 | 0.044 | 0.044 |
| 233 | — | 0.17 | 0.95 | 2.77 | — |
| 234 | — | 0.036 | 0.059 | — | 0.08 |
| 235 | — | 0.43 | 0.78 | — | — |
| 236 | — | 0.009 | 0.058 | 0.012 | 0.044 |
| 237 | — | 0.053 | 3.96 | 1.43 | — |
| 238 | — | 0.015 | 0.11 | 0.023 | — |
| 239 | — | 0.094 | 2.23 | 2.85 | — |
| 240 | — | 0.073 | 0.11 | 0.27 | 0.29 |
| 241 | — | 0.46 | 0.92 | 2.42 | 0.19 |
| 242 | — | 0.26 | 0.19 | — | — |
| 243 | — | 0.006 | 0.039 | 0.059 | — |
| 244 | — | — | — | 13.3 | — |
| 245 | — | 0.018 | 0.29 | 0.22 | 0.41 |
| 246 | — | 4.67 | 5.85 | — | 0.44 |
| 247 | — | 5.87 | 0.84 | — | — |
| 249 | — | — | 0.04 | — | 0.42 |
| 250 | — | 0.33 | 1.15 | — | 1.80 |
| 251 | — | 0.034 | 0.018 | — | 1.58 |
| 252 | — | 0.27 | 0.78 | — | 4.28 |
| 253 | — | 3.80 | 0.097 | — | — |
| 254 | — | 2.85 | 2.15 | — | — |
| 255 | — | 0.058 | 0.12 | — | 0.54 |
| 256 | — | 1.51 | 2.94 | — | 0.29 |
| 257 | — | 0.17 | 0.25 | — | — |
| 258 | — | 0.064 | 0.36 | — | — |
| 259 | — | 2.17 | 1.80 | — | — |
| 260 | — | — | 3.03 | — | — |
| 261 | — | 0.17 | 0.017 | — | 0.68 |
| 262 | — | — | — | — | 4.15 |
| 263 | — | 0.29 | 0.062 | — | — |
| 264 | — | 0.75 | 1.17 | — | — |
| 265 | — | 0.79 | 0.37 | 1.59 | — |
| 266 | — | 0.083 | 0.028 | 0.18 | — |
| 267 | — | 0.041 | 0.10 | 0.045 | 1.02 |
| 268 | — | 0.34 | 4.06 | 1.00 | — |
| 269 | — | 0.58 | 0.26 | — | — |
| 270 | — | 0.008 | 2.32 | 1.39 | — |
| 271 | — | 0.010 | 12.7 | 14.4 | — |
| 273 | — | 1.00 | 7.33 | 0.42 | — |
| 274 | — | 16.0 | 174 | 5.33 | — |
| 275 | — | 0.53 | 0.15 | 0.035 | — |
| 276 | — | 0.12 | 1.38 | 3.56 | — |
| 277 | — | 0.16 | 0.018 | — | — |
| 278 | — | 2.86 | — | 1.15 | — |
| 279 | — | 17.0 | 62.4 | — | 2.92 |
| 280 | — | 42.7 | 125 | — | 0.15 |
| 281 | — | 7.17 | 43.6 | — | — |
| 282 | — | 0.15 | 1.16 | — | — |
| 283 | — | 0.20 | 2.43 | 1.25 | 6.26 |
| 284 | — | 3.17 | 25.1 | 13.0 | — |
| 285 | — | 4.10 | 8.54 | — | — |
| 286 | — | 36.2 | 125 | — | — |
| 287 | — | 0.21 | 0.50 | — | — |
| 288 | — | 4.11 | 31.7 | — | — |
| 289 | — | 2.70 | 8.64 | 5.72 | 0.35 |
| 290 | — | 1.95 | 57.2 | — | 20.0 |
| 291 | — | 0.11 | 0.43 | — | 0.39 |
| 292 | — | 0.21 | 1.01 | — | 1.10 |
| 294 | 8.29 | — | 0.042 | 0.66 | 0.20 |
| 295 | 7.23 | 0.10 | 0.82 | 0.58 | 0.10 |
| 296 | — | 0.46 | 0.14 | 0.036 | — |
| 297 | — | 0.11 | 0.11 | 0.053 | — |
| 298 | — | 0.48 | 0.38 | 0.42 | — |
| 299 | — | 1.28 | 4.68 | 3.46 | — |
| 300 | — | 0.013 | 0.022 | — | — |
| 301 | — | 0.13 | 0.43 | — | — |
| 302 | — | 0.009 | 0.043 | — | 0.034 |
| 303 | — | 1.77 | 5.07 | — | — |
| 304 | — | 0.012 | 0.014 | 0.016 | 0.11 |
| 305 | — | 0.062 | 1.40 | 11.7 | 3.67 |
| 306 | — | 0.011 | 0.028 | — | 0.23 |
| 307 | — | 0.14 | 0.77 | — | — |
| 308 | — | 0.062 | 0.039 | 0.034 | 0.89 |
| 309 | — | 0.35 | 0.85 | 1.48 | — |
| 310 | — | 0.077 | 0.28 | — | — |
| 311 | — | 0.013 | 0.006 | — | — |
| 312 | — | 0.60 | 0.87 | — | — |
| 313 | — | 0.23 | 0.65 | — | 0.057 |
| 314 | — | 0.025 | 0.004 | — | 0.050 |
| 315 | — | 0.026 | 0.19 | — | 0.27 |
| 316 | — | 0.087 | 0.031 | — | — |
| 317 | — | 0.017 | 0.026 | — | 0.18 |
| 318 | — | 0.62 | 1.57 | — | 3.07 |
| 319 | — | 0.052 | 0.022 | — | 0.13 |
| 320 | — | 0.42 | 0.62 | — | 0.93 |
| 321 | — | 0.010 | 0.038 | — | — |

TABLE A-continued

In vitro DGK Inhibition IC$_{50}$ Activity Values

| Ex. No. | DGK alpha LIPGLO IC$_{50}$ (uM) | DGK alpha ADPGLO (Truncated) IC$_{50}$ (uM) | DGK zeta LIPGLO IC$_{50}$ (uM) | IFN-γ Whole Blood Normalized EC$_{50}$ (uM) | pERK Whole Blood Normalized IC$_{50}$ (uM) |
|---|---|---|---|---|---|
| 322 | — | 0.007 | 0.76 | — | — |
| 323 | — | 0.52 | 0.021 | — | 0.67 |
| 324 | — | 0.85 | 0.20 | — | 4.21 |
| 325 | — | 0.80 | 0.069 | — | 0.07 |
| 326 | — | — | — | — | 3.48 |
| 327 | — | 0.32 | 0.057 | — | 2.07 |
| 328 | — | 2.97 | 2.23 | — | 20.0 |
| 329 | — | 5.29 | 0.74 | — | 1.56 |
| 330 | — | 0.64 | 2.83 | — | 11.0 |
| 331 | — | 0.038 | 0.033 | — | 0.94 |
| 332 | — | 0.074 | 0.72 | — | — |
| 333 | — | 0.090 | 0.072 | 0.12 | 0.10 |
| 334 | — | 0.46 | 0.53 | 0.73 | 20.0 |
| 335 | — | 0.025 | 0.12 | — | 0.14 |
| 336 | — | 0.48 | 1.10 | — | 20.00 |
| 337 | — | 0.081 | 0.10 | — | 0.054 |
| 338 | — | 0.91 | 1.31 | — | 20.0 |
| 339 | — | 0.075 | 0.079 | — | 0.28 |
| 340 | — | 6.31 | 15.9 | — | 12.9 |
| 341 | — | 0.061 | 0.13 | — | 2.98 |
| 342 | — | 1.09 | 1.20 | — | 7.93 |
| 343 | — | 0.74 | 6.33 | — | 0.073 |
| 344 | — | 10.1 | 17.1 | — | 20.0 |
| 345 | — | 0.049 | 0.095 | — | 1.74 |
| 346 | — | 1.28 | 1.24 | — | 0.19 |
| 347 | — | 0.32 | 0.95 | — | 1.99 |
| 348 | — | 0.061 | 0.045 | — | 1.95 |
| 350 | — | 0.18 | 0.12 | — | 3.36 |
| 351 | — | 0.18 | 1.04 | — | 0.38 |
| 352 | — | 14.9 | 2.72 | — | — |
| 354 | — | — | 0.65 | — | 7.95 |
| 355 | — | — | 41.7 | — | 6.69 |
| 356 | — | 18.0 | 0.44 | — | 0.93 |
| 357 | — | 2.08 | 1.56 | — | 3.78 |
| 359 | — | 0.024 | 0.22 | — | — |
| 360 | — | 0.15 | 0.66 | — | — |
| 361 | — | 0.005 | 0.022 | 0.26 | — |
| 362 | — | 0.061 | 0.59 | 3.09 | — |
| 363 | — | 0.017 | 0.032 | 0.16 | 0.024 |
| 364 | — | 0.053 | 0.33 | — | 1.80 |
| 365 | — | 0.016 | 0.021 | — | 4.41 |
| 366 | — | 1.45 | 0.62 | — | — |
| 367 | — | 0.12 | 0.85 | — | — |
| 368 | — | 1.17 | 2.25 | — | — |
| 371 | — | 0.013 | 0.10 | 0.19 | 3.32 |
| 372 | — | 0.004 | 0.043 | 0.15 | — |
| 373 | 0.86 | — | 2.55 | 0.17 | — |
| 374 | 0.65 | — | 2.79 | 0.82 | — |
| 375 | 1.39 | — | 6.05 | 2.16 | — |
| 376 | 0.03 | — | 0.097 | 0.058 | — |
| 377 | 0.24 | — | 0.37 | 0.52 | — |
| 378 | — | 0.16 | 0.15 | — | — |
| 379 | — | 0.45 | 3.60 | — | — |
| 380 | — | 0.029 | 0.18 | — | — |
| 381 | — | 0.85 | 3.41 | — | — |
| 385 | — | 0.012 | 0.043 | 0.13 | 0.24 |
| 386 | — | 2.70 | 5.07 | 2.49 | — |
| 387 | — | 1.93 | 6.07 | 0.77 | — |
| 388 | — | 1.75 | 45.7 | 20.0 | — |
| 389 | — | 1.00 | 8.22 | — | 0.37 |
| 390 | — | 0.097 | 0.18 | 0.04 | 20.00 |
| 391 | — | 2.02 | 1.34 | 0.72 | 1.13 |
| 392 | — | 2.84 | 33.6 | — | 6.89 |
| 393 | — | 23.5 | 125 | — | 3.45 |
| 395 | — | 0.49 | 0.064 | — | 20.0 |
| 396 | — | 0.92 | 1.30 | — | — |
| 398 | — | 0.090 | 0.064 | — | — |
| 399 | — | 0.16 | 0.70 | — | 20.0 |
| 400 | — | 0.75 | 0.047 | — | 20.0 |
| 401 | — | 0.16 | 0.23 | — | 4.89 |
| 402 | 49.5 | — | 4.76 | 1.39 | 3.67 |
| 405 | 13.6 | — | 0.11 | 1.19 | 2.58 |
| 406 | — | 1.96 | 81.1 | — | 7.13 |
| 407 | — | 0.40 | 31.0 | — | 0.64 |
| 409 | — | 0.072 | 1.08 | — | 20.0 |
| 410 | — | 0.22 | 2.37 | — | — |
| 411 | — | 0.82 | 1.24 | — | 1.89 |
| 412 | — | 9.67 | 45.0 | — | 0.67 |
| 413 | — | 0.44 | 0.75 | — | — |
| 414 | — | 1.49 | 11.3 | — | 0.16 |
| 415 | — | 3.31 | 61.9 | — | 3.44 |
| 416 | — | 0.14 | 0.74 | — | 3.14 |
| 417 | — | 0.17 | 0.52 | — | 20.0 |
| 418 | — | 0.092 | 8.71 | — | 20.0 |
| 419 | — | 0.033 | 0.055 | — | 20.0 |
| 420 | — | 0.090 | 0.76 | — | — |
| 421 | — | 0.064 | 0.32 | 0.19 | — |
| 422 | — | 0.23 | 6.87 | — | — |
| 424 | — | 114.4 | 4.59 | — | — |
| 425 | — | 83.3 | 12.5 | — | — |
| 427 | — | 0.46 | 4.45 | — | — |
| 428 | — | — | 125 | 20.0 | — |
| 429 | — | — | 99.5 | 20.0 | — |
| 430 | — | — | 125 | 20.0 | 20.0 |
| 431 | — | 250 | 250 | 20.0 | 20.0 |
| 432 | — | — | 41.67 | 20.0 | — |
| 433 | — | 125 | 125 | 20.0 | — |
| 434 | — | — | 125 | 20.0 | 20.0 |
| 435 | — | 1.90 | 5.51 | 4.16 | 7.29 |
| 436 | — | 12.19 | 250 | 20.0 | — |
| 437 | — | 250 | 250 | — | — |
| 438 | — | 175 | 250 | — | — |
| 439 | — | 0.36 | 0.40 | — | 10.9 |
| 440 | — | 1.14 | 44.6 | — | 8.07 |
| 441 | — | 0.19 | 26.9 | — | 0.70 |
| 442 | — | 0.28 | 0.91 | — | — |
| 444 | — | 0.40 | 0.18 | — | — |
| 445 | — | 0.95 | 2.21 | — | 9.59 |
| 447 | — | 13.6 | 5.57 | — | 20.0 |
| 448 | — | 13.4 | 5.14 | — | 20.0 |
| 449 | — | 7.41 | 4.08 | — | 20.0 |
| 450 | — | 0.20 | 0.37 | — | 20.0 |
| 451 | — | — | — | — | 20.0 |
| 452 | — | — | — | — | 20.0 |
| 453 | — | 215 | 79.4 | — | — |
| 454 | — | 14.2 | 28.8 | — | — |
| 455 | — | 5.12 | 7.55 | — | — |
| 456 | — | 10.2 | 12.1 | — | — |
| 457 | — | 4.01 | 1.05 | — | — |
| 458 | — | 7.74 | 6.47 | — | — |
| 459 | — | 29.8 | 23.9 | — | — |
| 460 | — | 11.6 | 12.0 | — | — |

Table A lists in vitro DGK inhibition IC$_{50}$ activity values measured in the DGKα and DGKζ liposome assays.

The compounds of the present invention possess activity as an inhibitor(s) of one or both of the DGKα and DGKζ enzymes, and therefore, may be used in the treatment of diseases associated with the inhibition of DGKα and DGKζ activity.

Nucleotide sequence encoding hDGKα-(M1-S735)-Ct-TVMV-His:

(SEQ ID NO: 1)

```
   1 ATGGCCAAGG AGAGGGCCT AATAAGCCCC AGTGATTTTG CCCAGCTGCA
  51 AAAATACATG AATACTCCA CCAAAAAGGT CAGTGATGTC CTAAAGCTCT
 101 TCGAGGATGG CGAGATGGCT AAATATGTCC AAGGAGATGC CATTGGGTAC
 151 GAGGGATTCC AGCAATTCCT GAAAATCTAT CTCGAAGTGG ATAATGTTCC
 201 CAGACACCTA AGCCTGGCAC TGTTTCAATC CTTTGAGACT GGTCACTGCT
 251 TAAATGAGAC AAATGTGACA AAAGATGTGG TGTGTCTCAA TGATGTTTCC
 301 TGCTACTTTT CCCTTCTGGA GGGTGGTCGG CCAGAAGACA AGTTAGAATT
 351 CACCTTCAAG CTGTACGACA CGGACAGAAA TGGGATCCTG GACAGCTCAG
 401 AAGTGGACAA AATTATCCTA CAGATGATGC GAGTGGCTGA ATACCTGGAT
 451 TGGGATGTGT CTGAGCTGAG GCCGATTCTT CAGGAGATGA TGAAAGAGAT
 501 TGACTATGAT GGCAGTGGCT CTGTCTCTCA AGCTGAGTGG GTCCGGGCTG
 551 GGGCCACCAC CGTGCCACTG CTAGTGCTGC TGGGTCTGGA GATGACTCTG
 601 AAGGACGACG ACAGCACAT GTGGAGGCCC AAGAGGTTCC CCAGACCAGT
 651 CTACTGCAAT CTGTGCGAGT CAAGCATTGG TCTTGGCAAA CAGGGACTGA
 701 GCTGTAACCT CTGTAAGTAC ACTGTTCACG ACCAGTGTGC CATGAAAGCC
 751 CTGCCTTGTG AAGTCAGCAC CTATGCCAAG TCTCGGAAGG ACATTGGTGT
 801 CCAATCACAT GTGTGGGTGC GAGGAGGCTG TGAGTCCGGG CGCTGCGACC
 851 GCTGTCAGAA AAAGATCCGG ATCTACCACA GTCTGACCGG CTGCATTGT
 901 GTATGGTGCC ACCTAGAGAT CCACGATGAC TGCCTGCAAG CGGTGGGCCA
 951 TGAGTGTGAC TGTGGGCTGC TCCGGGATCA CATCCTGCCT CCATCTTCCA
1001 TCTATCCCAG TGTCCTGGCC TCTGGACCGG ATCGTAAAAA TAGCAAAACA
1051 AGCCAGAAGA CCATGGATGA TTTAAATTTG AGCACCTCTG AGGCTCTGCG
1101 GATTGACCCT GTTCCTAACA CCCACCCACT TCTCGTCTTT GTCAATCCTA
1151 AGAGTGGCGG GAAGCAGGGG CAGAGGGTGC TCTGGAAGTT CCAGTATATA
1201 TTAAACCCTC GACAGGTGTT CAACCTCCTA AAGGATGGTC CTGAGATAGG
1251 GCTCCGATTA TTCAAGGATG TTCCTGATAG CCGGATTTTG TGTGTGGTG
1301 GAGACGGCAC AGTAGGCTGG ATTCTAGAGA CCATTGACAA AGCTAACTTG
1351 CCAGTTTTGC CTCCTGTTGC TGTGTTGCCC CTGGGTACTG GAAATGATCT
1401 GGCTCGATGC CTAAGATGGG GAGGAGGTTA TGAAGGACAG AATCTGGCAA
1451 AGATCCTCAA GGATTTAGAG ATGAGTAAAG TGGTACATAT GGATCGATGG
1501 TCTGTGGAGG TGATACCTCA ACAAACTGAA GAAAAAGTG ACCCAGTCCC
1551 CTTTCAAATC ATCAATAACT ACTTCTCTAT TGGCGTGGAT GCCTCTATTG
1601 CTCATCGATT CCACATCATG CGAGAGAAAT ATCCGGAGAA GTTCAACAGC
1651 AGAATGAAGA ACAAGCTATG GTACTTCGAA TTTGCCACAT CTGAATCCAT
1701 CTTCTCAACA TGCAAAAAGC TGGAGGAGTC TTTGACAGTT GAGATCTGTG
1751 GGAAACCGCT GGATCTGAGC AACCTGTCCC TAGAAGGCAT CGCAGTGCTA
1801 AACATCCCTA GCATGCATGG TGGCTCCAAC CTCTGGGGTG ATACCAGGAG
1851 ACCCCATGGG GATATCTATG GGATCAACCA GGCCTTAGGT GCTACAGCTA
1901 AAGTCATCAC CGACCCTGAT ATCCTGAAAA CCTGTGTACC AGACCTAAGT
1951 GACAAGAGAC TGGAAGTGGT TGGGCTGGAG GGTGCAATTG AGATGGGCCA
```

```
2001 AATCTATACC AAGCTCAAGA ATGCTGGACG TCGGCTGGCC AAGTGCTCTG
2051 AGATCACCTT CCACACCACA AAAACCCTTC CCATGCAAAT TGACGGAGAA
2101 CCCTGGATGC AGACGCCCTG TACAATCAAG ATCACCCACA AGAACCAGAT
2151 GCCCATGCTC ATGGGCCCAC CCCCCCGCTC CACCAATTTC TTTGGCTTCT
2201 TGAGCGGATC CTCGGAGACA GTGCGGTTTC AGGGACACCA CCACCATCAC
2251 CACTGA
```

Amino acid sequence of hDGKα-(9-727)-TVMV-His:
(SEQ ID NO: 2)
```
0001 MASPSDFAQL QKYMEYSTKK VSDVLKLFED GEMAKYVQGD AIGYEGFQQF LKIYLEVDNV 0060
0061 PRHLSLALFQ SFETGHCLNE TNVTKDVVCL NDVSCYFSLL EGGRPEDKLE FTFKLYDTDR 0120
0121 NGILDSSEVD KIILQMMRVA EYLDWDVSEL RPILQEMMKE IDYDGSGSVS QAEWVRAGAT 0180
0181 TVPLLVLLGL EMTLKDDGQH MWRPKRFPRP VYCNLCESSI GLGKQGLSCN LCKYTVHDQC 0240
0241 AMKALPCEVS TYAKSRKDIG VQSHVWVRGG CESGRCDRCQ KKIRIYHSLT GLHCVWCHLE 0300
0301 IHDDCLQAVG HECDCGLLRD HILPPSSIYP SVLASGPDRK NSKTSQKTMD DLNLSTSEAL 0360
0361 RIDPVPNTHP LLVFVNPKSG GKQGQRVLWK FQYILNPRQV FNLLKDGPEI GLRLFKDVPD 0420
0421 SRILVCGGDG TVGWILETID KANLPVLPPV AVLPLGTGND LARCLRWGGG YEGQNLAKIL 0480
0481 KDLEMSKVVH MDRWSVEVIP QQTEEKSDPV PFQIINNYFS IGVDASIAHR FHIMREKYPE 0540
0541 KFNSRMKNKL WYFEFATSES IFSTCKKLEE SLTVEICGKP LDLSNLSLEG IAVLNIPSMH 0600
0601 GGSNLWGDTR RPHGDIYGIN QALGATAKVI TDPDILKTCV PDLSDKRLEV VGLEGAIEMG 0660
0661 QIYTKLKNAG RRLAKCSEIT FHTTKTLPMQ IDGEPWMQTP CTIKITHKNQ MPMLMGPPPR 0720
0721 SGSSETVRFQ GHHHHHH 0737
```

Nucleotide sequence encoding hDGKζ-(M1-A928)-transcript variant-2 Ct-TVMV-His:
(SEQ ID NO: 3)
```
  1 ATGGAGCCGC GGGACGGTAG CCCCGAGGCC CGGAGCAGCG ACTCCGAGTC
 51 GGCTTCCGCC TCGTCCAGCG GCTCCGAGCG CGACGCCGGT CCCGAGCCGG
101 ACAAGGCGCC GCGGCGACTC AACAAGCGGC GCTTCCCGGG GCTGCGGCTC
151 TTCGGGCACA GGAAAGCCAT CACGAAGTCG GGCCTCCAGC ACCTGGCCCC
201 CCCTCCGCCC ACCCCTGGGG CCCCGTGCAG CGAGTCAGAG CGGCAGATCC
251 GGAGTACAGT GGACTGGAGC GAGTCAGCGA CATATGGGGA GCACATCTGG
301 TTCGAGACCA ACGTGTCCGG GGACTTCTGC TACGTTGGGG AGCAGTACTG
351 TGTAGCCAGG ATGCTGCAGA AGTCAGTGTC TCGAAGAAAG TGCGCAGCCT
401 GCAAGATTGT GGTGCACACG CCCTGCATCG AGCAGCTGGA GAAGATAAAT
451 TTCCGCTGTA AGCCGTCCTT CCGTGAATCA GGCTCCAGGA ATGTCCGCGA
501 GCCAACCTTT GTACGGCACC ACTGGGTACA GAGCGACGC CAGGACGGCA
551 AGTGTCGGCA CTGTGGGAAG GGATTCCAGC AGAAGTTCAC CTTCCACAGC
601 AAGGAGATTG TGGCCATCAG CTGCTCGTGG TGCAAGCAGG CATACCACAG
651 CAAGGTGTCC TGCTTCATGC TGCAGCAGAT CGAGGAGCCG TGCTCGCTGG
701 GGGTCCACGC AGCCGTGGTC ATCCCGCCCA CCTGGATCCT CCGCGCCCGG
751 AGGCCCCAGA ATACTCTGAA AGCAAGCAAG AAGAAGAAGA GGGCATCCTT
801 CAAGAGGAAG TCCAGCAAGA AGGGCCTGA GGAGGGCCGC TGGAGACCCT
851 TCATCATCAG GCCCACCCCC TCCCCGCTCA TGAAGCCCCT GCTGGTGTTT
901 GTGAACCCCA AGAGTGGGGG CAACCAGGGT GCAAAGATCA TCCAGTCTTT
```

```
                                      -continued
 951 CCTCTGGTAT CTCAATCCCC GACAAGTCTT CGACCTGAGC CAGGGAGGGC

1001 CCAAGGAGGC GCTGGAGATG TACCGCAAAG TGCACAACCT GCGGATCCTG

1051 GCGTGCGGGG GCGACGGCAC GGTGGGCTGG ATCCTCTCCA CCCTGGACCA

1101 GCTACGCCTG AAGCCGCCAC CCCCTGTTGC CATCCTGCCC CTGGGTACTG

1151 GCAACGACTT GGCCCGAACC CTCAACTGGG GTGGGGGCTA CACAGATGAG

1201 CCTGTGTCCA AGATCCTCTC CCACGTGGAG GAGGGGAACG TGGTACAGCT

1251 GGACCGCTGG GACCTCCACG CTGAGCCCAA CCCCGAGGCA GGGCCTGAGG

1301 ACCGAGATGA AGGCGCCACC GACCGGTTGC CCCTGGATGT CTTCAACAAC

1351 TACTTCAGCC TGGGCTTTGA CGCCCACGTC ACCCTGGAGT TCCACGAGTC

1401 TCGAGAGGCC AACCCAGAGA AATTCAACAG CCGCTTTCGG AATAAGATGT

1451 TCTACGCCGG GACAGCTTTC TCTGACTTCC TGATGGGCAG CTCCAAGGAC

1501 CTGGCCAAGC ACATCCGAGT GGTGTGTGAT GGAATGGACT TGACTCCCAA

1551 GATCCAGGAC CTGAAACCCC AGTGTGTTGT TTTCCTGAAC ATCCCCAGGT

1601 ACTGTGCGGG CACCATGCCC TGGGGCCACC CTGGGGAGCA CCACGACTTT

1651 GAGCCCCAGC GGCATGACGA CGGCTACCTC GAGGTCATTG GCTTCACCAT

1701 GACGTCGTTG GCCGCGCTGC AGGTGGGCGG ACACGGCGAG CGGCTGACGC

1751 AGTGTCGCGA GGTGGTGCTC ACCACATCCA AGGCCATCCC GGTGCAGGTG

1801 GATGGCGAGC CCTGCAAGCT TGCAGCCTCA CGCATCCGCA TCGCCCTGCG

1851 CAACCAGGCC ACCATGGTGC AGAAGGCCAA GCGGCGGAGC GCCGCCCCCC

1901 TGCACAGCGA CCAGCAGCCG GTGCCAGAGC AGTTGCGCAT CCAGGTGAGT

1951 CGCGTCAGCA TGCACGACTA TGAGGCCCTG CACTACGACA AGGAGCAGCT

2001 CAAGGAGGCC TCTGTGCCGC TGGGCACTGT GGTGGTCCCA GGAGACAGTG

2051 ACCTAGAGCT CTGCCGTGCC ACATTGAGA GACTCCAGCA GGAGCCCGAT

2101 GGTGCTGGAG CCAAGTCCCC GACATGCCAG AAACTGTCCC CCAAGTGGTG

2151 CTTCCTGGAC GCCACCACTG CCAGCCGCTT CTACAGGATC GACCGAGCCC

2201 AGGAGCACCT CAACTATGTG ACTGAGATCG CACAGGATGA GATTTATATC

2251 CTGGACCCTG AGCTGCTGGG GGCATCGGCC CGGCCTGACC TCCCAACCCC

2301 CACTTCCCCT CTCCCCACCT CACCCTGCTC ACCCACGCCC CGGTCACTGC

2351 AAGGGGATGC TGCACCCCCT CAAGGTGAAG AGCTGATTGA GGCTGCCAAG

2401 AGGAACGACT TCTGTAAGCT CCAGGAGCTG CACCGAGCTG GGGCGACCT

2451 CATGCACCGA GACGAGCAGA GTCGCACGCT CCTGCACCAC GCAGTCAGCA

2501 CTGGCAGCAA GGATGTGGTC CGCTACCTGC TGGACCACGC CCCCCCAGAG

2551 ATCCTTGATG CGGTGGAGGA AAACGGGGAG ACCTGTTTGC ACCAAGCAGC

2601 GGCCCTGGGC CAGCGCACCA TCTGCCACTA CATCGTGGAG GCCGGGGCCT

2651 CGCTCATGAA GACAGACCAG CAGGGCGACA CTCCCCGGCA GCGGGCTGAG

2701 AAGGCTCAGG ACACCGAGCT GGCCGCCTAC CTGGAGAACC GGCAGCACTA

2751 CCAGATGATC CAGCGGGAGG ACCAGGAGAC GGCTGTGGGA TCCTCGGAGA

2801 CAGTGCGGTT TCAGGGACAC CACCACCATC ACCACTGA

Amino acid sequence of hDGKζ-(M1-A928)-transcript variant-2 Ct-TVMV-His:
                                                                (SEQ ID NO: 4)
0001 MEPRDGSPEA RSSDSESASA SSSGSERDAG PEPDKAPRRL NKRRFPGLRL FGHRKAITKS  0060

0061 GLQHLAPPPP TPGAPCSESE RQIRSTVDWS ESATYGEHIW FETNVSGDFC YVGEQYCVAR  0120
```

```
0121  mLQKSVSRRK CAACKIVVHT PCIEQLEKIN FRCKPSFRES GSRNVREPTF VRHHWVHRRR  0180

0181  QDGKCRHCGK GFQQKFTFHS KEIVAISCSW CKQAYHSKVS CFMLQQIEEP CSLGVHAAVV  0240

0241  IPPTWILRAR RPQNTLKASK KKRASFKRK SSKKGPEEGR WRPFIIRPTP SPLMKPLLVF  0300

0301  VNPKSGGNQG AKIIQSFLWY LNPRQVFDLS QGGPKEALEM YRKVHNLRIL ACGGDGTVGW  0360

0361  ILSTLDQLRL KPPPPVAILP LGTGNDLART LNWGGGYTDE PVSKILSHVE EGNVVQLDRW  0420

0421  DLHAEPNPEA GPEDRDEGAT DRLPLDVFNN YFSLGFDAHV TLEFHESREA NPEKFNSRFR  0480

0481  NKMFYAGTAF SDFLMGSSKD LAKHIRVVCD GMDLTPKIQD LKPQCVVFLN IPRYCAGTMP  0540

0541  WGHPGEHHDF EPQRHDDGYL EVIGFTMTSL AALQVGGHGE RLTQCREVVL TTSKAIPVQV  0600

0601  DGEPCKLAAS RIRIALRNQA TMVQKAKRRS AAPLHSDQQP VPEQLRIQVS RVSMHDYEAL  0660

0661  HYDKEQLKEA SVPLGTVVVP GDSDLELCRA HIERLQQEPD GAGAKSPTCQ KLSPKWCFLD  0720

0721  ATTASRFYRI DRAQEHLNYV TEIAQDEIYI LDPELLGASA RPDLPTPTSP LPTSPCSPTP  0780

0781  RSLQGDAAPP QGEELIEAAK RNDFCKLQEL HRAGGDLMHR DEQSRTLLHH AVSTGSKDVV  0840

0841  RYLLDHAPPE ILDAVEENGE TCLHQAAALG QRTICHYIVE AGASLMKTDQ QGDTPRQRAE  0900

0901  KAQDTELAAY LENRQHYQMI QREDQETAVG SSETVRFQGH HHHHH                  0945
```

What is claimed is:

1. A compound or a pharmaceutically acceptable salt thereof, having the structure:

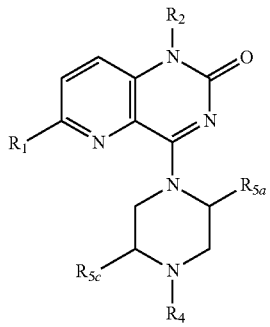

wherein:

$R_1$ is Cl or —CN;
$R_2$ is —CH$_3$ or —CD$_3$;
$R_4$ is —CHR$_{4a}$R$_{4b}$;
$R_{4a}$ is cyclopropyl, cyclobutyl, cyclohexyl, phenyl, pyridinyl, pyrimidinyl, oxadiazolyl, bicyclo[1.1.1]pentanyl, benzo[d][1,3]dioxolyl, or oxodihydrobenzo[d]oxazolyl, each substituted with zero to 3 substituents independently selected from F, Cl, Br, —CN, —CH$_3$, —CH(CH$_3$)$_2$, —C(CH$_3$)$_3$, —CH$_2$OH, —CHF$_2$, —CF$_3$, —CH$_2$Br, —CH$_2$NH$_2$, —CH$_2$NHC(O)OCH$_3$, —C(CH$_3$)$_2$CN, —OCH$_3$, —OCD$_3$, —OCH$_2$CH$_3$, —OCH(CH$_3$)$_2$, —OCHF$_2$, —OCF$_3$, —OCH$_2$CH$_2$CF$_3$, —OC(CH$_3$)$_2$CN, —OC(CH$_3$)$_2$CH$_2$OH, —OC(CH$_3$)$_2$CH$_2$OCH$_3$, —N(CH$_3$)$_2$, —C(O)OCH$_3$, cyclopropyl, cyanocyclopropyl, methylcyclopropyl, —O(cyclopropyl), —O((ethoxycarbonyl)cyclopropyl), morpholinyl, pyrrolidinonyl, tetrahydropyranyl, dioxolanyl, —CH$_2$(morpholinyl), —CH$_2$(difluoromorpholinyl), —CH$_2$(dimethylmorpholinyl), —CH$_2$(oxaazabicyclo[2.2.1]heptanyl), —CH$_2$(oxaazaspiro[3.3]heptanyl), —CH$_2$(methylpiperazinonyl), —CH$_2$(acetylpiperazinyl), —CH$_2$(piperidinyl), —CH$_2$(difluoropiperidinyl), —CH$_2$(methoxypiperidinyl), —CH$_2$(hydroxypiperidinyl), —C(CH$_3$)$_2$(morpholinyl), —OCH$_2$(cyclopropyl), —OCH$_2$(methylcyclopropyl), —OCH$_2$(methylazetidinyl), —OCH$_2$(oxetanyl), —OCH$_2$(tetrahydropyranyl), —OCH$_2$(thiazolyl), and —OCH$_2$CH$_2$(cyclopropyl);

$R_{4b}$ is:
(i) —CN, —CH$_3$, —CH$_2$CH$_3$, —CH$_2$CH$_2$CH$_3$, or —CH(CH$_3$)$_2$; or
(ii) phenyl, isoxazolyl, oxadiazolyl, thiazolyl, or triazolyl, each substituted with zero to 3 substituents independently selected from F, Cl, Br, —CH$_3$, —C(CH$_3$)$_3$, —CF$_3$, —OCF$_3$, and cyclopropyl; and $R_{5a}$ is —CH$_3$ or —CH$_2$CH$_3$; and
$R_{5c}$ is —CH$_3$, —CH$_2$CH$_3$, or —CH$_2$CH$_2$CH$_3$.

2. The compound according to claim 1 or a pharmaceutically acceptable salt thereof, wherein:

$R_{4a}$ is phenyl, pyridinyl, pyrimidinyl, oxadiazolyl, benzo[d][1,3]dioxolyl, or oxodihydrobenzo[d]oxazolyl, each substituted with 1 to 3 substituents independently selected from F, Cl, Br, —CN, —CH$_3$, —CH$_2$OH, —CH$_2$Br, —CH$_2$NH$_2$, —CH$_2$NHC(O)OCH$_3$, —CF$_3$, —C(CH$_3$)$_2$CN, —OCH$_3$, —OCD$_3$, —OCH$_2$CH$_3$, —OCH(CH$_3$)$_2$, —OCHF$_2$, —OCF$_3$, —OCH$_2$CH$_2$CF$_3$, —OC(CH$_3$)$_2$CN, —OC(CH$_3$)$_2$CH$_2$OH, —OC(CH$_3$)$_2$CH$_2$OCH$_3$, —N(CH$_3$)$_2$, —C(O)OCH$_3$, cyclopropyl, cyanocyclopropyl, methylcyclopropyl, —O(cyclopropyl), —O((ethoxycarbonyl)cyclopropyl), —OCH$_2$(cyclopropyl), —CH$_2$(piperidinyl), morpholinyl, pyrrolidinonyl, tetrahydropyranyl, dioxolanyl, —CH$_2$(morpholinyl), —CH$_2$(difluoromorpholinyl), —CH$_2$(dimethylmorpholinyl), —CH$_2$(oxaazabicyclo[2.2.1]heptanyl), —CH$_2$(oxaazaspiro[3.3]heptanyl), —CH$_2$(methylpiperazinonyl), —CH$_2$(acetylpiperazinyl), —CH$_2$(piperidinyl), —CH$_2$(difluoropiperidinyl), —CH$_2$(methoxypiperidinyl), —CH$_2$(hydroxypiperidinyl), —C(CH$_3$)$_2$(morpholinyl), —OCH$_2$(cyclopropyl), —OCH$_2$(methylcyclopropyl), —OCH$_2$(methylazetidinyl), —OCH$_2$(oxetanyl), —OCH$_2$(tetrahydropyranyl), —OCH$_2$(thiazolyl), and —OCH$_2$CH$_2$(cyclopropyl); and $R_{ab}$ is —CN, —CH$_3$, —CH$_2$CH$_3$, —CH$_2$CH$_2$CH$_3$, or —CH(CH$_3$)$_2$.

3. The compound according to claim 1 or a pharmaceutically acceptable salt thereof, having the structure:

$R_{4a}$ is phenyl, pyridinyl, or oxadiazolyl, each substituted zero to 3 substituents independently selected from with F, Cl, Br, —CN, —CH$_3$, —C(CH$_3$)$_3$, —CHF$_2$, —CF$_3$, —OCH$_3$, —OCH(CH$_3$)$_2$, —OCHF$_2$, —OCF$_3$, —OCH$_2$(cyclopropyl), and cyclopropyl; and $R_{4b}$ is phenyl, isoxazolyl, thiazolyl, or triazolyl, each substituted with 0 to 3 substituents independently selected from F, Cl, Br, —CH$_3$, —C(CH$_3$)$_3$, —CF$_3$, —OCF$_3$, and cyclopropyl.

4. The compound according to claim 1 or a pharmaceutically acceptable salt thereof, wherein:

$R_{5a}$ is —CH$_3$ or —CH$_2$CH$_3$; and
$R_{5c}$ is —CH$_2$CH$_3$ or —CH$_2$CH$_2$CH$_3$.

5. The compound according to claim 1 or a pharmaceutically acceptable salt thereof, having the structure:

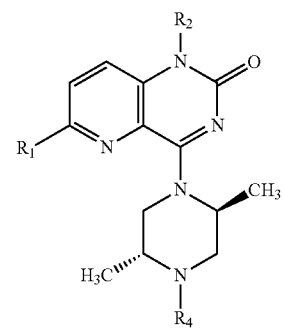

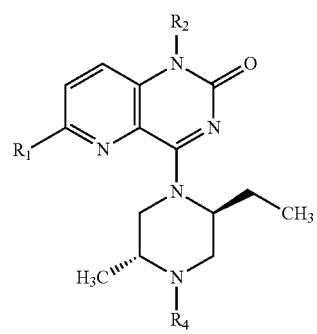

431
-continued
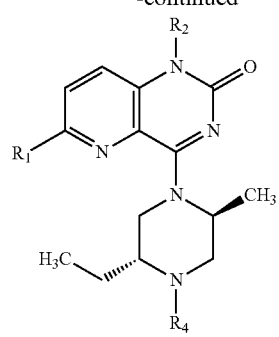
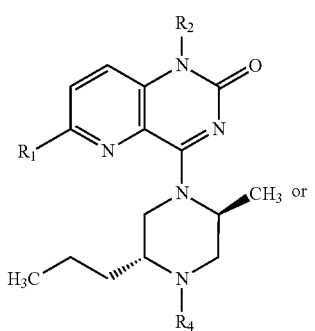 or
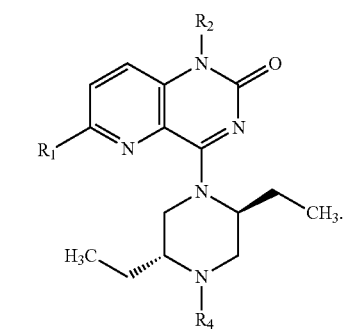
6. The compound according to claim 1 or a pharmaceutically acceptable salt thereof, wherein said compound is:
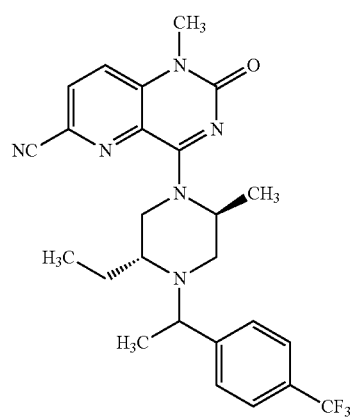
432
-continued
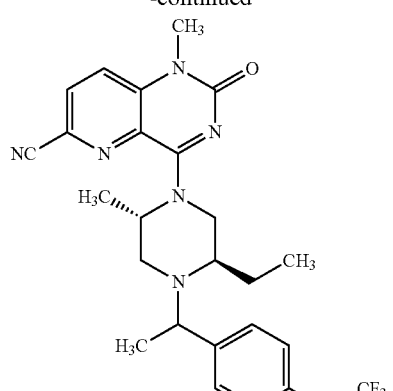
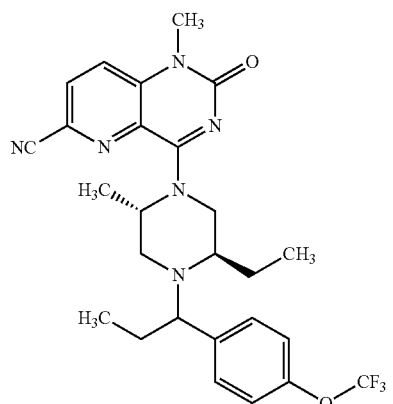
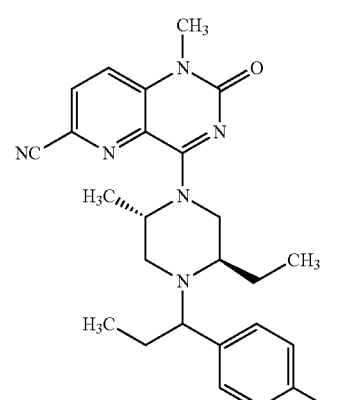
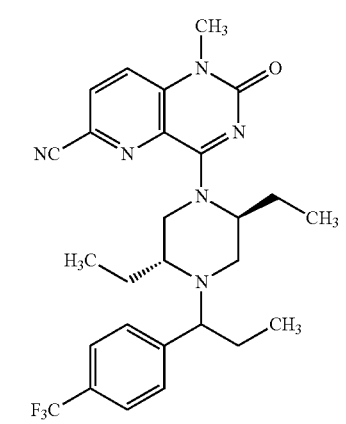

433
-continued
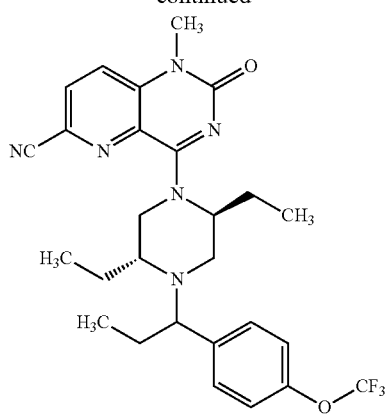
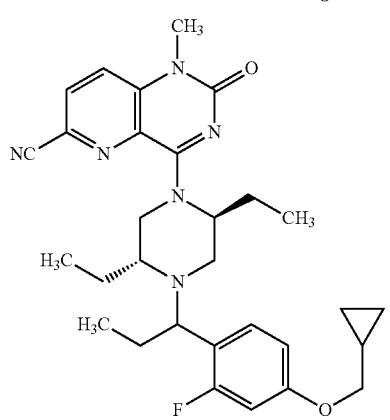
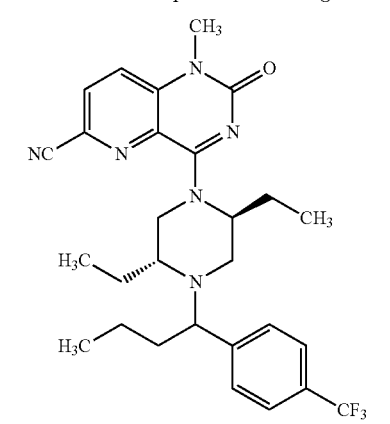
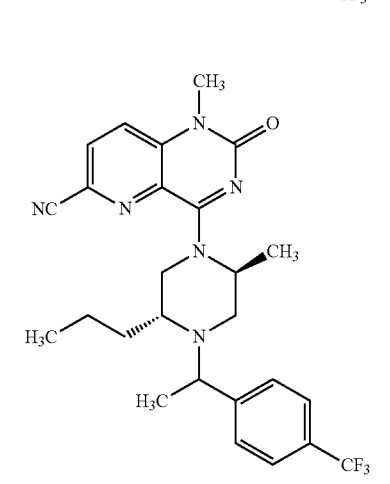
434
-continued
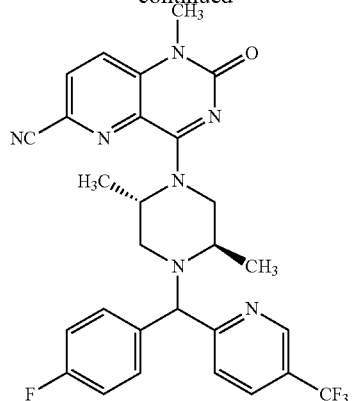
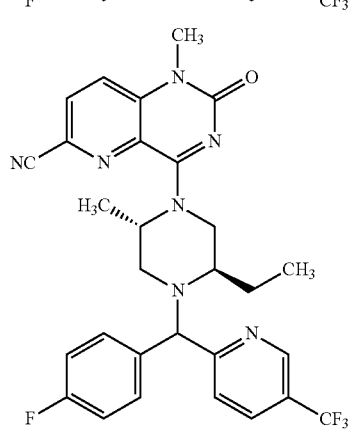
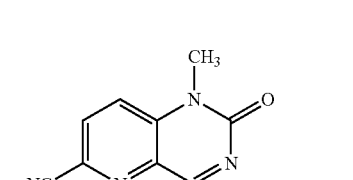
or
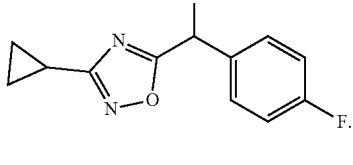

7. The compound according to claim 1 or a pharmaceutically acceptable salt thereof, wherein said compound is:

4-((2S,5R)-2,5-diethyl-4-((4-fluorophenyl)(5-(trifluoromethyl)pyridin-2-yl)methyl) piperazin-1-yl)-1-methyl-2-oxo-1,2-dihydropyrido[3,2-d]pyrimidine-6-carbonitrile (1-2);

4-((2s, 5r)-4-(1-(4-cyclopropylphenyl)ethyl)-2,5-dimethylpiperazin-1-yl)-1-methyl-2-oxo-1,2-dihydropyrido[3,2-d]pyrimidine-6-carbonitrile (3-4);

4-((2S,5R)-2,5-diethyl-4-(1-(4-(trifluoromethyl)phenyl)propyl)piperazin-1-yl)-1-methyl-2-oxo-1,2-dihydropyrido[3,2-d]pyrimidine-6-carbonitrile (5-6);

4-((2S,5R)-5-ethyl-2-methyl-4-(1-(4-(trifluoromethyl)phenyl)ethyl)piperazin-1-yl)-1-methyl-2-oxo-1,2-dihydropyrido[3,2-d]pyrimidine-6-carbonitrile (7-8);

4-((2S,5R)-2,5-diethyl-4-(1-(4-(trifluoromethoxy)phenyl)ethyl)piperazin-1-yl)-1-methyl-2-oxo-1,2-dihydropyrido[3,2-d]pyrimidine-6-carbonitrile (9-10);

4-((2S,5R)-2,5-diethyl-4-(1-(2-fluoro-4-methoxyphenyl)propyl)piperazin-1-yl)-1-methyl-2-oxo-1,2-dihydropyrido[3,2-d]pyrimidine-6-carbonitrile (11-12);

4-((2 S,5R)-4-(1-(2,2-difluorobenzo[d][1,3]dioxol-5-yl)ethyl)-2,5-diethylpiperazin-1-yl)-1-methyl-2-oxo-1,2-dihydropyrido[3,2-d]pyrimidine-6-carbonitrile (14-15);

4-((2S,5R)-2,5-diethyl-4-(1-(4-methoxyphenyl)ethyl)piperazin-1-yl)-1-methyl-2-oxo-1,2-dihydropyrido[3,2-d]pyrimidine-6-carbonitrile (16-17);

4-((2S,5R)-2,5-diethyl-4-(1-(4-isopropoxyphenyl)ethyl)piperazin-1-yl)-1-methyl-2-oxo-1,2-dihydropyrido[3,2-d]pyrimidine-6-carbonitrile (18-19);

4-((2S,5R)-2,5-diethyl-4-(1-(4-(trifluoromethyl)phenyl)ethyl)piperazin-1-yl)-1-methyl-2-oxo-1,2-dihydropyrido[3,2-d]pyrimidine-6-carbonitrile (20-21);

4-((2S,5R)-2,5-diethyl-4-(4-(trifluoromethoxy)benzyl)piperazin-1-yl)-1-methyl-2-oxo-1,2-dihydropyrido[3,2-d]pyrimidine-6-carbonitrile (22);

4-((2S,5R)-4-(1-(4-(cyclopropylmethoxy)phenyl)ethyl)-2,5-diethylpiperazin-1-yl)-1-methyl-2-oxo-1,2-dihydropyrido[3,2-d]pyrimidine-6-carbonitrile (23-24);

4-((2S,5R)-2,5-diethyl-4-(1-(2-fluoro-4-(trifluoromethyl)phenyl)ethyl)piperazin-1-yl)-1-methyl-2-oxo-1,2-dihydropyrido[3,2-d]pyrimidine-6-carbonitrile (25-26);

4-((2S,5R)-4-(1-(4-cyclopropylphenyl)ethyl)-2,5-diethylpiperazin-1-yl)-1-methyl-2-oxo-1,2-dihydropyrido[3,2-d]pyrimidine-6-carbonitrile (28-29);

4-((2S,5R)-2,5-diethyl-4-(1-(3-fluoro-4-(trifluoromethoxy)phenyl)ethyl)piperazin-1-yl)-1-methyl-2-oxo-1,2-dihydropyrido[3,2-d]pyrimidine-6-carbonitrile (30-31);

4-((2S,5R)-4-(1-(4-(cyclopropylmethoxy)-2-fluorophenyl)ethyl)-2,5-diethylpiperazin-1-yl)-1-methyl-2-oxo-1,2-dihydropyrido[3,2-d]pyrimidine-6-carbonitrile (32-33);

4-((2S,5R)-2,5-diethyl-4-((4-fluorophenyl)(isoxazol-3-yl)methyl)piperazin-1-yl)-1-methyl-2-oxo-1,2-dihydropyrido[3,2-d]pyrimidine-6-carbonitrile (34-35);

4-((2S,5R)-2,5-diethyl-4-(1-(4-(trifluoromethoxy)phenyl)propyl)piperazin-1-yl)-1-methyl-2-oxo-1,2-dihydropyrido[3,2-d]pyrimidine-6-carbonitrile (36-37);

4-((2S,5R)-2,5-diethyl-4-(1-(2-fluoro-4-(trifluoromethoxy)phenyl)ethyl)piperazin-1-yl)-1-methyl-2-oxo-1,2-dihydropyrido[3,2-d]pyrimidine-6-carbonitrile (38-39);

4-((2S,5R)-4-(1-(4-cyclopropyl-2-fluorophenyl)ethyl)-2,5-diethylpiperazin-1-yl)-1-methyl-2-oxo-1,2-dihydropyrido[3,2-d]pyrimidine-6-carbonitrile (40-41);

4-((2S,5R)-4-((5-cyclopropylisoxazol-3-yl)(4-(trifluoromethoxy)phenyl)methyl)-2,5-diethylpiperazin-1-yl)-1-methyl-2-oxo-1,2-dihydropyrido[3,2-d]pyrimidine-6-carbonitrile (42-43);

4-((2 S,5R)-2,5-diethyl-4-(1-(6-(trifluoromethyl)pyridin-3-yl)ethyl)piperazin-1-yl)-1-methyl-2-oxo-1,2-dihydropyrido[3,2-d]pyrimidine-6-carbonitrile (44-45);

4-((2S,5R)-5-ethyl-4-(4-fluorophenyl)(5-(trifluoromethyl)pyridin-2-yl)methyl)-2-methylpiperazin-1-yl)-1-methyl-2-oxo-1,2-dihydropyrido[3,2-d]pyrimidine-6-carbonitrile (46-47);

4-((2S,5R)-5-ethyl-2-methyl-4-(1-(4-(trifluoromethoxy)phenyl)ethyl)piperazin-1-yl)-1-methyl-2-oxo-1,2-dihydropyrido[3,2-d]pyrimidine-6-carbonitrile (48-49);

4-((2S,5R)-4-((4-cyclopropylthiazol-2-yl)(4-fluorophenyl)methyl)-5-ethyl-2-methylpiperazin-1-yl)-1-methyl-2-oxo-1,2-dihydropyrido[3,2-d]pyrimidine-6-carbonitrile (50-51);

4-((2S,5R)-5-ethyl-4-(1-(4-isopropoxyphenyl)ethyl)-2-methylpiperazin-1-yl)-1-methyl-2-oxo-1,2-dihydropyrido[3,2-d]pyrimidine-6-carbonitrile (52-53);

4-((2S,5R)-5-ethyl-4-(1-(4-methoxyphenyl)ethyl)-2-methylpiperazin-1-yl)-1-methyl-2-oxo-1,2-dihydropyrido[3,2-d]pyrimidine-6-carbonitrile (56-57);

4-((2S,5R)-5-ethyl-4-(1-(2-fluoro-4-(trifluoromethyl)phenyl)ethyl)-2-methylpiperazin-1-yl)-1-methyl-2-oxo-1,2-dihydropyrido[3,2-d]pyrimidine-6-carbonitrile (58-59);

4-((2S,5R)-4-(1-(4-cyanophenyl)ethyl)-5-ethyl-2-methylpiperazin-1-yl)-1-methyl-2-oxo-1,2-dihydropyrido[3,2-d]pyrimidine-6-carbonitrile (60-61);

4-((2S,5R)-4-(1-(4-cyclopropylphenyl)ethyl)-5-ethyl-2-methylpiperazin-1-yl)-1-methyl-2-oxo-1,2-dihydropyrido[3,2-d]pyrimidine-6-carbonitrile (63-64);

4-((2S,5R)-5-ethyl-4-(4-fluorophenyl)(6-(trifluoromethyl)pyridin-2-yl)methyl)-2-methylpiperazin-1-yl)-1-methyl-2-oxo-1,2-dihydropyrido[3,2-d]pyrimidine-6-carbonitrile (65-66);

4-((2S,5R)-4-(1-(4-(cyclopropylmethoxy)phenyl)ethyl)-5-ethyl-2-methylpiperazin-1-yl)-1-methyl-2-oxo-1,2-dihydropyrido[3,2-d]pyrimidine-6-carbonitrile (67-68);

4-((2S,5R)-4-(1-(4-(cyclopropylmethoxy)-2-fluorophenyl)ethyl)-5-ethyl-2-methylpiperazin-1-yl)-1-methyl-2-oxo-1,2-dihydropyrido[3,2-d]pyrimidine-6-carbonitrile (69-70);

4-((2 S,5R)-4-(1-(2,2-difluorobenzo[d][1,3]dioxol-5-yl)ethyl)-5-ethyl-2-methylpiperazin-1-yl)-1-methyl-2-oxo-1,2-dihydropyrido[3,2-d]pyrimidine-6-carbonitrile (71-72);

4-((2S,5R)-5-ethyl-4-(4-fluorophenyl)(isoxazol-3-yl)methyl)-2-methylpiperazin-1-yl)-1-methyl-2-oxo-1,2-dihydropyrido[3,2-d]pyrimidine-6-carbonitrile (73-74);

4-((2S,5R)-4-((5-cyclopropylpyridin-2-yl)(4-fluorophenyl)methyl)-5-ethyl-2-methylpiperazin-1-yl)-1-methyl-2-oxo-1,2-dihydropyrido[3,2-d]pyrimidine-6-carbonitrile (75-76);

4-((2S,5R)-4-(1-(4-(difluoromethoxy)phenyl)propyl)-5-ethyl-2-methylpiperazin-1-yl)-1-methyl-2-oxo-1,2-dihydropyrido[3,2-d]pyrimidine-6-carbonitrile (77-78);

4-((2 S,5R)-4-(1-(2,2-difluorobenzo[d][1,3]dioxol-5-yl)propyl)-5-ethyl-2-methylpiperazin-1-yl)-1-methyl-2-oxo-1,2-dihydropyrido[3,2-d]pyrimidine-6-carbonitrile (79-80);

4-((2S,5R)-5-ethyl-4-(1-(2-fluoro-4-(trifluoromethoxy)phenyl)ethyl)-2-methylpiperazin-1-yl)-1-methyl-2-oxo-1,2-dihydropyrido[3,2-d]pyrimidine-6-carbonitrile (81-82);

4-((2S,5R)-5-ethyl-2-methyl-4-(1-(4-(trifluoromethoxy)phenyl)propyl)piperazin-1-yl)-1-methyl-2-oxo-1,2-dihydropyrido[3,2-d]pyrimidine-6-carbonitrile (83-84);

4-((2S,5R)-5-ethyl-4-(1-(2-fluoro-4-(trifluoromethoxy)phenyl)propyl)-2-methylpiperazin-1-yl)-1-methyl-2-oxo-1,2-dihydropyrido[3,2-d]pyrimidine-6-carbonitrile (85-86);

4-((2S,5R)-5-ethyl-4-(4-fluorophenyl)(pyridin-2-yl)methyl)-2-methylpiperazin-1-yl)-1-methyl-2-oxo-1,2-dihydropyrido[3,2-d]pyrimidine-6-carbonitrile (87-88);

4-((2S,5R)-5-ethyl-2-methyl-4-(1-(4-(trifluoromethyl)phenyl)propyl)piperazin-1-yl)-1-methyl-2-oxo-1,2-dihydropyrido[3,2-d]pyrimidine-6-carbonitrile (89-90);

4-((2S,5R)-4-(1-(4-cyclopropyl-2-fluorophenyl)ethyl)-5-ethyl-2-methylpiperazin-1-yl)-1-methyl-2-oxo-1,2-dihydropyrido[3,2-d]pyrimidine-6-carbonitrile (91-92);

4-((2S,5R)-5-ethyl-2-methyl-4-(pyridin-2-yl(4-(trifluoromethoxy)phenyl)methyl) piperazin-1-yl)-1-methyl-2-oxo-1,2-dihydropyrido[3,2-d]pyrimidine-6-carbonitrile (93-94);

4-((2S,5R)-4-((4-chlorophenyl)(pyridin-2-yl)methyl)-5-ethyl-2-methylpiperazin-1-yl)-1-methyl-2-oxo-1,2-dihydropyrido[3,2-d]pyrimidine-6-carbonitrile (95-96);

4-((2 S,5R)-5-ethyl-4-(4-fluorophenyl)(6-(trifluoromethyl)pyridin-3-yl)methyl)-2-methylpiperazin-1-yl)-1-methyl-2-oxo-1,2-dihydropyrido[3,2-d]pyrimidine-6-carbonitrile (97-98);

4-((2S,5R)-4-((5-cyclopropylisoxazol-3-yl)(4-(trifluoromethoxy)phenyl)methyl)-5-ethyl-2-methylpiperazin-1-yl)-1-methyl-2-oxo-1,2-dihydropyrido[3,2-d]pyrimidine-6-carbonitrile (99-100);

4-((2S,5R)-4-((5-cyclopropylisoxazol-3-yl)(4-fluorophenyl)methyl)-5-ethyl-2-methylpiperazin-1-yl)-1-methyl-2-oxo-1,2-dihydropyrido[3,2-d]pyrimidine-6-carbonitrile (101-102);

4-((2S,5R)-4-((2-cyclopropylthiazol-5-yl)(4-fluorophenyl)methyl)-5-ethyl-2-methylpiperazin-1-yl)-1-methyl-2-oxo-1,2-dihydropyrido[3,2-d]pyrimidine-6-carbonitrile (103-104);

6-chloro-4-((2S,5R)-4-((3-cyclopropyl-1,2,4-oxadiazol-5-yl)(4-fluorophenyl)methyl)-2,5-dimethylpiperazin-1-yl)-1-methylpyrido[3,2-d]pyrimidin-2(1H)-one (105);

4-((2S,5R)-4-((3-cyclopropyl-1,2,4-oxadiazol-5-yl)(4-fluorophenyl)methyl)-2,5-dimethylpiperazin-1-yl)-1-methyl-2-oxo-1,2-dihydropyrido[3,2-d]pyrimidine-6-carbonitrile (106-107);

4-((2S,5R)-4-((3-(tert-butyl)-1,2,4-oxadiazol-5-yl)(4-fluorophenyl)methyl)-2,5-dimethylpiperazin-1-yl)-1-methyl-2-oxo-1,2-dihydropyrido[3,2-d]pyrimidine-6-carbonitrile (108-109);

4-((2S,5R)-4-((3-cyclopropyl-1,2,4-oxadiazol-5-yl)(4-fluorophenyl)methyl)-2,5-dimethylpiperazin-1-yl)-1-methyl-2-oxo-1,2-dihydropyrido[3,2-d]pyrimidine-6-carbonitrile (110-111);

4-((2S,5R)-4-((3-cyclopropyl-1,2,4-oxadiazol-5-yl)(4-fluorophenyl)methyl)-5-ethyl-2-methylpiperazin-1-yl)-1-methyl-2-oxo-1,2-dihydropyrido[3,2-d]pyrimidine-6-carbonitrile (112-113);

4-((2S,5R)-2-ethyl-4-((4-fluorophenyl)(5-(trifluoromethyl)pyridin-2-yl)methyl)-5-methylpiperazin-1-yl)-1-methyl-2-oxo-1,2-dihydropyrido[3,2-d]pyrimidine-6-carbonitrile (114-115);

4-((2S,5R)-2-ethyl-5-methyl-4-(1-(4-(trifluoromethyl)phenyl)ethyl)piperazin-1-yl)-1-methyl-2-oxo-1,2-dihydropyrido[3,2-d]pyrimidine-6-carbonitrile (116-117);

4-((2S,5R)-2-ethyl-4-(1-(2-fluoro-4-(trifluoromethyl)phenyl)ethyl)-5-methylpiperazin-1-yl)-1-methyl-2-oxo-1,2-dihydropyrido[3,2-d]pyrimidine-6-carbonitrile (118-119);

4-((2S,5R)-2-ethyl-4-((4-fluorophenyl)(6-(trifluoromethyl)pyridin-2-yl)methyl)-5-methylpiperazin-1-yl)-1-methyl-2-oxo-1,2-dihydropyrido[3,2-d]pyrimidine-6-carbonitrile (120-121);

4-((2S,5R)-2-ethyl-5-methyl-4-(1-(4-(trifluoromethoxy)phenyl)ethyl)piperazin-1-yl)-1-methyl-2-oxo-1,2-dihydropyrido[3,2-d]pyrimidine-6-carbonitrile (122-123);

4-((2 S,5R)-4-(bis(4-fluorophenyl)methyl)-2,5-dimethylpiperazin-1-yl)-1-methyl-2-oxo-1,2-dihydropyrido[3,2-d]pyrimidine-6-carbonitrile (124-125);

4-((2S,5R)-4-((4-fluorophenyl)(5-(trifluoromethyl)pyridin-2-yl)methyl)-2,5-dimethylpiperazin-1-yl)-1-methyl-2-oxo-1,2-dihydropyrido[3,2-d]pyrimidine-6-carbonitrile (126-127);

4-((2S,5R)-4-(1-(4-fluorophenyl)ethyl)-2,5-dimethylpiperazin-1-yl)-1-methyl-2-oxo-1,2-dihydropyrido[3,2-d]pyrimidine-6-carbonitrile (128-129);

4-((2S,5R)-2,5-dimethyl-4-(1-(4-(trifluoromethoxy)phenyl)ethyl)piperazin-1-yl)-1-methyl-2-oxo-1,2-dihydropyrido[3,2-d]pyrimidine-6-carbonitrile (131-132);

4-((2S,5R)-2,5-dimethyl-4-(1-(3,4,5-trifluorophenyl)ethyl)piperazin-1-yl)-1-methyl-2-oxo-1,2-dihydropyrido[3,2-d]pyrimidine-6-carbonitrile (138-139);

4-((2S,5R)-2,5-dimethyl-4-(1-(4-(trifluoromethyl)phenyl)ethyl)piperazin-1-yl)-1-methyl-2-oxo-1,2-dihydropyrido[3,2-d]pyrimidine-6-carbonitrile (140-141);

4-((2S,5R)-4-(1-(2-fluoro-4-(trifluoromethoxy)phenyl)ethyl)-2,5-dimethylpiperazin-1-yl)-1-methyl-2-oxo-1,2-dihydropyrido[3,2-d]pyrimidine-6-carbonitrile (142-143);

4-((2 S,5R)-4-(1-(2,4-difluorophenyl)ethyl)-2,5-dimethylpiperazin-1-yl)-1-methyl-2-oxo-1,2-dihydropyrido[3,2-d]pyrimidine-6-carbonitrile (144-145);

4-((2S,5R)-4-(1-(4-chloro-2-fluorophenyl)ethyl)-2,5-dimethylpiperazin-1-yl)-1-methyl-2-oxo-1,2-dihydropyrido[3,2-d]pyrimidine-6-carbonitrile (146-147);

4-((2S,5R)-4-(1-(3,4-difluorophenyl)ethyl)-2,5-dimethylpiperazin-1-yl)-1-methyl-2-oxo-1,2-dihydropyrido[3,2-d]pyrimidine-6-carbonitrile (148-149);

4-((2S,5R)-4-(1-(2-fluoro-4-(trifluoromethyl)phenyl)ethyl)-2,5-dimethylpiperazin-1-yl)-1-methyl-2-oxo-1,2-dihydropyrido[3,2-d]pyrimidine-6-carbonitrile (150-151);

4-((2S,5R)-4-(1-(2-fluoro-4-(trifluoromethoxy)phenyl)propyl)-2,5-dimethylpiperazin-1-yl)-1-methyl-2-oxo-1,2-dihydropyrido[3,2-d]pyrimidine-6-carbonitrile (152-153);

4-((2S,5R)-2,5-dimethyl-4-(1-(4-(trifluoromethoxy)phenyl)propyl)piperazin-1-yl)-1-methyl-2-oxo-1,2-dihydropyrido[3,2-d]pyrimidine-6-carbonitrile (154-155);

4-((2S,5R)-4-(1-(4-(difluoromethoxy)phenyl)ethyl)-2,5-dimethylpiperazin-1-yl)-1-methyl-2-oxo-1,2-dihydropyrido[3,2-d]pyrimidine-6-carbonitrile (156-157);

4-((2S,5R)-4-((4-cyclopropylthiazol-2-yl)(4-fluorophenyl)methyl)-2,5-dimethylpiperazin-1-yl)-1-methyl-2-oxo-1,2-dihydropyrido[3,2-d]pyrimidine-6-carbonitrile (158-159);

4-((2S,5R)-4-(1-(3-fluoro-4-(trifluoromethoxy)phenyl)ethyl)-2,5-dimethylpiperazin-1-yl)-1-methyl-2-oxo-1,2-dihydropyrido[3,2-d]pyrimidine-6-carbonitrile (160-161);

4-((2S,5R)-4-((4-fluorophenyl)(isoxazol-3-yl)methyl)-2,5-dimethylpiperazin-1-yl)-1-methyl-2-oxo-1,2-dihydropyrido[3,2-d]pyrimidine-6-carbonitrile (162-163);

4-((2S,5R)-4-((5-cyclopropylisoxazol-3-yl)(4-(trifluoromethoxy)phenyl)methyl)-2,5-dimethylpiperazin-1-yl)-1-methyl-2-oxo-1,2-dihydropyrido[3,2-d]pyrimidine-6-carbonitrile (164-165);

4-((2 S,5R)-4-(1-(2,2-difluorobenzo[d][1,3]dioxol-5-yl)ethyl)-2,5-dimethylpiperazin-1-yl)-1-methyl-2-oxo-1,2-dihydropyrido[3,2-d]pyrimidine-6-carbonitrile (166-167);

4-((2S,5R)-4-(1-(4-cyclopropyl-2-fluorophenyl)ethyl)-2,5-dimethylpiperazin-1-yl)-1-methyl-2-oxo-1,2-dihydropyrido[3,2-d]pyrimidine-6-carbonitrile (168-169);

4-((2S,5R)-4-((4-fluorophenyl)(2-(trifluoromethyl)thiazol-4-yl)methyl)-2,5-dimethylpiperazin-1-yl)-1-methyl-2-oxo-1,2-dihydropyrido[3,2-d]pyrimidine-6-carbonitrile (170-171);

6-chloro-4-((2S,5R)-2,5-diethyl-4-(1-(4-((1-hydroxy-2-methylpropan-2-yl)oxy) phenyl)ethyl)piperazin-1-yl)-1-methylpyrido[3,2-d]pyrimidin-2(1H)-one (186);

6-chloro-4-((2S,5R)-2,5-diethyl-4-(1-(4-((1-methoxy-2-methylpropan-2-yl)oxy) phenyl)ethyl)piperazin-1-yl)-1-methylpyrido[3,2-d]pyrimidin-2(1H)-one (187);

6-chloro-4-((2S,5R)-2,5-diethyl-4-(1-(4-((1-methoxy-2-methylpropan-2-yl)oxy) phenyl)ethyl)piperazin-1-yl)-1-methylpyrido[3,2-d]pyrimidin-2(1H)-one (188-189);

4-((2S,5R)-2,5-diethyl-4-(1-(4-(methoxy-d3)phenyl)ethyl)piperazin-1-yl)-1-methyl-2-oxo-1,2-dihydropyrido[3,2-d]pyrimidine-6-carbonitrile (190-191);

4-((2 S,5R)-4-(1-(6-cyclopropylpyridin-3-yl)ethyl)-2,5-diethylpiperazin-1-yl)-1-methyl-2-oxo-1,2-dihydropyrido[3,2-d]pyrimidine-6-carbonitrile (192-193);

4-((2S,5R)-2,5-diethyl-4-(1-(2-morpholino-4-(trifluoromethyl)phenyl)ethyl)piperazin-1-yl)-1-methyl-2-oxo-1,2-dihydropyrido[3,2-d]pyrimidine-6-carbonitrile (194-195);

4-((2S,5R)-4-(1-(4-(2-cyanopropan-2-yl)phenyl)ethyl)-2,5-diethylpiperazin-1-yl)-1-methyl-2-oxo-1,2-dihydropyrido[3,2-d]pyrimidine-6-carbonitrile (196-197);

4-((2S,5R)-4-(1-(4-(cyclopropylmethoxy)-2-fluorophenyl)propyl)-2,5-diethylpiperazin-1-yl)-1-methyl-2-oxo-1,2-dihydropyrido[3,2-d]pyrimidine-6-carbonitrile (198-199);

4-((2S,5R)-4-(1-(4-cyclopropylphenyl)propyl)-2,5-diethylpiperazin-1-yl)-1-methyl-2-oxo-1,2-dihydropyrido[3,2-d]pyrimidine-6-carbonitrile (200-201);

4-((2S,5R)-2,5-diethyl-4-(1-(3-methyl-2-oxo-2,3-dihydrobenzo[d]oxazol-5-yl)ethyl) piperazin-1-yl)-1-methyl-2-oxo-1,2-dihydropyrido[3,2-d]pyrimidine-6-carbonitrile (202-203);

4-((2 S,5R)-2,5-diethyl-4-(1-(2-morpholinopyrimidin-5-yl)ethyl)piperazin-1-yl)-1-methyl-2-oxo-1,2-dihydropyrido[3,2-d]pyrimidine-6-carbonitrile (206-207);

4-((2S,5R)-2,5-diethyl-4-(1-(4-(methoxy-d3)phenyl)propyl)piperazin-1-yl)-1-methyl-2-oxo-1,2-dihydropyrido[3,2-d]pyrimidine-6-carbonitrile (208-209);

4-((2S,5R)-2,5-diethyl-4-(4-fluorophenyl)(2-(trifluoromethyl)thiazol-4-yl)methyl) piperazin-1-yl)-1-methyl-2-oxo-1,2-dihydropyrido[3,2-d]pyrimidine-6-carbonitrile (210-211);

4-((2S,5R)-2,5-diethyl-4-(1-(4-methoxyphenyl)propyl)piperazin-1-yl)-1-methyl-2-oxo-1,2-dihydropyrido[3,2-d]pyrimidine-6-carbonitrile (212-213);

4-((2 S,5R)-2,5-diethyl-4-(1-(6-methoxypyridin-2-yl)ethyl)piperazin-1-yl)-1-methyl-2-oxo-1,2-dihydropyrido[3,2-d]pyrimidine-6-carbonitrile (214-215);

4-((2S,5R)-4-(1-(4-(cyclopropylmethoxy)phenyl)propyl)-2,5-diethylpiperazin-1-yl)-1-methyl-2-oxo-1,2-dihydropyrido[3,2-d]pyrimidine-6-carbonitrile (216-217);

4-((2S,5R)-2,5-diethyl-4-(1-(4-(1-methylcyclopropyl)phenyl)ethyl)piperazin-1-yl)-1-methyl-2-oxo-1,2-dihydropyrido[3,2-d]pyrimidine-6-carbonitrile (218-219);

4-((2 S,5R)-4-(1-(4-cyanophenyl)propyl)-2,5-diethylpiperazin-1-yl)-1-methyl-2-oxo-1,2-dihydropyrido[3,2-d]pyrimidine-6-carbonitrile (220-221);

4-((2S,5R)-4-(1-(4-(difluoromethoxy)phenyl)propyl)-2,5-diethylpiperazin-1-yl)-1-methyl-2-oxo-1,2-dihydropyrido[3,2-d]pyrimidine-6-carbonitrile (222-223);

4-((2 S,5R)-2,5-diethyl-4-(1-(6-(trifluoromethyl)pyridin-3-yl)propyl)piperazin-1-yl)-1-methyl-2-oxo-1,2-dihydropyrido[3,2-d]pyrimidine-6-carbonitrile (224-225);

4-((2 S,5R)-2,5-diethyl-4-(1-(2-(trifluoromethyl)pyrimidin-5-yl)ethyl)piperazin-1-yl)-1-methyl-2-oxo-1,2-dihydropyrido[3,2-d]pyrimidine-6-carbonitrile (226-227);

4-((2 S,5R)-2,5-diethyl-4-(1-(6-methylpyridin-3-yl)ethyl)piperazin-1-yl)-1-methyl-2-oxo-1,2-dihydropyrido[3,2-d]pyrimidine-6-carbonitrile (228-229);

4-((2S,5R)-2,5-diethyl-4-(1-(4-(2-oxopyrrolidin-1-yl)phenyl)ethyl)piperazin-1-yl)-1-methyl-2-oxo-1,2-dihydropyrido[3,2-d]pyrimidine-6-carbonitrile (230-231);

4-((2 S,5R)-4-(1-(4-(difluoromethoxy)-2-fluorophenyl)propyl)-2,5-diethylpiperazin-1-yl)-1-methyl-2-oxo-1,2-dihydropyrido[3,2-d]pyrimidine-6-carbonitrile (232-233);

4-((2 S,5R)-2,5-diethyl-4-(1-(4-isopropoxyphenyl)propyl)piperazin-1-yl)-1-methyl-2-oxo-1,2-dihydropyrido[3,2-d]pyrimidine-6-carbonitrile (234-235);

4-((2S,5R)-2,5-diethyl-4-(1-(p-tolyl)propyl)piperazin-1-yl)-1-methyl-2-oxo-1,2-dihydropyrido[3,2-d]pyrimidine-6-carbonitrile (236-237);

4-((2 S,5R)-4-(1-(4-chloro-2-fluorophenyl)propyl)-2,5-diethylpiperazin-1-yl)-1-methyl-2-oxo-1,2-dihydropyrido[3,2-d]pyrimidine-6-carbonitrile (238-239);

4-((2 S,5R)-4-(1-(6-(difluoromethoxy)pyridin-2-yl)ethyl)-2,5-diethylpiperazin-1-yl)-1-methyl-2-oxo-1,2-dihydropyrido[3,2-d]pyrimidine-6-carbonitrile (240-241);

4-((2S,5R)-2,5-diethyl-4-(1-(4-(trifluoromethyl)phenyl)butyl)piperazin-1-yl)-1-methyl-2-oxo-1,2-dihydropyrido[3,2-d]pyrimidine-6-carbonitrile (243-244);

4-((2 S,5R)-2,5-diethyl-4-(1-(6-(trifluoromethoxy)pyridin-2-yl)ethyl)piperazin-1-yl)-1-methyl-2-oxo-1,2-dihydropyrido[3,2-d]pyrimidine-6-carbonitrile (245-246);

4-((2 S,5R)-2,5-diethyl-4-(1-(4-(2-morpholinopropan-2-yl)phenyl)ethyl)piperazin-1-yl)-1-methyl-2-oxo-1,2-dihydropyrido[3,2-d]pyrimidine-6-carbonitrile (247-248);

4-((2S,5R)-2,5-diethyl-4-(1-(4-methoxyphenyl)-2-methylpropyl)piperazin-1-yl)-1-methyl-2-oxo-1,2-dihydropyrido[3,2-d]pyrimidine-6-carbonitrile (249-250);

4-((2S,5R)-4-(1-(4-(2-cyanopropan-2-yl)phenyl)propyl)-2,5-diethylpiperazin-1-yl)-1-methyl-2-oxo-1,2-dihydropyrido[3,2-d]pyrimidine-6-carbonitrile (251-252);

4-((2S,5R)-4-(1-(2-cyclopropylbenzo[d]oxazol-5-yl)ethyl)-2,5-diethylpiperazin-1-yl)-1-methyl-2-oxo-1,2-dihydropyrido[3,2-d]pyrimidine-6-carbonitrile (253-254);

4-((2S,5R)-4-(1-(4-cyclopropoxyphenyl)propyl)-2,5-diethylpiperazin-1-yl)-1-methyl-2-oxo-1,2-dihydropyrido[3,2-d]pyrimidine-6-carbonitrile (255-256);

4-((2S,5R)-4-((6-(difluoromethyl)pyridin-2-yl)(4-fluorophenyl)methyl)-2,5-diethylpiperazin-1-yl)-1-methyl-2-oxo-1,2-dihydropyrido[3,2-d]pyrimidine-6-carbonitrile (257-258);

ethyl (1 S,2S)-2-(4-(1-((2R,5 S)-4-(6-cyano-1-methyl-2-oxo-1,2-dihydropyrido[3,2-d]pyrimidin-4-yl)-2,5-diethylpiperazin-1-yl)ethyl)phenoxy)cyclopropane-1-carboxylate (259-260);

4-((2 S,5R)-2,5-diethyl-4-(1-(4-isopropoxyphenyl)-2-methylpropyl)piperazin-1-yl)-1-methyl-2-oxo-1,2-dihydropyrido[3,2-d]pyrimidine-6-carbonitrile (261-262);

4-((2S,5R)-4-(1-(4-(1-cyanocyclopropyl)phenyl)ethyl)-2,5-diethylpiperazin-1-yl)-1-methyl-2-oxo-1,2-dihydropyrido[3,2-d]pyrimidine-6-carbonitrile (263-264);

methyl 4-(1-((2R,5S)-4-(6-cyano-1-methyl-2-oxo-1,2-dihydropyrido[3,2-d]pyrimidin-4-yl)-2,5-diethylpiperazin-1-yl)ethyl)benzoate (265-266);

4-((2S,5R)-2,5-diethyl-4-(1-(4-(morpholinomethyl)phenyl)propyl)piperazin-1-yl)-1-methyl-2-oxo-1,2-dihydropyrido[3,2-d]pyrimidine-6-carbonitrile (267-268);

4-((2S,5R)-2,5-diethyl-4-(1-(4-(hydroxymethyl)phenyl)ethyl)piperazin-1-yl)-1-methyl-2-oxo-1,2-dihydropyrido[3,2-d]pyrimidine-6-carbonitrile (270-271);

4-((2S,5R)-4-(1-(4-(Bromomethyl)phenyl)ethyl)-2,5-diethylpiperazin-1-yl)-1-methyl-2-oxo-1,2-dihydropyrido[3,2-d]pyrimidine-6-carbonitrile (272);

4-((2S,5R)-2,5-diethyl-4-(1-(4-((4-methoxypiperidin-1-yl)methyl)phenyl)ethyl) piperazin-1-yl)-1-methyl-2-oxo-1,2-dihydropyrido[3,2-d]pyrimidine-6-carbonitrile (273-274);

4-((2S,5R)-4-(1-(4-((2,2-dimethylmorpholino)methyl)phenyl)ethyl)-2,5-diethylpiperazin-1-yl)-1-methyl-2-oxo-1,2-dihydropyrido[3,2-d]pyrimidine-6-carbonitrile (275-276);

4-((2S,5R)-4-(1-(4-((4,4-difluoropiperidin-1-yl)methyl)phenyl)ethyl)-2,5-diethylpiperazin-1-yl)-1-methyl-2-oxo-1,2-dihydropyrido[3,2-d]pyrimidine-6-carbonitrile (277-278);

4-((2S,5R)-4-(1-(4-((2-oxa-6-azaspiro[3.3]heptan-6-yl)methyl)phenyl)ethyl)-2,5-diethylpiperazin-1-yl)-1-methyl-2-oxo-1,2-dihydropyrido[3,2-d]pyrimidine-6-carbonitrile (279-280);

4-((2S,5R)-2,5-diethyl-4-(1-(4-(piperidin-1-ylmethyl)phenyl)ethyl)piperazin-1-yl)-1-methyl-2-oxo-1,2-dihydropyrido[3,2-d]pyrimidine-6-carbonitrile (281-282);

4-((2S,5R)-4-(1-(4-((4-acetylpiperazin-1-yl)methyl)phenyl)ethyl)-2,5-diethylpiperazin-1-yl)-1-methyl-2-oxo-1,2-dihydropyrido[3,2-d]pyrimidine-6-carbonitrile (283-284);

4-((2S,5R)-2,5-diethyl-4-(1-(4-((4-hydroxypiperidin-1-yl)methyl)phenyl)ethyl) piperazin-1-yl)-1-methyl-2-oxo-1,2-dihydropyrido[3,2-d]pyrimidine-6-carbonitrile (285-286);

4-((2S,5R)-2,5-diethyl-4-(1-(4-((4-methyl-3-oxopiperazin-1-yl)methyl)phenyl)ethyl) piperazin-1-yl)-1-methyl-2-oxo-1,2-dihydropyrido[3,2-d]pyrimidine-6-carbonitrile (287-288);

4-((2S,5R)-2,5-diethyl-4-(1-(4-(((R)-3-hydroxypiperidin-1-yl)methyl)phenyl)ethyl) piperazin-1-yl)-1-methyl-2-oxo-1,2-dihydropyrido[3,2-d]pyrimidine-6-carbonitrile (289-290);

4-((2S,5R)-4-(1-(4-(((2S,6R)-2,6-dimethylmorpholino)methyl)phenyl)ethyl)-2,5-diethylpiperazin-1-yl)-1-methyl-2-oxo-1,2-dihydropyrido[3,2-d]pyrimidine-6-carbonitrile (291-292);

4-((2S,5R)-4-((3-bromo-1-methyl-1H-1,2,4-triazol-5-yl)(4-fluorophenyl)methyl)-2,5-diethylpiperazin-1-yl)-1-methyl-2-oxo-1,2-dihydropyrido[3,2-d]pyrimidine-6-carbonitrile (293);

4-((2S,5R)-4-((3-cyclopropyl-1-methyl-1H-1,2,4-triazol-5-yl)(4-fluorophenyl) methyl)-2,5-diethylpiperazin-1-yl)-1-methyl-2-oxo-1,2-dihydropyrido[3,2-d]pyrimidine-6-carbonitrile (294-295);

4-((2S,5R)-5-ethyl-4-((4-fluorophenyl)(2-(trifluoromethyl)thiazol-4-yl)methyl)-2-methylpiperazin-1-yl)-1-methyl-2-oxo-1,2-dihydropyrido[3,2-d]pyrimidine-6-carbonitrile (296-297);

4-((2S,5R)-5-ethyl-2-methyl-4-(1-(3-methyl-2-oxo-2,3-dihydrobenzo[d]oxazol-5-yl) ethyl)piperazin-1-yl)-1-methyl-2-oxo-1,2-dihydropyrido[3,2-d]pyrimidine-6-carbonitrile (298-299);

4-((2S,5R)-4-(1-(4-cyclopropylphenyl)propyl)-5-ethyl-2-methylpiperazin-1-yl)-1-methyl-2-oxo-1,2-dihydropyrido[3,2-d]pyrimidine-6-carbonitrile (300-301);

4-((2S,5R)-4-(1-(4-cyclopropyl-2-fluorophenyl)propyl)-5-ethyl-2-methylpiperazin-1-yl)-1-methyl-2-oxo-1,2-dihydropyrido[3,2-d]pyrimidine-6-carbonitrile (302-303);

4-((2S,5R)-5-ethyl-4-(1-(4-methoxyphenyl)propyl)-2-methylpiperazin-1-yl)-1-methyl-2-oxo-1,2-dihydropyrido[3,2-d]pyrimidine-6-carbonitrile (304-305);

4-((2S,5R)-4-(1-(4-ethoxyphenyl)propyl)-5-ethyl-2-methylpiperazin-1-yl)-1-methyl-2-oxo-1,2-dihydropyrido[3,2-d]pyrimidine-6-carbonitrile (306-307);

4-((2S,5R)-4-(1-(4-(cyclopropylmethoxy)phenyl)propyl)-5-ethyl-2-methylpiperazin-1-yl)-1-methyl-2-oxo-1,2-dihydropyrido[3,2-d]pyrimidine-6-carbonitrile (308-309);

4-((2S,5R)-4-(1-(4-cyclopropoxyphenyl)propyl)-5-ethyl-2-methylpiperazin-1-yl)-1-methyl-2-oxo-1,2-dihydropyrido[3,2-d]pyrimidine-6-carbonitrile (311-312);

4-((2S,5R)-5-ethyl-4-(1-(4-methoxyphenyl)-2-methylpropyl)-2-methylpiperazin-1-yl)-1-methyl-2-oxo-1,2-dihydropyrido[3,2-d]pyrimidine-6-carbonitrile (313-314);

4-((2S,5R)-4-((6-(difluoromethyl)pyridin-2-yl)(4-fluorophenyl)methyl)-5-ethyl-2-methylpiperazin-1-yl)-1-methyl-2-oxo-1,2-dihydropyrido[3,2-d]pyrimidine-6-carbonitrile (315-316);

4-((2S,5R)-4-(1-(4-(2-cyanopropan-2-yl)phenyl)propyl)-5-ethyl-2-methylpiperazin-1-yl)-1-methyl-2-oxo-1,2-dihydropyrido[3,2-d]pyrimidine-6-carbonitrile (317-318);

4-((2S,5R)-4-(1-(3,4-difluorophenyl)propyl)-5-ethyl-2-methylpiperazin-1-yl)-1-methyl-2-oxo-1,2-dihydropyrido[3,2-d]pyrimidine-6-carbonitrile (319-320);

4-((2S,5R)-4-(1-(4-bromophenyl)propyl)-5-ethyl-2-methylpiperazin-1-yl)-1-methyl-2-oxo-1,2-dihydropyrido[3,2-d]pyrimidine-6-carbonitrile (321-322);

4-((2S,5R)-5-ethyl-4-(1-(4-isopropoxyphenyl)propyl)-2-methylpiperazin-1-yl)-1-methyl-2-oxo-1,2-dihydropyrido[3,2-d]pyrimidine-6-carbonitrile (323-324);

4-((2 S,5R)-4-(1-(4-(1-cyanocyclopropyl)phenyl)ethyl)-5-ethyl-2-methylpiperazin-1-yl)-1-methyl-2-oxo-1,2-dihydropyrido[3,2-d]pyrimidine-6-carbonitrile (325-326);

4-((2S,5R)-4-(1-(4-(cyclopropylmethoxy)-2,6-difluorophenyl)propyl)-5-ethyl-2-methylpiperazin-1-yl)-1-methyl-2-oxo-1,2-dihydropyrido[3,2-d]pyrimidine-6-carbonitrile (327-328);

4-((2S,5R)-5-ethyl-2-methyl-4-(1-(4-(tetrahydro-2H-pyran-4-yl)phenyl)ethyl) piperazin-1-yl)-1-methyl-2-oxo-1,2-dihydropyrido[3,2-d]pyrimidine-6-carbonitrile (329-330);

4-((2S,5R)-4-(1-(4-(1,3-dioxolan-2-yl)phenyl)propyl)-5-ethyl-2-methylpiperazin-1-yl)-1-methyl-2-oxo-1,2-dihydropyrido[3,2-d]pyrimidine-6-carbonitrile (331-332);

4-((2S,5R)-5-ethyl-4-(1-(4-isopropoxyphenyl)propyl)-2-methylpiperazin-1-yl)-1-methyl-2-oxo-1,2-dihydropyrido[3,2-d]pyrimidine-6-carbonitrile (330-334);

4-((2S,5R)-5-ethyl-2-methyl-4-(1-(4-(3,3,3-trifluoropropoxy)phenyl)propyl) piperazin-1-yl)-1-methyl-2-oxo-1,2-dihydropyrido[3,2-d]pyrimidine-6-carbonitrile (335-336);

4-((2S,5R)-5-ethyl-2-methyl-4-(1-(4-((tetrahydro-2H-pyran-4-yl)methoxy)phenyl) propyl)piperazin-1-yl)-1-methyl-2-oxo-1,2-dihydropyrido[3,2-d]pyrimidine-6-carbonitrile (337-338);

4-((2S,5R)-4-(1-(4-(2-cyclopropylethoxy)phenyl)propyl)-5-ethyl-2-methylpiperazin-1-yl)-1-methyl-2-oxo-1,2-dihydropyrido[3,2-d]pyrimidine-6-carbonitrile (339-340);

4-((2S,5R)-5-ethyl-2-methyl-4-(1-(4-(oxetan-3-ylmethoxy)phenyl)propyl)piperazin-1-yl)-1-methyl-2-oxo-1,2-dihydropyrido[3,2-d]pyrimidine-6-carbonitrile (341-342);

4-((2 S,5R)-5-ethyl-2-methyl-4-(1-(4-((1-methylazetidin-3-yl)methoxy)phenyl)propyl) piperazin-1-yl)-1-methyl-2-oxo-1,2-dihydropyrido[3,2-d]pyrimidine-6-carbonitrile (343-344);

4-((2S,5R)-5-ethyl-2-methyl-4-(1-(4-((1-methylcyclopropyl)methoxy)phenyl)propyl) piperazin-1-yl)-1-methyl-2-oxo-1,2-dihydropyrido[3,2-d]pyrimidine-6-carbonitrile (345-346);

4-((2S,5R)-5-ethyl-2-methyl-4-(1-(4-(thiazol-2-ylmethoxy)phenyl)propyl)piperazin-1-yl)-1-methyl-2-oxo-1,2-dihydropyrido[3,2-d]pyrimidine-6-carbonitrile (347-348);

4-((2S,5R)-4-(1-(3-bromo-4-(trifluoromethyl)phenyl)ethyl)-5-ethyl-2-methylpiperazin-1-yl)-1-methyl-2-oxo-1,2-dihydropyrido[3,2-d]pyrimidine-6-carbonitrile (349);

4-((2S,5R)-5-ethyl-2-methyl-4-(1-(3-(morpholinomethyl)-4-(trifluoromethyl)phenyl) ethyl)piperazin-1-yl)-1-methyl-2-oxo-1,2-dihydropyrido[3,2-d] pyrimidine-6-carbonitrile (350-351);

4-((2S,5R)-4-(1-(3-((dimethylamino)methyl)-4-(trifluoromethyl)phenyl)ethyl)-5-ethyl-2-methylpiperazin-1-yl)-1-methyl-2-oxo-1,2-dihydropyrido[3,2-d]pyrimidine-6-carbonitrile (352-353);

4-((2S,5R)-5-ethyl-2-methyl-4-(1-(3-(piperidin-1-ylmethyl)-4-(trifluoromethyl) phenyl)ethyl)piperazin-1-yl)-1-methyl-2-oxo-1,2-dihydropyrido[3,2-d]pyrimidine-6-carbonitrile (354-355);

4-((2S,5R)-4-(1-(3-cyano-4-(trifluoromethyl)phenyl)ethyl)-5-ethyl-2-methylpiperazin-1-yl)-1-methyl-2-oxo-1,2-dihydropyrido[3,2-d]pyrimidine-6-carbonitrile (356-357);

4-((2S,5R)-4-(1-(4-(aminomethyl)phenyl)ethyl)-5-ethyl-2-methylpiperazin-1-yl)-1-methyl-2-oxo-1,2-dihydropyrido[3,2-d]pyrimidine-6-carbonitrile (358);

methyl (4-(1-((2R,5S)-4-(6-cyano-1-methyl-2-oxo-1,2-dihydropyrido[3,2-d]pyrimidin-4-yl)-2-ethyl-5-methylpiperazin-1-yl)ethyl)benzyl)carbamate (359-360);

4-((2S,5R)-4-(1-(3-cyclopropyl-1,2,4-oxadiazol-5-yl)ethyl)-2,5-diethylpiperazin-1-yl)-1-methyl-2-oxo-1,2-dihydropyrido[3,2-d]pyrimidine-6-carbonitrile (361-362);

4-((2S,5R)-4-(1-(3-cyclopropyl-1,2,4-oxadiazol-5-yl)propyl)-2,5-diethylpiperazin-1-yl)-1-methyl-2-oxo-1,2-dihydropyrido[3,2-d]pyrimidine-6-carbonitrile (363-364);

4-((2S,5R)-4-(1-(3-cyclopropyl-1,2,4-oxadiazol-5-yl)-2-methylpropyl)-5-ethyl-2-methylpiperazin-1-yl)-1-methyl-2-oxo-1,2-dihydropyrido[3,2-d]pyrimidine-6-carbonitrile (365-366);

4-((2S,5R)-4-(1-(5-cyclopropyl-1,3,4-oxadiazol-2-yl)-2-methylpropyl)-5-ethyl-2-methylpiperazin-1-yl)-1-methyl-2-oxo-1,2-dihydropyrido[3,2-d]pyrimidine-6-carbonitrile (367-368);

2-((2R,5S)-4-(6-chloro-1-methyl-2-oxo-1,2-dihydropyrido[3,2-d]pyrimidin-4-yl)-2,5-diethylpiperazin-1-yl)-2-(4-fluorophenyl)acetonitrile (369);

6-chloro-4-((2S,5R)-4-((5-cyclopropyl-1,2,4-oxadiazol-3-yl)(4-fluorophenyl)methyl)-2,5-diethylpiperazin-1-yl)-1-methylpyrido[3,2-d]pyrimidin-2(1H)-one (370);

4-((2S,5R)-4-((5-cyclopropyl-1,2,4-oxadiazol-3-yl)(4-fluorophenyl)methyl)-2,5-diethylpiperazin-1-yl)-1-methyl-2-oxo-1,2-dihydropyrido[3,2-d]pyrimidine-6-carbonitrile (371-372);

4-((2S,5R)-4-(bis(4-chlorophenyl)methyl)-2,5-dimethylpiperazin-1-yl)-1-methyl-2-oxo-1,2-dihydropyrido[3,2-d]pyrimidine-6-carbonitrile (373-374);

4-((2S,5R)-4-((4-cyanophenyl)(4-fluorophenyl)methyl)-2,5-dimethylpiperazin-1-yl)-1-methyl-2-oxo-1,2-dihydropyrido[3,2-d]pyrimidine-6-carbonitrile (375);

4-((2S,5R)-4-(1-(4-((2-cyanopropan-2-yl)oxy)phenyl)ethyl)-2,5-dimethylpiperazin-1-yl)-1-methyl-2-oxo-1,2-dihydropyrido[3,2-d]pyrimidine-6-carbonitrile (376-377);

4-((2S,5R)-4-(1-(4-cyclopropylphenyl)propyl)-2,5-dimethylpiperazin-1-yl)-1-methyl-2-oxo-1,2-dihydropyrido[3,2-d]pyrimidine-6-carbonitrile (378-379);

4-((2S,5R)-4-(1-(4-cyclopropyl-2-fluorophenyl)propyl)-2,5-dimethylpiperazin-1-yl)-1-methyl-2-oxo-1,2-dihydropyrido[3,2-d]pyrimidine-6-carbonitrile (380-381);

6-chloro-4-((2S,5R)-4-(1-(4-(hydroxymethyl)phenyl)ethyl)-2,5-dimethylpiperazin-1-yl)-1-methylpyrido[3,2-d]pyrimidin-2(1H)-one (382);

4-((2S,5R)-4-(1-(4-(hydroxymethyl)phenyl)ethyl)-2,5-dimethylpiperazin-1-yl)-1-methyl-2-oxo-1,2-dihydropyrido[3,2-d]pyrimidine-6-carbonitrile (383);

4-((2S,5R)-4-(1-(4-(bromomethyl)phenyl)ethyl)-2,5-dimethylpiperazin-1-yl)-1-methyl-2-oxo-1,2-dihydropyrido[3,2-d]pyrimidine-6-carbonitrile (384);

4-((2S,5R)-4-(1-(4-((2,2-dimethylmorpholino)methyl)
  phenyl)ethyl)-2,5-dimethylpiperazin-1-yl)-1-methyl-2-
  oxo-1,2-dihydropyrido[3,2-d]pyrimidine-6-carboni-
  trile (385-386);
4-((2S,5R)-4-(1-(4-(((1S,4S)-2-oxa-5-azabicyclo[2.2.1]
  heptan-5-yl)methyl) phenyl)ethyl)-2,5-dimethylpiper-
  azin-1-yl)-1-methyl-2-oxo-1,2-dihydropyrido[3,2-d]
  pyrimidine-6-carbonitrile (387-388);
4-((2S,5R)-4-(1-(4-(((2S,6R)-2,6-dimethylmorpholino)
  methyl)phenyl)ethyl)-2,5-dimethylpiperazin-1-yl)-1-
  methyl-2-oxo-1,2-dihydropyrido[3,2-d]pyrimidine-6-
  carbonitrile (389);
4-((2 S,5R)-4-(1-(4-((4,4-difluoropiperidin-1-yl)methyl)
  phenyl)ethyl)-2,5-dimethylpiperazin-1-yl)-1-methyl-2-
  oxo-1,2-dihydropyrido[3,2-d]pyrimidine-6-carboni-
  trile (390-391);
4-((2S,5R)-4-(1-(4-((2-oxa-6-azaspiro[3.3]heptan-6-yl)
  methyl)phenyl)ethyl)-2,5-dimethylpiperazin-1-yl)-1-
  methyl-2-oxo-1,2-dihydropyrido[3,2-d]pyrimidine-6-
  carbonitrile (392-393);
6-chloro-1-methyl-4-((2S,5R)-2-methyl-5-propyl-4-(1-
  (4-(trifluoromethyl)phenyl) ethyl)piperazin-1-yl)
  pyrido[3,2-d]pyrimidin-2(1H)-one (394);
1-methyl-4-((2S,5R)-2-methyl-5-propyl-4-(1-(4-(trifluo-
  romethyl)phenyl)ethyl) piperazin-1-yl)-2-oxo-1,2-di-
  hydropyrido[3,2-d]pyrimidine-6-carbonitrile (395-
  396);
6-chloro-4-((2S,5R)-5-ethyl-2-methyl-4-(1-(4-(trifluo-
  romethyl)phenyl)ethyl) piperazin-1-yl)-1-(methyl-d$_3$)
  pyrido[3,2-d]pyrimidin-2(1H)-one (417-418);
4-((2S,5R)-5-ethyl-2-methyl-4-(1-(4-(trifluoromethyl)
  phenyl)ethyl)piperazin-1-yl)-1-(methyl-d3)-2-oxo-1,2-
  dihydropyrido[3,2-d]pyrimidine-6-carbonitrile (419-
  420);
6-chloro-4-((2S,5R)-2,5-diethyl-4-(1-(4-(trifluoromethyl)
  phenyl)propyl)piperazin-1-yl)-1-methylpyrido[3,2-d]
  pyrimidin-2(1H)-one (421-422);
6-chloro-4-((2S,5R)-2,5-diethyl-4-(1-(4-(trifluoromethyl)
  phenyl)ethyl)piperazin-1-yl)-1-methylpyrido[3,2-d]
  pyrimidin-2(1H)-one (426);
6-chloro-4-((2S,5R)-2,5-dimethyl-4-(1-(3-(trifluorom-
  ethyl)bicyclo[1.1.1]pentan-1-yl)propyl)piperazin-1-
  yl)-1-methylpyrido[3,2-d]pyrimidin-2(1H)-one (Di-
  astereomeric Mixture) (446);
4-((2S,5R)-2,5-dimethyl-4-(1-(3-(trifluoromethyl)bicyclo
  [1.1.1]pentan-1-yl)propyl) piperazin-1-yl)-1-methyl-2-
  oxo-1,2-dihydropyrido[3,2-d]pyrimidine-6-carboni-
  trile (447-449);
4-((2S,5R)-4-((4-fluorophenyl)(3-(trifluoromethyl)bicy-
  clo[1.1.1]pentan-1-yl)methyl)-2,5-dimethylpiperazin-
  1-yl)-1-methyl-2-oxo-1,2-dihydropyrido[3,2-d]pyrimi-
  dine-6-carbonitrile (450-452);
4-((2 S,5R)-4-(1-cyclopropylpropyl)-2,5-dimethylpiper-
  azin-1-yl)-1-methyl-2-oxo-1,2-dihydropyrido[3,2-d]
  pyrimidine-6-carbonitrile (453-455);
4-((2S,5R)-4-(1-(3,3-difluorocyclobutyl)propyl)-2,5-di-
  methylpiperazin-1-yl)-1-methyl-2-oxo-1,2-dihydro-
  pyrido[3,2-d]pyrimidine-6-carbonitrile (456-458); or
4-((2S,5R)-4-(1-(4,4-difluorocyclohexyl)propyl)-2,5-di-
  methylpiperazin-1-yl)-1-methyl-2-oxo-1,2-dihydro-
  pyrido[3,2-d]pyrimidine-6-carbonitrile (459-460).

8. The compound according to claim 1 or a pharmaceutically acceptable salt thereof, having the structure:

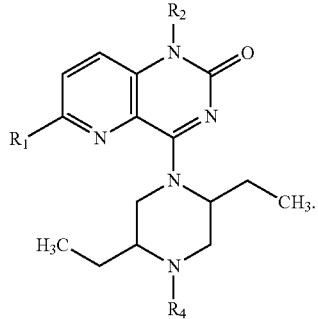

9. The compound according to claim 1 or a pharmaceutically acceptable salt thereof, having the structure:

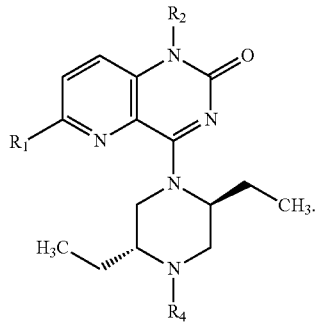

10. The compound according to claim 9 or a pharmaceutically acceptable salt thereof, wherein:

$R_1$ is —CN;

$R_2$ is —CH$_3$; and $R_{4b}$ is —CH$_3$, —CH$_2$CH$_3$, or —CH$_2$CH$_2$CH$_3$.

11. A compound having the structure:

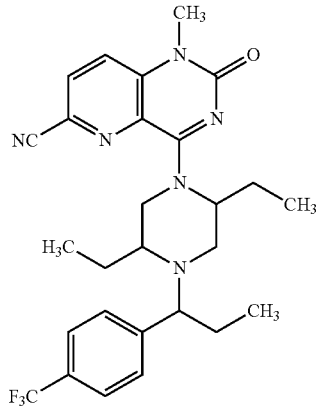 [SMILES: CCC1CN(C(CC)c2ccc(C(F)(F)F)cc2)C(CC)CN1c1nc(=O)n(C)c2ccc(C#N)nc12]

or a pharmaceutically acceptable salt thereof.

12. The compound according to claim 11 or a pharmaceutically acceptable salt thereof, having the structure:

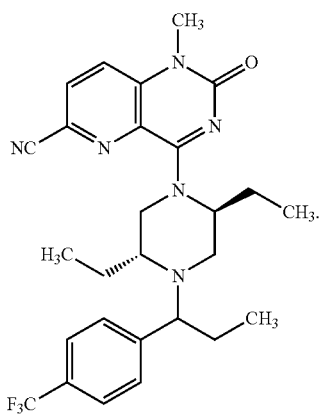 [SMILES: CCC(c1ccc(C(F)(F)F)cc1)N1C[C@H](CC)N(c2nc(=O)n(C)c3ccc(C#N)nc23)C[C@H]1CC]

13. A compound having the structure:

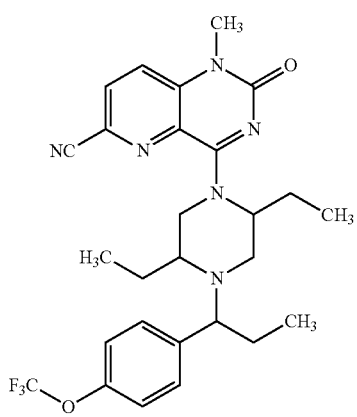 [SMILES: CCC1CN(C(CC)c2ccc(OC(F)(F)F)cc2)C(CC)CN1c1nc(=O)n(C)c2ccc(C#N)nc12]

or a pharmaceutically acceptable salt thereof.

14. The compound according to claim 13 or a pharmaceutically acceptable salt thereof, having the structure:

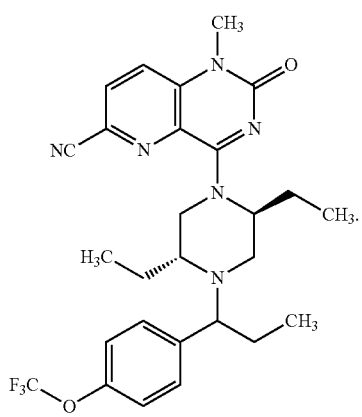 [SMILES: CCC(c1ccc(OC(F)(F)F)cc1)N1C[C@H](CC)N(c2nc(=O)n(C)c3ccc(C#N)nc23)C[C@H]1CC]

15. A compound having the structure:

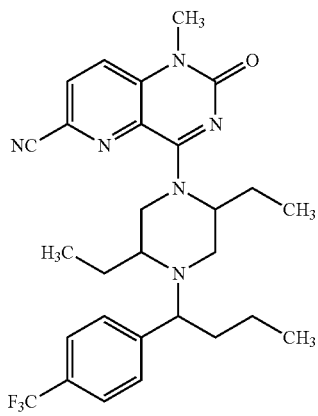 [SMILES: CCCC(c1ccc(C(F)(F)F)cc1)N1CC(CC)N(c2nc(=O)n(C)c3ccc(C#N)nc23)CC1CC]

or a pharmaceutically acceptable salt thereof.

16. The compound according to claim 15 or a pharmaceutically acceptable salt thereof, having the structure:

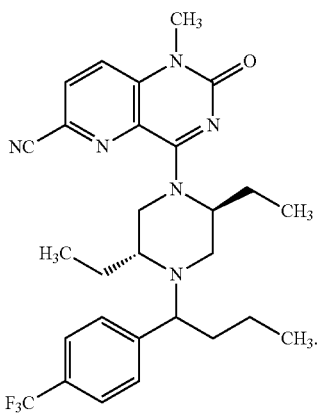 [SMILES: CCCC(c1ccc(C(F)(F)F)cc1)N1C[C@H](CC)N(c2nc(=O)n(C)c3ccc(C#N)nc23)C[C@H]1CC]

17. The compound according to claim 1 or a pharmaceutically acceptable salt thereof, wherein said compound is:
- 4-((2 S, 5R)-2,5-diethyl-4-((S)-1-(4-(trifluoromethyl)phenyl)propyl)piperazin-1-yl)-1-methyl-2-oxo-1,2-dihydropyrido[3,2-d]pyrimidine-6-carbonitrile;
- 4-((2 S, 5R)-2,5-diethyl-4-((R)-1-(4-(trifluoromethyl)phenyl)propyl)piperazin-1-yl)-1-methyl-2-oxo-1,2-dihydropyrido[3,2-d]pyrimidine-6-carbonitrile;
- 4-((2 S, 5R)-2,5-diethyl-4-((S)-1-(4-(trifluoromethoxy)phenyl)propyl)piperazin-1-yl)-1-methyl-2-oxo-1,2-dihydropyrido[3,2-d]pyrimidine-6-carbonitrile;
- 4-((2 S, 5R)-2,5-diethyl-4-((R)-1-(4-(trifluoromethoxy)phenyl)propyl)piperazin-1-yl)-1-methyl-2-oxo-1,2-dihydropyrido[3,2-d]pyrimidine-6-carbonitrile;
- 4-((2 S, 5R)-2,5-diethyl-4-((S)-1-(4-(trifluoromethyl)phenyl)butyl)piperazin-1-yl)-1-methyl-2-oxo-1,2-dihydropyrido[3,2-d]pyrimidine-6-carbonitrile; or
- 4-((2 S, 5R)-2,5-diethyl-4-((R)-1-(4-(trifluoromethyl)phenyl)butyl)piperazin-1-yl)-1-methyl-2-oxo-1,2-dihydropyrido[3,2-d]pyrimidine-6-carbonitrile.

18. A compound having the structure:

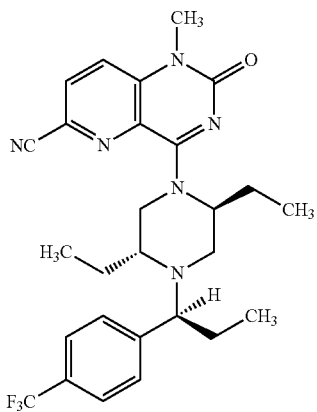 [SMILES: CC[C@H]1CN([C@@H](CC)c2ccc(C(F)(F)F)cc2)[C@H](CC)CN1c1nc(=O)n(C)c2ccc(C#N)nc12]

or a pharmaceutically acceptable salt thereof.

19. A compound having the structure:

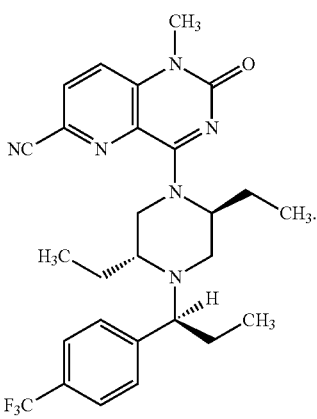 [SMILES: CC[C@H]1CN([C@@H](CC)c2ccc(C(F)(F)F)cc2)[C@H](CC)CN1c1nc(=O)n(C)c2ccc(C#N)nc12]

20. A pharmaceutically acceptable salt of the compound having the structure:

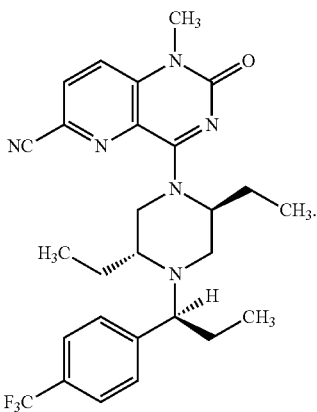 [SMILES: CC[C@H]1CN([C@@H](CC)c2ccc(C(F)(F)F)cc2)[C@H](CC)CN1c1nc(=O)n(C)c2ccc(C#N)nc12]

21. A compound having the structure:

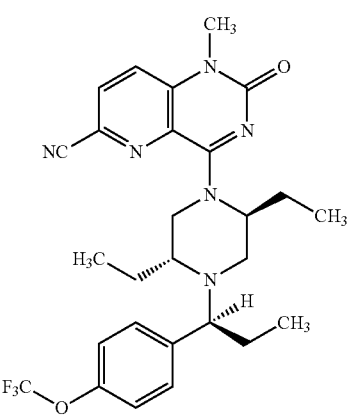 [SMILES: CC[C@H]1CN([C@@H](CC)c2ccc(OC(F)(F)F)cc2)[C@H](CC)CN1c1nc(=O)n(C)c2ccc(C#N)nc12]

or a pharmaceutically acceptable salt thereof.

22. A compound having the structure:

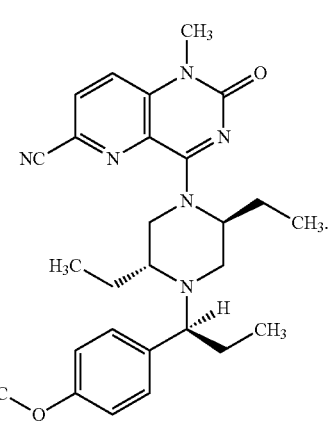

23. A pharmaceutically acceptable salt of the compound having the structure:

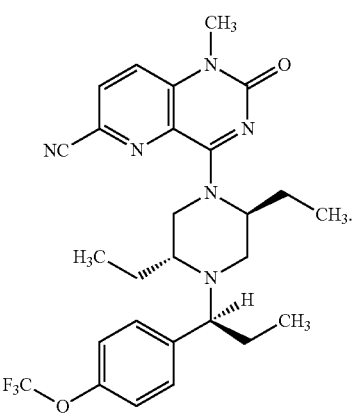 [SMILES: CC[C@H]1CN([C@@H](CC)c2ccc(OC(F)(F)F)cc2)[C@H](CC)CN1c1nc(=O)n(C)c2ccc(C#N)nc12]

24. A compound having the structure:

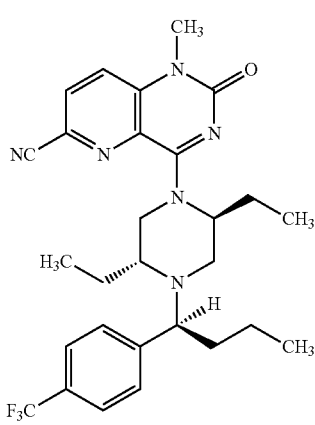 [SMILES: CCC[C@@H](c1ccc(C(F)(F)F)cc1)N1C[C@H](CC)N(c2nc(=O)n(C)c3ccc(C#N)nc23)C[C@H]1CC]

or a pharmaceutically acceptable salt thereof.

25. A compound having the structure:

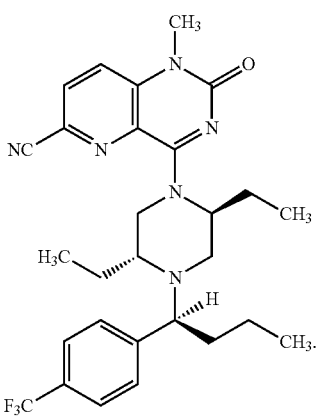 [SMILES: CCC[C@@H](c1ccc(C(F)(F)F)cc1)N1C[C@H](CC)N(c2nc(=O)n(C)c3ccc(C#N)nc23)C[C@H]1CC]

26. A pharmaceutically acceptable salt of the compound having the structure:

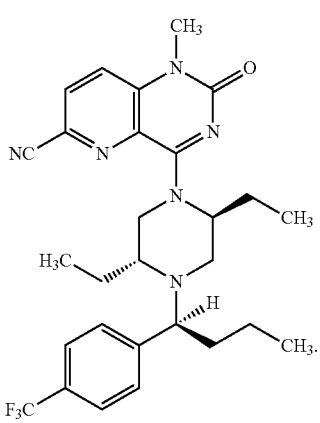 [SMILES: CCC[C@@H](c1ccc(C(F)(F)F)cc1)N1C[C@H](CC)N(c2nc(=O)n(C)c3ccc(C#N)nc23)C[C@H]1CC]

27. A pharmaceutical composition comprising a compound according to claim 1 or a pharmaceutically-acceptable salt thereof; and a pharmaceutically acceptable carrier.

28. A pharmaceutical composition comprising a compound according to claim 19; and a pharmaceutically acceptable carrier.

29. A pharmaceutical composition comprising the pharmaceutically acceptable salt of the compound according to claim 20; and a pharmaceutically acceptable carrier.

30. A pharmaceutical composition comprising a compound according to claim 22; and a pharmaceutically acceptable carrier.

31. A pharmaceutical composition comprising the pharmaceutically acceptable salt of the compound according to claim 23; and a pharmaceutically acceptable carrier.

32. A pharmaceutical composition comprising a compound according to claim 25; and a pharmaceutically acceptable carrier.

33. A pharmaceutical composition comprising the pharmaceutically acceptable salt of the compound according to claim 26; and a pharmaceutically acceptable carrier.

\* \* \* \* \*

UNITED STATES PATENT AND TRADEMARK OFFICE
CERTIFICATE OF CORRECTION

Page 1 of 3

PATENT NO. : 11,584,747 B2
APPLICATION NO. : 17/004058
DATED : February 21, 2023
INVENTOR(S) : Upender Velaparthi et al.

It is certified that error appears in the above-identified patent and that said Letters Patent is hereby corrected as shown below:

On the Title Page

Column 2 (Item (56) Other Publications), Line 7, delete "Inhyibitors" and insert -- Inhibitors --.

Column 2 (Item (56) Other Publications), Line 9, delete "Activites" and insert -- Activities --.

In the Claims

Claim 2, Column 430, Line 18 (Approx.), delete "$R_{ab}$" and insert -- $R_{4b}$ --.

Claim 7, Column 435, Line 7, delete "4-((2s, 5r)" and insert -- 4-((2S,5R) --.

Claim 7, Column 435, Line 22, delete "4-((2 S,5R)" and insert -- 4-((2S,5R) --.

Claim 7, Column 436, Line 5, delete "4-((2 S,5R)" and insert -- 4-((2S,5R) --.

Claim 7, Column 436, Line 8 (Approx.), delete "4-(4" and insert -- 4-((4 --.

Claim 7, Column 436, Line 37 (Approx.), delete "4-(4" and insert -- 4-((4 --.

Claim 7, Column 436, Line 49, delete "4-((2 S,5R)" and insert -- 4-((2S,5R) --.

Claim 7, Column 436, Line 53, delete "4-(4" and insert -- 4-((4 --.

Claim 7, Column 436, Line 64, delete "4-((2 S,5R)" and insert -- 4-((2S,5R) --.

Claim 7, Column 437, Line 12 (Approx.), delete "4-(4" and insert -- 4-((4 --.

Claim 7, Column 437, Line 31 (Approx.), delete "4-((2 S,5R)" and insert -- 4-((2S,5R) --.

Signed and Sealed this
Fourteenth Day of October, 2025

John A. Squires
*Director of the United States Patent and Trademark Office*

CERTIFICATE OF CORRECTION (continued)
U.S. Pat. No. 11,584,747 B2

Claim 7, Column 437, Line 31 (Approx.), delete "4-(4" and insert -- 4-((4 --.

Claim 7, Column 438, Line 22, delete "4-((2 S,5R)" and insert -- 4-((2S,5R) --.

Claim 7, Column 438, Line 25, delete "4-(4" and insert -- 4-((4 --.

Claim 7, Column 438, Line 45, delete "4-((2 S,5R)" and insert -- 4-((2S,5R) --.

Claim 7, Column 439, Line 17 (Approx.), delete "4-((2 S,5R)" and insert -- 4-((2S,5R) --.

Claim 7, Column 439, Line 41, delete "4-((2 S,5R)" and insert -- 4-((2S,5R) --.

Claim 7, Column 439, Line 62, delete "4-((2 S,5R)" and insert -- 4-((2S,5R) --.

Claim 7, Column 440, Line 1, delete "4-(4" and insert -- 4-((4 --.

Claim 7, Column 440, Line 8 (Approx.), delete "4-((2 S,5R)" and insert -- 4-((2S,5R) --.

Claim 7, Column 440, Line 20, delete "4-((2 S,5R)" and insert -- 4-((2S,5R) --.

Claim 7, Column 440, Line 26, delete "4-((2 S,5R)" and insert -- 4-((2S,5R) --.

Claim 7, Column 440, Line 29, delete "4-((2 S,5R)" and insert -- 4-((2S,5R) --.

Claim 7, Column 440, Line 33, delete "4-((2 S,5R)" and insert -- 4-((2S,5R) --.

Claim 7, Column 440, Line 40, delete "4-((2 S,5R)" and insert -- 4-((2S,5R) --.

Claim 7, Column 440, Line 44, delete "4-((2 S,5R)" and insert -- 4-((2S,5R) --.

Claim 7, Column 440, Line 50, delete "4-((2 S,5R)" and insert -- 4-((2S,5R) --.

Claim 7, Column 440, Line 53, delete "4-((2 S,5R)" and insert -- 4-((2S,5R) --.

Claim 7, Column 440, Line 60, delete "4-((2 S,5R)" and insert -- 4-((2S,5R) --.

Claim 7, Column 440, Line 64, delete "4-((2 S,5R)" and insert -- 4-((2S,5R) --.

Claim 7, Column 441, Line 19, delete "(1 S,2S)" and insert -- (1S,2S) --.

Claim 7, Column 441, Line 19, delete "((2R,5 S)" and insert -- ((2R,5S) --.

Claim 7, Column 441, Line 23, delete "4-((2 S,5R)" and insert -- 4-((2S,5R) --.

Claim 7, Column 443, Line 8, delete "4-((2 S,5R)" and insert -- 4-((2S,5R) --.

CERTIFICATE OF CORRECTION (continued)
U.S. Pat. No. 11,584,747 B2

Page 3 of 3

Claim 7, Column 443, Line 44, delete "4-((2 S,5R)" and insert -- 4-((2S,5R) --.

Claim 7, Column 443, Line 15 (Approx.), delete "4-((2 S,5R)" and insert -- 4-((2S,5R) --.

Claim 7, Column 445, Lines 48-49 (Approx.), delete "(Diastereomeric Mixture)" and insert -- (diastereomeric mixture) --.

Claim 7, Column 445, Line 58 (Approx.), delete "4-((2 S,5R)" and insert -- 4-((2S,5R) --.

Claim 17, Column 448, Line 47 (Approx.), delete "4-((2 S, 5R)" and insert -- 4-((2S,5R) --.

Claim 17, Column 448, Line 50 (Approx.), delete "4-((2 S, 5R)" and insert -- 4-((2S,5R) --.

Claim 17, Column 448, Line 54 (Approx.), delete "4-((2 S, 5R)" and insert -- 4-((2S,5R) --.

Claim 17, Column 448, Line 58 (Approx.), delete "4-((2 S, 5R)" and insert -- 4-((2S,5R) --.

Claim 17, Column 448, Line 61, delete "4-((2 S, 5R)" and insert -- 4-((2S,5R) --.

Claim 17, Column 448, Line 65, delete "4-((2 S, 5R)" and insert -- 4-((2S,5R) --.